(12) United States Patent
Wucherpfennig et al.

(10) Patent No.: US 11,597,934 B2
(45) Date of Patent: Mar. 7, 2023

(54) METHODS AND COMPOSITIONS FOR REDUCING IMMUNOSUPPRESSION BY TUMOR CELLS

(71) Applicants: Dana-Farber Cancer Institute, Inc., Boston, MA (US); The General Hospital Corporation, Boston, MA (US)

(72) Inventors: Kai W. Wucherpfennig, Brookline, MA (US); Glenn Dranoff, Sudbury, MA (US); Penghui Zhou, Quincy, MA (US); Donald Shaffer, Boston, MA (US); Nir Hacohen, Brookline, MA (US); Harvey I. Cantor, Wellesley, MA (US); Diana Alvarez Arias, Midland, MI (US)

(73) Assignees: DANA FARBER CANCER INSTITUTE, INC., Boston, MA (US); THE GENERAL HOSPITAL CORPORATION, Boston, MA (US)

( * ) Notice: Subject to any disclaimer, the term of this patent is extended or adjusted under 35 U.S.C. 154(b) by 98 days.

(21) Appl. No.: 17/102,787

(22) Filed: Nov. 24, 2020

(65) Prior Publication Data
US 2021/0139914 A1 May 13, 2021

Related U.S. Application Data

(60) Continuation of application No. 15/944,330, filed on Apr. 3, 2018, now Pat. No. 10,876,120, which is a
(Continued)

(51) Int. Cl.
*C12N 15/113* (2010.01)
*A61K 35/17* (2015.01)
(Continued)

(52) U.S. Cl.
CPC .......... *C12N 15/1137* (2013.01); *A61K 35/17* (2013.01); *A61K 39/0011* (2013.01);
(Continued)

(58) Field of Classification Search
CPC ... C07K 16/32; C07K 2317/55; C12N 5/0638
See application file for complete search history.

(56) References Cited

U.S. PATENT DOCUMENTS 8,809,288 B2    8/2014  Baier et al.
2004/0180338 A1  9/2004  Delepine et al.
(Continued)

FOREIGN PATENT DOCUMENTS

CN    103113470 A    5/2013
JP    2003533991 A   11/2003
(Continued)

OTHER PUBLICATIONS

Curran K.J., Pegram H.J., Brentjens R.J., Chimeric antigen receptors for T cell immunotherapy: current understanding and future directions. J Gene Med. Jun. 2012;14(6):405-15. doi: 10.1002/jgm. 2604. PMID: 22262649; PMCID: PMC4697438 (12 pages).
(Continued)

*Primary Examiner* — Terra C Gibbs
(74) *Attorney, Agent, or Firm* — Crowell & Moring LLP

(57) ABSTRACT

The present disclosure provides, in part, methods of discovering immunotherapy targets in vivo, therapeutic compositions (e.g., shRNA, immunoresponsive cells expressing shRNA and/or a chimeric antigen receptors (CAR)), and methods of use thereof.

20 Claims, 38 Drawing Sheets

Specification includes a Sequence Listing.

Related U.S. Application Data division of application No. 14/897,210, filed as application No. PCT/US2014/041739 on Jun. 10, 2014, now Pat. No. 9,944,931.

(60) Provisional application No. 61/929,821, filed on Jan. 21, 2014, provisional application No. 61/921,303, filed on Dec. 27, 2013, provisional application No. 61/833,298, filed on Jun. 10, 2013.

(51) Int. Cl.
| | |
|---|---|
| *C07K 14/725* | (2006.01) |
| *C12N 5/0783* | (2010.01) |
| *A61K 39/00* | (2006.01) |
| *C07K 16/32* | (2006.01) |
| *C12Q 1/6886* | (2018.01) |

(52) U.S. Cl.
CPC .. *A61K 39/001195* (2018.08); *C07K 14/7051* (2013.01); *C07K 16/32* (2013.01); *C12N 5/0638* (2013.01); *C12N 15/113* (2013.01); *C12Q 1/6886* (2013.01); *A61K 2039/5158* (2013.01); *A61K 2039/585* (2013.01); *C07K 2317/24* (2013.01); *C07K 2317/55* (2013.01); *C07K 2317/622* (2013.01); *C07K 2317/76* (2013.01); *C07K 2319/33* (2013.01); *C12N 2310/14* (2013.01); *C12N 2310/531* (2013.01); *C12N 2320/31* (2013.01); *C12N 2320/32* (2013.01); *C12Q 2600/178* (2013.01)

(56) References Cited

U.S. PATENT DOCUMENTS

| | | |
|---|---|---|
| 2010/0061984 A1 | 3/2010 | Greene et al. |
| 2010/0239656 A1 | 9/2010 | Astsaturov et al. |
| 2010/0260808 A1 | 10/2010 | Baier et al. |

FOREIGN PATENT DOCUMENTS

| | | |
|---|---|---|
| JP | 2011-507806 A | 3/2011 |
| WO | WO 01/90371 A1 | 11/2001 |
| WO | WO 2007/084775 A2 | 7/2007 |
| WO | WO 2008/033403 A2 | 3/2008 |
| WO | WO 2009/062199 A1 | 5/2009 |
| WO | WO 2012/038918 A1 | 3/2012 |
| WO | WO 2012/079000 A1 | 6/2012 |
| WO | WO 2013/121042 A1 | 8/2013 |

OTHER PUBLICATIONS

Ge Q., Ilves H., Dallas A., Kumar P., Shorenstein J., Kazakov S.A., Johnston B.H., Minimal-length short hairpin RNAs: the relationship of structure and RNAi activity. RNA. Jan. 2010;16(1):106-17. doi: 10.1261/rna.1894510. Epub Dec. 1, 2009. PMID: 19952116; PMCID: PMC2802021. (13 pages).

Notification of Reasons for Refusal dated Oct. 27, 2021 from corresponding Japanese Patent Application No. 2020-195684 (6 pages).

Iwamura K.; Kato T.; Miyahara Y.; Naota H.; Mineno J.; Ikeda H.; Shiku H.; "siRNA-mediated silencing of PD-1 ligands enhances tumor-specific human T-cell effector functions", Gene Therapy, Oct. 19, 2012 (10); pp. 959-966. DOI: 10.1038/gt.2011.185; PMID: 22113316. Epub Nov. 24, 2011.

Stromnes IM, Blattman JN, Tan X, Jeevanjee S., Gu H., Greenberg PD. Abrogating Cbl-b in effector CD8(+) T cells improves the efficacy of adoptive therapy of leukemia in mice. J Clin Invest. Oct. 2010;120(10):3722-34. doi 10.1172/JCI41991. Epub Sep. 20, 2010. PMID: 20890046; PMCID: PMC2947221 (13 pages).

GenBank: U26710.1, Human cbl-b mRNA (Aug. 30, 1996) (two pages).

Cheadle EJ, Rothwell DG, Bridgeman JS, Sheard VE, Hawkins RE, Gilham DE. Ligation of the CD2 co-stimulatory receptor enhances IL-2 production from first-generation chimeric antigen receptor T cells. Gene Ther. Nov. 2012;19(11):1114-20. doi: 10.1038/gt.2011.192. Epub Dec. 1, 2011. PMID: 22130449 (7 pages).

Notice of Preliminary Rejection dated Dec. 9, 2021 from corresponding Korean Patent Application No. 10-2021-7028677 (7 pages including English translation).

Article, Stephanie Wallner, Thomas Gruber, Gottfried Baier, Dominik Wolf, "Releasing the Brake: Targeting Cbl-b to Enhance Lymphocyte Effector Functions", *Journal of Immunology Research*, vol. 2012, Article ID 692639, 5 pages, 2012. https://doi.org/10.1155/2012/692639.

Article, Rao DD et al: "siRNA vs. shRNA: Similarities and differences", Advanced Drug Delivery Reviews, Elsevier, Amsterdam, NL, vol. 61, No. 9, Jul. 25, 2009 (Jul. 25, 2009), pp. 746-759, XP026142663, ISSN: 0169-409X, DOI: 10.1016/J.ADDR.2009.04.004 [retrieved on Apr. 20, 2009] the whole document*.

Extended European Search Report (9 pages) dated Sep. 9, 2021 from corresponding EP Application 21160675.1.

Ashton, J.M., et al.; "Gene sets identified with oncogene cooperativity analysis regulate in vivo growth and survival of leukemia stem cells"; Cell Stem Cell, vol. 11; Sep. 7, 2012; pp. 359-372.

Barr, F.A et al.; "Protein phosphatases and the regulation of mitosis"; Journal of Cell Science, vol. 124; Jul. 15, 2011; pp. 2323-2334.

Bellone, M., et al.; "Relevance of the tumor antigen in the validation of three vaccination strategies for melanoma"; Journal of immunology, vol. 165 Sep. 1, 2000; pp. 2651-2656.

Bollard, C.M et al.; "T-cell therapy in the treatment of post-transplant lymphoproliferative disease"; Nat Rev Clin Oncol, vol. 9; Sep. 2012; pp. 510-519.

Brahmer, J.R., et al. "Safety and activity of anti-PD-L1 antibody in patients with advanced cancer"; The New England Journal of Medicine, vol. 366, No. 26; Jun. 28, 2012; pp. 2455-2465.

Chiang, C.W., et al.; "Protein phosphatase 2A dephosphorylation of phosphoserine 112 plays the gatekeeper role for BAD-mediated apoptosis"; Mol Cell Biol, vol. 23, Sep. 2003; pp. 6350-6362.

Doody, K.M. et al.; "T-cell protein tyrosine phosphatase is a key regulator in immune cell signaling: lessons from the knockout mouse model and implications in human disease"; Immunological reviews; vol. 228; Mar. 6, 2009; pp. 325-341.

Eichhorn, P. et al.; "A RNA interface screen identifies the protein phosphatase 2A subunit PR55gamma as a stress-sensitive inhibitor of c-SRC"; PLoS Genetics, vol. 3, Issue 12; Dec. 2007; pp. 2381-2394; XP009170430.

Fidler, I.J.; "Biological behavior of malignant melanoma cells correlated to their survival in vivo"; Cancer research, vol. 35; Jan. 1975; pp. 218-224.

Gabrilovich, D.I. et al.; "Myeloid-derived suppressor cells as regulators of the immune system"; Nature Reviews—Immunology, vol. 9; Mar. 2009; pp. 162-174.

Galon, J., et al.; "Type, density, and location of immune cells within human colorectal tumors predict clinical outcome"; Science, vol. 313, Sep. 29, 2006; pp. 1960-1964.

Gerber, S.A. et al.; "Absolute quantification of proteins and phosphoproteins from cell lysates by tandem MS"; PNAS, vol. 100; Jun. 10, 2003; pp. 6940-6945.

Gorer, P.A.; "Studies in antibody response of mice to tumour inoculation"; Br J Cancer, vol. 4; Dec. 1950; pp. 372-379.

Hamanishi, J., et al.; Programmed cell death 1 ligand 1 and tumor-infiltrating CD8+ T lymphocytes are prognostic factors of human ovarian cancer:; PNAS, vol. 104, No. 9; Feb. 27, 2007; pp. 3360-3365.

Han, Q., et.al.; "Multidimensional analysis of the frequencies and rates of cytokine secretion from single cells by quantitative microengraving"; Lab on a Chip, vol. 10; Apr. 8, 2010; pp. 1391-1400.

Hinterleitner, R. et al.; "Adoptive Transfer of siRNA Cblb-Silenced CD8+ T Lymphocytes Augments Tumor Vaccine Efficacy in a B16 Melanoma Model" Plos One, vol. 7, No. 9; Sep. 2012; p. e44295; XP055141808.

Hodi, F.S., et al.; "Improved Survival with Ipilimumab in Patients with Metastatic Melanoma"; New England Journal of Medicine, vol. 363, No. 8; Aug. 19, 2010; pp. 711-723.

(56) References Cited

OTHER PUBLICATIONS

Hogquist, K.A., et al.; "T cell receptor antagonist peptides induce positive selection"; Cell, vol. 76, pp. 17-27; Jan. 14, 1994.
Kalos M, et al.; "T Cells with Chimeric Antigen Receptors Have Potent Antitumor Effects and Can Establish Memory in Patients with Advanced Leukemia"; Science Translational Medicine, vol. 3, Issue 95; Aug. 10, 2011; 11 pages.
Koller, B.H et al.; "Normal development of mice deficient in beta 2M, MHC class I proteins, and CD8+ T cells"; Science, vol. 248; Jun. 8, 1990; pp. 1227-1230.
Kurella, S., et al.; Transcriptional modulation of TCR, Notch and Wnt signaling pathways in SEB-anergized CD4+ T cells; Genes and Immunity, vol. 6; Jul. 21, 2005; pp. 596-608.
Lopes, A.R., et al.; "Bim-mediated deletion of antigen-specific CD8 T cells in patients unable to control HBV infection"; The Journal of clinical investigation, vol. 118; May 2008; pp. 1835-1845.
Luo, B., et al.; "Highly parallel identification of essential genes in cancer cells" PNAS, vol. 105, No. 51; Dec. 23, 2008; pp. 20380-20385.
Macian, F., et al.; "Transcriptional mechanisms underlying lymphocyte tolerance" Cell, vol. 109; Jun. 14, 2002; pp. 719-731.
Mahmoud, S.M., et al.; "Tumor-Infiltrating CD8+ Lymphocytes Predict Clinical Outcome in Breast Cancer"; Journal of Clinical Oncology, vol. 29, No. 15; May 20, 2011; pp. 1949-1955.
Milone et al.; "Chimeric Receptors Containing CD137 Signal Transduction Domains Mediate Enhanced Survival of T Cells and Increased Antileukemic Efficacy In Vivo"; Molecular Therapy, vol. 17; Apr. 21, 2009; pp. 1453-1464.
Mochida, S. et al.; "Greatwall phosphorylates an inhibitor of protein phosphatase 2A that is essential for mitosis"; Science, vol. 330, Nov. 25, 2010; pp. 1670-1673.
Muranski, P., et al.; "Tumor-specific Th17-polarized cells eradicate large established melanoma" Blood, vol. 112; Jul. 15, 2008; 362-373.
Overwijk, W.W., et al.; "Tumor regression and autoimmunity after reversal of a functionally tolerant state of self-reactive CD8+ T cells"; The Journal of experimental medicine, vol. 198; Aug. 18, 2003; pp. 569-580.
Pagès, F. et al; "In situ cytotoxic and memory T cells predict outcome in patients with early-stage colorectal cancer"; Journal of Clinical Oncology, vol. 27, No. 35; Dec. 10, 2009; pp. 5944-5951.
Paolino, M. et al.; "Cbl-b in T-cell activation"; Semin Immunopathol, vol. 32; Feb. 21, 2010; pp. 137-148.
Parish, I.A., et al.; "The molecular signature of CD8+ T cells undergoing deletional tolerance"; Blood, vol. 113; May 2009; pp. 4575-4585.
Restifo, N.P. et al.; "Adoptive immunotherapy for cancer: harnessing the T cell response"; Nature reviews—Immunology, vol. 12; Apr. 2012; pp. 269-281.
Riese, M.J. et al.; "Enhanced Effector Responses in Activated CD8+ T Cells Deficient in Diacylglycerol Kinases"; Cancer Research, vol. 73, No. 12; Apr. 10, 2013; pp. 3566-3577; XP055142357.
Shiao, S.L. et al.; "Immune microenvironments in solid tumors: new targets for therapy"; Genes & Development, vol. 25; Dec. 15, 2011; pp. 2559-2572.
Tamiya, T. et al.; "Suppressors of cytokine signaling (SOCS) proteins and JAK/STAT pathways: regulation of T-cell inflammation by SOCS1 and SOCS3"; Arteriosclerosis, Thrombosis, and Vascular Biology, vol. 31; May 2011; pp. 980-985.
Topalian, S.L. et al.; "Targeting the PD-1/B7-H1 (PD-L1) pathway to activate anti-tumor immunity"; Current opinion in immunology, vol. 24; Apr. 2012; pp. 207-212.
Topalian, S.L., et al.; "Safety, activity, and immune correlates of anti-PD-1 antibody in cancer"; The New England Journal of Medicine, vol. 366, No. 26; Jun. 28, 2012; pp. 2443-2454.
Turtle, C.J., et al.; Engineered T cells for anti-cancer therapy. Current opinion in immunology, vol. 24, Oct. 2012; pp. 633-639.
Westbrook, T.F., et al.; :A genetic screen for candidate tumor suppressors identifies REST; Cell, vol. 121; Jun. 17, 2005; pp. 837-848.
Wherry, E.J., et al.; "Molecular signature of CD8+ T cell exhaustion during chronic viral infection"; Immunity, vol. 27; Oct. 2007; pp. 670-684.
Xu, T., et al.; Microarray analysis reveals differences in gene expression of circulating CD8(+) T cells in melanoma patients and healthy donors; Cancer research, vol. 64; May 15, 2004; pp. 3661-3667.
Zender, L., et al.; "An oncogenomics-based in vivo RNAi screen identifies tumor suppressors in liver cancer"; Cell, vol. 135; Nov. 26, 2008; pp. 852-864.
Zha, Y., et al.; "T cell anergy is reversed by active Ras and is regulated by diacylglycerol kinase-alpha"; Nat Immunol, vol. 7; Nov. 2006; 1166-1173.
Zheng, Y. et al.; "Molecular regulation of T-cell anergy"; EMBO Reports, vol. 9; Jan. 1, 2008; pp. 50-55.
Zhou, P. et al.; "In vivo discovery of immunotherapy targets in the tumour microenvironment"; Nature, vol. 506, No. 7486; Jan. 29, 2014; pp. 52-57; XP055141914.
International Search Report completed Dec. 17, 2014 for International Application No. PCT/US2014/041739.
Office Action dated Jan. 5, 2018 for Japanese Application No. 2016-519595, including English translation.
Wang, W. et al.; "The application of the RNA interference technology in the treatment of pancreatic cancer's gene therapy"; International Journal of Digestive Diseases, vol. 27, No. 4; Aug. 25, 2007, vol. 27, No. 4; pp. 284-286; Abstract.
Quing Ge et al.; "Minimal-length short hairpin RNAs: The relationship of structure and RNAi activity"; RNA, vol. 16; Jan. 1, 2010; pp. 106-117.
Cancer Research Wales. News—No Two Cancers are the Same. https://www.cancerresearchwales.co.uk/blog/ no-two-cancers-are-the-same, downloaded on Feb. 25, 2020.
Stephens et al. (Nature, 2012 vol. 486:400-406).

FIG. 12a

| Gene Symbol | Function | Enrichment Fold |
|---|---|---|
| Ppp2r2d | Regulatory subunit of PP2A phosphatase | 17.2 |
| Arhgap5 | Negative regulator of Rho GTPases | 15.7 |
| Alk | Anaplastic lymphoma kinase (translocation of nucleophosmin and ALK in ALCL) | 13.5 |
| Egr2 | Transcription factor involved in T cell unresponsiveness, expression of Cblb | 10.2 |
| Ptpn2 | Inhibitor of T cell and cytokine signaling | 7.4 |

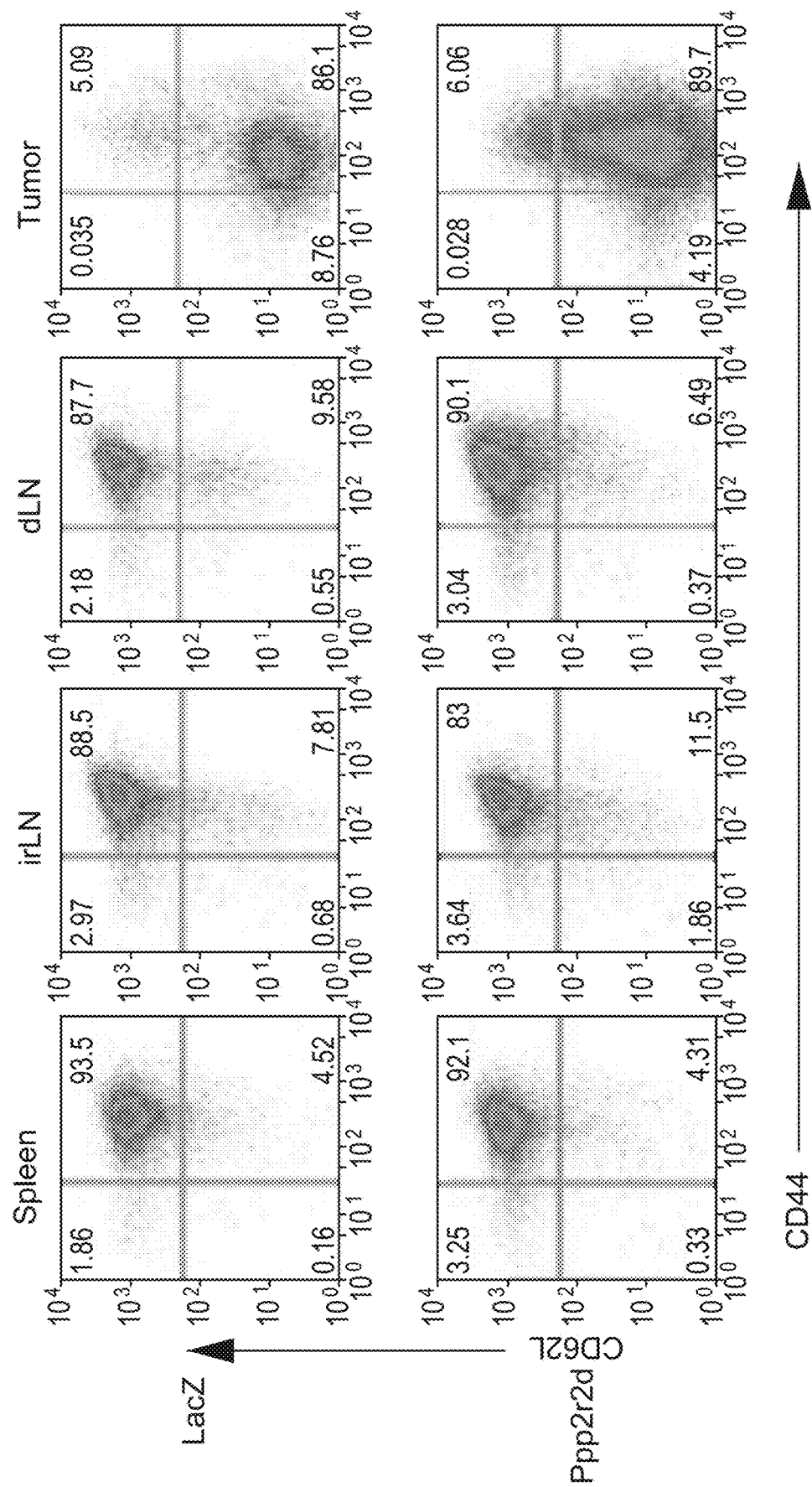

METHODS AND COMPOSITIONS FOR REDUCING IMMUNOSUPPRESSION BY TUMOR CELLS

RELATED APPLICATIONS

This application is a continuation of application Ser. No. 15/944,330, filed Apr. 3, 2018, which is a division of application Ser. No. 14/897,210, filed Dec. 9, 2015, now U.S. Pat. No. 9,944,931, which claims the benefit under 35 U.S.C. § 371 of International Application No. PCT/US2014/041739, filed Jun. 10, 2014, which claims priority to and the benefit of provisional applications U.S. Ser. No. 61/929,821, filed Jan. 21, 2014, U.S. Ser. No. 61/921,303, filed Dec. 27, 2013 and U.S. Ser. No. 61/833,298, filed Jun. 10, 2013, the contents of all of which are incorporated herein by reference in their entireties.

GOVERNMENT SUPPORT

This invention was made with government support under grant numbers R01 CA173750, A1073861, and P30 CA014051 awarded by The National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Dec. 9, 2015, is named 14293-469sequence listing_ST25.txt and is 351 KB in size.

TECHNICAL FIELD

This invention relates to methods of discovering immunotherapy targets in vivo, therapeutic compositions that modulate immunotherapy targets (e.g., shRNA, immunoresponsive cells expressing shRNA and, in some cases a receptor targeting a cancer cell, e.g., a chimeric antigen receptors (CAR)), and related methods of use.

BACKGROUND

Cytotoxic T cells play a central role in immune-mediated control of cancers[1-3], and monoclonal antibodies that target inhibitory receptors on T cells can induce significant clinical benefit in patients with advanced disease[4-6]. For survival, tumors have developed numerous immunosuppressive mechanisms to promote their own growth and to successfully evade the host immune system, effectively blocking the activity of T cells in the tumor microenvironment. This is a central issue in oncology because strong infiltration by CD8 T cells, which have cytotoxic function against tumor cells, is associated with a favorable prognosis in multiple types of human cancer[1,3,8]. This natural defense mechanism is severely blunted in the majority of patients by multiple inhibitory signals emanating from the tumor, its stroma, regulatory T cells and myeloid cell populations.[9-11] Various molecular and cellular immunosuppressive mechanisms responsible for tumor evasion have been identified. Certain of these mechanisms target immune antitumor effector cells. However, many of the regulatory mechanisms that result in loss of T cell function within immunosuppressive tumors remain unknown. Improving on the limited success of cancer immunotherapy requires new approaches to inhibit immunosuppressive pathways initiated by tumor cells to evade the host immune system.

SUMMARY

The present disclosure provides targets for inhibiting immunosuppressive pathways used by tumor cells to inactivate and/or suppress immune cells.

The disclosure also provides compositions and methods related to shRNA with therapeutic potential.

The disclosure also provides immunoresponsive cells, including T cells (e.g., cells targeting a tumor antigen) expressing at least one shRNA or other nucleic acid molecule capable of silencing genes that inhibit T cell function.

The disclosure also provides immunoresponsive cells, including T cells, harboring at least one vector expressing a shRNA and at least one chimeric antigen receptor directed to a tumor antigen.

In some embodiments, the disclosure provides immunoresponsive cells having tumor specificity comprising a vector encoding a shRNA capable of silencing genes that inhibit T cell function. In some aspects, the shRNA sequence reduces the expression of a gene selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ype2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In another aspect, the shRNA comprises 15 contiguous nucleotides complementary to a nucleic acid sequence selected from the group consisting of SEQ ID NOs: 604-620 and 653-678. In some aspects, the immunoresponsive cell further comprises a vector encoding a tumor-specific T-cell receptor. In some aspects, the immunoresponsive cell is selected from the group consisting of a tumor-infiltrating lymphocyte (TIL), a Natural Killer T cell (NKT), a cytotoxic T lymphocyte (CTL), and a CD4 T cell.

In some embodiments, the immunoresponsive cell comprises a vector encoding a CAR, wherein the CAR comprises an antigen binding domain, a transmembrane domain, and a stimulatory domain. In some aspects, the antigen binding domain binds a tumor antigen or pathogen antigen. Exemplary tumor antigens include, for example, prostate-specific membrane antigen (PSMA), Carcinoembryonic Antigen (CEA), CD19, CD20, CD22, ROR1, mesothelin, CD333/IL3Ra, c-Met, Glycolipid F77, EGFRvIII, GD-2, NY-ESO-1 TCR, ERBB2, BIRC5, CEACAM5, WDR46, BAGE, CSAG2, DCT, MAGED4, GAGE1, GAGE2, GAGE3, GAGE4, GAGE5, GAGE6, GAGE7, GAGE8, IL13RA2, MAGEA1, MAGEA2, MAGEA3, MAGEA4, MAGEA6, MAGEA9, MAGEA10, MAGEA12, MAGEB1, MAGEB2, MAGEC2, TP53, TYR, TYRP1, SAGE1, SYCP1, SSX2, SSX4, KRAS, PRAME, NRAS, ACTN4, CTNNB1, CASP8, CDC27, CDK4, EEF2, FN1, HSPA1B, LPGAT1, ME1, HHAT, TRAPPC1, MUM3, MYO1B, PAPOLG, OS9, PTPRK, TPI1, ADFP, AFP, AIM2, ANXA2, ART4, CLCA2, CPSF1, PPIB, EPHA2, EPHA3, FGF5, CA9, TERT, MGAT5, CEL, F42, CAN, ETV6, BIRC7, CSF1, OGT, MUC1, MUC2, MUM1, CTAG1A, CTAG2, CTAG, MRPL28, FOLH1, RAGE, SFMBT1, KAAG1, SART1, TSPYL1, SART3, SOX10, TRG, WT1, TACSTD1, SILV, SCGB2A2, MC1R, MLANA, GPR143, OCA2, KLK3, SUPT7L, ARTC1, BRAF, CASP5, CDKN2A, UBXD5, EFTUD2, GPNMB, NFYC, PRDX5, ZUBR1, SIRT2, SNRPD1, HERV-K-MEL, CXorf61, CCDC110, VENTXP1, SPA17, KLK4, ANKRD30A, RAB38, CCND1, CYPIB1, MDM2, MMP2, ZNF395, RNF43, SCRN1, STEAP1, 707-AP, TGFBR2, PXDNL, AKAP13, PRTN3, PSCA, RHAMM, ACPP, ACRBP, LCK, RCVRN, RPS2, RPL10A, SLC45A3, BCL2L1, DKK1, ENAH, CSPG4, RGS5, BCR, BCR-ABL, ABL-BCR, DEK, DEK-CAN, ETV6-AML1, LDLR-FUT, NPM1-ALK1, PML-RARA, SYT-SSX1, SYT-SSX2, FLT3, ABL1, AML1, LDLR, FUT1, NPM1, ALK, PML1, RARA, SYT, SSX1, MSLN, UBE2V1, HNRPL, WHSC2, EIF4EBP1, WNK2, OAS3, BCL-2, MCL1, CTSH, ABCC3, BST2, MFGE8, TPBG, FMOD, XAGE1, RPSA, COTL1, CALR3, PA2G4, EZH2, FMNL1, HPSE, APC, UBE2A, BCAP31, TOP2A, TOP2B, ITGB8, RPA1, ABI2, CCNI, CDC2, SEPT2, STAT1, LRP1, ADAM17, JUP, DDR1, ITPR2, HMOX1, TPM4, BAAT, DNAJC8, TAPBP, LGALS3BP, PAGE4, PAK2, CDKN1A, PTHLH, SOX2, SOX11, TRPM8, TYMS, ATIC, PGK1, SOX4, TOR3A, TRGC2, BTBD2, SLBP, EGFR, IER3, TTK, LY6K, IGF2BP3, GPC3, SLC35A4, HSMD, H3F3A, ALDH1A1, MFI2, MMP14, SDCBP, PARP12, MET, CCNB1, PAX3-FKHR, PAX3, FOXO1, XBP1, SYND1, ETV5, HSPA1A, HMHA1, TRIM68, and any combination thereof. In some aspects, the antigen binding domain is an antigen-binding fragment of an antibody (e.g., Fab or a scFv). The intracellular domains of such CARs contain cytoplasmic signaling domains derived from the T cell receptor and costimulatory molecules.

In some embodiments, the vector is a plasmid, retroviral vector, or lentiviral vector.

In some embodiments, the disclosure provides isolated nucleic acid molecules encoding a shRNA sequence. In another embodiment, the disclosure provides isolated nucleic acid molecules encoding a CAR. In yet another embodiment, the disclosure provides isolated nucleic acid molecules encoding a CAR and a shRNA sequence. In some aspects, the isolated nucleic acid encodes a shRNA sequence reduces the expression of a gene selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, or Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In another aspect, the isolated nucleic acid encodes a shRNA comprising 15 contiguous nucleotides complementary a nucleic acid sequence selected from the group consisting of SEQ ID NOs: 604-620 and 653-678.

In some embodiments, the isolated nucleic acid encodes a CAR comprising an antigen binding domain, a transmembrane domain, a stimulatory domain, and a co-stimulatory domain. In some embodiments, the antigen binding domain is an antigen-binding fragment of an antibody (e.g., Fab or a scFv). In some embodiments, the antigen binding domain is a cytoplasmic signaling domain derived from the T cell receptor and costimulatory molecules.

In some embodiments, the antigen-binding domain binds tumor antigen (e.g., a tumor antigen associated with a solid tumor, lymphoid tumor, melanoma, carcinoma, sarcomas, adenocarcinoma, lymphoma, leukemia, kidney, breast, lung, bladder, colon, ovarian, prostate, pancreas, stomach, brain, head and neck, skin, uterine, testicular, glioma, esophagus, and liver cancer).

In some embodiments the disclosure provides vectors comprising an isolated nucleic acid encoding a shRNA sequence, an isolated nucleic acid encoding a CAR, or an isolated nucleic acid encoding a CAR and a shRNA sequence. In some aspects, the vector is a plasmid, lentiviral vector, retroviral vector, adenoviral vector, adeno-associated viral vector. The shRNA can be operably linked to RNA polymerase II promoter or an RNA polymerase III promoter.

In yet other embodiments, the invention provides compositions comprising immunoresponsive cells according to the invention, and a pharmaceutically acceptable carrier.

In some embodiments, the disclosure provides immunoresponsive cells transfected with a first vector encoding a CAR and a second vector encoding a shRNA sequence. In some aspects, the shRNA sequence reduces the expression of a gene selected from the group consisting of Ppp2r2d, Eif2ak3, Arhgap5, Smad2, Akap81, Rbks, Egr2, Dgka, Cblb, Map3k3, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In another aspect, the shRNA comprise 15 contiguous nucleotides complementary a nucleic acid sequence selected from the group consisting of SEQ ID NOs: 604-620 and 653-678. In some aspects, the immunoresponsive cell further comprises a vector encoding a tumor-specific T-cell receptor. In some aspects, the immunoresponsive cell is selected from the group consisting of a tumor-infiltrating lymphocyte (TIL), a Natural Killer T cell (NKT), a cytotoxic T lymphocyte (CTL), and a CD4 T cell.

In some embodiments, the disclosure provides methods for treating cancer in a subject, the method comprising administering to the subject an autologous T cell modified to express a tumor-specific T-cell receptor or CAR and an shRNA, wherein the shRNA sequence reduces the expression of a gene selected from the group consisting of Ppp2r2d, Eif2ak3, Arhgap5, Smad2, Akap81, Rbks, Egr2, Dgka, Cblb, Map3k3, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In some aspects, the shRNA sequence comprises 15 contiguous nucleotides complementary to a nucleic acid sequence selected from the group consisting of: SEQ ID NOs: 604-620 and 653-678; and wherein the CAR comprises an antigen binding domain, a transmembrane domain, a stimulatory domain, and a co-stimulatory domain. In some aspects, the CAR comprises an antigen binding domain, a transmembrane domain, a stimulatory domain, and a co-stimulatory domain.

In some embodiments, the disclosure provides methods for treating cancer in a subject, the method comprising administering to the subject an autologous T cell modified to express a tumor-specific T-cell receptor or CAR and an shRNA of the invention. In yet another embodiment, the disclosure provides methods for treating cancer in a subject in need thereof by silencing genes that inhibit T cell function comprising administering to the subject an immunoresponsive cell comprising a vector, the vector encoding a tumor-specific T-cell receptor or a CAR and a shRNA sequence of the invention.

In some embodiments, the disclosure provides methods for identifying a gene that inhibits the function of an immunoresponsive T cell, the method comprising providing a population of immunoresponsive T cells harboring vectors expressing a shRNA, contacting the population of immunoresponsive T cells with an immunosuppressive tumor, determining whether a shRNA restores T cell function within the immunosuppressive tumor, and identifying a gene associated with a shRNA that restores T cell function within the tumor as a gene that inhibits the function of tumor-infiltrating T cells.

In some embodiments, the disclosure provides methods for increasing the immune response in a subject in need thereof, the method comprising administering a therapeutic agent that modulates the activity of a gene selected from the group consisting of Ppp2r2d, Eifak3, Arhgap5, Smad2, Akap8l, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

In some cases the sequence encoding an shRNA comprises a first sequence comprising 15-25 (15, 16, 17, 18, 19, 20, 21, 22, 23, 24 or 25) nucleotides complementary to any of SEQ ID NOs: 604-620 or SEQ ID NOs: 653-678 and a second sequence that is the reverse complement of the first sequence with one or no mismatches (i.e., is perfectly complementary to the first sequence), and a third sequence of 5-9 nucleotides positioned between the first and second sequences.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 12a is a table demonstrating enrichment of particular shRNAs in tumor versus spleen which was calculated based on deep sequencing results from the secondary screen.

FIG. 22a is a set of graphs showing representative flow cytometry plots demonstrating that the majority of adoptively transferred OT-I cells have a memory phenotype in lymph nodes but an effector phenotype in tumors. Cytokine pre-treated cells expressing Ppp2r2d or LacZ shRNAs were injected into mice bearing day 14 B16-Ova tumors. On day 7 following transfer, T cells were harvested from the indicated organs and stained with CD62L and CD44 antibodies. FACS analysis of shRNA-expressing OT-I cells was performed by gating on CD8/Thy1.1 double-positive cells.

DETAILED DESCRIPTION

Figure 1:
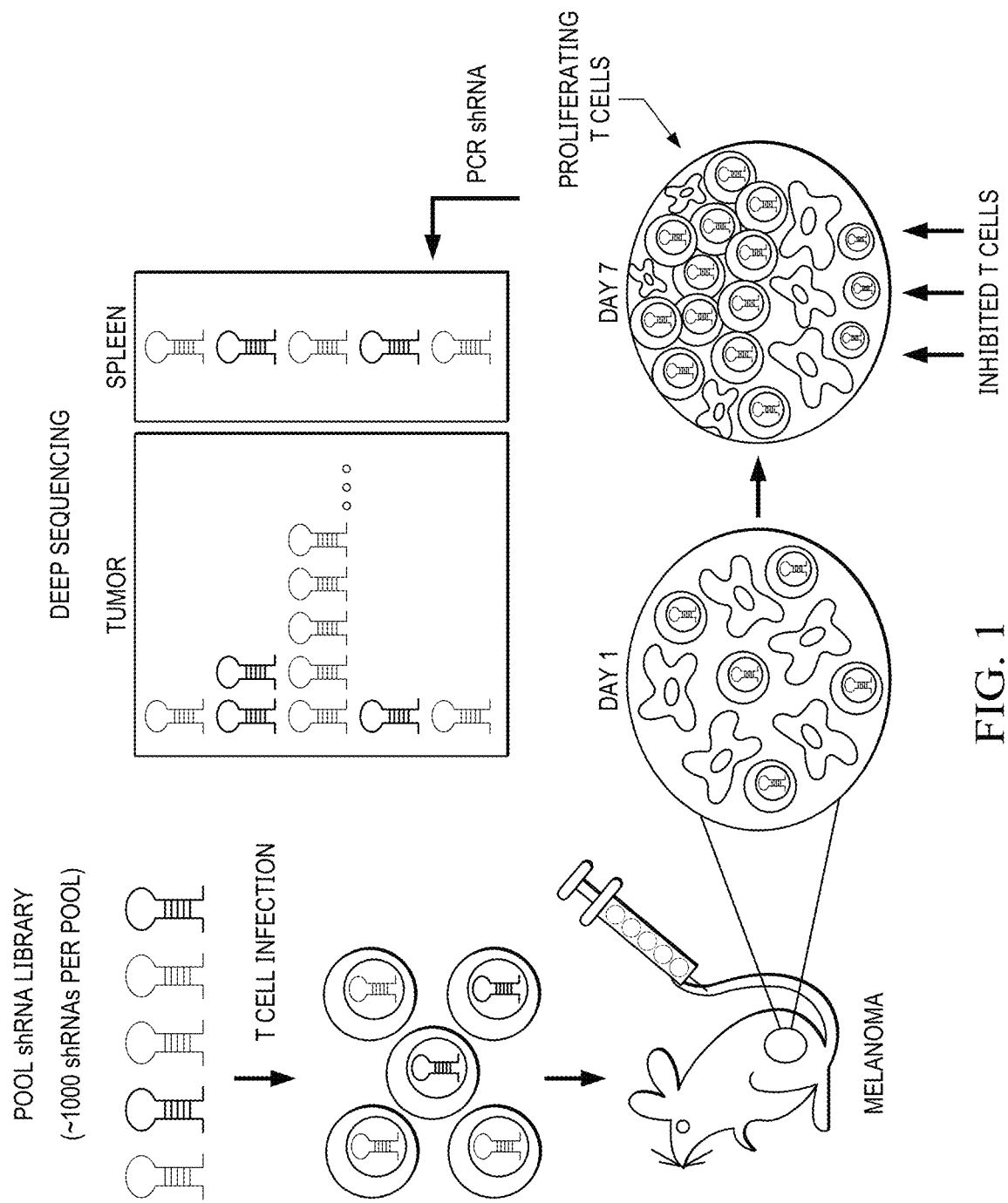
FIG. 1 is a schematic diagram demonstrating an exemplary approach for in vivo discovery of shRNAs that enhance T cell infiltration and accumulation within the tumor microenvironment.

The present disclosure is based, in part, on the observation that the regulatory mechanisms that result in loss of T cell function within immunosuppressive tumors can be systematically discovered in vivo using a pooled small hairpin RNA (shRNA) screening approach aimed at identifying genes that block the function of tumor infiltrating T-cells. As described in the background section above, tumor associated immunosuppressive mechanisms actively block the activity of T cells in the tumor microenvironment. The methods described herein identify shRNAs that enable robust T cell infiltration and accumulation in tumors, despite the multiple inhibitory signals. As described below, the methods identify shRNA that silence expression of genes responsible for immunosuppression by tumors, allowing for enhanced T cell infiltration and accumulation in tumors and resistance to apoptosis.

In some instances, the disclosure provides methods for specifically identifying regulatory mechanisms that result in the loss of T cell function within the tumor microenvironment. These methods can include: providing a population of T cells harboring vectors expressing a shRNA; contacting the population of T cells with an immunosuppressive tumor; determining whether a shRNA restores T cell function (e.g., restores ability of T cell to infiltrate and proliferate within the tumor microenvironment) within the immunosuppressive tumor; identifying a gene associated with a shRNA that restores T cell function within the tumor as a gene that inhibits T cell function within the tumor microenvironment.

The disclosure provides target genes for reducing the immunosuppressive effect of tumors. The expression of the target genes can be reduced in immune cells, e.g., T cells that recognize tumor associated antigens, and the reduction in expression of the target genes can increase the ability of the cells to evade tumor associated immunosuppressive mechanisms.

The disclosure provides shRNAs that reduce (e.g., silence, eliminate, knock down, knock out, or decrease) expression of genes that impair the function of tumor infiltrating T-cells. These shRNA were identified from the transfer of shRNA transduced T cells into tumors, followed by deep sequencing to quantify the representation of all shRNAs in the tumor and lymphoid organs. Representative shRNA disclosed herein include shRNA that reduce the activity of genes including, for example, Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

In some instances, the disclosure provides therapeutic compositions (e.g., including isolated nucleic acid molecules, vectors expressing nucleic acid molecules encoding the shRNA) related to the shRNAs that silence expression of genes that block the function of tumor infiltrating T-cells. In other aspects, the disclosure provides modified immunoresponsive cells (e.g., T cells, including Natural Killer T cells (NKT), a cytotoxic T lymphocytes (CTL), and a regulatory T cells) that harbor vectors capable of expressing the shRNA described herein. In another aspect, the modified immunoresponsive cells further harbor a vector capable of expressing a CAR having an antigen binding domain that targets a tumor specific antigen.

RNA Interference

One of the most important recent discoveries in biomedical research is the RNA interference (RNAi) pathway, which is used by cells to regulate the activity of many genes. The principles of RNAi have opened many new possibilities for the identification of therapeutic targets. RNA interference (RNAi) is an effective tool for genome-scale, high throughput analysis of gene function. The term "RNA interference" (RNAi), also called post transcriptional gene silencing (PTGS), refers to the biological process in which RNA molecules inhibit gene expression. An "RNA interfering agent" as used herein, is defined as any agent that interferes with or inhibits expression of a target gene, e.g., a target gene of the invention, by RNA interference (RNAi). Such RNA interfering agents include, but are not limited to, nucleic acid molecules including RNA molecules which are homologous to the target gene, e.g., a target gene of the invention, or a fragment thereof, short interfering RNA (siRNA), short hairpin RNA (shRNA), and small molecules which interfere with or inhibit expression of a target gene by RNA interference (RNAi).

"RNA interference (RNAi)" is a process whereby the expression or introduction of RNA of a sequence that is identical or highly similar to a target gene results in the sequence specific degradation or PTGS of messenger RNA (mRNA) transcribed from that targeted gene, thereby inhibiting expression of the target gene. This process has been described in plants, invertebrates, and mammalian cells. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene. These are the effector molecules for inducing RNAi, leading to posttranscriptional gene silencing with RNA-induced silencing complex (RISC). In addition to siRNA, which can be chemically synthesized, various other systems in the form of potential effector molecules for posttranscriptional gene silencing are available, including short hairpin RNAs (shRNAs), long dsRNAs, short temporal RNAs, and micro RNAs (miRNAs). These effector molecules either are processed into siRNA, such as in the case of shRNA, or directly aid gene silencing, as in the case of miRNA. The present invention thus encompasses the use of shRNA as well as any other suitable form of RNA to effect posttranscriptional gene silencing by RNAi. Use of shRNA has the advantage over use of chemically synthesized siRNA in that the suppression of the target gene is typically long-term and stable. An siRNA may be chemically synthesized, may be produced by in vitro by transcription, or may be produced within a host cell from expressed shRNA.

In one embodiment, a siRNA is a small hairpin (also called stem loop) RNA (shRNA). These shRNAs are composed of a short (e.g., 19-25 nucleotides) antisense strand, followed by a 5-9 nucleotide loop, and the complementary sense strand. Alternatively, the sense strand may precede the nucleotide loop structure and the antisense strand may follow. These shRNAs may be contained in plasmids, retroviruses, and lentiviruses.

As used herein, "gene silencing" induced by RNA interference refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without introduction of RNA interference. In one preferred embodiment, the mRNA levels are decreased by at least about 70%, about 80%, about 90%, about 95%, about 99%, about 100%.

The term "reduced" or "reduce" as used herein generally means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease, or any integer decrease between 10-100% as compared to a reference level.

The term "increased" or "increase" as used herein generally means an increase of at least 1% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any integer increase between 10-100% as compared to a reference level, or about a 2-fold, or about a 3-fold, or about a 4-fold, or about a 5-fold or about a 10-fold increase, or any increase between 2-fold and 10-fold or greater as compared to a reference level.

Immunoresponsive Cells

In some embodiments, the disclosure provides immunoresponsive cells, including T cells, cytotoxic T cells, tumor-infiltrating lymphocytes (TIL), regulatory (CD4) T cells, and Natural Killer (NKT) cells, expressing at least one of an antigen-recognizing receptor. In any aspect, the immunoresponsive cells express at least one tumor specific antigen-recognizing receptor. In some aspects, tumor cell antigen specific T cells, NKT cells, TIL, CTL cells or other immunoresponsive cells are used. Non-limiting examples of immunoresponsive cells include T cells, such as, for example, αβ-TCR+ T cells (e.g., CD8+ T cells or CD4+ T cells) γδ-TCR+ T cells, tumor-infiltrating lymphocytes (TIL), Natural Killer T cells (NKT), a cytotoxic T lymphocytes (CTL), and a CD4 T cells.

Nucleic Acid Compositions

In some embodiments, the disclosure provides isolated nucleic acids encoding shRNA sequences comprising a sequence at least 12, 15, 20 or 25 contiguous nucleotides complementary to a nucleic acid sequence selected from the group consisting of SEQ ID NOs: 604-620 and 653-678. The shRNA also includes the reverse complement of the contiguous nucleotide sequence and a short sequence located between the two sequences so that the two sequences form a stem loop shRNA that can be processed within a cell provide an siRNA that inhibits the expression of the protein encoded by one of SEQ ID NOs: 604-620 and 653-678, and compositions thereof.

Table 1 provides a list of genes identified here as being involved with tumor immunosuppression of T cells.

TABLE 1

| Gene | Human Gene Sequence | Human Sequence Accession No. | Murine Sequence Accession No. |
|---|---|---|---|
| Ppp2r2d | gtgtccggccaagcggcgccctgaaggcgtgtccggccgcagcttaggctctccgg gagtccccggagagtaggggcggccggcggcgctagtcttctggggagcgccgg gtgcacaccggaccactgcgggaggcctagggccgagggccgaggagctggcct gcgcccggcgaccccggcttccctccgcagtcgcccaggcgtcccttccccctac agccgagcggcgccgggcgcaggcgcattgggcgccccggcagccccgcgg | NM_018461 | NM_026391 |

TABLE 1-continued

| Gene | Human Gene Sequence | Human Sequence Accession No. | Murine Sequence Accession No. |
|---|---|---|---|
| | cccgccccgtccgctgcccgtccgaggaggcggagggcgatgacgtcatcgagc<br>ggggcgacgggcattgggcgccattttgaaaagggaaaaaaatccctccccggcg<br>gcggcggcggcggcggcggcgccggcggtggtggcggccccggggctgagcg<br>ctcggctgcagcggcgcggaggccgtctccctggtctgccgcggtccccgcccgtc<br>ccgccgccggctgccatggcaggagccggaggcggcggctgccccgcgggcgg<br>caacgacttccagtggtgcttctcgcaggtcaaggggccatcgacgaggacgtgg<br>ccgaagcggacatcatttccaccgttgagtttaattactctggagatcttcttgcaacag<br>gagacaagggcggcagagttgttattttcagcgtgaacaagagaataaaagccgcc<br>ctcattctagggagaatataatgtttacagcacctttcaaagtcatgaaccggagtttg<br>actatttgaaaagtctagaaattgaggaaaaaattaataaaattaggtggttaccacaac<br>agaatgctgctcattttcgactgtctacaaaggataaaactataaaattatgaaaataag<br>tgaacgggataaaagagcagaaggttataacctgaaagacgaagatggaagacttc<br>gagacccatttaggatcacggcgctacgggtcccaatattgaagcccatggatcttat<br>ggtagaagcgagtccacggcgaattttttgcaaatgctcacacatatcatataaattcca<br>tttcagtaaatagtgatcatgaaacatatctttctgcagatgacctgtgaattaatttatgg<br>cacttagaaatcacagatagaagctttaacatcgtggacatcaagcctgctaacatgg<br>aggagctgaccgaagtcatcactgcagccgagttccaccgcaccagtgcaacgtg<br>ttcgtctacagcagtagcaaagggaccatccgcctgtgtgacatgcgctcctcggcc<br>ctgtgcgacagacactccaagttttttgaagagcctgaagatcccagcagtaggtcctt<br>cttctcagaaataattttcatccatatccgatgtaaaattcagtcatagtgggcggtacatg<br>atgaccagagactacctgtcggtgaaggtgtgggacctcaacatggagagcaggcc<br>ggtggagaccaccaggtccacgagtacctgcgcagcaagctctgctctctctatga<br>gaacgactgcatctttgacaagtttgagtgttgctggaacggttcggatagcgccatca<br>tgaccgggtcctataacaacttcttcaggatgtttgatagagacacgcggagggatgt<br>gacccctggaggcctcgagagagagcagcaaaaccgcgcgccagcctcaaaccccg<br>gaaggtgtgtacgggggggtaagcggaggaaagacgagatcagtgtggacagtctg<br>gacttcaacaagaagatcctgcacacagcctggcaccccgtggacaatgtcattgcc<br>gtggctgccaccaataacttgtacatattccaggacaaaatcaactagagacgcgaac<br>gtgaggaccaagtcttgtcttgcatagttaagccggacattttttctgtcagagaaagg<br>catcattgtccgctccattaagaacagtgacgcacctgctacttcccttcacagacaca<br>ggagaaagccgcctccgctggaggcccggtgtggttccgcctcggcgaggcgcga<br>gacaggcgctgctgctcacgtggagacgctctcgaagcagagttgacggacactgc<br>tcccaaaaggtcattactcagaataaatgtatttatttcagtccggccttcctttccaattt<br>atagaccaaaaaattaacatccaagagaaaagttattgtcagataccgctcttctccaa<br>cttttccctctttctctgccatcacacttgggccttcactgcagcgtggtgtggccaccgt<br>ccgtgtcctctcggccttcctccgagtccaggtggactctgtggatgtgtggatgtggc<br>ccgagcaggctcaggcggcccactcacccacagcatccgccgccacccccttcgg<br>gtgtgagcgctcaataaaaacaacacactataaagtgtttttaaatccaaaaaaaaaa<br>aaaa (SEQ ID NO: 604) | | |
| Eif2ak3 | ggaaagtccaccttccccaacaaggccagcctgggaacatggagtggcagcggcc<br>gcagccaatgagagagcaaacgcgcggaaagtttgctcaatgggcgatgtccgag<br>ataggagtcactcaggtggcagcggcagaggccgggctgagacgtggccaggg<br>gaacacggctggctgtccaggccgtcggggcggcagtagggtccctagcacgtcct<br>tgccttcttgggagctccaagcggcgggagaggcaggcgtcagtggctgcgcctc<br>atgcctgcgcgcggggcgggacgctgatggagcgcgccatcagcccggggctgc<br>tggctacgggcgctgctgagctgctgctgctgctggggctcgcggcaaggacggtg<br>gccgcggggcgcgcccgtggcctcccagcgccgacggcggaggcggcgacgg<br>cctcggggcggccgctgctgctcccacctcagcgacgcgagtcaccggcggcgggcgc<br>cgtggctgccgccgaggtgactgtggaggacgctgaggcgctgccggcagcgc<br>gggagagcaggagctcggggtccggaaccagacgatgagacagagttgcgacc<br>gcgcggcaggtcattagtaattatcagcactttagatgggagaattgctgccttggatc<br>ctgaaaatcatgtaaaaagcagtgggatttggatgtgggatccggttccaggtgtca<br>tccagccttagcaaaccagaggtatttgggaataagatgatcattccttccctggatgg<br>agccctcttccagtgggaccaagaccgtgaaagcatgaaacagttcctttcacagtt<br>gaatcacttcttgaatcttcttataaatttggagatgatgttgattggaggaggaaaatct<br>ctgactacatatggactcagtgcatatagtggaaaggtgaggtatatctgacagctag<br>ggttgtcgcaatggatagtgacgaaatgaacaagaggaagacatcctgcttcta<br>cagcgtacccaaaaaactgttagagctgtcggacctcgcagtggcaatgagaagtg<br>gaatttcagtgttggccactttgaacttcggtatattccagacatggaaacgagagccg<br>gatttattgaaagcacctttaagcccaatgagaacacagaagagtctaaaattatttcag<br>atgtggaagaacaggaagctgccataatgacatagtgataaaggtttcggttgctga<br>ctggaaagttatggcattcagtaagaagggaggacatctggaatgggagtaccagttt<br>tgtactccaattgcatctgcctggttacttaaggatgggaaagtcattcccatcagtctttt<br>tgatgatacaagttatacatctaatgatgatgttttagaagatgaagaagacattgtaga<br>agctgccagaggagccacagaaaacagtgttttacttgggaatgtatagaggccagct<br>gtatctgcagtcatcagtcagaatttcagaaaagtttccttcaagtcccaaggctttgga<br>atctgtcagtaatgaaaacgcaattattccttaccaacaatcaaatggaaacccttaatt<br>cattctccttccagaactcctgtcttggtaggatctgatgaatttgacaaatgtctcagta<br>atgataagttttctcatgaagaatatagtaatggtgcacttttcaatcttgcagtatccatat<br>gataatggttattatctaccatactacaagaggggagaggaacaaacgaagcacacag<br>attacagtcagattcctcgacaacccacattacaacaagaatatccgcaaaaaggatc<br>ctgttcttcttttacactggtggaaagaaatagttgcaacgattttgttttgtatcatagcaa<br>caacgtttattgtgcgcaggcttttccatcctcatcctcacaggcaaaggaaggagtct<br>gaaactcagtgtcaaactgaaaataaatatgattctgtaagtggtgaagccaatgaca | NM_004836.5 | NM_010121.2 |

TABLE 1-continued

| Gene | Human Gene Sequence | Human Sequence Accession No. | Murine Sequence Accession No. |
|---|---|---|---|
| | gtagctggaatgacataaaaaactctggatatatatcacgatatctaactgattttgagc<br>caattcaatgcctgggacgtggtggctttggagttgttttgaagctaaaaacaaagta<br>gatgactgcaattatgctatcaagaggatccgtctccccaatagggaattggctcggg<br>aaaaggtaatgcgagaagttaaagccttagccaagcttgaacaccccgggcattgtta<br>gatatttcaatgcctggctcgaagcaccaccagagaagtggcaagaaaagatggatg<br>aaatttggctgaaagatgaaagcacagactggccactcagctctcctagcccaatgg<br>atgcaccatcagttaaaatacgcagaatggatccttttcgctacaaaagaacatattgaa<br>atcatagctccttcaccacaaagaagcaggtcttttttcagtagggatttcctgtgaccag<br>acaagttcatctgagagccagttctcaccactggaattctcaggaatggaccatgagg<br>acatcagtgagtcagtggatgcagcatacaacctccaggacagttgccttacagactg<br>tgatgtggaagatgggactatggatggcaatgatgaggggcactcctttgaactttgtc<br>cttctgaagcttctccttatgtaaggtcaagggagagaacctcctccttcaatagtatttga<br>agattctggctgtgataatgcttccagtaaagaagagccgaaaactaatcgattgcata<br>ttggcaaccattgtgctaataaactaactgctttcaagcccaccagtagcaaatcttcttc<br>tgaagctacattgtctatttctcctccaagaccaaccactttaagtttagatctcactaaaa<br>acaccacagaaaaactccagcccagttcaccaaaggtgtatctttacattcaaatgca<br>gctgtgcagaaaagaaaacctcaaagactggatgaatggacgatgtaccatagagg<br>agagagaggagcgtgtgtctgcacatcttcctgcagatcgcagaggcagtggag<br>tttcttcacagtaaaggactgatgcacagggacctcaagccatccaacatattctttaca<br>atggatgatgtggtcaaggttggagactttgggttagtgactgcaatggaccaggatg<br>aggaagagcagacggttctgaccccaatgccagcttatgccagacacacaggacaa<br>gtagggaccaaactgtatatgagcccagagcagattcatggaaacagctattctcata<br>aagtggacatcttttctttaggcctgattctatttgaattgctgtatccattcagcactcag<br>atggagaagagtcaggaccttaactgatgtaagaaatctcaaatttccaccattattact<br>cagaaatatccttgtgagtacgtgatggttcaagacatgctctctccatcccccatgga<br>acgacctgaagctataaacatcattgaaatgctgtatttgaggacttggactttccagg<br>aaaaacagtgctcagacagaggtctcgctccttgagttcatcgggaacaaaacattca<br>agacagtccaacaactcccatagccctttgccaagcaattagcccttaagttgtgctagc<br>aaccctaataggtgatgcagataatagcctacttcttagaatatgcctgtccaaaattgc<br>agacagtccaacaactcccatagccctttgccaagcaattagcccttaagttgtgctagc<br>ctggatttgggggcataacctaatttgagccaactcctgagttttgctatacttaaggaa<br>agggctatctttgctttgttagtctcgaaactggctgctggccaagctttatagccct<br>caccatttgcctaaggaggtagcagcaatccctaatatatatatatagtgagaactaaa<br>atggatatatttttataatgcagaagaaggaaagtcccctgtgtggtaactgtattgttc<br>tagaaatatgcttctagagatatgatgattttgaaaagatttctagaaaagctgactc<br>catttttgtccctggcgggtaaattaggaatctgcactattttggaggacaagtagcaca<br>aactgtataacggtttatgtccgtagttttatagtcctatttgtagcattcaatagctttattc<br>cttagatggttctagggtgggtttacagctttttgtacttttacctccaataaagggaaaat<br>gaagcttttatgtaaattggttgaaaggtctagttttggggagaaaaagccgtagtaa<br>gaaatggatcatatatattacaactaacttcttcaactatggacttttttaagcctaatgaaa<br>tcttaagtgtcttatatgtaatcctgtaggttggtacttcccccaaactgattataggtaac<br>agtttaatcatctcacttgctaacatgttttttatttttcactgtaaatatgtttatgttttatttata<br>aaaattctgaaatcaatccatttgggttggtggtacagaacacacttaagtgtgttaa<br>cttgtgacttcttttcaagtctaaatgatttaataaaaactttttttaaattaaaaaaaaaaaa<br>aaaaaa (SEQ ID NO: 605) | | |
| Arhgap5 | ctcggtgagcgcgccgaggaagagaggcgagcggagagtggaggaggaggcg<br>gcggcggcgggagcggtcccccaggaatgtcgctgccgccgccaccgccggggc<br>cgctgccgttgaggaggagacggaggagaccgacgttgttaggaagatgatcccta<br>tgatcttgaagatgtttctgcacagaaatgagggaaatacaaagaaccaaatacagttc<br>tgaaatttggggatctgtattttgagatgattttattttcagaatgagaagcatatctggttac<br>ctttatgaatgtagagacatgagaagagagttatgatggcaaaaaacaaagagcctc<br>gtcccccatcctataccatcagtatagttggactctctgggactgaaaaagacaaaggt<br>aactgtggagttggaaagtcttgtttgtgcaatagatttgtacgctcaaaagcagatgaa<br>tattatccagagcatacttctgtgcttagcaccattgacttggaggacgagtagtaaac<br>aatgatcacttttttgtactggggtgacataatacaaaatagtgaagatggagtagaatg<br>caaaattcatgtcattgaacaaacagagttcattgatgaccagactttcttgcctcatcg<br>gagtacgaatttgcaaccatatataaaacgtgcagctgcatctcaaattgcagtcagcag<br>aaaaactaatgtacatttgcactgatcagctaggcttagaacaagactttgaacagaag<br>caaatgcctgaagggaagctcaacgtagatggattttattatgcattgatgtaagtcaa<br>ggatgcaataggaagtttgatgatcaacttaaatttgtgaataaccttttttgtccagttatc<br>aaaatcaaaaaaacctgtaataatagcagcaactaaatgtgatgaatgcgtggatcatt<br>atcttagagaagttcaggcatttgcttcaaataaaaagaaccttcttgtagtggaaacat<br>cagcacgatttaatgtcaacattgaaacatgttttactgcactggtacaaatgttggataa<br>aactcgtagcaagcctaaaattattccctatttggatgcttataaaacacagagacaact<br>tgttgtcacagcaacagataagtttgaaaaacttgtgcagactgtgagagattatctag<br>caacttggaaaactgttagtaataaattaaaaaatcatcctgattatgaagaatacatca<br>acttagagggaacaagaaaggccagaaatacattctcaaaacatatagaacaactta<br>aacaggaacatataagaaaaggagagaagagtatataaatactttaccaagagcttt<br>caacactcttttgccaaatctagaagagattgaacatttgaattggtcagaagctttgaa<br>gttaatggaaaagagagcagatttccagttatgtttgtggtgctagttaaaaactccttg<br>ggatgaaactgaccatatagacaaaattaatgataggcggattccatttgacctcctga<br>gcactttagaagctgaaaaagtctatcagaaccatgtacagcatctgatatccgagaa<br>gaggagggtggaaatgaaggaaaaattcaaaaagactttgaaaaaaattcaattcatt<br>tcaccagggcagccatggggaggaagttatgtgctttgttatggaggatgaagcctaca | NM_<br>001030055.1 | NM_<br>009706.2 |

TABLE 1-continued

| Gene | Human Gene Sequence | Human Sequence Accession No. | Murine Sequence Accession No. |
|---|---|---|---|
| | aatatatcactgaggctgatagcaaagaggtatatggtaggcatcagcgagaaatagt tgaaaagccaaagaagagtttcaagaaatgcttttgagcattctgaactttttatgatt tagatcttaatgcaacacctagttcagatttaaatgagtgaaattcatacagttctgagtg aagaacctagatataaagctttacagaaacttgcacctgataggaatcccttctactta agcatataggatttgtttatcatcccactaaagaaacatgtcttagtggccaaaattgtac agacattaaagtggagcagttacttgctagtagtcttttacagttggatcatggccgctt aagattatatcacgatagtaccaatatagataaagttaacctttttatttagggaaggat ggccttgcccaagaactagcaaatgagataaggacacaatccactgatgatgagtat gccttagatggaaaaatttatgaacttgatatcggccggttgatgccaaatcgccttac ttttgagtcagttatggactgccgcctttaaaccacatgggtgcttctgtgtatttaattcc attgagtcattgagttttattggggaatttattgggaaaataagaactgaagcttctcaga tcagaaaagataaatacatggctaatcttccatttacattaattctggctaatcagagag attccattagtaagaatctaccaattctcaggcaccaagggcagcagttggcaaacaa gttgcaatgtcctttgtagatgtacctgctggtacatatcctcgtaaatttaatgaaaccc aaataaagcaagctctcagaggagtattggaatcagttaaacacaatttggatgtggtg agcccaattcctgccaataaggacttatcagaagctgttccttgagaattgtcatgtgcgc catgtgtggagatccatttagtgtggatcttattctttcacccttccttgattctcattcttgc agtgctgctcaagctggacagaataattccctaatgcttgataaaatcattggtgaaaa aaggaggcgaatacagatcacaatattatcataccactcttcaattggagtaagaaaa gatgaactagttcatgggtatatattagtttactctgcaaaacggaaagcttcgatggga atgcttcgagcatttctatcagaagttcaagacaccattcctgtacagctggtggcagtt actgacagccaagcagatttttttgaaaatgaggctatcaaagagttaatgactgaagg agaacacattgcaactgagatcactgctaaatttacagcactgtattctttatctcagtat catcggcaaactgaggtctttactctgtttttttagtgatgttcagagaaaaaaaaatatgat agaaaattcttatttgtctgataatacaagggaatcaacccatcaaagtgaagatgttttt ctaccatctcccagagactgttttccctataataactaccctgattcagatgatgacaca gaagcaccacctccttatagtccaattggggatgatgtacagttgcttccaacacctag tgaccgttccagatatagattagatttggaaggaaatgagtatcctattcatagtacccc aaactgtcatgaccatgaacgcaaccataaagtgcctccacctattaattcctaaacca gttgtacctaagacaaatgtgaaaaaactcgatccaaaccttttaaaaacaattgaagc tggtattggtaaaaatccaagaaagcagacttcccgggtgcctttggcacatcctgaa gatatggatccttcagataactatgcggttacccattgatacaattttcaaacagaaggg ctattctgatgagatttatgttgtcccagatgatagtcaaaatcgtattaaaattcgaaact catttgtaaataacacccaaggagatgaagaaatttgggttttctgatagaacctcaaaa agtcatggggaacggaggccttcaaaatacaaatataaatctaaaaccttgtttagtaa agccaagtcatactatagaagaacacattcagatgccagtgatgatgaggctttcacc acttctaaaacaaaaagaaaaggaagacatcgtggaagtgaagaagatccacttcttt ctcctgttgaaacttggaaaggtggtattgataatcctgcaatcacttctgaccaggagt tagatgataagaagatgaagaagaaaacccacaaagtgaaagaagataaaaagca gaaaaagaaaactaagaacttcaatccaccaacacgtagaaattgggaaagtaatta ctttgggatgcccctccaggatctggttacagctgagaagcccatacactactatttgttg agaaatgtgtggaatttattgaagatacagggttatgtaccgaaggactctaccgtgtc agcgggaataaaactgaccaagacaatattcaaaagcagtttgatcaagatcataata tcaatctagtgtcaatggaagtaacagtaaatgctgtagctggagcccttaaagctttct ttgcagatctgccagatccttttaattccatattctcttcatccagaactattggaagcagc aaaaatcccggataaaacagaacgtcttcatgccttgaaagaaattgttaagaaatttc atcctgtaaactatgatgtattcagatacgtgataacacatctaaacagggttagtcagc aacataaaatcaacctaatgacagcagacaacttatccatctgttttttggccaaccttga tgagacctgattttgaaaatcgagagttctgtctactactaagattcatcaatctgtgtt gaaacattcattcagcagtgtcagtttttcttttacaatggagaaattgtagaaacgacaa acattgtggctcctccaccaccttcaaacccaggacagttggtggaaccaatggtgcc acttcagttgccgccaccattgcaacctcagctgatacaaccacaattacaaacggat cctcttggtattatatgagtaggaagtgattgcaaacaggctggatttggacaaaaagc aaatctagacatgcatgtttcagggttcagtagtatacttcatgttttcatacagatatttca cattcaaaattacattttctcttttgaactagatggtattccttattcacttacattacaaatct aagaccatgtgataagcatgactggagaggtttaatttttataaacaaaaatagctataa agtacaaagctgctgctgcatgcaacccttattgcaatcagtatatcattcctgtggcaatt tctgtcaccttatattgtgaataaaattttctatagaaattaaatgatttaaaaactcaccta tatgaaacatttaatgcttttcagcctgctttctggctgattttgttatttgatgtgctaatttg ggcaacttaatttacattctggcagtcggtgtagataactaaaagcccagttaagtatttt ataatttcaggctactgaggccatgcttgggatgttgtttgaaagaaagaaaaaataca cttgacatatttcacatttctgtaccttcatctttacttccaagtaaacccgtggatctgatttg atgagggataaatgaacctatttctttttcacacataccaaggacatgcttgtggctaaa gtgagttgataatgttgtgcaaaggatagttgtcaccaactcatttctttatggtccataat gttaataaaattttgtatactgttaattctgtaaacagatgcatgttcaaagatctatgat ggtcttgtaatcttaatctaatatatttttagatattttaattttttccctatgggaacacatttt agtatagtgtagaaaatactccatgacattttcatataaggttatataacttttcatacata aacatgaaatttgttgtagaaaattctttaaaccaaacatttaaatctaggacttcaattta atttgttccttgaatctatttttatgtggccttaaaaaatatccaaaaaacccaagctaat atagcaataaaaactttgggtactgacagactcttttggagtgtttatattacaaatttgt attcatattcttttctgtgatgtgttgtactaaaatccaaaatggctttttgcaccatttttaag ccaattttttcctttgatgttggtaccagaattactataagtgactgctgcttttgggggta aacattttgttagtgaagataaaaccagaacactaaattatggataaaattttcagaata ggtggcacaggtaaatttcactaggttataatttgtgtagtaaagaaaaaatttatttggt caatgttatcttaattcatactacaattttaagattatcttatgtgtattatagtaaatagatga | | |

TABLE 1-continued

| Gene | Human Gene Sequence | Human Sequence Accession No. | Murine Sequence Accession No. |
|---|---|---|---|
| | ttttcagattcaaggctcctaagagtttgatttgctctgttttttcctaaaataaatattgtctc tcccaactgttaagttctaggtattgtacttccaattttaacttcagaaccaagatgttggc atgaaccaggctgctgttgaagtacatgtatattataaattatcttatttgtgttatactctta catgttatctttttaaagaaaacaaagtccctattattcctattgcaaagcacacaggaat taagaaagtacagtaattttttaaaaaaaaatccggtaaatgtagtattcttaacctgttcta tattacttataccctattgtctatatagcttttaatttatagttgtcagtttaactattggcatgtct ggcaaagaaaattaaactttaagagttttataaactgtttctaggttgctaaagaatttattt ttctactatatatggtatagacaaagcatcaaactatgtacaggaaaaaagcctgactat ttctatttggaagtaggctgaaaagagaatttttcaaaactgttcgtgtcttcagttcattct gtcataactttgctattgtaatatgtgaataccagtttatttaagctgttctcttttatactgta ttaatttaatgttcatctgcgtttagtaccattttttgttattaaaactggcatttaccgtttttca cattaacccaccttgcaccttccccaaacttatctccacttttctatgcattctatcattga tttgacacacttcatagtcagtcatttaaatactctacgtttggttcaattaaccagtaggtt acagttattgaaaattaaagtacagtttaaagctcagtctgttacactgaattgattgtgtt tgtttttgccaagggtttagatatgcttttaaatattagaaacatctaagaacagaataac ataattaaacttttttctggtaagttactggaaggtttcactgtttaggcacctatcatatga gactccttaaaggattaaaaagaataggatagtctcataattgtgagtaaacatcaaggc attatattttacaatactgaataaaaatttcatctacacacatgttgccattgtttcatttaagg ttcagtgcttatagttaactacaatattggacctaacaggatctagattagcaatataaag aagcatagtggtactctgtttcacactttcagtagatttattagaagtcaaattctattcaa cagacacttattaggatataacaactaatttaagaataaaaattccaggcacaatatatttttt ttaaatggtatttgttagtagtgcttctttccccttaacatttacagtgtaaatactgcaggta accgcaatctaagttagccaaaaagcagctttttttcccatactgtatgtaaataatgtag acctgggtttttttgtttatttgggtttgtttttttttttttgaggtactggaatctaattaatatctc ttaggtatcaacaaaagggaacaattggaatgagaatttaggccttagcttccatggtg atttttagttttttatacagtaataattgtgatgctatttgtcaactggatataaatacacatat aattttaaaaagtcaaagtgcttttgtttctttgtttaatgtaatttttgtgcttcacctacag gatgctgcagtaaattaaatatcagtgaagcttctgatgtataaagaatgctatgaataa aacattaagaagctgtgtaatttttaagttatagttgcctctattttttaccatttcattggtaaa aattagctaatttttttcaagtgaaatgaaaaataaaaatataaatttatcaatatgatgga aatcttattaaggagatgtattattgaattttcactgtacctgaaaaggagattcaaaatttt ttctggggatgtatataggtgaaaatttgatttttttaaattatcaggaaaacaagataatg cacagatttctaagactaagatcttacctggatgtgattttttgagctgtggctagacattc tttagagccactggaaatattttgaaaactattctagttatagcagagctgctaatattaa cgaatatatttgtgtcttcatggtttgtgactattaggccaaattttgtggtatatgttgtca gtctggatctggtgaggtctgttcaacatgaatctttgtgttatcttgaatttagtagtttca aggtacttaaattcttaacagtttctaatttgtttcaatacatgggacatggttgattttttt actgtattagaactcttggaagttcttagccttttcaggttatgaaatacctgaaagtaaa attttctaagattaataagggaagatactattcaaatcattttcttaggatagcatctttac atacaatgagaggattgtacaagcattaatctcatattccaacatccagttacttgatgtg atccaagtaccctggtcttttttgaagcagttaaaatctaattaattaacctttgggagtcttc actattcaattgatcctcatcattgtcctatttgcatgactccatttttttcctccactatatga gttttctttgtcaggggagaggagtgggaagagtcacagaatctcatattcacatctt aattaaattgtgtgaaattagtcttttgtggaaattctgtaggcagtatgattttgaaagc taaccaatgataattagcattttagttaatactaaatgcataaaattaaccctttgaaattt aatttggtgctggcagttctggtttagtcattttttaccagtagttagtagtattaagacctg cagtatatgcactttttgagtagctgtcaaataattgtagttgagaaacaacttgtttattct cacaattcagattttctattcagttttgtctcaaatagtaagttattgtgaacaatttaataac ggccctcctgttctagtttgcctaatattttagttaagattttagtgttttaacctatttttttaag ttttttttttgtattagattttttattttgaatagttatgtgggtttagtaattgacctatttattcatt gcttcactaattcatccagattagttttaagtgtgtatatgtatttgctcaccagatcatttttc ttgggaccttgaactgtgaatgtttttgtcctaaccatttaatattttctaggtacttgctgca agttcttgaactattttaccagctttaactttggggctcttagtttcttttctccagattcttgtt attttatttttatccaaataaatatttaggtgttctaagaa (SEQ ID NO: 606) | | |
| Smad2 | cggccggggaggcggggcgggccgtaggcaaagggaggtggggaggcggtggc cggcgactccccgcgccccgctcgcccccggcccttcccgcggtgctcggcctc gttcctttcctcctccgctccctcgtcttccataccgccccgccgggcgctttcggccg gcgtgcctcgcgcccaacgcgcggctggaggcgccaatcagcgggcggcaggg tgccagccccggggctgcgccggcgaatcggcgggccccgcgccagggtgg caggcgggtctacccgcgcggccgcggcggcggagaagcagctcgccagccag cagcccgccagccgccgggaggttcgatacaagaggctgttttcctagcgtggcttg ctgcctttggtaagaacatgtcgtccatcttgccattcacgccgccagttgtgaagaga ctgctgggatggaagaagtcagtcggtgggtctggaggagcaggcggaggagag cagaatgggcaggaagaaaagtggtgtgagaaagcagtgaaagtctggtgaaga agctaaagaaaacaggacgattagatgagcttgagaaagcccatcaccactcaaaact gtaatactaaatgtgttaccataccaagcacttgctctgaaatttggggactgagtacac caaatacgatagatcagtgggatacaacaggcctttacagcttctctgaacaaaccag gtctcttgatggtcgtctccaggtatcccatcgaaaaggattgccacatgttatatattgc cgattatggcgctggcctgatcttcacagtcatcatgaactcaaggcaattgaaaactg cgaatatgctttaatcttaaaaaggatgaagtatgtgtaaacccttaccactatcagag agttgagacaccagttttgcctccagtattagtgccccgacacaccgagatcctaaca gaacttccgcctctggatgactatactcactccattccagaaaacactaacttcccagc aggaattgagccacagagtaattatattccagaaacgccacctcctggatatatcagtg aagatggagaaacaagtgaccaacagttgaatcaaagtatggacacaggctctcca | NM_ 001003652 | NM_ 001252481 |

TABLE 1-continued

| | | Human Sequence Accession No. | Murine Sequence Accession No. |
|---|---|---|---|
| Gene | Human Gene Sequence | | |

```
gcagaactatctcctactactctttcccctgttaatcatagcttggatttacagccagttac
ttactcagaacctgcattttggtgttcgatagcatattatgaattaaatcagagggttgga
gaaaccttccatgcatcacagccctcactcactgtagatggctttacagacccatcaaa
ttcagagaggttctgcttaggtttactctccaatgttaaccgaaatgccacggtagaaat
gacaagaaggcatataggaagaggagtgcgcttatactacataggtggggaagttttt
gctgagtgcctaagtgatagtgcaatctttgtgcagagccccaattgtaatcagagata
tggctggcaccctgcaacagtgtgtaaaattccaccaggctgtaatctgaagatcttca
acaaccaggaatttgctgcttcttctggctcagtctgttaatcagggttttgaagccgtcta
tcagctaactagaatgtgcaccataagaatgagttttgtgaaagggtggggagcaga
ataccgaaggcagacggtaacaagtactccttgctggattgaacttcatctgaatgga
aagcatgtcataaagcttcaccaatcaagtcccatgaaaagacttaatgtaacaactctt
ctgtcatagcattgtgtggtccctatggactgtttactatccaaaagttcaagagaga
aaacagcacttgaggtctcatcaattaaagcaccttgtggaatctgtttcctatatttgaa
tattagatgggaaaattagtgtctagaaatactctcccattaaagaggaagagaagattt
taaagacttaatgatgtcttattgggcataaaactgagtgtcccaaaggtttattaataac
agtagtagttatgtgtacaggtaatgtatcatgatccagtatcacagtattgtgctgtttat
atacattttagtttgcatagatgaggtgtgtgtgcgctgcttcttgatctaggcaaac
ctttataaagttgcagtacctaatctgttattcccacttctctgttatttttgtgtgtctttttaa
tatataatatatcaagatttcaaattatttagaagcagattttcctgtagaaaaactaat
ttttctgccttttaccaaaaataaactcttggggaagaaaagtggattaacttttgaaat
ccttgaccttaatgtgttcagtggggcttaaacagtcattctttttgtggttttttgttttttttt
gttttttttttttaactgctaaatcttattataaggaaaccatactgaaaaccttccaagcct
cttttttccattcccattttgtcctcataatcaaaacagcataacatgacatcatcaccagt
aatagttgcattgatactgctggcaccagttaattctgggatacagtaagaattcatatg
gagaaagtcccttgtcttatgcccaaatttcaacaggaataattggcttgtataatctag
cagtctgttgatttatccttccacctcataaaaaatgcataggtggcagtataattatttc
agggatatgctagaattacttccacatatttatccctttttaaaaaagctaatctataaata
ccgttttttccaaaggtattttacaatatttcaacagcagaccttctgctcttcgagtagtttg
atttggtttagtaaccagattgcattatgaaatgggccttttgtaaatgtaattgtttctgca
aaatacctagaaaagtgatgctgaggtaggatcagcagatatgggccatctgttttttaa
agtatgttgtattcagtttataaattgattgttattctacacataattatgaattcagaatttta
aaaattgggggaaaagccattttatttagcaagtttttttagcttataagttacctgcagtct
gagctgttcttaactgatcctggttttgtgattgagacaatatttcatgctctgtagtgagagg
agatttccgaaactctgttgctagttcattctgcagcaaataattattatgtctgatgttga
ctcattgcagtttaaacatttcttcttgtttgcatcttagtagaaatggaaaataaccactc
ctggtcgtctttcataaattttcatatttttgaagctgtctttggtacttgttctttgaaatcat
atccacctgtctctataggtatcattttcaatactttcaacatttggtggtttttctattgggta
ctccccattttcctatatttgtgtgtatatgtatgtgttcatgtaaatttggttttagtaatttttt
attcattcaacaaatatttattgttcacctgtttgtaccaggaacttttcttgtcttgggta
aaggtgaacaagacaactacagttcctgcctttgctgagacagcagttacactaaccc
ttaattatcttacttgtctatgaaggagataaacagggtactgttgctggagaataacaga
tgggatgcttcaggtaggacatcaaggaaagcctctaaggaaaggatgcatgagcta
acacctgacattaaagaagcaagccaagtgaggagcatggggagataagatttcct
ggcaaagagaatagcatcaaatgcaaaaaggttcacactaaaggaaaacctgatta
ggtattaatgcttatacagaaacctctatacaaatccaaacttgaagatcagaatggtt
ctacagttcataacatttttgaaggtggccttattttgtgatagtctgcttcatgtgattctca
ctaacatatctccttcctcaacctttgctgtcaaaatttcatttgcaccacatcagtactact
taatttaacaagcttttgttgtgtaagctctcactgttttagtgccctgctgcttgcttccag
actttgtgctgtccagtaattatgtcttccactacccatcttgtgagcagagtaaatgtcct
aggtaataccactatcaggcctgtaggagatactcagtggagcctctgcccttcttttttc
ttacttgagaacttgtaatggtgttagggaacagttgtaggggcagaaaacaactctga
aagtggtagaaggtcctgatcttggtggttactcttgcattactgtgttaggtcaagcag
tgcctactatgctgtttcagtagtggagcgcatctctacagttctgatgcgatttttctgta
cagtatgaaattgggactcaactattgaaaacacctattgagcagttataccgttgag
cagttacttcctggttgtaattacatttgtgtgaatgtgtttgatgcttttttaacgagatgat
cttttttgtattttatctactgtggcctgatttttttttgttttctgcccctcccccccatttatag
gtgtggttttcatttttctaagtgatagaatcccctctttgttgaattttttgtctttatttaaatta
gcaacattacttaggattttattcttcacaatacgttaattttctaggaatgatgacctgag
aaccgaatggccatgctttctatcacatttctaagatgagtaatatttttttccagtaggttc
cacagagacacccttggggctggcttaggggaggctgttggagttctcactgactta
gtggcatatttattctgtactgaagaactgcatgggggttcttttggaaagagtttcattgc
tttaaaaagaagctcagaaagtctttataaccactggtcaacgattagaaaaatataact
ggatttaggcctaccttctggaataccgctgattgtgctcttttttatcctactttaaagaag
ctttcatgattagatttgagctatatcagttataccgattataccttataatacacattcagtt
agtaaacatttattgatgcctgttgtttgcccagccactgtgatggatattgaataataaa
aagatgactaggacggggccctgaccctgagctgtcttgtcttgtagaggttgtgt
tttttttcctcaggacctgtcactttggcagaaggaaatctgcctaatttttcttgaaagct
aaattttctttgtaagttttacaaattgtttaatacctagttgtatttttaccttaagccacat
tgagttttgcttgatttgtctgtcttttaaacactgtcaaatgctttcccttttgttaaaattatt
ttaatttcacttttttttgtgcccttgtcaatttaagactaagacctttgaaggtaaaacaaca
aacaaacatcagtcttagtctcttgctagttgaaatccaataaaagaaaatatataccca
gttggtttctctacctcttaaaagcttcccatatatacctttaagatccttctctttttttcttaa
ctactaaataggttcagcatttattcagtgttagataccctcttcgtctgagggtggcgta
ggtttatgttgggatataaagtaacacaagacaatcttcactgtacataaaatatgtcttc
atgtacagtctttactttaaaagctgaacattccaatttgcgcgcttccctcccaagcccct
```

TABLE 1-continued

| Gene | Human Gene Sequence | Human Sequence Accession No. | Murine Sequence Accession No. |
|---|---|---|---|
| | gcccaccaagtatctctttagatatctagtctgtggacatgaacaatgaatacttttttctt actctgatcgaaggcattgatacttagacatatcaaacatttcttcctttcatatgctttact ttgctaaatctattatattcattgcctgaattttattcttcctttctacctgacaacacacatc caggtggtacttgctggttatcctcttttcttgttagcctctgttttttgttttttttttttttgag agggagtctcgctctgttgcccaacctggagtgcagtggtgcgatcttggttcactgc aagctccgcctcccgggttcacgccatgcttctgcctcagcctcccaagtagctggga ctacaggcgcccaccaccacactcggctaatttttttgtattttttagtagagacggggttt caccgtgttggccaggatggtctcgatctcctgacctcgtgatctgtccacctcggctt cccaaagtgctgggattacaggcatgagccaccgcgcccagcctagccatattttat ctgcatatatcagaatgtttctctcctttgaacttattaacaaaaaaggaacatgcttttcat acctagagtcctaatttcttcatcatgaaggttgctattcaaattgatcaatcatttaattttt acaaatggctcaaaaattctgttcagtaaatgtctttgtgactggcaaatggcataaatta tgtttaagattatgaacttttctgacagttgcagccaatgtttttccctacgataccagatttc catcttggggcatattggattgttgtatttaagacagtcagaataatgatagtgtgtggtc tccagaggtagtcagaatcctgctattgagttcttttatatcttccttttcaatttttattac cattttgtttgtttagactacacttgtagggattgaggggcaaattatctcttggagtgga attcctgtgttttgagccttacaaccaggaaatatgagctatactagatagcctcatgata gcatttacgataagaacttatctcgtgtgttcatgtaattttttgagtaggaactgttttatct tgaatattgtagctaactatatatagcagaactgcctcagtctttttaagaaggaaataaa taatatatgtgtatgaatttatatatacatatacactcatagacaaacttaacagttggggt cattctaacagttaaaacaattgttccattgtttaaatctcagatcctggtaaaatgttctta atttgtctgtgttttcattttcctttcatggacagaccattggagtacattaattttcttaatctg ccatttggcagttcatttaatataccatttttggcaacttggtaactaagaatcacagcca aaatttgttaacatcaaagaaagtctgccatataccccgttactaaattattatacatcc agcagattagggatgtacttttacttaggggttaactttgttgttgttgataatactagattgc tcccctctttaattcttcttctggtgcaaggttgctgcttaagttaccctgggaaatactact acaaggtcaaattttctagtatcttacagcctgattgttaggtgattcagatctttgctcaat ataaatggattttccaagattctctgggccatccttgacccacaggtgatctcgctgga gtatattaacttaaatcagtgccagttggtttggtgccatgatatccataatgaatccag aacttcaccattgcttagatataagagtcccttggaagaataatgccactgatgatggg ggtcagaaggtgtattaactcaacatagagggcttttagattttcttcaaaaaaatttcg agaaaagtattctttttttccctccaaacagttaacagctcttagtttctccaaatatgctctt gatttacttattttttaattaaagatggtaatttattgaacaatgaaatccgtaatatatttgatt aaggacaaaagtgaagttttagaattataaaagtacttaaatattatatatttttccatttcat aattgttttccttctctgtggctttaaagttttttgactatttttacaatgttaatcactaggtaa cttgccatatttctggttctatattaagttctatccttataatgctgttattataaagctggttt ttagcatttgtctgtagcaatagaaattttactaagtctcgtttcccagtaagtttttttcttt tctcagtaagtccctaagaaaacatttgtttgccactcttactattcccaatcttggattgtt cgagctgaaaaaaaatttgatgagaattcaggaggatccttttctggtgaattttaggttc ctgctttaagaatgtggaaatccattgcttttatataactaatatacacacagattaattaaa attgtgagaaataattcacacatgacaagtaggtaacatgcagtggttttgaatttttttaa aaacccaactgttttgacaaaatatagaacccaaattggtactttcttagaccagtgtaac ctcacacctcagttttgcttttccaaccctgacttgaaaggcatatttgtatcttttttattagt gatagtgaagctgtgacactaacctttttatacaaaagagtaaagaaagaaaaactaca gcgattaagatgagaacagttctgcagttgttgaactagatccagcattgtaggcag aataaaaaatgttcatatctgagaatattcctttcgccatcttttcccaaggccagacctc ctggtggagcacagttaaaagtaacattctgggcctttgtaatcggagggctgtgtctc cagctggcagcctttgttttaatatataatgcaggactgtggaaaacagttggcataga atattttcacctaaaaagaaagaaaagacatacaaaactggattaattgcaaaaaga gaatacagtaaaataccatataactggacaaagctagaagaacctttagaagatttgtc tgaaaacagatttcaagagtgagcttttatacaagctcactaatttgcttgattactacca actcttcttaaagttaacacgtttaaggtatttctggacttcctagccttttagcaagcttag aggaactagccattagctagtgatgtaaaaatattttggggactgatgcccttaaaggtt atgcccttgaaagttcttacctttttctctagtgatattaaggaacgagtgggtagtgttctc agggtgaccagctgccctcaagtgcctgggattgagggtttccctggatgcgggact ttccctggatacaaaacttttagcagagtttttgtatatatgtggatttttctgataagtagca catcagaggccttaaccactgcccaaaagcgattctccattgagagtacatatcttgaa cttaagaaattcatttgctctgattttttaatcttgtaaagttttgctaaactcaaaacaagtc ccaggcacaccagaaggagctgaccaccttaggtgttcttgtgatttatccttacttccc tatgttgtcatagttgcttctaaactcagctgcactatggctgtcaacatttctgatacttat tgggatatgtgccatccagtcatttagtactttgaatggaacatgagatttataacacag gtaatcgctgaaggtaccagtatggtggtgagactcacacttagtgatccagctaagg taactgatgttataatggaacagagaagaggccaactagatagctaagttcttctgaac ctatgtgtatatgtaagtacaaatcatgcgtcctatgggggttaaacttaatctgaaattta cattttcatagtaaaaggaaaccaattgttgcagatttcttttcttgtgaggaaatacatg gcctttgatgctctggcgtctactgcatttcccagtctgttctgctcgagaagccagaat gtgttgttaacattttccgtgaatgttgtgttaaaatgattaaatgcatcagccaatggca agtgaaggaatgggtgtcctgatgcagactgagcagtttctcaattgtagcctcata ctcataaggtgcttaccagctagaacattgagcacgtgaggtgaaatttttttctctgat ggcattaactttgtaatgcaatatgatggatgcagaccttcttgtttccctctggaag tcctagtggctgcatccttggtgcactgtgatgagatattaaatgtgttcttttgtgagct ttcgttcatgattgtcaaaagtacgatgtggttcctttttattttattaaacaatgagctg aggctttattacagctggttttcaagttaaaattgttgaatactgatgtctttctcccaccta caccaaatattttagtctatttaaagtacaaaaaagttctgcttaagaaaacattgcttac atgtccctgtgatttctggtcaattttttatatatatttgtgtgcatcatctgtatgtgctttcactt | | |

TABLE 1-continued

| Gene | Human Gene Sequence | Human Sequence Accession No. | Murine Sequence Accession No. |
|---|---|---|---|
| | tttaccttgtttgctcttacctgtgttaacagccctgtcaccgttgaaaggtggacagtttt cctagcattaaaagaaagccatttgagttgtttaccatgttaaaaaaaaaaaaaaa (SEQ ID NO: 607) | | |
| Akap8l | gtgtgtggaggggaccctgtggttagcagcagctatcgcagcgtcggatgttcagag cagcagaagccggcgtcgtcggatgttgtgttgcccgccaccatgagctacacttgg ctttgtccagggatctgaaaccactttgcagtcgacatactcggataccagcgctcag cccacctgtgattatggatatggaactttggaactctgggacaaatagaggcttttcgagg gctatggctatggctatggctatggccaggataacaccaccaactatgggtatggtat ggccacttcacactcttgggaaatgcctagctctgacacaaatgcaaacactagtgcc tcgggtagcgccagtgccgattccgttttatccagaattaaccagcgcttagatatggt gccgcatttggagacagacatgtcaaggaggcgtgtacggctcaggtggagaaa gctatgactcttatgagtcctgcgactcgagggccgtcctgagtgagcgcgacctgta ccggtcaggctatgactacagcgagcttgaccctgagatgaaatggcctatgaggg ccaatacgatgcctaccgcgaccagttccgcatgcgtggcaacgacaccttcggtcc cagggcacagggctgggcccgggatgcccggagcggccgcaatggcctcag gctatgggcgcatgtgggaagaccccatgggggcccggggccagtgcatgtctggt gcctctcggctgccctcctcttctcccagaacatcatccccgagtacggcatgttcca gggcatgcgaggtgggggcgccttcccggggcggctcccgctttggtttcgggtttgg caatggcatgaagcagatgaggcggacctggaagacctggaccacagccgacttc cgaaccaagaagaagaagagaaagcagggcggcagtcctgatgagccagatagc aaagccaccgcacggactgctcggacaacagcgactcagacaatgatgagggca ccgaggggaagccacagagggccttgaaggcaccgaggctgtggagaagggct ccagagtggacggagaggatgaggagggaaaagaggatgggagagaagaaggc aaagaggatccagagaagggggccctaaccacccaggatgaaaatggccagacc aagcgcaagttgcaggcaggcaagaagagtcaggacaagcagaaaaagcggcag cgagaccgcatggtggaaaggatccagtttgtgtgttctctgtgcaaataccggacctt ctatgaggacgagatggccagccatcttgacagcaagttccacaaggaacactttaa gtacgtaggcaccaagctccctaagcagcggctgacttctgcaggagtacgtcac taacaagaccaagaagacagaggagctccgaaaaaccgtggaggaccttgatggc ctcatccaccaaatctacagagaccaggatctgacccaggaaattgccatggagcatt ttgtgaagaaggtggaggcagcccattgtgcagcctgcgacctcttcattcccatgca gtttgggatcatccagaagcatctgaagaccatggatcacaaccggaaccgcaggct catgatggagcagtccaagaagtcctccctcatggtggcccgcagtattctcaacaac aagctcatcagcaagaagctggagcgctacctgaagggcgagaacccttcaccga cagccccgaggaggagaaggagcaggaggaggctgagggcggtgccctggacg aggggcgcagggcgaagcggcagggatctcggagggcgcagagggcgtgcc ggcgcagcctcccgtgccccagagccagcccccggggccgtgtcgccgccacc gccgccgcccccagaggaggaggaggagggcgccgtgcccttgctgggagggg cgctgcaacgccagatccgcggcatctcgggcctcgacgtggaggacgacgagg aggggcggcggggcgcccgtgaccgagctcggggcgggggcgagcccgcgt ggccgaagctggaaaccaaacctaataaagtttttcccatcccaccaaaaaaaaaaa aaaaaaaaaa (SEQ ID NO: 608) | NM_014371 | NM_017476 |
| Rbks | accttttgagcgatggcggcgtctgggaacccagagggcagtggcaagaggaggt ggcggcggtggtagtggtgggctcctgcatgaccgacctggtcagtcttacttctcgtt tgccaaaaactggagaaaccatccatggacataagttttttattggctttggagggaaa ggtgccaaccagtgtgtccaagctgctcggcttggagcaatgacgtccatggtgtgta aggttggcaaagattctttttggcaatgatttatatagaaaacttaaaacagaatgatatttc tacagaatttacatatcagactaaagatgctgctacaggaacttgcttctataattgtcaat aatgaaggccagaatatcattgtcatagtggctggagcaaatttacttttgaatacgga ggatctgagggcagcagccaatgtcattagcagagccaaagtcatggtctgccagct cgaaataactccagcaacttcttttggaagccctaacaatggcccgcaggagtggagt gaaaaaccttgttcaatccagcccctgccattgctgacctggatctccagttctacaccc tctcagatgtgttctgctgcaatgaaagtgaggctgagattttaactggcctcacggtg ggcagcgctgcagatgctggggaggctgcattagtgctcttgaaaaggggctgcca ggtggtaatcattaccttaggggctgaaggatgtgtggtgctgtcacagacagaacct gagccaaagcacattcccacagagaaagtcaaggctgtggatcaccgggtctgg tgacagctttgtgggagctctgccttctacctggcttactatccaaatctgtccttggaa gacatgctcaacagatccaatttcattgcagcagtcagtgtccaggctgcaggaacac agtcatcttaccttacaaaaaagaccttccgcttactctgttttgattgctattagtccca aaataaatatacctgggaataaatgtacttggggtggctgctcctggctaatgcttat tagaaaatgtcctcgtccctttctttgcaaatttagttcttttacgaagtcatcctcaag cttcaattttatttataacgatgattcttttgctttccatgcatttgcacaaaacaaccagaat taaagattccacaacc (SEQ ID NO: 609) | NM_022128 | NM_153196 |
| Egr2 | aactgagcgaggagcaattgattaatagctcggcgaggggactcactgactgttataa taacactacaccagcaactcctggcttcccagcagccggaacacagacaggagaga gtcagtggcaaatagacattttcttatttcttaaaaaacagcaacttgtttgctactttatt tctgttgatttttttttcttggtgtgtggtggttgtttttaagtgtggagggcaaaaggag ataccatcccaggctcagtccaaccctctccaaaacggcttttctgcacactccaggta gcgagggagttgggtctccaggttgtgcgaggagcaaatgatgaccgccaaggcc gtagacaaaatcccagtaactctcagtggttttgtgcaccagctgtctgacaacatcta cccggtggaggacctcgccgccacgtcggtgaccatctttcccaatgccgaactgg gaggcccccttgaccagatgaacggagtggccggagatggcatgatcaacattgac | NM_000399 | NM_010118 |

TABLE 1-continued

| Gene | Human Gene Sequence | Human Sequence Accession No. | Murine Sequence Accession No. |
|---|---|---|---|
| | atgactggagagaagaggtcgttggatctcccatatcccagcagctttgctcccgtctc<br>tgcacctagaaaccagaccttcacttacatgggcaagttctccattgaccctcagtccc<br>ctggtgccagctgctacccagaaggcataatcaatattgtgagtgcaggcatcttgca<br>agggtcacttccccagcttcaaccacagcctcatccagcgtcacctctgcctcccc<br>aacccactggccacaggacccctgggtgtgtgcaccatgtcccagacccagcctga<br>cctggaccacctgtactctccgccaccgcctcctcctccttattctggctgtgcaggag<br>acctctaccaggaccttctgcgttcctgtcagcagccaccacctccacctcttcctctc<br>tggcctaccaccacctccttcctatcccccaagccagccacggacccaggtct<br>cttcccaatgatcccagactatcctggattcttcatctcagtgccagagacctaca<br>tggtacagctggcccagaccgtaagccctttccctgcccactggacccctgcgggt<br>gcccctccactcactccactctctacaatccgtactttacctgggggcccagt<br>gctggggtgaccggaccagggccagtggaggcagcgagggaccccggctgcct<br>ggtagcagctcagcagcagcagcagccgccgccgccgccgcctataacccacacc<br>acctgccactgcggcccattctgaggcctcgcaagtacccttacagaccagcaag<br>acgccggtgcacgagaggccctaccgtgcccagcagaaggctgcgaccggcgg<br>ttctcccgctctgacgagctgacacggcacttccgaatccacactcggcataagccc<br>ttccagtgtcggatctgcatgcgcaacttcagccgcagtgaccacctccaccaccata<br>tccgcacccacaccggtgagaagcccttcgcctgtgactactgtggccgaaagtttg<br>cccggagtgatgagaggaagcgccacaccaagatccacctgagacagaaagagc<br>ggaaaagcagtgccccctctgcatcggtcgcagcccctctacagcctcctgctctg<br>ggggcgtgcagcctgggggtaccctgtgcagcagtaacagcagcagtcttggcgg<br>agggccgctcgcccccttgctcctctcggacccggacaccttgagatgagactcaggc<br>tgatacaccagctcccaaaggtcccggaggcccttgtccactggagctgcacaaca<br>aacactaccacccttcctgtccctctctcccctttgttgggcaaagggcttggtggagc<br>tagcactgccccctttccacctagaagcaggttcttcctaaaacttagcccattctagtct<br>ctcttaggtgagttgactatcaacccaaggcaaaggggaggctcagaaggaggtgg<br>tgtggggaccctggccaagagggctgaggtctgaccctgctttaaagggttgtttga<br>ctaggttttgctaccccacttccccttattttgacccatcacaggttttgacctggatgt<br>cagagttgatctaagacgttttctacaataggttgggagatgctgatcccttcaagtgg<br>ggacagcaaaaagacaagcaaaactgatgtgcactttatggcttgggactgatttggg<br>ggacattgtacagtgagtgaagtatagcctttatgccacactctgtggccctaaaatgg<br>tgaatcagagcatatctagttgtctcaaccttgaagcaatatgtattataaactcagag<br>aacagaagtgcaatgtgatggggaacatagcaatatctgtctcctttcgagttgtttg<br>agaaatgtaggctatttttcagtgtatatccactcagattttgtgtatttttgatgtacactg<br>ttctctaaattctgaatctttgggaaaaaatgtaaagcatttatgatctcagaggttaactt<br>atttaaggggatgtacatatattctctgaaactaggatgcatgcaattgtgttggaagt<br>gtccttggtgcctgtgtgatgtagacaatgttacaaggtctgcatgtaaatgggttgcc<br>ttattatggagaaaaaaatcactccctgagtttagtatggctgtatatttctgcctattaata<br>tttggaattttttttagaaagtatattttttgtatgctttgttttgtgacttaaaagtgttaccttttg<br>tagtcaaatttcagataagaatgtacataatgttaccggagctgatttgtttggtcattag<br>ctcttaatagttgtgaaaaaataaatctattctaacgcaaaaccactaactgaagttcag<br>ataatggttttgtgactatagtgtaaataaatacttttcaacaataaaaaaaaaaaa<br>aa (SEQ ID NO: 610) | | |
| Dgka | agttcctgccagtgagtccctaggcctccatctctctcccttgctgtaccaccttcacca<br>ccatccatgcgaccccaagagcctttaatgactctagaagagactccaggcagggga<br>agctgaaaggaccttttcactcccctactttttggccagggccttctgtgccacctgccaag<br>accagcaggcctaccctctgaagaggtccaagcaacggaagtactactacgaagct<br>gcctttctggccatccttgagaaaaaatagacagatggccaaggagaggggcctaata<br>agccccagtgattttgcccagctgcaaaaatacatggaatactccaccattaaaggtca<br>gtgatgtcctaaagctcttcgaggatggcgagatggctaaatatgtccaaggagatgc<br>cattgggtacgagggattccagcaattcctgaaaatctatctcgaagtggataatgttc<br>ccagacacctaagcctggcactgtttcaatcctttgagactggtcactgcttaaatgag<br>acaaatgtgacaaaagatgtggtgtgtctcaatgatgttttcctgctacttttccttctgg<br>agggtggtcggccagaagacaagttagaattcaccttcaagctgtacgacacggaca<br>gaaatgggatcctggacagctcagaagtggacaaaattatcctacagatgatgcgag<br>tggctgaatacctggattgggatgtgtctgagctgaggccgattcttcaggagatgatg<br>aaagagattgactatgatggcagtggctctgtctctcaagctgagtgggtccgggctg<br>gggccaccaccgtgccactgctagtgctgctgggtctggagatgactctgaaggac<br>gacggacagcacatgtggaggcccaagaggttcccagaccagtctactgcaatct<br>gtgcgagtcaagcattggtcttggcaaacagggactgagctgtaacctctgtaagtac<br>actgttcacgaccagtgtgccatgaaagccctgcctttgtgaagtcagcacctatgcca<br>agtctcggaaggacattggtgtccaatcacatgtgtgggtgcgaggaggctgtgagt<br>ccgggcgctgcgaccgctgtcagaaaaagatccggatctaccacagtctgaccggg<br>ctgcattgtgtatggtgccacctagagatccacgatgactgcctgcaagcggtgggc<br>catgagtgtgactgtgggctgctccgggatcacatcctgcctccatcttccatctatccc<br>agtgtcctggcctctggaccggatcgtaaaaatagcaaaacaagccagaagaccat<br>ggatgatttaaatttgagcacctctgaggctctgcggattgaccctgttcctaacaccca<br>cccacttctcgtctttgtcaatcctaagagtggcgggaagcaggggcaaagggtgct<br>ctggaagttccagtatatattaaaccctcgacaggtgttcaacctcctaaaggatggtc<br>ctgagatagggctccgattattcaaggatgttcctgatagccggattttggtgtgtggtg<br>gagacggcacagtaggctggattctagagaccattgacaaagctaacttgccagtttt<br>gcctcctgttgctgtgttgcccctgggtactggaaatgatctggctcgatgcctaagat<br>ggggaggaggttatgaaggacagaatctggcaaagatcctcaaggatttagagatg<br>agtaaagtggtacatatggatcgatggtctgtggaggtgatacctcaacaaactgaag | NM_001345 | NM_016811 |

TABLE 1-continued

| Gene | Human Gene Sequence | Human Sequence Accession No. | Murine Sequence Accession No. |
|---|---|---|---|
| | aaaaaagtgacccagtccccttcaaatcatcaataactacttctctattggcgtggatg<br>cctctattgctcatcgattccacatcatgcgagagaaatatccggagaagttcaacagc<br>agaatgaagaacaagctatggtacttcgaatttgccacatctgaatccatcttctcaaca<br>tgcaaaaagctggaggagtctttgacagttgagatctgtgtgggaaaccgctggatctga<br>gcaacctgtccctagaaggcatcgcagtgctaaacatccctagcatgcatggtggctc<br>caacctctggggtgataccaggagaccccatggggatatctatgggatcaaccagg<br>ccttaggtgctacagctaaagtcatcaccgaccctgatatcctgaaaacctgtgtacca<br>gacctaagtgacaagagactggaagtggttgggctggagggtgcaattgagatggg<br>ccaaatctataccaagctcaagaatgctggacgtcggctggccaagtgctctgagatc<br>accttccacaccacaaaaaccctcccatgcaaattgacggagaaccctggatgcag<br>acgccctgtacaatcgtagtcacccacaagaaccagatgcccatgctcatgggccca<br>cccccccgctccaccaatttctttggcttcttgagctaataggggacaccccttggcctcc<br>aagccagccttgaacccacctccctgtccctggactctactcccgaggctctgtacatt<br>gctgccacatactcctgccagcttggggagtgttccttcaccctcacagtatttattat<br>cctgcaccacctcactgttcccatgcgcacacacatacacaccccaaaacacat<br>acattgaaagtgcctcatctgaataaaaatgacttgtgtttcccctttgggatctgctaaaa<br>aaaaaaaaaaaaaaaaaaaaaaaaaa (SEQ ID NO: 611) | | |
| Cblb | ctgggtcctgtgtgtgccacaggggtggggtgtccagcgagcggtctcctcctcctg<br>aagtgctgctgcggcgtcccgccggcctccccgagtcgggcgggagggagagc<br>gggttgtggatttgtcttgacggtaattgttgcgtttccacgtctcggaggcctgcgcgct<br>gggttgctccttcttcgggagcgagctgttacagcgatcccactccagccgggggct<br>ccccacacacactgggctgcgtgcgtgtggagtgggacccgcgcacacgcgtgtct<br>aggacagctacggcgccgaaagaacttaaaattccagatggcaaactcaatgaatg<br>gcagaaacccggtggtcgaggaggaaatcccgaaaaggtcgaattttgggtatta<br>ttgatgctattcaggatgcagttggaccccctaagcaagctgccgcagatcgcagga<br>ccgtggagaagacttggaagacatggacaaagtggtaagactgtgccaaaatccca<br>aacttcagttgaaaaatagcccaccatatatacttgatattttgcctgatacatatcagca<br>tttacgacttatattgagtaaatatgatgacaaccagaaacttgcccaactcagtgagaa<br>tgagtactttaaaatctacattgatttgccttatgaaaagtcaaacgggcaataagact<br>cttaaagaaggcaaggagagttatgtatgaagaacagtcacaggacagacgaaatc<br>tcacaaaactgtcccttatcttcagtcacatgctggcagaaatcaaagcaatcttccca<br>atggtcaattccaggagataactttcgtatcacaaaagcagatgctgctgaattctgg<br>agaaagtttttggagacaaaactatcgtaccatggaaagtattcagacagtgccttcat<br>gaggtccaccagattagctctgcctggaagcaatggctctaaaatcaacaattgattt<br>aacttgcaatgattacatttcagttttgaatttgatattttaccaggctgtttcagccttgg<br>ggctctattttgcggaattggaatttcttagctgtgacacatccagttatcatgcatttct<br>cacatatgatgaagttaaagcacgactacagaaatatagcaccaaacccggaagcta<br>tatttccggttaagttgcactcgattgggacagtgggccattggctatgtgactgggg<br>atgggaatatcttacagaccatacctcataacaagcccttattcaagccctgattgatg<br>gcagcagggaaggattttatctttatcctgatgggaggagttataatcctgatttaactg<br>gattatgtgaacctacacctcatgaccatataaaagttacacaggaacaatatgaattat<br>attgtgaaatgggctccacttttcagctctgtaagatttgtgcagagaatgacaaagatg<br>tcaagattgagccttgtgggcatttgatgtgcacctcttgccttacggcatggcaggag<br>tcggatggtcagggctgcccttttctgtcgttgtgaaataaaaggaactgagcccataat<br>cgtggacccctttgatccaagagatgaaggctccaggtgttgcagcatcattgacccc<br>tttggcatcccgatgctagacttggacgacgatgatgatcgtgaggagtccttgatgat<br>gaatcggttggcaaacgtccgaaagtgcactgacaggcagaactcaccagtcacat<br>caccaggatcctctcccctgcccagagaagaaagccacagcctgacccactccag<br>atcccacatctaagcctgccacccgtgcctcctcgcctggatctaattcagaaaggca<br>tagttagatctccctgtggcagcccaacgggttcaccaaagtcttctccttgcatggtg<br>agaaaacaagataaaccactcccagcaccacctcctcccttaagagatcctcctccac<br>cgccacctgaaagacctccaccaatcccaccagacaatagactgagtagacacatc<br>catcatgtggaaagcgtgccttccagagacccgccaatgcctcttgaagcatggtgc<br>cctcgggatgtgtttgggttctaatcagcttgtgggatgtcgactcctagggagggct<br>ctccaaaacctgaatcacagcgagttcaaatgtcaatggaaggcacagtagagtgg<br>gctctgacccagtgcttatgcggaaacacagacgccatgatttgcctttagaaggagc<br>taaggtcttttccaatgtcaccttggaagtgaagaaatatgattgttcctccccggcttttct<br>cctcctcctccagttaccaccctcctccctagcataaagtgtactggtccgttagcaaat<br>tctctttcagagaaaacaagagacccagtagaggaagatgatgatgaatacaagattc<br>cttcatcccaccctgtttccctgaattcacaaccatctcattgtcataatgtaaaacctcct<br>gttcggtcttgtgataatggtcactgtatgctgaatggaacacatggtccatcttcagag<br>aagaaatcaaacatccctgacttaagcatatatttaaagggagatgttttttgattcagcct<br>ctgatcccgtgccattaccacctgccaggcctccaactcgggacaatccaaagcatg<br>gttcttcactcaacaggacgccctctgattatgatcttctcatccctccattaggtgaaga<br>tgcttttgatgccctccctccatctctcccacctccccatcctcctgcaaggcatagtct<br>cattgaacattcaaaacctcctggctccagtagccggccatcctcaggacaggatcttt<br>ttcttcttccttcagatccctttgttgatctagcaagtggccaagttcctttgcctcctgcta<br>gaaggttaccaggtgaaaatgtcaaaactaacagaacatcacaggactatgatcagc<br>ttccttcatgttcagatggttcacaggcaccagccagaccccctaaaccaccaccgtg<br>caggactgcaccagttaattcaccacagattaaccccatgggcctgaggcggcattgg<br>aaaatgtcgatgcaaaaattgcaaaactcatgggagagggttatgcctttgaaggagt<br>gaagagagccttagagatagcccagaataatgtcgaagttgcccggagcatcctccg<br>agaatttgccttcctcctccagtatccccacgtctaaatctatagcagccagaactgta<br>gacaccaaaatggaaagcaatcgatgtattccaagagtgtggaaataaagagaactg | NM_170662 | NM_001033238 |

TABLE 1-continued

| Gene | Human Gene Sequence | Human Sequence Accession No. | Murine Sequence Accession No. |
|---|---|---|---|
| | agatggaattcaagagagaagtgtctcctcctcgtgtagcagcttgagaagaggcttg<br>ggagtgcagcttctcaaaggagaccgatgcttgctcaggatgtcgacagctgtggctt<br>ccttgttttgctagccatatttttaaatcaggggtgaactgacaaaaataatttaaagacg<br>tttacttcccttgaactttgaacctgtgaaatgctttaccttgttttacagtttggcaaagttg<br>cagttgttcttgttttagtttagttttgttttggtgttttgatacctgtactgtgttcttcacag<br>acccttttgtagcgtggtcaggtctgctgtaacatttcccaccaactctcttgctgtccaca<br>tcaacagctaaatcatttattcatatggatctctaccatcccatgccttgcccaggtcca<br>gttccatttctctcattcacaagatgctttgaaggttctgatttttcaactgatcaaactaatg<br>caaaaaaaaaaagtatgtattcttcactactgagtttcttctttggaaaccatcactattg<br>agagatgggaaaaacctgaatgtataaagcattatttgtcaataaactgcctttgtaa<br>ggggttttcacataacata (SEQ ID NO: 612) | | |
| Mdfic | cccaggccggctctggcctcctgacccagacagcgcagggcgcgagggatcgcg<br>cggccgagcccgggtcgcgccgctcccagcatcggggccgctagccaagagttcg<br>aggccttcccgatccggatgtgatgaaaaagagcaacagagggagaagtgtttcag<br>gattgtaggagtggaagaggggaaagagaggcagagaggggaaggccccctc<br>gcaggggagccggctggagtgagctggctggaaagaggggcggagtgcgcgg<br>agtcagagccgccaccgctgccgcagttgccgccactgcggcgtctgggctgagc<br>cggagggaggcgggaggacgcgcaggggcggccgccgcgtcgtcaggccac<br>cggggcgaaaatgcggccgctgccggaggctcgctaactttccggggcggaagag<br>gaggaggaggaggaggaagggggcttggagctacgggggggatgcggagaag<br>cagtcagttccctgcacccagcacctcacagcccttcctccgtgcgccctgccgggc<br>ggcgagctaggcggcagcggcgcggcgcgggctcggcggagcggcccatgtcc<br>ggcgcgggcgaagccctcgctcccgggcccgtggggccgcagcgcgtggccga<br>ggcgggcggccgcagctgggctccacagcccagggaaaatgtgataaagacaat<br>actgagaaagatataactcaagctaccaatagccacttcacacatggagagatgcaa<br>gaccagtccatttggggaaatccttcggatggtgaactcattagaacccaacctcagc<br>gcttgcctcagcttcagacttcagcccaggtgccaagtggtgagggaaataggcaaga<br>taaagaacggccacacaggtctgagcaatgtgaaatggaattcaccacgggggccaaa<br>cacggatccgcagataatcgcaaactttcagcacctgtttctcaaaaaatgcatagaaa<br>aattcagtccagcagtctgtaaacagcgatatcagtaagaagagcaaagtaaatgct<br>gtcttttcccaaaagacaggctcttcacctgaagattgttgtgtccactgtatcctggctt<br>gcttgttctgcgaattcctgacccttttgcaacattgtcctcggacaaccctcatgtggca<br>tctgcacctcagaagcctgctgctgttgctgtggtgacgagatgggggatgattgtaa<br>ctgcccttgtgatatggactgtggcatcatggatgcctgttgtgaatcatcagactgctt<br>ggaaatctgtatggaatgctgtggaatttgttttccttcataaatatttatcttttgtttgtgtt<br>aaaactggagagtgtttaaaaatttcctttgggggaagaaaagcacattgtaagatt<br>ctcatgaaacaacatggaatttgcactgttaactcattattgtaagtaatctctgaaagcc<br>tttttacttaaccaaatctacatggtttaatatgtgaaattttaactactttaactagtttata<br>aatttcttaatatgttacaataacttagggacattttgacacccccttcccaaatgttaaa<br>tgcctctctccttttttaccgatatttctgtttctttttaaccgttctcaggagcacttttgctccaa<br>atatattattttttcagtgtgtatttaaacgaggcagttttatttttgatatgtatcattcatgatt<br>gaaaggaagcagtcttggccaggcacggtggcttacacctgtaaccctggcattttg<br>ggaggccaaggtgggcagattgcctgagctcaggagttcgagaccagccagggca<br>acatggtgaaaccccatctctactaaaatacaaaaagttagctgggcttggcggtgtg<br>cgcctgtagtcccagctactcaggaggctgaggcaggagaattgcttgaacccgag<br>aggcggaagttgcagtgagccgagattgtgccactgaactccaacctgcactccagc<br>ctgggcaacagagcgagactccatctctaaataaataaatttaataaataaataa<br>ataaataaataaacaaaccagtctctttattttaaaagaaacttttaggaaacaaacccat<br>aatagttgggaaccagtgttgatctctctcccttaccttctccacttgttcaacagactct<br>gaatgccgactgtgtggactctcttcctcagactgtggggacagatacaattccactcc<br>tgtccacaggaacatgagatttagcagactaaggagatctgtaaagaatgaaccatac<br>cacaaggcatactgaagtgaggattataagagaaataaactcaaaatgctgttggaat<br>atgcagagaattgctaccagaatattcagtcaaggtttcagggagagttgcatttttgag<br>gactctcttagaatgagtgattcacctgctatttaaatgaatttttttagattttttgacaaaga<br>tttaggtggacaccctaaactgtgtgtgcctttaaccagttaaaagaacagtgccttcag<br>cattctttttattagttgtaggaatacagcttttttgaaaagctataaagtttaaattaacta<br>aaaatatgcattttcttacacataatttaaatgttatcatactttttttgatgaaacataatgc<br>cttagtaaaatagctctatttaataaagaagattgagtactctgacacatttcatttattatta<br>ggaaattttaatattaaaatcccagtgttctgagttattgaaaggcatcttttattttgaga<br>gctttaggtctttttgggatgagaacattttagttgtttagtttgtttcttaagcagtgctattt<br>tttgtaaacacagataaatggaaaccattcttttcaatgcagaagaaatctagatatcc<br>ctactgtgaccaaatttctgtattacgattttatgttaaattaaactaatatggcaggttata<br>atgatccttaagtgtaaagaaatcagtcaattacaagagtaattgtatagttattgagacc<br>tctagtgtgtggcttagatgaaagggagagtaaattttcataccatgctctctcctactca<br>gtttgatctctcaaaattgtagtttggtttgatttaatatattcttagtagaaattttgaaag<br>tatgctttgggattaataattattttttaattttttctggctgaatatcaaattgatagtaacaac<br>agaagcataatttttaggaaggctttcgcaaacctagcctttaagagaggttttttaacct<br>gaagcatgagaatatatcacctgtggttctccatgagatgaaacgtagtttctagttata<br>tcattacttaaagggcttaaaaagaaaaaacttagcaaacttttgaatcttttattgct<br>atttacacatatacacacataacaaacacctttaaattttgggatctgaatataattctgt<br>aaacagctgtcttcatttttctcctcttaagaacttaattcatttgttcataaaatataagg<br>aaatctttatactattttacagtaaccacaatctaaatatttacatatacccaaaattaactt<br>atgctcatatattaggatgtgagaatatcatctgtttatggacacatgaaacctcctaatg<br>acctggaattgttagaatatttgacttttttatatgcaaagtttttcaaccaagtggtttgtcta | NM_001166345 | NM_175088 |

TABLE 1-continued

| Gene | Human Gene Sequence | Human Sequence Accession No. | Murine Sequence Accession No. |
|---|---|---|---|
| | atatttaaacatgtactggcacaatttgtgatgaaaatattagcacatttgcaataatgttt<br>ctccataacagagaatgttaatggataccagaattttattttgtatttatgttcatagtactt<br>ttcctcttgtctactccagacagttattccataaagcatttgtataattaaaaggaaaaca<br>gaaaaaggaaaagtaggcaaatgtgaaaatagtttcaatatatcttatgatttcttcatgt<br>aaaatgttttgttgaagtatatggctatcatgactaagtgctagaatttatagttacaggc<br>ggtgtccttttaaatgtggaaaggcttttaaaatattttaaaactggacctgtattatcctg<br>aatacactatatgaaaattttaaaaatgacttctttattttgctttaccgtatgtttatatcta<br>attgacatattgactaatgtttgaaagaattcaaccataagtttaaaatctgaaggttatctt<br>tatcatgtttcatccctgtctgaagatttcctagtcttcttatgtaaatcacatgactcatgtc<br>cgtaaatgaactatgaaagattacgatcagtttatgatcattgacatgtgatttcaaaaca<br>cagtgttcttttaaaaatctataatatgtcaaaatacaagttttttttttttacatcgttttagta<br>agttaatttcatttatttacttgggagctatatttccacttagaaaaactaaggtaattttaca<br>atatatgctgagattaaaaaccaaggtaaaaatgatcaaacatatatgaaattgagtctt<br>agatttaatgaatacactcgaaaataaatgatcagaagaattttcatctaaggcataga<br>gtggcgaaattttgtaaatgctcgcagttagcatctaactattaacaatacagtatgactt<br>tatttaggagaaggcttttttatttagaaaattattttttacagtgtatcaactgtatc<br>cattttcctcacctggatagtcaatgttatctgagcagttcaaggagtaaccaaggcaa<br>ccttatgtaataactttccattcttatccatacaaactctttcagtgccctagattctaatgt<br>tataaacgtcaaacatcactgcccttacataaataagactcgagacttattttacataaat<br>aagtatcttgccttcttgaatgctagttaaatgcttagatttacctaactgcctaatgaatc<br>aggttatttgttaataagattattttttcaaattattttaagacctttatgccccttccaattactt<br>gtgatttgtaggcctgtaggattgttgcatctaatctgactggcaacagaaaatgtcatc<br>aaatactataatatccattttgttttctttgcactaatacaacagaacatatcattttttgttta<br>aacaatggttaatatattaatagggtttgttccacacttactatttatagttttttataatcaag<br>cattgggtattaaaagagaatccttcaaccccttcatcttcgtatgcttatacaataaattg<br>cagtgagtgt (SEQ ID NO: 613) | | |
| Entpd1 | agggaagaagggagaaagagagagagatttgaatatacattgcttcaaggatgcaa<br>aaaattacaacctgtcctttctagtcaatgaaaaagacagggtttgaggttccttccgaaac<br>ggggccggctaatttagcccctcccacgagcccaagggtctgttatatctctgtttcctt<br>gaggacctctctcacggagacggaccacagcaagcagaggctgggggggggaaa<br>gacgaggaaagaggaggaaaacaaaagctgctacttatggaagatacaaaggagt<br>ctaacgtgaagacatttgctccaagaatatcctagccatcctggctctcctctatcat<br>agctgtgatagctttgctgctgtgggggttgacccagaacaaagcattgccagaaaac<br>gtaagtatgggatgtgctggatgcgggttcttctcacacaagtttatacatctataagt<br>ggccagcagaaaaggagaatgacacaggcgtggtgcatcaagtagaagaatgcag<br>ggttaaaggtcctggaatctcaaaattgttcagaaagtaaatgaaataggcatttacct<br>gactgattgcatggaaagagctagggaagtgattccaaggtcccagcaccaagaga<br>cacccgtttacctgggagccacggcaggcatgcggttgctcaggatgaaagtgaa<br>gagttggcagacagggttctggatgtggtggagaggagcctcagcaacttcccctt<br>gacttccagggtgccaggatcattactggccaagaggaaggtgcctatggctggat<br>actatcaactatctgctgggcaaattcagtcagaaaacaaggtggttcagcatagtccc<br>atatgaaaccaataatcaggaaacctttggagcttggaccttgggggagcctctaca<br>caagtcacttttgtaccccaaaaccagactatcgagtcccagataatgctctgcaatt<br>cgcctctatggcaaggactacaatgtctacacacatagctcttgtgctatgggaagga<br>tcaggcactctggcagaaactggccaaggacattcaggttgcaagtaatgaaattctc<br>agggacccatgctttcatcctggatataagaaggtagtgaacgtaagtgacctttacaa<br>gaccccctgcaccaagagatttgagatgactcttccattccagcagtttgaaatccagg<br>gtattggaaactatcaacaatgccatcaaagcatcctggagctcttcaacaccagttac<br>tgcccttactcccagtgtgccttcaatgggattttcttgccaccactccaggggg attttg<br>gggcattttcagctttttactttgtgatgaagttttttaaacttgacatcgagaaagtctctca<br>ggaaaaggtgactgagatgatgaaaaagttctgtgctcagccttgggaggagataaa<br>aacttcttacgctggagtaaaggagaagtacctgagtgaatactgcttttctggtacct<br>acattctctccctccttctgcaaggctatcatttcacagctgattcctgggagcacatcc<br>atttcattggcaagatccagggcagcgacgccggctggactttgggctacatgctga<br>acctgaccaacatgatcccagctgagcaaccattgtccacacctctctcccactccac<br>ctatgtcttcctcatggttctattctccctggtcctttttcacaggtggccatcataggcttgct<br>tatctttcacaagccttcatatttctgaaagatatggtatagcaaaagcagctgaaatat<br>gctggctggagtgaggaaaaaaatcgtccagggagcattttcctccatcgcagtgttc<br>aaggccatccttccctgtctgccagggccagtcttgacgagtgtgaagcttccttggct<br>tttactgaagcctttcttttggaggtattcaatatcctttgcctcaaggacttcggcagata<br>ctgtctctttcatgagttttttcccagctacaccttttctccttttgtactttgtgcttgtataggttt<br>taaagacctgacacctttcataatctttgctttataaaagaacaatattgactttgtctaga<br>agaactgagagtcttgagtcctgtgataggaggctgagctggctgaaagaagaatct<br>caggaactggttcagttgtactcttaagaaccccttctctctcctgtttgccatccatta<br>agaaagccatatgatgcctttggagaaggcagacacacattccattcccagcctgctc<br>tgtgggtaggagaattttctacagtaggcaaatatgtgctaaagcaaagagttttataa<br>ggaaatatatgtgctcatgcagtcaatacagttctcaatcccacccaaagcaggtatgt<br>caataaatcacatattcctaggtgatacccaaatgctacagagtggaacctcagacct<br>gagatttgcaaaagcagatgtaaatatatgcattcaaacatcagggcttactatgagg<br>taggtggtatatacatgtcacaaatataaaatcagttacaactcagggtcactaataat<br>gcatcttccaatgcatattttattatggtaaaatatacataaatataattcaccatttttaaca<br>tttaattcatattaaatacgtacaaatcagtgacatttagtacattcacagtgttgtgccac<br>catcaccactatttagttccagaacatttgcatcatcaatacattgtctagagacaagact | NM_001776 | NM_009848 |

TABLE 1-continued

| Gene | Human Gene Sequence | Human Sequence Accession No. | Murine Sequence Accession No. |
|---|---|---|---|
| | atcctgggtaggcagaaaccatagatcttttgtgtttacagctatggaaaccaactgtac cataaagatagttcactgagttttaaagccaagccacatcttattttccaaggtttaattt agtgagagggcagcattagtgtggagtggcatgcttttgccctatcgtggaatttacac atcagaatgtgcaggatccaagtctgaaagtgttgccacccgtcacacaacatgggct ttgtttgcttattccatgaagcagcagctatagaccttaccatggaaacatgaagagac cctgcacccctttccttaaggattgctgcaagagttacctgttgagcaggattgactggt gatgtttcattctgaccttgtcccaagctctccatctctagatctggggactgactgttga gctgatgggaaagaaaagctctcacacaaaccggaagccaaatgtcccctatctct tgaatgatcaagtcacttttgacaacatccaggtgaatataaaaacttaataaagctgtg gaaaggaactcttaatcttcttttctgctacttaggttaaattcactttgatcttgattaggaa tcaaaattcgaattgggacatgttcaaattcttcttgtggtagttgcctatactgtcatcg ctgctgttggttgagcattgtggtgtaccacgctgtgctcaagggtattacattcttc ttctcatttaatcctcacaacaatctgaagaaggtaggtattacaattcccacttcataga aacagaaactgaggttcagagaggttaagtcatttgcccaaatggctgagccaaagc ctaccatgtacctaacctttatttcttcccgaacataccaggctgtctcctcataacttc caagcatgcacttaaaactccacatgaatacaaggttcatgggacttggtattcataga aagggaggcagaaagctggtctgttcctgataggcttgtaatttaattttcattctgttcat gtgctttggatggaagcacatctggcatatgatgctaatcagtggttcccataccctg gcttcctaattttaatgtttgctcacagcatagtagattgacatcaaatagtggccgatga tgatgaaaataaaggtcaaataagttgagccaataacagccgcttttttccttctgtctgc gtatacaaagcactgtcatgcacacaatctattctgaccctcacaacaacccataagg gtgtaaatagtatttccatttacaaatgaggatcacacaaactactacatggcagagca gatactccaactcatgtcttctggttgaagcctattgcttttcttttctaaacactttccctc agcaagttggaattagacttcacaagtctccttcagagaacacaaatcttttcttattcca ttcctgtttggttgcctacgtccaatctcccctcccagagatgccaaaaaaaaaatc ctttaaggtatttgggagccaaactcaacttgttaaaatctcaaattatggagacaatca gcagacacaacctaaccccaattattttggcaggaaggttggtttagaggcagatcca gcaatctgctttgggccactctgggtggggtaggtgaaataagattggtcactgttaac taatttttaatattggattggccattggttatcactgattaccattctcccctggattttcacc caggactcaaaacttggttctgctaaccctgttcctttatgaggaaccttttaaagattcc tttataaggtgggagtttttttctatgaacctataggggagaaaaaagatcagcagaag tcattacttttttttttttttttttttttgagagagagtctcactccattgcccaggctggag tgcagtggtgctatctcggctcactgcaacctccgcctcctggttcaagcaattctcct gcctcagcctcccgagtagctgggattgcaggtgccaccaccacacccggctaatt tttgtatttttagtaaagacaggtttcaccatgttggccaggctggtctccaactcccaa tctcaggtgatcctattgcctcgggctcccaaagtgctgggattacaggagtgagcca ccatgcctggccagaagtggttacttctgtagacaaaagaaataatgctacttaatcagg cttctctgtgtgacaagaaagagaaagaaataaagaagtttcaattcatccaattcttaa taagaaatatgtaaataaaattttttaaaattacacttcattttaatgttgtatcagtcaaggt ccctgcaagagatggatggtatggtacactcaaactgggtaacacaggagagttttca gaaagcaactaaatccaaaatactatcaaggaatcaatataaaaatttgttaatattttt catactaaatttttcaaaatattttgtgtctattacatttacagcacatcttaattaggactag ctgtgtgttcacctcacatgtggcttgtagctaccatactggacagcacatgtccaaaa aaatacacgtaaagttaaagtttaaaagacacaggaactaagccctcattgtctttccct tgggaggtagtttaaagagctatagatgctgtaacattcttgctattatttattatatatgac attattcctaaaaaagcttttgagatcctaggttgtattcctcaggttttgttgccttcccat gaagatgtgaaggcagggatgcctgttattcagtccaagatgcatgacaagagacat gggaaagtttcatctggatttaaagattaattcttgatgcttacattccatactcaaaatgt aaatttgaatattaaaataaagatgattttttttttggagctagtcttgctctgttgcccagg ctggaatgcagtggcatgatcatggctcactgcagcctcgacctcccaagctcaagc aaggctcaggtgtgcacctaagtagctaggactacaggtgtgcaccaccatgtcta gctatttttttttctgtagagacaggggttttcctatgttgtccaggctggtctcgaactcctg ccctcaagcaatcctcctgccttggcctcccaaagtgttgagattacaggcgtaagcc actgcacctggccaagatgaatattttaatagctcacagaacaaagtttgccacataat gataaaattactatgaaaatatatttccctttattgtcagtttaaaagatgaactgagtttca cccaaactggtctggcccctctctgattcaaataccaatagttgctctgattcaattttcca actgttagaacatgacagctgctcataactagctttgcttactaaccatgtttctttccattt gtattaggtccttttacttttataacagcctcaaagtttcatgaattgctgcagtaaacattg attttcatgtttgtgagtctgcaagccagctgggcagctctacttcaggtggtaagggtg gatcagacctattccatatacctcttgttctccttgtccagtggtttctagggatatgttctc atgatgaacccgcgagggctcgtgaaagtgagaggaaactaggatgcctcttaag gtcttggtcaggatggggtctcctgtcacttctgtcacaggctattgtaagtcatatgag caagctcaataaaatataaacaagtcagatgaaacagtgggaggaatggcaaagtcat atggccaaggccatgagtgattaattttaacacaggaaaaagtttaagcattaaatgc gattatttaatatacaatgtcttattaactgaaatataaaatgtgtttactgtaaaatataatc tgtttatctcaccaaagaaatattatctttaaaaaatgtcattacttctaagacatcatcagt ctgcaacttctttccatttgccttaatcaggatgctgtggcagctcccacattagcctcgc attctaaactggtagatgtcctaggaaaccatacatctatgtattttttcttatttttatacgttt aggacaatgtatagctaattacccaacttttttatttgcatacaaatctaatacaactgaac acaatcagtttttatcacagtataatggattttttcaatagtgaggaggtgcctccatgag cctttctcttagaaaagtggcattcaagactcttcatttgaagtgaagattgctatgtctttt gcattgctctattttacataaaattaagttataaattgacactataatcaaagacaccatga tcagtgatgtttgatcaccctcatcagcactagagttgacttgtttttataacccctttgcat gtatgttgaatagcaaagttcatcagagaacatgtattagtcaatggtaagtaagatact ctcatctaagaaataacatcacctcttctaatgaagttctaagaagagagggaagaaa | | |

TABLE 1-continued

| Gene | Human Gene Sequence | Human Sequence Accession No. | Murine Sequence Accession No. |
|---|---|---|---|
| | aagtcttgggagctagtcagggaatagtgtgtatttgcaattacctaaactgaactctac cattttctcctaacccagttcctcctcctgtgttttttcatgattaatgccacccctgcctcaa tgaaccaagatcagctccatcactgggacctcccattctgcctgtgcaatattttcttttt ttatttctccttctaatattactgttattgctccagtaaagagctgtaatatattttacctgga ctgataccaggaatggtggtgttgcttccaatctgttgctgctagattaatctttgcaaag cacaggcttaatttcattgctgctcaactaaaaccactggtggctttccattgcctacaa aataaagtcaacctocccatcagacattcaaggctttcaatgatccatggccgccagct cttccaggctcatatcccactccactcctctgatgtttcctacactacactacactatac tacactacagccaggtagaatgactgttcacccaacaccactcaggttgtcttctcaac ttggaatactcttgcaccttcaaagctcatttcaaatgcccttcatttgtgaagccttctc caaatttccaagtcagaatgtctcttccttgtgctaccacaaccctttaactgagcctcca ttagtgcactgagacattctgttcagtgtctgggtgaagcttcctggtgaaaaatatgtt acctatttctttctgaaaagttggattcagggatattatcacggacctaaggtaatagttct agccaacctccctgtccactgccaggccgactacaaacccttctgttgctggcgagct ggtccgcaccactagttctgcttcactctatttatctcttgatgtaaccatcttctttctcca ggtttaagaaccagcccaactcctggttccctgatgaagcttttattccccctagccaca tggaactttttccttttggaacatgcctttagtttctgtgtagtttgccatgcagcacttcatt gtacacattattaaaacagaattttaaggattagaatgaaccttaaaagatcatgcatctc aaaatttaatgtacatacaaattacccagggattttgttgaaataaaaattatttaattttaa ttaatataaattaattcagtaggtctggggtgaggcctgaggtttacatttccaacaagct gccaggtaaagccaatacatctgtccaggaatcacactttgcgtatcaaaggtctagat gacattatcattccaaagagtttcttttacaggctctcagatcagtgttcatccactacctg actactgtcattcacaggcattctgttccacagcaggccagctaacgtggtatttacaa agctcactcctcttatacaacaatccaagtgttcttttgtcagttgtctgtgcccagga gatccctctctgccttgccttgccctctgcctttggagaccagcacctcatactcagtga aggcctggagtgcttaagagggatttcttccagctctcttgccctggtcttcagtgtatta gatgtattacctccatgctctcagtagaggcccataggaaagagtaggtaggttatgc cagctcacacgcatccttaaaaatggtttagaagtttagctggtttcttattactcctgtct atggatgtttccttctgtcactctactagggatgaaacagctaatcatgttcaatagttac atttagattggttttttaaaaactatgattgtattagttcgtttccatgctgctgataaagacat atctgagactggaaacaaaaaggggtttaattggacttacagttccacatggctgggga ggcctcaaaatcaggtggggaggcaaaaggtacttcttacgtggtggcatcaagagca aaatgaggaagaagcaaaagcagaaactcttcataaacccaccagatcttgtgggac ttattatcacgagaatagcacagaaaagactggcctccatgattcaattacctcccact gcgtccctcccacaacatgtgggaattctgggagatacaattcaagttgagatttgggt ggggacacagccaaaccatatcattcctccctgggctcctccaaatttcataatcctca catttcaaaaccaatcattccttcccaacagttccccaaagtcttaactcaattcagcatta acccaaaagtccacagtccaaagtctcatctgagacaaggcaagtcccttccacttac aagcctgtaaaagcaagctagttacctcctagatacaatggggggtacaggtattggg taaatacagctgttccaaatgagagaaattggccaaaacaaaggggttacagggtcc atgcaagtctgaaatccagtggggcagtcaaattttaaagctccataatgatctcctttg actccatgtctcacattcaggtcatgctgatgcaagagataggttcccatggtcttgtgc agctccgcccctgtggctttgcagagtacagcctccctcctggctgctttctcaggctg atgttgagtgtctgtagcttttccaggcacaagatgcaagttggtggttgatctaccattc tgggtcaccattctggggtctaccgttctgggactgtggccttcttctcacagctcca ctaggcagtgcccaacagggactctgtgtgggggctctgccccacatttcccttcca cactgccctaggagaggttcccatgagggctctgcccctgcagcaaacttttgcctg gacatccaggtgtttccatatatattctgaaatctaggcagaggttcccaaatctcaattc ttgacatctctgcacccacaggctcaacatcacatggaagctgccaatgcttggggcc tctaccctctgaagccacagcccaagctctatgttggctccttcagccatggctggag cagctgggacacagggcaccaagtccctaggctgcacacagcacagagaccctgg gcccagcccacaaaaccacttttctcctgggcctctgggcctgtgatgggaggg ctgccatgaaggtctctgacatgacctggagacattttccccatggtcaggggattaa cattaggctccttgctgcttatgcaaatttagcagccagcttgaatttctccttaaaaaaa atgggttttctttttctactgcatcatcaggctgcagattttccacatttatgctcttgtttcc ctttaaaacagaatgtttttaacagcacccaagtcaccttttgaatgctttgctgcttaga aatttattccaccagatacccctaagtcatctctctcaagctctaagttccacaaatctcta gggcaagggtgaaatgctgccagtctccttgctaaaacataacaagggtcacctttac ttcagttcccaacaaggtcttcatctccatctgagaccacctcagcctggaccttattgtt catatcactatcagtattttgtcaatgccattcacagtctctaggaggttccaaactttcc tacattttcctatcttcttctgagccctccagattatttcaacacccagttccaaagttgctt ccacattttcgggtatcttttcagcaatgccccactctactggtactattagtccattttcat gctgctgataaagacatacctgagactgggaacaaaaagaggtttaattggacttata gttccacctggctggggaggcctcagaatcatggcaggaggtgaaaggcatttctta cacggcagcagcaagagaaaatgaagaagcagcaaaagcagaaaccctgata aaaccatcagatctcgtgagacttattcactatcacaagaatagcatgggaaagacca gcccccttgattcaattacctcccctgggtcctgtgggaattctggaaggtacaattca atttgagatttgggtggggacacagccaaaccatatcaatgattttgtactttaaccag ctgaatgaagtacaatctcttgctatatgacacaataattatttgcaaaatgagtaaac atatcataaggaaattatttttacaaggtttgaaacctgaaatgcagtctattatcatcat aactaaaaatagagcctcaataaacagattcccagttttgaaaatgcaacatttgtactc cacattgtcagttttcttaggtatatttataaatactcctataaaaatgtaaagaaacacat aatgtagattgctaatttataataacacaagttgattttgacatccaacttattaattatga aatgacttttggcctagtaacaatgaaaatgggggcaaatacagataaatggtaattctt agaatgaactactcagcaccaattctaagttttcttgatggtaaatcataatgttcccttt | | |

TABLE 1-continued

| Gene | Human Gene Sequence | Human Sequence Accession No. | Murine Sequence Accession No. |
|---|---|---|---|
| | ctcctcggttctgcaatctataggcatcccataattgtaatcaatagcttaaaaatatgtct<br>ctctgtcctattctgtatctgtatctcttggattttttacctttgcaatagtcaactgaaccatc<br>ttcttggagtactcatgaagatggaagtctacatggagaatacaggatgaatccactct<br>gtctcctgcagtgaagtctgtttgaaggatgtatttggctgtcttctggacaggccattct<br>aataacagaaacaaacaagttattttaaaacttattggaatattcaaatattaaccaaagt<br>agaaaatataatacacatccatgtgcccatcacagaacttcactgattatcatcattta<br>gccagtcttgaagaagcaagtgctaattacaatcacaaatgaaacaagattcagactt<br>catgaagagcactgcgctataataaaagaagaaatgagcacatacattcttttactgac<br>agtcaaatggtgaaggtgggcagaatcattatgtgatgcaacatggcaaaagtataca<br>gacagtgcatccagaggaaggcaccttgctgaatgactagaatggaagtaggagac<br>attttgcaggccccttcatcctgcaggagaaccagaaccacagcagctctatttgc<br>ctattcctctttaaattacaaagttaaaatttgggagtagtagaaaatcaattggttatctta<br>tagagtctcctagaatatttcattggcattgagaaggtggaaaatgcaaattatatactttt<br>aaaatgtaaatttgcttttcacatatgcttaaagcctaaaacctcttaataaacttcttctga<br>aatata (SEQ ID NO: 614) | | |
| Dgkz | ggagagtgtctctaaggtgacactcgggtgcgcggcagcagcggcggttgcagga<br>ggagagtgtctctaaggtgacactcgggtgcgcggcagcagcggcggttgcagga<br>gctcgctctccgcccgggctccggctccgctccagccgtccgggggcgccgcgg<br>cgcgcagagcgcagcaccccgactccagccaggagccccgcccccccggagc<br>gcaggaggacccgcgcccgcctctcccaggcgcagcgcccagcatctcgctgctc<br>ctgtcgtctaagcgtcggcgtcgctagggacctgcggatcccggcgctcccctccct<br>ccccgcctcgcgtccccggcccgggcggactggagactcgaacttgagcgggtgc<br>ccgaaaggccgcaggagccgcgggcggaaggcggccgcacgatggccgaggg<br>gcagggcggcggagggcagcgctgggactggctggcggcggccgggcagcc<br>gaggaggaggtggtgcggcggcgtttgccggcgcggggaggaggcccaggtcgc<br>gcagccctggcccgagggttcccggggcacggccgctgggcccccggtggagga<br>gcgtttccgccagctgcacctacgaaagcaggtgtcttacaggaaagccatcaccaa<br>gtcgggcctccagcacctggccccccctccgcccacccctgggcccgtgcagc<br>gagtcagagcggcagatccggagtacaggactggacgagtcagcgacatatg<br>gggagcacatctggttcgagaccaacgtgtccggggacttctgctacgttggggagc<br>agtactgtgtagccaggatgctgaagtcagtgtttcgaagaaagtgcgcagcctgca<br>agattgtggtgcacacgccctgcatccgagcagctggagaagataaaattccgctgtaa<br>gccgtccttccgtgaatcaggctccaggaatgtccgcgagccaacctttgtacggca<br>ccactgggtacacagacgacgccaggacggcaagtgtcggcactgtgggaaggg<br>attccagcagaagttcaccttccacagcaaggagattgtggccatcagctgctcgtgg<br>tgcaagcaggcataccacagcaaggtgtcctgcttcatgctgcagcagatcgagga<br>gccgtgctcgctgggggtccacgcagccgtggtcatcccgcccacctggatcctcc<br>gcgcccgaggccccagaatactctgaaagcaagcaagaagaagaagggctt<br>ccttcaagaggtagtccagcaagaaagggcctgaggagggccgctggagacccctt<br>catcatcaggcccaccccctccccgctcatgaagcccctgctggtgtttgtgaaccc<br>aagagtgggggcaaccaggtgcaaagatcattccagtctttcctctggtatctcaatc<br>cccgacaagtcttcgacctgagccagggagggcccaaggaggcgctggagatgta<br>ccgcaaagtgcacaacctgcggatcctggcgtgcggggcgacggcacggtggg<br>ctggatcctctccaccctggaccagctacgcctgaagccgccaccccctgttgccatc<br>ctgccctgggtactggcaacgacttggcccgaaccctcaactggggtgggggcta<br>cacagatgagcctgtgtccaagatcctctcccacgtggaggagggaacgtggtac<br>agctggaccgctgggacctccacgctgagcccaaccccgaggcagggcctgagg<br>accgagatgaaggcgccaccgaccggttgccctggatgtcttcaacaactacttca<br>gcctgggcttgacgcccacgtcacccctggagttccacgagtctcgagaggccaacc<br>cagagaaattcaacagccgcttttcggaataagatgttctacgccgggacagctttctct<br>gacttcctgatgggcagctccaaggacctggccaagcacatccgagtggtgtgtgat<br>ggaatggacttgactcccaagatccaggacagaaacccagtgtgttgttttcctgaa<br>catcccaggtcctgtgcgggcaccatgccctggggcaccctggggagcaccac<br>gactttgagccccagcggcatgacgacggctacctcgaggtcattggcttcaccatg<br>acgtcgttggccgcgctgcaggtgggcggacacggcgagcggctgacgcagtgtc<br>gcgaggtggtgctcaccacatccaaggccatcccggtgcaggtggatggcgagcc<br>ctgcaagcttgcagcctcacgcatccgcatcgccctgcgcaacaggccaccatggt<br>gcagaaggccaagcggcggagcgccgcccccctgcacagcgaccagcagccgg<br>tgccagagcagttgcgcatccaggtgagtcgcgtcagcatgcacgactatgaggcc<br>ctgcactacgacaaggagcagctcaaggaggcctctgtgccgctgggcactgtggt<br>ggtccaggagacagtgacctagagctctgccgtgcccacattgagagactccagc<br>aggagcccgatggtgctggagcaagtccccgacatgccagaaactgtcccccaa<br>gtggtgcttcctggacgccaccactgccagccgcttctacaggatcgaccgagccca<br>ggagcacctcaactatgtgactgagatcgcacaggatgagatttatatcctggaccct<br>gagctgctgggggcatcggcccggcctgacctcccaaccccaacttccctctccc<br>acctcaccctgctcacccacgcccggtcactgcaagggatgctgcaccccctca<br>aggtgaagagctgattgaggctgccaagaggaacgacttctgtaagctccaggagct<br>gcaccgagctgggggcgacctcatgcaccgagacgagcagagtcgcacgtcctg<br>caccacgcagtcagcactggcagcaaggatgtggtccgctacttctgtggaccacg<br>cccccagagatccttgatgcggtggaggaaaacggggagacctgtttgcaccaag<br>cagcggccctgggccagcgcaccatctgccactacatcgtggaggccggggcctc<br>gctcatgaagacagaccagcagggcgacactccccggcagcgggctgagaaggc<br>tcaggacaccgagctggccgcctacctggaaaccggcagcactaccagatgatcc<br>agcggggaggaccaggagacggctctgtagcgggccgcccacgatcagcaggatt | NM_201532 | NM_13806 |

TABLE 1-continued

| Gene | Human Gene Sequence | Human Sequence Accession No. | Murine Sequence Accession No. |
|---|---|---|---|
| | ggacaatgccggccaggggacgagcgagcgccttccttgcccacctcactgccacattcca gtgggacggccacggggggacctaggccccagggaaagagccccatgccgccc cctaaggagccgcccagacctagggctggactcaggagctgggggggcctcacct gttccctgaggaccccgccggaccccgaggctcacagggaacaagacacggct gggttggatatgcctttgccggggttctggggcagggcgctccctggccgcagcag atgccctcccaggagtggaggggctggagaggggaggccttcgggaagaggctt cctgggcccctggtcttcggccgggtcccagcccccgctcctgccccacccac ctcctccgggcttcctcccggaaaactcagcgcctgctgcacttgcctgccctgctttg cttggcacccgctccggcgaccctccccgctccctgtcatttcatcgcggactgtgc ggcctgggggtgggggcgggactctcacggtgacatgtttacagctgggtgtgac tcagtaaagtggatttttttttctttaaaaaaaa (SEQ ID NO: 615) | | |
| Vamp7 | attggaggagcgctcccactcccaagaggccacgcgtagacggggcgcttcatgc attggaggagcgctcccactcccaagaggccacgcgtagacggggcgcttcatgc ggaagtcagcggcgtccggtcccagcctcctctgggagcgggcagttggcgaccct gcactgacccgcgtccctccgtcccgagcccgcgccctcagagggtgcccgga cagactgaagccatggcgattcttttttgctgttgttgccaggggaccactatccttgcc aaacatgcttggtgtggaggaaacttcctggaggtgacagagcagattctggctaag atacctcctgaaaataacaaactaacgtactcacatgccaattatttgtttcattacatctg ccaagacaggattgtatatctttgtatcactgatgatgattttgaacgttcccgagccttta attttctgaatgagagaaagaagagcttccagactacttacggttcaagagcacagac agcacttccatatgccatgaatagcgagttctcaagtgtcttagctgcacagctgaagc atcactctgagaataagggcctagacaaagtgatggagactcaagcccaagtggatg aactgaaaggaatcatggtcagaaacatagatctggtagctcagcgaggagaaagat tggaattattgattgacaaaacagaaaatcttgtggattcttctgtcaccttcaaaactac cagcagaaatcttgctcgagccatgtgtatgaagaacctcaagctcactattatcatcat catcgtatcaattgtgttcatctatatcattgtttcacctctctgtggtggatttacatggcc aagctgtgtgaagaaataggaaagaagaagttaccattaaccaaggatatgagagaa caaggagtctaaaagcaatccatgtgactcaagccttttcacatactgacagatggtatct gccagtctcttcaaccctcttctcacttttaatatcttgttccatgcctccaggtttatcttt gtcttatctaccagtttattcctgtgaacttcagattgaaccattcattgcagcagtagcct taaaaaggcttttgtttatttctttggtttgttaactagtgtcatctatttagagaaacatttt gttttttaattgctcaaagtgtcgccgctagtcttatgagctcttactaaaactatggag aaactttgtatgtgcacacaaaagtattcaagagacagtattgctaacatctcatcttaat gtcttttgttattgagaagttttaggtgcttcaaaacaatataaatgataatagttgttattt ggggaattgtaatgatgttggtgctgcttccttctaagagctcagacaagtaaagtatg aaacattcttatttcagttagatggggaacattttgctagccattagaagcacacagaa ttatccttgtcctcctaatattgactttcaggaataaagttcagtgtgctgatcattcacaat acagtggatagcttgatatcttctgttttcccattgcagttgatttgagaagataaaggttt aaatattgttgaaagttgcagttttttaaatgtgttccttttttcttctgtgaatatttagggcaa tcgtgtcgctaatagaatatgtagtagaggggggtgggaggtaaattcctctgacttgc caaagaaaaagaagggaaccacagtggatatgctagcattttagctgtgcaaaggga ggtagtgtgggaaaagtgttttccattctgggaaaagcccaaaccgaatacggtcagc agtcaactccagggtttgggcttgattcctgttgaataatagttttgagcattctttgtggtt aaataaattcttaaatctgcctagttttgatgaattcttttgtgaacttgaaagagaatag acagtatgacatatagaattaatacaaaacagtttaacaaccattaactgcagttaag aattattggactgtaatcatatcgctactggcatctgttatctagttttgcatttctggtgtgt atctgaaaggaagacatttctaccctagatccaattgcatttatttatcaataagtgccat taaattgaaattatattacattttacaattctcaatgaatgaacaaattagtctgtagaatc tagccacctgtttagcctagtcatgtgccttgaacatatatgtgtcccatttatctggctca tggtacctgttcttctatccaaacctttcaattcatgctacctgattcatttatttgacataga tcttaggcccacttgaactcttttcttgtttatctagcatagcacaaacgttttttccagtcttc tttatcaacactaatgcctcttaattgcatcagtatttcctattggaaaatacatctgttcca gaaaaacatttggcattcctgaataattccaaatgttttttaactcaaagaaaaaaggttta aagcttatttccctttcttatacacacctgaatttaaattgatgtgcatgttttagggatcaat tacctaactgttccttggtctatttatgtataagaatgcttttttaaagcacatgtctcatttta aatgacgcacaaactgaagatgtaataaaatttaagagtaataacaataaaaaaa (SEQ ID NO: 616) | NM_005638 | NM_011515 |
| Hipk1 | gcagagtctgcagtgcggaggggccgggaagtccaggccccgcactcgatccac gctggctccctacggaggcccacctactcgaggcccaccgactcctactgcaatcag tactatgcgatcgtcctagagagtccattcagctgcacttcccgcctcagtcatggcatca cagctgcaagtgttttcgccccatcagtgtcgtcgagtgcctctgcagtgcgaaga aactgttaaatagagcccctctggctgggatgtttcaggacagagtagcaacgacaaat atttttacccacagcaaaaccctcccagccacacaagggcaagccaactcctctcacc aggtagcaaatttcaacatccctgcttacgaccagggcctcctcctcccagacctag agtggagcatattgttgtaacagccgctgatagctcgggcagtgctgctacatcaacc ttccaaagcagccagaccctgactcacagaagcaacgtttctttgcttgagccatatca aaaatgtggattgaaacgaaaaagtgaggaagttgacagcaacggtagtgtgcagat catagaagaacatccccctctcatgctgcaaaaacaggactgtggtgggtgctgctgc cacaaccaccactgtgaccacaaagagtagcagttccagcgtggaaggggattacc agctggtccagcatgagatcctttgctctatgaccaatagctatgaagtgcttggagttcc tagccgggggacatttggacaggtggctaagtgctggaagaggagcaccaagga aattgtggctattaaaatcttgaagaaccacccctcctatgccagacaaggacagattg aagtgagcatcctttcccgcctaagcagtgaaaatgctgatgagtataattttgtccgtt | NM_198268 | MM_010432 |

TABLE 1-continued

| Gene | Human Gene Sequence | Human Sequence Accession No. | Murine Sequence Accession No. |
|---|---|---|---|
| | catacgagtgctttcagcataagaatcacacctgccttgtttttgaaatgttggagcaga actatatgattttctaaagcaaaacaaatttagcccactgccactcaagtacatcagac caatcttgcagcaggtggccacagccttgatgaagctcatagagtcttggtctgatcca cgctgaccttaagcctgaaaacatcatgctggttgatccagttcgccagccctaccga gtgaaggtcattgactttggttctgctagtcacgtttccaaagctgtgtgctcaacctact tacagtcacgttactacagagctcctgaaattattcttgggttaccattttgtgaagctatt gatatgtggtcactgggctgtgtgatagctgagctgttcctgggatggcctcttatcct ggtgcttcagaatatgatcagattcgttatatttcacaaacacaaggcttgccagctgaa tatcttctcagtgccggaacaaaaacaaccaggttttttcaacagagatcctaatttggg gtacccactgtggaggcttaagacacctgaagaacatgaactggagactggaataaa atcaaagaagctcggaagtacatttaaattgcttagatgacatggctcaggtcaatat gtctacagacctggagggaacagacatgttggcagagaaggcagaccgaagagaa tacattgatctgttaaagaaaatgctcacaattgatgcagataagagaattacccctcta aaaactcttaaccatcagtttgtgacaatgactcaccttttggattttccacatagcaatc atgttaagtcttgttttcagaacatggagatctgcaagcggagggttcacatgtatgata cagtgagtcagatcaagagtcccttcactacacatgttgccccaaatacaagcacaaa tctaaccatgagcttcagcaatcagctcaatacagtgcacaatcaggccagtgttctag cttccagttctactgcagcagctgctactctttctctggctaattcagatgtctcactacta aactaccagtcagctttgtacccatcatctgctgcaccagttcctggagttgcccagca gggtgtttccttgcagcctggaacccaccagatttgcactcagacagatccattccaac agacatttatagtatgtccacctgcgttttcaaactggactacaagcaacaacaaagcat tctggattccctgtgaggatggataatgctgtaccgattgtacccaggcaccagctg ctcagccactacagattcagtcaggagttctcacgcagggaagctgtacaccactaat ggtagcaactctccaccctcaagtagccaccatcacaccgcagtatgcggtgcccttt actctgagctgcgcagccggccggccggcgctggttgaacagactgccgctgtact gcaggcgtggcctggagggactcagcaaattctcctgccttcaacttggcaacagttg cctggggtagctctacacaactctgtccagcccacagcttatgattccagaggccatg gggagtggacagcagctagctgactggaggaatgcccactctcatggcaaccagta cagatcttttcatgcagcagccatccttgctgactaaccatgtgacattggccactgctc agcctctgaatgttggtgttgcccatgttgtcagacaacaacaatccagttccctccctt cgaagaagaataagcagtcagctccagtctcttccaagtcctctctagatgttctgcctt cccaagtctattctctggttgggagcagtccctccgcaccacatcttcttataattcctt ggtccctgtccaagatcagcatcagcccatcatcattccagatactcccagccctcctg tgagtgtcatcactatccgaagtgacactgatgaggaagaggacaacaaatacaagc ccagtagctctggactgaagccaaggtctaatgtcatcagttatgtcactgtcaatgatt ctccagactctgactcttctttgagcagcccttattccactgatacctgagtgctctccg caccccgcactatcattgtgcctccactgaaaactgcacttgtgactgcactgtagcaa cccaggcctcaggtctcctgagcaataagactaagccagtcgcttcagtgagtgggc agtcatctggatgctgtatcaccccacagggtatcgagctcaacgcggggggacc agtgcagcacaaccactcaatcttagccagaaccagcagtcatcggcggctccaac ctcacaggttgagaagcagcaacccagcccccccgcaggcagcaggcgtttgtggcc cctctctcccaagccccctacaccttccagcatggcagcccgctacactcgacaggg cacccacaccttgccccggcccctgctcacctgccaagccaggctcatctgtatacgt atgctgccccgacttctgctgctgcactgggctcaaccagctccattgctcatcttttctc cccacagggttcctcaaggcatgctgcagcctataccactcacccagcacttttggtg caccaggtccctgtcagtgtgggcccagcctcctcacttctgccagcgtggcccctg ctcagtaccaacaccagtttgccacccaatcctacattgggtcttcccgaggctcaaca atttacactggatacccgctgagtcctaccaagatcagccagtattcctacttatagttg gtgagcatgagggaggaataatcatggctaccttctcctggccctgcgttcttaatatt gggctatggagagatcctccttacccctcttgaaatttcttagccagcaacttgttctgca ggggcccactgaagcagaaggttttttctctgggggaacctgtctcagtgttgactgca ttgttgtagtcttcccaaagtttgccctatttttaaattcattattttttgtgacagtaattttggt acttggaagagttcagatgcccatcttctgcagttaccaaggaagagagattgttctga agttaccctctgaaaaatattttgtctctctgacttgatttctataaatgcttttaaaaacaa gtgaagccctctttatttcattttgtgttattgtgattgctggtcaggaaaaatgctgata gaaggagttgaaatctgatgacaaaaaaagaaaaattacttttgtttgtttataaactca gacttgcctattttattttaaaagcggcttacacaatctcccttttgtttattggacatttaaa cttacagagtttcagttttgttttaatgtcatattatacttaatgggcaattgttattttttgcaa aactggttacgtattactctgtgttactattgagattctctcaattgctcctgtgttttgttata aagtagtgtttaaaaggcagctcaccatttgctggtaacttaatgtgagagaatccatat ctgcgtgaaaacaccaagtattctttttaaatgaagcaccatgaattctttttaaatttatttt ttaaaagtctttctctctctgattcagcttaaattttttttatcgaaaaagccattaaggtggtt attattacatggtggtggtggttttattatttgcaaaatctctgtctctattatgagatactggc attgatgagctttgcctaaagattagtatgaattttcagtaatacacctctgttttgctcatc tctcccttctgttttatgtgatttgtttggggagaaagctaaaaaacctgaaaccagata agaacatttcttgtgtatagcttttatacttcaaagtagcttcctttgtatgccagcagcaa attgaatgctctcttattaagacttatataatcaagtgcatgtaggaattgcaaaaaatatttt aaaaatttattactgaatttaaaaatatttagaagttttgtaatggtggtgttttaatatttta cataattaaatatgtacatattgattagaaaaataacaagcaatttttcctgctaaccca aaatgttatttgtaatcaaatgtgtagtgattacactttgaattgctactagtgtgtatgtg atcctccagtgttatcccggagatggattgatgtctccattgtatttaaaccaaaatgaac tgatacttgttggaatgtatgtgaactaattgcaattatattagagcatattactgtagtgct gaatgagcaggggatttgcctgcaaggagaggagttcccttggaattgttttgcacag gtgtgtctggtgaggagtttttcagtgtgtgtctcttccttccctttatcctccttcccttatt gtagtgccttatatgataatgtagtggttaatagagtttacagtgagcttgccttaggatg | | |

TABLE 1-continued

| Gene | Human Gene Sequence | Human Sequence Accession No. | Murine Sequence Accession No. |
|---|---|---|---|
| | gaccagcaagcccccgtggacccctttagttgttcaccgggatttatcagaacaggatta gcagctgtattgtgtaatgcattgttctcagtttccctgccaacattgaaaaataaaaca gcagcttttctcctttaccaccacctctacccctttccattttggattctcggctgagttctc acagaagcattttccccatgtggctctctcactgtgcgttgctaccttgcttctgtgagaa ttcaggaagcaggtgagaggagtcaagccaatattaaatatgcattcttttaaagtatgt gcaatcacttttttgaatgaatttttttttccttttcccatgtggcagtccttcctgcacatagt tgacattcctagtaaaatatttgcttgttgaaaaaaacatgttaacagatgtgtttatacca aagagcctgttgtattgcttaccatgtccccatactatgaggagaagttttgtggtgccg ctggtgacaaggaactcacagaaaggttttcttagctggtgaagaatatagagaagga accaaagcctgttgagtcattgaggcttttgaggtttcttttttaacagcttgtatagtcttg gggcccttcaagctgtgaaattgtccttgtactctcagctcctgcatggatctgggtcaa gtagaaggtactgggggatggggacattcctgcccataaaggatttggggaaagaag attaatcctaaaatacaggtgtgttccatctgaattgaaaatgatatatttgagatataatttt taggactggttctgtgtagatagagatggtgtcaaggaggtgcaggatggagatggg agatttcatggagcctggtcagccagctctgtaccaggttgaacaccgaggagctgtc aaagtatttggagtttcttcattgtaaggagtaagggcttccaagatggggcaggtagt ccgtacagcctaccaggaacatgttgtgttttcttttttttttaaaatcattatattgagttgt gttttcagcactatattggtcaagatagccaagcagtttgtataatttctgtcactagtgtc atacagttttctggtcaacatgtgtgatctttgtgtctccttttttgccaagcacattctgattt tcttgttggaacacaggtctagtttctaaaggacaaattttttgttccttgtctttttttctgtaa tcctgcaccccagtccaataagcagataccacttaagataggagtctaaactccacag aaaaggataataccaagagcttgtattgttaccttagtcacttgcctagcagtgtgtggc tttaaaaactagagatttttcagtcttagtctgcaaactggcatttccgatttccagcata aaaatccacctgtgtctgctgaatgtgtatgtatgtgctcactgtggctttttagattctgtcc ctgggggttagccctgttggccctgacaggaagggaggaagcctggtgaatttagtga gcagctggcctgggtcacagtgacctgacctcaaaccagcttaaggctttaagtcctc ggttcagtgtagccactctgggctcatagggacacttggtcactccagagttttttaatag ctcccaggaggtgatattattttcagtgctcagctgaaataccaaccccaggaataaga actccatttcaaacagttctggccattctgagcctgcttttgtgattgctcatccattgtcct ccactagaggggctaagcttgactgcccttagccaggcaagcacagtaatgtgtgttt tgttcagcattatatgcaaaaattcactagttgagatggtttgttttaggataggaaatga aattgcctctcagtgacaggagtggcccgagcctgcttcctattttgattttttttttttttttaa ctgatagatggtgcagcatgtctacatggttgtttgttgctaaactttatataatgtgtggtt tcaattcagcttgaaaaataatctcactacatgtagcagtacattatatgtacattatatgt aatgttagtatttctgctttgaatccttgatattgcaatgaattcctactttattaaatgtatt tgatatgctagttattgtgtgcgatttaaactttttttgctttctcccttttttttggttgtgcgctt tcttttacaacaagcctctagaaacagatagtttctgagaattactaggctatgtttgtaat gcagatgtacttagggagtatgtaaaataatcattttaacaaaagaaatagatatttaaa atttaatactaactatgggaaaagggtccattgtgtaaaacatagtttatctttggattcaa tgtttgtcttggttttacaaagtagcttgtattttcagtattttctacataatatggtaaaatg tagagcaattgcaatgcatcaataaaatgggtaaattttctgacttatgtggctgttttttga cttctgttataggatataaagggggatcaataaatgacatctttgaaagtgaaaa (SEQ ID NO: 617) | | |
| Nuak2 | gtgctttactgcgcgctctggtactgctgtggctccccgtcctggtgcgggacctgtgc cccgcgcttcagccctcccgcacagcctactgattcccctgccgcccttgctcacct cctgctcgccatggagtcgctggttttcgcgcggcgctccggcccccactccctcggc cgcagagctagcccggccgctggcggaagggctgatcaagtcgcccaagccccta atgaagaagcaggcggtgaagcggcaccaccacaagcacaacctgcggcaccgc tacgagttcctggagacctgggccaaaggcacctacgggaaggtgaagaaggcgc gggagagctccggggcgcctggtggccatcaagtcaatccggaaggacaaaatcaa agatgagcaagatctgatgcacatacggagcgagattgagatcatgtcatcactcaa ccaccctcacatcattgccatccatgaagtgtttgagaacagcagcaagatcgtgatc gtcatggagtatgccagccggggcgacctttatgactccatcgacgagcggcagca gctcagtgagcgcgaagctaggcattcttccggcagatcgtctctgccgtgcactatt gccatcagaacagagttgtccaccgagatctcaagctggagaacatcctcttggatgc caatgggaatatcaagattgctgacttcggcctctccaacctctactatcaaggcaagt tcctgcagacattctgtgggagccccctctatgcctcgcagagattgtcaatgggaa gccctacacaggcccagaggtggacagctggtccctgggtgttctcctctacatcctg gtgcatggcaccatgcccttgatgggcatgaccataagatcctagtgaaacagatca gcaacggggcctaccgggagccacctaaaccctctgatgcctgtgcctgatccgg tggctgttgatggtgaacccaccgccggccaccctggaggatgtggccagtca ctggtgggtcaactgggctacgccacccgagtgggagagcaggaggctccgcat gagggtgggcaccctggcagtgactctgcccgcgcctccatggctgactggctccg gcgttcctcccgcccctcctggagaatggggccaaggtgtgcagcttcttcaagca gcatgcacctggtggggaagcaccaccctggcctggagcgccagcattcgctca agaagtcccgcaaggagaatgacatggcccagtctctccacagtgacacggctgat gacactgcccatcgccctggcaagagcaacctcaagctgccaaagggcattctcaa gaagaaggtgcagcctctgcagaaggggtacaggaggaccctccggagctcagc ccaatccctgcgagccccagggcaggctgccccgctgctccccaagaaggcattct caagaagccccgacagcgcgagtcgctgctactactcctctcccgagccccagtgaatc tggggagctcttggacgcaggcgacgtgtttgtgagtggggatcccaaggagcaga agcctccgcaagcttcagggctgctcctccatcgcaaaggcatcctcaaactcaatg gcaagtctctcccagttcagccttggagctcgcggccccaccaccttcggctccctgg atgaactcgccccacctcgcccctggcccgggccagccgaccctcaggggctgt | NM_030952 | NM_ 001195025 |

TABLE 1-continued

| Gene | Human Gene Sequence | Human Sequence Accession No. | Murine Sequence Accession No. |
|---|---|---|---|
| | gagcgaggacagcatcctgtcctctgagtcctttgaccagctggacttgcctgaacgg<br>ctcccagagcccccactgcggggctgtgtgtctgtggacaacctcacggggcttgag<br>gagcccccctcagagggccctggaagctgcctgaggcgctggcggcaggatcctt<br>gggggacagctgcttttccctgacagactgccaggaggtgacagcgacctaccgac<br>ggtcaggctctcagatgcagctggttgcaccccgaggggagatgccttctcccccac<br>ctcccaggacctgcatcccagctcagaaggctcagttgggtttgcagtggagccctg<br>agcagggctggatatgggaagtaggcaaatgaaatgcgccaagggttcagtgtctgt<br>cttcagccctgctgaacgaagaggatactaaagagagggggaacgggaatgcccgc<br>gacagagtccacattgcctgtttcttgtgtacatgggggggccacagagacctggaa<br>agagaactctcccagggccatcctcctgcatcccatgaatactctgtacacatggtgc<br>cttctaaggacagctccttccctactcattccctgcccaagtggggccagacctcttta<br>cacacacattcccgttcctaccaaccaccagaactgatggtggcaccctaatgtgca<br>tgaggcatcctgggaatggtctggagtaacgcttcgttattttttattttt atttttattt attat<br>ttatttttttgagacggagtttcgctcttggtgcccaggctagagtgcaatggcgcgatc<br>tcagctcacctcaacctccgcctcccggttcaagcgattctcctgcctcagcctccct<br>agtagctgggattacaggcgcccgccaccatgcccggctaattttgtatttttagtaga<br>gacagggtttctccatgttggtcaggctggtctcaaactcccgacctcaggtgatccac<br>ccacctcggcctcccaaagtgctgggattacaggcgtgagccaccgcgcccacct<br>aacccttccttatttagcctaggagtaagagaacacaatctctgtttcttcaatggttctct<br>tcccttttccatcctccaaacctggcctgagcctcctgaagttgctgctgtgaatctgaa<br>agacttgaaaagcctccgcctgctgtgtggacttcatctcaaggggcccagcctcctc<br>tggactccaccttggacctcagtgactcagaacttctgcctctaagctgctctaaagtc<br>cagactatggatgtgttctctaggccttcaggactctagaatgtccatatttattttttatgtt<br>cttggctttgtgttttaggaaaagtgaatcttgctgttttcaataatgtgaatgctatgttct<br>gggaaaatccactatgacatctaagttttgtgtacagagagatattttttgcaactatttcc<br>acctcctcccacaaccccccacactccactccacactcttgagtctctttacctaaiggt<br>ctctacctaatggacctccgtgccaaaaagtaccattaaaaccagaaaggtgattgg<br>aaaaaaaaaaaaaaaaaaaaaaaaaaaaaaaaaaaaaaaaa (SEQ ID<br>NO: 618) | | |
| Alk | agctgcaagtggcgggcgcccaggcagatgcgatccagcggctctgggggcggc<br>agcggtggtagcagctggtacctcccgccgcctctgttcggagggtcgcggggcac<br>cgaggtgcttccggccgccctcggtcggcacccaaagccggggcgctgatga<br>tgggtgaggaggggcggcaagatttcgggcgcccctgccctgaacgccctcagc<br>tgctgccgccggggccgctccagtgcctgcgaactctgaggagccgaggcgccgg<br>tgagagcaaggacgctgcaaacttgcgcagcgcgggggctgggattcacgcccag<br>aagttcagcaggcagacagtccgaagccttcccgcagcggagagatagcttgagg<br>gtgcgcaagacgggcagcctccgccctcggttcccgcccagaccgggcagaagag<br>cttggaggagccaaaaggaacgcaaaaggcggccaggacagcgtgcagcagctg<br>ggagccgccgttctcagcctttaaaagttgcagagattggaggctgccccgagaggg<br>gacagaccccagctccgactgcgggggggcaggagaggacggtaccaactgcca<br>cctcccttcaaccatagtagttcctctgtaccgagcgcagcgagctacagacggggg<br>cgcggcactcggcgcggagagcggggaggctcaaggtcccagccagtgagcccag<br>tgtgcttgagtgtctctggactcgcccctgagcttccaggtctgtttcatttagactcctg<br>ctcgcctccgtgcagttgggggaaagcaagagacttgcgcgcacgcacagtcctct<br>ggagatcaggtggaaggagccgctgggtaccaaggactgttcagagcctcttcccat<br>ctcggggagagcgaagggtgaggctgggcccggagagcagtgtaaacggcctcc<br>tccggcgggatgggagccatcgggtccctgtggctcctgccgctgctgctttccacg<br>gcagctgtgggctccgggatggggaccggccagcgcgcgggctcccagctgcg<br>gggccgccgctgcagccccgggagccactcagctactcgcgcctgcagaggaag<br>agtctggcagttgacttcgtggtgccctcgctcttccgtgtctacgcccgggaccctact<br>gctgccaccatcctcctcggagctgaaggctggcaggcccgaggcccgcggctcg<br>ctagctctggactgcgccccgctgctcaggttgctggggccggcgccgggggtctc<br>ctggaccgccggttcaccagcccggcagaggcccggacgctgtccagggtgctg<br>aagggcggctccgtgcgcaagctccggcgtgccaagcagttggtgctggagctgg<br>gcgaggaggcgatcttggagggttgcgtcgggcccccggggaggcggctgtgg<br>ggctgctccagttcaatctcagcgagctgttcagttggtggattcgccaaggcgaagg<br>gcgactgaggatccgcctgatgcccgagaagaaggcgtcggaagtgggcagagtt<br>gggaaggctgtccgcggcaattcgcgcctcccagccccgccttctcttccagatcttc<br>gggactggtcatagctccttggaatcaccaacaaacatgccttctccttctcctgattatt<br>ttacatggaatctcacctggataatgaaagactccttcccttcctgtctcatcgcagcc<br>gatatggtctggagtgcagctttgacttccccctgtgagctggagtattcccctccactgc<br>atgacctcaggaaccagagctggtcctggcgccgcatccctccgaggaggcctcc<br>cagatggacttgctggatgggcctggggcagagcgttctaaggagatgcccagagg<br>ctcctttctccttctcaacacctcagctgactccaagcacaccatcctgagtccgtggat<br>gaggagcagcagtgagcactgcacactggccgtctcggtgcacaggcacctgcag<br>ccctctgaaggtacattgcccagctgctgccccacaacgaggctgcaagagagat<br>cctcctgatgcccactccagggaagcatggttggacagtgctccagggaagaatcg<br>gccgtccagacaacccatttcgagtgggcctggaatacatctccagtggaaaccgca<br>gcttgtctgcagtggacttcttttgccctgaagaactgcagtgaaggaacatcccagg<br>ctccaagatggccctgcagagctccttcacttgttggaatgggacttcctccagcttg<br>ggcaggcctgtgacttccaccaggactgtgcccagggagaagatgagagccagat<br>gtgccggaaactgcctgtgggttttactgcaactttgaagatggcttctgtggctggac<br>ccaaggcacactgtcaccccacactcctcaatggcaggtcaggaccctaaaggatg<br>cccggttccaggaccaccaagaccatgtctcattgctcagtaccactgatgtccccgc | NM_004304 | NM_007439 |

TABLE 1-continued

| Gene | Human Gene Sequence | Human Sequence Accession No. | Murine Sequence Accession No. |
|---|---|---|---|
| | ttctgaaagtgctacagtgaccagtgctacgtttcctgcaccgatcaagagctctccat gtgagctccgaatgtcctggctcattcgtggagtcttgaggggaaacgtgtccttggtg ctagtggagaacaaaaccgggaaggagcaaggcaggatggtctggcatgtcgccg cctatgaaggcttgagcctgtggcagtggatggtgtttgcctctcctcgatgtgtctgac aggttctggctgcagatggtcgcatggtggggacaaggatccagagccatcgtggct tttgacaatatctccatcagcctggactgctacctcaccattagcggagaggacaagat cctgcagaatacagcaccccaaatcaagaaacctgtttgagagaaacccaaacaagg agctgaaaccggggaaaattcaccaagacagaccccccatctttgaccctacagttc attggctgttcaccacatgtggggccagcgggcccatggccccacccaggcacag tgcaacaacgcctaccagaactccaacctgagcgtggaggtggggagcgagggcc ccctgaaaggcatccagatctgtgaaggtgccagccaccgacacctacagcatctcg ggctacggagctgctggcggaaaggcgggaagaacaccatgatgcggtcccac ggcgtgtctgtgctgggcatcttcaacctggagaaggatgacatgctgtacatcctgg ttgggcagcagggagaggacgcctgccccagtacaaaccagttaatccagaaagtc tgcattggagagaacaatgtgatagaagaagaaatccgtgtgaacagaagcgtgcat gagtgggcaggaggcggaggaggaggggtggagccacctacgtattttaagatga aggatggagtgccggtgcccctgatcattgcagccggaggtggtggcagggcctac ggggccaagacagacacgttccacccagagagaccaggagaataactcctcggttct agggctaaacggcaattccggagccgcaggtggtggaggtggctggaatgataac acttccttgctctgggccgaaaatctttgcaggagggtgccaccggaggacattcct gccctcaggccatgaagaagtgggggtgggagacaagaggggggtttcggagggg gtggagggggtgctcctcaggtggaggaggcggaggatatataggcggcaatgc agcctcaaacaatgaccccgaaatggatggggaagatggggtttccttcatcagtcc actgggcatcctgtacacccccagctttaaaagtgatggaaggccacggggaagtga atattaagcattatctaaactgcagtcactgtgaggtagacgaatgtcacatggaccct gaaagccacaaggtcatctgcttctgtgaccacgggacggtgctggctgaggatgg cgtctcctgcattgtgtcacccaccccggagccacacctgccactctcgctgatcctct ctgtggtgacctctgccctcgtggccgcctggtcctggcattctccggcatcatgatt gtgtaccgccgaagcaccaggagctgcaagccatgcagatggagctgcagagcc ctgagtacaagctgagcaagctccgcacctcgaccatcatgaccgactacaacccca actactgctttgctggcaagacctcctccatcagtgacctgaaggaggtgccgcgga aaaacatcaccttcattcggggtctgggccatggcgcctttggggaggtgtatgaag gccaggtgtccggaatgcccaacgacccaagcccccctgcaagtggctgtgaagac gctgcctgaagtgtgctctgaacaggacgaactggatttcctcatggaagccctgatc atcagcaaattcaaccaccagaacattgttcgctgcattggggtgagcctgcaatccct gcccggttcatcctgctggagctcatggcggggggagacctcaagtcctcctccg agagacccgcctcgcccgagccagcctcctccctggccatgctggaccttctgca cgtggctcgggacattgcctgtggctgtcagtattttggaggaaaaaccacttcatccac cgagacattgctgccagaaactgcctcttgacctgtcaggccctggaagagtggcc aagattggagacttcgggatggcccgagacatctacagggcgagctactatagaaa gggaggctgtgccatgctgccagttaagtggatgcccccaggcctttcatggaag gaatattcacttctaaaacagacacatggtcctttggagtgctgctatgggaaatcttttc tcttggatatatgccataccccagcaaaagcaaccaggaagttctggagtttgtcacca gtggaggccggatggacccacccaagaactgccctgggcctgtataccggataatg actcagtgctggcaacatcagcctgaagacaggcccaactttgccatcattttggaga ggattgaatactgcacccaggaccggatgtaatcaaccgctttgccgatagaata tggttccacttgtggaagaggaagagaaagtgcctgtgaggcccaaggaccctgagg gggttcctcctctcctggtctctcaacaggcaaaacgggaggaggagcgcagccca gctgccccaccacctctgcctaccacctcctctggcaaggctgcaaagaaacccaca gctgcagagatctctgttcgagtccctagagggccggccgtggaaggggggacacgt gaatatggcattctctcagtccaaccctccttcggagttgcacaaggtccacggatcca gaaacaagccaccagcttgtgaacccaacgtacggctcctggtttacagagaaac ccaccaaaaagaataatcctatagcaaagaaggagccacacgacaggggtaacctg gggctggagggaagctgtactgtcccaccctaacgttgcaactgggagacttccggg ggcctcactgctcctagagcccttcgctgactgccaatatgaaggaggtacctctgt tcaggctacgtcacttcccttgtgggaatgtcaattacggctaccagcaacagggcttg cccttagaagccgctactgccctggagctggtcattacgaggataccattctgaaaa gcaagaatagcatgaaccagcctgggccctgagctcggtcgcacactcacttctcttc cttgggatccctaagaccgtggaggagagaggcaatggctccttcacaaaccag agaccaaatgtcacgttttgttttgtgccaactattttgaagtaccaccaaaaaagctgt attttgaaaatgctttagaaaggttttgagcatgggttcatcctattctttcgaaagaaga aaatatcataaaaatgagtgataaatacaaggcccagatgtgctaaggttttat gcatgtttgttgtatacttccttatgcttctttcaaattgtgtgtgtctgcttcaatgtagtca gaattagctgcttctatgtttcatagttgggtcatagatgtttccttgccttgttgatgtgg acatgagccatttgaggggagagggaacggaaataaaggagttatttgtaatgacta aaa (SEQ ID NO: 619) | | |
| Pdzk1ip1 | gcccgtcttcgtgtctcctccctcccctcgcttcctccttcctagctcctctcctccaggg ccagactgagcccaggttgatttcaggcggacaccaatagactccacagcagctcca ggagcccagacaccggcggccagaagcaaggctaggagctgctgcagccatgtc ggctccagcctcctcattctgggcctgctcacggcagtgccacctgccagctgtca gcaaggcctggggaaccttcagccctggatgcagggccttatcgcggtggccgtgtt cctggtcctcgttgcaatcgcctttgcagtcaaccacttctggtgccaggaggagccg gagcctgcacacatgatcctgaccgtcggaaacaaggcagatggagtcctggtggg aacagatggaaggtactcttcgatggccgcagtttcaggtccagtgagcatgagaa | NM_005764 | NM_ 001164557 |

TABLE 1-continued

| Gene | Human Gene Sequence | Human Sequence Accession No. | Murine Sequence Accession No. |
|---|---|---|---|
| | tgcctatgagaatgtgcccgaggaggaaggcaaggtccgcagcaccccgatgtaac cttctctgtggctccaaccccaagactcccaggcacatgggatggatgtccagtgcta ccacccaagcccctcttctttgtgtggaatctgcaatagtgggctgactccctccag ccccatgccggccctacccgcccagaagtatagccagccaaggttggagctcaga ccgtgtctaggttggggctcggctgtggccctggggtctcctgctcagctcagaaga gccttctggagaggacagtcagctgagcacctcccatcctgctcacacgtccttccc ataactatggaaatggccctaatttctgtgaaataaagacttttgtatttctggggctga ggctcagcaacagcccctcaggcttccagtga (SEQ ID NO: 620) | | |
| Inpp5b | aaatgtagtcactgtcccggaacctggggcagcggagtcccgtgcgcctgtggtg acagctcaggagggtgtgtgcgctcagcaggggccagcatggaccagtctgtggc aatccaggagacgctggctgaggggaatactgcgtcatcgccggtgcaaggtgtgc ggagcacggcggccaggaacacgctctcttcctctatacgcaccggaggatggcca ttaccggggacgatgtctctctggaccagatagtgccagtctcgcgggattttacgctg gaagaagtgtccccagatggtgaactctacatccttggacagatgtgaccgtccagc tggacacagcagagcttttgcctcgtattccaactgcccttgttcacaaaccaggat gttcctccacgaagttgccagggcctgtccaggcttcgattctgcgacccgggatcct gaattcctgtggctgtctcggtataggtgcgcagagctggagctggagatgccaacg ccgcgcggttgtaactcggccctagttacctggccagggtacgcgacaattggcgga ggtggttctaactttgatggtttgagaccaaatggaagggagtgcctatggaccaaa gctccaggggtcaagataaaccagaaagcttgcaaccaagacagaataaatccaag tccgaaattactgacatggttcgctcctccactatcacagtgtcggacaaggctcatatt ttatccatgcagaagtttggactgcgagatacaattgtgatatcacatctactacagaa agaagaggattacacctatatccagaacttcaggttttttgcgggaacatacaatgtaa atgggcagtcccccaaagaatgcctccggctgtggctgagcaatggtatccaggcc ccagatgtctattgtgtaggggttccaggagcttgatctgagtaaggaagcttttttcttc acgataccccaaaggaggaagagtggttcaaagctgtgtcagagggtcttcatccag atgccaaatatgcaaaggtgaagcttatccgactggttgggattatgctgctgttatatg tcaaacaggagcatgcagcttatatctcagaagtggaagccgactgtgggggaca ggaatcatgggaggatgggcaacaagggaggcgtggcgatcaggttccagttcc acaacaccagcatctgcgttgtgaattctcacttggcagcccacattcaagagtatga gaggaggaaccaggactataaggacatttgttctcgaatgcagttagtcagcctgac ccaagcctccccctctcaccatcagcaaccatgatgtgatcttgtggctgggggacc tcaactacaggatagaagagctggatgtggaaaaagtgaaaaagctcatcgaagag aaggactttcaaatgctgtatgcatatgatcagctgaaaattcttggtggccgcaaaga ctgtctttgaaggcttcacagagggtgagctcacattccagcctacttacagtatgata cgggctctgacgactgggataccagtgagaagtgccgtgctcctggtgtgatc ggattctctggaaagggaagaacatcactcagctgagttaccagagccacatggccc tgaagaccagtgaccacaagcctgtcagctcagtgtttgacatcggggtgagggtcg taaatgacgagctttaccggaagacactggaggaaattgttcgctccctggataagat ggaaaatgccaacattccttctgtgtccctgtccaagcgagagttctgttttcagaatgt gaagtacatgcaattgaaagtagaatccttacaattcataatggacaagtaccctgtca ttttgaattcatcaacaagcctgatgaagagtcttactgtaagcagtggctgaatgccaa ccccagcagaggcttcctcctgccagattctgatgttgagattgacttggagctcttcgt aaataagatgacagctacaaagctcaactcgggtgaagacaaaattgaggacattct ggttctgcacttggacaggggaaaggattactttttgtctgtgtctgggaactacctgcc cagctgttttgggtctcccattcatacactgtgttacatgagagagccaatcttggacct accacttgaaaccattagtgagctgactctgatgccagtatggactggagatgatggg agccagttggatagcccccatggaaatccccaaagagctctggatggttgattacc tgtaccgaaatgctgtccagcaggaagatctgtttcagcaaccaggcctgaggtcag aatttgaacatatcagggactgcttggatactggaatgattgataacctctctgccagca atcattctgtagccgaagccctgctgcttttcctggagagccttcagagcctgtcatct gttacagcacctaccataactgcttggagtgttctggcaactacacagcaagcaaaca ggtcatttctactctcccatattccacaaaaatgtcaccactgtctgatggcgtttttgc gagaactgctgaaaaattcagcaaaaaatcatttggatgagaatattctagctagcata tttggcagcttattgcttcgaaacccagctggtcaccaaaagcttgatatgacagagaa gaagaaggctcaagaatttattcaccagttcctctgcaacccactctgagcctctctctc ctcctattttacttgaggctgccaattaccagcccccacctgttcagctcaagagatgcc ttaagataattatgtgaggccacttggtagcaagaatggcagctatttcctgagcctagt accccaattaagccaccattggttagcacactcagcgctgtgagtcgtgaagacac gggagaaatccaccataataaaaactgacattcaattttcaactttagttatttaacacag atttttttatttttatttttttttatttttgagacggagttttgctctgtcgcgcagggtggagtg cggtggcacgatctcggctcactgcaacctctgcctcctgggtgcaagcaattatcct gcctcagcctcccgagtagctgggactgcaggcacacactgccacgcccagctaat tttttgcatttagtagagacgggggtttcaccgtgttgcccaggctgttctaaaactcctg aactcaggtaatctgcctgcctcggcctccccaagtgctaggattacagatgtgagcc accacgcccggccttttttttttttttttttcttttttgagatggagtttcactcttgttgcccagg ctggagtcgcttggcgtggtcttggctcactgcaacctctgcctcttggttcaagcaa ttctcctgcctcagcctctcgagtagctgggattataggcgtccgccaccatgcctggc taattttagtgtgtattagtatagacacgtttcaccatggtggccaggctggtctcgaa tgcctggcctcaggtgatccacctgcctggcctcccaaagtgctgggattacaggca tgaaccaccacgcctggcctaaaatgtttttaaataaagtacttgtactcactcacccta cctccagggcatagtcagtctgggctgagatcccatgatcagatatttgatggaaag tcctgaaaggccaatgagttggatggcaagaatgcaggcagaagctgctggataaa ataggctacagccacctcagatgctttcagtgctctgtctgaggatgtgtatatgcatat | NM_005540 | NM_008385 |

TABLE 1-continued

| Gene | Human Gene Sequence | Human Sequence Accession No. | Murine Sequence Accession No. |
|---|---|---|---|
| | gcaaactcgaccccegttcctgcccagataatggctcaataactctgaggctggttgc<br>tcagcctctgagggcaatacaggcatttaaaaaattaaaatgaccaggcacagtggct<br>cacgcctgtaatctcggcactttgggagactgaggtgggagcatcacttgagaccag<br>gagtttgggaccaggctgggcaacacagggagaccccctctctacaaaaacatttta<br>aaaaattagagggtgtggtgatgcatgcctgtggtcccagttacttgggaggctgac<br>gtgggtggctcacttgagcacaggagtttgaggctgcagtgacctatgaccacatca<br>ctgtacgccagcccgggtgagagagggagaccccgtctctaaaaataaaatgtaaa<br>atcactgaaaaaatgagtgttcggtgaaacaagtgggattttctgggccagcaagtctt<br>ccaaactgtatatgatgcatcctgtctccatgtgtaatatattttaatgataaatgtattttta<br>acagtgaaaaaaaaaaaaaa (SEQ ID NO: 653) | | |
| Socs1 | ggcagctgcacggctcctggccccggagcatgcgcgagagccgccccggagcgc<br>cccggagccccccgccgtcccgcccgcggcgtcccgcgctcgccgccagcgca<br>ccccggacgctatggcccaccctccggctgcccttctgtaggatggtagcaca<br>caaccaggtggcagccgacaatgcagtctccacagcagcagagccccgacggcg<br>gccagaaccttcctcctcttcctcctcctcgccgcggcccccgcccgcggcc<br>gtgccccgcggtcccggtcccgccccggcgacacgcacttccgcacattccgtt<br>cgcacgccgattaccggcgcatcacgcgcgccagcgcgctcctggacgcctgcgg<br>attctactgggggcccctgagcgtgcacggggcgcacgagcggctgcgcgccgag<br>cccgtgggcaccttcctggtgcgcgacagccgccagcggaactgcttttttcgcccctta<br>gcgtgaagatggcctcgggacccacgagcatccgcgtgcactttcaggccggccg<br>cttttcacctggatggcagccgcgagagcttcgactgcctcttcgagctgctggagcac<br>tacgtggcggcgccgcgccgcatgctgggggccccgctgcgccagcgccgcgtg<br>cggccgctgcaggagctgtgccgccagcgcatcgtggccaccgtgggccgcgag<br>aacctggctcgcatccccctcaaccccgtcctccgcgactgctgagctgctcttccccctt<br>ccagatttgaccggcagccgccgtgcacgcagcattaactgggatgccgtgtta<br>tttttgttattacttgcctggaaccatgtgggtaccctccccggcctgggttggagggag<br>cggatgggtgtagggcgaggcgcctcccgcccctcggctggagacgaggccgca<br>gaccccttctcacctcttgaggggtcctccccctcctggtgctccctctgggtccccc<br>tggttgttgtagcagcttaactgtatctggagccaggacctgaactcgcacctcctacc<br>tcttcatgtttacatatacccagtatctttgcacaaaccaggggtgggggagggtctct<br>ggctttatttttctgctgtgcagaatcctatttttatatttttaaagtcagtttaggtaataaac<br>tttattatgaaagtttttttttt (SEQ ID NO: 654) | NM_003745 | NM_001271603 |
| Jun | gacatcatgggctatttttaggggttgactggtagcagataagtgttgagctcgggctg<br>gataagggctcagagttgcactgagtgtggctgaagcagcgaggcgggagtggag<br>gtgcgcggagtcaggcagacagacagacacagccagccagccaggtcggcagta<br>tagtccgaactgcaaatcttattttctttttcaccttctctctaactgcccagagctagcgcc<br>tgtggctcccggactggtgtttcgggagtgtccagagagcctggtctccagccgccc<br>ccgggaggagagccctgctgccatggcgctgttgacagcggcggaaagcagcgg<br>tacccacgcgcccgcggggggaagtcggcgagcggctgcagcagcaaagaactttt<br>cccggctggggaggtccggagacaagtggcagttgtcccggagcgaacgtttgcaag<br>cctttcctgcgtcttaggcttctccacggcggtaaagaccagaaggcggcggagagc<br>cacgcaagagaagaaggacgtgcgctcagcttcgctcgcaccggttgttgaacttgg<br>gcgagcgcgagccgggctgccgggcgcccccctcccccctagcagcggaggagg<br>ggacaagtcgtcggagtccggcgggccaagacccgccgccggccggccactgca<br>gggtccgcactgatccgctccgcgggagagccgctgctctgggaagtgagttcgc<br>ctgcggactccgaggaaccgctgcgcccgaagagcgctcagtgagtgaccgcgac<br>ttttcaaagccgggtagcgcgcgcgagtcgacaagtaagagtgcgggaggcatctt<br>aattaaccctgcgctccctggagcgagctggtgaggagggcgcagcggggacgac<br>agccagcgggtgcgtgcgctcttagagaaactttccctgtcaaaggctccggggg<br>cgcgggtgtccccgcgcttgccagagcccgttgcggccccgaaacttgtgcgcgca<br>gcccaaactaacctcacgtgaagtgacggactgttctatgactgcaaagatggaaac<br>gaccttctatgacgatgccctcaacgcctcgttcctccgtccgacgggaccttat<br>ggctacagtaaccccaagatcctgaaacagagcatcaccctgaacctggccgaccc<br>agtgggagcctgaagccgcacctccgcgccaagaactcggacctcctcacctcgcc<br>cgacgtggggctgctcaagctggcgtcgcccgagctggagcgcctgataatccagt<br>ccagcaacgggcacatcaccaccaccgccgaccccacccagttcctgtgccccaa<br>gaacgtgacagatgagcaggagggcttcgccgagggcttcgtgcgcgccctggcc<br>gaactgcacagccagaacacgctgcccagcgtcacgtcggcggcgcagccggtca<br>acggggcaggcatggtggctcccgcggtagcctcggtggcaggggcagcggca<br>gcggcggcttcagcgccagcctgcacagcgagccgccggtctacgcaaacctcag<br>caacttcaaccagcgcgcgctgagcagcggcggcgggcgccctcctacggcgc<br>ggccggcctggcctttcccgcgcaacccagcagcagcagcagccgccgcacca<br>cctgccccagcagatgcccgtgcagcacccgcggctgcaggccctgaaggagga<br>gcctcagacactgcccgatgcccggccagacaccgccccctgctccccatgcac<br>atggagtcccaggagcggatcaaggcggagaggaagcgcatgaggaaccgcatc<br>gctgcctccaagtgccgaaaaaggaagctggagagaatcgcccggctggaggaaa<br>aagtgaaaaccttgaaagctcagaactcggagctggcgtccacggccaacatgctc<br>agggaacaggtggcacagcttaaacagaaagtcatgaaccacgttaacagtgggtg<br>ccaactcatgctaacgcagcagttgcaaacatttttgaagagagaccgtcggggctg<br>aggggcaacgaagaaaaaaaataacacagagagacagacttgagaacttgacaag<br>ttgcgacggagagaaaaagaagtgtccgagaactaaagccaagggtatccaagtt<br>ggactgggttgcgtcctgacggcgccccagtgtgcacgagtgggaaggacttggc<br>gcgccctcccttggcgtggagccaggagcggccgcctgcgggctgccccgctttt | NM_002228 | NM_010591 |

TABLE 1-continued

| Gene | Human Gene Sequence | Human Sequence Accession No. | Murine Sequence Accession No. |
|---|---|---|---|
| | gcggacgggctgtccccgcgcgaacggaacgttggacttttcgttaacattgaccaa<br>gaactgcatggacctaacattcgatctcattcagtattaaaggggggaggggaggg<br>ggttacaaactgcaatagagactgtagattgcttctgtagtactccttaagaacacaaa<br>gcgggggagggttgggaggggcggcaggagggaggtttgtgagagcgaggc<br>tgagcctacagatgaactctttctggcctgccttcgttaactgtgtatgtacatatatatat<br>tttttaatttgatgaaagctgattactgtcaataaacagcttcatgcctttgtaagttatttctt<br>gtttgtttgtttgggtatcctgcccagtgttgtttgtaaataagagatttggagcactctga<br>gtttaccatttgtaaataagtatataatttttttttatgtttttgtttctgaaaattccagaaaggat<br>atttaagaaaatacaataaactattggaaagtactcccctaacctcttttctgcatcatctg<br>tagatactagctatctaggtggagttgaaagagttaagaatgtcgattaaaatcactctc<br>agtgcttcttactattaagcagtaaaaactgttctctattagactttagaaataaatgtacc<br>tgatgtacctgatgctatggtcaggttatactcctcctccccccagctatctatatgaatt<br>gcttaccaaaggatagtgcgatgtttcaggaggctggaggaaggggggttgcagtg<br>gagagggacagcccactgagaagtcaaacacttcaaagtttggattgtatcaagtggc<br>atgtgctgtgaccatttataatgttagtagaaattaacaataggtgcttattctcaaagca<br>ggaattggtggcagattttacaaaagatgtatccttccaattttggaatcttctctttgacaa<br>ttcctagataaaaagatggcctttgcttatgaatatttataacagcattcttgtcacaataa<br>atgtattcaaataccaaaaaaaaaaaaaaa (SEQ ID NO: 655) | | |
| Nptxr | cggccgcggcgacagctccagctccggctccggctccggctccggctcc<br>cgcgcctgccccgctcggcccagcgcgcctgggctccgcgccccgaccccgtcg<br>ccgcgcctgcgggggcctcgggcgcccccgccgcccgcctcacgctgaagttcc<br>tggccgtgctgctggccgcgggcatgctggcgttcctcggtgccgtcatctgcatcat<br>cgccagcgtgcccctggcggcagcccggcgcgggcgctgcccggccggcgccg<br>acaatgcttcggtcgcctcgggcgccgcgcgtccccgggcccgcagcggagcct<br>gagcgcgctgcacggcgcgggcggttcagccgggcccccgcgctgcccgggg<br>cacccgcggcagcgcgcacccgctgccgcccgggcccctgttcagccgcttcct<br>gtgcacgccgctggagctgcctgcccgtcggggcccagcaggggggacgcggc<br>gggcgctgcgccgggcgagcgcgaagagctgctgctgctgcagagcacggccga<br>gcagctgcgccagacggcgctgcagcaggaggcgcatccgcgccgaccagg<br>acaccatccgtgagctcaccggcaagctgggccgctgcgagagcggcctgccgcg<br>cggcctccagggcgccgggccccgccgcgacaccatggccgacgggccctggg<br>actcgcctgcgctcattctggagctggaggacgccgtgcgcgccctgcgggacccc<br>atcgaccgcctggagcaggagcttccagcccgtgtgaacctctcagctgccccagc<br>cccagtctctgctgtgcccaccggcctacactccaagatggaccagctggaggggc<br>agctgctggcccaggtgctggcactggagaaggagcgtgtggccctcagccacag<br>cagccgccggcagaggcaggaagtggaaaaggagttggacgtcctgcagggtcgt<br>gtggctgagctggagcacgggtcctcagcctacagtcctccagatgccttcaagatc<br>agcatccccatccgtaacaactacatgtacgcccgcgtgcggaaggctctgcccga<br>gctctacgcattcaccgcctgcatgtggctgcggtccaggtccagcggcaccggcc<br>agggcaccccccttctcctactcagtgcccgggcaggccaacgagattgtactgctag<br>aggcgggccatgagcccatggagctgctgatcaacgacaaggtggcccagctgcc<br>cctgagcctgaaggacaatggctggcaccacatctgcatcgcctggaccacaaggg<br>atggcctatggtctgcctaccaggacggggagctgcagggctccggtgagaacctg<br>gctgcctggcaccccatcaagcctcatgggatcctctatcttgggccaggagcaggat<br>accctgggtggccggtttgatgccaccccaggcctttgtcggtgacattgcccagtttaa<br>cctgtgggaccacgccctgacaccagcccaggtcctgggcattgccaactgcactg<br>cgccactgctgggcaacgtccttccctgggaagacaagttggtggaggcctttgggg<br>gtgcaacaaaggctgccttcgatgtctgcaaggggagggccaaggcatgagggc<br>caccctcatccagggcccctcccttgcctgccacttttggggacttgaggggggtcatat<br>tccctcctcagcctgcccacgcactggccttccctcctgcccactcctggctgtgcct<br>cccatttcccctcacctgtacccacacctccagaatgccctgcctgcgagtgtgtccc<br>ctgtccccacctgagtggggaggagcgtctcaagtgaacagtgggagcctgcccac<br>ctggcactgcactggagttgtctcttaccccaccctccctgcccatcaactgtatctgat<br>ttcactaattttgacagcaccccagtagggtaggattgtgtatgaggggggaccccac<br>tatctcagtggtgggggtggccgcccgcccccttgtccccatgcaacaggcccagt<br>ggcttccccttcagggcatcaacaggctgtagaaggggatgacgaggacatcagtt<br>ggttagacttttccctcctccctcttttccaccagctgccagtctgcccagtgggatctc<br>gatggagcctcccccccccccccaccatgcctccctcttcctcctctttcctcctctcttt<br>gtgtgtagcggtttgaatgttggttccatgcctggcccagcccaccctcagtctccagg<br>acattcctttcccagctccagcctggagggaagggacaaagaccccaggaggcc<br>aaagggctgcagtcacccctttgtgctcacccatagtgatgggcactggtatagtcatc<br>gctctcccctccatgccaaggacaggaatggaccgcttcagcctgggctgggagca<br>gccctaaggtagaggcctcatgcccaggagacccacctctggcagagccacatt<br>acctaccctgtgcatggtcctggggcagcaaggaagaagctcagagggtggggag<br>aagcatgaagcagtgacagagcactgggtgagagggagaagaccttggttcctag<br>ccagcccgctaatgtgctgtgtggccttctgtaagtccctgccctctctgggcctggc<br>cttcctcattcgtgagctgaggcccctcgctttggtcatttgctctccagattgggtgtgag<br>cttctctgtgaaccaggtggatatgtggggaaagctctggtgaccctgggcttcgcag<br>gggtagatcccaggactcggcagtggatgggatgcagccagtcatgggttagggtc<br>agcagagactcagagtccagggcaaggttcaaggcagactaacctcatgcatggatt<br>gtaaaaaaccagctcccttttggatcaacccagcctggcacccttgcctgtctgagagt<br>gtctcaaagggctgatgcgcttcctggtcccccttgagtcatcaccagcttccccaagag<br>agtgtcagaatcttaagagctgagaggccgggcacggtggctcacgcctgtaatccc<br>agcactttgggaggctgagacaggcagatcacttgaggtcaggagttcgaagtcag | NM_014293 | NM_030689 |

TABLE 1-continued

| Gene | Human Gene Sequence | Human Sequence Accession No. | Murine Sequence Accession No. |
|---|---|---|---|
| | cctggccaacgtggtgaaacccccatcttcactaaaaatacaaaacttagctggttaggt<br>ggtgcatgcctgtagtcccagctactcgggaggccgaggcagaagaatctcttgaac<br>tgaggaggtggaggttgcagtgagccgagatcacgccattgcactccagcctgggc<br>aacagagcaagaaccatctcaaaaaaataataataatcttaaagatgagaaaagcca<br>ccccatctggcaccacagctgcatcttgcttgtgagaaatggggaagagttcaggga<br>ggacacgtgacctgcacaggatcacagagcatggggcagagccaggactagagct<br>cagggcatctgactccctcttcagtgttcttcccctccatgttgcctgccctgaagac<br>ctttgagttcagtctacacctaagcaggtagacatccgcgaggtcagatgctttccaac<br>atgacacctgaacatcttcctttatgcaacacccaaacatcttggcatccccaccccag<br>gaagtgcggggaggaggtttatgatccctgggcgcttcggcagaatggagagctga<br>ggtgtccctcccctgctagtcacctaccaggtgtctgagcagctgcatgctccctggct<br>caagtgggcactgtaccttttgcctgccttttttgttccctatctccactccctgaggccac<br>ttagcctgagacatgatgcaagagctgcaggccggggggctcagtgccatggaagc<br>tactccaagttgcattgcctcccgcgcccagatcctgctttccatttcgagaacataaat<br>agattgcccagccctccagtacaatcccactggaagaaaaggcaatggcgggctt<br>cagccagacctgctgagacctaggttgccacggtaacagccaaagacatcaaccca<br>agtgctgggtcaagtgtctcatcatactggcactgttgctggggtgacggcagaattc<br>agaacttcaatttcagtgacgccaagcttgatgtgtttctgttattgttttgaagaaggtag<br>ctcttgtggaggacttgggagaaggatgggtcttaggaaggaggtgacagcacttg<br>catggtcacttgagcccacacacacgctcaaccccaagtccttttatgctttgtcacagt<br>gaagatgagacctctgacgtccaagccttgttcctgtgctgcatcacccactcagcttt<br>ccaaagggaacaggaacaaatttccccagcaccactgtttgggtcccgcttttcctatc<br>ttctgctgccccctgagcacatccaagcagacagggaaagaggagtcagacatggcc<br>cagtcacatcctgagctgctcctggctgataaccacgatggagcccgtgtttgtcctgc<br>catctggcactgcactgagtgtggcacaggcaccgtcctgttgatctcacaacacagt<br>tctaagttaggacgttcttggctccgttagacaggtgaggaaactggggcacagaga<br>ggtgatgtcatctgcctggtgtatatcagctagcaagtgatggagcccagatttcaaa<br>ccaaaggggttacgtccaggggctgagttcccactcacctgtgtagagtgccatct<br>gggcaccattgctccagacgtgttccgaccccttcccagcccacagggcttgaagt<br>gaaggaacagaggcagcgggtgggccagccccagggcaggggtccccttggtga<br>agccgtgccaggggctcagctgcttcagggaatgtgtccctcccaccatgggcca<br>gagcttcagcccttctttagctcagctagagttcacaggagagccaaaaagaaaag<br>gaagagagcatctcccgagtcctgggcagggaaggggagggaaattgctgcttct<br>ccaactcttgcttggggccaagccctgcaccagttgcttcccagctgttatctgccaga<br>tcttcccatcttgtggcatgtggtgcccccaccaacatcccaaggggaccaatcccctt<br>gccaccactttgcatcacctgggaccacagatttggacaggaagggctctgagaaga<br>ggccaaagccctcattttacagatgaggaagctgaagcccggggaggggagcgac<br>cctcaaggccaccccagctggacacgggagacttgagcccagccttctgactgcattc<br>agccctctctaggacgcagcagcctctccccagcactgagtcccccctcctttgtgtgt<br>cccagcacccttggcctgagtaaacttggaaaggggctccctcccagagaagggac<br>tactctcttcacccctttattccagctgcctgccacccccagacccccacctcccaccct<br>gaccccccgacccctgggtggggaagggctcacatgggcccaggctgagtgtgag<br>tgagcatgtcaagttgtctgacactgtgacattagtgcaccctactgacaaccctccc<br>cagccttgcccctttctcctctccctgttttgtacataaattgttatgagctgcaacatgt<br>gtgcgtgtgtgcgtgtgtgtgtgtatgtgtgtgatctgtgtcatggttttgttac<br>cttttgttttttgtaaacttgaatgttcaaaataaacatgctgtttactctgagaaaaaaaa<br>aaaaaaa (SEQ ID NO: 656) | | |
| Socs3 | gcggctcccgacttggactccctgctccgctgctgccgcttcggccccgcacgcagcc<br>gcggctccgacttggactccctgctccgctgctgccgcttcggccccgcacgcagcc<br>agccgccagccgcccgcccggcccagctcccgcgcggccccttgccgcggtcc<br>ctctcctggtccccctcccggttggtccgggggtgcgcaggggggcagggcgggcgc<br>ccaggggaagctcgagggacgcgcgcgcgaaggctcctttgtggacttcacggcc<br>gaaacatctgggcgcagccgggccaccgctggccgtctcgcccgcgtcgcc<br>ttggggacccgaggggctcagccccaaggacggagacttcgattcgggaccagc<br>ccccggatgcggtagcggccgagtgcggaggccgcgaagcagagcagccg<br>ccgccgcgcagatccacgctggctccgtgcgccatggtcacccacagcaagtttcc<br>cgccgcgggatgagccgcccctggacaccagcctgcgcctcaagaccttcagct<br>ccaagagcgagtaccagccggtggtgaacgcagtgcgcaagctgcaggagagcg<br>gatctactggagcgcagtgaccggcggcgaggcgaacctgctgctcagtgccgag<br>cccgccggcacctttctgatccgcgacagctcggaccagccacttcttcacgctc<br>agcgtcaagacccagtctctggaccaagaacctgcgcatccagtgtgaggggggca<br>gcttctctctgcagagcgatccccggagcacgcagcccgtgccccgcttcgactgcg<br>tgctcaagctggtgcaccactacatgccgccccctggagcccctccttcccctcgcc<br>acctactgaaccctcctccgaggtgcccgagcagccgtctgcccagccactccctcg<br>gagtcccccagaagagcctattacatctactccgggggcgagaagatcccccctggt<br>gttgagccggcccctctcctccaacgtggccactcttcagcatctctgtcggaagacc<br>gtcaacgccacctggactcctatgagaaagtcacccagctgcgcgggccattcg<br>gcagttcctggaccagtacgatgccccgctttaaggggtaaagggcgcaaagggca<br>tgggtcgggagagggggacgcaggccccctcttcctccgtggcacatgggcaaagcac<br>aagaggcaaccaggagagagtcctgtagctctggggggaaagagggcggacag<br>gccccctcctctgccctctccctgcagaatgtggcaggcggacctggaatgtgttgga<br>gggaaggggggagtaccctgagtctccagcttctccggaggagccagctgtcctg<br>gtgggacgatagcaaccacaagtggattctccttcaattcctcagcttcccctctgcct<br>ccaaacaggggacacttcgggaatgctgaactaatgagaactgccagggaatcttca | NM_003955 | NM_007707 |

TABLE 1-continued

| Gene | Human Gene Sequence | Human Sequence Accession No. | Murine Sequence Accession No. |
|---|---|---|---|
| | aactttccaacggaacttgtttgctcttttgatttggttttaaacctgagctggttgtggagcc<br>tgggaaaggtggaagagagagaggtcctgagggcccccagggctgcgggctggcg<br>aaggaaatggtcacaccccccgcccacccccaggcgaggatcctggtgacatgctcc<br>tctccctggctctcggggagaagggcttggggtgacctgaagggaaccatcctggta<br>ccccacatcctctcctccgggacagtcaccgaaaacacaggttccaaagtctacctg<br>gtgcctgagagcccaggggcccttcctccgttttaagggggaagcaacatttggaggg<br>gatggatgggctggtcagctggtctccttttcctactcatactataccttcctgtacctgg<br>gtggatggagcgggaggatggaggagacgggacatcttttcacctcaggctcctggt<br>agagaagacaggggattctactctgtgcctcctgactatgtctggctaagagattcgc<br>cttaaatgctcccctgtcccatggagagggacccagcataggaaagccacatactcag<br>cctggatgggtggagaggctgagggactcactggagggcaccaagccagcccac<br>agccagggaagtgggggaggggggggcggaaaccatgcctcccagctgagcactg<br>ggaatgtcagcccagtaagtattggccagtcaggcgcctcgtggtcagagcagagc<br>caccaggtcccactgccccgagccctgcacagcccctcctcctgcctgggtgggggg<br>aggctggaggtcattggagaggctggactgctgccaccccgggtgctcccgctctg<br>ccatagcactgatcagtgacaatttacaggaatgtagcagcgattgaattacaggaa<br>cagttttttgttttttgttttgttttttgttttgtggggggggcaactaaacaaacacaaagt<br>attctgtgtcaggtattgggctggacagggcagttgtgtgttgggtggttttttttctctat<br>tttatgtttgtttcttgttattaataatgtttacaatctgcctcaatcactctgtcttttataaag<br>attccacctccagtcctctctcctcccccttactcaggcccttgaggctattaggagatg<br>cttgaagaactcaacaaaatcccaatccaagtcaaactttgcacatatttatatttatattc<br>agaaaagaaacatttcagtaatttataataaagagcactatttttttaatgaaaaac<br>(SEQ ID NO: 657) | | |
| F11r | gaggcagctcctgtggggaaaggcgccagtgcgccgaggcgggagtggcggc<br>gaggcagctcctgtggggaaaggcgccagtgcgccgaggcgggagtggcggc<br>ggggtaacacctggccgaggtgactcgttctgaagagcagcggttccttacaccaat<br>cggaacgtgcaggggtggggagctggccaatcaggcgcggagggcggggccgg<br>gcggggttccacctggcggctggctctcagtcccctcgctgtagtcgcgggagctgtg<br>tctgttcccaggagtccttcggcggctgttgtgtcgggagcctgatcgcgatggggac<br>aaaggcgcaagtcgagaggaaactgttgtgcctcttcatattggcgatcctgttgtgct<br>ccctggcattgggcagtgttacagtgcactcttctgaacctgaagtcagaattcctgag<br>aataatcctgtgaagagtcctgtgcctactcgggcttttcttctccccgtgtggagttgga<br>agtttgaccaaggagacaccaccagactcgtttgctataataacaagatcacagcttc<br>ctatgaggaccgggtgaccttcttgccaactggtatcaccttcaagtccgtgacacgg<br>gaagacactgggacatacacttgtatggtctctgaggaaggcggcaacagctatggg<br>gaggtcaaggtcaagtcatcgtgcttgtgcctccatccaagcctacagttaacatccc<br>ctcctctgccaccattgggaaccgggcagtgctgacatgctcagaacaagatggttc<br>cccaccttctgaatacacctggttcttaagatgggatagtgatgcctacgaatcccaaa<br>agcacccgtgccttcagcaactcttcctatgtcctgaatcccacaacaggagagctgg<br>tctttgatccctgtcagcctctgatactggagaatacagctgtgaggcacggaatgg<br>gtatgggacacccatgacttcaaatgctgtgcgcatgaagctgtggagcggaatgt<br>gggggtcatcgtggcagccgtccttgtttaccctgaactcctgggaatcttggttttgg<br>catctggtttgcctatagccgaggccactttgacagaacaaagaaagggacttcgagt<br>aagaaggtgatttacagccagcctagtgcccgaagtgaaggagaattcaaacagac<br>ctcgtcattcctggtgtgagcctggtcggctcaccgcctatcatctgcatttgccttactc<br>aggtgctaccggactctggcccctgatgtctgtagtttcacagaatgccttatttgtcttc<br>tacaccccacagggccccctacttcttcggatgtgtttttaataatgtcagctatgtgccc<br>catcctccttcatgcctccctcccttttcctaccactgctgagtgcctggaacttgttta<br>aagtgtttattccccatttctttgagggatcaggaaggaatcctgggtatgccattgactt<br>cccttctaagtagacagcaaaaatggcgggggtcgcaggaatctgcactcaactgcc<br>cacctggctggcagggatctttgaataggtatcttgagcttggttctgggctcttttccttg<br>tgtactgacgaccagggccagctgttctagagcgggaattagaggctagagcggct<br>gaaatggttgtttggtgatgacactgggtccttccatctctggggcccactctctctgt<br>cttccatgggaagtgccactgggatccctctgccctgtcctcctgaatacaagctga<br>ctgacattgactgtgtctgtggaaaatgggagctcttgttgtggagagcatagtaaattt<br>tcagagaacttgaagccaaaaggatttaaaaccgctgctctaaagaaaagaaaactg<br>gaggctgggcgcagtggctcacgcctataatcccagaggctgaggcaggcggatc<br>acctgaggtcaggagttcaagatcagcctgaccaacatggagaaaccctactaaaaa<br>tacaaagttagccaggcatagtggtgcatgcctgtaatcccagctgctcaggagcctg<br>gcaacaagagcaaaactccagctcaaaaaaaaaagaaagaaaagaaagctggag<br>ctggtggcttaggccatcacccttccccttggctggaactactggacagacccttttgag<br>atgtgcctgtggtgctgtggagatgtgtgtagtggtcttagctctctttgttgagcttgtgtgt<br>gtgttgtgtagtcttagagtatgctgaaattgggcgtgtgttggagggcttcttagctctt<br>tggtgagattgtatttctatgtgtttgtatcagctgaatgttgctggaaataaaaccttggtt<br>tgtcaaggtcttttttttgtgggaagtaagtttggggaaaaggtcttttgagggttcctagg<br>ctccttttgtacaacaggaaaatgcctcaaagcatgcttcccagcaacctggggctgg<br>ttcccagtgcctggtcctgcccttcctggttcttatctcaaggcagagcttctgaatttc<br>aggccttcattccagagccctcttgtggccaggccttcctttgctggaggaaggtaca<br>caggtgaagctgatgctgtacttggggatctccttggcctgttccaccaagtgaga<br>gaaggtacttactcttgtacctcctgttcagccaggtgcattaacagacctccctacag<br>ctgtaggaactactgtcccagagctgaggcaaggggatttctcaggtcatttggagaa<br>caagtgctttagtagtagtttaaagtagtaactgctactgtatttagtggggtggaattca<br>gaagaaatttgaagaccagatcatgggtggtctgcatgtgaatgaacaggaatgagc<br>cggacagcctggctgtcattgctttcttcctccccatttggacccttctctgcccttacatt | NM_016946 | NM_172647 |

TABLE 1-continued

| Gene | Human Gene Sequence | Human Sequence Accession No. | Murine Sequence Accession No. |
|---|---|---|---|
| | tttgtttctccatctaccaccatccaccagtctatttattaacttagcaagaggacaagtc<br>aagggccctcttggcttgattttgcttcttttctttctgtggaggatatactaagtgcgacttt<br>gccctatcctatttggaaatccctaacagaattgagttttctattaaggatccaaaaaga<br>aaaacaaaatgctaatgaagccatcagtcaagggtcacatgccaataaacaataaatt<br>ttccagaagaaatgaaatccaactagacaaataaagtagagccttatgaaatggttcagt<br>aaagatgagtttgttgttttttgttttgttttgttttgtttttttaaagacggagtctcgctctgt<br>cacccaggctggagtgcagtggtatgatcttggctcactgtaacctccgcctcccggg<br>ttcaagccattctcctgcctcagtctcctgagtagctgggattacggggtgcgtgccacc<br>atgcctggctaatttttgtgttttagtagagacagggttttcaccatgttggtcgggctgg<br>tctcaaactcctgacctcttgatccgcctgccttggcctcccaaagtgatgggattaca<br>gatgtgagccaccgtgccgagccaaggatgagatttttaaagtatgttcttgttctgtgt<br>catggttggaagacagagtaggaaggatatggaaaaggtcatgggaagcagagg<br>tgattcatggctctgtgaatttgaggtgaatggttccttattgtctaggccacttgtgaag<br>aatatgagtcagttattcccagccttggaatttacttctagcttacaatggacctttga<br>actggaaaacaccttgtctgcattcactttaaaatgtcaaaactaatttttataataaatgtt<br>tattttcacattgagtttgtttaaatcctgaagttcttacctttaagagaattgggactcctag<br>agtgattggacattcaaaatattcctgatagtcttgttaattaagagattaggatatcttc<br>cattaccttgataattacgttttaatttagcttttttcattggcctgtgttaaatgcaaataac<br>cccacaatggacatttcctatgttaaagtgacatttagggggataaaaaatgagagcagt<br>tccatggattttggtgtttccctgagacatgaactcagcataatctgggataaaatgatt<br>gagtgttaaggatgtgtttgttgttcctgtcgttttttttattttcttcaaagtatacaacatggt<br>ttgatatgcacatacatttgtgtaatgattgccatggtcaattaacacatcaccattttgtg<br>tgtgtgtgtgtgtgtgggtgtgagggagtcagctccgagccaggctggagtgcaatg<br>gtacaaccttggctcactgcaacctccacctcctgggttcaagcaattctcttgcctcag<br>cctcctaagtagctgggactataggcgtgtgccaccatgcccagctaatttttttgtatttt<br>agtagagacgggggttttcaccatgttggccaggatgatctcgatcccttgacctcatgat<br>ccgcccacctcggcctcccaaagtgctgggattacaggcgtgagtcactgcacccg<br>gccacatcacctcccattttctatcttacgtattcagaacttgttcatcttgtaactgaaag<br>cgtgtaccctttgaccaacactgttttcctgtcttaacaggatctacagatcaaggaca<br>ggggaggggatagtggaggaaaacggagttagtcgtttctaaatgaggggacagt<br>atgtttcttggggcctgaggacagcttaataaaagtagacaaatgaagaaaaacaacaa<br>tttgcattaaaaaatatccaattctttta (SEQ ID NO: 658) | | |
| Fyn | agagcatcagcaagagtagcagcgagcagcccgcgctggtggcggcggcgcgtcg<br>ttgcagttgcgccatctgtcaggagcggagccggcgaggaggggggctgccgcggg<br>cgaggaggaggggtcgccgcgagccgaaggccttcgagacccgcccgccgccc<br>ggcggcgagagtagaggcgaggttgttgtgcgagcgcgcgtcctctctccgcccg<br>ggcgcgccgcgcttctcccagcgcaccgaggaccgcccgggcgcacacaaagcc<br>gccgcccgcgccgcaccgccgcggcggccgccgcccgcgccagggagggattcg<br>gccgccgggccggggacaccccggcgccgcccctcggtgctctcggaaggccc<br>accggctccccgggcccgccggggacccccccggagccgcctcggccgcgccgga<br>ggagggcgggagaggaccatgtgagtgggctccggagcctcagcgccgcgca<br>gttttttttgaagaagcaggatgctgatctaaacgtggaaaaagaccagtcctgcctctg<br>ttgtagaagacatgtggtgtatataaagtttgtgatcgttggcggacattttggaatttag<br>ataatgggctgtgtgcaatgtaaggataaaagaagcaacaaaactgacggaggagag<br>ggacggcagcctgaaccagttgctctgggtaccgctatggcacagaccccacccctc<br>agcactacccagcttcggtgtgacctccatcccaactacaacaacttccacgcagc<br>cggggccaaggactcaccgtctttggttggtgtgaactcttcgtctcatacggggac<br>cttgcgtacgagaggaggaacaggagtgacactctttgtggcccttttatgactatgaa<br>gcacggacagaagatgacctgagttttttcacaaaggagaaaaatttcaaatattgaaca<br>gctcggaaggagattggtgggaagcccgctccttgacaactgtggagagacaggttac<br>attcccagcaattatgtggctccagttgactctatccaggcagaagagtggtactttgg<br>aaaacttggccgaaaagatgctgagcgacagctattgtcctttggaaacccaagagg<br>tacctttcttatccgcgagagtgaaaccaccaaaggtgcctcattcactttctatccgtgat<br>gggatgatatgaaaggagaccatgtcaaacattataaaattcgcaaacttgacaatg<br>gtggatactacattaccacccgggcccagtttgaaacacttcagcagcttgtacaacat<br>tactcagagagagctgcaggtctctgctgccgcctagtagttccctgtcacaaaggga<br>tgccaaggcttaccgatctgtctgtcaaaaccaaagtgtctgggaaatccctcgaga<br>atccctgcagttgatcaagagactgggaaatgggcagtttgggaagtatggatggg<br>tacctggaatggaaacacaaaagtagccataaagactcttaaaccaggcacaatgtc<br>ccccgaatcattccttgaggaagcgcagatcatgaagaagctgaagcacgacaagc<br>tggtccagctctatgcagtggtgtctgaggagcccatctacatcgtcaccgagtatatg<br>aacaaaggaagtttactggatttcttaaaagatggagaaggaagagctctgaaattac<br>caaatcttgtggacatgcagcacaggggctgcaggaatggcttacatcgagcgca<br>tgaattatatccatagagatctgcgatcagcaaacattctagtggggaatggactcatat<br>gcaagattgcttcggattggcccgattgatagaagacaatgagtacacagcaa<br>gacaaggtgcaaagttcccccatcaagtggacgtgccccgaggcagccctgttgcgg<br>gaggttcacaatcaagtctgacgtgtggtcttttggaatcttactcacagagcggtcac<br>caaaggaagagtgccatacccaggcatgaacaaccgggaggtgctggagcaggtg<br>gagcgaggctacaggatgccctgcccgcaggactgcccatctctctgcatgagctc<br>atgatccactgctggaaaaaggaccctgaagaacgcccccacttttgagtacttgcaga<br>gcttcctggaagactactttacccgcgacagagcccagtaccaacctggtgaaaacc<br>tgtaaggcccgggtctgcggagagaggccttgtcccagaggctgccccacccctcc<br>ccattagctttcaattccgtagccagctgctccccagcagcggaaccgcccaggatc<br>agattgcatgtgactctgaagctgacgaacttccatgcccctcattaatgacacttgtcc | NM_002037 | NM_001122892 |

TABLE 1-continued

| Gene | Human Gene Sequence | Human Sequence Accession No. | Murine Sequence Accession No. |
| --- | --- | --- | --- |
| | ccaaatccgaacctcctctgtgaagcattcgagacagaaccttgttatttctcagactttt<br>ggaaaatgcattgtatcgatgttatgtaaaaggccaaacctctgttcagtgtaaatagtt<br>actccagtgccaacaatcctagtgcttttccttttttaaaaatgcaaatcctatgtgattttaa<br>ctctgtcttcacctgattcaactaaaaaaaaaaaagtattatttttccaaattgtggcctcttt<br>gtctaaaacaatttaaatttttttttcatgttttaacaaaaaccaatcaggacaggtgtttgttt<br>ttgttttcttttttataaatatgaatatatataatattttatgtccctgtacatatacaatgtggg<br>tgctaatgtggagactgtggccggcctgagccaccaagctgcgggacccagaggg<br>aggattttactgcaagtcagcatcaaagcaccggtgttattctgaaaacaccagtggc<br>ctcattttttggcttttgcaaagcatgaattttttcatttggattgatcttttcctggttcatgact<br>gtacctgtaggtggttgttacttttgactcttttcaggaaccaccccccaagctgaatttac<br>aagttctgttagcactatttgcttcaacttactgcgatttgttctcaaaacttaaaaataag<br>caagcaaatggctgatactaccaagagaacttggaagatggataccacacaaacttctt<br>gtataaaaatatgaatgctgaaatgtttcagacattttttaatttaataaacctgtaaccaca<br>tttaagtgatcttttaaacccatagcattgtttgtcatggcaacccgctttaactttctcatgc<br>aactaaaatttctgggggaaatgagggtgggggttgtacatttcccattgtaaaataag<br>tgttttaaatgtcctgtactgctaacgaatgacttttctatatgtccaggagttctccagtgg<br>aataactatgcactactttacatttcatggggatgcacaaaaacaaaaagtattacattt<br>ttagttgctgtttgtaccaaccttaaattacatatgtttaacaacaacaaatcaaaatcct<br>atactattgagttttttaatactgactagcaactctgaagtcttaattcctttttttgttatgattt<br>atttgtgagtttacatttttaaattgtttaactttcttaatttagtaattaaaaagagagcatttt<br>acatttgaa (SEQ ID NO: 659) | | |
| Ypel2 | gccgcggcggtggcgagactgtggctttaagagcgtgccgggagcccgagccc<br>cagccgggccgcgcttcgccgctgcgcaccccagcggagccaagccccacgctg<br>gccggacagggccgcctgtcgccgggctgctgagaactagccctagacctctgcgt<br>gagggttcttctgccgaagacatccaccagtgtgtggagcctgccacacccacccgct<br>gccaaaccacggcctttacctgtgtcttccggtgtttcccgtgcgacccatcctgtggg<br>agtgcctcgtgggctgccccagagttcaccccacactcagcagcaccaatggtgaa<br>gatgacaagatcgaagactttccaggcatatctgccctcctgccaccggacctacag<br>ctgcattcactgcagagctcacttggccaatcatgatgaacttttttttccaagtcattcca<br>aggaagtcaaggacgagcataccctcttaactcagtagttaatgtgggctgtgggcct<br>gcagaagagcgagtgttgctttacaggactgcatgcagtcgcagacatttactgtgaa<br>aactgcaaaaccactctgggctggaaatacgaacatgctttgaaagcagccagaaa<br>tataaagaaggcaaatacatcattgaactagcacacatgatcaaggacaatggctggg<br>gactgattggacagcatctttcccaacccagtgtccacgtgaacgccattcaaccgaa<br>cattcttcccaagcgtgagagagtgactgacacttggttccatccatttagggggccttg<br>ccatccggggcatcctcccacccctgacgccatctttctggtggctctgcctctaaatcg<br>ctgtctctctgtctctttgcttgtatctgtttgtgagttgatcctggcttctctctctgttctag<br>ttttggctgaaaacaaaacaacaaaaggaacagatccttgaccgcatggcggcagcc<br>caccttggtaagggcccagggcccatgcgagagctgcctgatggcctcttgtcagg<br>agagcagtggcacggggcgtgaggaagagggaaaggggaaactctaagggtcc<br>tggcgcggggaaggggtggaagggtggaggtaggaacaaaattgcgccgctcctg<br>gagacctgataacttaggcttgaaataattgacttgtctaaaaggacaaagagaaaaa<br>aaaaatacctcatgactgcattctactgactagaagcttctgttcctgacaccaaatgt<br>gccaggttagcaaatgagcacaagatgtggccctgattctagttggtggggcaaggg<br>cctggttctcctgggctgagtggggagtgtcctggcagcagcgagtgacctgggc<br>agtggccaggtgggtgcgatgactctgatgcctcactcagtctctgggcaatcatcat<br>ctttgcctctagccaccgtagataaggtgtgaagggactgctgtttgcaatgggcttac<br>catccaaatatcccaaaggctttgaccagcaaccaagtaaaatcagtaattgaggaga<br>gcagggcacaaaggggctgcagtttgggagctcctgaagaaatggctcagatattg<br>agtcagagaaataaaaagtaggatcagttagcaattctaactgcccttccttctgaccc<br>ctcataagaggagtgtggtgagggagggagactgggtagggtcatcccaggagga<br>ggggtttacattggaaccagttcaggttcggtgcatctttcctcttcggttttacagtggc<br>ttccgtgggatcgtcaatttcttgttcttagagtttcgggtgttttctccagtcgttgttactgt<br>agactgtagaaagcacgggcccaggctctgagcttagtaataaccttggctggtaga<br>ttcctcatgcccctaattgtcccacttaggcctgaatgtcttgcatggagagaaatctcct<br>gtcagtgtggtccagcagcagggaggagttctgcccaaattccgtatcaccccttcc<br>cccatccaagcatccttcgattagggaagtggagagcacatccctgtaaggcccata<br>agagaaagaggagtttgttacatttaatcaacactgtgaagtctgttctacagcaattca<br>gccattacacagtatatgactgaaactcatttaactgggttaatttcatttcttagactgaa<br>tatattattgttaagatacgtgtgcgtgttaggtaattctcagcatctcctccaagtaggc<br>cgaccttctcggaaaattcaccctaaaagtctcacaaaagaatggtttcatggggaga<br>ttctgtaaagtgatgaactgagatgaaagcagccaacagcccaggagcttttcagaat<br>agcgtctgcagcagaaccagtttccattcagagcgcgtccttggtggaaatgcttttttg<br>tgtgtctccacgcgctgatggtggaatgggagcccaagacgtgtgggcttagaaat<br>caacttttgttccccaaggcttcttgtccagatcttttccagtgcttttcatagccctgggag<br>atcaagttgttctcccacttactgcaaggtagactgaagttcagaagaaatactgaat<br>ttctgctcccagaagaatagtttctctggctcacaggcccaagttctcaatgaaatcgttt<br>tttaacttcacattcctaagctggcttcccggcacagaagccatggatttcccctctctc<br>ccttcccctcctcaaggaaatagtcttccttttatggattttcattggagtctcttcacagc<br>gattgtcctggctgtttattgatagtccttcccataagaaaatgggggtttaaacatgggt<br>aggtattttgtctttcaaactcaaatggaatgtggtgacataaactagacatggggtgc<br>cctcaagttttccaaggggaccaatgtgccactgttcttccttggggatgaggcctttga<br>ctgttggatggatcagagcaggctccagtcagaccctggttctgaatgttttttttttcgg<br>tgactatccagtgagccttcagtgggtgcaaggcgccatacttgctgtgagagagctg | NM_<br>001005404 | NN_<br>001005341 |

TABLE 1-continued

| Gene | Human Gene Sequence | Human Sequence Accession No. | Murine Sequence Accession No. |
|---|---|---|---|
| | agtagagtgttggttttccataattacaggggaaaaaagtcattaggctttccctttgtgtcagtgaaaccaaagtgcttcttacaacgttcgctctgttcatgggttgtctatctaacattgagcagcattggagaggccacagctgagctatggagatgctaaattaactcatggcctcagtcagttcattcttaatttcctcaccaaattattgacttagagcataaccaaagacctcattcattcaccccaggtgggttggggtaattggagtttgttggtgaagtttgggggcgggtgttgggagtagagacagggtaaggggacgtgagaaagggaaaggcatgaagttctatacctcagccagcagctgccttcgtttggaactgaagtccagccagcagactctctagctccatctccccctgtgccaccctaggtcatatgaccttggccaccttggagtagacccagaccctcgggacccgggacattagtctcaggctgctgatggattgatttgacatgaaccaaacacagccaaactcgatacccacaagctgtcagctgaacctgactgagtgttcttcctgagttcacgaggataggctagagtgcattttactggtggatcagtgtgtgcgaaagagatgacccttataaagagattttcaagtggatatatataaagaaacagttgcttgtaaaatatactttgtaaataatatttaatttttttaaataatatatttggtgctgtttttctcagatcccctgagagcacttttttattttccttttaaattctatggtttcctttgcatttcttgaagtatattttaagggaaacagtgatcaccaatacatgttttcagttttttttttttttaaggtctctatcactttaatctggatcaaggctttgaagcaatgcctctctgcatttttcccagtggaacagactctgcagtacattaatcaggttgagaattgaaatattttcttgcatcagtattggctagaaaagaaaataaataaaaccaagttaatttagtagtaacaacttacagtgattcttcctgttggaagaatttccaacaaatcagaatcacgttttagttgtgcgtgtgcgcgcacacgtgtgtaaaaagcactttcgattgtgcctcctgttttctcgagtggggacactttaactacagtttacacctcgggcgcataaagttttttcttctctttctctctggttgtttctgtttctgagtggaccaacagcagaacccacgaggatttgttttgagtatggagctgttgcgggtttgctccttttttcttgctttgcgtgctcagttttttacagactgtaaaggagatgtgttgtttgtgaagatggagcagagtcaaatctgtgcttctaactgagatgagagtgtattaatcacgtatcgcagggctccagctgttttagaagccacatcatgttaaacattaactggtttggattaaaagaacattaatattataatacacatatcttagtggtaaacagcttttttttttttaaggtcagattgcctcaggtttagaaagaggctgagaaatcaaatcttgaacacaatcaacttacatattttaaaggaatctgcctcaaatgagaaaatatgctagttatctagatagaggaaagagatatttactttttttaaaaattaaaatagttatgaaatctggcagaaaaggtaaagcctagaagaaactatgaaagctattctcatgttaccaaattctatctgcgcattttgtttttgtataacatttcggtgacagtgggagtcggttccctttcccaacctgcagagactatcttccaatacagaatctgtcttttttatgcttgtgtttacaaactgtatttgttgggtttggttttgtttcttttggtggcaattcaggtcacttttgcttcattataattgtcttcacctatcctgtatttgtacatagtgattcagtattagagaaaagtgcaagtttctgtcatatttccaatagtgttggtgctcatttgagaaaataaaagttttcaaatattaactcttaaaaaaaaaa (SEQ ID NO: 660) | | |
| Pkd1 | cccctcccctcccgatcctcatcccccttgccctccccccagcccagggacttttccggaaagttttttattttccgtctgggctctcggagaaagaagctcctggctcagcggctgcaaaactttcctgctgccgcgccgccagccccgccctccgctgcccggccctgcgcccgccgagcgatgagcgccctccggtcctgcgggccgcccagtccgctgctgcccgtggcggcggcagctgccgcagcggccgccgcactggtcccagggtccgggcccgggcccgcgccgttcttggctcctgtcgcggccccggtcggggggcatctcgttccatctgcagatcggcctgagccgtgagccggtgctgctgctgcaggactcgtccggggactacagcctggcgcacgtccgcgagatggcttgctccattgtcgaccagaagttccctgaatgtggtttctacggaatgtatgataagatcctgctttttcgccatgacccttacctctgaaaacatccttcagctggtgaaagcggccagtgatatccaggaaggcgatcttattgaagtggtcttgtcagcttccgccacctttgaagactttcagattcgtccccacgctctctttgttcattcatacagagctccagctttctgtgatcactgtggagaatgctgtggggctggtacgtcaaggtcttaaatgtgaagggtgtggtctgaattaccataagagatgtgcattttttaaatacccaacaattgcagcggtgtgaggcggagaaggctctcaaacgtttccctcactggggtcagcaccatccgcacatcatctgctgaactctctacaagtgccctgatgagccccttctgcaaaaatcaccatcagagtcgtttattggtcgagagaagaggtcaaattctcaatcatacatttggacgaccaattcaccttgacaagattttgatgtctaaagttaaagtgccgcacacatttgtcatccactcctacttcccggcccacagtgtgccagtactgcaagaagcttctgaaggggcttttcaggcagggcttgcagtgcttaagattgcagattatactgccataaacgttgtgcaccgaaagtaccaaacaactgccttggcgaagtgaccattaatggagatttgcttagccctggggcagatctgatgtggtcatgggaagggagtgatgacaatgatagtgaaaggaacagtgggctcatggatgatatggaagaagcaatggtccaagatgcagagatggcaatggcagagtgccagaacgacagtggcgagatgcaagattcagacccagaccacgaggacgccaacagaaccatcagtccatcaacaagcaacaatatcccactcatgagggtagtgcagtctgtcaaacacacaagaggaaaagcagcacagtcatgaaagaagaatggatggtccactacaccagcaaggacacgctgcggaaacggcactattggagattggatagcaaatgtattaccctcttcagaatgacacaggaagcaggtactacaaggaaattccttttctctgaaattttgtctctggaaccagtaaaaacttcagctttaattcctaatggggccaatcctcattgtttcgaaatcactacggcaaatgtagtgtattatgtgggagaaaatgtggtcaatccttccagcccatcaccaaataacagtgttctcaccagtggcgttggtgcagatgtggccaggatgtgggagatagccatccagcatgcccttatgcccgtcattcccaaggggtcctccgtgggtacaggaaccaacttgcacagagatatctctgtgagtattttcagtatcaaattgcacagttcaagaaaatgttggacatcagcacagtatatcagatttttcgtgatgaagtactgggttctggacagtttggttggttgtatgtgggaaaacatcgtaaaacaggaagagatgtagctattaaaatcattgacaaattacgatttccaacaaaacaagaaagccagcttcgtaatgaggttgcaattctacagaacctccatcacatcctggtgtttgtaaatttggagtgtatgtttgagacgcctgaaagagtgtttgttgttatggaaaaactccatggagacatgctggaaatgatcttgtcaagtgaaaaggg | NM_002742 | NM_008858 |

TABLE 1-continued

| Gene | Human Gene Sequence | Human Sequence Accession No. | Murine Sequence Accession No. |
|---|---|---|---|
| | caggttgccagagcacataacgaagttttaattactcagatactcgtggctttgcggc<br>accttcattttaaaaatatcgttcactgtgacctcaaaccagaaaatgtgttgctagcctc<br>agctgatcctttttcctcaggtgaaactttgtgattttggttttgcccggatcattggagag<br>aagtcttccggaggtcagtggtgggtaccccccgcttacctggctcctgaggtcctaa<br>ggaacaagggctacaatcgctctctagacatgtggtctgttggggtcatcatctatgta<br>agcctaagcggcacattcccatttaatgaagatgaagacatacacgaccaaattcaga<br>atgcagctttcatgtatccaccaaatccctggaaggaaatatctcatgaagccattgatc<br>ttatcaacaatttgccgcaagtaaaaatgagaaagcgctacagtgtggataagaccttg<br>agccaccccttggctacaggactatcagacctggttagatttgcgagagctggaatgca<br>aaatcggggagcgctacatcacccttttgaaagtgtttgacctgaggtgggagaagtat<br>gcaggcgagcaggggagcagtaccccacacacctgatcaatccaagtgctagcca<br>cagtgacactcctgagactgaagaaacagaaatgaaagccctcggtgagcgtgtca<br>gcatcctctgagttccatcctctataatctgtcaaaacactgtggaactaataaatacata<br>cggtcaggtttaacatttgccttgcagaactgccattatttttctgtcagatgagaacaaa<br>gctgttaaactgttagcactgttgatgtatctgagttgccaagacaaatcaacagaagc<br>atttgtattttgtgtgaccaactgtgttgtatttttttcaaaagttccctgaaacacgaaacttg<br>ttattgtgaatgattcatgttatatttaatgcattaaacctgtctccactgtgcctttgcaaat<br>cagtgttttcttactggagcttcattttggtaagagacagaatgtatctgtgaagtagttc<br>tgtttggtgtgtcccattggtgagtcattgtaaacaaactcttgaagagtcgattatttcc<br>agtgttctatgaacaactccaaaacccatgtgggaaaaaaatgaatgaggagggtag<br>ggaatattaatcctaagacacttttatgcatgattcaagttttaatgtatagttttgatttcctt<br>gcctgcctggtgtgcctcagttttatttaaactcaagacaatgcacctagctgtgcaaga<br>cctagtgctcttaagcctaaatgccttagaaatgtaaactgccatatataacagatacatt<br>tccctcttcttataatactctgttgtactatggaaatcagtgctcagcaacctttcacct<br>ttgtgtatttttcaataataaaaaatattcttgtcaaaa (SEQ ID NO: 661) | | |
| Ptpn2 | gctcgggcgccgagtctgcgcgctgacgtccgacgctccaggtactttccccacgg<br>ccgacagggcttggcgtgggggcggggcgcggcgcgcagcgcgcatgcgccgc<br>agccgcagcgctctccccggatcgtgcggggcctgagcctctccgccggccgcagg<br>ctctgctcgcgccagctcgctcccgcagccatgcccaccaccatcgagcgggagtt<br>cgaagagttggatactcagcgtcgctggcagccgctgtacttggaaattcgaaatga<br>gtcccatgactatcctcatagagtggccaagtttcagaaaacagaaatcgaaacaga<br>tacagagatgtaagccacatatgatcacagtcgtgttaaactgcagaaatgctgagaatg<br>attatattaatgccagtttagttgacatagaagaggcacaaaggagttacatcttaacac<br>agggtccacttcctaacacatgctgccatttctggcttatggtttggcagcagaagacc<br>aaagcagttgtcatgctgaaccgcattgtggagaaagaatcggttaaatgtgcacagt<br>actggccaacagatgaccaagatgctgtttaaagaaacagattcagtgtgaagc<br>tcttgtcagaagatgtgaagtcgtattatacagtttcatctactacaattagaattatatcaa<br>tagtggtgaaaccagaacaatatctcacttttcattatactacctggccagattttggagtc<br>cctgaatcaccagcttcatttctcaatttcttgtttaaagtgagagaatctggctccttgaa<br>ccctgaccatgggcctgcgggtgatccactgtagtgcaggcattgggcgctctggcac<br>cttctctctggtagaatcttgtcttgttttgatggaaaaaggagatgatataacataaaa<br>caagtgttactgaacatgagaaaataccgttatgggtcttattcagaccccagatcaact<br>gagattctcatacatggctataatagaaggagcaaatttgtataaagggagattctagta<br>tacagaaacgatggaaagaacttttctaaggaagacttatctcctgcctttgatcattcac<br>caaacaaaataatgactgaaaaagacaatgggaacagaataggtctagaagaagaa<br>aaaactgacaggtgaccgatgtacaggactttcctcttttaaatgcaagatttcaatggagg<br>agaacagtgagagtgctctacgaaacgtattcgagaggacagaaaggccaccac<br>agctcagaaggtgcagcagatgacaagagggctaaatgagaatgaacgaaaaaga<br>aaaaggtggttatattggcaacctattctcactaagatggggtttatgtcagtcattttggt<br>tggcgcttagttggctggacactgtttttttcagcaaaatgccctataaacaattaattttg<br>cccagcaagcttctgcactagtaactgacagtgctacattaatcataggggtttgtctgc<br>agcaaacgcctcatatcccaaaaacggtgcagtagaatagacatcaaccagataagt<br>gatatttacagtcacaagcccaacatctccaggactcttgactgcaggttcctctgaacc<br>ccaaactgtaaatggctgtctaaaatataaagacattcatgtttgttaaaaactggtaaattttt<br>gcaactgtattcatacatgtcaaacacagtatttcacctgaccaacattgagatatcctt<br>atcacaggatttgtttttggaggctatctgattttaacctgcacttgatataagcaataaa<br>tattgtggttttatctacgttattggaaagaaaatgacattttaaataatgtgtgtaatgtata<br>atgtactattgacatgggcatcaacacttttattcttaagcatttcagggtaaatatatttta<br>taagtatctatttaatctttttgtagttaactgtacatttaagagctcaatttgaaaaatctgtt<br>actaaaaaataaattgtatgtcgattgaattgtactggatacattttccatttttctaaaga<br>gaagtttgatatgagcagttagaagttggaataacaatttctactatattttttgcatttcttt<br>tatgttttacagttttcccccattttaaaaagaaaagcaaacaaagaaacaaaagttttttcct<br>aaaaatatctttgaaggaaaattctccttactgggatagtcaggtaaacagttggtcaag<br>actttgtaaagaaattggtttctgtaaatcccattattgatatgtttattttcatgaaaatttc<br>aatgtagttggggtagattatgatttaggaagcaaaagtaagaagcagcattttatgatt<br>cataaatttcagtttactagactgaagttttgaagtaaacacttttcagtttcttctacttcaa<br>taaatagtatgattatatgcaaaccttacattgtcattttaacttaatgaatatttttaaagc<br>aaactgtttaatgaatttaactgctcatttgaatgctagctttcctcagatttcaacattcca<br>ttcagtgtttaattgtcttacttaaacttgaaattgttgttacaaatttaattgctaggaggc<br>atggatagcatacattattatggatagcataccttatttcagtggttttcaaactatgctcat<br>tggatgtccaggtgggtcaagaggttactttcaaccacagcatctctgccttgtctcttta<br>tatgccacataagatttctgcataaggcttaagtattttaaaggggggcagttatcatttttta<br>aaacagtttggtcgggcgcggtggctcatgcctgtaatcccagcactttgggaggctg<br>aagtgggcagatcacctgaggtcaggagttcaagaccagcctggccaacgtggtga | NM_002828 | NM_008977 |

TABLE 1-continued

| Gene | Human Gene Sequence | Human Sequence Accession No. | Murine Sequence Accession No. |
|---|---|---|---|
| | aacaccatctctactaaaaatgcaaaaattagctgggcatggtggagggcacctgtaa<br>tctcagctactcaggaggctgaggtaggagaattgcttgaacccaggagatggaggt<br>tgcagtgagctgagatcacgtcactgcactccagccagggcgacagagcgagactc<br>catctcaaaagaaacaaacaaaaaaaaacagtttgggccgggtgtggtggctcacgct<br>tgtaatcccagcacttcggaaggccaaggcgggcggatcacgaggtcaagagatg<br>gagactgtcctggccaacatggtgaaatcccttctttactaaaaatacaaaaattatctg<br>ggcgtggtggtgcatgccggtagtcccagctccttgggttggctaaggcaggagaatc<br>acttgaacccgggaggcagaggttgcagtgagccgagattgcaccactgcactcca<br>gcctggcaacagagcaagacttcgtctc (SEQ ID NO: 662) | | |
| Grk6 | cggctggctgcgcggccggggaggcggggaggccgcggcgcggtcactgcg<br>agccgagccgagccgccgagccgcgccgatcgccatccggcctcggcactg<br>cgcgcgatcccgccggcggcgcggcccggcggggccaggcggcgccacagcc<br>catggagctcgagaacatcgtagcgaacacggtgctactcaaggcccgggaaggt<br>ggcggtggaaatcgcaaaggcaaaagcaagaaatggcggcagatgctccagttcc<br>ctcacatcagccagtgcgaagagctgcggctcagcctcgacgtgactatcacagc<br>ctgtgcgagcggcagcccattgggcgcctgctgttccgagagttctgtgccacgagg<br>ccggagctgagccgctgcgtcgccttcctggatgggggtggccgagtatgaagtgac<br>cccggatgacaagcggaaggcatgtgggcggcagctaacgcagaattttctgagcc<br>acacgggtcctgacctcatccctgaggtcccccggcagctggtgacgaactgcacc<br>cagcggctggagcagggtccctgcaaagacccttttccaggaactcacccggctgac<br>ccacgagtacctgagcgtggcccctttttgccgactacctcgacagcatctacttcaac<br>cgtttcctgcagtggaagtggctggaaaggcagccagtgacccttaaaacaccttcag<br>gcaataccgagtcctgggcaaaggtggctttggggaggtgtgcgcctgccaggtgc<br>gggccacaggtaagatgtatgcctgcaagaagctagagaaaaagcggatcaagaa<br>gcggaaggggaggccatgcgcgtgaacgagaagcagatcctgggagaaagtgaa<br>cagtaggtttgtagtgagcttggcctacgcctatgagaccaaggacgcgctgtgcctg<br>gtgctgacactgatgaacgggggcgacctcaagttccacatctaccacatgggccag<br>gctggcttccccgaagcgcgggccgtcttctacgcgccgagatctgctgtggcctg<br>gaggacctgcaccgggacgcatcgtgtacagggacctgaagcccgagaacatctt<br>gctggatgaccacggccacatccgcatctctgacctgggactagctgtgcatgtgcc<br>cgagggccagaccatcaaagggcgtgtgggcaccgtggtttacatggctccggag<br>gtggtgaagaatgaacggtacacgttcagccctgactggtgggcgctcggctgcctc<br>ctgtacgagatgatcgcaggccagtcgcccttccagcagaggaagaagaagatcaa<br>gcgggaggaggtggagcggctggtgaaggaggtccccgaggagtattccgagcg<br>ctttttccccgcaggcccgctcactttgctcacagctcctctgcaaggaccctgccgaa<br>cgcctgggtgtcgtggggcagtgcccgcgaggtgaaggagcaccccctctttaa<br>gaagctgaacttcaagcggctgggagctggcatgctggagccgccgttcaagcctg<br>accccaggccatttttactgcaaggatgttctggacattgaacagttctctacggtcaag<br>ggcgtggagctggagcctaccgaccaggacttctaccagaagtttgccacaggcag<br>tgtgcccatcccctggcagaacgagatggtggagaccgagtgcttccaagagctga<br>atgtctttgggctggatggctcagttcccccagacctggactggaagggccagccac<br>ctgcacctcctaaaaagggactgctgcagagactcttcagtcgccaagattgctgtgg<br>aaactgcagcgacagcgaggaagagctccccacccgcctctagcccccagcccga<br>ggcccccaccagcagttggcggtagcagctactccgagcgccgtttacagtttttgca<br>cagtgatcttccccattgtccactcaagtcgtggcctggggaacacagacggagctgt<br>ccccagtgtcctccgtccctcagcccctggcctggctgagtttggcagggcctgggc<br>catccctgggacaaaggtgcgtcccttcagctcttctccgtggagctcggggctttctg<br>tatttatgtatttgtacgaatgtatatagcgaccagagcattcttaattcccgccgcagac<br>ctggccccgccttggctcctgggggcagccagccctggctgggagagcggga<br>gctggcagaggagccactgccaaactcaaggctcctctggcccagcttggatggct<br>gagggtggtcacaccctgagccttcagcactgtgctggccacccggcctctgagt<br>aagactcgtgcctcccctgctgccctgggctcaggctgctaccctctggggcccaa<br>agctgtccttctcagtgcttgtcagcgctgggtctggggcctctgtatgccctaggcc<br>tgtgccaaagtggccagagattgggctgcctgtgatacccatcagcccactgccccg<br>gccggcccagaaggtctgcctctgccttccagctcccacagcctggtccctgatact<br>gggctctgtcctgcagacacctctttcagaaacgcccaagcccagcccctaggagg<br>gggtggggcatccctggtcaaccctcaaacattccggactccctcataacaataga<br>cacatgtgcccagcaataatccgcccttcctgtgtgcgcctgtggggtgcgtgcgc<br>gcgcgtgtgtacctgtgtgggtgaaggggataggggcgaggctgtgcctgtgcccca<br>ggtcccagccctggcccttcccagactgtgatggccatcctggtcccagtgttagggt<br>agcatgggattacagggccctgtttttttccatatttaaagccaattttttattactcgttttgtc<br>caacgtaa (SEQ ID NO: 663) | NM_001004106 | NM_001038018 |
| Cdkn2a | cgagggctgcttccggctggtgcccccgggggagacccaacctggggcgacttca<br>gggtgccacattcgctaagtgctcggagttaatagcacctcaccgagcactcgctc<br>acggcgtcccttgcctggaaagataccgcggtccctccagaggatttgagggaca<br>gggcggaggggctcttccgccagcaccggaggaagaatgaggagggggctgg<br>ctggtcaccagagggtggggcggaccgcgtgcgctcggcggctgcggagagggg<br>gagagcaggcagcggcggcggggagcagcatggagccggcggcggggagca<br>gcatggagcttcggctgactggctggccacggccgcgccggggtcggtaga<br>ggaggtgcgggcgctgctggaggcggggcgctgcccaacgcaccgaatagtta<br>cggtcggaggccgatccaggtcatgatgatgggcagcgccgagtggcggagctg<br>ctgctgctccacggcgcggagccaactgcgccgacccgccactctcacccgac<br>ccgtgcacgacgctgcccggagggcttcctggacacgctggtggtgctgcaccg | NM_000077 | NM_001040654 |

TABLE 1-continued

| Gene | Human Gene Sequence | Human Sequence Accession No. | Murine Sequence Accession No. |
|---|---|---|---|
| | ggccggggcgcggctggacgtgcgcgatgcctggggccgtctgcccgtggacctg gctgaggagctgggccatcgcgatgtcgcacggtacctgcgcgcggctgcggggg gcaccagaggcagtaaccatgcccgcatagatgccgcggaaggtccctcagacatc cccgattgaaagaaccagagaggctctgagaaacctcgggaaacttagatcatcagt caccgaaggtcctacagggccacaactgcccccgccacaaccccaccccgctttcgt agttttcatttagaaaatagagctttaaaaatgtcctgccttttaacgtagatatatgccttcccccactaccgtaaatgtccatttatatcattttttatatattcttataaaaatgtaaaaaagaaaaacaccgcttctgccttttcactgtgttggagttttctggagtgagcactcacgccctaagcgcacattcatgtgggcattcttgcgagcctcgcagcctccggaagctgtcgacttcatgacaagcattttgtgaactagggaagctcagggggttactggcttctcttgagtcacactgctagcaaatggcagaaccaaagctcaaataaaaataaaataattttcatcattcactcaaaaaaaaaaaaaaa (SEQ ID NO: 664) | | |
| Sbf1 | gggcgggccggctggctgggaagatggcggcgggaacctgggccgccgccgccgccgccgccgccgcggagcgaaccaggggtgtccggggtgcgcggtccagggccggggccgggccatgagcgcgccgtcctcgagtccccgagccgcggagcccgcccgcgcccctcgggccgcccccgcgtccctcgccatggcgcggctcgcggactacttcgtgctggtggcgttcgggccgcacccgcgcgggagtggggaaggccagggccagattctgcagcgcttcccagagaaggactgggaggacaacccattcccccagggcatcgagctgttttgccagcccagcgggtggcagctgtgtcccgagaggaatccaccgaccttctttgttgctgtcctcaccgacataactccgagcgccactactgcgcctgcttgaccttctgggagccagcggagccttcacaggaaacgacgcgcgtggaggatgccacagagagggaggaagaggggggatgagggaggccagacccacctgtctcccacagcacctgcccccatctgcccagctgtttgcaccgaagacgctgtactggtgtcgcgactcgaccacacgagtgttcaggaacagccttggcctcatctatgccatccacgtggagggcctgaatgtgtgcctggagaacgtgattgggaacctgctgacgtgcactgtgccctggctggggctcgcagaggacgatctctttgggggctggtgaccggcaggtcatccagactccactggccgactcgctgcccgtcagcgctgcagcgtggccctgctcttccgccagctaggcatcaccaacgtgctgtctttgttctgtgccgccctcacgagcacaaggttctcttcctgtcccgagctaccagcgggctcgcgatgcctgtagggccttcctggcactgctgtttcctctcagatacagcttcacctatgtgcccatcctgccggctcagctgctggaggtcctcagcacacccacgcccttcatcattgggtcaacgcggccttccaggcagagaccaggagctgctcgatgtgattgttgctgatctggatggagggacggtcaccattcctgagtgtgtgcacattccacccttgccagagccactgcagagtcagacgcacagtgtgctgagcatggtcctggacccggagctggagttggctgacctcgccttccctccgcccacgacatccacctcctccctgaagatgcaggacaaggagctgcgcgcggtcttcctgcgggctgttcgctcagctgctgcagggctatcgctggtgcctgcacgtcgtgcgcatccacccggagcctgtcatccgcttccataaggcagccttcctgggccagcgtgcgggctggtagaggacgatttcctgatgaaggtgctggagggcatggcctttgctggctttgtgtcagagcgtgggtcccataccgccctacggacctgttcgatgagctggtggcccacgaggtggcaaggatgcgggcggatgagaaccaccccccagcgtgtcctgcgtcacgtccagaaactggcagagcagctctacaagaacgagaacccgtacccagccgtggcgatgcacaaggtacgaggcccggtgagagcagccacctgcgacgggtgccccgaccttccccggctggatgagggcaccgtgcagtggatcgtggaccaggctgcagccaagatgcagggtgcacccccagctgtgaaggccgagaggaggaccaccgtgccctcagggccccccatgactgccatactggagcggtgcagtgggctgcatgtcaacagcgcccggcggctgaggttgtgcgcaactgcatctcctacgtgtttgaggggaaaatgcttgaggccttagaagctgctcccagccgtgttgagggccctgaaggggcgagctgcccgccgctgcctcgcccaggagctgcacctgcatgtgcagcagaacctgcgctcctggaccaccagcagtttgactttgtcgtccgtatgatgaactgctgcctgcaggactgcacttctctgacgagcatggcattgcggcggctctgctgcctctggtcacagccttctgccggaagctgagcccgggggtgacgcagtttgcatacagctgtgtgcaggagcacgtggtgtggagcacgccacagttctgggaggccatgttctatggggatgtgcagactcacatccgggccctctacctggagcccacggaggacctggcccccgcccaggaggttggggaggcaccttcccaggaggacgagcgctctgccctagacgtggcttctgagcagcggcgcttgtggccaactctgagtcgtgagaagcagcaggagctggtgcagaaggaggagagcacggtgttcagccaggccatccactatgccaaccgcatgagctacctcctcctgcccctggacagcagcaagaacggtcctacttcgggagcgtgccgggctgggcgacctgagagcgccagcaacagcctgggcaccaacagcatggctggcagtgtggccgagagctatgacacggagagcggcttcgaggatgcagagacctgcgacgtagctggggctgtggtccgcttcatcaaccgctttgtggacaaggtctgcacggagagtggggtcaccagcgaccacctcaaggggagcatgtcatggtgccagacattgtccagatgcacatcgagaccctggaggccgtgcagcgggagagccggaggctgccgcccatccagaagcccaagctgctgcggccgcgcctgctgccggtgaggagtgtgtgctggacggcctgcgcgtctacctgctgccggatgggcgtgagggggcgcggggggcagtgctggggaccagcattgctcccagctgagggcgccgtcttcctcaccacgtacgggtcatcttcacggggatgcccacggaccccctggttggggagcaggtggtggtccgctcatcccgtggctgcgctgaccaaggagaagcgcatcagcgtccagacccctgtgaccagctcctgcaggacgggctccagctgcgctcctgcacattccagctgctgaaaatggcctttgacgaggaggtggggtctgtggacagcgccgagctcttccgtaagcagctgcataagctgcggtaccgccgggacatcagggccacctttgcgttcaccttgggctctgcccacacacctggccggcaccgcgagtcaccaaggacaagggtcctcccctcagaaccctgtcccggaacctggtcaagaacgccaagaagaccatcgggcggcagcatgtcactcgcaagaagtacaaccccccagctggagcaccggggccagccgccccctgaggaccaggaggacgagatctcagtgtcg | NM_002972 | NM_001170561 |

TABLE 1-continued

| Gene | Human Gene Sequence | Human Sequence Accession No. | Murine Sequence Accession No. |
|---|---|---|---|
| | gaggagctggagcccagcacgctgaccccgtcctcagccctgaagccctccgacc gcatgaccatgagcagcctggtggaaagggcttgctgtcgcgactaccagcgcctc ggtctgggcaccctgagcagcagcctgagccgggccaagtctgagcccttccgcat ttctccggtcaaccgcatgtatgccatctgccgcaacgctacccagggctgctgatcgtg ccccagagtgtccaggacaacgccctgctgcgcgtgtcccgctgctaccgccagaa ccgcttcccgtggtctgctggcgcagcgggcggtccaaggcggtgctgctgcgct ctggaggcctgcatggcaaaggtgtcgtcggcctcttcaaggcccagaacgcacctt ctccaggccagtcccaggcggactcgagtagcctggagcaggagaagtacctgca ggctgtggtcagctccatgccccgctacgccgacgcgtcgggacgcaacacgctta gcggcttctcctcagcccacatgggcagtcacgttcccagccccagagccagggtc accacgctgtccaaccccatggcggcctcggcctccagacggaccgcaccccgag gtaagtggggcagtgtccggaccagtggacgcagcagtggccttggcaccgatgtg ggctcccggctagctggcagagacgcgctggccccacccccaggccaacgggggc cctcccgacccgggcttcctgcgtccgcagcgagcagccctctatatccttgggac aaagcccagctcaaggggtgtgcggtcagaccccctgcagcagtgggagctggtgc ccattgaggtattcgaggcacggcaggtgaaggctagcttcaagaaggcggctgaaag catgtgtcccaggctgccccgctgctgagcccagcccagcctccttcctgcgctcact ggaggactcagagtggctgatccagatccacaagctgctgcaggtgtctgtgctggt ggtggagctcctggattcaggctcctccgtgctggtgggcctggaggatggctggga catcaccaccaggtggtatccttggtgcagctgctctcagaccccttctaccgcacg ctggagggctttcgcctgctggtggagaaggagtggctgtccttcggccatcgcttca gccaccgtggagctcacaccctggccgggcagagcagcggcttcacaccgtcttc ctgcagttcctggactgcgtacaccaggtccacctgcagttccccatggagtttgagtt cagccagttctacctcaagttcctcggctaccaccatgtgtcccgccgtttccggacct tcctgctcgactctgactatgagcgcattgagctggggctgctgtatgaggagaagg aggaacgcaggggccaggtgccgtcaggtctgtgtgggagtatgtggaccggct gagcaagaggacgcctgtgttccacaattacatgtatgcgcccgaggacgcagagg tcctgcggccctacagcaacgtgtccaacctgaaggtgtgggacttctacactgagg agacgctggccgagggccctccctatgactgggaactggccaggggccccctga accccagaggaagaacggtctgatggaggcgctccccagagcaggcgccgcgt ggtgtggccctgttacgacagctgcccgcgggcccagcctgacgccatctcttcgcc tgctggaggagctgcagaggaggagacagagttgggccaacccgctgagcgctg gaaggacacctgggaccgggtgaaggctgcacagcgcctcgagggccggccaga cggccgtggcaccctagctccctccttgtgtccaccgcaccccaccacgtcgctc gctgggtgtgtacctgcaggaggggcccgtgggctccaccctgagcctcagcctgg acagcgaccagagtagtggctcaaccacatccggctcccgtcaggctgcccgctgc agcaccagcaccctgtacagccagttccagacagcagagagtgagaacaggtccta cgagggcactctgtacttagaaggggccttcatgaagccttggaaggcccgctggt tcgtgctggacaagaccaagcaccagctgcgctactacgaccaccgtgtggacaca gagtgcaagggtgtcatcgacttggcggaggtggaggctgtggcacctggcacgcc cactatgggtgccctaagactgtggacgagaaggccttcttttgacgtgaagacaac gcgtcgcgtttacttacttctgtgcccaggacgtgccctcggcccagcagtgggtgga ccggatccagagctgcctgtcggacgcctgagcctcccagcccttgcccggctgctct gcttccggtcgttaccgaccactaggggtgggcagggccgccccggccatgtttaca gccccggccctcgacagtattgaggccccgagccccagcacttgtgtgtacagcc cccgtccccgccccgccccgccggccggccctaacttatttttggcgtcacagctga gcaccgtgccgggaggtggccaaggtacagcccgcaatgggcctgtaaatagtcc ggcccgtcagcgtgtgctggtccagccagcggctgcaggcgagtttctagaacca gagtctatataaagagagaactaacgccacgctcctgtgcctgccttccccactcccc ggctgcctgctctcggcctacccagttgggtcccatctgccctatccaggcccacct ggcggaggttggcatctttctcgtgagcctctcctggtgcctgggtccacccagctc ggcctgcatgtccctgggagtgactttgctctgggggcggatcgagcaggaggcttc actggggacagcttgattccctccacgcctcagggctggtctaggggccggcacgg ctggagaggaagcccccatccctacccaggggatgcagaagctgacctcacagag gcttgggggtgaaagggtgggtggtcatttgacccccagaaggctgttgcaggtccag aggacacttgaggtggacgtcagtttctggctagacccgagctgaagggatggagg ccggaggcggggggggggggggacagtgggctcccaggggaatgcaggttga ccacatctggctcctgccaggcaacgagcagcatctggcagagtaagggggccaac gcccatggggatggaccctctcagttcttgggaattctgccccaaaagtcctttccct ggggtctcagagggcccccgtccttcccttcaggtgtcactgtggcccctcactgctc ttttcctattcaaacctgagtcccaccaggcccagggcttcacctgctgagctgttgtgt ccctgcctgtgacgaggcctggccaggggtgcaggagcagaaggtggggagggtt atagacgctgcaaaggccaagagaacatctgagagtggcagctggtgacctggcca gaggggctggtgaggggcagagaacctggatgaggctgggtccctcaggtggtc ctctcaagtgggagttcgagcatcagttttttttagtgaggataaagttcttattacag ctgcagaggcagggcccagtgctggcaggtggggggcaagaccctccctgtg ggacgttgaagccaaggatggccttggaccctgtcaggcccagcatggtcccgcca cctcccccaccccacaggtggtgtgggacacctgggcgagatgtgagggtgggct cacttgagccactgaaaccagccaggtcttccctcaggccggacagatggcgcctg accgaagttcctggcacctggaaaaccccacaggtcagagtaagggcaggaaaggac cctgccctcctgttccacgtctgtgggggggagaggacaaatgccaggcacagggt aggcggcgagaacaaggcactcaatgtgtagctggggcagagactcggcctctgg ggagctgagcgggttccctccaccccccaaccgtggtggaaagacaattcgctgg ggcggggtgggggtctggtctccacctgcccctcccactcagccactgaggacaag gtggggcccaggcttctggagggggagctggcacaaaaggaagtcctgggggttg | | |

TABLE 1-continued

| Gene | Human Gene Sequence | Human Sequence Accession No. | Murine Sequence Accession No. |
| --- | --- | --- | --- |
| | atgtgtttgagcgttaggcgaagtggttccccccatcccccaaacggaaaaatgtcag tatttgctaagctgtagagacctgatgccgtgatgtggcctgttccgcctccacccatta cacggggataacgctggggggtggcgggcccacaaaagaggtgctggaggagac tctcccacccctggccgggccggggctttggggccggaaggttcacagtacgcggt ttgtccgaacgtcacggcttttattgggagttgggggctttggggtgccctgtcaggtga tcagaacattaaaaatggactcaacgtaaaaaaaaaaaaaaaaa (SEQ ID NO: 665) | | |
| Lpmk | gccgtcagggccccagggagcgcggggcgccgctgctgctgttcttcggctcggtt ctgtctaccgggcagcgccggggccggcggctgcggcggcagaggaacaggag ccgggagccgcgttccgccgagagttgggcagaggagcgcccgcgccccggcg gcgtcatgggccccctccccgcgcttcagttgggcaccagccgcgggattcccccg ggcctcctcgcgcccgagcctgagcgaccctcgggttctccggcgcccctccctc gccctatttttttttcctactctcgctgccgttaccgcttctgctctccgttatggcaacaga gccaccatcccccctccgggtcgaggcgccgggcccccagaaatgcggacctca ccgggcgatcgagtccaccccgagggcaccccgcagccggcgggcggccgactc cgcttcctcaacggctgcgtgcccctctcgcatcaggtggccgggcacatgtacggg aaggacaaagtgggtatactgcaacatccagatggcacagttttgaaacagttacaac cacctccaaggggcccaagagagctggaattctataatatggtttatgctgctgaagt tttgatggtgttcttctagagctacgaaaatatttgccaaaatattatggcatctggtcacc tcccactgcaccaaacgatttatacctaaaactggaagatgtgacccataaatctttataa gccctgtataatggatgtaaagataggccaaaaaagctatgatccttttgcctcatctga aagattcagcaacaggtcagcaagtacccattaatgaagagattgggttcttggtg cttggcatgagggtttatcatgttcattccgattactatgagacagaaaaccagcattac ggaagaagcttaacaaaagaaactataaaggatggagtctccagatttttttcataatgg gtactgcttaagaaaagatgctgttgctgccagtattcagaagattgagaaaattctgc agtggtttgaaaaccagaagcagcttaatttttacgcaagttcattactctttgtaatgaa ggttcatctcagccaaccactacaaaattgaatgacagaacttggcagaaaagttttt gtccaaaggacaactgtcagacacagaagtactagagtacaataataactttcatgtgt taagttccacagctaatggaaaaatagagtcttcagtgggcaaaagcttgtccaagat gtatgcgcgtcacaggaaaatatatacaaaaaagcatcacagtcagacttcattgaaa gttgaaaatctggagcaagcaatgggtggaaaagcatgtcacaggaacatttaaat ggaaatgtacttttcccaactggaaaaagttttctaccatcttcccactggttgccaagag attgctgaagtagaagtgcgaatgatagattttgctcatgtgttccctagcaacacaata gatgagggatatgtttatgggctaaagcatttaatttctgtacttcgaagtatttaagacaa ttgaatcctctgagcagtctttttaaggggtgggcaatcataatgaagagggcagt caatatctgcaccttaatgctatgtaaaaaatttgtattagagtcgacattttatttgtcttt atacttttgaagaatggttaacttttttataatcttactcaggaaaactaactatttgttcat tagaaaactatgaagaataaagaaacttaggaatgttaagcagggaatgtggtggtac atggcttaaacatcttttttggctcaagcaaaatgcaaaccattattcagtcattaagagtt tagaagctttctgtagccaattcatgaaatctctgtccacccagccttgacaatgagcc atatctaaaatattacattattagaacacctaccaaaatctcgaaagcacaggttgatgt ccttagtattgctatgtatgaagttactaaaactggagaaaattctacttcagaaataagt actgtttaggttttatattaaaagttcagaccagcatatcaaagggtgctccttagtgaaa tgatttagaattgttgcattccaaaagcaggttttctcttttaattttttacatctctctctcaaa atattatacttcatgaaaagacaattgatgtggatgacaacaacaaagtcttgaaatta agggcacactaattgtccttactgggggttaggggaagagagatattatttcttaggaac aattatattttcctttacaatctttcattcatgagaaaattggaatataaatttattacattgtg aaagtatcataaaccatataccctttgtatctaaatgcagcttcaaaaaagtaaataattga agttttatttctcctctaaataacttgaatttttttctttaaaaatttatgtatttatatgtccccca tttagttaagtggtagtgtaaatgttttgttgctaaaaacagtttctcagaattatagtaagc aatgaaagacaatatctaattaggttgttatcaaaaatactgtgtgtaaattagtccgtaa tataggtttggtgcgtatctataacatgcttctatttcactcttcctcaaaacagttttatat tatgttgaccagtgaaattgtaacttaatttcatggggacaggggcagtgctacagttcc tggaattaattagatttgtattatctttgtttcacacccaccaccttaaaaattaaatcaacta gttatttgtcataaaaacatttaaaactttgagtcttcaaatacatttgatgttaatgctgcc attacttgcacttccattcactaataacatttctaggtagttatcagttttgtcatattcctgg aaaatattttggggttgtaaattctttctcctcttttttcttcggagttacaaattgaatttttaa atccgagcacctttattgtggtgtggagaaaattatcacaattttatgtttattttaccttctc agccttctctgagggcactttgcaaatacctgagtccaaacagaagtaccaactaaat gctctatgaactctatccttagtaaatctattaaacctgaataatttaaaagatcatgttcat tttgtaatagcaaaatttgatataatttttttatttagaattgtgtttatcataggggacttcc aatttttcttcacttttttgaatggatattggctatagtttatgtttaacgggaatgaatttca agtcataatcatcagaatttttagttaactttatcttttacaatatggattttgttgttatttgg atagtggttcaataaatcttaagctcagataattaaacactattttgaatcttaacaagata ctgaggcttttttttgtatggagtatatacctatgtacaatgaatttaataaacttaagt attgtcagatttttttgcacattttagctcaataaaatcttaatgttcaagattttttttatctgcat ttggaaatacaattttgtaaaatcaatgtcttaccttttgatacaatagatcatgttttgtttt taataaagcaagaagccctttttatctgttgtttttcagggaagggattaacatttaattctg ttgtttacattttgttatccaatgctcatttttatgttgcttttataagtaggcttagg tataacagaataagtatctgtttatctaatctacatgtgactatcttagtctctctcggtcac ttaatatattgctgaaatttaccactgtgggatgaatgatcgctattcaccaagtatattt gaacatgtaaatgcttaagaaataagcataatgcggatatagtttgggttaataggattc tcatagtttttttttcccctatgaaacataagtaatgattttagtgtatttcttatggaatacact cattttaaaaaggactttaagaaattgtggatgtgaataataccttctctctaataaaaattta | NM_152230 | NM_027184 |

TABLE 1-continued

| Gene | Human Gene Sequence | Human Sequence Accession No. | Murine Sequence Accession No. |
|---|---|---|---|
| | aattgtataatagttttataatatttacattaattgatattttaatatggatagacattgcatag attcaaataaattaaaatcaatgatataaatgctaaatattttatctaaatagttttcaagaaa cagttatggaaatgtgtatattaaatggctctaatgtggagcttgtggtatttcaactcagt attcattattagttgtgtgtctggaaagattgtacttacttttcctccttttacactacagtttgct cttatggggctctaaactgttaactgaagaaccttcgtctgtattttgattgagcataattt agtattttatgatttccaagatgatgttcttatgtctatcaagtctatgtatcaaatttataac atcatttaagaaaaaggaatttccacagatacttcagttgcaattttttgtttcatgctactg aaaatacatttgtttctaggggttggaatattatagaagatgtaggatgaaagaaaacg atagaacaacgaaagaattctgtttatgaaattacaggaattgtgtccactatggtaaag cattgtcattttagtacatttctcttagtagtttggcattttatactttaaaacttgttttgctttt aaaaattgtttataatgcttaccctctttctccagtgcctttagtcttgatttgatatgtttgta ccctcagttaccctttctattacatgttttttgatgttttcatagcctaggaaacatcgattcct ttttaataattgtcaatctgattatttaaagaggtaacaattatctgttaatgctttggaaaa acaagtagggttgcctttggaggccaggcttcttagttcattcaaaaatattccttggatt tatgccatgtattaagcattttagccccagtattacaactgtgaaccaaacggataag gccctaaccattttcagcattctctttggatggggtgggatttgggacttttaattaaaata gagatatagaaaaataggcatctaaataagataataagtgtgggttgaaatgaagca tctaacaatagttgaagttagaagtaatattttacagtattgtaacctctatttaagtttggg tatttgttacagatagcataaaaaagccttaattttcactttccttgctggcaaaggtaca tttatttagactgtccatttaaagtaatgtttaacataaacattactgtgaaaaacattccat tacatatttcccaagcaaatgagctgcatcttcatactgtatttacaatttagtacaacagt tttaggcctcaatcttaacatcactggtattttaaatttggcaatgaatatgaaattacttt gacttacagattgattatattattactttgaaatgcattaatttcttagaaaagtttggagc ctctatcttttttgagaaatacttaaattctcattacttatattaatagcctgtactaagtga tttgtcatcttaagtttaaatttttacctactgtccacttaaatataattaacagtctgtaaag tgaaatagttttaagtatgatgtatgatgcacctgcatataaatgaaaatggcgtgcaca aagacactttactatgggaactgtactggaagatttatgaagcatgtgaaattgcacct gtatttagtcacagttactttggttaaatgtataaatgtctttagggttttttttttaaatgtgtt tgtaatttgtactattgtgggggtatacttggactgcagggtgttattgtcaatgtgtgattt gtgttttatttatagaatcatctaatgtgatataccaatttttataagtgatatttacataatt ctaataactgtatatttgacaacctattatttatgattgcattggaa (SEQ ID NO: 666) | | |
| Rock1 | gctggttccccttccgagcgtccgcgccccgcatgcgcagtctgccccggcggtctc gctggttccccttccgagcgtccgcgccccgcatgcgcagtctgccccggcggtctc cgtttgtttgaacaggaaggcggacatattagtccctctcagccccctcgccccacc ccccaggcattcgccgccggcgactcgcccttccccggctgggccgcgcagccctc ccagaagctcccccatcagcagccgccgggacccaactatcgtcttcctcttcgccc gctctccagccttttcctctgctaagtctccatcgggcatcgacctcgccctgccccacc ggacaccgtagcagcagcccagcagcgacgggacaaaatggggagagtgaggct gtcctgcgtgcaccagctcgtggccgagactgatcggtgcgtcggggccgggccga gtagagccggggacgcggggctagaccgtctacagcgcctctgagcggagcggg cccggcccgtggcccgagcggcggccgcagctggcacagctcctcacccgccctt tgctttcgcctttcctcttctccctccttgttgcccggagggagtctccaccctgcttctc tttctctacccgctcctgcccatctcgggacgggaccccctccatggcgacggcggc cggggcccgctagactgaagcacctcgcggagcgacgaggctggtggcgacgg cgctgtcggctgtcgtgaggggctgccgggtgggatgcgactttgggcgtccgagc ggctgtgggtcgctgttgccccggcccggggtctggagagcggaggtcccctcag tgaggggaagacgggggaaccgggcgcacctggtgaccctgaggttccggctcct ccgccccgcggctgcgaaccaccgcggaggaagttggttgaaattgctttccgctg ctggtgctggtaagagggcattgtcacagcagcagcaacatgtcgactggggacag ttttgagactcgatttgaaaaaatggacaacctgctgcgggatcccaaatcggaagtg aattcggattgttttgctggatggattggatgctttggtatatgatttggattttcctgcctta agaaaaaacaaaaattattgacaacttttttaagcagatataaagacacaataaataaat cagagatttacgaatgaaagctgaagattatgaagtagtgaaggtgattggtagaggt gcatttggagaagttcaattggtaaggcataaatccaccaggaaggtatatgctatgaa gcttctcagcaaatttgaaatgataaagagatctgattctgctttttctgggaagaaagg gacatcatggcttttgccaacagtccttgggttgttcagctttttatgcattccaagatga tcgttatctctacatggtgatgaatacatgcctggtggagatcttgtaaacttaatgag caactatgatgtgcctgaaaaatgggcacgattctatactgcagaagtagttcttgcatt ggatgcaatccattccatgggttttattcacagagatgtgaagcctgataacatgctgct ggataaataggacattttgaagttagcagattttggtatttgtatgaagatgaataagga aggcatggtacgatgtgatacagcggttggaacacctgattatatttcccctgttagtatt aaaatcccaaggtggtgatggttattatggaagagaatgtgaaggtgtcggttggg gtattttatacgaaatgcttgtaggtgatacacctttttatgcagattctaggttggaactt acagtaaaattatgaaccataaaaattcaataccttttcctgatgataagacatatcaaa agaagcaaaaaaccttatttgtgccttccttaagacagggaagtgaggttagggcga aatggtgtagaagaaatcaaacgacatctcttcttcaaaaatgaccagtgggcttggg aaacgctccgagacactgtagcaccagttgtacccgatttaagtagtgacattgatact agtaattttgatgacttggaagaagataaaggagaggaagaaacattccctattcctaa agctttcgttggcaatcaactaccttttgtaggatttacatattatagcaatcgtagatactt atcttcagcaaatcctaatgataacagaactagctccaatgcagataaaagcttgcag gaaagtttgcaaaaaacaatctataagctggaagaacagttgcatttatgaaatgcagt taaaagatgaaatggagcagaagtgcagaacctcaaacataaaactagacaagata atgaaagaattggatgaagagggaaatcaaagaagaaatctagaatctacagtgtctc | NM_005406 | NM_009071 |

TABLE 1-continued

| Gene | Human Gene Sequence | Human Sequence Accession No. | Murine Sequence Accession No. |
|---|---|---|---|
| | agattgagaaggagaaaatgttgctacagcatagaattaatgagtaccaaagaaaag ctgaacaggaaaatgagaagagaagaaatgtagaaaatgaagtttctacattaaagg atcagttggaagacttaaagaaagtcagtcagaattcacagcttgctaatgagaagct gtcccagttacaaaagcagctagaagaagccaatgacttacttaggacagaatcgga cacagctgtaagattgaggaagagtcacacagagatgagcaagtcaattagtcagtt agagtccctgaacagagagttgcaagagagaaatcgaattttagagaattctaagtca caaacagacaaagattattaccagctgcaagctatattagaagctgaacgaagagac agaggtcatgattctgagatgattggagacctttcaagctcgaattacatcttttacaaga ggaggtgaagcatctcaaacataatctcgaaaaagtggaaggagaaagaaaagag gctcaagacatgcttaatcactcagaaaaggaaaagaataatttagagatagatttaaa ctacaaacttaaatcattacaacaacggttagaacaagaggtaaatgaacacaaagta accaaagctcgtttaactgacaaacatcaatctattgaagaggcaaagtctgtggcaat gtgtgagatggaaaaaaagctgaaagaagaaagagaagctcgagagaaggctgaa aatcgggttgttcagattgagaaacagtgttccatgctagacgttgatctgaagcaatct cagcagaaactagaacatttgactggaaataaagaaaggatggaggatgaagttaag aatctaaccctgcaactggagcaggaatcaaataagcggctgttgttacaaaatgaatt gaagactcaagcattgaggcagacaattgaaaaggtttagaaaagcagatgaaaca ggaaataaatactttattggaagcaaagagattattagaatttgagttagctcagcttac gaaacagtatagaggaaatgaaggacagatgcgggagctacaagatcagcttgaag ctgagcaatatttctcgacactttataaaacccaggtaaaggaactttaaagaagaaatt gaagaaaaaaacagagaaaatttaaagaaaatacagttaactacaaaataaaaaaaa aactcttgctactcagttggatctagcagaaacaaaagctgagtctgagcagttggcg cgaggccttctggaagaacagtattttgaattgacgcaagaaagcaagaaagctgctt caagaaatagacaagagattacagataaagatcacactgttagtcggcttgaagaag cagagaaaatgaagaaggcagaggaagaatataaactggagaaggaggaggaga tcagtaatcttaaggctgcctttgaaaagaatatcaacactgaacgaacccaaaaaca caggctgttaacaaattggcagaaataatgaatcgaaaagattttaaaattgatagaaa gaaagctaatacacaagatttgagaaagaaagaaaaggaaatcgaaagctgcaac tggaactcaaccaagaaagagagaaattcaaccagatggtagtgaaacatcagaag gaactgaatgacatgcaagcgcaattggtagaagaatgtgcacataggaatgagctt cagatgcagttggccagcaaagagagtgatattgagcaattgcgtgctaaacttttgg acctctcggattctacaagtgttgctagttttcctagtgctgatgaaactgatggtaacct cccagagtcaagaattgaaggttggcttcagtaccaaatagcaggaaatatcaaacga tatggctggaagaaacagtatgttgtggtaagcagcaaaaaaaattttgttctataatgac gaacaagataaggagcaatccaatccatctatggtattggacatagataaactgtttca cgttagacctgtaacccaaggagatgtgtatagagctgaaactgaagaaattcctaaa atattccagatactatatgcaaatgaaggtgaatgtagaaaaagatgtagagatggaac cagtacaacaagctgaaaaaactaatttccaaaatcacaaaggccatgagtttattcct acactctaccactttcctgccaattgtgatgcctgtgccaaacctctctggcatgttttaa gccacccctgccctagagtgtcgaagatgccatgttaagtgccacagagatcactta gataagaaagaggacttaatttgtccatgtaaagtaagttatgatgtaacatcagcaag agatatgctgctgttagcatgttctcaggatgaacaaaaaaaatgggtaactcatttagt aaagaaaatcccttagaatccaccatctggttttgttcgtgatccctcgaacgctttct acaagatccactgcaaatcagtctttccggaaagtggtcaaaaatacatctggaaaaa ctagttaaccatgtgactgagtgccctgtgaaatcgtgtgggatcgtacctgataaacc aggatctttaacctatgcagagcagacaggctgtactttgacacaaatatcacaggctt cagggttaagattgctgtttttctgtccttgctttggcacaacacactgagggttttttttatt gcgggtttgcctacaggtagattagattaattattactatgtaatgcaagtacagttggg ggaaagcttaggtagatatattttttttataaaggtgctgctttttggattttataagaaaat gcctgtcagtcgtgatagaacagagttttcctcatatgagtaagaggaagggacttca ctttcaagtggaacagccatcactatcaagatcagctcatggaaggagtaaagaaaat atctcaaaatgagacaaactgaagttttgttttttttttaatgacttaagtttttgtgctcttgc aagactatacaaaactattttaagaaagcagtgatatcacttgaacttcagtgccctcac tgtagaatttaaaagccttactgttgattgcccatgttggactttgatggagaaattaaata tctttcatttttgcKtttcaaaatactgtatatgtttcagcaagtttggggaatgggagagg acaaaaaaagttacatttaatctatgcattttttgccaagccatattgagttattttactact agagacattaggaaactaactgtacaaaagaaccaagtttaaaagcattttgtggggt acatcatttctataattgtataatgtatttcttttgtggttttaaatgataaagacattaagttaa caaacatataagaaatgtatgcactgttttgaaatgtaaattattcttagaacactttcaatg ggggttgcattgtccttttagtgccttaatttgagataattattttactgccatgagtaagta tagaaatttcaaaaaatgtattttcaaaaaattatgtgtgtcagtgagttttttcattgataatt ggtttaatttaaaatattttagaggtttgttggactttcataattgagtacaatcttttgcatca aactacctgctacaataatgactttataaaactgcaaaaaatgtagaaggttgcaccaa cataaaaaggaaatatgcaatacatccatgatgttttccagttaacataggaattacca gataaatactgttaaactcttgtccagtaacaagagttgattcatatggacagtatgattt attgtttatttttttaaccaaatacctcctcagtaatttataatgctttgcagtaatgtgtatc agataagaagcactggaaaaccgatcgtctctaggatgatatgcatgtttcaagtggta ttgaaagccgcactgatggatatgtaataataaacatatctgttattaatatactaatgact ctgtgctcatttaatgagaaataaaagtaatttatggatgggtatcttta attttttactgcaa aaatgttgtgaaattccatggttagattaaagagctagggagaggaaatttt (SEQ ID NO: 667) | | |
| Stk17b | gaacggcgatgccccagacgcggctgcagttttcaaaccgcgactgcaagcttcgg tagtcctctccgctgctgtcgccaggagtcacttcacgagtagccaggtcacaaccgt cggcccttgtctggaaaagtaaaagtggatcctgccacgttcggagctccctggcgc | NM_004226 | NM_133810 |

TABLE 1-continued

| Gene | Human Gene Sequence | Human Sequence Accession No. | Murine Sequence Accession No. |
|---|---|---|---|
| | ctcgtccggctggagctagagatctcgtcctgtggcggccccggcgtggggcgg gacagcggcccctggagggggcagtcccgggagaacctgcggcggccggagc ggtaaaaataagtgactaaagaagcagacctgggaatcacctaacatgtcgaggag gagatttgattgccgaagtatttcaggcctactaactacaactcctcaaattccaataaa aatggaaaactttaataatttctatatttcttacatctaaagagctagggagaggaaattt gctgtggttagacaatgtatatcaaaatctactggccaagaatatgctgcaaaatttcta aaaaagagaagaagaggacaggattgtcgagcagaaattttacacgagattgctgtg cttgaattggcaaagtcttgtccccgtgttattaatcttcatgaggtctatgaaaatacaa gtgaaatcattttgatattggaatatgctgcaggtggagaaattttcagcctgtgtttacct gagttggctgaaatggtttctgaaaatgatgttatcagactcattaaacaaatacttgaa ggagtttattatctacatcagaataacattgtacaccttgatttaaagccacagaatatatt actgagcagcatatacctctcggggacattaaaatagtagattttggaatgtctcgaa aaatagggcatgcgtgtgaacttcgggaaatcatgggaacaccagaatattagctcc agaaatcctgaactatgatcccattaccacagcaacagatatgtggaatattggtataat agcatatatgttgttaactcacacatccacctttgtgggagaagataatcaagaaacata cctcaatatttctcaagttaatgtagattattcggaagaaacttttctcatcagtttcacagct ggccacagactttattcagagcctttagtaaaaaatccagagaaaagaccaacagca gagatatgcctttctcattcttggctacagcagtgggactttgaaaacttgtttcaccctg aagaaacttccagttcctctcaaactcaggatcattctgtaaggtcctctgaagacaag acttctaaatcctcctgtaatgaaacctgtggtgatagagaagacaaagagaatatccc agaggatagcagcatggtttccaaaagatttcgtttcgatgactcattacccaatcccc atgaacttgttcagatttgctctgtttagcactttttcttttgactcatttggactgaatttgaa attttatatccactccagtgagattatgatttgtagcttcatatatgacatgtttatattgtaa atgcacttttccatggaataatttagggaagtgttttaatgttaaattactagttgctagcat gttatgatttcatatcctgagatagctctgcagataagaaaatatttaaatatatgacaaa aagtaaaattgtacatgtgagtttacatgttaatgaaataattcaacttcaaatgaacttac cagaatgttttgcatatcaacaaaaaaagtggcttgagttttattatagttggtgtaaact gaacacagtgaagacattggaatttaataggttctctctctaaggtgactcttataccat gcctctatcaacatatttgtttaggaaagcagtatgaagtttaagccaaaataatttcta cttttatagatgctcaagagacatttctacaattgaaaatgtctttcaattacaaatatttgaa acttcgtaagattttcattctctgtggtctgttatatgagagagatcctttttactagagcaa agagggagttagaaacctgatcagggatattctttacaagttggagcagaggaaaga gtagcatgccttcgtattttaacgcaaatgtcttttcctcctcccaacctacttgagatct gataaggtctggaagatggagatatttggtatgcaagtgtagagttttttaatcctccag aatttctagagtagaagatacttaggtatagttaaatattagtattttagtcaaacatattt attaattgaatatagaagaaaatgttgacacactcagacagcttactgaattttagatgtc ttctgcatcttagaataaagccagtcattcagagttctaaaagtatgcataaaaaaattac agcaccggtaggtctattaacacagtgcccgagtcagcggtagcaagactgatgtga tcataaaaacatgacatcaggctcgtctgaagttcttgtgtgaaattcctagtgagtgagg aggctcagcttaaagccatctgcagagtggcccctcattgtggtcttttgctgggacca atgcaagagactagggagacaaaatgtttgcttatggctagagactatatccagccc taatgatggggaaagttagtcctttttcgggtaatcttttatgaatttttcacctgatgaccgt tatattggtctgttatcatgttacgataactgtgatctcatgaccatgttgctgtatcagaa gaaatagtttgacaaatggtaacattcaacctgatgttccccctttagacctttaacttctc aaaatttttggtaagtttccaaattctttaataataacttaaaacttttttgaataactacaggt cactttatttgaccacatggtgaattccttttaatgtcttcagcatttgttaaggaaaagtttt ctctacttgtgtgtgtatgtgtgcacatgtgtgtatgtacaggtgtatgtatatatctataga tagatacaatacattctttagacacttttcaagattctttgctgtggtatttttgtgctcaact caggtgccaaaggagattttttttttttttttttttgagatggagttttgctctgtactcag gctggagtgcagtggcatgatctcagctcacggcaacctctgcctcccgggttcaag caattctcctgtctcagcctcctgagtagtgggattacaggcgcatgccaccgtgccc agctaattttgtatttttagtagagacggggtttcaccatgttggccaggctggtcacaa actcctgactttcaagtgatccacccgcctcggcctcccaaagtgctgggattacaggc gtgagccactgcgccccgcccaggagctcttttcttatgacatataaattatgacattt atattctttatatgactttatgttctcttcttatgacatttaaattctttaagtagtttgttggtcc aataaactagacgttgtataatctaaattgagcccttgtatatctaaaactgatgagttgtt tctaaattgttgattgtccatttacttgcctttggtattaagataatgcaagtaaagtttagta agtcattggataatgaaatgattatgtttctgaagacatattatatttttaattttttagagga atcatgccatccccaaaaaatcaagaaatatttgaatttgaaattataagttcatttgtta aaagacattttacaaatgtctgaaaatcttaaaatactttacatctaccttttaagtagtag aatacagagctgtaaatttccatgccttttttcctgatattaagtttatagtaaaaaagca actagtgattgcacaaagaatataaaaatccactcttttttacaaaggtgtgaattaaata acgttattgattggaatatgaaaatagaccaatcatttaagagcttttttagcaaatgattc aattcttactctttttctcccaagattgaaaagcataatgtatttctcaaagtaggaatcta gagagcccctataagtggacaaatgtcagtaacacttgaacacatgagaagataagt gttatgttgtgataatttaaagttaaatttgcttttttgggtaggatccctaaatagatgggat ttttaaatagatgatatatagatgacaattgcaattgtcattttaattattttcccctacagtaa agaacctagctctgagcagtgaaattgtaatgcacttaaaggaagtaagccgttaa ctgactctagtggagcgatctccaactgttttggcactagggacgggttttgtggaaga aaattttccacaggactgggggtttaggggggtggtttcaggatgctcaagtacatta catttatcattagattctcataaggagcatgcaacctagatctcttgcacgtgtggttcac agcaggattcgagctcctttgagaatctaatgccatggctgatctaacaggaaactga gctcaggcagtaatgcttggcaccgcccccacccttctatgcagcccggtcgtggcc tggggactggggacccctgctctagtcagtaataaggtacttgtgccagaatataaat caacacattgcttcctttatcaaagaagtcttgttatttaaaaaaagtcaactgagccagt | | |

TABLE 1-continued

| Gene | Human Gene Sequence | Human Sequence Accession No. | Murine Sequence Accession No. |
|---|---|---|---|
| | atgattagtgatgtaattgattttcattctggcacaagcctctttcattctggacagctcac aaatagttaatggaccatgctttgaatagccttcctctaagcaacatttataaatactgat attttagaactgtaacatttcttctgttttatttttgaattttcagtttgatatcttgtccttattcat tgttgtataaacaactgtacttttaatttcaagtagtattaaaagtatttcacttcagtttggg gggattattatcaatttataattttatttaaagtattttaaagaaaattgtaaattttccataaa ttacaacttcctgccatattttattaaataataatcttgcttaaggcatatagacagacatta ttatgagtattccagtaaaaaaaatctacatcaacttgaccattctggctaaaaattaaaa agcactttttatatctgtggttgtcatttgtttcaaagcattctaaatttattgttcttaaaag tatgtctgcatgttctagcctttgacctaggtcatctatgaaccctctttgtgtctaataaac atatctgtaaaggcaaaaaaaaaaaaaaaaaa (SEQ ID NO: 668) | | |
| Mast2 | taggcaggcggctgagccggcggcgggtggcctgcccaacgtgtgctgggtggg agaaggcgaggcgtcagcgatgctgtctcttccgtgaggagcgcagaggaggtcg cggcgccggaggcccagaaggccgaaggcgccgcgggctggggtcggtggc ttagggagcccgtccggccatggtggccgcgggtggtggttggcgcggctgcgctg cggccggggcagtgcggagccgggacagtcgcggcgctgacgcccgcgggcc ccagctgcagatatgaagcggagccgctgccgcgaccgaccgcagccgccgccg cccgaccgccgggaggatggagttcagcgggcagcggagctgtctcagtctttgcc gccgcgccggcgagcgccgcccgggaggcagcggctggaggagcggacgggc cccgcggggcccgagggcaaggagcaggatgtagtaactggagttagtcccctgct cttcaggaaactcagtaatcctgacatattttcatccactggaaaagttaaacttcagcg acaactgagtcaggatgattgtaagttatggagaggaaacctggccagctctctatcg ggtaagcagctgctccctagtccagcagtgtacatagcagtgtgggacaggtgactt ggcagtcgtcaggagaagcatcaaacctggttcgaatgagaaaccagtcccttggac agtctgcaccttctcttactgctggcctgaaggagttgagccttccaagaagaggcag cttttgtcggacaagtaaccgcaagagcttgattgtgacctctagcacatcacctacac taccacggccacactcaccactccatggccacacaggtaacagtcctttggacagcc ccggaatttctctccaaatgcacctgctcacttttctctttgttcctgcccgtaggactgat gggcggcgctggtctttggcctctttgccctcttcaggatatggaactaacactcctag ctccactgtctcatcatcatgctcctcacaggaaaagctgcatcagttgccttttccagcc tacagctgatgagctgcactttttgacgaagcatttcagcacagagagcgtaccagat gaggaaggacggcagtccccagccatgcggcctcgctcccggagcctcagtcccg gacgatccccagtatcctttgacagtgaaataataatgatgaatcatgtttacatagaaa gattcccaaaggccaccgcacaaatggaagagcgactagcagagtttatttcctcca acactccagacagcgtgctgcccttggcagatggagccctgagctttattcatcatca ggtgattgagatggcccgagactgcctggataaatctcggagtggcctcattacatca caatacttctacgaacttcaagataattttggagaaactttacaagatgctcatgagcgc tcagagagctcagaagtggcttttgtgatgcagctggtgaaaaagctgatgattatcat tgcccgcccagcacgtctcaggaatgcctggagtttgaccctgaagagttctaccac cttttagaagcagagagggccacgccaaagagggacaagggattaaatgtgacatt ccccgctacatcgttagccagctgggcctcacccgggatcatagaagaaatggc ccagttgagcagctgtgacagtcctgacactccagagacagatgattctttttgagggc catggggcatctctgccatctaaaaagacaccctgaagaggacttcgagaccatta agctcatcagcaatggcgcctatggggctgtatttctggtgcggcacaagtccacccg gcagcgctttgccatgaagaagatcaacaagcagaacctgatcctacggaaccagat ccagcaggccttcgtggagcgtgacatactgacttttgctgagaaccccctttgtggtc agcatgttctgctcctttgataccaagcgccacttgtgcatggtgatggagtacgttgaa gggggagactgtgccactctgctgaagaatattgggggccctgcctgtggacatggtg cgtctatactttgcggaaactgtgctggcctggagtacttacaacaactatggcatcgt gcatcgtgacctcaagcctgacaacctcctaattacatccatggggcacatcaagcct acggactttggactgtcaaaattggcctcatgagtctgacaacgaacttgtatgagg gtcatattgaaaaggatgcccgggaattcctggacaagcaggtatgcgggacccca gaatacattgcgcctgaggtgatcctgcgcagggctatgggaagccagtggactg gtgggccatgggcattatcctgtatgagttcctggtgggctgcgtccctcttttttggagat actccggaggagctattgggcaggtgattagtgatgagattgtgtggcctgagggt gatgaggcactgccccagacgccaggacctcacctccaaactgctccaccagaa ccctctgagagacttggcacaggcagtgcctatgaggtgaagcagcacccattctttt actggtctggactggacaggacttctccgccagaaggctgaatttattcctcagttgga gtcagaggatgatactagctattttgacacccgctcagagcgttaccaccacatggac tcggaggatgaggaagaagtgagtgaggatgcctgccttgagatccgccagttctct tcctgctctccaaggttcaacaaggtgtacagcagcatggagcggctctcactgctcg aggagcgccggaccaccccccgaccaagcgcagcctgagtgaggagaaggag gaccattcagatggcctggcagggctcaaaggccgagaccggagctgggtgattg gctcccctgagatattacggaagcggctgtcggtgtctgagtcatcccacacagaga gtgactcaagccctccaatgacagtgcgacgccgctgctcaggcctcctggatgcgc ctcggttcccggagggccctgaggaggccagcagcaccctcaggaggcaaccac aggagggtatatgggtcctgacaccccatctggagagggggtatctgggcctgtca ctgaacactcaggggagcagcggccaaagctgatgagggaagctgttggccgag cagtggttccagtccagctatggagacccgaggccgtgggacctcacagctggctg agggagccacagccaaggccatcagtgacctgctgtgcgtagggccgccaccg gctgctctctgggactcaacagagaagcgcactgctcgccctgtcaacaaagtgat tccccgttggccagccccatgtcccacattctcagtcgtccaacccatcatcccggg actcttctccaagcagggacttcttgccagcccttggcagcatgaggcctcccatcatc atccaccgagctggcaagaagtatggcttcaccctgcgggccattcgcgtctacatg ggtgactccgatgtctacaccgtgcaccatatggtgtgtggcacgtggaggatggagt | NM_015112 | NM_001042743 |

TABLE 1-continued

| Gene | Human Gene Sequence | Human Sequence Accession No. | Murine Sequence Accession No. |
|---|---|---|---|
| | ccggccagtgaggcagggcttcgtcaaggtgacctcatcacccatgtcaatgggga acaaggtggccatttcaacaactccctggagaacacatccattaaagtggggccag ctcggaagggcagctacaaggccaagatggcccgaaggagcaagaggagccgc ggcaaggatgggcaagaaagcagaattaaggagctccctgttccgcaagatcacca agcaagcatccctgctccacaccagccgcagccttttcttcccttaaccgctccttgtca tcaggggagagtgggccaggctctcccacacacagccacagcattcccccgatc tcccactcaaggctaccgggtgaccccgatgctgtgcattcagtgggagggaattc atcacagagcagctccccagctccagcgtgcccagttcccagccggctctgggc acacgcgccagctccctccacggtctggcacccaagctccaacgccagtaccgc tctccacggcgcaagtcagcaggcagcatcccactgtcaccactggcccacacccc ttctccccaccccaacagcttcacctcagcggtccccatgcccctgtctggccat gtagcccaggcctttcccacaaagcttcacttgtcacctccctgggcaggcaacta cacggcccaagagtgcggagccaccccgttcaccactactcaagagggtgcagtc ggctgagaaactggcagcagcacttgccgcctctgagaagaagctagccacttctcg caagcacagccttgacctgccccactctgaactaaagaaggaactgccgcccaggg aagtgagccctctggaggtagttggagccaggagtgtgctgtctggcaaggggggcc ctgccagggaagggggtgctgcagcctgctccctcacgggccctaggcaccctcc ggcaggaccgagccgaacgacgggagtcgctgcagaagcaagaagccattcgtg aggtggactcctcagaggacgacaccgaggaagggcctgagaacagccagggtg cacaggagctgagcttggcacctcacccagaaagtgagccaggtggcccctaaa ggagcaggacagagtggggaagaggatcctttcccgtccagagacccctaggagcc tgggcccaatggtccccaagcctattgacagggatcacactggggcctcccagaatg gaaagtcccagtggtccccacaggaggctcgggagcccacaagccattgaggagg ctgccagctcctcctcagcaggccccaacctaggtcagtctggagccacagaccc catccctcctgaaggttgctggaaggcccagcacctccacaccaggcactaacagc actttctcccagcacttcggggactcacccccaccagcagttgctctcctcccagctcca cctctgggaagctgagcatgtggtcctggaaatcccttattgagggcccagacacgg catccccaagcagaaaggcaaccatggcaggtgggctagccaacctccaggatttg gaaaacaactccagcccagcctaagaacctgtctcccagggagcagggggaaga cacagccacctagtgcccccagactggcccatccatcttatgaggatcccagccagg gctggctatgggagtctgagtgtgcacaagcagtgaaagaggatcagccctgagc atcacccaagtgcctgatgcctcaggtgacagaaggcaggacgttccatgccgagg ctgccccctcacccagaagtctgagcccagcctcaggagggccaagaaccaggg ggccatcaaaaagcatcaggatttggcttttggttccagatgagcttttaaagcaaacata gcagttgtttgccatttcttgcactcagacctgtgtaatatatgctcctggaaaccatcaa aaaaaaaaaaaaaaaa (SEQ ID NO: 669) | | |
| Pdp1 | agagtgggcaggccgggggtgagggctcgcgctccgggagctgcacggggctgc gtggaaagagcgccgagcggtggcgtcgttgtcgccccctcctcgtcgggaagaat cgtttggtctcctgccgtgcccggttcgtattcccactccctgccacgagccgccccg tccgggatcctccacccgtccaaagttgtgaggggcgccgggcgtgctcgcggat cggcggccgcgggcgtgcggagggctggacgagccctggagcgccaggagaat gtgtgtgtgtcccgggcccagacgaattggaatcccagtcagaagttccagcctgcc actgttctctgatgccatgccagcaccaactcaactgttttttcctctcatccgtaactgtg aactgagcaggatctatgcactgcatgttactgccaccacaaacatctctgttgttcct catcgtacattcctcagagtcgactgagatacacacctcatccagcattttgctaccttt gcaggccaaaggagaactggtggcagtacacccaaggaaggagatatgcttccac accacagaaattttacctcacacctccacaagtcaatagcatccttaaagctttatgaat acagtttcaaagtgccagaatttgacggcaaaaatgtcagttctatccttggatttgaca gcaatcagctgcagcaaatgcacccattgaggaccggagaagtgcagcaacctgc ttgcagaccagagggatgcttttgggggttttttgatgccatgcaggttgtgcttgttcc caggcagtcagtgaaagactcttttattatattgctgtctctttgttaccccatgagacttt gctagagattgaaaatgcagtggagagcggccgggcactgctacccattctccagtg gcacaagcaccccaatgaattactttagtaaggaggcatccaaattgtactttaacagctt gaggacttactggcaagagcttatagacctcaacactggtgagtcgactgatattgat gttaaggaggctctaattaatgccttcaagaggcttgataatgacatctccttggaggc gcaagttggtgatcctaattcttttctcaactacctggtgcttcgagtggcattttctggag ccactgcttgtgtggcccatgtggatggtgttgaccttcatgtggcaatactggcgat agcagagccatgctgggtgtgcaggaagaggacggctcatggtcagcagtcacgct gtctaatgaccacaatgctcaaaatgaaagagaactagaacggctgaaattggaaca tccaaagagtgaggccaagagtgtcgtgaaacaggatcggctgcttggcttgctgat gccatttagggcatttggagatgtaaagttcaaatggagcattgaccttcaaaaagaga gtgatagaatctggcccagaccagttgaatgacaatgaatataccaagtttattcctcct aattatcacacacctccttatctcactgctgagccagaggtaacttaccaccgattaag gccacaggataagtttctggtgttggctactgatggggtgtgggagactatgcataggc aggatgtggttaggattgtgggtgagtacctaactggcatgcatcaccaacagccaat agctgttggtggctacaaggtgactctgggacagatgcatggccttttaacagaaagg agaaccaaaatgtcctcggtatttgaggatcagaacgcagcaacccatctcattcgcc acgctgtgggcaacaacgagtttgggactgttgatcatgagcgcctctctaaaatgctt agtcttcctgaagagctcgtccgaatgtacagagatgacattacaatcattgtagttcag ttcaattctcatgttgtagggggcgtatcaaaaccaagaatagtgagtggctcttcactg gcaattctcaaatgatatacatttaaagggcagattttttaaaaagatactactataataa acatttccagttggtcattctaagcatttacccttttgatactctagctagtcaggtactcc aaattgactttgcagcagggtggcagggtcaggagagtctggtcctgcctagctcag atttcatggcacctgcacttgaagcaagtcacttctcttcatcacaggtgtcttgaaacatta | NM_001161779 | NM_001098231 |

TABLE 1-continued

| Gene | Human Gene Sequence | Human Sequence Accession No. | Murine Sequence Accession No. |
|---|---|---|---|
| | gcttcttttaccaacctgagaaaattaggatgacctggcaaataagatcagaataggc<br>caaaagcaagtatcttgctgtgtgtagtctcttggttaaagtgaagaaacagtactgttc<br>acacctttcttcactgagattccagtgtacatgagaacatatatttattgcatgattttctag<br>atacacagtctatgcattattcatatacatttattttagcctaaagtggttttcaaatccagtt<br>cttcaagccataaatgaccaagatccaagcaatctgaatttgttttttgtgaaatttgactg<br>gaatgcttcttaagtggaataactatactccgttatccacccgatttcctaatgtaattgaa<br>agattttctattttgccacacacttggagacaataaggggttttttagttttatctactcttctatt<br>gaagttaaagaaagaaaaaaagattttttttatttgtattaatgaaaagcttagttttaaaat<br>aaggagatccagaataaaaagaagagactgatctcttcaattattgtcatctgtagcca<br>ccttgcacatcactcttatgtaatccccaaaggcttggcatgccgtaagtgtgtggtgg<br>gtagactgctgccggggaatcgtacttcttatttagtaatgataagacttttcattattttttg<br>gaattttaaagatgacataaataagtttaaatatcaattttggggagtaaggtttaatattgc<br>catcgggtattgagacaggaggaagtttctgttttttctccatttagacataggtcaattaa<br>aatatttgggtttaaaatgactaaatgcttcaaacatattgtagcttaagatatatgtgttaa<br>gatatacatgagaaacttttaaaaggtaactactgtgcatgcctgatgcttaataagaat<br>acttagtggcatcaaatgtttgcagcagtctccataattatattcagtcccttctaatactg<br>tatcaatgtaaatgaaataaatatttttcaaattggcttttttgatatgcatcaagtggcatttt<br>gttcctgtgtttaatagtgatagtatacagctgtgcacatattgtcatcaatattctagca<br>tcactgttaaggctgtgattatgtttgatattcacctggattttaatacaagccaatatcag<br>cttcccattgtgtaatacttgggtgtttaggagtcttttcacatttttgggggatatgaact<br>agatgttcaagaactccttctggactgtggatactgaatcagtgtactattggctgcaga<br>atagtttcaattgaaaatagactcaggaagattgctgctcagaatatcataatgttt att<br>ttttgaggtgtttttgttttatttgtgtgtttatttttttttaagtcagcttggaacttttttcctgg<br>gtagtatttgggagagggaaaggctgtactatatatttatttctaaatgttttgactgggc<br>attttttccttttaatgaaatatgtggactgctctagcaaacccctatttttcagctactatttgaat<br>attcttgaacaccaccactgaagagtttcatatacaccaaataatgtctcatctctatagt<br>acagggaatataaaaattggtttcctgtggtcatgatcaagatagtagtattattacacaa<br>gaaacttggtctgcagtctggaagcttgtctgctctatagaaatgaaaatgcagcatga<br>agttgacattgtggaaatgaaagtaattgggtattagaaatctgaaagtactgtcatcta<br>aaagcaattgtgattttattgtaattggttgtcactgttgtacggtgtctagaattaaagaa<br>tacatgtaaactttcatggtatttagccttcttaaattttttaaaatttaaactttctaaccta<br>tgtattcaacttctgtatttataataatcagtggttcatgttatataatacacccttaactagt<br>taaatggaatgttggtatggtacagagtaccatatgctaaagaaaactgtcttataaaag<br>atgtatatgtgtgaagacatgaaagtttaatgtacagaatggttggagaaatgcctatg<br>gtgaattaaagcttcatatctgctactgaaaaaaaaaaaaaaaa (SEQ ID NO: 670) | | |
| Yes1 | ggaggaggtggagagtgaggcggaggcgtggggagcccgggaactccctcctcc<br>tgaagtaacgcgtcccgggccggctagccgtcgttgctgccgccgggcgcccgg<br>gacgaggaggtggaggagggagagggccccgcgggcctcgcctccgcccctccgc<br>cacctcgagctgcgctagcagcgactcatgagagcgcggccggaggacagatttg<br>ataatgggctgcattaaaagtaaagaaaacaaaagtccagccatttaatacagacctg<br>aaaatactccagagcctgtcagtacaagtgtgagccattatggagcagaacccacta<br>cagtgtcaccatgtccgtcatcttcagcaaagggaacagcagttaatttcagcagtcttt<br>ccatgacaccatttggaggatcctcaggggtaacgccttttggaggtgcatcttcctca<br>ttttcagtggtgccaagttcatatcctgctggtttaacaggtggtgttactatatttgtggc<br>cttatatgattatgaagctagaactacagaagaccttcaataagaagggtgaaagatt<br>tcaaataattaacaatacggaaggagattggtgggaagcaagatcaatcgctacagg<br>aaagaaatggttatatcccgagcaattatgtagcgcctgcagattccattcaggcagaa<br>gaatggtattttggcaaaatggggagaaaagatgctgaaagattacttttgaatcctgg<br>aaatcaacgaggtattttcttagtaagagagagtgaaacaactaaaggtgcttattccct<br>ttctattcgtgattgggatgagataaggggtgacaatgtgaaacactacaaaattagga<br>aacttgacaatggtggatactatatcacaaccagagcacaatttgatactctgcagaaa<br>ttggtgaaacactacacagaacatgctgatggtttatgccacaagttgacaactgtgtg<br>tccaactgtgaaacctcagactcaaggtctagcaaaagatgcttgggaaatccctcga<br>gaatcttgcgactagaggttaaactaggacaaggatgtttcggcgaagtgtggatgg<br>gaacatggaatggaaccacgaaagtagcaatcaaaacactaaaaccaggtacaatg<br>atgccagaagctttccttcaagattgctcagtttaatgaaaaaattaagacatgataaact<br>tgttccactatatgctgttgtttctgaagaaccaatttacattgtcactgaatttatgtcaaa<br>aggaagcttattagatttccttaaggaaggagatgaaagtatttgaagcttccaaagc<br>tggttgatatggctgctcagattgctgatggtatggcatatattgaaagaatgaactatat<br>tcaccgagatctccgggctgctaatattcttgtaggagaaatcttgtgtgcaaaatgg<br>agactttggtttagcaaggttaattgaagacaatgaatacacagcaagacaaggtgca<br>aaatttccaatcaaatggacagctcctgaagctgcactgtatggtcggtttacaataaa<br>gtctgatgtctggtcatttggaattctgcaaacagaactagtaacaaagggccgagtg<br>ccatatccaggtatggtgaaccgtgaagtactagaacaagtgggcaggatacag<br>gatgccgtgccctcaggggctgtccagaatccctccatgaattgatgaatctgtgttgga<br>agaaggaccctgatgaaagaccaacatttgaatatattcagtcctccttggaagactac<br>ttcactgctacagagccacagtaccagccaggagaaatttataattcaagtagcctat<br>tttatatgcacaaatctgccaaaatataaagaaacttgtgtagattttctcacaggaatcaaa<br>agaagaaaatcttctttactctgcatgtttttaatggtaaactggaatcccagatatggttg<br>cacaaaaccactttttttttccccaagtatttaaactctttatgtaccaatgatgaatttatcag<br>cgtatttcagggtccaaacaaaatagagctaagatactgatgacagtgtgggtgacag<br>catggtaatgaaggcagtgaggctcctgcttatttataaatcatttcctttcttttttttccc<br>caaagtcagaattgctcaaagaaaaattatttattgttacagataaaacttgagagataaa | NM_005433 | NM_009535 |

TABLE 1-continued

| Gene | Human Gene Sequence | Human Sequence Accession No. | Murine Sequence Accession No. |
|---|---|---|---|
| | aagctataccataataaaatctaaaattaaggaatatcatgggacctaataattccattc<br>cagttttttaaagtttcttgcatttattattctcaaaagttttttctaagttaaacagtcagtat<br>gcaatcttaatatatgctttctttttgcatggacatgggccaggttttcaaaaggaatataa<br>acaggatctcaaacttgattaaatgttagaccacagaagtggaatttgaaagtataatg<br>cagtacattaattttttcatgttcatggaactgaaagaataagaacttttcacttcagtcctt<br>ttctgaagagtttgacttagaataatgaaggtaactagaaagtgagttaatcttgttttga<br>ggttgcattgattttttaaggcaatatataattgaaactactgtccaatcaaaggcgaaat<br>gttttgatctttagatagcatgcaaagtaagacccagcattttaaaagcccttttttaaaaa<br>ctagacttcgtactgtgagtattgcttatatgtccttatggggatgggtgccacaaatag<br>aaaatatgaccagatcagggacttgaatgcacttttgctcatggtgaatatagatgaac<br>agagaggaaaatgtatttaaaagaaatacgagaaaagaaagtgaaagttttacaagtt<br>agagggatggaagtaatgtttaatgttgatgtcatggagtgacagaatggctttgctg<br>gcactcagagctcctcacttagctatattctgagactttgaagagttataaagtataacta<br>taaaactaatttttcttacacactaaatgggtatttgttcaaaataatgaagttatggcttca<br>cattcattgcagtgggatatggttttatgtaaaacattttagaactccagttttcaaatca<br>tgtttgaatctacattcactttttttttgtttcttttttgagacggagtctcgctctgtcgccca<br>ggctggagtcagtggcgcgatctcggctcactgcaagctctgcctcccaggttcac<br>accattctcctgcctcagcctcccgagtagctgggactacaggtgcccaccacg<br>cctggctagtttttgtatttttagtagagacgcagtttcaccgtgttagccaggatggtct<br>cgatctcctgaccttgtgatctgcccgcctcggcctcccaaagtgctgggattacagg<br>cgtgagccaccgcgcccagcctacattcacttctaaagtctatgtaatggtggtcattttt<br>ttcccttttagaatacattaaatggttgatttggggaggaaaacttattctgaatattaacg<br>gtggtgaaaaggggacagttttacccctaaagtgcaaaagtgaaacatacaaaataag<br>actaattttaagagtaactcagtaatttcaaaatacagatttgaatagcagcattagtgg<br>tttgagtgtctagcaaaggaaaaattgatgaataaaatgaaggtctggtgtatatgttta<br>aaatactctcatatagtcacactttaaattaagccttatattaggccccctctatttcaggat<br>ataattcttaactatcattatttacctgattttaatcatcagattcgaaattctgtgccatggc<br>atatatgttcaaattcaaaccatttttaaatgtgaagatggacttcatgcaagttggcag<br>tggttctggtactaaaaattgtggttgttttttctgtttacgtaacctgcttagtattgacact<br>ctctaccaagagggtcttcctaagaagagtgctgtcattatttcctcttatcaacaacttg<br>tgacatgagatttttaagggctttatgtgaactatgatattgtaattttctaagcatattca<br>aaagggtgacaaaattacgtttatgtactaaatctaatcaggaaagtaaggcaggaaa<br>agttgatggtaacattaggttttaactgaatgggagcagttccttatataataacaattgtat<br>agtagggataaaacactaactttaatgtgtattcattttaaattgttctgtattttaaattgcc<br>aagaaaaacaactttgtaaatttggagatattttccaacagcttacgtcttcagtgtctta<br>atgtggaagttaaccccttaccaaaaagggaagttggcaaaacagccttctagcacac<br>tttttaaatgaataatggtagcctaaacttaatattttttaaagtattgtaatattgttttgtgt<br>gataattgaaataaaaagttctcattgaatgcacctattaatcgttttagttgctattcatatt<br>ctcattcgttttttaaaaactgatattttctgaatttattcttccattgagaaaaaaatgttca<br>gttacttgtaactactgagcagaatttaatcaatcctttattaaattcagaacattattgaa<br>(SEQ ID NO: 671) | | |
| Met | gccctcgccgccgcggcgccccgagcgctttgtgagcagatgcggagccgagtg<br>gagggcgcgagccagatgcggggcgacagctgacttgctgagaggaggcgggg<br>aggcgcggagcgcgcgtgtggtccttgcgccgctgacttctccactggttcctgggc<br>accgaaagataaacctctcataatgaaggccccgctgtgcttgcacctggcatcctc<br>gtgctcctgtaaccttggtgcagaggagcaatggggagtgtaaagaggcactagca<br>aagtccgagatgaatgtgaatatgaagtatcagcttcccaacttcaccgcggaaacac<br>ccatccagaatgtcattctacatgagcatcacattttccttggtgccactaactacatttat<br>gttttaaatgaggaagaccttcagaaggttgctgagtacaagactgggcctgtgctgg<br>aacacccagattgtttcccatgtcaggactgcagcagcaaagccaatttatcaggagg<br>tgtttggaaagataacatcaacatggctctagttgtcgacacctactatgatgatcaact<br>cattagctgtggcagcgtcaacagagggacctgccagcgacatgtctttccccacaat<br>catactgctgacatacagtcggaggttcactgcatattctcccacagatagaagagc<br>ccagccagtgtcctgactgtgtggtgagcgccctgggagccaaagtccttcatctgt<br>aaaggaccggttcatcaacttctttgtaggcaataccataaattcttcttattccccagtc<br>atccattgcattcgatatcagtgagaaggctaaaggaaacgaaaagtggttttatgtttt<br>gacggaccagtcctacattgatgttttacctgagttcagagattcttaccccattaagtat<br>gtccatgcctttgaaagcaacaattttatttacttcttgacggtccaaagggaaactctag<br>atgctcagacttttcacacaagaataatcaggttctgttccataaactctggattgcattc<br>ctacatggaaatgcctctggagtgtattctcacagaaaagagaaaaaagagatccac<br>aaaggaaagtgtttaatatacttcaggctgcgtatgtcagcaggcctgggcccag<br>cttgctagacaaataggagccagcctgaatgatgacattcttttcggggtgttcgcaca<br>aagcaagccagattcagccgaaccaatggatcgatctgccatgtgtgcattccctatca<br>aatatgtcaacgacttcttcaacaagatcgtcaacaaaaacaatgtgagatgtctccag<br>cattttttacggacccaatcatgagcactgctttaataggacacttctgagaaattcatca<br>ggctgtgaagcgcgcgtgatgaatatcgaacagagtttaccacagctttgcagcgc<br>gttgacttattcatgggtcaattcagcgaagtcctcttaacatctatatccaccttcattaa<br>aggagacctcaccatagctaatcttgggacatcagaggggtcgcttcatgcaggttgtg<br>gtttctcgatcagcaccatcaacccctcatgtgaattttctcctggactcccatccagtgt<br>ctccagaagtgattgtggagcatacattaaaccaaaatggctacacactggttatcact<br>gggaagaagatcacgaagatcccattgaatggcttgggctgcagacatttccagtcct<br>gcagtcaatgcctctctgccccaccccttttgttcagtgtggctggtgccacgacaaatgt | NM_001127500 | NM_008591 |

TABLE 1-continued

| Gene | Human Gene Sequence | Human Sequence Accession No. | Murine Sequence Accession No. |
|---|---|---|---|
| | gtgcgatcggaggaatgcctgagcgggacatggactcaacagatctgtctgcctgca atctacaaggttttcccaaatagtgcaccccttgaaggagggacaaggctgaccatat gtggctgggactttggatttcgg aggaataataaatttgatttagagaaaactagagttctccttggaaatgagagctgcac cttgactttaagtgagagcacgatgaatacattgaaatgcacagttggtcctgccatga ataagcatttcaatatgtccataattatttcaaatggccacgggacaacacaatacagta cattctcctatgtggatcctgtaataacaagtatttcgccgaaatacggtcctatggctg gtggcactttacttactttaactggaaattacctaaacagtgggaattctagacactttttc aattggtggaaaaacatgtactttaaaaagtgtgtcaaacagtattcttgaatgttatacc ccagcccaaaccatttcaactgagtttgctgttaaattgaaaattgacttagccaaccga gagacaagcatcttcagttaccgtgaagatcccattgtctatgaaattcatccaaccaa atcttttattagtacttggtggaaagaacctctcaacattgtcagtttttctattttgctttgcc agtggtgggagcacaataacaggtgttgggaaaaacctgaattcagttagtgtcccg agaatggtcataaatgtgcatgaagcaggaaggaactttacagtggcatgtcaacatc gctctaattcagagataatctgttgtaccactccttccctgcaacagctgaatctgcaac tcccccctgaaaaccaaagccttttcatgttagatgggatcctttccaaatactttgatctc attttatgtacataatcctgtgtttaagccttttgaaaagccagtgatgatctcaatgggca atgaaaatgtactggaaattaagggaaatgatattgaccctgaagcagttaaaggtga agtgttaaaagttggaaataagagctgtgagaatatacacttttcattctgaagccgtttt atgcacggtcccccaatgacctgctgaaattgaacagcgagctaaatatagagtggaa gcaagcaatttcttcaaccgtcatggaaaagtaatagttcaaccagatcagaatttcac aggattgattgctggtgttgtctcaatatcaacagcactgttattactactttgggttttcct gtggctgaaaagagaaagcaaattaaagatctgggcagtgaattagttcgctacgat gcaagagtacacactcctcatttggataggcttgtaagtgcccgaagtgtaagcccaa ctacagatatggtttcaaatgaatctgtagactaccgagctacttttccagaagatcagt ttcctaattcatctcagaacggttcatgccgacaagtgcagtatcctctgacagacatgt cccccatcctaactagtggggactctgatatatccagtccattactgcaattatactgtcc acattgacctcagtgctctaaatccagagctggtccaggcagtgcagcatgtagtgatt gggcccagtagcctgattgtgcatttcaatgaagtcataggaagagggcatttttggttg tgtatatcatgggactttgttggacaattgatggcaagaaaattcactgtgctgtgaaatc cttgaacagaatcactgacataggagaagtttcccaatttctgaccgagggaatcatca gggtctccgctggtggtcctaccatacatgaaacatggagatcttcgaaatttcattcg aaatgagactcataatccaactgtaaaagatcttattggattggtcttcaagtagccaa aggcatgaaatatcttgcaagcaaaaagtttgtccacagagacttggctgcaagaaac tgtatgctggatgaaaaattcacagtcaaggttgctgattttggtcttgccagagacatg tatgataaagaatactatagtgtacacaacaaaacaggtgcaaagctgccagtgaagt ggatggctttggaaagtctgcaaactctaaagtttaccaccaagtcagatgtgtggtcc tttggcgtgctcctctgggagctgatgacaagaggagccccaccttatcctgacgtaa acacctttgatataactgtttacttgttgcaagggagaagactcctacaacccgaatact gcccagaccccttatatgaagtaatgctaaaatgctggcacccctaaagccgaaatgc gcccatccttttctgaactggtgtcccggatatcagcgatcttctctactttcattgggga gcactatgtccatgtgaacgctacttatgtgaacgtaaaatgtgtcgctccgtatccttct ctgttgtcatcagaagataacgctgatgatgaggtggacacacgaccagcctccttct gggacacatcatagtgctagtactatgtcaaagcaacagtccacactttgtccaatggt tttttcactgcctgacctttaaaaggccatcgatattctttgccttgccaaaattgcactat tataggacttgtattgttatttaaattactggattctaaggaatttcttatctgacagagcat cagaaccagaggcttggtcccacaggccacggaccaatggcctgcagccgtgaca acactcctgtcatattggagtccaaaacttgaattctgggttgaatttttttaaaaatcaggt accacttgatttcatatgggaaattgaagcaggaaatattgagggcttcttgatcacag aaaactcagaagagatagtaatgctcaggacaggagcggcagccccagaacaggc cactcatttagaattctagtgttttcaaaacacttttgtgtgttgtatggtcaataacattttc attactgatggtgtcattcacccattaggtaaacattcccttttaaatgtttgtttgttttga gacaggatctcactctgttgccagagcttttagtgcagtggtgtgatcatatctcactgc aacctccacctcccagcctcaagcctcccgaatagctgggactacaggcgcacacc accatccccggctaattttttgtattttttgtagagacggggttttgccatgttgccaaggct ggtttcaaactcctggactcaagaaatccacccacctcagcctcccaaagtgctagga ttacaggcatgagccactgcgcccagccctataaattttgtatagacattcctttggtt ggaagaatatttataggcaatacagtcaaagtttcaaaatagcatcacacaaaacatgt ttataaatgaacaggatgtaatgtacatagatgacattaagaaaatttgtatgaaataatt tagtcatcatgaaatatttagttgtcatataaaaacccactgtttgagaatgatgctactct gatctaatgaatgtgaacatgtagatgttttgtgtgtattttttaaatgaaaactcaaaata agacaagtaatttgttgataaatattttaaagataactcagctgtttgtaaagcaggat acgttttactaaaaggttcattggttccaatcacagctcataggtagagcaaagaaagg gtgaatgaattgaaaagattagcctctgtctcggtggcaggttcccacctcgcaagca attggaaacaaaacttttggggagtttttattttgcattagggtgtgttttatgttaagcaaa acatactttagaaacaaatgaaaaaggcaattgaaaatcccagctcacctctgatg gaatagccaccctgagcagaactttgtgatgcttcattctgtggaattttgtgcttgctac tgtatagtgcatgtggtgtaggttactctaactggttttgtcgacgtaaacatttaaagtgt tataatttttataaaaatgtttatttttaatgatatgagaaaaatttgttaggccacaaaaac actgcactgtgaacatttttagaaaaggtatgtcagactgggattaatgacagcatgattt tcaatgactgtaaattgcgataaggaaatgtactgattgccaatacaccccaccctcatt acatcatcaggacttgaagccaagggttaacccagcaagctacaaagagggtgtgtc acactgaaactcaatagttgagtttggctgttgttgcaggaaaatgattataactaaaag ctctctgatagtgcagagacttaccagaagacacaaggaattgtactgaagagctatt acaatccaaatattgccgtttcataaatgtaattagtaatactaattcacagagtattgta | | |

TABLE 1-continued

| Gene | Human Gene Sequence | Human Sequence Accession No. | Murine Sequence Accession No. |
|---|---|---|---|
| | aatggtggatgacaaaagaaaatctgctctgtggttaagaaagaactgtctctaccag<br>ggtcaagagcatgaacgcatcaatagaaagaactcggggaaacatcccatcaacag<br>gactcacacacttgtatatacattcttgagaacactgcaatgtgaaaatcacgtttgctatt<br>ataaacttgtccttagattaatgtgtctggacagattgtgggagtaagtgattcttctaag<br>aattagatacttgtcactgcctatacctgcagctgaactgaatggtacttcgtatgttaat<br>agttgttctgataaatcatgcaattaaagtaaagtgatgcaacatcttgtaaaaaaaaaaaaaaaaaaa (SEQ ID NO: 672) | | |
| Ppm1g | agttgctaaggaaatgactgcccgcagcgcctggccccgccgcgcaggccgggcg<br>gggtctggagcggcgccgtttccgcttccgctccctcacagctcccgtcccgttaccg<br>cctcctggccggcctcgcgccttcaccggcaccttgcgtcggtcgcgccgcgggg<br>cctgctcctgccgcgcgcaccccccggggcttcggctccggcacgggtcgcgccca<br>gctttcctgcacctgaggccgccggccagccgccgccatgggtgcctacctctccca<br>gcccaacacggtgaagtgctccggggacggggtcggcgccccgcgcctgccgct<br>gccctacggcttctccgccatgcaaggctggcgcgtctccatggaggatgctcacaa<br>ctgtattcctgagctggacagtgagacagccatgttttctgctctacgatggacatggag<br>gggaggaagttgccttgtactgtgccaaatatcttcctgatatcatcaaagatcagaag<br>gcctacaaggaaggcaagctacagaaggctttagaagatgccttcttggctattgacg<br>ccaaattgaccactgaagaagtcattaaagagctggcacagattgcagggcgaccc<br>actgaggatgaagatgaaaaagaaaaagtagctgatgaagatgatgtggacaatga<br>ggaggctgcactgctgcatgaagaggctaccatgactattgaagagctgctgacacg<br>ctacgggcagaactgtcacaaggggcctccccacagcaaatctggaggtgggaca<br>ggcgaggaaccagggtcccagggcctcaatggggaggcaggacctgaggactca<br>actagggaaactccttcacaagaaaatggccccacagccaaggcctacacaggcttt<br>tcctccaactcggaacgtgggactgaggcaggccaagttggtgagcctggcattccc<br>actggtgaggctgggccttcctgctcttcagcctctgacaagctgcctcgagttgctaa<br>gtccaagttctttgaggacagtgaggatgagtcagatgaggcggaggtagaagagg<br>aagacagtgaggaatgcagcgaggaagaggatggctacagcagtgaggaggcag<br>agaatgaggaagatgaggatgacaccgaggaggctgaagaggacgatgaagaag<br>aagaagaagagatgatggtgccagggatggaaggcaaagaggagcctggctctga<br>cagtggtacaacagcggtggtgccctgatacgagggaagcagttgattgtagcca<br>acgcaggagactctcgctgtgtggtatctgaggctggcaaagctttagacatgtcctat<br>gatcacaaaccagaggatgaagtagaactagcacgcatcaagaatgctggtggcaa<br>ggtcaccatggatgggcgagtcaacgggggcctcaacctctccagagccattgggg<br>accacttctataagagaaacaagaacctgccacctgaggaacagatgattcagccct<br>tcctgacatcaaggtgctgactctcactgacgaccatgaattcatggtcattgcctgtga<br>tggcatctggaatgtgatgagcagccaggaagttgtagattcaatcaaagatca<br>gccagcgtgatgaaaatggggagcttcggttattgtcatccattgtggaagagctgct<br>ggatcagtgcctggcaccagacacttctgggttggttcagagtgtgtttaacatgac<br>ctgcatcatcatttgcttcaagccccgaaacacagcagagctccagccagagagtgg<br>caagcgaaaactagaggaggtgctctctactgagggggctgaagaaaatgcaaca<br>gcgacaagaagaagaaggccaagcgacactagcagtgcatccagacccctgcccac<br>ctagactgttttctgagccctcggacctgagactgagttttgtctttttcctttagccttag<br>cagtgggtatgaggtgtgcaggggggagctgggtggcttcactccgcccattccaaag<br>agggctctccctccacactgcagccgggagcctctgctgtccttccagccgcctctg<br>ctcctcgggctcatcaccggttctgtgcctgtgctctgttgtgttggagggaaggactg<br>gcggttctggttttactctgtgaactttatttaaggacattctttttattggcggctccatg<br>gccctcggccgcttgcaccgctctctgttgtacacttttcaatcaacacttttcagacta<br>aaggccaaaacctaa (SEQ ID NO: 673) | NM_177983 | NM_008014 |
| Blvrb | Ggcgtggcccttcgagccagctccgcccgttgttctggcttgagtagggcagag<br>agcaccgcccaggagccagtgggttcccgcgcgtgccgagactctgaggcttgca<br>cccccacgatcccgtacgatggccgtcaagaagatcgcgatcacggcgccactgg<br>ccagaccgggacaccagctctggcgcaggcggtgcaagcaggttacgaagtgaca<br>gtggtggtgcgggactcctccaggctgccatcagaggggcccggcgggcccacg<br>tggtagtgggagatgttctgcagggagccgatgtggacaagaccgtggctgggcag<br>gacgctgtcatggtgctgctggggacccgcaatgacctcagtcccacgacagtgatg<br>tccgagggcgcccggaacattgtggcagccatgaaggacatggtggtggacaaggt<br>cgtggcctttacctcggctacctgctgtgggacccctaccaaggtgcccgcaggact<br>ggaggctgtgactgatgaccacatccggatgcacaaggtgagcgggaatcaggcc<br>tgaagtttcgtgggtgtgatgccgcagacataggagaccagccactaactggggcg<br>tacacagtgaccgtggatggacgaggggccctcaagggtcatgtcgaaacatgacctg<br>ggccatttcatgctgcgctgcctccaccaccgatgagtacgacggacacaggacctag<br>ccctcccaccagtaccagtagcactctgtcccattgggagggtggcattctggga<br>catgaggagcaaaggaaggggggcaataaatgttgagccaagagcttcaaattactct<br>agagaaaccgacaaaaaaaaaaaaaaaaaaa (SEQ ID NO: 674) | NM_000713 | NM_144923 |
| Tnk1 | ggaactcggggtgcggccctcgccggccccgggccagcggccaggtccccgccc<br>tccgcgggatttactcctgtcccgcctcctcggatttagcccaggcagcctggaggt<br>tccgcatcgccgcttgaccaggtggagctggagcctggtactctagg<br>gcctaccctgagctcaccatctgaaggagagtgccatcatccttaggaactccttctcc<br>agacatgcttcctgaggctggctccctgtggctactgaagctgctccgggacatccag<br>ttggcccagttttactgccatccttgaggagcttaatgtcactcggccagagcactt<br>cgactttgtaaagcctgaggacctggacggcattggcatgggctggcctgcccagc<br>gcagactgtccgaagctctgaaaaggctacgttctgggcctaagtctaagaactgggt | NM_001251902 | NM_031880 |

TABLE 1-continued

| Gene | Human Gene Sequence | Human Sequence Accession No. | Murine Sequence Accession No. |
|---|---|---|---|
| | ctacaagatccttggaggttttgcccctgagcacaaggagcccaccctgccctcgga<br>cagcccacggcacctccctgagccagagggggggcctcaagtgtctgatcccagag<br>ggtgctgtttgcagaggggagctgctggttcaggctgcttcggtgtggtgcaccga<br>gggctgtggacgctgcccagtggcaagagtgtcccagtggctgtcaagtccctccg<br>ggtaggtcccgaaggcccgatgggcacagaactgggggacttcctgcgagaggta<br>tcggtcatgatgaacttggagcacccacacgtgctgcgtctgcacggccttgtactgg<br>gccagcctctgcagatggtgatggagctggcgccactgggctccctgcacgcgcgc<br>ctaacggccccggccccgacaccccgctgctcgtggccctgctctgcctcttcctg<br>cggcagctggcgggagccatggcgtacctgggggcccgcgggctggtgcaccga<br>gacctcgctacgcgcaacctactgctggcgtcgccgcgcaccatcaaggtggctga<br>cttcgggctggtgcggcctctgggcggtgcccggggccgctacgtcatgggcggg<br>ccccgccctatccctacgcctggtgtgcccagagagcctgcgcacggagccttc<br>tcgtctgcctcggacgtgtggatgtttggggtgacgctgtgggagatgttctccggg<br>ggcgaggaaccctgggcggggtcccaccgtacctcatcctgcagcggctggagg<br>acagagcccggctgcctaggcctcccctctgctccagggccctctactccctcgcctt<br>gcgctgctgggcccccaccctgccgaccggcctagcttttcccacctggagggc<br>tgctgcaagaggccgggccttcggaagcatgctgtgtgagggatgtcacagaacca<br>ggcgcccgaggatggagactggtgaccccatcacagtcatcgagggcagctcctc<br>tttccacagccccgactccacaatctggaagggccaggatggtcgcaccttcaaagt<br>gggcagcttcccagcctcggcagtgacgctggcagatgcgggggcttgccagcc<br>acccgtccagtccacagaggcaccctgcccggggagatcaacacccaggaagca<br>tagatggagacagaaagaaggcaaatctagggatgcgcccccagcacgggggcca<br>gaggaggaacatgcccctggagaggatgaaaggcatttccaggagtctggagtcag<br>ttctgtccctcggtcctcgtcccacaggggggtggttcaagcccccctgaaattcgaca<br>agccagagctgtgcccagggacctccaggcctgcctccacgcccacctttatcctc<br>tagctctcctcagcccagccagccctctagggagaggcttccctggcccaaaagaaa<br>accccacacaatcaccccatgggaatgcctggagcccgtaaagccgctgccctct<br>ctggaggcctcttgtccgatcctgagttgcagaggaagattatggaggtggagctga<br>gtgtgcatggggtcacccaccaggagtgccagacagcactaggagccactgggg<br>agatgtggtttctgccatccggaacctcaaggtagatcagtccttccacctgagtagcc<br>ggtccagagctgactgctggcgcatcctggagcattaccagtgggacctctcagctg<br>ccagccgctatgtcctggccaggccctgagctcagcttctgcgggcacagacacca<br>gcatgaaaagcctaggccctgagggcctggccacatgggacaagcggaacca<br>gaacaaggtcccgacaggggtagacgttccacctggggagatcccacctgccgtag<br>gcacatggaggaggagcccagagttgggcactggcaaatgtcctcctcctcccatg<br>ctcctggcttctgaaggctgaagctcctttggctgggccaagaaggatctagtctgcc<br>cactacattctcaaacaagaggacttggaggaaaagagctgctatacatcatatgcag<br>aggaagcttctacgcgctagagaggatcaaggggccacactggaccatgtgaacag<br>ccatcctgaactgccatcagctaccacactggactctgcagggcagccatcctggat<br>gatggaagccaccatattgacttgggggtataggcccaaactgccttcgtttggtccag<br>ggccatcgtgggtgatgacgattgctctcttgcactcaaggacattgtgatgctggtagt<br>atggattatgagatggactagcccctgccccagcccagctctcacattcccctttgttttt<br>tcccataccaactgcttctaccctcccctattacatacttctttcaatgtccaaaaagttac<br>aaagtttatatgaatgtaacatataaaaaaa (SEQ ID NO: 675) | | |
| Prkab2 | actgggcggactccgcgccgccggccttgtagccattttaggaggaatcgctggtcg<br>ccagcgaggggtgcggcttcaatttcaataactttattggtggcctgatctgcagaaca<br>gccatcacatatgtggccctggaggttgggagcgcatcgcccgaggtggtccccg<br>acgagctgcagccatgggaaacaccaccagcgaccgggtgtccggggagcgcca<br>cggcgccaaggctgcacgctccgagggcgcaggcggccatgcccgggggaagg<br>agcacaagatcatggtggggagtacggacgaccccagcgtgttcagcctccctgac<br>tccaagctccctggggacaaagagtttgtatcatggcagcaggatttggaggactcc<br>gtaaagcccacacagcaggcccggcccactgttatccgctggtctgaaggaggcaa<br>ggaggtcttcatctctgggtccttcaacaattggagcaccaagattccactgattaaga<br>gccataatgactttgttgccatcctggacctccctgagggagagcaccaatacaagtt<br>ctttgtggatggacagtgggttcatgatccatcagagcctgtggttaccagtcagcttg<br>gcacaattaacaatttgatccatgtcaagaaatctgattttgaggtgttcgatgctttaaa<br>gttagattctatggaaagttctgacatcttgtagagaccttttccagctcaccccccagg<br>gccttatggtcaagaaatgtatgcgtttcgatctgaggaaagattcaaatccccaccca<br>tccttcctcctcatctacttcaagttattcttaacaaagacactaatatttcttgtgacccag<br>ccttactccctgagcccaaccatgttatgctgaaccatctctatgcattgtccattaagg<br>acagtgtgatggtccttagcgcaaaccatcgctacaagaagaagtatgttactactctg<br>ctatacaagcccatttgaagggatcccttcttgcctctaaggattcaggagaagcatct<br>cccttgcatttctggactgaaccagtcttacctgagactggaaggctgatttgctttgag<br>gctgatatgtgtgtttcagagcctctgagtaggatgctctgcttttgcatttgattgcagat<br>gagagctttgagttcacggaatttattttaagaaaaaaaaaatatacatatgagaagaa<br>ggtaaatggaagcctcctagccccagctagaagtaagtttctgcctgtgggttttcacc<br>aagacctgtttgggggcgctgcaggaataactatataggaagattttcctaaaatgaa<br>agaacagcaaactcttaggatccttgttgggtggagattctatcactgctaccttggctc<br>tccaaggaatgggcttgtgctagaccgctgccctacttaacagctgcctcattgcaag<br>ggcagttttcttgcatgggttctctatattcccagagtatgtggcacaatctgtgttgttta<br>tatgataccagatgccccacaagaacccttattcctcatttcacattcttcctttaatag<br>cctccttcagatcccatacctgaccctctctaacacaaaacttattgggtaagtgactttt<br>gaaaagttttgtggcacctgacccacccccagacactagggctatcagaaggtctcctt<br>tttagcccagcacaggcccaggccacttttgtcgtgtttgttttaacttctaaagaaaattttt | NM_005399 | NM_182997 |

TABLE 1-continued

| Gene | Human Gene Sequence | Human Sequence Accession No. | Murine Sequence Accession No. |
|---|---|---|---|
| | gtttcagcattataagttaaggcagaatgcagaacacctacatttttgttttagtttggtgc<br>caaggctcaggctgttttttggcaaattcccgaaagttttcccactttgcctggccctgca<br>ctgtcttttcttctatgtaaacagttctgtaggcaggagtggaacccgggagtattttc<br>atgtctttcatccttgaaagattttttatgtgcagcatttttttttttaattaaaaaatgcctttc<br>attggtcttaagagaccgcattggagaatttcaggcttttgataaatgcttcttcaaagag<br>attttcttctctagtctagccttccacattcttagattaatatggccaaccctgtacacatca<br>ctacactaaacactgctctagataaactgctcaagttcatttaactcatttgatgcaccta<br>aagggggttcctcattttaaagattttgttaggccaagaagcaagagagtattcctagtatt<br>cccaaccatgaaaagtatcattctttgcaccaaatgttaacaaaatcattttgttctcctgc<br>ctcttcttttaaaggtgtttgatgattaagtggggtcactgaattccatttgtggactgaa<br>aagtattcaatccacttttgggggttcagagataaaacattttttcccaagtagctgggct<br>cttccattttgcagattttttgtcaaataatcaacactaaaggagctaaactgtttttatgaat<br>gagagactccctgactgctcagatgaccctagccacactgaaagggcacctacagg<br>tcagtttagctacctcctgtctttcccatgcaaagctgataacacagttgtctttggacttg<br>tagacctcttggattccaggtgtgatggagtaaagtgtgggattgttgttttgctgggat<br>ggccacctctgcagcaaaaggcttttgtggagaaccttttatgttcccaaccacttttttg<br>aatggtgtgccatttaaaaatccaggccagatcctattataaccaactctcaggatttac<br>agccttcagttgtactagaattttgtttaatccaatactcattaaataagtgggccacttag<br>gaagattcaaaatcttggttattacatgaagtttgttatatttcttgtcaacagtattgaaat<br>gtaatatgtatgttcatgtatgaaaattttactccacacagtgtttcagtagagtggg<br>gcaggaaaagagatctcttcgatttctttcaggcctgaggcttttgtgaaatgcgtcagc<br>cccctgtgacagtaggttttgatgctagtgatcttcagatctttctctctggaaatgtgca<br>gagagtgtcagtttcccaagttctgaggtaactctcagcccagatgtgaaatgggagc<br>ctaccagctggtatagaagggaatgggtaggaggcactgggtgctgactcattcagc<br>actgtccctttctatactgctgatacatcccatggttctgagaagccttatctcagtctatt<br>tggaagagagggaggaagagaaggaagtaacccaaagtactactcatttatcattgt<br>atattgattagttaaagggataattaatttaatgctgaggagagtttgacagattttgaaa<br>atgagtaaaggcaaaaaaattttttttagccttatttttgcttttgggaattttacagagtca<br>aagtaggcagaataagaaaatagttcttcaggagggccgacctttaaagaacttcaac<br>atagtttcggaattgtggggaagaagaagtgactgagctgagaagtaataatagaat<br>aaagggttgagtaacttacaactgaaaatgatctctttttaaaagaaattaaatcagaca<br>ccacatggtggtgtccttggatctcactgtacagaattagcagtgtataaccatcttctct<br>tttcatcttgttccaattctctcctcttttcctttccattctgctttaagctcatgtgtcaggcag<br>actttaccagagtgtcagacattacctaaaacacatacgttagccatgctgctggtatg<br>gagattattccacaccatgattattagcctcctttaagctgaatgggatttaaccattctag<br>gcaacaccctgaagggcatacctaacctcaatagtgttggcttttaaaacgtatgtttg<br>tatggtagagaaactttgtaaaagaagattccaagagaagtttgtgaggatcctacaa<br>acccaggcccactcactttgctctttattctttctagtatcttgtagatctaatgggtctggg<br>ataaaaactttgaaaagtgtcaatattccatgtatgctgctgaaatgaagttaagtttgga<br>aagaagtgatacctctagactgggtttatattaatctgggatataaatgaagaagacata<br>ctaatagaactccttgcttttaattggggaaataggggcttaataattttgacctcaactaa<br>aaatgatatgcaatagtctctgtgtgtgtttgaaatacattgtgttctcagagatttctacat<br>tctcacgttctagtgattggggcatgggcttaatagcagatgtacagtgtattcctgcat<br>tattgtgattcccttaaagcccagttcttgctgtcttctaccaggggctgctgactccag<br>ttacccatggaatgcaggacctgggaggggtagccattaggggtcttcaaaactcttg<br>gatctaagcatttgtcactccttaagtgccaatcacaattggatatggaaggactgtgatt<br>tctgcaatgaacccaaacttttagagtaaaaagccaaatttaaattataagaaagaagg<br>gaaaaagagaaaaactcaagtctattacttgtagagtccaattcttagcaatggaatc<br>gctctaggattctagtttgggctttgtctggatttgcttttctcagttgtgctttgaagtgaat<br>aagcttttgttacaaattaattttttattagttccaatattagttggagttaacttgaattgattg<br>tatgtagcacagcacttttgcagtaagattggtgtgaaatactaaacactatggattttgt<br>aggtgtcaggttaaatggtcaagggatacctctcattaagtcatatattaggtattgatga<br>tcttacttcttttctgttcccagtacaaaacacttacctaacccagcttgtggttttaggac<br>agccaaagctcactgttgttggttagtcctaatcactcacgggtctcataaatgagact<br>tgtttgaattttggtacattggagcatgttggttggtattacacggcagcatttcgaatga<br>gtgcagctctgtgtctgtcagaaaggagagataagactactttgaagggaattaaatat<br>gtgagtcctcttttaatggtgcttttgtaacctttaatgctgaggtacagagctgctttttc<br>aatatttcataaaggagtggcagacaagagtggattttaaagctgttcttcaaacgtaat<br>ttgtcactggactctgacacacctggaaattatatgatatgatacatacagaaatgttgt<br>gggtttttccataaaactttaataaaagtattatacagcaataaaaaaaaaaaaaa<br>(SEQ ID NO: 676) | | |
| Trpm7 | gcgcgctcacgtggtccgtcccccagcccgtcgccggcggaggcgggcgcggg<br>gcgccgctcacgtggtccgtcccccagcccgtcgccggcggaggcgggcgcggg<br>cgcgtccctgtgccagtcacccggaggagttggtcgcacaattatgaaagactcgg<br>cttctgctgctagcgccggagctgagttagttctgagaaggtttccctgggcgttccttg<br>tccggcggcctctgctgccgcctccggagacgcttcccgatagatggctacttggcc<br>gcggaggaggaggaggtggagttgctgccccttccggagtccgcccccgtgaggaga<br>atgtcccagaaatcctggatagaaagcactttgaccaagagggaatgtgtatatattat<br>accaagttccaaggaccctcacagatgcctccaggatgtcaaatttgtcagcaactc<br>gtcaggtgtttttgtggtcgcttggtcaagcaacatgcttgttttactgcaagtcttgccat<br>gaaatactcagatgtgaaattgggtgaccatttttaatcaggcaatagaagaatggtctg<br>tggaaaagcatttcagaacagagcccaacggatgcttatggagtcataaatatcaagg<br>gggttctcattcctacagagctaagtatgtgaggctatcatatgacaccaaacctgaag<br>tcattctgcaacttctgcttaaagaatggcaaatggagttacccaaacttgttatctctgt | NM_017672 | NM_021450 |

TABLE 1-continued

| Gene | Human Gene Sequence | Human Sequence Accession No. | Murine Sequence Accession No. |
|---|---|---|---|
| | acatgggggcatgcagaaatttgagcttcacccacgaatcaagcagttgcttggaaa<br>aggtcttattaaagctgcagttacaactggagcctggattttaactggaggagtaaaca<br>caggtgtggcaaaacatgaggagatgccctcaaagaacatgcttccagatcatctcg<br>aaagatttgcactatcggaatagctccatggggagtgattgaaaacagaaatgatcttg<br>ttgggagagatgtggttgctccttatcaaaccttattgaaccccctgagcaaattgaatg<br>ttttgaataatctgcattcccatttcatattggtggatgatggcactgttggaaagtatgg<br>ggcggaagtcagactgagaagagaacttgaaaaaactattaatcagcaaagaattca<br>tgctaggattggccagggtgtccctgtggtggcacttatattttgagggtgggccaaat<br>gttatcctcacagttcttgaataccttcaggaaagcccccctgttccagtagttgtgtgtg<br>aaggaacaggcagagctgcagatctgctagcgtatattcataaacaaacagaagaa<br>ggagggaatcttcctgatgcagcagagcccgatattatttccactatcaaaaaaacatt<br>taactttggccagaatgaagcacttcatttatttcaaacactgatggagtgcatgaaaag<br>aaaggagcttatcactgttttccatattgggtcagatgaacatcaagatatagatgtagc<br>aatacttactgcactgctaaaaggtactaatgcatctgcatttgaccagcttatccttaca<br>ttggcatgggatagagttgacattgccaaaaatcatgtatttgtttatggacagcagtgg<br>ctggttggatccttggaacaagctatgcttgatgctcttgtaatgatagagttgcattttg<br>taaaacttcttattgaaaatggagtaagcatgcataaattccttaccattccgagactgg<br>aagaacttacaacactaaacaaggtccaactaatccaatgctgtttcatcttgttcgag<br>acgtcaaacagggaaatcttcctccaggatataagatcactctgattgatataggactt<br>gttattgaatatctcatgggaggaacctacagatgcacctatactaggaaacgttttcga<br>ttaatatataatagtcttggtggaaataatcggaggtctggccgaaatacctccagcag<br>cactcctcagttgcgaaagagtcatgaatctttttggcaataggcagataaaaaggaa<br>aaaatgaggcataaccatttcattaagacagcacagccctaccgaccaaagattgata<br>cagttatggaagaaggaaagaagaaaagaaccaaagatgaaattgtagacattgatg<br>atccagaaaccaagcgctttccttatccacttaatgaacttttaatttgggcttgccttatg<br>aagaggcaggtcatggcccgttttcatggcaacatggtgaagaatcaatggctaaag<br>cattagttgcctgtaagatctatcgttcaatggcatatgaagcaaagcagagtgacctg<br>gtagatgatacttcagaagaactaaaacagtattccaatgattttggtcagttggccgtt<br>gaattattagaacagtccttcagacaagatgaaaccatggctatgaaaagctcacttat<br>gaactgaagaactggagtaattcaacagccttaagttagcagtttcttcaagacttaga<br>cctttttgtagctcacacctgtacacaaatgttgttatctgatatgtggatgggaaggctg<br>aatatgaggaaaaattcctggtacaaggtcatactaagcatttttagttccacctgccata<br>ttgctgttagagtataaaactaaggctgaaatgtcccatatcccacaatctcaagatgct<br>catcagatgacaatggatgacagcgaaaacaactttcagaacataacagaagagatc<br>cccatggaagtgttttttaagaagtacggattttggatagtaatgaaggaaagaatgaga<br>tggagatacaaatgaaatcaaaaaagcttccaattacgcgaaagttttatgcctttatc<br>atgcaccaattgtaaaattctggtttaacacgttggcatatttaggattttctgatgcttttata<br>catttgtggttcttgtacaaatggaacagttaccttcagttcaagaatggattgttattgctt<br>atattttttacttatgccattgagaaagtccgtgagatctttatgtctgaagctgggaaagt<br>aaaccagaagattaaagtatggtttagtgattacttcaacatcagtgatacaattgccat<br>aattctttcttcattggatttggactaagatttggagcaaaatggaacttttgcaaatgcat<br>atgataatcatgttttttgtggctggaagattaatttactgtcttaacataatattttggtatgt<br>gcgtttgctagattttctagctgtaaatcaacaggcaggacccttatgtaatgatgattgg<br>aaaaatggtggccaatatgttctacattgtagtgattatggctcttgtaaacttagttttgg<br>tgttcccagaaaggcaatacttatcctcatgaagcaccatcttggactcttgctaaaga<br>tatagtttttcaccccatactggatgatttttggtgaagtttatgcatacgaaattgatgtgtg<br>tgcaaatgattctgttatccctcaaatctgtggtcctgggacgtggttgactccatttcttc<br>aagcagtctacctctttgtacagtatatcattatggttaatcttcttattgcatttttcaacaa<br>tgtgtatttacaagtgaaggcaatttccaatattgtatggaagtaccagcgttatcatttta<br>ttatggcttatcatgagaaaccagttctgcctcctccacttatcattcttagccatatagttt<br>ctctgttttgctgcatatgtaagagaagaaagaaagataagacttccgatggaccaaa<br>acttttccttaacagaagaagatcaaaagaaacttcatgattttgaagagcagtgtgttga<br>aatgtatttcaatgaaaaagatgacaaatttcattctgggagtgaagagagaattcgtgt<br>cactttttgaaagagtggaacagatgtgcattcagattaaagaagttggagatcgtgtca<br>actacataaaaagatcattacaatcattagattctcaaattggccatttgcaagatctttca<br>gccctgacggtagatacattaaaaacactcactgcccagaaagcgtcggaagctagc<br>aaagttcataatgaaatcacacgagaactgagcatttccaaacacttggctcaaaacct<br>tattgatgatggtccttttaagaccttctgtatggaataagcatggtgttgtaaatacactt<br>agctcctctcttcctcaaggtgatcttgaaagtaataatccttttcattgtaatattttaatga<br>aagatgacaaagatccccagtgtaatatatttggtcaagacttacctgcagtaccccag<br>agaaaagaatttaattttccagaggctggttcctcttctggtgccttattcccaagtgctg<br>tttccctccagaactgcgacagaactacatggggtagaactcttaaaaatatttaata<br>aaaatcaaaaattaggcagttcatctactagcataccacatctgtcatccccaccaacc<br>aaattttttgttagtacaccatctcagccaagttgcaaaagccacttggaaactggaacc<br>aaagatcaagaaactgtttgctctaaagctacagaaggagataatacagaatttggag<br>catttgtaggacacagagatagcatggatttacagaggtttaaagaaacatcaaacaa<br>gataaaaatactatccaataacaatacttctgaaaacactttgaaacgagtgagttctctt<br>gctggatttactgactgtcacagaacttccattcctgttcattcaaaacaagcagaaaaa<br>atcagtagaaggccatctaccgaagacactcatgaagtagattccaaagcagctttaa<br>taccggattggttacaagatagaccatcaaacagagaaatgccatctgaagaaggaa<br>cattaaatggtctcacttctccattttaagccagctatggatacaaattactattattcagct<br>gtggaaagaaataacttgatgaggttatcacagagcattccatttacacctgtgcctcc<br>aagagggggagcctgtcacagtgtatcgtttggaagagagttcacccaacatactaaat<br>aacagcatgtcttcttggtcacaactaggcctctgtgccaaaatagagtttttaagcaaa<br>gaggagatgggaggagggtttacgaagagctgtcaaagtacagtgtacctggtcaga | | |

TABLE 1-continued

| Gene | Human Gene Sequence | Human Sequence Accession No. | Murine Sequence Accession No. |
| --- | --- | --- | --- |
| | acatgatatcctcaaatcagggcatctttatattatcaaatcttttcttccagaggtggtta<br>atacatggtcaagtatttacaaagaagatacagttctgcatctctgtctgagagaaattc<br>aacaacagagagcagcacaaaagcttacgtttgcctttaatcaaatgaaacccaaatc<br>cataccatattctccaaggttccttgaagttttcctgctgtattgccattcagcaggacag<br>tggtttgctgtgaagaatgtatgactggagaatttagaaaatacaacaataataatgg<br>agatgagattattccaactaatactctggaagagatcatgctagcctttagccactgga<br>cttacgaatatacaagaggggagttactggtacttgatttgcaaggtgaggtgaaaatt<br>tgactgacccatctgtgataaaagcagaagaaaagagatcctgtgatatggtttttggc<br>ccagcaaatctaggagaagatgcaattaaaaacttcagagcaaaacatcactgtaatt<br>cttgctgtagaaagcttaaacttccagatctgaagaggaatgattatacgcctgataaa<br>attatatttcctcaggatgagccttcagatttgaatcttcagcctggaaattccaccaaag<br>aatcagaatcaactaattctgttcgtctgatgttataatattaatattaagaatcattggttt<br>Igcctgcacctcacagaaatgaactgtgtcacttttccctcgggaggaaattgtttggta<br>atatagaaaggtgtatgcaagttgaatttgctgactccagcacagttaaaaggtcaatat<br>tcttttgacctgattaatcagtcagaaagtccctataggatttgagctggcagctgagaa<br>attttaaaggtaattgataattagtatttataaattttaaagggctctttgtatagcagagg<br>atctcatttgactttgttttgatgagggtgatgctctacttatgtggtacaataccattaac<br>caaaggtaggtgtccatgcagattttattggcagctgttttattgccattcaactaggga<br>aatgaagaaatcacgcagccttttggttaaatggcagtcaaaattttcctcagtgtattta<br>gtgtgttcagtgatgatatcactggttcccattctttgtttgttggccacgggaaggg<br>aaatgacttgttctaattctaggttcacagaggtatgagaagcctgaactgaagaccatt<br>ttcaagagggacggtatttatgaatcagggttaggctccatatttaaagatagagccag<br>ttttttttttttaaatagaacccaaattgtgtaaaaatgttaattgggtttttttaaacattgttttat<br>caagtcactgttaagtagaagaaagccatggtaaactgatacataacctaaattataaa<br>agcagaaacctaactcactcgtcaagggttagttaccttttgaggaaagttaaagtactt<br>ttttcccctatctgtatctatagcaacaacccagaacttacaaacttcgccaaagatttgatt<br>gattgttatatcaaatcagaatgtaaacatgaactcttgcatatatttaaaattgtgttgga<br>acatttgaacatgaatgctgtttgtggtacttaagaaaattaattcagttggattatcattatg<br>tgatactggcagattgcagtgcaaccttatgccaataaaatgtaatttaacagccccag<br>atattgttgaatattcaacaataacaagaaaagcttttcatctaagtttttatgctttaattttt<br>ttctattttttcttttcaagtaccttggtactaattttaattttatttggaagggagcagtat<br>aaagcttatttgtatttagtagtgtatctcatagatacagacaaggcaagagatgataag<br>ctgtttaaatagtgtaaatattgattggggtggggagaaagaaaaagtgtattacttaa<br>agatactatatacgttttgtatatcattaaatctttaaaagaaatgaaataaatttattgttta<br>cagatgtttagtgagtttaatcattctgaaaaattatctgacattttcagggtgtcaatttga<br>gtatcagtttttttaaatgaaccatttgtatacctgtgcttttgatctcctgtcctgtacaatg<br>tttaaattaatactgatttcttactgtcttcttaagaaatctttttttgttaggccaaaaagg<br>gcaatatgggctgtctgttgattttaattttatattgattattttcacaggattataaatagtag<br>ctatactttttttttttttttttttttttgagacggagtctcgctctgttgcttgggctggagtgca<br>gtggtgcgatctcagctcaccacaaccgccgccttccgggtttaagtgattctcctgcc<br>tcagcctcccgagtagctgggactacaggcacacgccaccatgcccagctaattata<br>tattttttagtagagacagggttttcactatgttggccagtgtggtcacaaactcctgacctt<br>gtgagccaccgcacctgttctgctaacacttatttagtgcctactgtgtaccagacatta<br>ctctaagtatttcacatatattaacctacttaatcgttataacaatgttataaagaaataggt<br>gttattatcctgttttgcagatttgaaagtcaaggtgctagagaggtaaagtaacgtcca<br>taagattcttacgtttatttaataataagtagcaacggtaggatttgaacccaggctggct<br>gcctttcatctatactgtttttgttttgttttgttttgttttgttttgttttgtttgtcttggtggggc<br>atggtggctcatgcctgtaatcccagcacttcgggaggccaaggcaggtggatcact<br>tgggctcaggagtttgagaccagcctgggcaacatggcaaaatcctatctctgctaaa<br>aaaaaaaatacaaaaattaggccaggtgcagtggctcatgcctgtaatcccagcactt<br>tgggaggccaaggtgggcggatcacaaggtcaggagttcgagaccagcctgacca<br>acatagtgaaaccccgtctctactaaaaatacaaaaattagctgggcatggcggtga<br>gtgcctgtaatcccagctactcaggagtctgaggcaggagaattgcttgaacctggg<br>aggtggaggttgcagtgagctgagatcgtgccattgcgctccagcctgggcaacagt<br>gcgagactccgtcaaaaaaaaaaaaataactggatgtgatggtgtgcacctgtagttc<br>cagctacttgggagactgaggtggaggatcacttgagcctgggagactgaggcag<br>cagtgagctgagatcatgccactgctttccaacctgggcaacagagtgagatcctgtc<br>tcagaaagaaaaaaaaaaaaagacaacctcttgctctgttgcccaggctggagtgt<br>agtagcgtgatcatagctcactgcagccgtaaactcctgggctcaagcaatcctcctg<br>ccactgcctcttgattaggtggaaccacaggcatgcaccaccacacgtacctaatttta<br>tatatatatttttttattttttcattttttattttttttttgtttttttgagttgaagtctcactctgttg<br>cccaggccggagtacagtggcacaatcttggctcactgcaacctctgcctcccaagatc<br>aagcaattctcgtgcttcagcctccaaagtagctgagattacaggtacccaccattatg<br>cctggctgattttttgtatttttcgtagagacaaggttcaccttgttggccaggctgatctc<br>aaactcctgacctcaagtgatccacctcccccggctacccaaagtactgggattatag<br>gtgtgagccaccatgcctgggtaacacccaactaattttaaatatatatttttgtagagat<br>ggggtctagccttgttgcccacgctggtctcaaattcctgggctcaagtgatcctctcg<br>cctgagcttcccaaagtggtagaattgcaggcatgaattgctgcacccagcctcatct<br>gtgctgtgaattatgtgctgtattgactctcaagcatgatgaccattggtggtttctgtac<br>catttcctgttacttactgaaacacacctactccattaacttcttgggttaagtctagaaa<br>gtaacagtttacttgtaaaccacatttcttatccccaataagtatttttataagattattaaag<br>ttcattattactaccctatgatgtgaaagtgtcatttgcttaatcttttttaaatttttattctcaa<br>cctcatcttactgaagagaataaaactcttttaccatattcttaaaatgtggaattctcggc<br>caggtgcagtggctcacgcctgtaattccatcactttgggaggccaaggtgggjggat<br>catctgaggtcaggagttcaagaccagcctggccaacatggtgagtaccccgtctcta | | |

TABLE 1-continued

| Gene | Human Gene Sequence | Human Sequence Accession No. | Murine Sequence Accession No. |
|---|---|---|---|
|  | ctaaaaatacaaaaattatctgggtgtggtggcgcgtgcctgtaggcccagctactca<br>ggaggctgaggcaggagaattgatgaacccaagaggtggaggttgcagtgagcct<br>agattgctgccactgcactccagcctgggtgacagcagaactctgtctcaaaaaaaa<br>catgtggaattcttttctgcaaatgttctctaatagtataccttcttcagtctctcgatatatg<br>tatgctattattttacaagtaatacatgttgattgtattggaaattatagaaaagattatattg<br>gattgtttagaaaatattttaaatgtgaagaaaaatataaaaattactcccttgttccactt<br>tccccactctcaagttagactatgttgttttcatagttagtttgctagcagtctaccccact<br>agattatatgcttcacagagggaagggaccctcaagaatcactggattgagtagcac<br>ccaatacccttgcttgctgcctggtttgtgatgggcatactgtaagaaaaaaaaatctgaa<br>tgacaaaatgttttccataataccagacttcctcttgaagagatgggtcgtaatgttgta<br>gtcttacatgcttacgtagacaatcaaagcaagaatactcaataaatggctatttaccac<br>ttgaaagaaa (SEQ ID NO: 677) | | |
| Ppp3cc | aaggcggaagggtggggagggcggcgctcggggcgggaggcccggccgggtc<br>cgctaggacagcggggccgctgggaagttgtgagagcggcgctcggggcgcgc<br>ttgcgtgcacgagggcccgggccgcgagcagccgcggccgtcccggtcgccacc<br>cttagcagcggtcgcggtcggtgccgaagcggtgttccccgccttagccgctggcg<br>cctcccaagagagcggccggtgggccctcgtcctgtcagtggcgtcggaggccgg<br>cgctgcggtggccgcgcccttctggtgctcggacaccgctgaggagccggggccg<br>ggcacggctggctgacggctccgggcagctaaggctgcccgaggagaaggcggc<br>ggccgcggcgtaggcgcacgtccggcgggctcctggagcctggaggaggccga<br>ggggaccatgtccggaggcgcttccacctctccaccaccgaccgcgtcatcaaag<br>ctgtccccttcctccaacccaacggcttactttcaaggaagtatttgagaatgggaaa<br>cctaaagttgatgttttaaaaaaccatttggtaaaggaaggacgactggaagaggaag<br>tagccttaaagataatcaatgatggggagccatcctgaggcaagagaagactatgat<br>agaagtagatgctccaatcacagtatgtggtgatattcatggacaattctttgacctaat<br>gaagttatttgaagttggaggatcacctagtaacacacgctacctctttctgggtgacta<br>tgtggacagaggctattcagtatagagtgtgtgctgtattatggagtttaaagattaat<br>catcccaaaacattgtttctgcttcggggaaatcatgaatgcaggcatcttacagactat<br>ttcaccttcaaacaggaatgtcgaatcaaatattcggaacaggtgtatgatgcctgtatg<br>gagacatttgactgtcttcctcttgctgccctcttaaaccagcagtttctctgtgtacatgg<br>aggaatgtcacctgaaattacttctttagatgacattaggaaattagacaggtttacgga<br>acctcccgccttggacctgtgtgtgacctgctttggtctgatccctcagaggattatgg<br>caatgagaagaccttggagcactatacccacaacactgtccgagggtgctcttatttct<br>acagttaccctgcagtttgtgaattttttgcagaacaataatttactatcaattatcagagcc<br>catgaagcccaagatgctgggtatcgaatgtacaggaagagccaagccacaggcttt<br>ccatcacttattacaattttctctgcccccaattacctagatgtctataacaataaagctgc<br>tgtgttgaaatatgaaaacaatgtcatgaatatcaggcagtttaactgttctccacaccc<br>ctactggcttccaaacttttatggatgttttcacatggtctttgccttttgttggggaaaag<br>tcacagagatgctggtaaatgtgctcaacatatgctctgatgacgaactgatttctgatg<br>atgaagcagaagatcactacattccaagctatcagaaaggaagcactacagttcgtaa<br>ggagatcatcaggaataagatcagagccattgggaagatggcacgggtcttttcaatt<br>cttcggcaagaaagtgagagtgtgctgactctcaagggcctgactcccacaggcaca<br>ctccctctgggcgtcctctcaggaggcaagcagactatcgagacagccacagtaga<br>agcggtagaggcccgggaagccatcagagggttctcgcttcagcacaagatccgg<br>agttttgaagaagcgcgaggtctggaccgaattaatgagcgaatgccaccccgaaa<br>ggatagcatacacgctggtgggccaatgaaatctgtaacctcagcacactcacatgct<br>gcgcacaggagcgaccaagggaagaaagcccattcatgacttagagtcctgccgtg<br>gctcaggtggatctaaaactcaagaacaaattctatttatttattattggaaaatgaaaag<br>caactcaaaacaacttcaacgtggaggtgcatttataattcagtctgcatttattctgtaa<br>aaaggtggctgttttataaattcttttaatttatgttcaatatatataaaaagtgcatctgtttt<br>gttttttcccttttttctccataattttaagaaatgaatctgattgttgtcaacacatttgtgaag<br>tcttgtgctataaaggggaacttcccctaataaaagggccttggaaacctcaaacctg<br>ggtttctgacttgaaaaaaaaaaaaaa (SEQ ID NO: 678) | NM_001243974 | NM_008915 |

In some aspects, the nucleic acids of the compositions encode the shRNA sequences targeting the sequences provided in Table 2. Table 2 further demonstrates enrichment in tumor versus spleen for the selected shRNA based on deep sequencing analysis ("Enrich Fold").

TABLE 2

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Akap8l | 54194 | ND000290 | CGAAACCGCAGGCTTATGATG | 1 | 0.5 | AKAP8L | 26993 |
| Akap8l | 54194 | ND000285 | CAGACTGCTCAGACAACAGTG | 2 | 0.7 | AKAP8L | 26993 |
| Akap8l | 54194 | TRCN0000288034 | CCACAAGGAACACTTCAAATA | 3 | 1.0 | AKAP8L | 26993 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Akap8l | 54194 | ND000291 | AGACCTCTACCGGTCAAGCTA | 4 | 1.1 | AKAP8L | 26993 |
| Akap8l | 54194 | ND000286 | ATAGAGGCTACGAGAACTATG | 5 | 1.4 | AKAP8L | 26993 |
| Akap8l | 54194 | TRCN0000288033 | CCAGAACATCATACCCGAGTA | 6 | 1.6 | AKAP8L | 26993 |
| Akap8l | 54194 | ND000289 | TTAGATATGATGCCGCACTTG | 7 | 1.7 | AKAP8L | 26993 |
| Akap8l | 54194 | TRCN0000088483 | CCCACCTGTGATTATGGATAT | 8 | 1.8 | AKAP8L | 26993 |
| Akap8l | 54194 | ND000288 | GGCGAGAATCCTTTCACTGAC | 9 | 1.9 | AKAP8L | 26993 |
| Akap8l | 54194 | TRCN0000088486 | CGAGAACTATGGTTATGGCTA | 10 | 2.1 | AKAP8L | 26993 |
| Akap8l | 54194 | ND000292 | CAAATACCGGACCTTCTATGA | 11 | 2.8 | AKAP8L | 26993 |
| Akap8l | 54194 | TRCN0000307538 | GATATCTGAAGGGCGAGAATC | 12 | 3.8 | AKAP8L | 26993 |
| Akap8l | 54194 | TRCN0000307539 | ACCGGTCAAGCTATGACTATG | 13 | 4.4 | AKAP8L | 26993 |
| Akap8l | 54194 | ND000287 | TTGGATTTGGCAATGGCATGA | 14 | 7.1 | AKAP8L | 26993 |
| Akap8l | 54194 | TRCN0000088487 | CCGAAACCACTTTGCAGTCTA | 15 | 11.8 | AKAP8L | 26993 |
| Alk | 11682 | TRCN0000361004 | ACCTAGAGGAGAATCACTTTA | 16 | 0.2 | ALK | 238 |
| Alk | 11682 | TRCN0000023725 | GCCTTCATGGAAGGGATATTT | 17 | 0.4 | ALK | 238 |
| Alk | 11682 | TRCN0000361067 | CGGGCCTGTATACCGGATAAT | 18 | 0.7 | ALK | 238 |
| Alk | 11682 | TRCN0000361003 | GTGGAGCCACCTACGTGTTTA | 19 | 0.9 | ALK | 238 |
| Alk | 11682 | ND000299 | GGAATCTGACCTGGACGATGA | 20 | 1.0 | ALK | 238 |
| Alk | 11682 | ND000293 | CTTCGTTGTACCCTCGCTCTT | 21 | 1.1 | ALK | 238 |
| Alk | 11682 | ND000298 | GAAGGGATATTTACCTCTAAA | 22 | 1.3 | ALK | 238 |
| Alk | 11682 | TRCN0000023728 | CCGGGATATTGCTGCTAGAAA | 23 | 1.7 | ALK | 238 |
| Alk | 11682 | TRCN0000023724 | GCATCGCATTGGAGGCTATAA | 24 | 2.1 | ALK | 238 |
| Alk | 11682 | ND000297 | GGGCCTGTATACCGGATAATG | 25 | 2.4 | ALK | 238 |
| Alk | 11682 | TRCN0000023726 | CGGAGGATATATAGGTGGCAA | 26 | 2.9 | ALK | 238 |
| Alk | 11682 | ND000300 | ATCGAATACGGTCCAGTAGTA | 27 | 3.4 | ALK | 238 |
| Alk | 11682 | ND000296 | TGCTTCCGCGTAGTCAGAAAT | 28 | 3.8 | ALK | 238 |
| Alk | 11682 | ND000294 | CCTGCGGCAATGTCAACTATG | 29 | 9.4 | ALK | 238 |
| Alk | 11682 | TRCN0000023727 | CCCGAACGTCAACTATGGTTA | 30 | 9.5 | ALK | 233 |
| Alk | 11682 | ND000295 | GGCGAGGAGACGATTCTTGAA | 31 | 13.5 | ALK | 238 |
| Arhgap5 | 11855 | TRCN0000321111 | TGGTACATATCCTCGTAAATT | 32 | 0.5 | ARHGAP5 | 394 |
| Arhgap5 | 11855 | TRCN0000360350 | ATTGCAATCAGTATATCATTC | 33 | 0.8 | ARHGAP5 | 394 |
| Arhgap5 | 11855 | TRCN0000360421 | GATCATGAACGTAACCATAAA | 34 | 1.2 | ARHGAP5 | 394 |
| Arhgap5 | 11855 | TRCN0000360349 | TGATAATAGCAGCAACTAAAT | 35 | 1.3 | ARHGAP5 | 394 |
| Arhgap5 | 11855 | TRCN0000321112 | AGCATGACTGGAGAGGTTTAA | 36 | 1.4 | ARHGAP5 | 394 |
| Arhgap5 | 11855 | TRCN0000321110 | TGATAGTCAGAATCGAATTAT | 37 | 1.4 | ARHGAP5 | 394 |
| Arhgap5 | 11855 | TRCN0000321109 | GAACTGGTTCATGGGTATATA | 38 | 1.5 | ARHGAP5 | 394 |
| Arhgap5 | 11855 | TRCN0000012706 | GCAAGCTCTAAGAGGAGTATT | 39 | 3.6 | ARHGAP5 | 394 |
| Arhgap5 | 11855 | TRCN0000012707 | CCTGATCCTTTGATTCCATAT | 40 | 6.0 | ARHGAP5 | 394 |
| Arhgap5 | 11855 | TRCN0000321181 | ACAGATCCTCTTGGTATTATA | 41 | 8.3 | ARHGAP5 | 394 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Arhgap5 | 11855 | TRCN0000012703 | GCACGATTTAATGTCAACATT | 42 | 15.7 | ARHGAP5 | 394 |
| Blvrb | 233016 | ND000310 | CTCAGTCCCACTACAGTAATG | 43 | 0.8 | BLVRB | 645 |
| Blvrb | 233016 | ND000308 | TGACCACATCCGGATGCATAA | 44 | 1.0 | BLVRB | 645 |
| Blvrb | 233016 | ND000306 | GCCTCACCACCAATGAGTATG | 45 | 1.2 | BLVRB | 645 |
| Blvrb | 233016 | ND000309 | TGAGAAATGACACAAATAGAG | 46 | 1.2 | BLVRB | 645 |
| Blvrb | 233016 | ND000303 | TGCAAGAGTCAGGGCTGAAAT | 47 | 1.3 | BLVRB | 645 |
| Blvrb | 233016 | ND000301 | GGAAGCTGTCATCGTGCTACT | 48 | 1.5 | BLVRB | 645 |
| Blvrb | 233016 | ND000304 | GCATAAGATTCTGCAAGAGTC | 49 | 1.9 | BLVRB | 645 |
| Blvrb | 233016 | TRCN0000042385 | CCTCAGTCCCACTACAGTAAT | 50 | 2.2 | BLVRB | 645 |
| Blvrb | 233016 | ND000302 | TCGAGGGTCATATCCAAGCAT | 51 | 2.4 | BLVRB | 645 |
| Blvrb | 233016 | TRCN0000324726 | GAACATCGTGACAGCCATGAA | 52 | 3.0 | BLVRB | 645 |
| Blvrb | 233016 | TRCN0000042384 | CCAATGAGTATGACGGACACA | 53 | 3.1 | BLVRB | 645 |
| Blvrb | 233016 | ND000307 | GAGGGTCATGCATCCTGAGAA | 54 | 3.1 | BLVRB | 645 |
| Blvrb | 233016 | ND000305 | TAGGAGACCAACCACTAACTG | 55 | 5.3 | BLVRB | 645 |
| Blvrb | 233016 | TRCN0000324662 | GCTGAAATACGTGGCAGTGAT | 56 | 5.3 | BLVRB | 645 |
| Blvrb | 233016 | TRCN0000042386 | CGGATGCATAAGATTCTGCAA | 57 | 8.0 | BLVRB | 645 |
| Cblb | 208650 | ND000027 | TCTACATCGATAGTCTCATGA | 58 | 0.7 | CBLB | 868 |
| Cblb | 208650 | TRCN0000244603 | CTACACCTCACGATCATATAA | 59 | 0.9 | CBLB | 868 |
| Cblb | 208650 | TRCN0000244605 | TGAGCGAGAATGAGTACTTTA | 60 | 0.9 | CBLB | 868 |
| Cblb | 208650 | ND000026 | ATCGAACATCCCAGATTTAGG | 61 | 1.0 | CBLB | 868 |
| Cblb | 208650 | ND000029 | TAAAGTGTACTGGTCCATTAG | 62 | 1.4 | CBLB | 868 |
| Cblb | 208650 | TRCN0000244607 | CTTGTACTCCAGTACCATAAT | 63 | 1.5 | CBLB | 868 |
| Cblb | 208650 | ND000028 | GTATGAGACAGAAGGACTGAG | 64 | 1.5 | CBLB | 868 |
| Cblb | 208650 | TRCN0000244604 | CCAGATTTAGGCATCTATTTG | 65 | 1.6 | CBLB | 868 |
| Cblb | 208650 | ND000031 | TCAGCACTTGAGACTTATATT | 66 | 1.7 | CBLB | 868 |
| Cblb | 208650 | ND000024 | TACACCTCACGATCATATAAA | 67 | 2.1 | CBLB | 868 |
| Cblb | 208650 | ND000033 | AACACAGACGCCATGATTTGC | 68 | 5.1 | CBLB | 868 |
| Cblb | 208650 | ND000032 | AAGATGTCAAGATTGAGCCTT | 69 | 5.3 | CBLB | 868 |
| Cblb | 208650 | TRCN0000244606 | CCCTGATTTAACCGGATTATG | 70 | 6.1 | CBLB | 868 |
| Cblb | 208650 | ND000030 | AGCCAGGTCCAATTCCATTTC | 71 | 10.0 | CBLB | 868 |
| Cblb | 208650 | ND000025 | CGAGCGATCCGGCTCTTTAAA | 72 | 10.8 | CBLB | 868 |
| Cdkn2a | 12578 | ND000317 | CTTGGTGAAGTTCGTGCGATC | 73 | 0.6 | CDKN2A | 1029 |
| Cdkn2a | 12578 | TRCN0000257162 | CGCTCTGGCTTTCGTGAACAT | 74 | 0.8 | CDKN2A | 1029 |
| Cdkn2a | 12578 | TRCN0000362594 | GATGATGATGGGCAACGTTCA | 75 | 0.9 | CDKN2A | 1029 |
| Cdkn2a | 12578 | TRCN0000231228 | TCCCAAGAGCAGAGCTAAATC | 76 | 0.9 | CDKN2A | 1029 |
| Cdkn2a | 12578 | TRCN0000362666 | TCTTGGTGAAGTTCGTGCGAT | 77 | 1.0 | CDKN2A | 1029 |
| Cdkn2a | 12578 | TRCN0000362596 | ACGGGCATAGCTTCAGCTCAA | 78 | 1.1 | CDKN2A | 1029 |
| Cdkn2a | 12578 | TRCN0000222730 | GCTCGGCTGGATGTGCGCGAT | 79 | 1.1 | CDKN2A | 1029 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Cdkn2a | 12578 | TRCN0000231225 | TTGAGGCTAGAGAGGATCTTG | 80 | 1.2 | CDKN2A | 1029 |
| Cdkn2a | 12578 | TRCN0000222731 | CATCAAGACATCGTGCGATAT | 81 | 2.1 | CDKN2A | 1029 |
| Cdkn2a | 12578 | TRCN0000077815 | GTGAACATGTTGTTGAGGCTA | 82 | 2.3 | CDKN2A | 1029 |
| Cdkn2a | 12578 | TRCN0000077816 | GTCTTTGTGTACCGCTGGGAA | 83 | 3.3 | CDKN2A | 1029 |
| Cdkn2a | 12578 | TRCN0000362595 | CTAGCGATGCTAGCGTGTCTA | 84 | 4.1 | CDKN2A | 1029 |
| Cdkn2a | 12578 | TRCN0000222729 | GTGATGATGATGGGCAACGTT | 85 | 5.6 | CDKN2A | 1029 |
| Cdkn2a | 12578 | TRCN0000231226 | GCTCAACTACGGTGCAGATTC | 86 | 6.9 | CDKN2A | 1029 |
| Cdkn2a | 12578 | TRCN0000231227 | TCAAGACATCGTGCGATATTT | 87 | 7.2 | CDKN2A | 1029 |
| Dgka | 13139 | TRCN0000024825 | GAGCTAAGTAAGGTGGTATAT | 88 | 0.7 | DGKA | 1606 |
| Dgka | 13139 | TRCN0000368765 | GCGATGTACTGAAGGTCTTTG | 89 | 0.7 | DGKA | 1606 |
| Dgka | 13139 | ND000059 | TCAGTGATGTGTACTGCTACT | 90 | 0.8 | DGKA | 1606 |
| Dgka | 13139 | ND000054 | GTATATCTCGACCGATGGTTC | 91 | 1.0 | DGKA | 1606 |
| Dgka | 13139 | TRCN0000378505 | TGATGCGAGTGGCCGAATATC | 92 | 1.1 | DGKA | 1606 |
| Dgka | 13139 | TRCN0000024828 | CCTAGGATTTGAACAATTCAT | 93 | 1.2 | DGKA | 1606 |
| Dgka | 13139 | ND000058 | AAAGATTCTCAAGGATATAGA | 94 | 1.6 | DGKA | 1606 |
| Dgka | 13139 | ND000056 | GAGGGATGTTCCATCACCTTC | 95 | 1.9 | DGKA | 1606 |
| Dgka | 13139 | ND000053 | TACAGACATCCTTACACAACC | 96 | 2.0 | DGKA | 1606 |
| Dgka | 13139 | TRCN0000024824 | GCCGAATATCTAGACTGGGAT | 97 | 3.4 | DGKA | 1606 |
| Dgka | 13139 | TRCN0000024827 | CGGCTGGAAGTGGTAGGAATA | 98 | 3.5 | DGKA | 1606 |
| Dgka | 13139 | ND000055 | GTTCCTCAGTTCCGGATATTG | 99 | 5.0 | DGKA | 1606 |
| Dgka | 13139 | TRCN0000024826 | CCTGAGCTGTAACTTCTGTAA | 100 | 6.8 | DGKA | 1606 |
| Dgka | 13139 | ND000057 | TGCGAACAGAGCATTAGCCTT | 101 | 7.8 | DGKA | 1606 |
| Dgka | 13139 | TRCN0000361167 | TGTTCCTCAGTTCCGGATATT | 102 | 10.2 | DGKA | 1606 |
| Dgkz | 104418 | ND000063 | CACCTTCCACAGCAAGGAGAT | 103 | 0.4 | DGKZ | 8525 |
| Dgkz | 104418 | ND000061 | ATCGTGGTGCATACCCAATGC | 104 | 0.4 | DGKZ | 8525 |
| Dgkz | 104418 | TRCN0000278613 | CCTGGATGTCTTTAACAACTA | 105 | 0.7 | DGKZ | 8525 |
| Dgkz | 104418 | ND000060 | CGAGTAGTGTGTGACGGAATG | 106 | 0.9 | DGKZ | 8525 |
| Dgkz | 104418 | ND000065 | CACATCTGGTTTGAGACCAAC | 107 | 1.4 | DGKZ | 8525 |
| Dgkz | 104418 | TRCN0000278690 | GAGAAGTTCAACAGCCGCTTT | 108 | 1.6 | DGKZ | 8525 |
| Dgkz | 104418 | ND000069 | ACTGTGCAGGCACCATGCCCT | 109 | 2.0 | DGKZ | 8525 |
| Dgkz | 104418 | ND000068 | AGAAGCTGTTCAGATCTAGGG | 110 | 2.8 | DGKZ | 8525 |
| Dgkz | 104418 | TRCN0000297512 | GTGGACTTCAAAGAATTCATT | 111 | 3.6 | DGKZ | 8525 |
| Dgkz | 104418 | ND000064 | ACTACGAGGCTCTACATTATG | 112 | 5.2 | DGKZ | 8525 |
| Dgkz | 104418 | ND000067 | AGTACATAATTTGAGGATTCT | 113 | 5.5 | DGKZ | 8525 |
| Dgkz | 104418 | TRCN0000278682 | CGAGGCTCTACATTATGACAA | 114 | 6.0 | DGKZ | 8525 |
| Dgkz | 104418 | TRCN0000278614 | CCTGTAAGATCGTGGTGCATA | 115 | 6.4 | DGKZ | 8525 |
| Dgkz | 104418 | ND000052 | GAAACCGCAGTGCATCGTCTT | 116 | 7.7 | DGKZ | 8525 |
| Dgkz | 104418 | ND000066 | CAGCATCACGGATTCGAATTG | 117 | 14.0 | DGKZ | 8525 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Egr2 | 13654 | TRCN0000218224 | AGGATCCTTCAGCATTCTTAT | 118 | 0.4 | EGR2 | 1959 |
| Egr2 | 13654 | ND000075 | AGCTCTGGCTGACACACCAG | 119 | 0.6 | EGR2 | 1959 |
| Egr2 | 13654 | TRCN0000081682 | CCAGGATCCTTCAGCATTCTT | 120 | 0.6 | EGR2 | 1959 |
| Egr2 | 13654 | TRCN0000081678 | GCTGTATATTTCTGCCTATTA | 121 | 1.3 | EGR2 | 1959 |
| Egr2 | 13654 | TRCN0000235777 | ACTATTGTGGCCGCAAGTTTG | 122 | 1.3 | EGR2 | 1959 |
| Egr2 | 13654 | TRCN0000235775 | AGCGGGTACTACCGTTTATTT | 123 | 1.6 | EGR2 | 1959 |
| Egr2 | 13654 | TRCN0000235778 | CTGTATATTTCTGCCTATTAA | 124 | 2.4 | EGR2 | 1959 |
| Egr2 | 13654 | ND000073 | GTGACCACCTTACTACTCACA | 125 | 3.2 | EGR2 | 1959 |
| Egr2 | 13654 | ND000074 | GTTTGCCAGGAGTGACGAAAG | 126 | 3.9 | EGR2 | 1959 |
| Egr2 | 13654 | TRCN0000081681 | CCTTCACCTACATGGGCAAAT | 127 | 4.0 | EGR2 | 1959 |
| Egr2 | 13654 | TRCN0000081680 | CCAGAAGGTATCATCAATATT | 128 | 5.1 | EGR2 | 1959 |
| Egr2 | 13654 | TRCN0000081679 | CCACTCTCTACCATCCGTAAT | 129 | 5.2 | EGR2 | 1959 |
| Egr2 | 13654 | ND000072 | CCGTGCCAGAGAGATCCACAC | 130 | 5.6 | EGR2 | 1959 |
| Egr2 | 13654 | ND000071 | CAATAGGTTGGGAGTTGCTGA | 131 | 8.6 | EGR2 | 1959 |
| Egr2 | 13654 | TRCN0000235776 | ACTCTCTACCATCCGTAATTT | 132 | 10.2 | EGR2 | 1959 |
| Eif2ak3 | 13666 | TRCN0000321872 | CCATGAGTTCATCTGGAACAA | 133 | 0.4 | EIF2AK3 | 9451 |
| Eif2ak3 | 13666 | ND000328 | CATAGCTCCTTCTCCTGAAAG | 134 | 0.9 | EIF2AK3 | 9451 |
| Eif2ak3 | 13666 | ND000332 | GATGACTGCAATTACGCTATC | 135 | 1.1 | EIF2AK3 | 9451 |
| Eif2ak3 | 13666 | ND000325 | GTCGCCATTTATGTCGGTAGT | 136 | 1.1 | EIF2AK3 | 9451 |
| Eif2ak3 | 13666 | ND000325 | TGGAAACAACTACTCCCATAA | 137 | 1.1 | EIF2AK3 | 9451 |
| Eif2ak3 | 13666 | TRCN0000321873 | GTGACCCATCTGCACTAATTT | 138 | 1.3 | EIF2AK3 | 9451 |
| Eif2ak3 | 13666 | ND000329 | GCATGATGGCAACCATTATGT | 139 | 1.3 | EIF2AK3 | 9451 |
| Eif2ak3 | 13666 | ND000330 | ATCCCGATATCTAACAGATTT | 140 | 1.6 | EIF2AK3 | 9451 |
| Eif2ak3 | 13666 | ND000333 | TGTCGCCGATGGGATAGTGAT | 141 | 1.9 | EIF2AK3 | 9451 |
| Eif2ak3 | 13666 | TRCN0000321805 | GCCACTTTGAACTTCGGTATA | 142 | 2.0 | EIF2AK3 | 9451 |
| Eif2ak3 | 13666 | TRCN0000028759 | CCATACGATAACGGTTACTAT | 143 | 4.8 | EIF2AK3 | 9451 |
| Eif2ak3 | 13666 | TRCN0000321806 | CCTCTACTGTTCACTCAGAAA | 144 | 5.8 | EIF2AK3 | 9451 |
| Eif2ak3 | 13666 | ND000327 | CATACGATAACGGTTACTATC | 145 | 5.9 | EIF2AK3 | 9451 |
| Eif2ak3 | 13666 | ND000331 | CGTGACCCATCTGCACTAATT | 146 | 7.3 | EIF2AK3 | 9451 |
| Eif2ak3 | 13666 | TRCN0000028799 | GCCTGTTTGATGATACAAGTT | 147 | 13.4 | EIF2AK3 | 9451 |
| Entpd1 | 12495 | ND000082 | GAATGTAAGTGAGCTCTATGG | 148 | 0.3 | ENTPD1 | 953 |
| Entpd1 | 12495 | TRCN0000222348 | CCGAACTGATACCAACATCCA | 149 | 0.4 | ENTPD1 | 953 |
| Entpd1 | 12495 | TRCN0000222346 | CCCATGCTTTAACCCAGGATA | 150 | 0.4 | ENTPD1 | 953 |
| Entpd1 | 12495 | TRCN0000222345 | COETGGTTTCACCTCTATCTT | 151 | 0.8 | ENTPD1 | 953 |
| Entpd1 | 12495 | TRCN0000222344 | CCAAGGACATTCAGGTTTCAA | 152 | 0.9 | ENTPD1 | 953 |
| Entpd1 | 12495 | ND000085 | CAGGAACAGAGTTGGCTAAGC | 153 | 1.0 | ENTPD1 | 953 |
| Entpd1 | 12495 | ND000078 | TTAACCCAGGATACGAGAAGG | 154 | 1.1 | ENTPD1 | 953 |
| Entpd1 | 12495 | ND000081 | ACTATCTCAGCCATGGCTTTG | 155 | 1.2 | ENTPD1 | 953 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Entpd1 | 12495 | ND000077 | TTCAAGTGGTGGCGTCCTTAA | 156 | 1.3 | ENTPD1 | 953 |
| Entpd1 | 12495 | ND000076 | GACTTTGGGCTACATGCTGAA | 157 | 1.4 | ENTPD1 | 953 |
| Entpd1 | 12495 | ND000080 | GGCATGCGCTTGCTTAGAATG | 158 | 1.9 | ENTPD1 | 953 |
| Entpd1 | 12495 | ND000084 | GCACTGGAGACTACGAACAGT | 159 | 1.9 | ENTPD1 | 953 |
| Entpd1 | 12495 | ND000083 | GTGGATTACTATTAACTATCT | 160 | 6.5 | ENTPD1 | 953 |
| Entpd1 | 12495 | TRCN0000222347 | GCTCCTGGGAACAGATTCATT | 161 | 7.3 | ENTPD1 | 953 |
| Entpd1 | 12495 | ND000079 | ACCATTTGATCAGTTTCGAAT | 162 | 13.3 | ENTPD1 | 953 |
| F11r | 16456 | TRCN0000284518 | GCTGATTCCCAGGACTATATT | 163 | 0.6 | F11R | 50848 |
| F11r | 16456 | TRCN0000124868 | GTATCGCTGTATAACTATGTA | 164 | 0.6 | F11R | 50848 |
| F11r | 16456 | ND000093 | ATTGACCTGCACCTACTCT | 165 | 0.6 | F11R | 50848 |
| F11r | 16456 | ND000094 | GCCGGGAGGAAACTGTTGT | 166 | 0.6 | F11R | 50848 |
| F11r | 16456 | TRCN0000271840 | CCTGGTTCAAGGACGGGATAT | 167 | 0.7 | F11R | 50848 |
| F11r | 16456 | TRCN0000271841 | TTCGGTGTACACTGCTCAATC | 168 | 0.7 | F11R | 50848 |
| F11r | 16456 | TRCN0000271792 | CACCGGGTAAGAAGGTCATTT | 169 | 0.9 | F11R | 50848 |
| F11r | 16456 | ND000088 | ACTTGCATGGTCTCCGAGGAA | 170 | 0.9 | F11R | 50848 |
| F11r | 16456 | ND000086 | GTAACACTGATTLTCCTTGGA | 171 | 1.0 | F11R | 50848 |
| F11r | 16456 | ND000090 | GTTATAACAGCCAGATCACAG | 172 | 1.1 | F11R | 50848 |
| F11r | 16456 | ND000092 | TAGCTGCACAGGATGCCTTCA | 173 | 1.3 | F11R | 50848 |
| F11r | 16456 | ND000087 | GGTTTGCCTATAGCCGTGGAT | 174 | 1.9 | F11R | 50848 |
| F11r | 16456 | TRCN0000271794 | CCTATAGCCGTGGATACTTTG | 175 | 4.3 | F11R | 50848 |
| F11r | 16456 | ND000091 | CTCCGTTGTCCATTTGCCTTA | 176 | 4.6 | F11R | 50848 |
| F11r | 16456 | ND000089 | CCACCCTCTGAATATTCCTGG | 177 | 6.8 | F11R | 50849 |
| Fyn | 14360 | TRCN0000023383 | CATCCCGAACTACAACAACTT | 178 | 0.7 | FYN | 2534 |
| Fyn | 14360 | TRCN0000023381 | CCTTTGGAAACCCAAGAGGTA | 179 | 0.9 | FYN | 2534 |
| Fyn | 14360 | TRCN0000361148 | TCTGAGACAGAAGCGTGTTAT | 180 | 1.4 | FYN | 2534 |
| Fyn | 14360 | TRCN0000023379 | GCTCGGTTGATTGAAGACAAT | 181 | 1.4 | FYN | 2534 |
| Fyn | 14360 | TRCN0000361213 | TTGACAATGGTGGATACTATA | 182 | 1.9 | FYN | 2534 |
| Fyn | 14360 | TRCN0000361149 | TCTTCACCTGATTCAACTAAA | 183 | 1.9 | FYN | 2534 |
| Fyn | 14360 | TRCN0000023382 | GCTCTGAAGTTGCCAAACCTT | 184 | 2.0 | FYN | 2534 |
| Fyn | 14360 | TRCN0000361212 | CACTGTTTGTGGCGCTTTATG | 185 | 2.3 | FYN | 2534 |
| Fyn | 14360 | TRCN0000361152 | CATCGAGCGCATGAATTATAT | 186 | 2.9 | FYN | 2534 |
| Fyn | 14360 | TRCN0000023380 | CCTGTATGGAAGGTTCACAAT | 187 | 6.5 | FYN | 2534 |
| Fyn | 14360 | ND000111 | TCGATGTTATGTCAAAGGCC | 188 | 0.5 | FYN | 2534 |
| Fyn | 14360 | ND000112 | ACCACACAAACTTCCTGTAT | 189 | 0.7 | FYN | 2534 |
| Fyn | 14360 | ND000115 | ACAGCTCCTGTCCTTTGGAAA | 190 | 1.0 | FYN | 2534 |
| Fyn | 14360 | ND000113 | GCAGCGAAACTGACAGAGGAG | 191 | 4.1 | FYN | 2534 |
| Fyn | 14350 | ND000114 | ACACTGTTTGTGGCGCTTTAT | 192 | 4.4 | FYN | 2534 |
| Grk6 | 26385 | ND000356 | TGACTACCACAGCCTATGTGA | 193 | 0.5 | GRK6 | 2870 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Grk6 | 26385 | TRCN0000022851 | CGAGAAACAGATCTTGGAGAA | 194 | 0.6 | GRK6 | 2870 |
| Grk6 | 26385 | ND000355 | CTAACCTTGCTTAGCAACTGT | 195 | 0.6 | GRK6 | 2870 |
| Grk6 | 26385 | ND000359 | AGGAATGAGCGCTACACGTTC | 196 | 1.0 | GRK6 | 2870 |
| Grk6 | 26385 | TRCN0000022853 | TCTTGGAGAAAGTGAACAGTA | 197 | 1.1 | GRK6 | 2870 |
| Grk6 | 26385 | TRCN0000022850 | GCGCCTGTTATTTCGTGAGTT | 198 | 1.1 | GRK6 | 2870 |
| Grk6 | 26385 | TRCN0000361581 | GAACAGTTCTCTACAGTTAAA | 199 | 1.1 | GRK6 | 2870 |
| Grk6 | 26385 | ND000354 | CAGGCTATTTATTGCAAGGAT | 200 | 1.2 | GRK6 | 2870 |
| Grk6 | 26385 | ND000357 | GAGCTTAGCCTACGCCTATGA | 201 | 1.3 | GRK6 | 2870 |
| Grk6 | 26385 | TRCN0000022852 | GCAAAGGCAAGAGCAAGAAAT | 202 | 1.3 | GRK6 | 2870 |
| Grk6 | 26385 | TRCN0000361580 | CCATGGCTCTCAACGAGAAAC | 203 | 2.7 | GRK6 | 2870 |
| Grk6 | 26385 | ND000358 | TCTATGCTGCTGAGATCTGCT | 204 | 4.2 | GRK6 | 2870 |
| Grk6 | 26385 | TRCN0000361508 | GCCGACTAATGCAGAACTTTC | 205 | 4.5 | GRK6 | 2870 |
| Grk6 | 26385 | ND000360 | CGCCTGTTATTTCGTGAGTTC | 206 | 5.8 | GRK6 | 2870 |
| Grk6 | 26385 | TRCN0000022849 | CGCCGACTAATGCAGAACTTT | 207 | 11.0 | GRK6 | 2870 |
| Hipk1 | 15257 | ND000371 | CTACCTGCAATCACGCTACTA | 208 | 0.3 | HIPK1 | 204851 |
| Hipk1 | 15257 | ND000374 | AGCGGAGGGTTCACATGTATG | 209 | 0.4 | HIPK1 | 204851 |
| Hipk1 | 15257 | TRCN0000361231 | CAACCAGTACAGCACTATTAT | 210 | 0.4 | HIPK1 | 204851 |
| Hipk1 | 15257 | TRCN0000361237 | TACCCTTTTTCTGGCTAATTC | 211 | 0.7 | HIPK1 | 204851 |
| Hipk1 | 15257 | TRCN0000368011 | AGCCTGAAGGCGAGGTCTAAT | 212 | 1.1 | HIPK1 | 204851 |
| Hipk1 | 15257 | ND000375 | CATTGGCACCCGTACTATCAT | 213 | 1.1 | HIPK1 | 204851 |
| Hipk1 | 15257 | TRC80000023157 | GCTTCAGAATACGATCAGATT | 214 | 1.2 | HIPK1 | 204851 |
| Hipk1 | 15257 | ND000375 | GAAGACTCTTAACCACCAATT | 215 | 1.8 | HIPK1 | 204851 |
| Hipk1 | 15257 | TRCN0000361233 | ATACGATCAGATTCGCTATAT | 216 | 1.9 | HIPK1 | 204851 |
| Hipk1 | 15257 | ND000372 | CTGTCATACATTTGGTCTCTT | 217 | 2.7 | HIPK1 | 204851 |
| Hipk1 | 15257 | ND000377 | GCTACTAGCCCTGAGTTCTTA | 218 | 3.4 | HIPK1 | 204851 |
| Hipk1 | 15257 | TRCN0000361232 | TATAACTTTGTCCGTTCTTAT | 219 | 4.5 | HIPK1 | 204851 |
| Hipk1 | 15257 | ND000373 | CTCGCTGCTAAACTACCAATC | 220 | 6.3 | HIPK1 | 204851 |
| Hipk1 | 15257 | ND000378 | GCCAATCATCATTCCAGATAC | 221 | 6.7 | HIPK1 | 204851 |
| Hipk1 | 15257 | TRCN0000023154 | CGCTCCAAATACAAGCACAAA | 222 | 12.3 | HIPK1 | 204851 |
| Inpp5b | 16330 | TRCN0000080903 | GCTTAGAGGTTCCTGGATAAA | 223 | 0.5 | INPP5B | 3633 |
| Inpp5b | 16330 | TRCN0000080906 | CCTTTGGTTCACACACCAGAA | 224 | 0.7 | INPP5B | 3633 |
| Inpp5b | 16330 | ND000130 | CTGTTAGTGACCTGACGTTGA | 225 | 0.8 | INPP5B | 3633 |
| Inpp5b | 16330 | TRCN0000305895 | ATATTCTAGCTAGCATATTTG | 226 | 0.8 | INPP5B | 3633 |
| Inpp5b | 16330 | TRCN0000311434 | GGCCAGAGTTTGACCTATAA | 227 | 1.4 | INPP5B | 3633 |
| Inpp5b | 16330 | ND000131 | GAGTCCTTCACGATTCATAAT | 228 | 1.4 | INPP5B | 3633 |
| Inpp5b | 16330 | TRCN0000080905 | CGGATCTCCTATCCATACATT | 229 | 1.5 | INPP5B | 3633 |
| Inpp5b | 16330 | ND000128 | GTATCGGACAAGGCTCACATT | 230 | 1.6 | INPP5B | 3633 |
| Inpp5b | 16330 | ND000129 | TTCGAGACACAATCGTGAGAT | 231 | 1.9 | INPP5B | 3633 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Inpp5b | 16330 | ND000127 | CTGTCCAAGCCGCAAACATGT | 232 | 3.1 | INPP5B | 3633 |
| Inpp5b | 16330 | ND000133 | CTCAAGCTTGTATTCCAACTT | 233 | 4.3 | INPP5B | 3633 |
| Inpp5b | 16330 | ND000132 | ATATAAGGGACTGTCTAGATA | 234 | 4.6 | INPP5B | 3633 |
| Inpp5b | 16330 | TRCN0000080904 | CGAGTCCTTCACGATTCATAA | 235 | 6.2 | INPP5B | 3633 |
| Inpp5b | 16330 | TRCN0000080907 | CCGAGTCCTTCACGATTCATA | 236 | 8.1 | INPP5B | 3533 |
| Inpp5b | 16330 | ND000134 | CGTCCGACTGGTTGGGATTAT | 237 | 9.5 | INPP5B | 3633 |
| Ipmk | 69718 | TRCN0000024840 | CCCAGATGGTACAGTTCTGAA | 238 | 0.5 | IPMK | 253430 |
| Ipmk | 69718 | ND000384 | CGAGGCTGTGTGGGTTCTATA | 239 | 0.5 | IPMK | 253430 |
| Ipmk | 69718 | TRCN0000360733 | TTGCCGTGCTTCGGAGTATTT | 240 | 0.6 | IPMK | 253430 |
| Ipmk | 69718 | TRCN0000360808 | GATGCGATTGCCGCCAGTATT | 241 | 0.7 | IPMK | 253430 |
| Ipmk | 69718 | TRCN0000024839 | CCTAACGAAAGAGACCCTGAA | 242 | 0.8 | IPMK | 253430 |
| Ipmk | 69718 | ND000383 | ATTGCCGTGCTTCGGAGTATT | 243 | 1.1 | IPMK | 253430 |
| Ipmk | 69718 | ND000380 | AGCGGAAGTACGGATGATAGA | 244 | 1.3 | IPMK | 253430 |
| Ipmk | 69718 | TRCN0000360807 | GAGGCTCTGTGGGTTCTATAT | 245 | 1.4 | IPMK | 253430 |
| Ipmk | 69718 | ND000379 | TGCCCAAATACTACGGCGTCT | 246 | 1.7 | IPMK | 253430 |
| Ipmk | 69718 | TRCN0000024843 | CGGCAAGGACAAAGTGGGCAT | 247 | 2.9 | IPMK | 253430 |
| Ipmk | 69718 | ND000381 | CTAGCAACACAGTCGATGAGG | 248 | 3.2 | IPMK | 253430 |
| Ipmk | 69718 | TRCN0000360732 | ACCAAACGATGTGTACCTAAA | 249 | 4.0 | IPMK | 253430 |
| Ipmk | 69718 | TRCN0000024841 | ACCCTGTATAATGGACGTGAA | 250 | 4.1 | IPMK | 253430 |
| Ipmk | 69718 | ND000382 | CCTGTATAATGGACGTGAAGA | 251 | 4.7 | IPMK | 253430 |
| Ipmk | 69718 | TRCN0000024842 | CACCAAACGATGTGTACCTAA | 252 | 6.9 | IPMK | 253430 |
| Jun | 16476 | TRCN0000229526 | GAACAGGTGGCACAGCTTAAG | 253 | 0.5 | JUN | 3725 |
| Jun | 16476 | TRCN0000042693 | CGGCTACAGTAACCCTAAGAT | 254 | 0.5 | JUN | 3725 |
| Jun | 16476 | TRCN0000055205 | CTACGCCAACCTCAGCAACTT | 255 | 0.7 | JUN | 3725 |
| Jun | 16476 | TRCN0000055206 | CGGTGCCTACGGCTACAGTAA | 256 | 0.8 | JUN | 3725 |
| Jun | 16476 | TRCN0000042695 | GCTTAAGCAGAAAGTCATGAA | 257 | 0.9 | JUN | 3725 |
| Jun | 16476 | TRCN0000360499 | AGCGCATGAGGAACCGCATTG | 258 | 0.9 | JUN | 3725 |
| Jun | 16476 | TRCN0000360498 | CCTATCGACATGGAGTCTCAG | 259 | 0.9 | JUN | 3725 |
| Jun | 16476 | TRCN0000042697 | GAAGCGCATGAGGAACCGCAT | 260 | 1.0 | JUN | 3725 |
| Jun | 16476 | TRCN0000360511 | ATTCGATCTCATTCAGTATTA | 261 | 1.1 | JUN | 3725 |
| Jun | 16476 | TRCN0000360572 | GGATCGCTCGGCTAGAGGAAA | 262 | 1.2 | JUN | 3725 |
| Jun | 16476 | TRCN0000055207 | GCGGATCAAGGCAGAGAGGAA | 263 | 3.1 | JUN | 3725 |
| Jun | 16476 | TRCN0000229528 | GGCATGTGCTGTGATCATTTA | 264 | 3.2 | JUN | 3725 |
| Jun | 16476 | TRCN0000042694 | ACGCAGCAGTTGCAAACGTTT | 265 | 3.3 | JUN | 3725 |
| Jun | 16476 | TRCN0000055203 | GCGGGGTAACTGCAATAAGAT | 266 | 5.2 | JUN | 3725 |
| Jun | 16476 | TRCN0000229525 | CAGTAACCCTAAGATCCTAAA | 267 | 5.5 | JUN | 3725 |
| Jun | 16476 | TRCN0000229527 | GCTAACGCAGCAGTTGCAAAC | 268 | 5.8 | JUN | 3725 |
| Jun | 16476 | TRCN0000218856 | GAAAGTCATGAACCACGTTAA | 269 | 6.4 | JUN | 3725 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Mast2 | 17776 | TRCN0000225743 | AGCAACAACAGGAAGGTATAT | 270 | 0.4 | MAST2 | 23139 |
| Mast2 | 17776 | TRCN0000022896 | GCATCCACGAACAAGACCATA | 271 | 0.7 | MAST2 | 23139 |
| Mast2 | 17776 | TRCN0000225741 | TTGAGACCAAGCGTCACTTAT | 272 | 1.0 | MAST2 | 23139 |
| Mast2 | 17776 | ND000396 | CCGCAAGAGCTTGATTGTAAC | 273 | 1.2 | MAST2 | 23139 |
| Mast2 | 17776 | TRCN0000022898 | GCTGGTTCTGAAGAGTGGAAA | 274 | 1.2 | MAST2 | 23139 |
| Mast2 | 17776 | ND000392 | GATATTACGGAAGCGGTTATC | 275 | 1.3 | MAST2 | 23139 |
| Mast2 | 17776 | ND000393 | ACGAATACCACGGTCCCAAAT | 276 | 1.4 | MAST2 | 23139 |
| Mast2 | 17776 | ND0218393 | GTGGAAACAAGGTATCAATTT | 277 | 1.5 | MAST2 | 23139 |
| Mast2 | 17776 | ND000397 | GAAGTGTGCTATCCGGGAAAG | 278 | 1.6 | MAST2 | 23139 |
| Mast2 | 17776 | ND000395 | GCCTCATTACGTCACACTATT | 279 | 1.6 | MAST2 | 23139 |
| Mast2 | 17776 | TRCN0000022895 | CCTCATTACGTCACACTATTT | 280 | 1.9 | MAST2 | 23139 |
| Mast2 | 17776 | TRCN0000225742 | ACTTGTATGAGGGTCATATTG | 281 | 4.1 | MAST2 | 23139 |
| Mast2 | 17776 | TRCN0000022897 | CGAATGAGAAACCAATCCCTT | 282 | 4.2 | MAST2 | 23139 |
| Mast2 | 17776 | ND000394 | GCATCAAACCTGGTTCGAATG | 283 | 4.3 | MAST2 | 23139 |
| Mast2 | 17776 | TRCN0000022894 | CCCTGTCAACAAAGTAATCAA | 284 | 5.1 | MAST2 | 23139 |
| Mdfic | 16543 | TRCN0000237997 | GGAGGAAACAGGCAAGATAAA | 285 | 0.2 | MDFIC | 29969 |
| Mdfic | 16543 | TRCN0000237994 | TGATGCGGGACCAGTCCATTT | 286 | 0.4 | MDFIC | 29969 |
| Mdfic | 16543 | ND000148 | TGTAATGAGGACAATACGGAG | 287 | 0.4 | MDFIC | 29969 |
| Mdfic | 16543 | TRCN0000362432 | TCCTGACCCTCTGCAACATTG | 288 | 0.6 | MDFIC | 29969 |
| Mdfic | 16543 | TRCN0000237996 | TGACATGGACTGCGGCATCAT | 289 | 0.8 | MDFIC | 29969 |
| Mdfic | 16543 | TRCN0000095981 | CGAAGCATGTAATGAGGACAA | 290 | 1.0 | MDFIC | 29969 |
| Mdfic | 16543 | TRCN0000095982 | GACATCAGTAAGAAGAGTAAA | 291 | 1.1 | MDFIC | 29969 |
| Mdfic | 16543 | TRCN0000237998 | TGCCAAGTGACAGGTTATAAA | 292 | 1.1 | MDFIC | 29969 |
| Mdfic | 16543 | TRCN0000095983 | TGCAACATTGTCCTGGGACAA | 293 | 1.5 | MDFIC | 29969 |
| Mdfic | 16543 | TRCN0000237995 | ATCGTCAGACTGTCTAGAAAT | 294 | 1.6 | MDFIC | 29969 |
| Mdfic | 16543 | TRCN0000095980 | CCGTGGAGAATCACAAGATAT | 295 | 2.6 | MDFIC | 29969 |
| Mdfic | 16543 | TRCN0000362509 | GTTTATCTATTGGAGGTTAAA | 296 | 4.4 | MDFIC | 29969 |
| Mdfic | 16543 | ND000147 | GAAGAGTAAAGTAAATGCTGT | 297 | 5.1 | MDFIC | 29969 |
| Mdfic | 16543 | TRCN0000095979 | CGCCGGATGTATGTGGTTTAA | 298 | 7.2 | MDFIC | 29969 |
| Mdfic | 16543 | TRCN0000362431 | GCCGGATGTATGTGGTTTAAT | 299 | 10.0 | MDFIC | 29969 |
| Nptxr | 73340 | TRCN0000219475 | CTTGGTCTCTCCCATCATATA | 300 | 0.5 | NPTXR | 23467 |
| Nptxr | 73340 | ND000150 | ACAGCAACTGGCACCATATCT | 301 | 0.8 | NPTXR | 23467 |
| Nptxr | 73340 | TRCN0000219474 | GATACCTTGGGAGGCCGATTT | 302 | 0.8 | NPTXR | 23467 |
| Nptxr | 73340 | ND000155 | GGCCAATGAGATCGTGCTTCT | 303 | 1.0 | NPTXR | 23467 |
| Nptxr | 73340 | ND000154 | GTAGCCTTTGACCCTCAAATC | 304 | 1.0 | NPTXR | 23467 |
| Nptxr | 73340 | ND000152 | CAATGGAGCTGCTGATCAACG | 305 | 1.0 | NPTXR | 23467 |
| Nptxr | 73340 | TRCN0000219472 | GACAGCAACTGGCACCATATC | 306 | 1.1 | NPTXR | 23467 |
| Nptxr | 73340 | ND000158 | TTGGTCTCTCCCATCATATAC | 307 | 1.3 | NPTXR | 23467 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Nptxr | 73340 | ND000159 | ATACCTTGGAGGCCGATTTG | 308 | 1.3 | NPTXR | 23467 |
| Nptxr | 73340 | ND000133 | CCTGTCAGTTTCAGGACTTTG | 309 | 2.0 | NPTXR | 23467 |
| Nptxr | 73340 | ND000156 | TCCGCAACAACTACATGTACG | 310 | 2.1 | NPTXR | 23467 |
| Nptxr | 73340 | ND000157 | ATAAGCTGGTAGAGGCCTTTG | 311 | 3.9 | NPTXR | 23467 |
| Nptxr | 73340 | ND000149 | CGGTGCCGTCATCTGCATCAT | 312 | 6.6 | NPTXR | 23467 |
| Nptxr | 73340 | TRCN0000219473 | CAAGCCACACGGCATCCTTAT | 313 | 7.0 | NPTXR | 23467 |
| Nptxr | 73340 | ND000151 | TCAAGCCACACGGCATCCTTA | 314 | 7.2 | NPTXR | 23467 |
| Nuak2 | 74137 | ND000434 | TTGGACTTGCCTGAACGTCTT | 315 | 0.2 | NUAK2 | 81788 |
| Nuak2 | 74137 | TRCN0000361812 | TTTGACGGGCAGGATCATAAA | 316 | 0.4 | NUAK2 | 81788 |
| Nuak2 | 74137 | TRCN0000024271 | GCCAATGGAAACATCAAGATT | 317 | 0.7 | NUAK2 | 81788 |
| Nuak2 | 74137 | TRCN0000361873 | GTGTAGTGACTGCCATTATTT | 318 | 0.7 | NUAK2 | 81788 |
| Nuak2 | 74137 | ND000436 | CCAAGGTGTGCAGCTTCTTCA | 319 | 1.6 | NUAK2 | 81788 |
| Nuak2 | 74137 | ND000431 | CCTGATCCGGTGGCTGTTAAT | 320 | 1.7 | NUAK2 | 81788 |
| Nuak2 | 74137 | TRCN0000378457 | GGGCTCATCAAGTCGCCTAAA | 321 | 1.8 | NUAK2 | 81788 |
| Nu3k2 | 74137 | TRCN0000024270 | CCGAAAGGCATTCTCAAGAAA | 322 | 2.1 | NUAK2 | 81788 |
| Nu3k2 | 74137 | TRCN0000024273 | GTCGCCTAAACCTCTGATGAA | 323 | 2.1 | NUAK2 | 81788 |
| Nuak2 | 74137 | TRCN0000024272 | CCGAGGCGATCTGTATGATTA | 324 | 2.1 | NUAK2 | 81788 |
| Nuak2 | 74137 | TRCN0000378409 | GAAGTCTCGACAGCGTGAATC | 325 | 2.8 | NUAK2 | 81788 |
| Nuak2 | 74137 | ND000435 | TCGGACCGCTGTTTGACTTCA | 326 | 2.8 | NUAK2 | 81788 |
| Nuak2 | 74137 | ND000433 | TAGCAGCAAGATTGTGATTGT | 327 | 4.5 | NUAK2 | 81788 |
| Nuak2 | 74137 | ND000432 | AGTCTCGACAGCGTGAATCTG | 328 | 5.4 | NUAK2 | 81788 |
| Nuak2 | 74137 | TRCN0000024269 | CCCAAGGAAAGGCATCCTTAA | 329 | 13.1 | NUAK2 | 81788 |
| Pdzk1ip1 | 67182 | TRCN0000244507 | GATGGCAGATACTCCTCAATG | 330 | 0.4 | PDZK1IP1 | 10158 |
| Pdzk1ip1 | 67182 | ND000172 | GGGAATGGATGGCAGATACTC | 331 | 0.5 | PDZK1IP1 | 10158 |
| Pdzk1ip1 | 67182 | ND000176 | CTCCCTCACCTCTCTAGAATC | 332 | 0.6 | PDZK1IP1 | 10158 |
| Pdzk1ip1 | 67182 | ND000170 | TGCAATCGTCTTCGCCGTCAA | 333 | 0.8 | PDZK1IP1 | 10158 |
| Pdzk1ip1 | 67182 | ND000173 | CATTGCTGTCGCTGTGTTCTT | 334 | 1.2 | PDZK1IP1 | 10158 |
| Pdzk1ip1 | 67182 | TRCN0000244505 | ACAAGAATGCCTACGAGAATG | 335 | 1.7 | PDZK1IP1 | 10158 |
| Pdzk1ip1 | 67182 | ND000174 | TTCTTGGTCCTTGTTGCAATC | 336 | 2.0 | PDZK1IP1 | 10158 |
| Pdzk1ip1 | 67182 | TR0ND000244509 | GGAGCACAGTGATGATCATTG | 337 | 2.5 | PDZK1IP1 | 10158 |
| Pdzk1ip1 | 67182 | ND000171 | ACTGCTCTACAGGAATCTACT | 338 | 2.5 | PDZK1IP1 | 10158 |
| Pdzk1ip1 | 67182 | ND000175 | CTGTCAACAAGGTCTAGGAAA | 339 | 4.8 | PDZK1IP1 | 10158 |
| Pdzk1ip1 | 67182 | TRCN0000244508 | CCTCATTGCTGTCGCTGTGTT | 340 | 6.3 | PDZK1IP1 | 10158 |
| Pdzk1ip1 | 67182 | TRCN0000244506 | TCTACAGGAATCTACTGAAAC | 341 | 12.9 | PDZK1IP1 | 10158 |
| Pkd1 | 18763 | ND000445 | CAAGTCCTATGACCCTAATTT | 342 | 0.5 | PKD1 | 5310 |
| Pkd1 | 18763 | TRCN0000304664 | GGTGGACACCACTCAGTATTA | 343 | 0.8 | PKD1 | 5310 |
| Pkd1 | 18763 | TRCN0000072086 | CCAACTCAACATCACCGTAAA | 344 | 0.8 | PKD1 | 5310 |
| Pkd1 | 18763 | TRCN0000304612 | ACACAATACCACGCATATTTA | 345 | 0.9 | PKD1 | 5310 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Pkd1 | 18763 | ND000447 | GGCCGCTTCAAATATGAAATA | 346 | 1.2 | PKD1 | 5310 |
| Pkd1 | 18763 | ND000444 | TTCACTAGGAGTGGCATATTC | 347 | 1.3 | PKD1 | 5310 |
| Pkd1 | 18763 | ND000442 | CATCTATAAGGGTAGTCTTTC | 348 | 1.4 | PKD1 | 5310 |
| Pkd1 | 18763 | ND000441 | GTTATTACCTCTCTTGTTTCT | 349 | 1.8 | PKD1 | 5310 |
| Pkd1 | 18763 | ND000446 | GTAGTCTACCCTGTCTATTTG | 350 | 2.9 | PKD1 | 5310 |
| Pkd1 | 18763 | TRCN0000072084 | GCCCTGTACCTTTCAACCAAT | 351 | 4.9 | PKD1 | 5310 |
| Pkd1 | 18763 | ND000443 | CATGTCATCGAGTACTCTTTA | 352 | 6.2 | PKD1 | 5310 |
| Pkd1 | 18763 | TRCN0000304611 | CAACTGATGGTGTCCTATATA | 353 | 7.7 | PKD1 | 5310 |
| Pkd1 | 18763 | TRCN0000072085 | CCATCATTGAAGGTGGCTCAT | 354 | 8.9 | PKD1 | 5310 |
| Pkd1 | 18763 | TRCN0000072087 | GCTTCACTACTCTTCCTGCTT | 355 | 9.9 | PKD1 | 5310 |
| Pkd1 | 18763 | TRCN0000331808 | CGCTCGCACTTTCAGCAATAA | 356 | 47.6 | PKD1 | 5310 |
| Ppm1g | 14208 | TRCN0000326875 | GAGGATGATAAAGACAAAGTA | 357 | 0.3 | PPM1G | 5496 |
| Ppm1g | 14208 | TRCN0000326874 | GCTTTCCTCAGCCCATTACAA | 358 | 0.5 | PPM1G | 5496 |
| Ppm1g | 14208 | ND000458 | GAGATGATGGTCCCTGGAATG | 359 | 0.8 | PPM1G | 5496 |
| Ppm1g | 14208 | TRCN0000375841 | TGACCACAGAGGAAGTCATTA | 360 | 1.1 | PPM1G | 5496 |
| Ppm1g | 14208 | TRCN0000081212 | GATGCCTTCTTGGCTATTGAT | 361 | 1.1 | PPM1G | 5496 |
| Ppm1g | 14208 | TRCN0000306418 | CCATGGATGGACGAGTCAATG | 362 | 1.2 | PPM1G | 5496 |
| Ppm1g | 14208 | ND000460 | TGACGCGATATGGGCAGAACT | 363 | 1.2 | PPM1G | 5496 |
| Ppm1g | 14208 | ND000464 | GCTACCATGACTATTGAAGAG | 364 | 1.3 | PPM1G | 5496 |
| Ppm1g | 14208 | ND000462 | TGGCAAAGCTTTAGATATGTC | 365 | 2.1 | PPM1G | 5496 |
| Ppm1g | 14208 | ND000465 | CATGGATGGACGAGTCAATGG | 366 | 2.9 | PPM1G | 5496 |
| Ppm1g | 14208 | TRCN0000081210 | CTTCGGTTATTGTCATCCATT | 367 | 3.0 | PPM1G | 5496 |
| Ppm1g | 14208 | ND000459 | TGCCTGTGCTCTGTTGTGTTG | 368 | 3.6 | PPM1G | 5496 |
| Ppm1g | 14208 | ND000461 | CAAATTAGTGAGCCCGGTACT | 369 | 6.2 | PPM1G | 5496 |
| Ppm1g | 14208 | TRCN0000081209 | GCCTTGTACTGTGCCAAATAT | 370 | 7.1 | PPM1G | 5496 |
| Ppm1g | 14208 | ND000463 | CATGACGTGCATCATCATTTG | 371 | 8.5 | PPM1G | 5496 |
| Ppp2r2d | 52432 | ND000490 | ACTTCGAGACCCATTTAGAAT | 372 | 0.7 | PPP2R2D | 55844 |
| Ppp2r2d | 52432 | ND000488 | CAGAAGATCCCAGCAGTAGAT | 373 | 0.9 | PPP2R2D | 55844 |
| Ppp2r2d | 52432 | TRCN0000030899 | GCCACCAATAACTTGTATATA | 374 | 1.0 | PPP2R2D | 55844 |
| Ppp2r2d | 52432 | TRCN0000430828 | ATAGTGATCATGAAACATATC | 375 | 1.3 | PPP2R2D | 55844 |
| Ppp2r2d | 52432 | ND000487 | ATATGTACGCCGGTCAATTAG | 376 | 1.4 | PPP2R2D | 55844 |
| Ppp2r2d | 52432 | TRCN0000425449 | ATGCTCATACATATCACATAA | 377 | 1.5 | PPP2R2D | 55844 |
| Ppp2r2d | 52432 | TRCN0000427220 | TCATCTCCACCGTTGAGTTTA | 378 | 1.6 | PPP2R2D | 55844 |
| Ppp2r2d | 52432 | ND000491 | GATCTGAGAATTAACCTATGG | 379 | 1.7 | PPP2R2D | 55844 |
| Ppp2r2d | 52432 | TRCN0000080901 | CCATTTAGAATTACGGCACTA | 380 | 1.9 | PPP2R2D | 55844 |
| Ppp2r2d | 52432 | TRCN0000080902 | CGGTTCAGACAGTGCCATTAT | 381 | 2.0 | PPP2R2D | 55844 |
| Ppp2r2d | 52432 | ND000489 | CACCGTTGAGTTTAACTACTC | 382 | 4.0 | PPP2R2D | 55844 |
| Ppp2r2d | 52432 | ND000486 | GCTCAATAAAGGCCATTACTC | 383 | 4.9 | PPP2R2D | 55844 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Ppp2r2d | 52432 | TRCN0000431278 | GAGAATTAACCTATGGCATTT | 384 | 8.3 | PPP2R2D | 55844 |
| Ppp2r2d | 52432 | ND000492 | CCACAGTGGTCGATACATGAT | 385 | 16.3 | PPP2R2D | 55844 |
| Ppp2r2d | 52432 | TRCN0000080900 | CCCACATCAGTGCAATGTATT | 386 | 17.2 | PPP2R2D | 55844 |
| Ppp3cc | 19057 | ND000512 | CCCGAGGTCTAGACCGAATTA | 387 | 0.1 | PPP3CC | 5533 |
| Ppp3cc | 19057 | ND000510 | TCACAGTGTGTGGTGATGTTC | 388 | 0.4 | PPP3CC | 5533 |
| Ppp3cc | 19057 | TRCN0000012695 | GCTGTATCTATGGAGCTTAAA | 389 | 0.4 | PPP3CC | 5533 |
| Ppp3cc | 19057 | TRCN0000012693 | CCTATGAGCAAATCACATTTA | 390 | 0.4 | PPP3CC | 5533 |
| Ppp3cc | 19057 | ND000511 | AGGAATGTCGGATCAAGTATT | 391 | 0.7 | PPP3CC | 5533 |
| Ppp3cc | 19057 | TRCN0000012694 | CGGCTAACTTTGAAGGAAGTT | 392 | 0.9 | PPP3CC | 5533 |
| Ppp3cc | 19057 | TRCN0000012696 | CGGATGAAGAAATGAACGTAA | 393 | 1.2 | PPP3CC | 5533 |
| Ppp3cc | 19057 | ND000508 | ACCTAGTAATACTCGCTACCT | 394 | 1.4 | PPP3CC | 5533 |
| Ppp3cc | 19057 | ND000513 | CTGTATCTATGGAGCTTAAAG | 395 | 1.6 | PPP3CC | 5533 |
| Ppp3cc | 19057 | ND000515 | AGAAATGAACGTAACCGATGA | 396 | 1.8 | PPP3CC | 5533 |
| Ppp3cc | 19057 | ND000514 | CAAACAACTTAAACTTGGAGG | 397 | 2.4 | PPP3CC | 5533 |
| Ppp3cc | 19057 | ND000507 | TGTAATTCAGTCGCATTTATT | 398 | 2.6 | PPP3CC | 5533 |
| Ppp3cc | 19057 | ND000506 | GGACAATTCTTTGACCTGATG | 399 | 4.2 | PPP3CC | 5533 |
| Ppp3cc | 19057 | TRCN0000012697 | CGAGGTCTAGACCGAATTAAT | 400 | 4.3 | PPP3CC | 5533 |
| Ppp3cc | 19057 | ND000509 | TTCCGTCACTTATTACGATTT | 401 | 4.4 | PPP3CC | 5533 |
| Prkab2 | 108097 | ND000529 | CTGTGGTTACCAGTCAGCTTG | 402 | 0.2 | PRKAB2 | 5565 |
| Prkab2 | 108097 | TRCN0000025112 | GTATGTCACCACGCTGCTGTA | 403 | 0.4 | PRKAB2 | 5565 |
| Prkab2 | 108097 | ND000527 | CCCTCACCTACTCCAAGTTAT | 404 | 0.7 | PRKAB2 | 5565 |
| Prkab2 | 108097 | TRCN0000361908 | TATGAGTTCACGGAGTTTATT | 405 | 0.7 | PRKAB2 | 5565 |
| Prkab2 | 108097 | TRCN0000025111 | CGCAACCCATCGCTACAAGAA | 406 | 0.8 | PRKAB2 | 5565 |
| Prkab2 | 108097 | TRCN0000025109 | CATCGCTACAAGAAGAAGTAT | 407 | 0.9 | PRKAB2 | 5565 |
| Prkab2 | 108097 | ND000528 | CAATTGGAGCACCAAGATCCC | 408 | 1.1 | PRKAB2 | 5565 |
| Prkab2 | 103097 | ND000530 | AGTGGGTTCATGATCCGTCAG | 409 | 1.1 | PRKAB2 | 5565 |
| Prkab2 | 108097 | ND000526 | ACCGTTATCCGCTGGTCTGAA | 410 | 1.8 | PRKAB2 | 5565 |
| Prkab2 | 108097 | TRCN0000361952 | GATCTGAGGAGAGATTCAAAT | 411 | 2.0 | PRKAB2 | 5565 |
| Prkab2 | 108097 | TRCN0000361953 | CTTAACAAGGACACGAATATT | 412 | 2.3 | PRKAB2 | 5565 |
| Prkab2 | 108097 | TRCN0000361910 | CTCTGATAAAGAGTCATAATG | 413 | 2.6 | PRKAB2 | 5565 |
| Prkab2 | 108097 | TRCN0000025110 | CGCTGCTGTATAAGCCCATCT | 414 | 4.1 | PRKAB2 | 5565 |
| Prkab2 | 108097 | ND000525 | CTTACGGTCAAGAAATGTATG | 415 | 4.8 | PRKAB2 | 5565 |
| Prkab2 | 108097 | TRCN0000025113 | CATTAAGGACAGTGTGATGGT | 416 | 7.0 | PRKAB2 | 5565 |
| Ptpn2 | 19255 | ND000532 | TCCGAACACATGCTGCCATTT | 417 | 0.5 | PTPN2 | 5771 |
| Ptpn2 | 19255 | TRCN0000029891 | GCCAAGATTGACAGACACCTA | 418 | 1.0 | PTPN2 | 5771 |
| Ptpn2 | 19255 | TRCN0000279253 | AGACTATTCTGCAGCTATAAA | 419 | 1.0 | PTPN2 | 5771 |
| Ptpn2 | 19255 | TRCN0000029893 | CCGTTATACTTGGAAATTCGA | 420 | 1.0 | PTPN2 | 5771 |
| Ptpn2 | 19255 | TRCN0000279254 | AGTATCGAATGGGACTTATTC | 421 | 1.2 | PTPN2 | 5771 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Ptpn2 | 19255 | ND000534 | TTATATTAATGCCAGCTTAGT | 422 | 1.4 | PTPN2 | 5771 |
| Ptpn2 | 19255 | ND000531 | ATGTTCATGACTTGAGACTAT | 423 | 1.7 | PTPN2 | 5771 |
| Ptpn2 | 19255 | TRCN0000279329 | ATATGATCACAGTCGTGTTAA | 424 | 2.2 | PTPN2 | 5771 |
| Ptpn2 | 19255 | TRCN0000279252 | CGGTGGAAAGAACTTTCTAAA | 425 | 2.2 | PTPN2 | 5771 |
| Ptpn2 | 19255 | ND000533 | CCATATCTCACTTCCATTATA | 426 | 4.7 | PTPN2 | 5771 |
| Ptpn2 | 19255 | TRCN0000279330 | TCTCCTACATGGCCATAATAG | 427 | 5.0 | PTPN2 | 5771 |
| Ptpn2 | 19255 | TRCN0000029890 | CGGTGGAAAGAACTTTCTAAA | 428 | 5.1 | PTPN2 | 5771 |
| Ptpn2 | 19255 | ND000535 | TATCGAATGGGACTTATTCAG | 429 | 5.5 | PTPN2 | 5771 |
| Ptpn2 | 19255 | TRCN0000029892 | CCTGTCTTGTTCTGATGGAAA | 430 | 7.4 | PTPN2 | 5771 |
| Rbks | 71336 | ND000536 | TCGCTGCAGTCAGTGTACAGG | 431 | 0.4 | RBKS | 611132 |
| Rbks | 71336 | ND000543 | GGCCTTCTACCTGGCTTACTA | 432 | 0.6 | RBKS | 611132 |
| Rbks | 71336 | ND000537 | CTGCAATGATTCTCCTAGAAC | 433 | 0.9 | RBKS | 611132 |
| Rbks | 71336 | ND000544 | AGTGGTGGGTTCCTGCATGAC | 434 | 0.9 | RBKS | 611132 |
| Rbks | 71336 | ND000539 | ATATGCCAGCTAGAAATAAGC | 435 | 1.1 | RBKS | 611132 |
| Rbks | 71336 | TRCN0000078936 | GTGATGATATGCCAGCTAGAA | 436 | 1.2 | RBKS | 611132 |
| Rbks | 71336 | ND000538 | CATATTTCTACAGAGTTTACA | 437 | 1.7 | RBKS | 611132 |
| Rbks | 71336 | TRCN0000078934 | TCAATAATGAAGGCCAGAATA | 438 | 1.9 | RBKS | 611132 |
| Rbks | 71336 | ND000545 | GCTGCCAGGTTGTGGTCATCA | 439 | 2.7 | RBKS | 611132 |
| Rbks | 71336 | TRCN0000078937 | TGATGATATGCCAGCTAGAAA | 440 | 4.0 | RBKS | 611132 |
| Rbks | 71336 | ND000541 | CAAGGTTGGCAACGATTCTTT | 441 | 4.1 | RBKS | 611132 |
| Rbks | 71336 | ND000542 | GAGCCTGTTCCAAAGCACATT | 442 | 5.0 | RBKS | 611132 |
| Rbks | 71336 | TRCN000078935 | CCAAAGCACATTCCCACTGAA | 443 | 5.7 | RBKS | 611132 |
| Rbks | 71336 | ND000540 | CATTAGCCGAGCCAAAGTGAT | 444 | 12.8 | RBKS | 611132 |
| Rbks | 71336 | TRCN0000078933 | GCCTCCATAATTGTCAATAAT | 445 | 13.9 | RBKS | 611132 |
| Rock1 | 19877 | ND000568 | CATACTGTTAGTCGGCTTGAA | 446 | 0.6 | ROCK1 | 6093 |
| Rock1 | 19877 | ND000567 | ATGACATGCAAGCGCAATTGG | 447 | 0.7 | ROCK1 | 6093 |
| Rock1 | 19877 | ND000555 | GCCTACAGGTAGATTAGATTA | 448 | 0.9 | ROCK1 | 6093 |
| Rock1 | 19877 | ND000569 | AGTTCAATTGGTGAGGCATAA | 449 | 1.0 | ROCK1 | 6093 |
| Rock1 | 19877 | TRCN0000361452 | CTAGCAAAGAGAGTGATATTG | 450 | 1.2 | ROCK1 | 6093 |
| Rock1 | 19877 | TRCN0000022901 | CCTGGTTTATGATTTGGATTT | 451 | 1.6 | ROCK1 | 6093 |
| Rock1 | 19877 | TRCN0000022900 | CGGGAGTTACAAGATCAACTT | 452 | 1.7 | ROCK1 | 6093 |
| Rock1 | 19877 | TRCN0000022902 | CCGTGCAAAGTAAGTTACGAT | 453 | 1.8 | ROCK1 | 6093 |
| Rock1 | 19877 | TRCN0000022899 | GCAGAAATAATGAATCGCAAA | 454 | 2.0 | ROCK1 | 6093 |
| Rock1 | 19877 | ND000566 | ATCAAGATCAGATCGTGGAAG | 455 | 2.2 | ROCK1 | 6093 |
| Rock1 | 19877 | TRCN0000361453 | TTCAATTGGTGAGGCATAAAT | 456 | 2.3 | ROCK1 | 6093 |
| Rock1 | 19877 | TRCN0000022903 | GCAGTGTCTCAAATTGAGAAA | 457 | 4.1 | ROCK1 | 6093 |
| Rock1 | 19877 | TRCN0000361455 | TGTGGGATGCTACCTGATAAA | 458 | 4.4 | ROCK1 | 6093 |
| Rock1 | 19877 | TRCN0000361522 | CTACAGGTAGATTAGATTAAT | 459 | 5.6 | ROCK1 | 6093 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Rock1 | 19877 | TRCN0000361521 | CAACTTTCTAAGCAGATATAA | 460 | 6.5 | ROCK1 | 6093 |
| Sbf1 | 77980 | ND000571 | CAGTATGTTACTCGTAAGAAG | 461 | 0.2 | SBF1 | 6305 |
| Sbf1 | 77980 | TRCN0000081099 | GCAGTATGTTACTCGTAAGAA | 462 | 0.4 | SBF1 | 6305 |
| Sbf1 | 77980 | ND000575 | TGCTAAGTTGTTTCTAGAACC | 463 | 0.8 | SBF1 | 6305 |
| Sbf1 | 77980 | ND000570 | CGATACTATGACCACCGAATG | 464 | 0.8 | SBF1 | 6305 |
| Sbf1 | 77980 | TRCN0000081101 | CGAGAGGAATCCACCAACTTT | 465 | 0.9 | SBF1 | 6305 |
| Sbf1 | 77980 | TRCN0000081102 | GCGATACTATGACCACCGAAT | 466 | 1.5 | SBF1 | 6305 |
| Sbf1 | 77980 | ND000578 | CTAACTTATTGTGGTGTCATG | 467 | 1.5 | SBF1 | 6305 |
| Sbf1 | 77980 | ND000574 | TCTTGCTGGACTCTGATTATG | 468 | 1.6 | SBF1 | 6305 |
| Sbf1 | 77980 | ND000572 | GGCTAGATGAGGGCACAATTC | 469 | 2.2 | SBF1 | 6305 |
| Sbf1 | 77980 | ND000573 | GAAGACAACACGTCGCGTTTA | 470 | 3.1 | SBF1 | 6305 |
| Sbf1 | 77980 | ND000577 | TACGGAATTGCATCTCCTATG | 471 | 3.2 | SBF1 | 6305 |
| Sbf1 | 77980 | TRCN0000081098 | CACGCGGACATCTATGACAAA | 472 | 4.8 | SBF1 | 6305 |
| Sbf1 | 77980 | ND000579 | TTACCACATACCGCGTCATCT | 473 | 5.6 | SBF1 | 6305 |
| Sbf1 | 77980 | TRCN0000081100 | CCCTACAGCAATGTGTCCAAT | 474 | 6.0 | SBF1 | 6305 |
| Sbf1 | 77980 | ND000576 | GACTTTGTCGTCCGCATGATG | 475 | 6.9 | SBF1 | 6305 |
| Smad2 | 17126 | ND000208 | AGATCAGTGGGACACAACAGG | 476 | 0.4 | SMAD2 | 4087 |
| Smad2 | 17126 | TRCN0000039336 | TGGTGTTCAATCGCATACTAT | 477 | 1.0 | SMAD2 | 4087 |
| Smad2 | 17126 | ND000205 | GTAATTACATCCCAGAAACAC | 478 | 1.1 | SMAD2 | 4087 |
| Smad2 | 17126 | TRCN0000089334 | CGGTTAGATGAGCTTGAGAAA | 479 | 1.2 | SMAD2 | 4087 |
| Smad2 | 17126 | TRCN0000089333 | CCAGTAGTAGTGCCTGAAGTA | 480 | 1.2 | SMAD2 | 4087 |
| Smad2 | 17126 | ND000207 | TAACCCGAATGTGCACCATAA | 481 | 1.2 | SMAD2 | 4087 |
| Smad2 | 17126 | ND000199 | CCCAACTGTAACCAGAGATAC | 482 | 1.4 | SMAD2 | 4087 |
| Smad2 | 17126 | TRCN0000089335 | CCACTGTAGAAATGACAAGAA | 483 | 1.5 | SMAD2 | 4087 |
| Smad2 | 17126 | ND000200 | CCTCCGTCGTAGTATTCATGT | 484 | 1.9 | SMAD2 | 4087 |
| Smad2 | 17126 | ND000201 | GCCAGTGGTGAAGAGACTTCT | 485 | 1.9 | SMAD2 | 4087 |
| Smad2 | 17126 | ND000203 | CTCGGCACACGGAGATTCTAA | 486 | 6.7 | SMAD2 | 4087 |
| Smad2 | 17126 | ND000204 | GACAGTATCCCAAAGGTTATT | 487 | 7.1 | SMAD2 | 4087 |
| Smad2 | 17126 | ND000202 | GAGTGCGCTTGTATTACATAG | 488 | 7.1 | SMAD2 | 4087 |
| Smad2 | 17126 | TRCN0000089337 | CTAAGTGATAGTGCAATCTTT | 489 | 19.3 | SMAD2 | 4087 |
| Smad2 | 17126 | ND000206 | TGCCTAAGTGATAGTGCAATC | 490 | 30.3 | SMAD2 | 4087 |
| Socs1 | 12703 | ND000214 | TETCGAGCTGCTGGAGCACTA | 491 | 0.6 | SOCS1 | 8651 |
| Socs1 | 12703 | ND000219 | TCGAGCTGCTGGAGCACTACG | 492 | 1.2 | SOCS1 | 8651 |
| Socs1 | 12703 | TRCN0000231240 | TCGCCAACGGAACTGCTTCTT | 493 | 1.4 | SOCS1 | 8651 |
| Socs1 | 12703 | ND000218 | ACTTCTGGCTGGAGACCTCAT | 494 | 1.5 | SOCS1 | 8651 |
| Socs1 | 12703 | TRCN0000067420 | GCGAGACCTTCGACTGCCTTT | 495 | 1.7 | SOCS1 | 8651 |
| Socs1 | 12703 | TRCN0000067418 | CGACACTCACTTCCGCACCTT | 496 | 1.8 | SOCS1 | 8651 |
| Socs1 | 12703 | ND000220 | CTACCTGAGTTCCTTCCCCTT | 497 | 1.8 | SOCS1 | 8651 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Socs1 | 12703 | TRCN0000231238 | TTCCGCTCCCACTCCGATTAC | 498 | 1.8 | SOCS1 | 8651 |
| Socs1 | 12703 | TRCN0000231241 | TAACCCGGTACTCCGTGACTA | 499 | 1.9 | SOCS1 | 8651 |
| Socs1 | 12703 | ND000216 | TACTCCGTGACTACCTGAGTT | 500 | 2.4 | SOCS1 | 8651 |
| Socs1 | 12703 | ND000211 | CCTCCGCTCCCACTCCGATTA | 501 | 2.6 | SOCS1 | 8651 |
| Socs1 | 12703 | TRCN0000067422 | GCGCGACAGTCGCCAACGGAA | 502 | 2.7 | SOCS1 | 8651 |
| Socs1 | 12703 | TRCN0000231239 | TGGACGCCTGCGGCTTCTATT | 503 | 2.9 | SOCS1 | 8651 |
| Socs1 | 12703 | TRCN0000067419 | CGCATCCCTCTTAACCCGGTA | 504 | 3.4 | SOCS1 | 8651 |
| Socs1 | 12703 | ND000212 | TACATATTCCCAGTATCTTTG | 505 | 3.6 | SOCS1 | 8651 |
| Socs1 | 12703 | TRCN0000231242 | GCGCCTTATTATTTCTTATTA | 506 | 4.1 | SOCS1 | 8651 |
| Socs1 | 12703 | TRCN0000067421 | CCGTGACTACCTGAGTTCCTT | 507 | 5.8 | SOCS1 | 8651 |
| Socs1 | 12703 | ND000215 | GGAGGGTCTCTGGCTTCATTT | 508 | 7.8 | SOCS1 | 8651 |
| Socs1 | 12703 | ND000213 | TTCGCGCTCAGCGTGAAGATG | 509 | 8.4 | SOCS1 | 8651 |
| Socs1 | 12703 | ND000217 | ATCCCTUTAACCCGGTACTC | 510 | 8.5 | SOCS1 | 8651 |
| Socs3 | 12702 | ND000222 | CGAGAAGATTCCGCTGGTACT | 511 | 0.3 | SOCS3 | 9021 |
| Socs3 | 12702 | TRCN0000067472 | GCTGCAGGAGAGCGGATTCTA | 512 | 0.4 | SOCS3 | 9021 |
| Socs3 | 12702 | TRCN0000231180 | GGCTAGGAGACTCGCCTTAAA | 513 | 0.7 | SOCS3 | 9021 |
| Socs3 | 12702 | TRCN0000067468 | GCTAGGAGACTCGCCTTAAAT | 514 | 0.8 | SOCS3 | 9021 |
| Socs3 | 12702 | ND000227 | GAGAGCTTACTACATCTATTC | 515 | 0.9 | SOCS3 | 9021 |
| Socs3 | 12702 | ND000221 | GGGAGTTCCTGGATCAGTATG | 516 | 1.0 | SOCS3 | 9021 |
| Socs3 | 12702 | TRCN0000067470 | CAAGAGAGGTTACTACATCTA | 517 | 1.1 | SOCS3 | 9021 |
| Socs3 | 12702 | TRCN0000231179 | CAGTATGATGCTCCACTTTAA | 518 | 1.2 | SOCS3 | 9021 |
| Socs3 | 12702 | ND000223 | CAAGCTGGTGCACCACTACAT | 519 | 1.3 | SOCS3 | 9021 |
| Socs3 | 12702 | ND000224 | ACCTGGACTCCTATGAGAAAG | 520 | 1.4 | SOCS3 | 9021 |
| Socs3 | 12702 | TRCN0000067471 | CTTCTTCACGTTGAGCGTCAA | 521 | 1.6 | SOCS3 | 9021 |
| Socs3 | 12702 | ND000228 | TCGGGAGTTCCTGGATCAGTA | 522 | 1.7 | SOCS3 | 9021 |
| Socs3 | 12702 | ND000226 | TGCAGGAGAGCGGATTCTACT | 523 | 1.9 | SOCS3 | 9021 |
| Socs3 | 12702 | ND000225 | CCTGGTGGGACAATACCTTTG | 524 | 3.3 | SOCS3 | 9021 |
| Socs3 | 12702 | TRCN0000067469 | GATCAGTATGATGCTCCACTT | 525 | 4.6 | SOCS3 | 9021 |
| Socs3 | 12702 | TRCN0000231176 | TCTTCACGTTGAGCGTCAAGA | 526 | 4.7 | SOCS3 | 9021 |
| Socs3 | 12702 | TRCN0000231177 | CGCTTCGACTGTGTACTCAAG | 527 | 4.9 | SOCS3 | 9021 |
| Socs3 | 12702 | ND000229 | GGAGCAAAAGGGTCAGAGGGG | 528 | 5.3 | SOCS3 | 9021 |
| Stk17b | 98267 | ND000590 | AGTGGGACTTTGGAAGCTTGT | 529 | 0.3 | STK17B | 9262 |
| Stk17b | 98267 | ND000597 | CATCTGGACTGACTCGGAAAT | 530 | 0.5 | STK17B | 9262 |
| Stk17b | 98267 | ND000596 | ATGCTGCGGGTGGAGAAATTT | 531 | 0.6 | STK17B | 9262 |
| Stk17b | 98267 | ND000588 | TATCTGAATATTTCTCAAGTG | 532 | 0.6 | STK17B | 9262 |
| Stk17b | 98267 | ND000593 | TTTACCTGAGTTAGCCGAAAT | 533 | 0.7 | STK17B | 9262 |
| Stk17b | 98267 | ND000589 | GTTAACTCATACATCACCATT | 534 | 1.1 | STK17B | 9262 |
| Stk17b | 98267 | ND000594 | CCTATACCATAACTCTATTAC | 535 | 1.3 | STK17B | 9262 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Stk17b | 98267 | ND000592 | CTCAACTATGATCCCATTACC | 536 | 1.3 | STK17B | 9262 |
| Stk17b | 98267 | ND000591 | AGACCTCCAAGTCCTCCTGTA | 537 | 1.4 | STK17B | 9262 |
| Stk17b | 98267 | TRCN0000024255 | GCTGTGGTTAGACAATGTATA | 538 | 1.6 | STK17B | 9262 |
| Stk17b | 98267 | ND000595 | TATTGGCATAATAGCGTATAT | 539 | 3.6 | STK17B | 9262 |
| Stk17b | 98267 | TRCN0000024256 | GCTTGTTTCATCCTGAGGAAA | 540 | 4.0 | STK17B | 9262 |
| Stk17b | 98267 | TRCN0000024258 | TCCTCAACTATGATCCCATTA | 541 | 4.2 | STK17B | 9262 |
| Stk17b | 98267 | TRCN0000024254 | GCAGAAGCTAAGGACGAATTT | 542 | 4.4 | STK17B | 9262 |
| Stk17b | 98267 | TRCN0000024257 | CAGAATAACATTGTTCACCTT | 543 | 6.4 | STK17B | 9262 |
| Tnk1 | 83813 | ND000599 | TGCCCAGCGCAGACTTAATGA | 544 | 0.3 | TNK1 | 8711 |
| Tnk1 | 83813 | TRCN0000023704 | CGTGACACTCTGGGAAATGTT | 545 | 0.6 | TNK1 | 8711 |
| Tnk1 | 83813 | ND000602 | GTGTCCCACCATATCTCATCC | 546 | 0.7 | TNK1 | 8711 |
| Tnk1 | 83813 | ND000600 | AGTAGCAATACCGGATCACTG | 547 | 0.7 | TNK1 | 8711 |
| Tnk1 | 83813 | TRCN0000023706 | GCGGGAAGTATCTGTCATGAT | 548 | 0.8 | TNK1 | 8711 |
| Tnk1 | 83813 | ND000603 | AGAGGATGCGAGGCATTTCCA | 549 | 1.1 | TNK1 | 8711 |
| Tnk1 | 83813 | ND000601 | GGACAGAGAGAAGGCAACGTT | 550 | 1.1 | TNK1 | 8711 |
| Tnk1 | 83813 | TRCN0000361891 | AGAATTGGGTGTACAAGATAC | 551 | 1.3 | TNK1 | 8711 |
| Tnk1 | 83813 | TRCN0000023707 | CCACCTATTATCTGCAACTCT | 552 | 1.6 | TNK1 | 8711 |
| Tnk1 | 83813 | TRCN0000023705 | GCCTCTGATGTGTGGATGTTT | 553 | 1.7 | TNK1 | 8711 |
| Tnk1 | 83813 | TRCN0000361890 | TGCAGAGGATGCGAGGCATTT | 554 | 1.8 | TNK1 | 8711 |
| Tnk1 | 83813 | TRCN0000361889 | TGGCGTGACACTCTGGGAAAT | 555 | 2.0 | TNK1 | 8711 |
| Tnk1 | 83813 | TRCN0000023708 | CAGACTTAATGAAGCCCTGAA | 556 | 5.2 | TNK1 | 8711 |
| Tnk1 | 83813 | TRCN0000361892 | GTGTTGTACATCGAGGGTTAT | 557 | 5.2 | TNK1 | 8711 |
| Tnk1 | 83813 | ND000398 | CCAGAACTTCGGCGTACAAGA | 558 | 7.6 | TNK1 | 8711 |
| Trpm7 | 58800 | ND000607 | GAAGTATCAGCGGTATCATTT | 559 | 0.4 | TRPM7 | 54822 |
| Trpm7 | 58800 | TRCN0000274774 | ATGGATTGTTATCGCTTATAT | 560 | 0.7 | TRPM7 | 54822 |
| Trpm7 | 58800 | ND000606 | GCTTGGAAAGGGTCTTATTAA | 561 | 0.9 | TRPM7 | 54822 |
| Trpm7 | 58800 | ND000608 | ATTGAATCCCTTGAGCAAATT | 562 | 0.9 | TRPM7 | 54872 |
| Trpm7 | 58800 | TRCN0000274712 | CCTTATCAAACCCTATTGAAT | 563 | 1.1 | TRPM7 | 54827 |
| Trpm7 | 58800 | TRCN0000274773 | CCAAAGATCAAGAACCCATTT | 564 | 1.2 | TRPM7 | 54822 |
| Trpm7 | 58800 | ND000604 | TAGAGGTAATGTTCTCATTGA | 565 | 1.2 | TRPM7 | 54822 |
| Trpm7 | 58800 | ND000610 | ACCGGATTGGTTACGAGATAG | 566 | 1.5 | TRPM7 | 54822 |
| Trpm7 | 58800 | TRCN0000274772 | ACCTGGTGCAGGACCATTAAC | 567 | 1.7 | TRPM7 | 54822 |
| Trpm7 | 58800 | ND000605 | TAGACTTTCTAGCCGTAAATC | 568 | 2.9 | TRPM7 | 54822 |
| Trpm7 | 58800 | TRCN0000274711 | CTAGACTTTCTAGCCGTAAAT | 569 | 3.1 | TRPM7 | 54822 |
| Trpm7 | 58800 | TRCN0000023957 | CCTCAGGATGAGTCATCAGAT | 570 | 3.5 | TRPM7 | 54822 |
| Trpm7 | 58800 | TRCN0000023956 | CCTGGTATAAGGTCATATTAA | 571 | 4.9 | TRPM7 | 54822 |
| Trpm7 | 58800 | TRCN0000023955 | GCTCAGAATCTTATTGATGAT | 572 | 5.3 | TRPM7 | 54822 |
| Trpm7 | 58800 | ND000609 | GCCCTAACAGTAGATACATTG | 573 | 5.9 | TRPM7 | 54822 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Vamp7 | 20955 | TRCN0000115068 | CTTACTCACATGGCAATTATT | 574 | 0.6 | VAMP7 | 6845 |
| Vamp7 | 20955 | TRCN0000380436 | GCACAACTGAAGCATCACTCT | 575 | 0.8 | VAMP7 | 6845 |
| Vamp7 | 20955 | TRCN0000336075 | GCACAAGTGGATGAACTGAAA | 576 | 0.9 | VAMP7 | 6845 |
| Vamp7 | 20955 | TRCN0000336077 | TTACGGTTCAAGAGCACAAAC | 577 | 1.0 | VAMP7 | 6845 |
| Vamp7 | 20955 | TRCN0000380733 | TAAGAGCCTAGACAAAGTGAT | 578 | 1.0 | VAMP7 | 6845 |
| Vamp7 | 20955 | ND000255 | AGCCATGTGTATGAAGAATAT | 579 | 1.2 | VAMP7 | 6845 |
| Vamp7 | 20955 | ND000258 | TCCAGGAGCCCATACAAGTAA | 580 | 1.4 | VAMP7 | 6845 |
| Vamp7 | 20955 | ND000255 | ATAAACTAACTTACTCACATG | 581 | 1.5 | VAMP7 | 6845 |
| Vamp7 | 20955 | TRCN0000336014 | GCCGCCACATTTCGTTGTAAA | 582 | 1.8 | VAMP7 | 6845 |
| Vamp7 | 20955 | TRCN0000353419 | GCACTTCCTTATGCTATGAAT | 583 | 1.9 | VAMP7 | 6845 |
| Vamp7 | 20955 | TRCN0000115066 | GCCTTAAGATATGCAATGTTA | 584 | 2.2 | VAMP7 | 6845 |
| Vamp7 | 20955 | ND000257 | CTGAAAGGAATAATGGTCAGA | 585 | 4.0 | VAMP7 | 6845 |
| Vamp7 | 20955 | ND000239 | CTCCTTGTAAATGATACACAA | 586 | 9.8 | VAMP7 | 6845 |
| Vamp7 | 20955 | TRCN0000353291 | CTTTGCCTGTCATATAGTTTG | 587 | 10.5 | VAMP7 | 6845 |
| Vamp7 | 20955 | TRCN0000115069 | TCGAGCCATGTGTATGAAGAA | 588 | 11.3 | VAMP7 | 6845 |
| Yes1 | 22612 | ND000617 | ATCCCTAGCAATTACGTAGTG | 589 | 0.5 | YES1 | 7525 |
| Yes1 | 22612 | TRCN0000339152 | TGGTTATATCCCTAGCAATTA | 590 | 0.5 | YES1 | 7525 |
| Yes1 | 22612 | ND000614 | TATGCTTCACTCGGCATGTTT | 591 | 0.6 | YES1 | 7525 |
| Yes1 | 22612 | ND000616 | ATTCCAGATACGGTTACTCAA | 592 | 0.6 | YES1 | 7525 |
| Yes1 | 22612 | ND000613 | TTTAAGAAGGGTGAACGATTT | 593 | 0.7 | YES1 | 7525 |
| Yes1 | 22612 | ND000612 | CACGACCAGAGCTCAGTTTGA | 594 | 0.8 | YES1 | 7525 |
| Yes1 | 22612 | ND000615 | CAGGTATGGTAAACCGTGAAG | 599 | 0.8 | YES1 | 7525 |
| Yes1 | 22612 | ND000611 | GGAGTGGAACATGCTACAGTT | 596 | 1.0 | YES1 | 7525 |
| Yes1 | 22612 | ND000618 | CCTCATECTCAGTGGTGTCAA | 597 | 2.6 | YES1 | 7525 |
| Yes1 | 22612 | ND000619 | TCGAGAATCATTGCGACTAGA | 598 | 2.8 | YES1 | 7525 |
| Yes1 | 22612 | TRCN0000339083 | CCAGGTACAATGATGCCAGAA | 599 | 2.8 | YES1 | 7525 |
| Yes1 | 22612 | TRCN0000339150 | GCGGAAAGATTACTTCTGAAT | 600 | 3.9 | YES1 | 7525 |
| Yes1 | 22612 | TRCN0000023616 | GCTGCTCTGTATGGTCGATTT | 601 | 4.1 | YES1 | 7525 |
| Yes1 | 22612 | TRCN0000023618 | CCTTGTATGATTATGAAGCTA | 602 | 5.4 | YES1 | 7525 |
| Yes1 | 22612 | TRCN0000023617 | GCCAGTCATTATGGAGTGGAA | 603 | 9.7 | YES1 | 7525 | shRNAs demonstrating an at least ≥3 shRNAs fold enrichment in tumor relative to spleen indicate amore active target sequence region.

In some aspects, the nucleic acids of the compositions encode the shRNA sequences targeting the human Ppp2r2d and Cblb sequences provided in Table 2a.

TABLE 2a

| # | Gene | Human shRNA Target Sequence |
|---|---|---|
| 1 | Ppp2r2d | CCCGCACCAGTGCAACGTGTT (SEQ ID NO: 636) |
| 2 | Ppp2r2d | TCATAGTGGGCGGTACATGAT (SEQ ID NO: 637) |

TABLE 2a-continued

| # | Gene | Human shRNA Target Sequence |
|---|---|---|
| 3 | Ppp2r2d | GAGAATTAATTTATGGCACTT (SEQ ID NO: 638) |
| 4 | Ppp2r2d | CCATTTAGGATCACGGCGCTA (SEQ ID NO: 639) |
| 5 | Ppp2r2d | ATAGTGATCATGAAACATATC (SEQ ID NO: 375) |
| 6 | Ppp2r2d | GCCACCAATAACTTGTACATA (SEQ ID NO: 640) |
| 7 | Ppp2r2d | CGGTTCGGATAGCGCCATCAT (SEQ ID NO: 641) |
| 8 | Ppp2r2d | TCATTTCCACCGTTGAGTTTA (SEQ ID NO: 642) |
| 9 | Ppp2r2d | ATGCTCACACATATCATATAA (SEQ ID NO: 643) |
| 1 | Cblb | CGGGCAATAAGACTCTTTAA (SEQ ID NO: 644) |
| 2 | Cblb | TGCCCAGGTCCAGTTCCATTTC (SEQ ID NO: 645) |
| 3 | Cblb | TCCTGATTTAACTGGATTATG (SEQ ID NO: 646) |
| 4 | Cblb | ATCAAACATCCCTGACTTAAG (SEQ ID NO: 647) |
| 5 | Cblb | CTACACCTCATGACCATATAA (SEQ ID NO: 648) |
| 6 | Cblb | TACACCTCATGACCATATAAA (SEQ ID NO: 649) |
| 7 | Cblb | TCAGTGAGAATGAGTACTTTA (SEQ ID NO: 650) |
| 8 | Cblb | CCTGACTTAAGCATATATTTA (SEQ ID NO: 651) |
| 9 | Cblb | TCTACATTGATAGCCTTATGA (SEQ ID NO: 652) |

In other embodiments, the disclosure provides isolated nucleic acids encoding shRNA sequences complementary to a Ppp2r2d target sequence identical to at least 12, at least 15, at least 20, or at least 25 contiguous nucleotides set forth in SEQ ID NO: 372, 373, 374, 375, 376, 377, 378, 378, 379, 380, 381, 382, 383, 384, 385, or 386.

In other embodiments, the disclosure provides isolated nucleic acids encoding a shRNA comprising a sequence complementary to a human Pp2r2d sequence that corresponds to a murine target sequence set forth in SEQ ID NO: 372, 373, 374, 375, 376, 377, 378, 378, 379, 380, 381, 382, 383, 384, 385, or 386.

In other embodiments, the disclosure provides isolated nucleic acids encoding shRNA sequences complementary to a Eif2ak3 target sequence identical to at least 12, at least 15, at least 20, or at least 25 contiguous nucleotides set forth in SEQ ID NO: 133, 134, 135, 136, 137, 138, 139, 140, 141, 142, 143, 144, 145, 146 or 147.

In other embodiments, the disclosure provides isolated nucleic acids encoding a shRNA comprising a sequence complementary to a human Eifak3 sequence that corresponds to a murine target sequence set forth in SEQ ID NO: 133, 134, 135, 136, 137, 138, 139, 140, 141, 142, 143, 144, 145, 146 or 147.

In other embodiments, the disclosure provides isolated nucleic acids encoding shRNA sequences complementary to an Arhgap5 target sequence identical to at least 12, at least 15, at least 20, or at least 25 contiguous nucleotides set forth in SEQ ID NO: 32, 33, 34, 35, 36, 37, 38, 39, 40, 41, or 42.

In other embodiments, the disclosure provides isolated nucleic acids encoding a shRNA comprising a sequence complementary to a human Arhgap5 sequence that corresponds to a murine target sequence set forth in SEQ ID NO: 32, 33, 34, 35, 36, 37, 38, 39, 40, 41, or 42.

In other embodiments, the disclosure provides isolated nucleic acids encoding shRNA sequences complementary to a Smad2 target sequence identical to at least 12, at least 15, at least 20, or at least 25 contiguous nucleotides set forth in SEQ ID NO: 476, 477, 478, 479, 480, 481, 482, 483, 484, 485, 486, 487, 488, 489, or 490.

In other embodiments, the disclosure provides isolated nucleic acids encoding a shRNA comprising a sequence complementary to a human Smad2 sequence that corresponds to a murine target sequence set forth in SEQ ID NO: 476, 477, 478, 479, 480, 481, 482, 483, 484, 485, 486, 487, 488, 489, or 490.

In other embodiments, the disclosure provides isolated nucleic acids encoding shRNA sequences complementary to an Akap81 target sequence identical to at least 12, at least 15, at least 20, or at least 25 contiguous nucleotides set forth in SEQ ID NO: 1, 2, 3, 4, 5, 6, 7, 8, 9, 10, 11, 12, 13, 14, or 15.

In other embodiments, the disclosure provides isolated nucleic acids encoding a shRNA comprising a sequence complementary to a human Akap81 sequence that corresponds to a murine target sequence set forth in SEQ ID NO: 1, 2, 3, 4, 5, 6, 7, 8, 9, 10, 11, 12, 13, 14, or 15.

In other embodiments, the disclosure provides isolated nucleic acids encoding shRNA sequences complementary to a Rbks target sequence identical to at least 12, at least 15, at least 20, or at least 25 contiguous nucleotides set forth in SEQ ID NO: 431, 432, 433, 434, 435, 436, 437, 438, 439, 440, 441, 442, 443, 444, or 445.

In other embodiments, the disclosure provides isolated nucleic acids encoding a shRNA comprising a sequence complementary to a human Rbks sequence that corresponds to a murine target sequence set forth in SEQ ID NO: 431, 432, 433, 434, 435, 436, 437, 438, 439, 440, 441, 442, 443, 444, or 445.

In other embodiments, the disclosure provides isolated nucleic acids encoding shRNA sequences complementary to an Egr2 target sequence identical to at least 12, at least 15, at least 20, or at least 25 contiguous nucleotides set forth in SEQ ID NO: 118, 119, 120, 121, 122, 123, 124, 125, 126, 127, 128, 129, 130, 131, or 132.

In other embodiments, the disclosure provides isolated nucleic acids encoding a shRNA comprising a sequence complementary to a human Egr2 sequence that corresponds to a murine target sequence set forth in SEQ ID NO: 118, 119, 120, 121, 122, 123, 124, 125, 126, 127, 128, 129, 130, 131, or 132.

In other embodiments, the disclosure provides isolated nucleic acids encoding shRNA sequences complementary to a Dgka target sequence identical to at least 12, at least 15, at least 20, or at least 25 contiguous nucleotides set forth in SEQ ID NO: 88, 89, 90, 91, 92, 93, 94, 95, 96, 97, 98, 99, 100, 101, 102, 103, 104, 105, 106, 107, 108, 109, 110, 111, 112, 113, 114, 115, 116 or 117.

In other embodiments, the disclosure provides isolated nucleic acids encoding a shRNA comprising a sequence complementary to a human Dgka sequence that corresponds to a murine target sequence set forth in SEQ ID NO: 88, 89, 90, 91, 92, 93, 94, 95, 96, 97, 98, 99, 100, 101, 102, 103, 104, 105, 106, 107, 108, 109, 110, 111, 112, 113, 114, 115, 116 or 117.

In other embodiments, the disclosure provides isolated nucleic acids encoding shRNA sequences complementary to a Cblb target sequence identical to at least 12, at least 15, at least 20, or at least 25 contiguous nucleotides set forth in SEQ ID NO: 58, 59, 60, 61, 62, 63, 64, 65, 66, 67, 68, 69, 70, 71, or 72.

In other embodiments, the disclosure provides isolated nucleic acids encoding a shRNA comprising a sequence complementary to a human Cblb sequence that corresponds to a murine target sequence set forth in SEQ ID NO: 58, 59, 60, 61, 62, 63, 64, 65, 66, 67, 68, 69, 70, 71, or 72.

In other embodiments, the disclosure provides isolated nucleic acids encoding shRNA sequences complementary to a Mdfic target sequence identical to at least 12, at least 15, at least 20, or at least 25 contiguous nucleotides set forth in SEQ ID NO: 285, 286, 287, 288, 289, 290, 291, 292, 293, 294, 295, 296, 297, 298, or 299.

In other embodiments, the disclosure provides isolated nucleic acids encoding a shRNA comprising a sequence complementary to a human Mdfic sequence that corresponds to a murine target sequence set forth in SEQ ID NO: 285, 286, 287, 288, 289, 290, 291, 292, 293, 294, 295, 296, 297, 298, or 299.

In other embodiments, the disclosure provides isolated nucleic acids encoding shRNA sequences complementary to an Entpd1 target sequence identical to at least 12, at least 15, at least 20, or at least 25 contiguous nucleotides set forth in SEQ ID NO: 148, 149, 150, 151, 152, 153, 154, 155, 156, 157, 158, 159, 160, 161, or 162.

In other embodiments, the disclosure provides isolated nucleic acids encoding a shRNA comprising a sequence complementary to a human Entpd1 sequence that corresponds to a murine target sequence set forth in SEQ ID NO: 148, 149, 150, 151, 152, 153, 154, 155, 156, 157, 158, 159, 160, 161, or 162.

In other embodiments, the disclosure provides isolated nucleic acids encoding shRNA sequences complementary to a Vamp7 target sequence identical to at least 12, at least 15, at least 20, or at least 25 contiguous nucleotides set forth in SEQ ID NO: 574, 575, 576, 577, 578, 579, 580, 581, 582, 583, 584, 585, 586, or 587.

In other embodiments, the disclosure provides isolated nucleic acids encoding a shRNA comprising a sequence complementary to a human Vamp7sequence that corresponds to a murine target sequence set forth in SEQ ID NO: 574, 575, 576, 577, 578, 579, 580, 581, 582, 583, 584, 585, 586, or 587.

In other embodiments, the disclosure provides isolated nucleic acids encoding shRNA sequences complementary to a Hipk1 target sequence identical to at least 12, at least 15, at least 20, or at least 25 contiguous nucleotides set forth in SEQ ID NO. 208, 209, 210, 211, 212, 213, 214, 215, 216, 217, 218, 219, 220, 221, or 222.

In other embodiments, the disclosure provides isolated nucleic acids encoding a shRNA comprising a sequence complementary to a human Hipk1 sequence that corresponds to a murine target sequence set forth in SEQ ID NO: 208, 209, 210, 211, 212, 213, 214, 215, 216, 217, 218, 219, 220, 221, or 222.

In other embodiments, the disclosure provides isolated nucleic acids encoding shRNA sequences complementary to a Nuak2 target sequence identical to at least 12, at least 15, at least 20, or at least 25 contiguous nucleotides set forth in SEQ ID NO: 315, 316, 317, 318, 319, 320, 321, 322, 323, 324, 325, 326, 327, 328, or 329.

In other embodiments, the disclosure provides isolated nucleic acids encoding a shRNA comprising a sequence complementary to a human Nuak2 sequence that corresponds to a murine target sequence set forth in SEQ ID NO: 315, 316, 317, 318, 319, 320, 321, 322, 323, 324, 325, 326, 327, 328, or 329.

In other embodiments, the disclosure provides isolated nucleic acids encoding shRNA sequences complementary to an Alk target sequence identical to at least 12, at least 15, at least 20, or at least 25 contiguous nucleotides set forth in SEQ ID NO: 16, 17, 18, 19, 20, 21, 22, 23, 24, 25, 26, 27, 28, 29, 30, or 31.

In other embodiments, the disclosure provides isolated nucleic acids encoding a shRNA comprising a sequence complementary to a human Alk sequence that corresponds to a murine target sequence set forth in SEQ ID NO: 16, 17, 18, 19, 20, 21, 22, 23, 24, 25, 26, 27, 28, 29, 30, or 31.

In other embodiments, the disclosure provides isolated nucleic acids encoding shRNA sequences complementary to a Pdzk1ip1 target sequence identical to at least 12, at least 15, at least 20, or at least 25 contiguous nucleotides set forth in SEQ ID NO: 330, 331, 332, 333, 334, 335, 336, 337, 338, 339, 340, or 341.

In other embodiments, the disclosure provides isolated nucleic acids encoding a shRNA comprising a sequence complementary to a human Pdzk1ip1 sequence that corresponds to a murine target sequence set forth in SEQ ID NO: 330, 331, 332, 333, 334, 335, 336, 337, 338, 339, 340, or 341.

In other embodiments, the disclosure provides isolated nucleic acids encoding shRNA sequences complementary to a Blvrb target sequence identical to at least 12, at least 15, at least 20, or at least 25 contiguous nucleotides set forth in SEQ ID NO: 52, 53, 54, 55, 56 or 57.

In other embodiments, the disclosure provides isolated nucleic acids encoding a shRNA comprising a sequence complementary to a human Blvrb that corresponds to a murine target sequence set forth in SEQ ID NO: 52, 53, 54, 55, 56 or 57.

In other embodiments, the disclosure provides isolated nucleic acids encoding shRNA sequences complementary to a Cdkn2a target sequence identical to at least 12, at least 15, at least 20, or at least 25 contiguous nucleotides set forth in SEQ ID NO: 83, 84, 85, 86 or 87.

In other embodiments, the disclosure provides isolated nucleic acids encoding a shRNA comprising a sequence complementary to a human Cdkn2a that corresponds to a murine target sequence set forth in SEQ ID NO: 83, 84, 85, 86 or 87.

In other embodiments, the disclosure provides isolated nucleic acids encoding shRNA sequences complementary to a F11r target sequence identical to at least 12, at least 15, at least 20, or at least 25 contiguous nucleotides set forth in SEQ ID NO: 175, 176 or 177.

In other embodiments, the disclosure provides isolated nucleic acids encoding a shRNA comprising a sequence complementary to a human F11r that corresponds to a murine target sequence set forth in SEQ ID NO: 175, 176 or 177.

In other embodiments, the disclosure provides isolated nucleic acids encoding shRNA sequences complementary to a Fyn target sequence identical to at least 12, at least 15, at least 20, or at least 25 contiguous nucleotides set forth in SEQ ID NO: 187, 191 or 192.

In other embodiments, the disclosure provides isolated nucleic acids encoding a shRNA comprising a sequence complementary to a human Fyn that corresponds to a murine target sequence set forth in SEQ ID NO: 187, 191 or 192.

In other embodiments, the disclosure provides isolated nucleic acids encoding shRNA sequences complementary to a Grk6 target sequence identical to at least 12, at least 15, at least 20, or at least 25 contiguous nucleotides set forth in SEQ ID NO: 204, 205, 206 or 207.

In other embodiments, the disclosure provides isolated nucleic acids encoding a shRNA comprising a sequence complementary to a human Grk6 that corresponds to a murine target sequence set forth in SEQ ID NO: 204, 205, 206 or 207.

In other embodiments, the disclosure provides isolated nucleic acids encoding shRNA sequences complementary to an Inpp5b target sequence identical to at least 12, at least 15, at least 20, or at least 25 contiguous nucleotides set forth in SEQ ID NO: 232, 234, 235, 236 or 237.

In other embodiments, the disclosure provides isolated nucleic acids encoding a shRNA comprising a sequence complementary to a human Inpp5b that corresponds to a murine target sequence set forth in SEQ ID NO: 232, 234, 235, 236 or 237.

In other embodiments, the disclosure provides isolated nucleic acids encoding shRNA sequences complementary to an Impk target sequence identical to at least 12, at least 15, at least 20, or at least 25 contiguous nucleotides set forth in SEQ ID NO: 248, 249, 250, 251 or 252.

In other embodiments, the disclosure provides isolated nucleic acids encoding a shRNA comprising a sequence complementary to a human Impk that corresponds to a murine target sequence set forth in SEQ ID NO: 248, 249, 250, 251 or 252.

In other embodiments, the disclosure provides isolated nucleic acids encoding shRNA sequences complementary to a Jun target sequence identical to at least 12, at least 15, at least 20, or at least 25 contiguous nucleotides set forth in SEQ ID NO: 263, 264, 265, 266, 267, 268 or 269.

In other embodiments, the disclosure provides isolated nucleic acids encoding a shRNA comprising a sequence complementary to a human Jun that corresponds to a murine target sequence set forth in SEQ ID NO: 263, 264, 265, 266, 267, 268 or 269.

In other embodiments, the disclosure provides isolated nucleic acids encoding shRNA sequences complementary to a Mast2 target sequence identical to at least 12, at least 15, at least 20, or at least 25 contiguous nucleotides set forth in SEQ ID NO: 281, 282, 283 or 284.

In other embodiments, the disclosure provides isolated nucleic acids encoding a shRNA comprising a sequence complementary to a human Mast2 that corresponds to a murine target sequence set forth in SEQ ID NO: 281, 282, 283 or 284. In other embodiments, the disclosure provides isolated nucleic acids encoding shRNA sequences complementary to a Nptxr target sequence identical to at least 12, at least 15, at least 20, or at least 25 contiguous nucleotides set forth in SEQ ID NO: 311, 312, 313 or 314.

In other embodiments, the disclosure provides isolated nucleic acids encoding a shRNA comprising a sequence complementary to a human Nptxr that corresponds to a murine target sequence set forth in SEQ ID NO: 311, 312, 313 or 314.

In other embodiments, the disclosure provides isolated nucleic acids encoding shRNA sequences complementary to a Pkd1 target sequence identical to at least 12, at least 15, at least 20, or at least 25 contiguous nucleotides set forth in SEQ ID NO: 351, 352, 353, 354, 355 or 356.

In other embodiments, the disclosure provides isolated nucleic acids encoding a shRNA comprising a sequence complementary to a human Pkd1 that corresponds to a murine target sequence set forth in SEQ ID NO: 351, 352, 353, 354, 355 or 356.

In other embodiments, the disclosure provides isolated nucleic acids encoding shRNA sequences complementary to a Ppm1g target sequence identical to at least 12, at least 15, at least 20, or at least 25 contiguous nucleotides set forth in SEQ ID NO: 367, 368, 369, 370 or 371.

In other embodiments, the disclosure provides isolated nucleic acids encoding a shRNA comprising a sequence complementary to a human Ppm1g that corresponds to a murine target sequence set forth in SEQ ID NO: 367, 368, 369, 370 or 371.

In other embodiments, the disclosure provides isolated nucleic acids encoding shRNA sequences complementary to a Ppp3cc target sequence identical to at least 12, at least 15, at least 20, or at least 25 contiguous nucleotides set forth in SEQ ID NO: 399, 400 or 401.

In other embodiments, the disclosure provides isolated nucleic acids encoding a shRNA comprising a sequence complementary to a human Ppp3cc that corresponds to a murine target sequence set forth in SEQ ID NO: 399, 400 or 401.

In other embodiments, the disclosure provides isolated nucleic acids encoding shRNA sequences complementary to a Prkab2 target sequence identical to at least 12, at least 15, at least 20, or at least 25 contiguous nucleotides set forth in SEQ ID NO: 414, 415 or 416.

In other embodiments, the disclosure provides isolated nucleic acids encoding a shRNA comprising a sequence complementary to a human Prkab2 that corresponds to a murine target sequence set forth in SEQ ID NO: 414, 415 or 416.

In other embodiments, the disclosure provides isolated nucleic acids encoding shRNA sequences complementary to a Ptpn2 target sequence identical to at least 12, at least 15, at least 20, or at least 25 contiguous nucleotides set forth in SEQ ID NO: 426, 427, 428, 429 or 430.

In other embodiments, the disclosure provides isolated nucleic acids encoding a shRNA comprising a sequence complementary to a human Ptpn2 that corresponds to a murine target sequence set forth in SEQ ID NO: 426, 427, 428, 429 or 430.

In other embodiments, the disclosure provides isolated nucleic acids encoding shRNA sequences complementary to a Rock1 target sequence identical to at least 12, at least 15, at least 20, or at least 25 contiguous nucleotides set forth in SEQ ID NO: 457, 458, 459 or 460.

In other embodiments, the disclosure provides isolated nucleic acids encoding a shRNA comprising a sequence complementary to a human Rock1 that corresponds to a murine target sequence set forth in SEQ ID NO: 457, 458, 459 or 460.

In other embodiments, the disclosure provides isolated nucleic acids encoding shRNA sequences complementary to a Sbf1 target sequence identical to at least 12, at least 15, at least 20, or at least 25 contiguous nucleotides set forth in SEQ ID NO: 470, 471, 472, 473, 474 or 475.

In other embodiments, the disclosure provides isolated nucleic acids encoding a shRNA comprising a sequence complementary to a human Sbf1 that corresponds to a murine target sequence set forth in SEQ ID NO: 470, 471, 472, 473, 474 or 475.

In other embodiments, the disclosure provides isolated nucleic acids encoding shRNA sequences complementary to a Socs1 target sequence identical to at least 12, at least 15, at least 20, or at least 25 contiguous nucleotides set forth in SEQ ID NO: 504, 505, 506, 507, 508, 509 or 510.

In other embodiments, the disclosure provides isolated nucleic acids encoding a shRNA comprising a sequence complementary to a human Socs1 that corresponds to a murine target sequence set forth in SEQ ID NO: 504, 505, 506, 507, 508, 509 or 510.

In other embodiments, the disclosure provides isolated nucleic acids encoding shRNA sequences complementary to a Socs3 target sequence identical to at least 12, at least 15, at least 20, or at least 25 contiguous nucleotides set forth in SEQ ID NO: 524, 525, 526, 527 or 528.

In other embodiments, the disclosure provides isolated nucleic acids encoding a shRNA comprising a sequence complementary to a human Socs3 that corresponds to a murine target sequence set forth in SEQ ID NO: 524, 525, 526, 527 or 528.

In other embodiments, the disclosure provides isolated nucleic acids encoding shRNA sequences complementary to a Stk17b target sequence identical to at least 12, at least 15, at least 20, or at least 25 contiguous nucleotides set forth in SEQ ID NO: 539, 540, 541, 542 or 543.

In other embodiments, the disclosure provides isolated nucleic acids encoding a shRNA comprising a sequence complementary to a human Stk17b that corresponds to a murine target sequence set forth in SEQ ID NO: 539, 540, 541, 542 or 543.

In other embodiments, the disclosure provides isolated nucleic acids encoding shRNA sequences complementary to a Tnk1 target sequence identical to at least 12, at least 15, at least 20, or at least 25 contiguous nucleotides set forth in SEQ ID NO: 556, 557 or 558.

In other embodiments, the disclosure provides isolated nucleic acids encoding a shRNA comprising a sequence complementary to a human Tnk1 that corresponds to a murine target sequence set forth in SEQ ID NO: 556, 557 or 558.

In other embodiments, the disclosure provides isolated nucleic acids encoding shRNA sequences complementary to a Trpm7 target sequence identical to at least 12, at least 15, at least 20, or at least 25 contiguous nucleotides set forth in SEQ ID NO: 569, 570, 571, 572 or 573.

In other embodiments, the disclosure provides isolated nucleic acids encoding a shRNA comprising a sequence complementary to a human Trpm7 that corresponds to a murine target sequence set forth in SEQ ID NO: 569, 570, 571, 572 or 573.

In other embodiments, the disclosure provides isolated nucleic acids encoding shRNA sequences complementary to a Yes1 target sequence identical to at least 12, at least 15, at least 20, or at least 25 contiguous nucleotides set forth in SEQ ID NO: 600, 601, 602 or 603.

In other embodiments, the disclosure provides isolated nucleic acids encoding a shRNA comprising a sequence complementary to a human Yes1 that corresponds to a murine target sequence set forth in SEQ ID NO: 600, 601, 602 or 603. In any embodiment, a human sequence that corresponds to a murine target sequence is a sequence which perfectly corresponds to the human gene sequence, and for example, can have none, 1, 2, 3 or 4 nucleotide mismatches with the at least 12, at least 15, at least 20, or at least 25 contiguous nucleotides of the selected murine target sequence.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, adeno-associated virus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term "percent sequence identity" refers to the degree of identity between any given query sequence and a subject sequence. A percent identity for any query nucleic acid or amino acid sequence, e.g., a transcription factor, relative to another subject nucleic acid or amino acid sequence can be determined as follows.

As used herein, the term "complementary nucleotide sequence," also known as an "antisense sequence," refers to a sequence of a nucleic acid that is completely complementary to the sequence of a "sense" nucleic acid encoding a protein (e.g., complementary to the coding strand of a double-stranded cDNA molecule or complementary to an mRNA sequence). Herein, nucleic acid molecules are provided that comprise a sequence complementary to at least about 15, 16, 17, 18, 19, 20, 21, 22, 23, 24, or 25 nucleotides or an entire gene coding strand, or to only a portion thereof.

As used herein, the term "correspond to a nucleotide sequence" refers to a nucleotide sequence of a nucleic acid encoding an identical sequence. In some instances, when antisense nucleotides (nucleic acids) or siRNA's (small inhibitory RNA) hybridize to a target sequence a particular antisense or small inhibitory RNA (siRNA) sequence is substantially complementary to the target sequence, and thus will specifically bind to a portion of an mRNA encoding polypeptide. As such, typically the sequences of those nucleic acids will be highly complementary to the mRNA target sequence, and will have no more than 1, 2, 3, 4, 5, 6, 7, 8, 9, or 10 base mismatches throughout the sequence. In many instances, it may be desirable for the sequences of the nucleic acids to be exact matches, i.e. be completely complementary to the sequence to which the oligonucleotide specifically binds, and therefore have zero mismatches along the complementary stretch. Highly complementary sequences will typically bind quite specifically to the target sequence region of the mRNA and will therefore be highly efficient in reducing, and/or even inhibiting the translation of the target mRNA sequence into polypeptide product.

As used herein, the term "vector" refers to any viral or non-viral vector, as well as any plasmid, cosmid, phage or binary vector in double or single stranded linear or circular form that may or may not be self transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this invention.

Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom, Thus, a gene encodes a protein if transcription and translation of mRNA corresponding to that gene produces the protein in a cell or other biological system, Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

Vectors capable of directing the expression of genes to which they are operatively linked are referred to herein as "expression vectors". Thus, an "Expression vector" is a specialized vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

In some aspects, the disclosure provides modified cells that harbor vectors capable of expressing the shRNA described herein and further modified to express a CAR. In one aspect the shRNA and the CAR are expressed on the same vector. In another aspect, the shRNA and the CAR are expressed on separate vectors.

In some embodiments, the modified cells described herein are immunoresponsive cells. In some aspects, the immunoresponsive cells express at least one of an antigen-recognizing receptor. In any aspect, the immunoresponsive cells express at least one of an tumor specific antigen-recognizing receptor. In some aspects, tumor cell antigen specific T cells, NKT cells, TIL, CTL cells or other immunoresponsive cells are used. Non-limiting examples of immunoresponsive cells include T cells, such as, for example, $\alpha\beta$-TCR+ T cells (e.g., CD8+ T cells or CD4+ T cells) $\gamma\delta$-TCR+ T cells, tumor-infiltrating lymphocytes (TIL), Natural Killer T cells (NKT), a cytotoxic T lymphocytes (CTL), and a CD4 T cells.

Compositions comprising the immunoresponsive cells of the invention (e.g., T cells, NKT cells, TILs, CTL cells, or their progenitors) can be provided systemically or directly to a subject for the treatment of a cancer. In one embodiment, cells of the invention are directly injected into an organ of interest (e.g., an organ affected by a cancer). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NKT cells, TILs, CTL cells in vitro or in vivo.

The modified immunoresponsive cells can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells will be administered, eventually reaching $1\times10^{10}$, or more. Immunoresponsive cells of the invention can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage).

The cells can be introduced by injection, catheter, or the like. If desired, factors can also be included, including, but not limited to, interleukins, e.g. IL-2, IL-3, IL-6, and IL-11, as well as the other interleukins, the colony stimulating factors, such as G-, M- and GM-CSF, interferons, e.g. .gamma.-interferon and erythropoietin.

Compositions of the invention include pharmaceutical compositions comprising the immunoresponsive cells of the invention or their progenitors and a pharmaceutically acceptable carrier. Administration can be autologous or heterologous. For example, immunoresponsive cells, or progenitors can be obtained from one subject, and administered to the same subject or a different, compatible subject.

Chimeric Antigen Receptors

In some instances, the invention provides chimeric antigen receptors (CARs) comprising an antigen binding domain directed to a tumor cell antigen. A CAR is an artificially constructed hybrid protein or polypeptide containing an extracellular portion that recognizes a tumor cell antigen (e.g., the antigen binding domains of an antibody (scFv) and a cyplasmic signaling domain derived from the T cell receptor and costimulatory domain. (Kalos M, et al., Sci Transl Med. 2011 Aug. 10; 3(95)) Kalos et al. describes the generation of CAR T cells that target CD19 and demonstrates the CAR modified T-cells mediated potent antitumor effect in chronic lymphocytic leukemia patients. Characteristics of CARs include their ability to redirect T-cell specificity and reactivity toward a selected target in a non-MHC-restricted manner, exploiting the antigen-binding properties of monoclonal antibodies. The CAR-modified T-cells have the potential to replicate in vivo and long term persistence allows for sustained tumor control and obviate the need for repeated infusions of antibody. (Kalos M, et al., Sci Transl Med. 2011 Aug. 10; 3(95)) The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains. CAR-modified T cells are described in detail in WO2012/079000 and WO2012/09999 and in Milone et al. 2009 Mol. Ther. 17:1453.

A CAR combines the binding site of a molecule that recognizes an antigen being targeted (i.e., an "antigen binding domain") with one or more domains of conventional immune receptors responsible for initiating signal transduction that leads to lymphocyte activation (e.g., the "stimulatory domain" or "signaling domain").

In some embodiments, the binding portion used is derived from the structure of the Fab (antigen binding) fragment of a monoclonal antibody (mAb) that has high affinity for the tumor antigen being targeted. Because the Fab is the product of two genes, the corresponding sequences are usually combined via a short linker fragment that allows the heavy-chain to fold over the light-chain derived peptides into native configuration, creating a single-chain fragment variable (scFv) region.

Fv or (scFv) antibody fragments comprise the VH and VL domains of antibody, wherein these domains are present in a single polypeptide chain. Generally the Fv polypeptide further comprises a polypeptide linker between the VH and VL domains, which enables the scFv to form the desired structure for antigen binding.

In some embodiments, the binding portion used is derived from a cytoplasmic signaling domain derived from T cell receptor and costimulatory molecules.

In some embodiments, the signaling portion of CARs contains usually the intracellular domains of the zeta (ζ) chain of the TCR/CD3 complex[25] or, less commonly, of the gamma (γ) chain of the immunoglobulin receptor FcεRI[26, 27] or the CD3-epsilon (ε) chain,[28] with the transmembrane region being derived from the same molecule.

In some aspects, the CARs comprise an antigen binding domain, a transmembrane domain, a stimulatory domain, and a co-stimulatory domain. Further embodiments of the invention provide related nucleic acids, recombinant expression vectors, host cells, populations of cells, antibodies, or antigen binding portions thereof, and pharmaceutical compositions relating to the CARs of the invention.

In one aspect, the antigen binding domain binds to a tumor cell antigen. The term "tumor cell antigen" or "tumor antigen" as used herein refers to any polypeptide expressed by a tumor that is capable of inducing an immune response. Non-limiting examples of tumor antigens include, for example, prostate-specific membrane antigen (PSMA), Carcinoembryonic Antigen (CEA), CD19, CD20, CD22, ROR1, mesothelin, CD333/IL3Ra, c-Met, Glycolipid F77, EGFRvIII, GD-2, NY-ESO-1 TCR, ERBB2, BIRC5, CEACAM5, WDR46, BAGE, CSAG2, DCT, MAGED4, GAGE1, GAGE2, GAGE3, GAGE4, GAGE5, GAGE6, GAGE7, GAGE8, IL13RA2, MAGEA1, MAGEA2, MAGEA3, MAGEA4, MAGEA6, MAGEA9, MAGEA10, MAGEA12, MAGEB1, MAGEB2, MAGEC2, TP53, TYR, TYRP1, SAGE1, SYCP1, SSX2, SSX4, KRAS, PRAME, NRAS, ACTN4, CTNNB1, CASP8, CDC27, CDK4, EEF2, FN1, HSPA1B, LPGAT1, ME1, HHAT, TRAPPC1, MUM3, MYO1B, PAPOLG, OS9, PTPRK, TPI1, ADFP, AFP, AIM2, ANXA2, ART4, CLCA2, CPSF1, PPIB, EPHA2, EPHA3, FGF5, CA9, TERT, MGAT5, CEL, F4.2, CAN, ETV6, BIRC7, CSF1, OGT, MUC1, MUC2, MUM1, CTAG1A, CTAG2, CTAG, MRPL28, FOLH1, RAGE, SFMBT1, KAAG1, SART1, TSPYL1, SART3, SOX10, TRG, WT1, TACSTD1, SILV, SCGB2A2, MC1R, MLANA, GPR143, OCA2, KLK3, SUPT7L, ARTC1, BRAF, CASP5, CDKN2A, UBXD5, EFTUD2, GPNMB, NFYC, PRDX5, ZUBR1, SIRT2, SNRPD1, HERV-K-MEL, CXorf61, CCDC110, VENTXP1, SPA17, KLK4, ANKRD30A, RAB38, CCND1, CYPIB1, MDM2, MMP2, ZNF395, RNF43, SCRN1, STEAP1, 707-AP, TGFBR2, PXDNL, AKAP13, PRTN3, PSCA, RHAMM, ACPP, ACRBP, LCK, RCVRN, RPS2, RPL10A, SLC45A3, BCL2L1, DKK1, ENAH, CSPG4, RGS5, BCR, BCR-ABL, ABL-BCR, DEK, DEK-CAN, ETV6-AML1, LDLR-FUT, NPM1-ALK1, PML-RARA, SYT-SSX1, SYT-SSX2, FLT3, ABL1, AML1, LDLR, FUT1, NPM1, ALK, PML1, RARA, SYT, SSX1, MSLN, UBE2V1, HNRPL, WHSC2, EIF4EBP1, WNK2, OAS3, BCL-2, MCL1, CTSH, ABCC3, BST2, MFGE8, TPBG, FMOD, XAGE1, RPSA, COTL1, CALR3, PA2G4, EZH2, FMNL1, HPSE, APC, UBE2A, BCAP31, TOP2A, TOP2B, ITGB8, RPA1, ABI2, CCNI, CDC2, SEPT2, STAT1, LRP1, ADAM17, JUP, DDR1, ITPR2, HMOX1, TPM4, BAAT, DNAJC8, TAPBP, LGALS3BP, PAGE4, PAK2, CDKN1A, PTHLH, SOX2, SOX11, TRPM8, TYMS, ATIC, PGK1, SOX4, TOR3A, TRGC2, BTBD2, SLBP, EGFR, IER3, TTK, LY6K, IGF2BP3, GPC3, SLC35A4, HSMD, H3F3A, ALDH1A1, MFI2, MMP14, SDCBP, PARP12, MET, CCNB1, PAX3-FKHR, PAX3, FOXO1, XBP1, SYND1, ETV5, HSPA1A, HMHA1, TRIM68 and any combination thereof.

The present invention relates generally to the use of T cells genetically modified to stably express a shRNA of the invention and a desired CAR. T cells expressing a CAR are generally referred to as CAR T cells. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular stimulatory domain (e.g., signaling domain). Thus, in addition to an antigen binding domain the CAR can include the intracellular domains of the zeta (chain of the TCR/CD3 complex, the gamma (γ) chain of the immunoglobulin receptor FcεRI26, 27 or the CD3-epsilon (ε) chain. The CAR can also include a transmembrane region being from the same molecules or other type I transmembrane proteins such as CD4, CD8 and CD28.

In one embodiment, the CAR of the invention comprises an extracellular domain having an antigen recognition domain, a transmembrane domain, and a cytoplasmic domain.

In one embodiment, the transmembrane domain that naturally is associated with one of the domains in the CAR is used. In another embodiment, the cytoplasmic domain can be designed to comprise a stimulatory domain and a costimulatory domain.

A CAR can include intracytoplasmatic portion of co-stimulatory molecules, such as CD28, CD134/OX40, CD137/4-1BB, Lck, ICOS or DAPO.

The disclosure also relates to a strategy of Adoptive cell therapy (ACT). ACT is a procedure in which therapeutic lymphocytes are administered to patients in order to treat cancer. This approach entails the ex vivo generation of tumor specific T cell lymphocytes and infusing them to patients. In addition to the lymphocyte infusion the host may be manipulated in other ways which support the take of the T cells and their immune response, for example, preconditioning the host (with radiation or chemotherapy) and administration of lymphocyte growth factors (such as IL-2). One method for generating such tumor specific lymphocytes involves the expansion of antigen specific T cells.

In one embodiment, the invention provides generating T cells expressing a shRNA of the invention and a desired CAR directed to a tumor antigen. The modified T cells can be generated by introducing a vector (e.g., plasmid, lentiviral vector, retroviral vector, adenoviral vector, adeno-associated viral vector) encoding both 1) an shRNA capable of reducing expression of a target gene described herein and 2) a desired CAR into the cells. The modified T cells of the invention are able to replicate in vivo resulting in long term persistence that can lead to tumor control.

In one aspect, the disclosure provides methods of treating cancer comprising administering a composition capable of silencing genes that inhibit T cell function. In one embodiment, the methods relate to administering T cell expressing a shRNA of the invention and a desired CAR directed to a tumor antigen. In one aspect the T cell to be administered comprises a vector encoding a shRNA of the invention and a desired CAR directed to a tumor antigen.

Pharmaceutical Formulations

In some instances, therapeutic compositions disclosed herein can include, in addition to the tumor targeting T cells, compounds, drugs, and/or agents used for the treatment of cancer. Such compounds, drugs, and/or agents can include, for example, chemotherapy drugs, small molecule drugs or antibodies that stimulate the immune response to a given cancer. In other instances, therapeutic compositions can include, for example, one or more small molecule inhibitors that silence, reduces, eliminates, knocks down, knocks out, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc. Accordingly, the invention provides one or more inhibitors of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc.

In one aspect, the invention provides one or more inhibitors of Ppp2r2d.

In another aspect, the invention provides one or more inhibitors of Eif2ak3.

In another aspect, the invention provides one or more inhibitors of Arhgap5.

In another aspect, the invention provides one or more inhibitors of Smad2.

In another aspect, the invention provides one or more inhibitors of Akap81.

In another aspect, the invention provides one or more inhibitors of Rbks.

In another aspect, the invention provides one or more inhibitors of Egr2.

In another aspect, the invention provides one or more inhibitors of Dgka.

In another aspect, the invention provides one or more inhibitors of Cblb.

In another aspect, the invention provides one or more inhibitors of Map3k3.

In another aspect, the invention provides one or more inhibitors vMdfic.

In another aspect, the invention provides one or more inhibitors of Entpd1.

In another aspect, the invention provides one or more inhibitors of Dgkz.

In another aspect, the invention provides one or more inhibitors of Vamp7.

In another aspect, the invention provides one or more inhibitors of Nuak2.

In another aspect, the invention provides one or more inhibitors of Hipk1.

In another aspect, the invention provides one or more inhibitors of Alk. In one embodiment, the inhibitor of Alk includes, for example, for example CH5424802 (Hoffmann-La Roche), LDK378 (Novartis), Crizotinib and PF-02341066 (Pfizer) or AP26113 (Ariad Pharmaceuticals).

In another aspect, the invention provides one or more inhibitors of Pdzk1ip1.

In some instances, therapeutic compositions can include, for example, cytokines, chemokines and other biologic signaling molecules, tumor specific vaccines, cellular cancer vaccines (e.g., GM-CSF transduced cancer cells), tumor specific monoclonal antibodies, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy.

In some instances, therapeutic compositions disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm).

In some instances, pharmaceutical compositions can include an effective amount of one or more peptides. The terms "effective amount" and "effective to treat," as used herein, refer to an amount or a concentration of one or more peptides for a period of time (including acute or chronic administration and periodic or continuous administration) that is effective within the context of its administration for causing an intended effect or physiological outcome.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

Methods

In some instances, methods can include selection of a human subject who has or had a condition or disease (e.g., cancer). In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease).

The term "subject," as used herein, refers to any animal. In some instances, the subject is a mammal. In some instances, the term "subject", as used herein, refers to a human (e.g., a man, a woman, or a child). Samples for use in the methods can include serum samples, e.g., obtained from the selected subject.

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

Methods of Use

In some embodiments, the disclosure provides methods for increasing the immune response in a subject in need thereof. The disclosure provides therapies that are particularly useful for the treatment of subjects having cancer. In some instances, the disclosure provides methods of treatment that include administering to a subject a composition disclosed herein.

Provided herein are methods for treating and/or preventing cancer or symptoms of cancer in a subject comprising administering to the subject a therapeutically effective amount of a composition capable of silencing genes that inhibit T cell function (e.g., an immunoresponsive T cell expressing a shRNA of the invention and a desired CAR directed to a tumor antigen). In some cases the T cell is derived from the patient to be treated and has been modified to express the CAR and an shRNA that reduces expression of a target gene described herein.

In some embodiments, the cancer is a carcinoma, sarcomas, adenocarcinoma, lymphoma, leukemia, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), and multiple myeloma. In some embodiments, the cancer is melanoma. In some embodiments, the cancer is a plasma cell malignancy, for example, multiple myeloma (MM) or pre-malignant condition of plasma cells. In some embodiments the subject has been diagnosed as having a cancer or as being predisposed to cancer.

As used herein, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), and multiple myeloma.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The terms "treat" or "treating," as used herein, refers to partially or completely alleviating, inhibiting, ameliorating, and/or relieving the disease or condition from which the subject is suffering. In some instances, treatment can result in the continued absence of the disease or condition from which the subject is suffering.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by increasing T cell accumulation and infiltration within the tumor.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

It is also within the scope of the present invention to combine any of the methods and any of the compositions disclosed herein with one or more therapeutic agents. A therapeutic agent includes, but is not limited to, small molecules, peptides, antibodies, ribozymes, antisense oligonucleotides, chemotherapeutic agents and radiation.

It is also within the scope of the present invention to combine any of the methods and any of the compositions disclosed herein with conventional cancer therapies and various drugs in order to enhance the efficacy of such therapies through either reducing the doses/toxicity of conventional therapies and/or to increase the sensitivity of conventional therapies. One conventional therapy is the use of radiation therapy. Another conventional therapy is the use of chemotherapeutic drugs that can be divided into: alkylating agents, antimetabolites, anthracyclines, plant alkaloids, topoisomerase inhibitors, and antitumour agents. All of these drugs affect cell division or DNA synthesis and function in some way. Other conventional cancer therapies are agents that do not directly interfere with DNA. Examples of such agents for which to combine with the present invention may include for example "small-molecule" drugs that block specific enzymes involved in cancer cell growth. Monoclonal antibodies, cancer vaccines, angiogenesis inhibitors, and gene therapy are targeted therapies that can also be combined with the compositions and methods disclosed herein because they also interfere with the growth of cancer cells.

Methods of Screening Test Compounds

Included herein are methods for screening test compounds, e.g., polypeptides, polynucleotides, inorganic or organic large or small molecule test compounds, to identify agents useful in the treatment of cancer e.g., test compounds that silence, reduces, eliminates, knocks down, knocks out, modulates, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to silence, reduces, eliminates, knocks down, knocks out, modulates, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc activity or gene expression.

A test compound that has been screened by a method described herein and determined to silence, reduces, eliminates, knocks down, knocks out, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc, can be considered a candidate compound. A candidate compound that has been screened, e.g., in an in vivo model of a disorder, e.g., cancer, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that inhibiting immunosuppressive pathways used by tumor cells to inactivate and/or suppress immune cells) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

EXAMPLES

The invention is further described in the following examples, which do not limit the scope of the invention described in the claims.

Recent work has shown that cytotoxic T cells play a central role in immune-mediated control of cancers-, and monoclonal antibodies that target inhibitory receptors on T cells can induce significant clinical benefit in patients with advanced disease[4-6]. However, many of the regulatory mechanisms that result in loss of T cell function within immunosuppressive tumors remain unknown. In the following examples, the inventors demonstrate that such regulatory mechanisms can be systematically discovered in vivo in the tumor microenvironment. The inventors postulated that shRNAs targeting key inhibitors would enable robust T cell infiltration and accumulation in tumors, despite multiple inhibitory signals. Using a pool shRNA screening approach aimed at identifying genes that block the function of tumor-infiltrating CD8 T cells, candidate shRNA were discovered by transfer of shRNA-transduced T cells into tumor-bearing mice, followed by deep sequencing to quantify the representation of all hairpins in tumors and lymphoid organs. The majority of shRNAs induced T cell accumulation in tumors but not the spleen, demonstrating feasibility of discovering shRNAs with differential action across tissues. One of the targets was Ppp2r2d, a regulatory subunit of the PP2A phosphatase[7]. Control shRNA-transduced T cells underwent apoptosis upon recognition of melanoma cells, while Ppp2r2d shRNA-transduced T cells accumulated in tumors due to enhanced proliferation and resistance to apoptosis. Ppp2r2d shRNA-expressing T cells also significantly delayed tumor growth. This in vivo approach has widespread applications to dissect complex immune functions in relevant tissue microenvironments.

Immune cells perform complex surveillance functions throughout the body and interact with many different types of cells in distinct tissue microenvironments. Therapeutic targets for modulating immune responses are typically identified in vitro and tested in animal models at a late stage of the process. Here the inventors have addressed the challenge of how targets for immune modulation can be systematically discovered in vivo. This is a central issue in oncology because strong infiltration by CD8 T cells—which have cytotoxic function against tumor cells—is associated with a favorable prognosis in multiple types of human cancer[1,3,8]. Unfortunately, this natural defense mechanism is severely blunted in the majority of patients by multiple inhibitory signals emanating from the tumor, its stroma, regulatory T cells and myeloid cell populations.[9-11]

Pooled shRNA libraries have been shown to be powerful discovery tools[12-14]. The inventors reasoned that shRNAs capable of restoring CD8 T cell function can be systematically discovered in vivo by taking advantage of the extensive proliferative capacity of T cells following triggering of the T cell receptor by a tumor-associated antigen. When introduced into T cells, only a small subset of shRNAs from a pool will restore T cell proliferation resulting in their enrichment within tumors. Over-representation of active shRNAs within each pool can be quantified by deep sequencing of the shRNA cassette from tumors and secondary lymphoid organs (FIG. 1).

Experimental animals. C57BL/6 mice, TRP-1 mice (transgenic mice expressing T-cell receptor (TCR) specific for tyrosinase-related protein 1)[23], pmel-1 mice (transgenic mice expressing TCR specific for gp100)[18], and b2m−/− mice[24] were purchased from The Jackson Laboratory. The Rag1−/− OT-I mice[16] were purchased from Taconic Farms, Inc. Mice were bred at the Dana-Farber Cancer Institute animal facility. All experimental procedures were approved by the Dana-Farber Cancer Institute Animal Care and Use Committee.

Cell lines. B16 melanomas, an aggressive tumor that is difficult to treat, express the surrogate tumor antigen Ovalbumin (Ova), which is recognized by CD8 T cells from OT-I T cell receptor transgenic mice[16,17]. EL4 thymoma[38] and B16-F10 melanoma[15] cells were maintained in RPMI 1640 supplemented with 10% FBS, 2 mM L-glutamine, 100 µg/ml streptomycin and 100 µg/ml penicillin. Ovalbumin-expressing B16 tumor cells (16-Ova) were maintained in the same media with addition of 600 µg/mL G418 (Invitrogen).

Vectors and shRKA Sequences. shRNAs were selected for 255 genes over-expressed in dysfunctional T cells (anergic or exhausted state). pLKO.3G vector was obtained from The RNAi Consortium. pLKO-Thy1.1, pLKO-Ametrine, pLKO-RFP, pLKO-TFP vectors were modified from pLKO.3G vector by replacing GFP with the corresponding reporter gene. Murine Ppp2r2d and Cblb sequences targeted by 10 selected shRNAs are provided in Table 3 (listed in order of shRNA activity (highest to lowest)). The LacZ target sequence targeted by a control shRNA is also listed. All other target sequences can be found in Table 2.

TABLE 3

| # | Gene | Clone ID | Murine shRNA Target Sequence |
|---|------|----------|------------------------------|
|   | LacZ | TRCN0000072227 | GCGCTAATCACGACGCGCTGT (SEQ ID NO: 621) |
| 1 | Ppp2r2d | TRCN0000080900 | CCCACATCAGTGCAATGTATT (SEQ ID NO: 386) |
| 2 | Ppp2r2d | ND000492 | CCACAGTGGTCGATACATGAT (SEQ ID NO: 385) |
| 3 | Ppp2r2d | TRCN0000431278 | GAGAATTAACCTATGGCATTT (SEQ ID NO: 384) |
| 4 | Ppp2r2d | ND000486 | GCTCAATAAAGGCCATTACTC (SEQ ID NO: 383) |
| 5 | Ppp2r2d | TRCN0000080901 | CCATTTAGAATTACGGCACTA (SEQ ID NO: 380) |
| 6 | Ppp2r2d | TRCN0000430828 | ATAGTGATCATGAAACATATC (SEQ ID NO: 375) |
| 7 | Ppp2r2d | TRCN0000080899 | GCCACCAATAACTTGTATATA (SEQ ID NO: :374) |
| 8 | Ppp2r2d | TRCN0000080902 | CGGTTCAGACAGTGCCATTAT (SEQ ID NO: 381) |
| 9 | Ppp2r2d | TRCN0000427220 | TCATCTCCACCGTTGAGTTTA (SEQ II) NO: 378) |
| 10 | Ppp2r2d | TRCN0000425449 | ATGCTCATACATATCACATAA (SEQ ID NO: 377) |
| 1 | Cblb | ND000025 | CGAGCGATCCGGCTCTTTAAA (SEQ ID NO: 72) |
| 2 | Cblb | ND000030 | AGCCAGGTCCAATTCCATTTC (SEQ ID NO: 71) |
| 3 | Cblb | TRCN0000244606 | CCCTGATTTAACCGGATTATG (SEQ ID NO: 70) |
| 4 | Cblb | ND000026 | ATCGAACATCCCAGATTTAGG (SEQ ID NO: 61) |
| 5 | Cblb | TRCN0000244603 | CTACACCTCACGATCATATAA (SEQ ID NO: 59) |
| 6 | Cblb | ND000024 | TACACCTCACGATCATATAAA (SEQ ID NO: 67) |
| 7 | Cblb | TRCN0000244605 | TGAGCGAGAATGAGTACTTTA (SEQ. ID NO: 60) |
| 8 | Cblb | TRCN0000244604 | CCAGATTTAGGCATCTATTTG (SEQ ID NO: 65) |
| 9 | Cblb | TRCN0000244607 | CTTGTACTCCAGTACCATAAT (SEQ ID NO: 63) |
| 10 | Cblb | ND000027 | TCTACATCGATAGTCTCATGA (SEQ ID NO: 58) |

Antibodies and flow cytometry. Single-cell suspensions were stained in PBS, 2% FBS with labeled antibodies at 4° C. for 20 minutes, followed by two washes with ice-cold PBS, 2% FBS. Cells were analyzed/sorted using a FACSAria (BD Biosciences) and FlowJo software (TriStar). Antibodies used were specific for CD4, CD8, Vα2, Vβ5.1/5.2, Thy1.1, CD25, CD44, CD62L, CD69, CD122, CD127, IFNγ, TNFα (BioLegend), PD-1, TIM-3, LAG-3, granzyme B, and H-2Kb (BioLegend), Vα3.2 (eBioscience), Vβ13, Vβ14 (BD Biosciences), phospho-Akt (Ser473) and phospho-Bad (Ser112) (Cell Signaling). Apoptotic cells were detected by labeling with annexin V (BioLegend) or activated caspase-3 antibody (Cell Signaling). Mouse anti-CD3/CD28 beads were purchased from Invitrogen.

T cell isolation from tumors. B16-Ova melanomas were cut into small pieces in petri dishes containing 5 mL of PBS, 2% FBS and washed with PBS. Tumors were resuspended in 15 mL RPMI supplemented with 2% FBS, 50 U/mL Collagenase Type IV (Invitrogen), 20U/mL DNase (Roche), samples incubated at 37° C. for 2 hours and tissue further dissociated using a gentleMACS Dissociator (Miltenyi Biotech). Suspensions were washed three times with PBS and passed through a 70 μM strainer. Lymphocytes were isolated by density gradient centrifugation and then either analyzed or sorted by flow cytometry using a FACSAria (BD Biosciences).

T cell apoptosis. Cytokine pre-treated OT-I cells were transduced with LacZ or Ppp2r2d shRNAs and injected into mice bearing day 14 B16-Ova tumors. After 7 days, intracellular staining was performed using an activated caspase-3 antibody (Cell Signaling) and CD8/Thy1.1 double-positive T cells were gated in the FACS analysis.

Immunofluorescence and immunohistochemistry. B16-Ova tumors from mice treated with OT-I T cells expressing LacZ or Ppp2r2d shRNAs (GFP-expressing vector) were cryopreserved in optimal cutting temperature (O.C.T.) compound (Tissue-Tek). 10 μm-sections from cryopreserved tumors were were permeabilized with 0.2% Triton X-100, fixed in 4% paraformaldehyde and stained with a GFP antibody (Molecular Probes) in combination with DAPI. For TUNEL detection, sections were stained with TACS 2 TdT Blue Label (Trevigen) based on manufacturer's directions. Samples were visualized using a laser-scanning confocal microscope (Leica SP5X) and analyzed with ImageJ software (NIH).

qRT-PCR assay. Total RNA was extracted using TRIzol reagent (Invitrogen). RNA was reverse transcribed with the High Capacity cDNA Reverse Transcription kit (Applied Biosystems). Real time quantitative PCR reactions were performed as triplicates using an ABI 7900HT instrument with SYBR green (ABI). Rpl23 levels were used for normalization. The following primers were used. Ppp2r2d forward GGAAGCCGACATCATCTCCAC (SEQ ID NO: 622), Ppp2r2d reverse GTGAGCGCGGCCTTTATTCT (SEQ ID NO: 623); Cblb forward GGTCGCATTTTGGG-GATTATTGA (SEQ ID NO: 624), Cblb reverse TTTGGCACAGTCTTACCACTTT (SEQ ID NO: 625); Rpl23 forward CTGTGAAGGGAATCAAGGGA (SEQ ID NO: 626) and Rpl23 reverse TGTCGAATTAC-CACTGCTGG (SEQ ID NO: 627).

Microarray Analysis. IL-7/IL-15 cultured OT-I T cells were transduced with one of five experimental shRNAs (Ppp2r2d, Arhgap5, Alk, Egr2, Ptpn2) or a LacZ control shRNA. Infected cells were sorted to purity using GFP encoded by the vector as a reporter. T cells ($5 \times 10^6$) were injected i.v. into mice bearing day 14 B16-Ova tumors. Seven days later, shRNA-expressing OT-I T cells (CD8+GFP+) were isolated from tumors and spleens. Cells were sorted twice to high purity and total RNA was extracted using TRIzol reagent (Invitrogen) for Affymetrix gene expression profiling (Mouse Genome 430 2.0 Arrays). Arrays for each shRNA were done in triplicate (6 mice per group).

Nanowell Analysis of Cytokine Production at a Single Cell Level

Materials. Antibodies used for T cell activation were anti-mouse CD3 and anti-mouse CD28 (Biolegend). Antibodies used to capture secreted cytokines were anti-mouse IFNγ (Biolegend), anti-mouse IL-2 (Biolegend), anti-mouse TNFα (Biolegend) and anti-mouse GM-CSF (Biolegend).

Detection antibodies were anti-mouse IFNγ (Biolegend), anti-mouse IL-2 (Biolegend), anti-mouse TNFα (Biolegend) and anti-mouse GM-CSF (Biolegend), and they were fluorescently labeled with appropriate Alexa Fluor dyes (Invitrogen) following manufacturer's instructions. The lipids used to prepare supported bilayers were: 1,2-dioleoyl-sn-glycero-3-phosphocholine (DOPC) and 1,2-dioleoyl-sn-glycero-3-phosphoethanolamine-N-(cap biotinyl) (Biotinyl Cap PE) (Avanti Polar Lipids).

Fabrication of PDMS arrays of nanowells and preparation of supported lipid bilayers. The array of nanowells was manufactured by injecting polydimethylsiloxane (PDMS, Dow Corning) prepared at a 10:1 base/catalyst weight ratio into a custom-built mold encasing a micropatterned silicon master. Arrays of nanowells were cured at 70° C. for 4-16 h. Each array comprised 72×24 blocks, each containing a 7×7 (50 μm×50 μm×50 μm) subarray of nanowells (total of 84,672 wells). The PDMS arrays adhered directly to a 3"×1" glass slide forming a 1 mm thick layer. Supported lipid bilayers were prepared as described previously14. Bilayers were generated by applying DOPC liposomes containing 2 mol % biotin-Cap-PE lipids on the PDMS array of nanowells. The surfaces were rinsed with deionized water to remove excess liposomes. Before use, the lipid bilayer was blocked with BSA in PBS (100 μg/mL) for 45 minutes. The bilayer was then incubated with 1 μg/mL of streptavidin in a solution of 100 μg/mL BSA in PBS, followed by incubation with biotinylated CD3 and CD28 antibodies. The device was rinsed extensively with PBS before adding the cells.

Microengraving. Capture antibodies were diluted in borate buffer (50 mM sodium borate, 8 mM sucrose, and 50 mM NaCl, pH 9.0) to a final concentration of 10 μg/mL and deposited on the surface of epoxy-modified slides for 1 h at room temperature. Slides were blocked with 3% non-fat milk in PBST (PBS with 0.05% (v/v) Tween 20) for 30 min at room temperature and washed with PBS before placing them into contact with the PDMS array of nanowells. A suspension of T cells was dispensed onto the surface of the nanowells, modified with a supported lipid bilayer in media and allowed to settle into the wells. The density of suspended cells applied to the array was optimized empirically to maximize well occupancy by single cells (typically ~30% of wells). After incubation of the cell-loaded wells, a glass slide coated with capture antibodies was then placed onto the loaded array for cytokine capture. The microarray and glass slide were held together by compression in a hybridization chamber (Agilent Technologies, G2534A) and incubated for 1h at 37° C. with 5% $CO_2$. The glass slide was then separated from the array and placed in PBS. After microengraving, slides were incubated for 30 min with blocking buffer (PBS, 10 mg/mL BSA, 0.05% (v/v) Tween-20, 2% mouse serum and 2 mM sodium azide), washed with PBST (PBS+ 0.05% v/v Tween-20), and then incubated with fluorescence detection antibodies at 1 μg/mL for 45 min at 25° C. The slides were washed with PBST and PBS, rinsed briefly with water, and dried with a $N_2$ stream. Reference slides were generated at the end of each experiment with the same detection antibodies used on the printed slides. For reference slides, antibodies were diluted in water, spotted onto blank poly-L-lysine slides (1 μL/spot), and the reference slides were dried under vacuum. Slides were scanned using a Genepix 4200AL microarray scanner (Molecular Devices). The median fluorescence intensity of each spot was extracted using Genepix Pro.

On-chip image-based cytometry. Before imaging, T cells were stained with CellMask™ Plasma Membrane Stain (Invitrogen, Life Technologies) and SYTOX green (for detection of dead cells, Life Technologies). The cell-loaded arrays of nanowells were mounted face-up on the microscope with a coverslip placed on top of the array. Images were acquired on an automated inverted epifluorescence microscope (Carl Zeiss). Transmitted light and epifluorescence micrographs were collected block-by-block (7×7 microwells per block). The resulting collection of images was analyzed using a custom program to determine the number of cells present in each well and the mean fluorescence intensity of each label. Only viable T cells were considered for the analysis. Although the cells expressed GFP, the fluorescence intensity of GFP was negligible under the utilized microscope acquisition setting compared to SYTOX green, enabling identification of dead cells.

Data analysis. Data extracted from both on-chip cytometry and printed cytokines were matched in Microsoft Excel using unique identifiers assigned to each well within the array. The dataset was filtered to include wells containing only single cells. To compensate from signal bleed-through and convert the measured fluorescence intensity for the captured cytokines from a given cell into a rate of secretion, the data from standard calibration curves (from reference slides) prepared with known amounts of detection antibodies was used to convert measured intensities to a number of molecules, as described previously (Han, Q., et. al., Multidimensional analysis of the frequencies and rates of cytokine secretion from single cells by quantitative microengraving. Lab Chip 10, 1391-1400, doi:10.1039/b926849a (2010).

Example 1: In Vivo RNAi Discovery of Immunotherapy Targets

Two large primary screens were performed, with the first focusing on genes over-expressed in dysfunctional T cells (T cell anergy or exhaustion; 255 genes, 1,275 shRNAs divided into two pools), and the second on kinases/phosphatases (1,307 genes, 6,535 shRNAs divided into seven pools) (Table 4). In these primary screens, each gene was represented by ~5 shRNAs.

TABLE 4

| | | T cell Dysfunction | Kinase/ Phosphatase | shRNA Enrichment |
|---|---|---|---|---|
| 1st Screen | Genes | 255 | 1307 | 4-10×: 123 |
| | shRNAs | 1275 | 6535 | 10-20×: 17 |
| | Candidate Genes | 32 | 82 | >20×: 1 |
| 2nd Screen | Genes | 32 | 43 | 4-10×: 191 |
| | shRNAs | 480 | 645 | 10-20×: 27 |
| | Candidate Genes | 17 | 26 | >20×: 1 | shRNAs targeting 255 genes over-expressed in dysfunctional T cells (anergic or exhausted state)[37] and 1,307 kinase/phosphatase genes (~5 shRNAs per gene) were obtained from The RNAi Consortium (TRC; Broad Institute, Cambridge, Mass., USA). Nine pools were created and shRNAs subcloned into the pLKO-Thy1.1 lentiviral vector. Each pool also contained 85 negative-control shRNAs (number of shRNAs: GFP, 24; LacZ, 20; luciferase 25; RFP 16). OT-I T cells isolated by negative selection (Stemcell Technologies) were cultured with IL-7 (5 ng/mL, Peprotech) and IL-15 (100 ng/mL, Peprotech) in complete RPMI media (RPM 11640, 10% FBS, 20 mM HEPES, 1 mM sodium pyruvate, 0.05 mM 2-mercaptoethonal, 2 mM L-glutamine, 100 μg/ml streptomycin and 100 μg/ml penicillin). On day 2, OT-I T cells were spin-infected with lentiviral pools (nine lentiviral shRNA pools and a LacZ control shRNA lentiviral vector control) supplemented with protamine sulfate (5 μg/mL) in 24-well plates coated with retronectin (5 μg/mL) at a multiplicity of infection (MOI) of 15. Typically, ~5×10$^6$ OT-1 T cells were infected for each pool.

Figure 2:
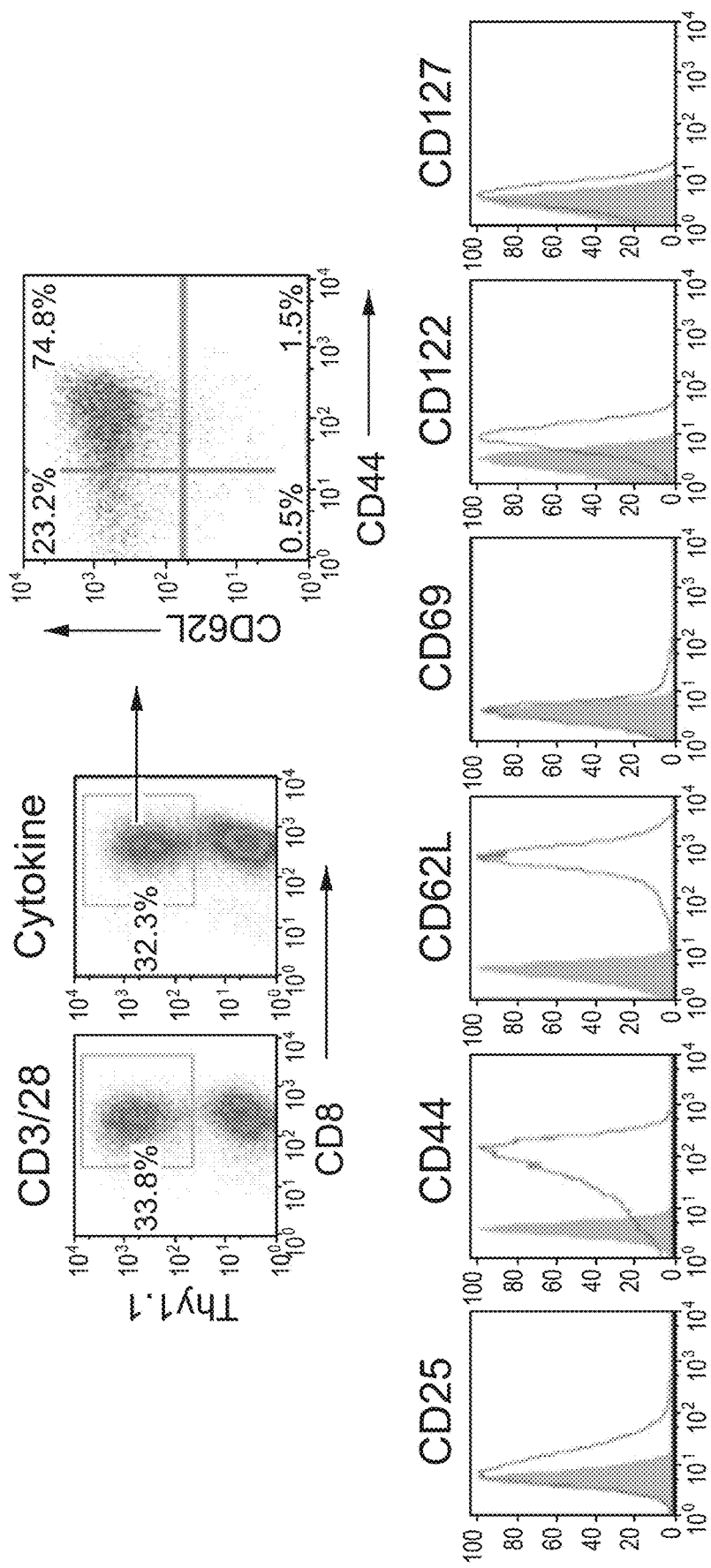
FIG. 2 is a set of graphs showing representative flow cytometry plots of CD8$^+$ T cells from Rag1−/−/OT-I TCR transgenic mice following infection with an shRNA vector. Transduction efficiency was determined based on expression of the Thy1.1 reporter encoded by the lentiviral vector. Cytokine-cultured T cells expressing the LacZ control shRNA were then stained with a panel of activation markers (black lines; isotype control, shaded). The majority of infected T cells exhibited a central memory phenotype (CD62L$^+$ CD44$^+$).
Figure 3:
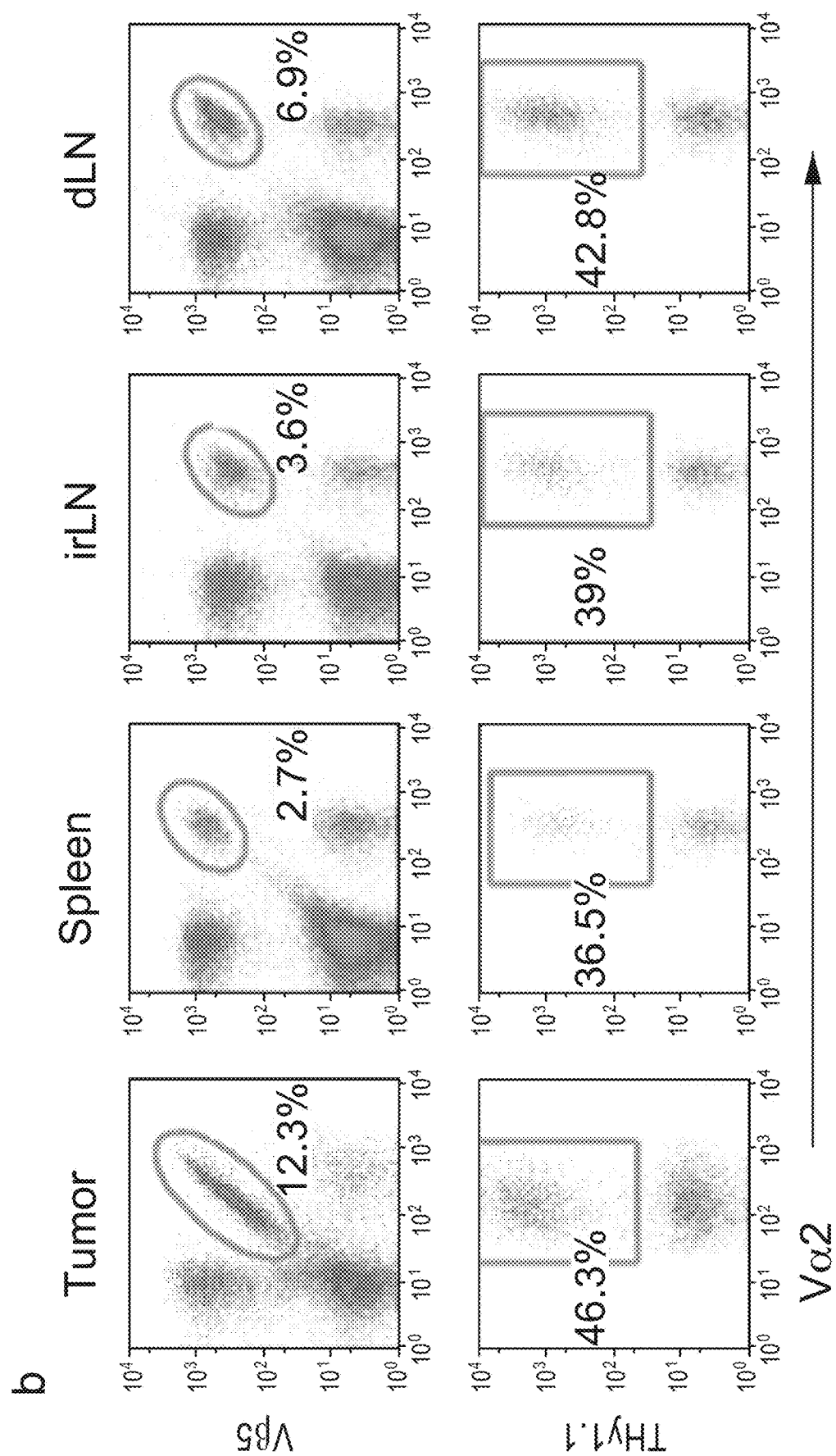
FIG. 3 is a set of graphs showing representative flow cytometry plots of OT-I T cells sorted from tumors and secondary lymphoid organs for deep sequencing analysis (dLN, tumor-draining lymph node; irLN, irrelevant lymph node). CD8$^+$Vα2$^+$Vβ5$^+$Thy1.1$^+$ cells were sorted and genomic DNA was extracted for PCR amplification of the shRNA cassette.

Following infection, OT-I cells were cultured with IL-7 (2.5 ng/mL), IL-15 (50 ng/mL) and IL-2 (2 ng/mL) in complete RPMI media. On day 5, live shRNA-transduced T were enriched using a dead cell removal kit (Miltenyi), and infected cells were positively selected based on Thy1.1 marker (Stemcell Technologies) to 50-60% Thy1.1 positivity. Successful transduction was monitored by surface expression of the Thy1.1 reporter (FIG. 2). T cells (5×10$^6$) were injected i.v. into C57BL/6 mice bearing day 14 B16-Ova tumors (15 mice per shRNA pool)(number of animals chosen to provide sufficient cells for T cell isolation and PCR). Genomic DNA was isolated from 5×10$^6$ enriched OT-I cells as the start population for deep sequencing. Seven days later, shRNA-expressing T cells (CD8$^+$Vα2$^+$Vβ5$^+$Thy1.1$^+$) were isolated by flow cytometry from tumors, spleens, tumor-draining lymph nodes and irrelevant lymph nodes for isolation of genomic DNA, followed by PCR amplification of the shRNA cassette. (FIG. 3) Genomic DNA was isolated (Qiagen) and deep-sequencing templates were generated by PCR of the shRNA cassette. Representation of shRNAs in each pool was analyzed by deep sequencing using an Illumina Genome Analyzer[30]. Data were normalized using the average reads of control shRNAs in each pool. Kinase/phosphatase genes were selected for the secondary screen based on expression levels in T cells.

For certain genes, shRNAs were over-represented in all tested tissues compared to the starting T cell population (e.g. SHP-1), indicative of enhanced proliferation independent of TCR recognition of a tumor antigen. For other genes, there was a selective loss of shRNAs within tumors (e.g. ZAP-70, a critical kinase in the T cell activation pathway). We focused our analysis on genes whose shRNAs showed substantial over-representation in tumor but not spleen, a secondary lymphoid organ. Substantial T cell accumulation in tumors was observed for a number of shRNAs, despite the immunosuppressive environment. For secondary screens, we created focused pools in which each candidate gene was represented by ~15 shRNAs.

Figure 4:
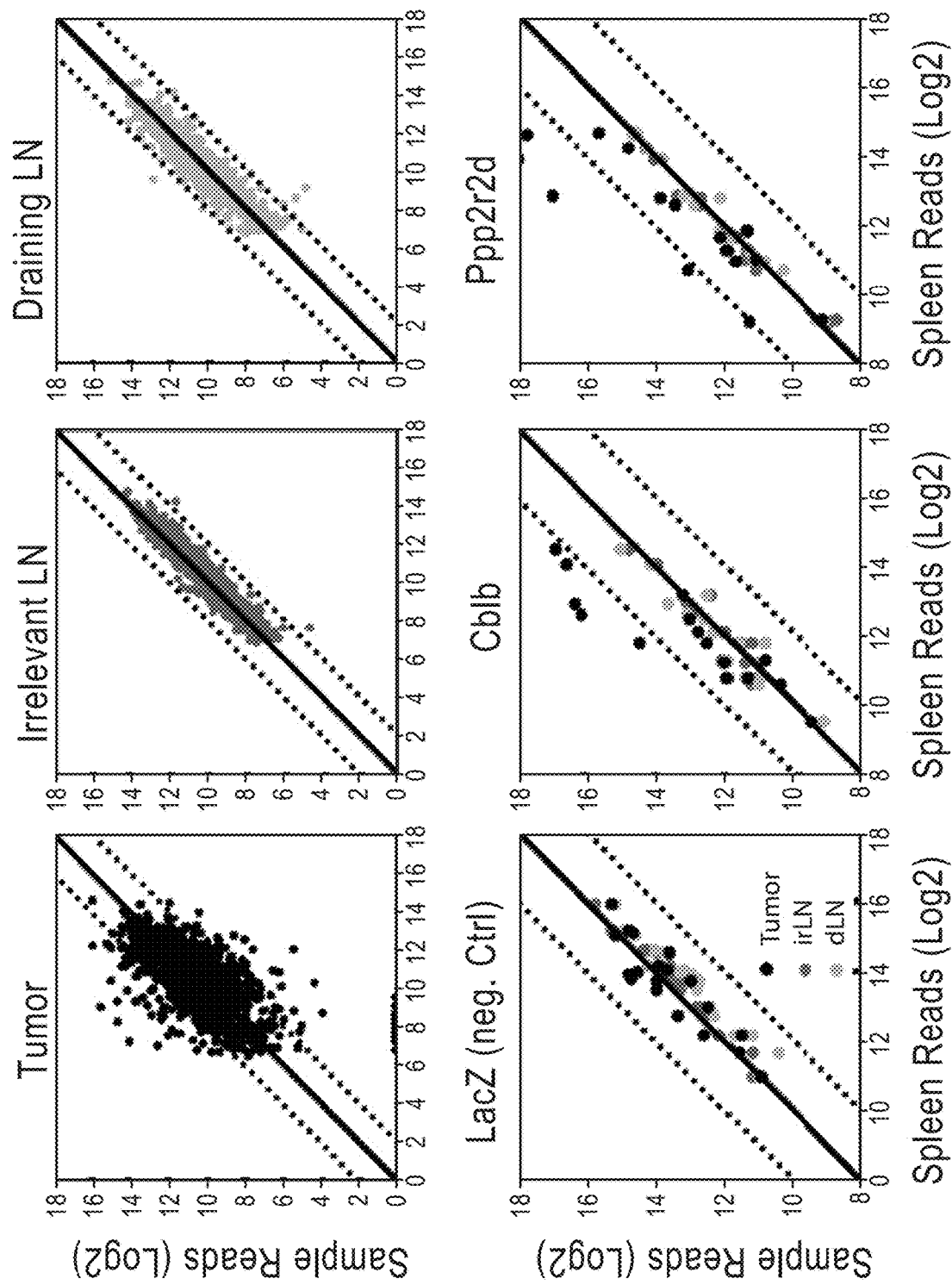
FIG. 4 is a set of graphs showing deep sequencing data from in vivo shRNA pool screen. Upper row, sequence reads for all genes in a pool in tumor, irrelevant (irLN) and draining lymph node (dLN); lower row, three individual genes (LacZ, negative control) are plotted in comparison to spleen for tumors, irrelevant lymph nodes (irLN) and tumor-draining lymph nodes (dLN). Sequence reads are plotted for these tissues versus spleen. Dashed lines indicate a deviation by log 2 from diagonal.
Figure 5:
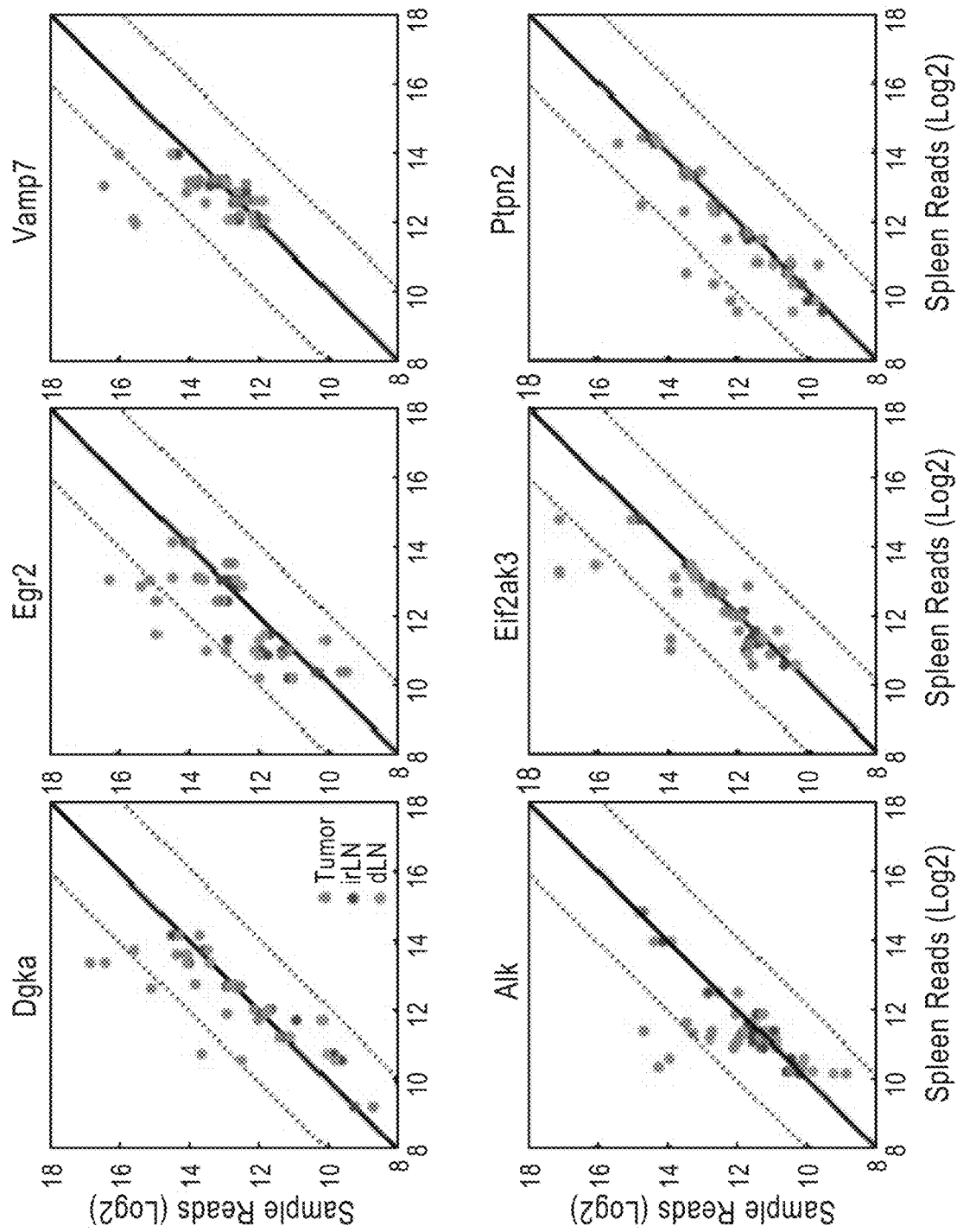
FIG. 5 is a set of graphs showing deep sequencing data from T cell dysfunction screen. shRNA sequencing reads for genes positive in secondary screen are plotted in comparison to spleen for tumors, irrelevant lymph nodes (irLN) and tumor-draining lymph nodes (dLN), with dashed lines indicating a deviation of log 2 from the diagonal. Data show enrichment of particular shRNAs representing these genes in tumors compared to spleens or lymph nodes.

Primary data from this analysis are shown for three genes in FIG. 4: LacZ (negative control), Cblb (an E3 ubiquitin ligase that induces T cell receptor internalization)[19] and Ppp2r2d (not previously studied in T cells). For both Ppp2r2d and Cblb, five shRNAs were substantially increased in tumors compared to spleen, while no enrichment was observed for LacZ shRNAs. Overall, 43 genes met the following criteria: ≥4-fold enrichment for 3 or more shRNAs in tumors compared to spleen (Table 5, FIG. 4, FIG. 5). The set included gene products previously identified as inhibitors of T cell receptor signaling (including Cblb, Dgka, Dgkz, Ptpn2) as well as other well-known inhibitors of T cell function (e.g. Smad2, Socs1, Socs3, Egr2), validating our approach (Table 5, Table 6).[20-22] Table 5 describes the functional classification of candidate genes from the secondary screen.

TABLE 5

| Function | Genes |
| --- | --- |
| Inhibition of TCR signaling | Cblb, Dgka, Dgkz, Fyn, Inpp5b, Ppp3cc, Ptpn2, Stk17b, Tnk1 |
| Phosphoinositol metabolism | Dgka, Dgkz, Impk, Inpp5b, Sbf1 |
| Inhibitory cytokine signaling pathways | Smad2, Socs1, Socs 3 |
| AMP signaling, inhibition of mTOR | Entpd1, Prkab2, Nuak |
| Cell cycle | Cdkn2a, Pkd1, Ppp2r2d |
| Actin and microtubules | Arhgap5, Mast2, Rock 1 |
| Potential nuclear functions | Blvrb, Egr2, Impk, Jun, Ppm1g |
| Role in cancel cells | Alk, Arhgap5, Eif2ak3, Hipk1, Met, Nuak, Pdzklip, Rock1, Yes1 |

Secondary screens were performed focusing on genes whose shRNAs showed substantial over-representation in tumor but not spleen, a secondary lymphoid organ. Substantial T cell accumulation in tumors was observed for a number of shRNAs, despite the immunosuppressive environment. For these secondary screens, ~10 additional shRNAs were synthesized for each gene (IDT) for a total of ~15 shRNAs per gene. These focused pools contained 85 negative-control shRNAs. Two control shRNAs (one for RFP, one for luciferase) showed some enrichment in tumors relative to spleen (4.0 and 5.1-fold, respectively). Cut-off in the secondary screen was defined as ≥3 shRNAs with ≥4 fold enrichment in tumor relative to spleen. Screening results were validated at a cellular level by introducing individual shRNAs into T cells, along with a reporter protein (GFP, TFP, RFP or Ametrine fluorescent proteins, Thy1.1). This approach enabled simultaneous testing of five shRNAs in an animal (three mice per group). Proliferation of shRNA-transduced T cells was visualized based on CFSE dilution after 24 hours as well as 3, 5 and 7 days. In addition, intracellular staining was performed on days 3, 5 and 7 for IFNγ, TNF and isotype controls. Results from the primary and secondary screen of T cell dysfunction pool shRNA library are provided in Table 6. Genes for which at least 3 shRNAs showed >4 fold enrichment in tumors are listed, along with a brief description of their function. Results from secondary screen of kinase and phosphatase shRNA libraries are shown in Table 7.

TABLE 6

| Symbol | Total # shRNAs | Enrichment (fold) | Function |
| --- | --- | --- | --- |
| Dgkz | 6 | 5.2-14.0 | Phosphorylates and thereby inactivates DAG |
| Egr2 | 6 | 4.0-10.2 | Transcription factor involved in T cell unresponsiveness, expression of Cblb |
| Smad2 | 5 | 6.7-30.3 | TGF beta signaling pathway |
| Cblb | 5 | 4.1-10.8 | E3 ubiquitin ligase (degradation of TCR and signaling molecules; ko mice reject tumors) |
| Inpp5b | 5 | 4.3-9.5 | Inositol polyphosphate-5-phosphatase, hydrolyzes PIP2 |
| Socs1 | 5 | 4.1-8.5 | Inhibitor of cytokine signaling |

TABLE 6-continued

| Symbol | Total # shRNAs | Enrichment (fold) | Function |
|---|---|---|---|
| Jun | 5 | 5.2-6.4 | Persistent AP-1 activation in tumor-infiltrating T cells leads to upregulated PD-1 |
| Entpd1 | 4 | 6.5-13.3 | Extracellular degradation of ATP to AMP (an inhibitory signal through AMP kinase) |
| Vamp7 | 4 | 4.0-11.3 | Vesicle associated transmembrane protein |
| Dgka | 4 | 5.0-10.2 | Phosphorylates and thereby inactivates DAG |
| Mdfic | 4 | 4.4-10.0 | Inhibits viral gene expression, interacts with cyclin T1 and T2 |
| Nptxr | 4 | 4.0-7.2 | Pentraxin Receptor |
| F11r | 4 | 4.6-6.8 | Cell migration |
| Socs3 | 4 | 4.6-6.3 | Inhibitor of cytokine signaling |
| Pdzklip1 | 3 | 4.8-12.9 | Pdzk1 interacting protein, expression correlates with tumor progression |
| Fyn | 3 | 4.1-6.5 | inhibits activation of resting T cells (through Csk) |
| Ypel2 | 3 | 4.6-5.1 | Function unknown |

TABLE 7

| Symbol | Total # shRNAs | Enrichment (fold) | Function |
|---|---|---|---|
| Rbks | 6 | 4.0-12.8 | Ribokinase carbohydrate metabolism |
| Pkd1 | 6 | 4.9-9.9 | Cell cycle arrest (activates JAK/STAT pathway) |
| Ppp2r2d | 5 | 4.0-17.2 | Regulatory subunit of PP2A phosphatase |
| Eif2ak3 | 5 | 4.8-13.4 | ER stress sensor, resistance of cancer cells to chemotherapy |
| Ptpn2 | 5 | 4.7-7.4 | Inhibitor of T cell and cytokine signaling |
| Hipk1 | 4 | 4.5-12.3 | Interacts with p53 and c-myb, knockout mice develop fewer carcinogen-induced tumors |
| Grk6 | 4 | 4.2-11 | Regulator of particular G-protein coupled receptors |
| Cdkn2a | 4 | 4.1-7.2 | G1 cell cycle arrest and apoptosis in T cells |
| Sbf1 | 4 | 4.8-6.9 | Activates MTMR2, which dephosphorylates PI(3)P and PI(3,5)P2 |
| Ipmk | 4 | 4.0-6.9 | Inositol polyphosphate kinase, nuclear functions such as chromatin remodeling |
| Rock1 | 4 | 44.1-6.5 | Rho kinase, inhibitors have shown activity in mouse models of cancer |
| Stk17b | 4 | 4.0-6.4 | Inhibitor of T cell signaling forms complex with protein kinase D |
| Mast2 | 4 | 4.1-5.1 | Microtubule-associated serine/threonine kinase |
| Arhgap5 | 3 | 6.0-15.7 | Negative regulator of Rho GTPases, inhibition can reduce cancer cell invasion |
| Alk | 3 | 9.6-13.5 | Anaplastic lymphoma kinase (translocation of nucleophosmin and ALK in ALCL) |
| Nuak | 3 | 4.5-13.1 | Member of AMP-activated protein kinase-related kinase family, oncogene in melanoma |
| Akap8I | 3 | 4.4-11.8 | A-kinase anchoring protein, recruits cAMP-dependent protein kinase (PKA) to chromatin |
| Pdp1 | 3 | 4.1-9.8 | Pyruvate dehydrogenase phosphatase 1, regulation of glucose metabolism |
| Yes1 | 3 | 5.4-9.7 | Src family kinase, oncogene in several tumors |
| Met | 3 | 4.1-8.9 | Receptor tyrosine kinase, involved in hepatocellular and other cancers |
| Ppm1g | 3 | 6.2-8.2 | Dephosphorylates spliceosome substrates and histones H2A-H2B |
| Blvrb | 3 | 5.3-8.0 | Biliverdin reductase, also transcription factor, arrest of cell cycle |
| Tnk1 | 3 | 5.2-7.6 | Downregulates Ras pathway (phosphorylation of Grb2), inhibition of NF-kB pathway |
| Prkab2 | 3 | 4.1-7.0 | Subunit of AMP kinase, inhibits fatty acid synthesis and mTOR pathway |
| Trpm7 | 3 | 4.9-5.9 | Ion channel and serine-threonine kinase |
| Ppp3cc | 3 | 4.2-4.4 | Regulatory subunit of calcincurin (phosphatase in T cell receptor signaling) |

Example 2: shRNA-Driven Expansion of CD4 and CD8 T Cells in B16 Melanomas

Figure 6:
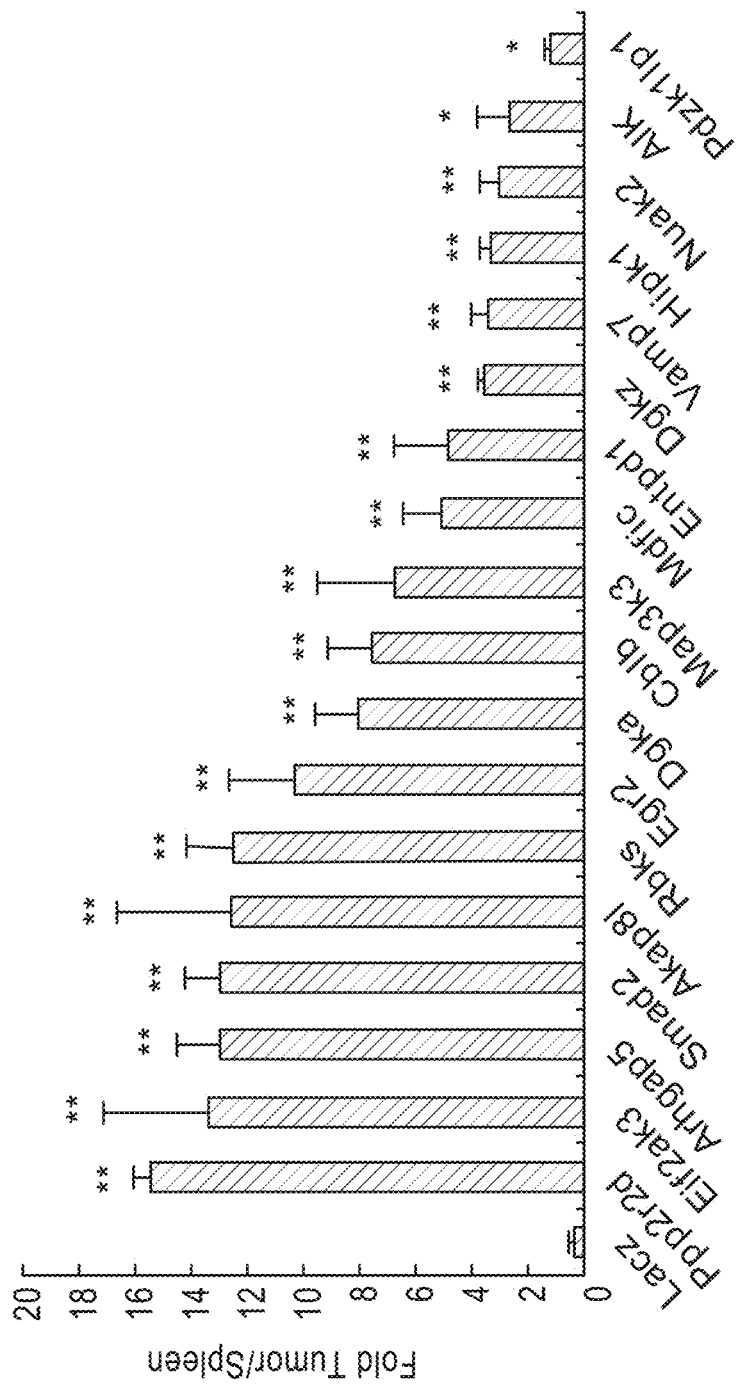
FIG. 6 is a graph showing flow cytometry based quantification of OT-I CD8$^+$ T cell enrichment in tumors relative to spleen. The percentage of shRNA-expressing OT-I T cells was determined by flow cytometry in tumors/spleens by gating on reporter proteins in CD8$^+$Vα2$^{30}$ Vβ5$^+$ T cells. Statistical significance was determined for each experimental shRNA against LacZ shRNA (fold enrichment tumor/spleen) (n=3; *p<0.05, *p<0.01, Student's t-test).
Figure 7:
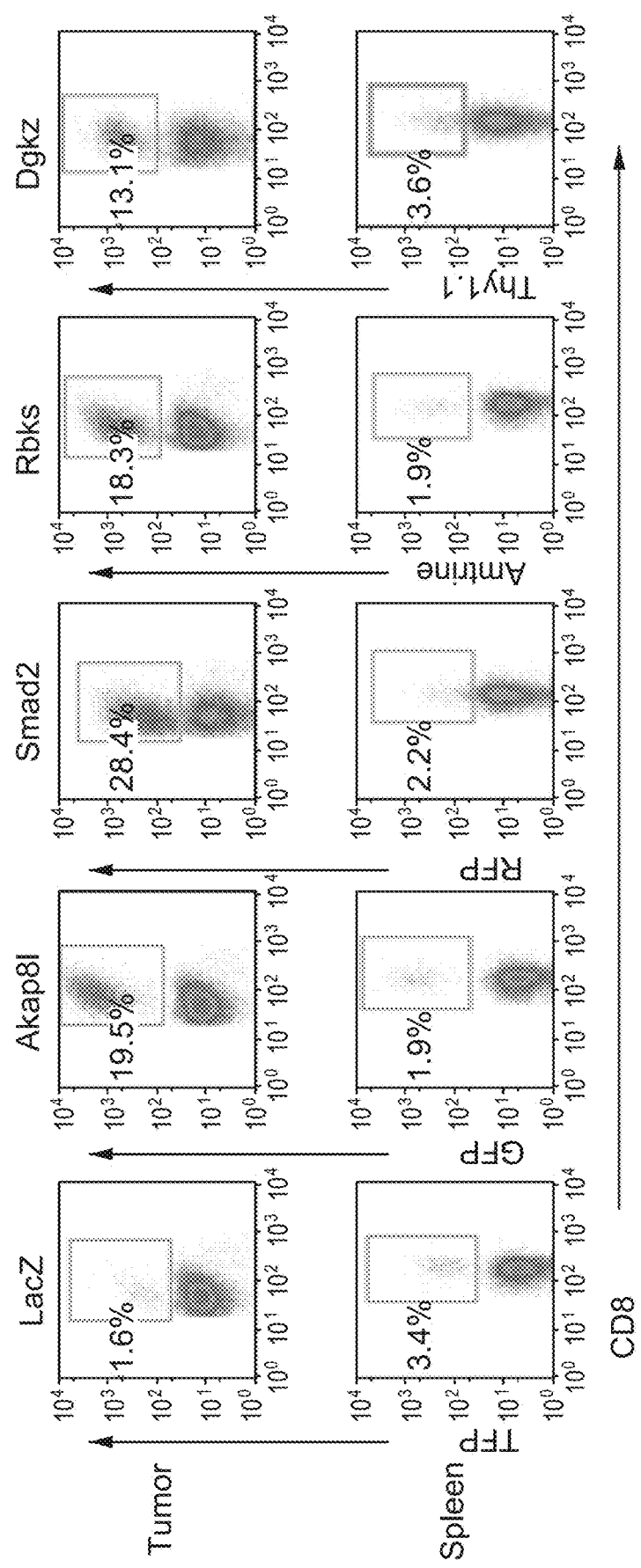
FIG. 7 is a set of graphs showing representative flow cytometry plots of cell enrichment in tumor transduced with shRNA vectors (LacZ, Akap8I, Smad2, Rbks, Dgkz). The percentage of shRNA-expressing OT-I T cells was determined by flow cytometry in tumors/spleens by gating on reporter proteins in CD8$^+$Vα2$^+$Vβ5$^+$ T cells.

Positive shRNAs from deep sequencing analysis were cloned into lentiviral vectors encoding five different reporter proteins (GFP, TFP, RFP or Ametrine fluorescent proteins, Thy1.1). Cytokine-pretreated OT-1IT cells were transduced with lentiviral vectors driving expression of a single shRNA and a reporter protein; $1 \times 10^6$ T cells of each population were mixed and co-injected i.v. into C57BL/6 mice bearing day 14 B16-Ova tumors. After seven days T cells were isolated from tumors, spleens and lymph nodes, and the percentage of reporter-positive CD8'V$\alpha$2$^+$V$\beta$5$^+$ T cells was determined by flow cytometry based on co-introduced reporters. Fold-enrichment in tumors compared to spleen was calculated based on the percentage of OT-I T cells in each organ expressing a particular reporter. When the control LacZ shRNA was expressed in CD8 OT-I T cells, the frequency of shRNA-expressing CD8 OT-I T cells was lower in tumors compared to spleen (~2-fold). In contrast, experimental shRNAs induced accumulation of CD8 OT-I T cells in tumors but not the spleen (FIG. 6, FIG. 7). For seven of these shRNAs (e.g., Ppp2r2D, Eif2ak3, Arhgap5, Smad2, Akap8I, Rbks and Egr2), T cell accumulation in tumors was >10-fold relative to spleen. The strongest phenotype was observed with shRNAs targeting Ppp2r2d, a regulatory subunit of the PP2A phosphatase7.

Figure 8A:
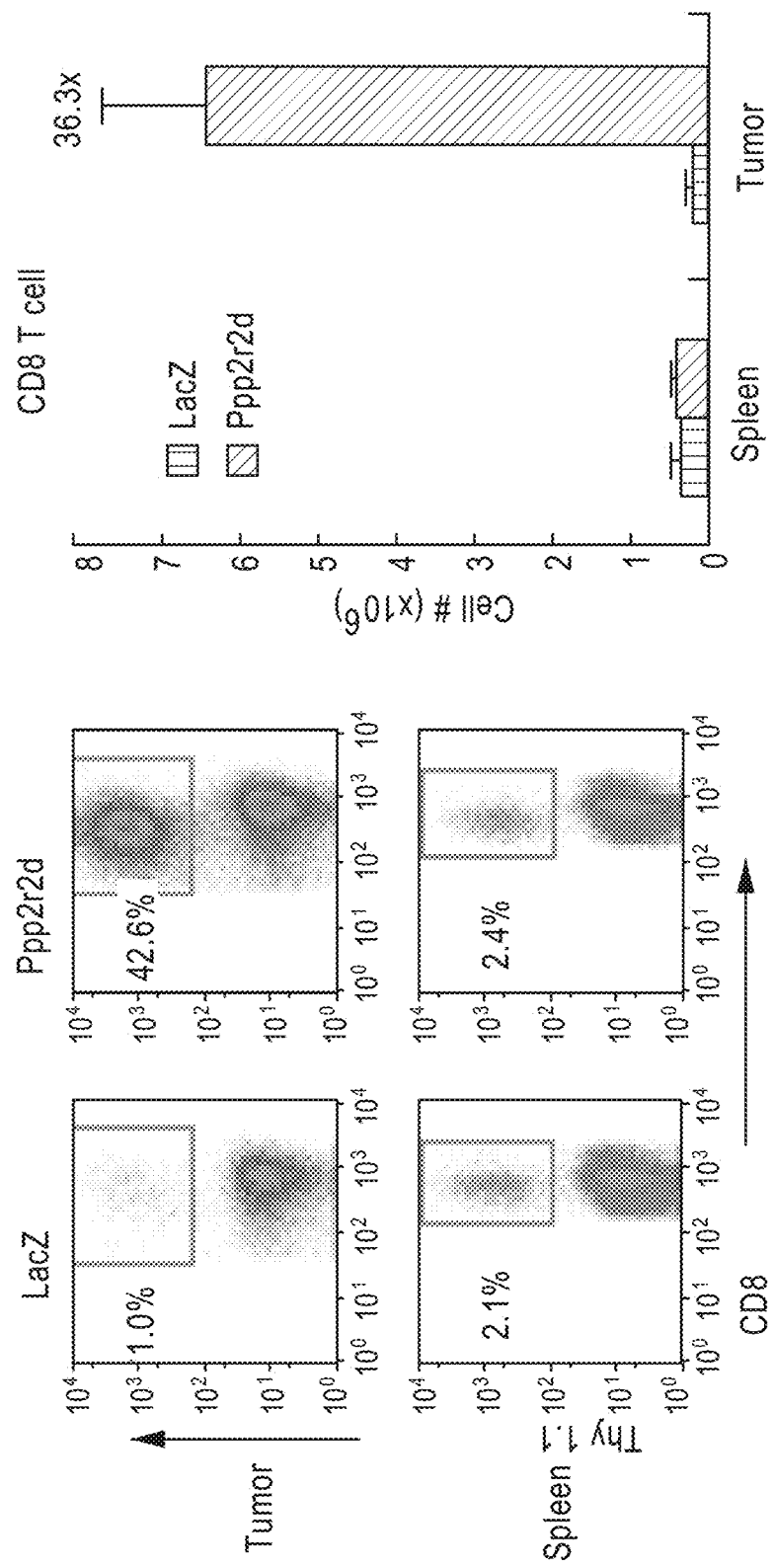
FIGS. 8a-8b are a set of graphs showing flow cytometry-based quantification of CD4+ and CD8+ T cell enrichment in tumors. shRNA-expressing T cells were identified in tumors and spleens using Thy1.1 reporter (% Thy1.1+CD8 T cells or CD4+ T cells, top and bottom panels). Total numbers of LacZ or Ppp2r2d shRNA-expressing T cells were determined in tumors and spleens 7 days following transfer of 2×106 shRNA-expressing cells (right panels). Fold-enrichment of Ppp2r2d versus LacZ shRNA-expressing T cells in tumors is indicated.
Figure 8B:
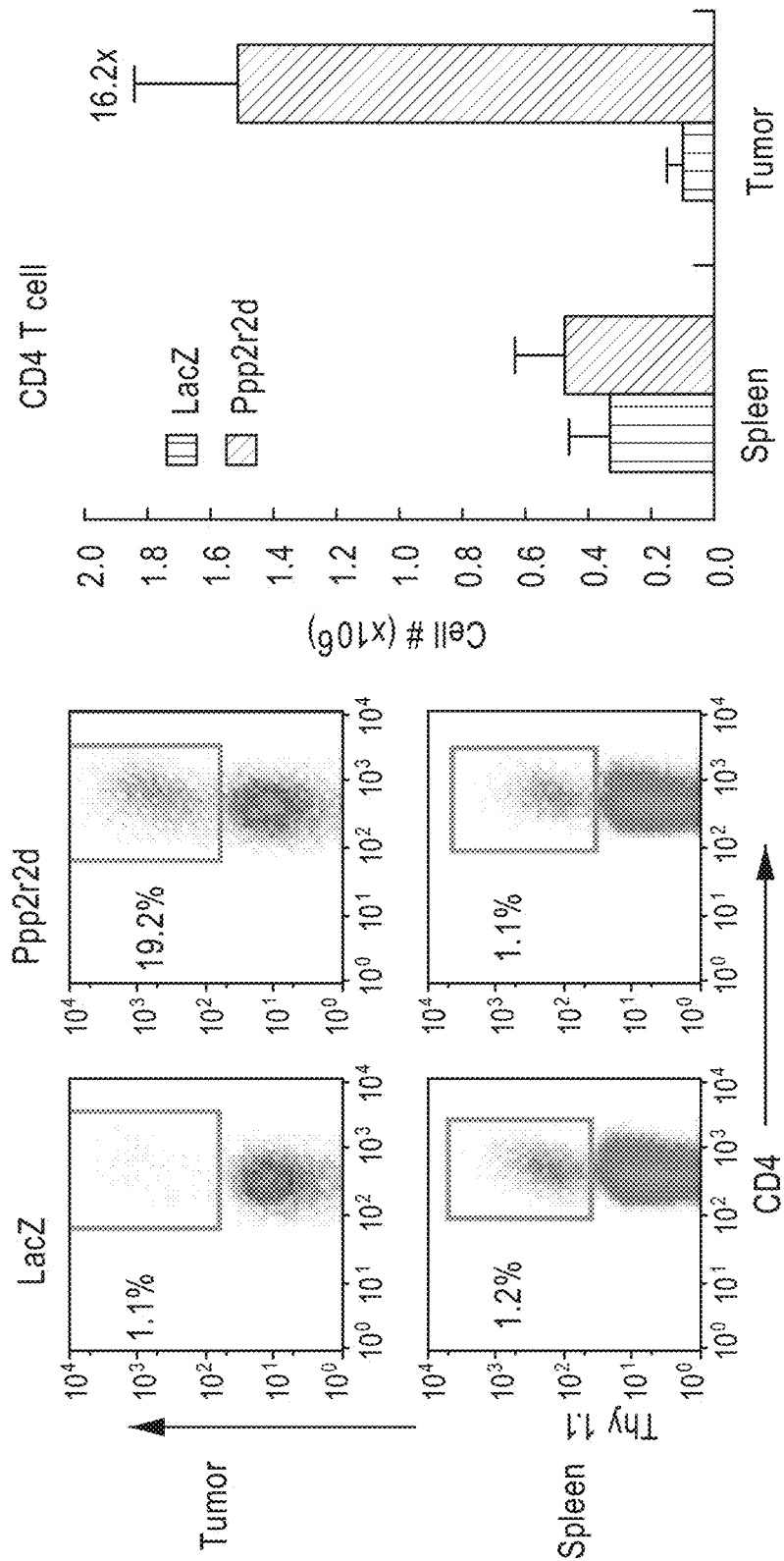
Figure 9:
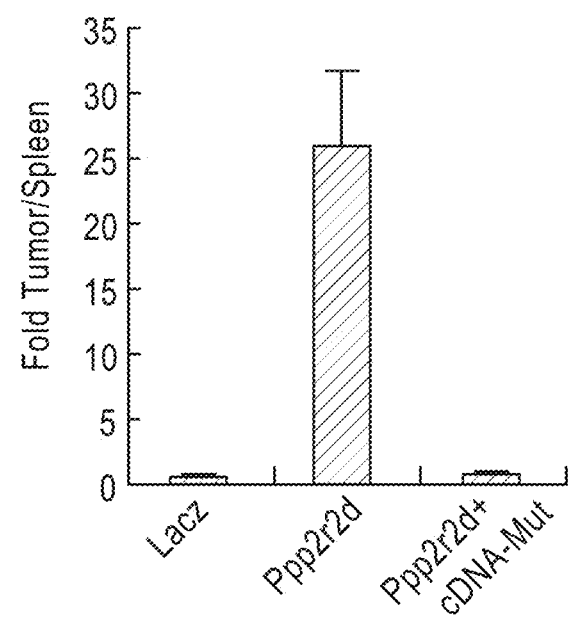
FIG. 9 is a graph showing reversal of Ppp2r2d shRNA-mediated T cell expansion in tumors by Ppp2r2d cDNA with a mutated shRNA binding site but preserved protein sequence. The three cell populations were identified based on co-expressed reporters; fold-enrichment was calculated based on percentage of reporter-positive cells in tumors versus spleens.

CD8$^+$ OT-I or CD4$^+$ TRP-1 T cells expressing Ppp2r2d or LacZ shRNAs were injected into mice bearing day 14 B16-Ova tumors. shRNA-expressing T cells were identified in tumors and spleens using Thy1.1 reporter (FIG. 8a, % Thy1.1$^+$ CD8 T cells, left panels). Total numbers of LacZ or Ppp2r2d shRNA-expressing T cells were determined in tumors and spleens 7 days following transfer of 2×10$^6$ shRNA-expressing cells (FIG. 8a, right panels). Fold-enrichment of Ppp2r2d versus LacZ shRNA-expressing T cells in tumors is indicated. Ppp2r2d shRNA not only induced accumulation of OT-I CD8 T cells, but also CD4 T cells (from TRP-1 TCR transgenic mice), with T cell numbers in tumors being significantly higher when Ppp2r2d rather than LacZ shRNA was expressed (36.3-fold for CD8; 16.2-fold for CD4 T cells) (FIGS. 8a-8b).

Figure 17:
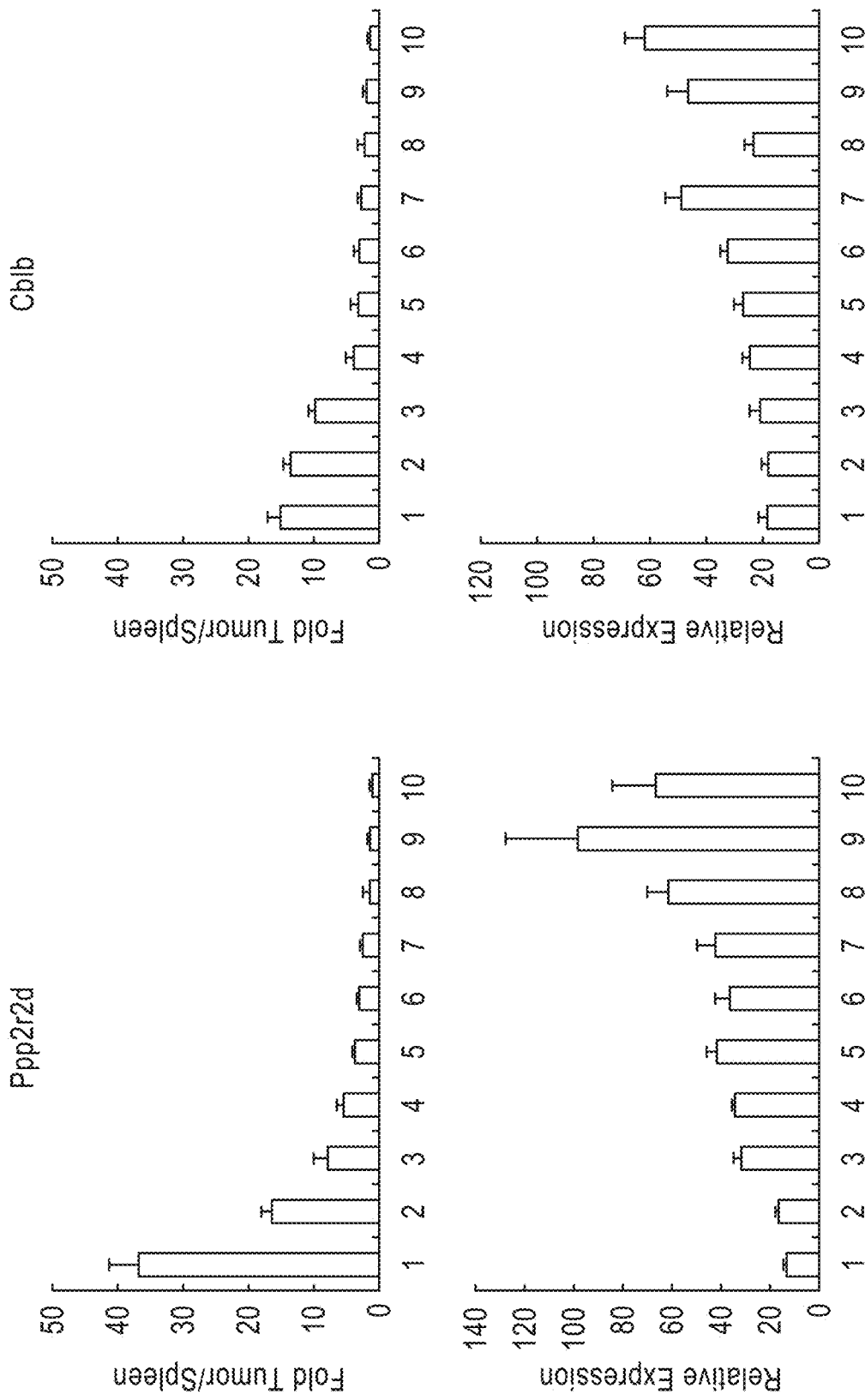
FIG. 17 is a set of graphs demonstrating FACS analysis of T cell enrichment in tumors compared to spleen for cells expressing a panel of Ppp2r2d or Cblb shRNAs (upper panels). Ppp2r2d and Cblb mRNA levels were measured by qPCR prior to T cell transfer (lower panels). Data represent biological replicates (n=3), each value represents mean+/−s.d.

T cell enrichment in tumors compared to spleen for cells expressing a panel of Ppp2r2d or Cblb shRNAs (FIG. 17, upper panels) Ppp2r2d and Cblb mRNA levels were also measured by qPCR prior to T cell transfer (FIG. 17, lower panels). The strongest T cell enrichment in tumors was observed for shRNAs with >80% knock-down efficiency at the mRNA level (shRNAs #1 and 2 for both Ppp2r2d and Cblb). CD8 T cell accumulation correlated with the degree of Ppp2r2d knock-down, and two Ppp2r2d shRNAs with the highest in vivo activity induced the lowest levels of Ppp2r2d mRNA (FIG. 17).

Figure 18:
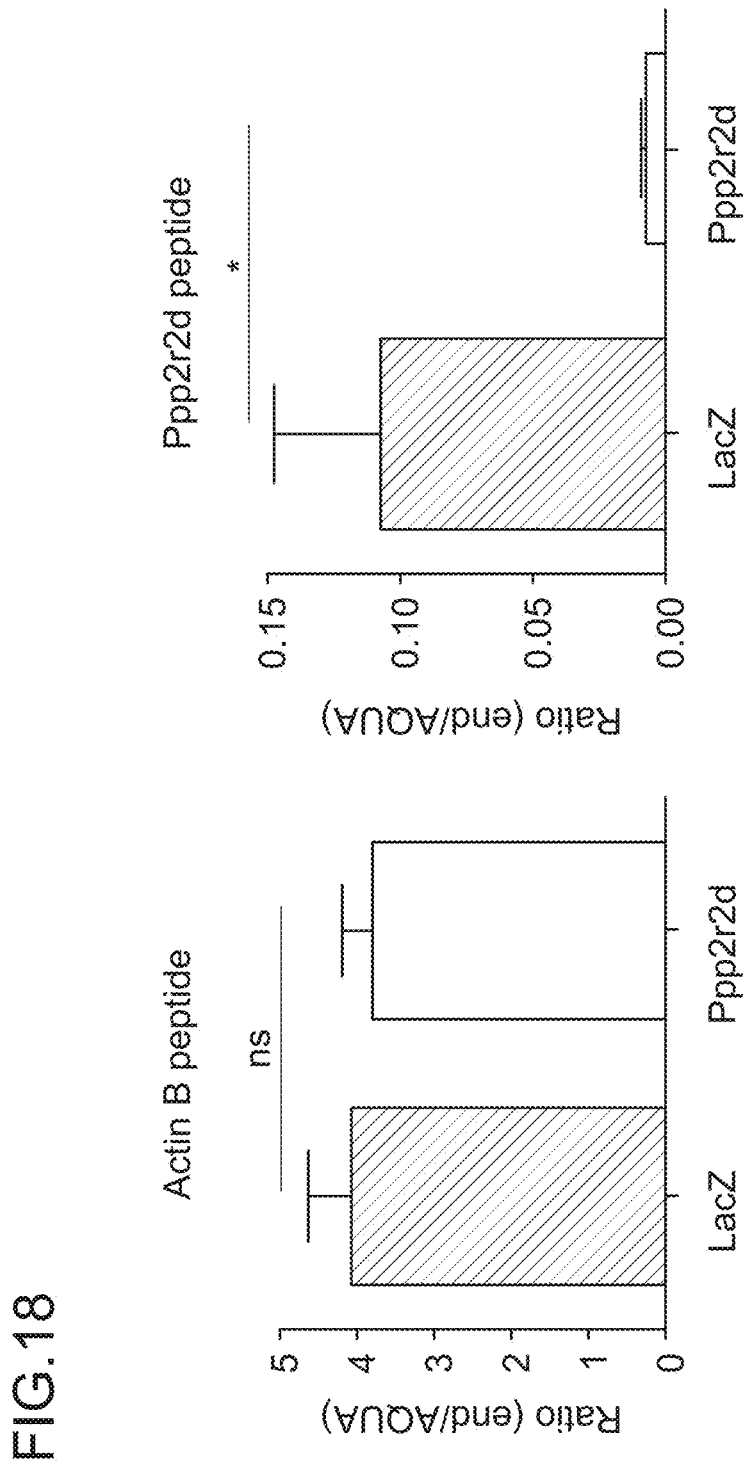
FIG. 18 is a set of graphs demonstrating Ppp2r2d protein quantification by mass spectrometry with labeled synthetic peptides (AQUA, ratio of endogenous to AQUA peptides). Representative data from two independent experiments (a-d); Two-sided student's t-test, *P<0.05, **P<0.01; mean+/−s.d.

Ppp2r2d knockdown was also confirmed at the protein level using a quantitative mass spectrometry approach (FIG. 18). A previously reported approach for absolute quantification (AQUA) of proteins from cell lysates by mass spectrometry was used to measure the effect of Ppp2r2d shRNA expression at the protein level (Gerber, S. A., Rush, J., Stemman, O., Kirschner, M. W. & Gygi, S. P. Absolute quantification of proteins and phosphoproteins from cell lysates by tandem MS. PNAS, 100, 6940-6945 (2003). This strategy is based on a 'selective reaction monitoring' approach in which a synthetic peptide with incorporated stable isotopes is used as an internal standard for mass spectrometry analysis. OT-I cells expressing LacZ or Ppp2r2d shRNAs were sorted to purity using FACS. Cells (1×10$^6$) were lysed in 1 ml of MPER extraction reagent (Pierce) containing a Protease Inhibitor Cocktail (Sigma), 1 mM EDTA and 1 mM PMSF for 15 minutes on ice with occasional vortexing. Cell debris was removed by centrifugation and the protein supernatant was filtered (0.2 μm SpinX centrifuge filter, Costar). Protein concentration was determined by Bradford assay (Biorad) and UV280 nm analysis (Nanodrop instrument); 0.1 mg of cellular protein was separated by SDS-PAGE and stained with Coomassie blue reagent (Pierce). Gel bands corresponding to a MW range of 45-60 kDa were excised followed by in-gel digestion of proteins with trypsin. Eluted peptides were spiked with 300 fmol of isotopically labeled Ppp2r2d (FFEEPEDPSS[13C-15N-R]—OH)(SEQ ID NO: 628) and Actin B (GYSFTTTAE[13C-15N-R]—OH) (SEQ ID NO: 629) peptides (21st Century Biochemicals) for quantification by LC MS/MS (LTQ XL Orbitrap, Thermo Scientific). The Ppp2r2d peptide was chosen from a region of the protein that differs from other regulatory subunits of PP2A. Initially, a LC-MS/MS run of a LacZ shRNA sample was analyzed to localize the Ppp2r2d and Actin B peptides that were being monitored. The absolute quantification AQUA peptides co-eluted with the corresponding endogenous peptides from the reverse-phase column, yet their higher MW (10 Da) enabled the ratio of peak intensity for endogenous and AQUA peptides to be determined using abundant peptide fragment ions. Triplicate samples were analyzed by SDS-PAGE-LC-MS/MS and statistical significance was determined using Graphpad Prism 6.0 software using a two-sided Student t-test (F test, *p=0.0062).

Figure 19:
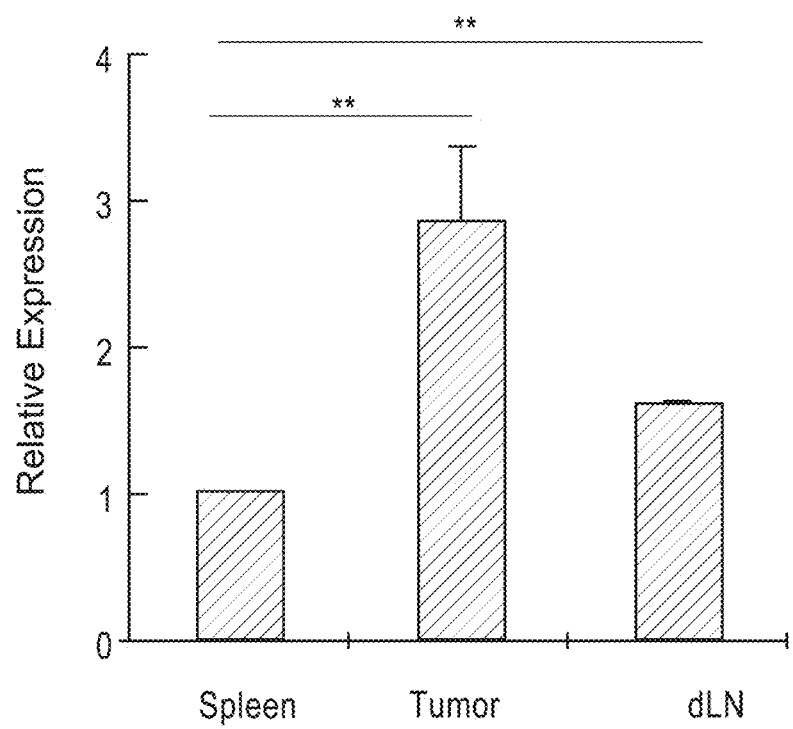
FIG. 19 is a graph demonstrating qPCR analysis for Ppp2r2d mRNA in tumor-infiltrating OT-I T cells (day 7).

The specificity of Ppp2r2d shRNA was determined. Ppp2r2d shRNA activity was specific because the phenotype was reversed when a mutated Ppp2r2d cDNA (with wild-type protein sequence, but mutated DNA sequence at the shRNA binding site) was co-introduced with the Ppp2r2d shRNA (FIG. 9, 10a-c). Furthermore, OT-1 CD8 T cells over-expressed Ppp2r2d in tumors compared to spleen (in the absence of any shRNA expression), suggesting that it is an intrinsic component of the signaling network inhibiting T cell function in tumors (FIG. 19).

Figures 10A, 10B:
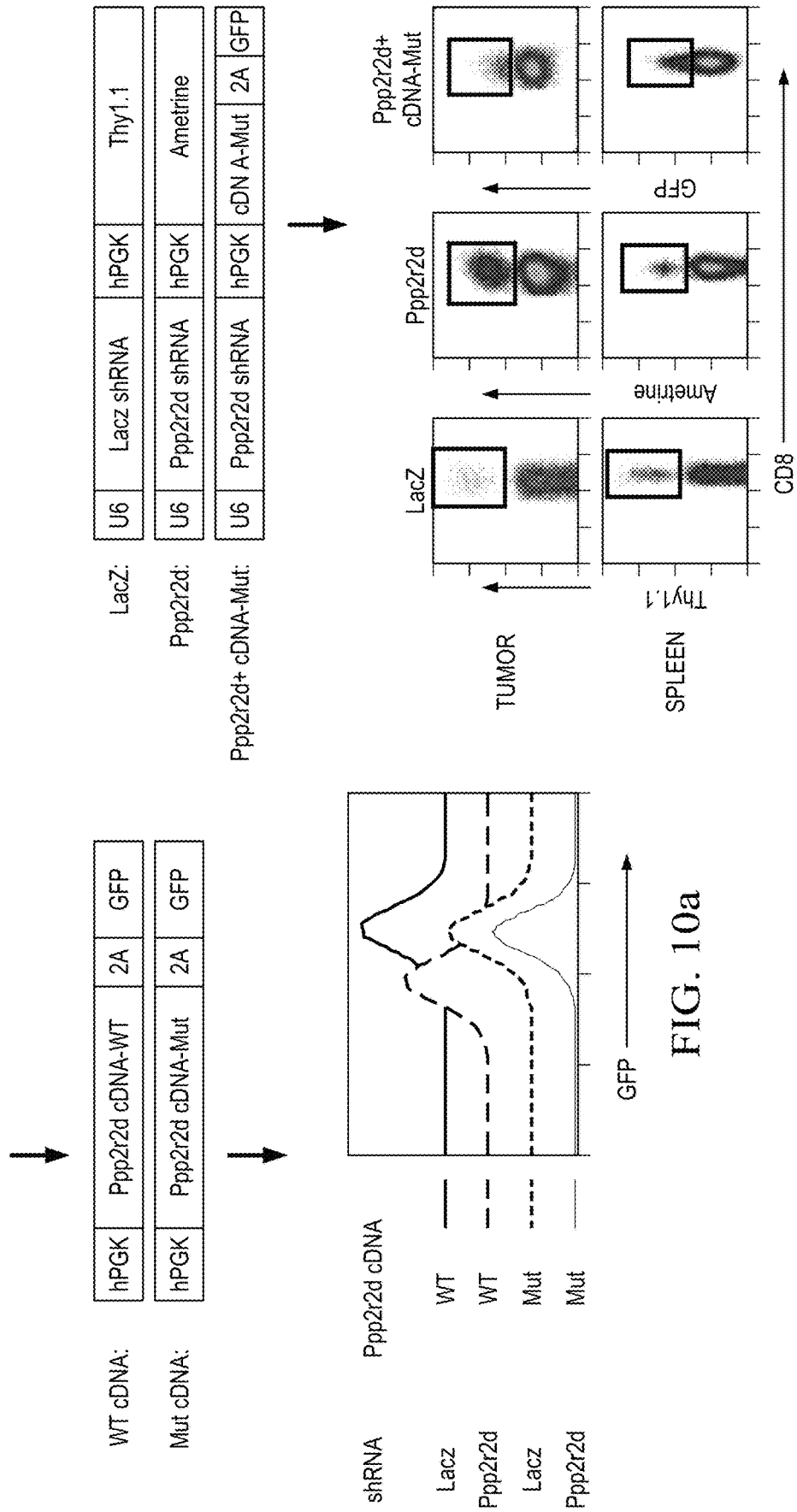
FIG. 10a describes the generation of mutant Ppp2r2d cDNA with preserved protein sequence but disrupted shRNA binding site. EL4 cells were transduced with mutant or wild type Ppp2r2d cDNA on a vector also containing GFP. GFP-positive cells were sorted to purity and transduced with LacZ or Ppp2r2d shRNA vectors expressing a Thy1.1 reporter. shRNA-transduced (Thy1.1$^+$) cells were analyzed by flow cytometry for GFP expression. The Ppp2r2d shRNA reduced GFP levels when wild-type Ppp2r2d, but not when mutant Ppp2r2d was expressed. (SEQ ID NOS. 679-681 shown.)
FIG. 10b demonstrates that expression of Ppp2r2d mutant cDNA prevents phenotype induced by Ppp2r2d shRNA. OT-I T cells were transduced with a vector encoding LacZ shRNA, Ppp2r2d shRNA or Ppp2r2d shRNA plus mutant Ppp2r2d cDNA. The different cell populations were normalized for transduction efficiency and co-injected into B16-Ova tumor bearing mice. The percentage of each T cell population in tumors and spleens was quantified by gating on CD8$^{30}$ Vα2$^+$Vβ5$^+$ T cells; transduced cells were detected based on expression of Thy1.1 or Ametrine/GFP fluorescent reporters (representative data from 2 independent experiments, n=3 mice per experiment).

OT-1 T cells transduced with lentiviral vectors driving expression of LacZ shRNA, Ppp2r2d shRNA, Ppp2r2d shRNA. Mutant Ppp2r2d cDNA with preserved protein sequence but disrupted shRNA binding site were generated. Wild-type Ppp2r2d cDNA was isolated by RT-PCR using forward primer GGATCCATGGCAGGAGCTGGAGGC (SEQ ID NO: 630) and reverse primer: GCTAGCATTAAT-TTTGTCCTGGAATATATACAAGTTATTGGTGG (SEQ ID NO: 631). The target sequence of Ppp2r2d shRNA, CCCACATCAGTGCAATGTATT (SEQ ID NO: 632) was mutated to TCCCCACCAATGTAACGTGTT (SEQ ID NO: 633) by overlapping PCR (which conserves protein coding sequence) using forward primer: TCCATCCCCAC-CAATGTAACGTGTTTGTTTACAGCAGCAGCAAGG (SEQ ID NO: 634) and reverse primer: AAACAAACACGTTACATTGGTGGGGATG-GAACTCTGCGGCAGTGA (SEQ ID NO: 635). (FIG. 10a) Both wild-type and mutant Ppp2r2d cDNAs were cloned into a modified pLKO.3 vector with a 2A ribosomal skip peptide-GFP sequence (resulting in stoichiometric Ppp2r2d and GFP expression in cells). Constructs were introduced into EL4 thymoma cells. GFP-expressing EL4 cells were sorted to purity and then transduced with LacZ or Ppp2r2d shRNA lentiviral vectors driving expression of a Thy1.1 reporter. shRNA-transduced (Thy1.1$^+$) cells were analyzed by flow cytometry for GFP expression. The Ppp2r2d shRNA reduced GFP levels when wild-type Ppp2r2d. The Ppp2r2d shRNA was not able to reduce expression of the GFP reporter in cells expressing the mutant Ppp2r2d cDNA, demonstrating that the shRNA binding site had been successfully mutated. (FIG. 10a)

Expression of Ppp2r2d mutant cDNA also prevents phenotype induced by Ppp2r2d shRNA. (FIG. 10b) Ppp2r2d shRNA was cloned into the mutant Ppp2r2d cDNA-2A-GFP construct which resulted in co-expression of Ppp2r2d shRNA and mutated Ppp2r2d cDNA in one vector. OT-I T cells were separately infected with lentiviruses encoding LacZ shRNA (Thy1.1), Ppp2r2d shRNA (Ametrine) or Ppp2r2d shRNA plus mutant Ppp2r2d cDNA (GFP). (FIG. 10b) These three populations there then mixed at the same ratio and injected into mice bearing day 14 B16-Ova tumors.

On day 7, each T cell population was quantified in tumors and spleens by gating on OT-I (CD8$^+$V$\alpha$2$^+$V$\beta$5$^+$)-T cells followed by analysis of populations marked by Thy1.1, Ametrine or GFP expression. The percentage of each T cell population in tumors and spleens was quantified by gating on V$\alpha$2$^+$V$\beta$5$^+$ T cells; transduced cells were detected based on expression of Thy1.1 or Ametrine/GFP fluorescent reporters and the results are shown in FIG. 10b. (representative data from 2 independent experiments, n=3 mice per experiment).

Figure 10C:
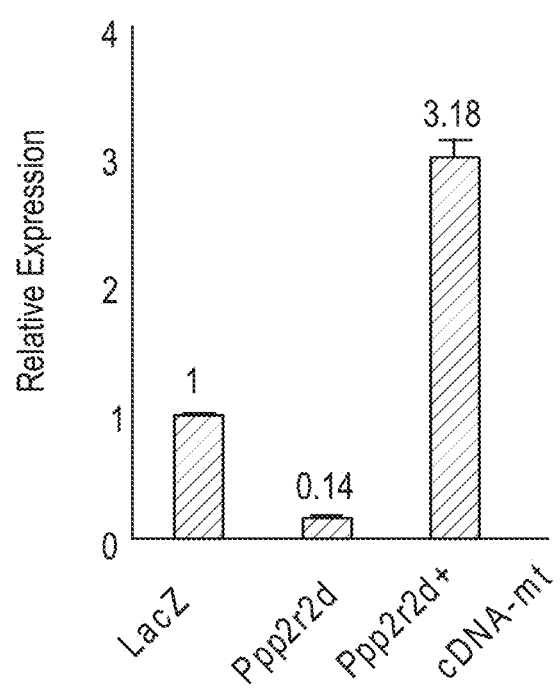
FIG. 10c is a graph demonstrating real-time PCR analysis for Ppp2r2d expression in OT-I T cells transduced with LacZ shRNA, Ppp2r2d shRNA, and Ppp2r2d shRNA plus Ppp2r2d mutant cDNA. Data represent biological replicates (n=3), each value represents mean+/−s.d.
Figure 11:
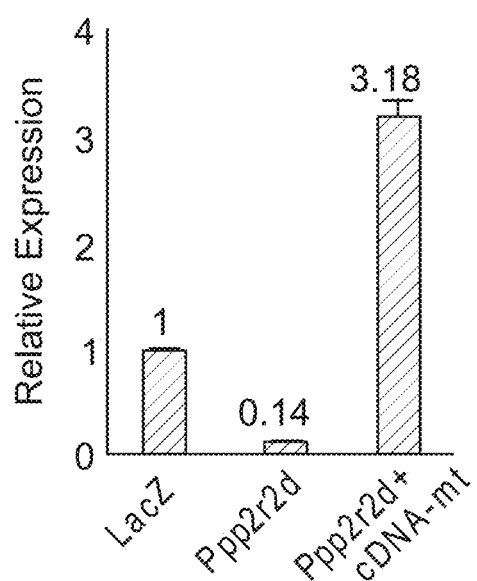
FIG. 11 is a graph demonstrating real-time qPCR analysis for Ppp2r2d mRNA levels in OT-I T cells transduced with LacZ shRNA or one of three Ppp2r2d shRNAs identified in the screen.

FIG. 10c provides real-time PCR analysis for Ppp2r2d expression in OT-I T cells transduced with LacZ shRNA, Ppp2r2d shRNA, and Ppp2r2d shRNA plus Ppp2r2d mutant cDNA. Also, the Ppp2r2d shRNA with the highest in vivo activity was associated with the lowest levels of Ppp2r2d mRNA (FIG. 11).

Figure 12B:
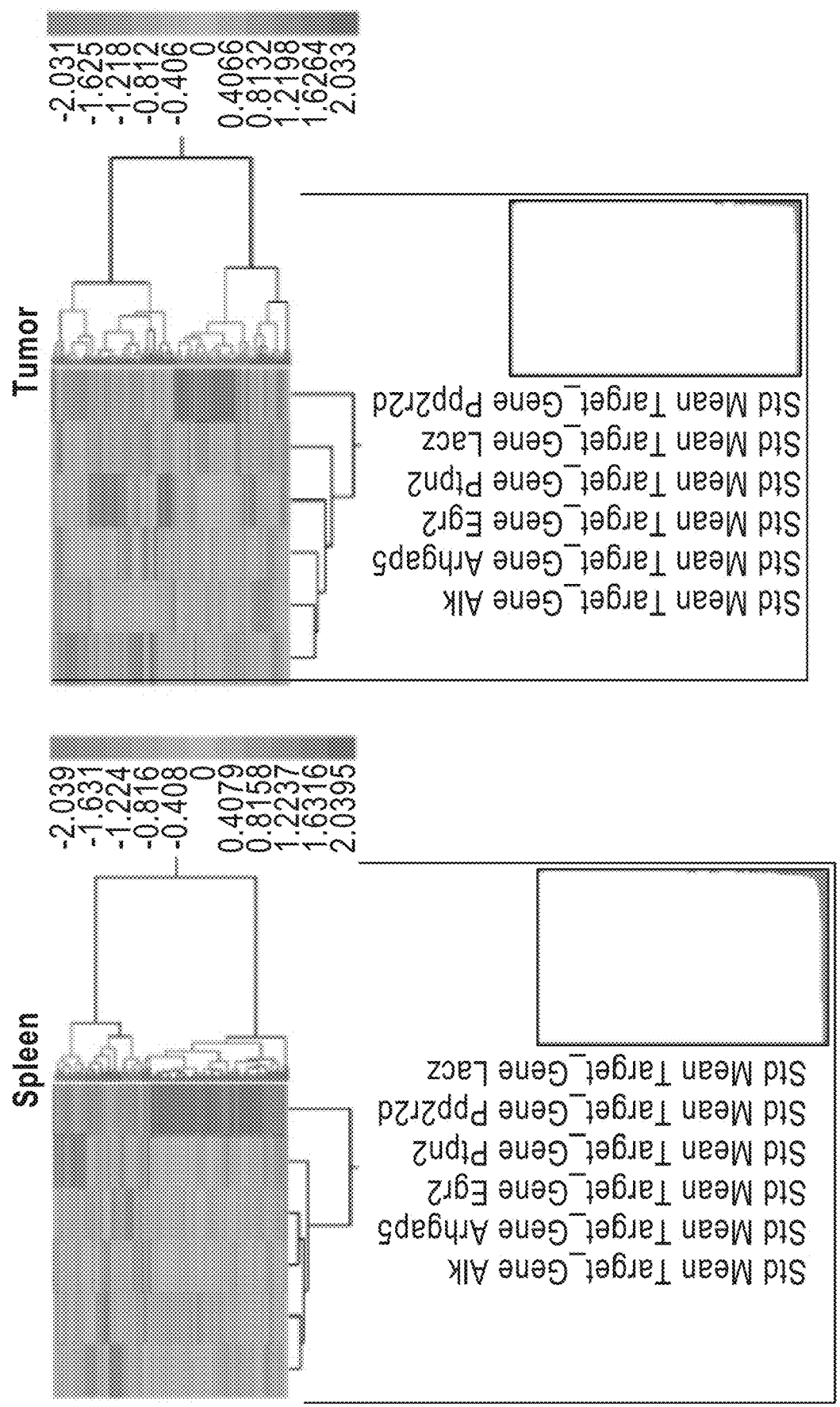
FIG. 12b demonstrates clustering of mean expression levels for mRNAs found to be significantly regulated by T cells in or tumors expressing the LacZ control shRNA or one of five experimental shRNAs. Significant expression differences were defined as an Anova p value <0.01 between T cells expressing LacZ control shRNA or one of five experimental shRNAs (Alk, Arhgap5, Egr2, Ptpn2 or Ppp2r2d) (JMP-Genomics 6.0, SAS Institute Inc.). mRNAs significantly regulated in one or more treatment groups are shown after clustering (Fast Ward).
Figure 12C:
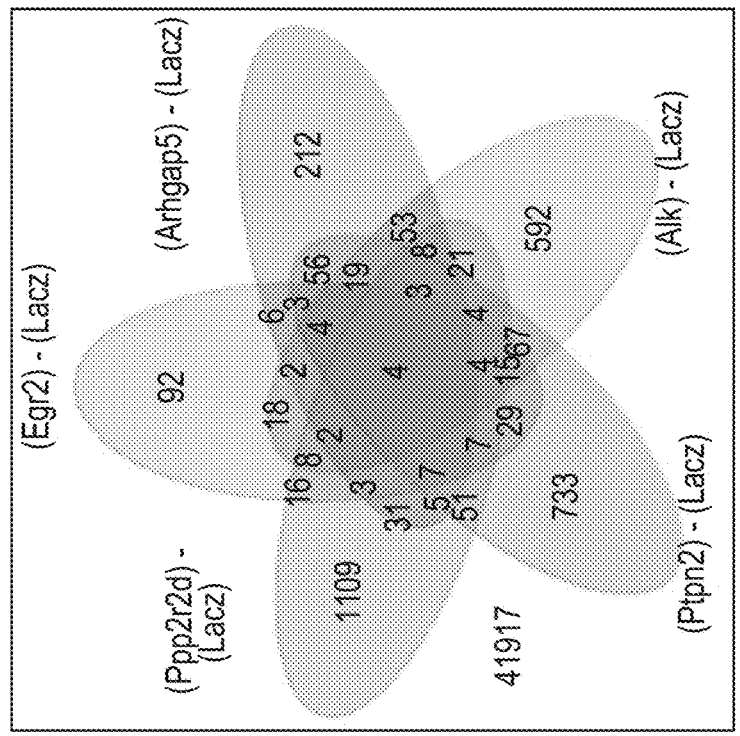
FIG. 12c is a Venn diagram showing overlaps between expression signatures for tumor-infiltrating T cells transduced with one of the five experimental shRNAs (signatures defined as an Anova p<0.01 as described above). Indicated are the numbers of overlapping probe IDs for any combination of the 5 signatures, as indicated by the overlapping ovals. The significance of the overlaps versus that expected by random chance (Fishers Exact Test) is shown in the accompanying table.

Microarray analysis of tumor-infiltrating T cells expressing experimental or control shRNAs showed that each shRNA induced a distinct set of gene expression changes, with some overlap between particular shRNAs (FIG. 12a-c). Two genes (Egr2 and Ptpn2) have known functions in T cells. Enrichment in tumor versus spleen was calculated based on deep sequencing results from the secondary screen. (FIG. 12a) Clustering of mean expression levels for mRNAs found to be significantly regulated by T cells in spleens or tumors expressing the LacZ control shRNA or one of five experimental shRNAs. (FIG. 12b) Significant expression differences were defined as an Anova p value <0.01 between T cells expressing LacZ control shRNA or one of five experimental shRNAs (Alk, Arhgap5, Egr2, Ptpn2 or Ppp2r2d) (JMP-Genomics 6.0, SAS Institute Inc.). mRNAs significantly regulated in one or more treatment groups are shown after clustering (Fast Ward). FIG. 12c is a Venn diagram showing overlaps between expression signatures by tumor-infiltrating T cells transduced with one of the five experimental shRNAs (signatures defined as an Anova p<0.01 as described above). Indicated are the numbers of overlapping probe IDs for any combination of the 5 signatures, as indicated by the overlapping ovals. The significance of the overlaps versus that expected by random chance (Fishers Exact Test) is shown in the accompanying table.

Example 3: Changes in T Cell Function Induced by Ppp2r2d

Figure 13A:
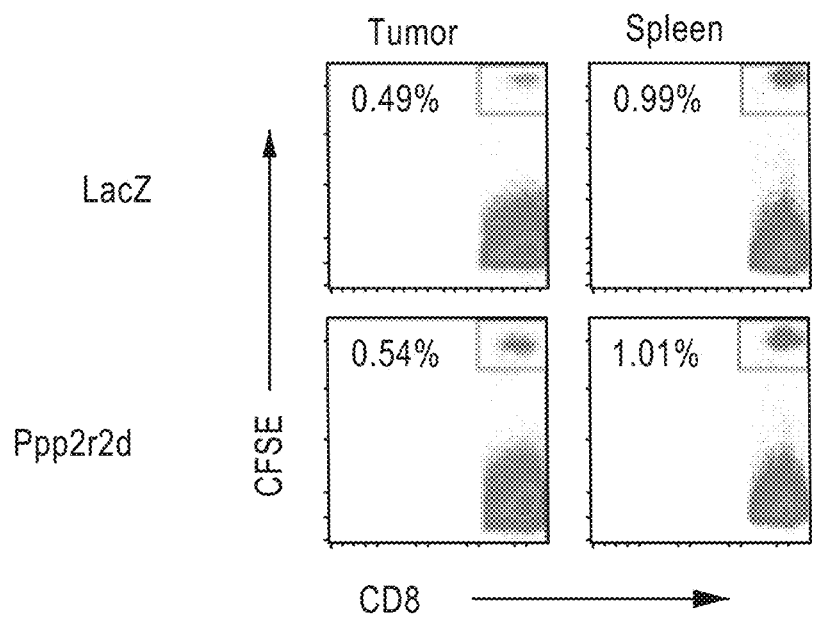
FIG. 13a is a set of graphs showing representative flow cytometry plots of demonstrating the frequency of Ppp2r2d or LacZ shRNA-transduced CD8 T cells in tumors on day 1.
Figure 13B:
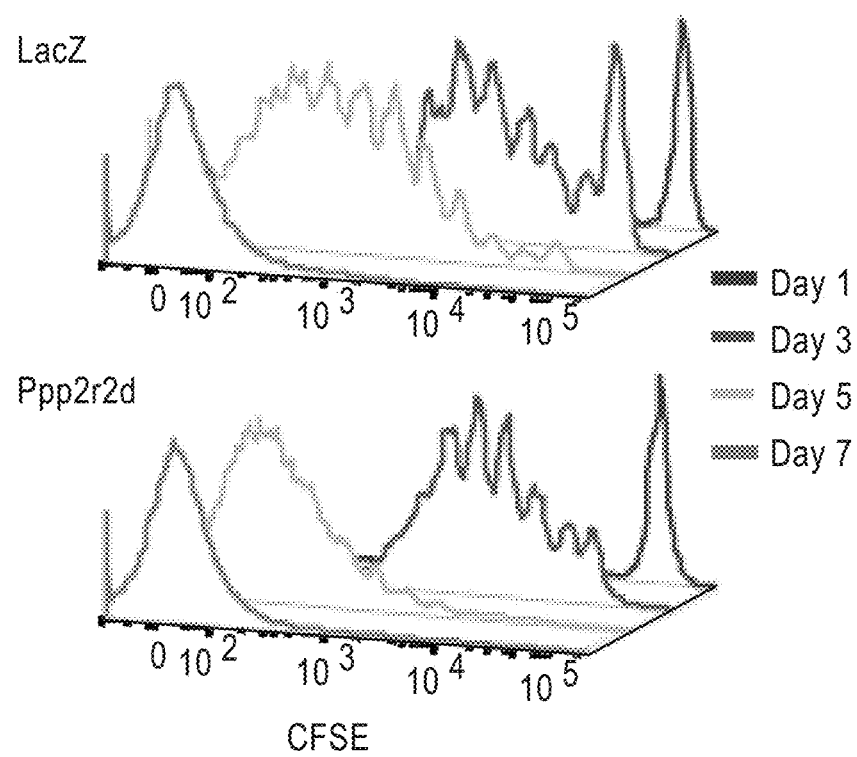
FIG. 13b are a pair of graphs demonstrating the degree of proliferation (based on CFSE dilution) by Ppp2r2d shRNA-transduced CD8 T cells compared to LacZ shRNA-transduced T cells in tumors on days 1, 3, 5, and 7.
Figure 13C:
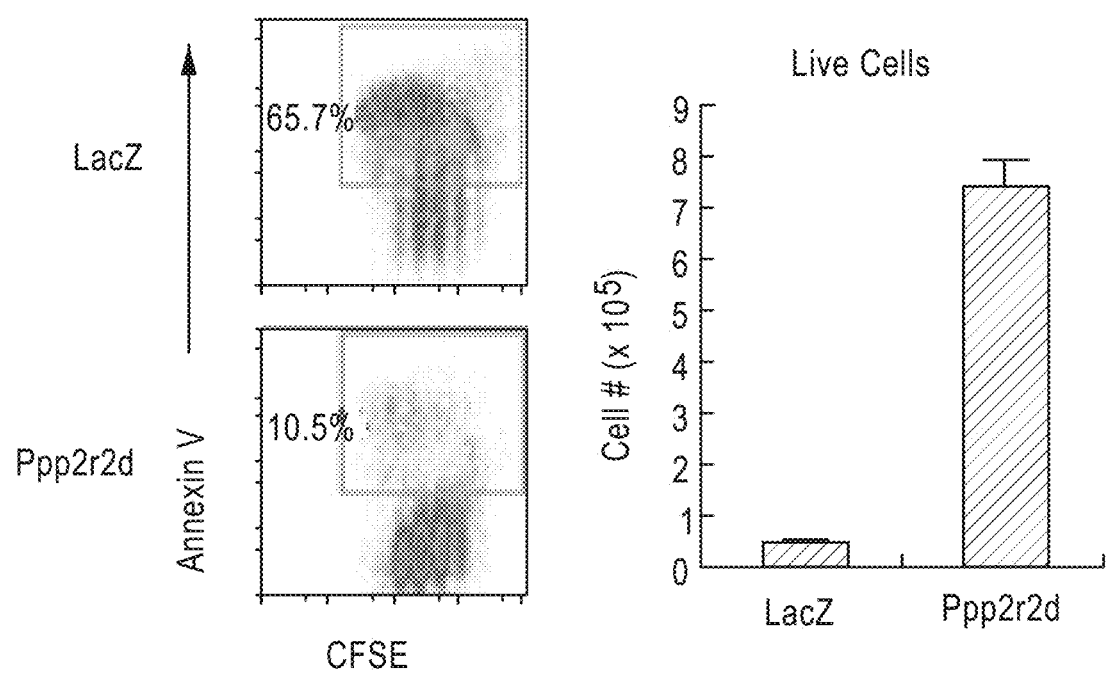
FIG. 13c is a set of graphs demonstrating that Ppp2r2d-silencing inhibits T cell apoptosis upon encounter of tumor cells. CFSE-labeled OT-I T cells were co-cultured with B16-Ova tumor cells for 72 hours. Cells were stained with CD8 and annexin V.
Figure 13D:
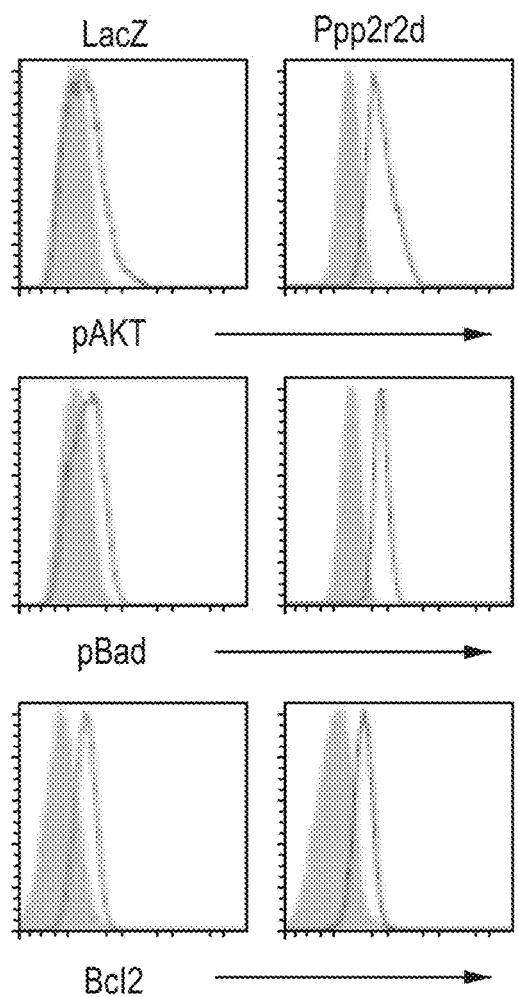
FIG. 13d is a set of graphs demonstrating intracellular staining for anti-apoptotic proteins. OT-I T cells expressing LacZ or Ppp2r2d shRNA were co-cultured with B16-Ova tumor cells for 48 hours and then stained with isotype control (grey) and phospho-AKT (Ser473), phospho-Bad (Ser 112) or Bcl-2 antibodies.
Figure 13E:
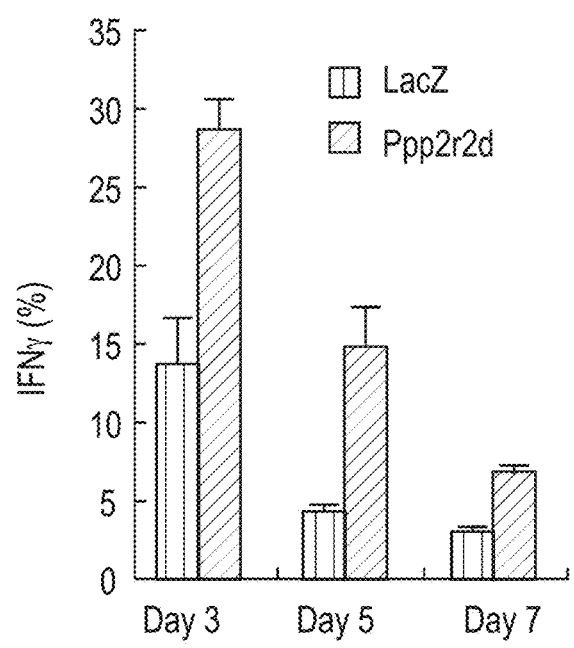
FIG. 13e is a graph demonstrating increased IFN-γ secretion by Ppp2r2d-silenced T cells. OT-I T cells isolated from B16-Ova tumor-bearing mice were assayed for IFN-γ expression by intracellular staining.
Figure 13F:
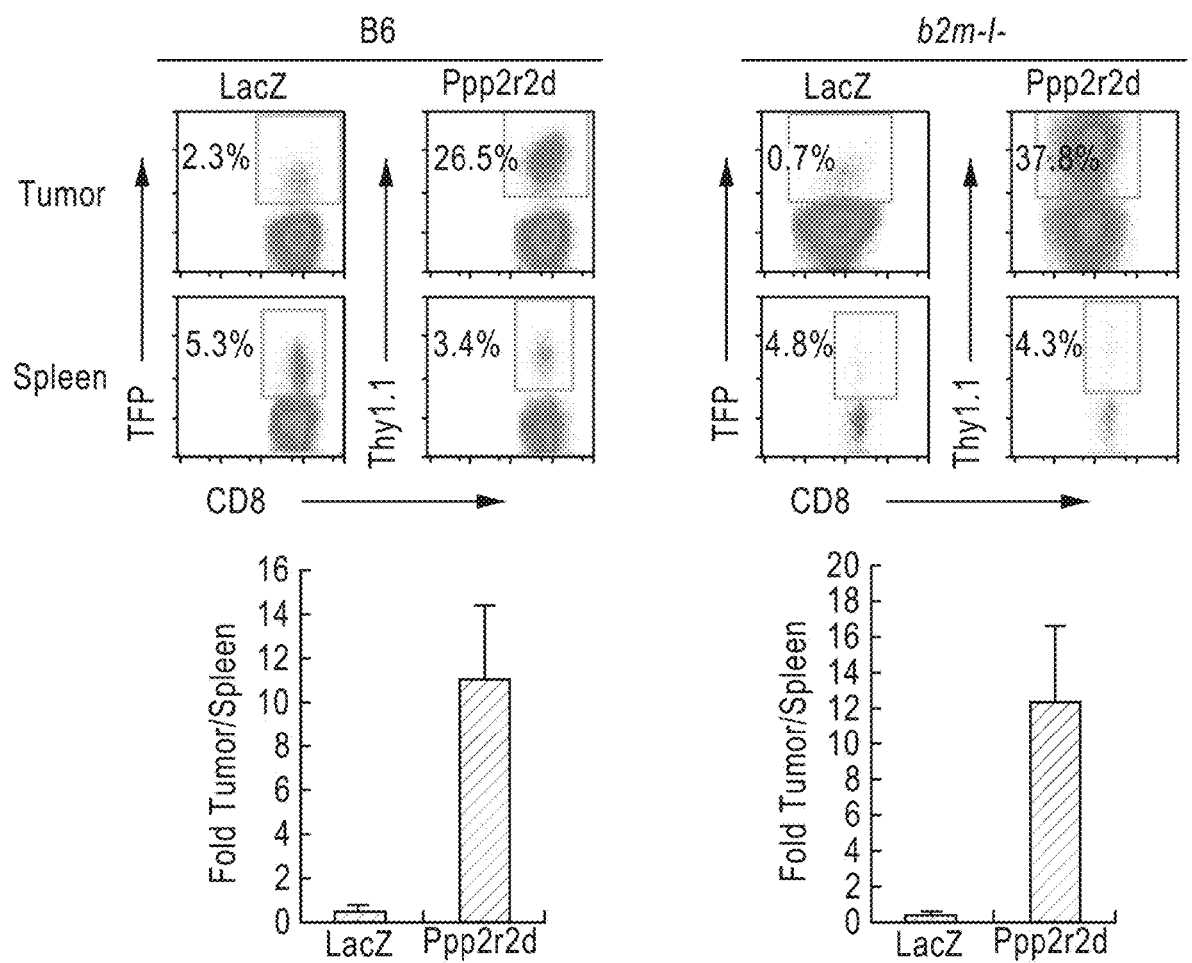
FIG. 13f is a set of graphs demonstrating Ppp2r2d-silenced T cells expand in tumors even without presentation of tumor antigens by professional antigen presenting cells. LacZ or Ppp2r2d shRNA-expressing OT-I T cells were transferred into day 14 B16-Ova tumor-bearing C57BL/6 or b2m−/− mice. shRNA-expressing T cells were identified based on expression of teal fluorescent protein (TFP) or Thy1.1 (fold enrichment in tumors compared to spleens).
Figure 13G:
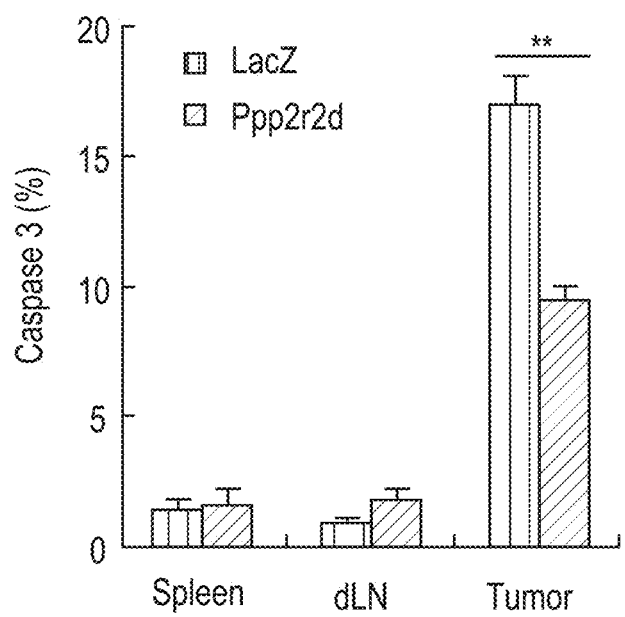
FIG. 13g is a graph demonstrating that Ppp2r2d-silencing inhibits T cell apoptosis upon encounter of tumor cells. CFSE-labeled OT-I T cells were co-cultured with B16-Ova tumor cells for 72 hours (activated caspase-3).
Figure 15:
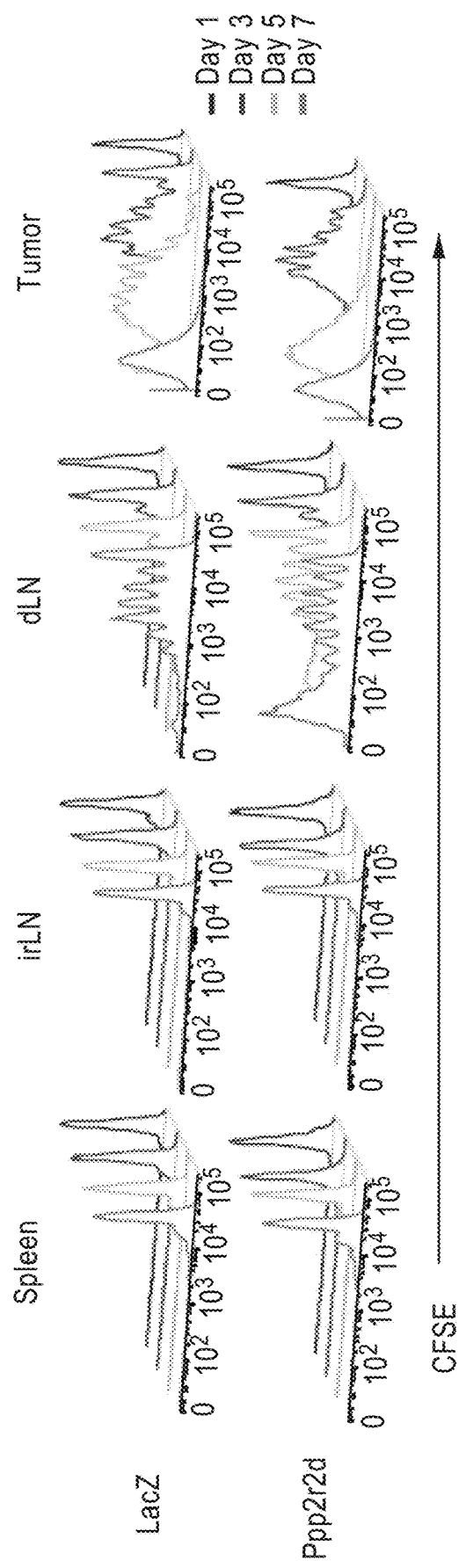
FIG. 15 is a set of graphs demonstrating accumulation of Ppp2r2d shRNA-expressing T cells in tumors and tumor-draining lymph nodes, but not other secondary lymphoid organs. OT-I T cells expressing Ppp2r2d or LacZ shRNAs were labeled with CFSE and injected into B16-Ova tumor-bearing mice. T cells were isolated from the indicated organs on days 1, 3, 5 and 7 to examine the extent of T cell accumulation based on dilution of the CSFE dye.
Figure 20A:
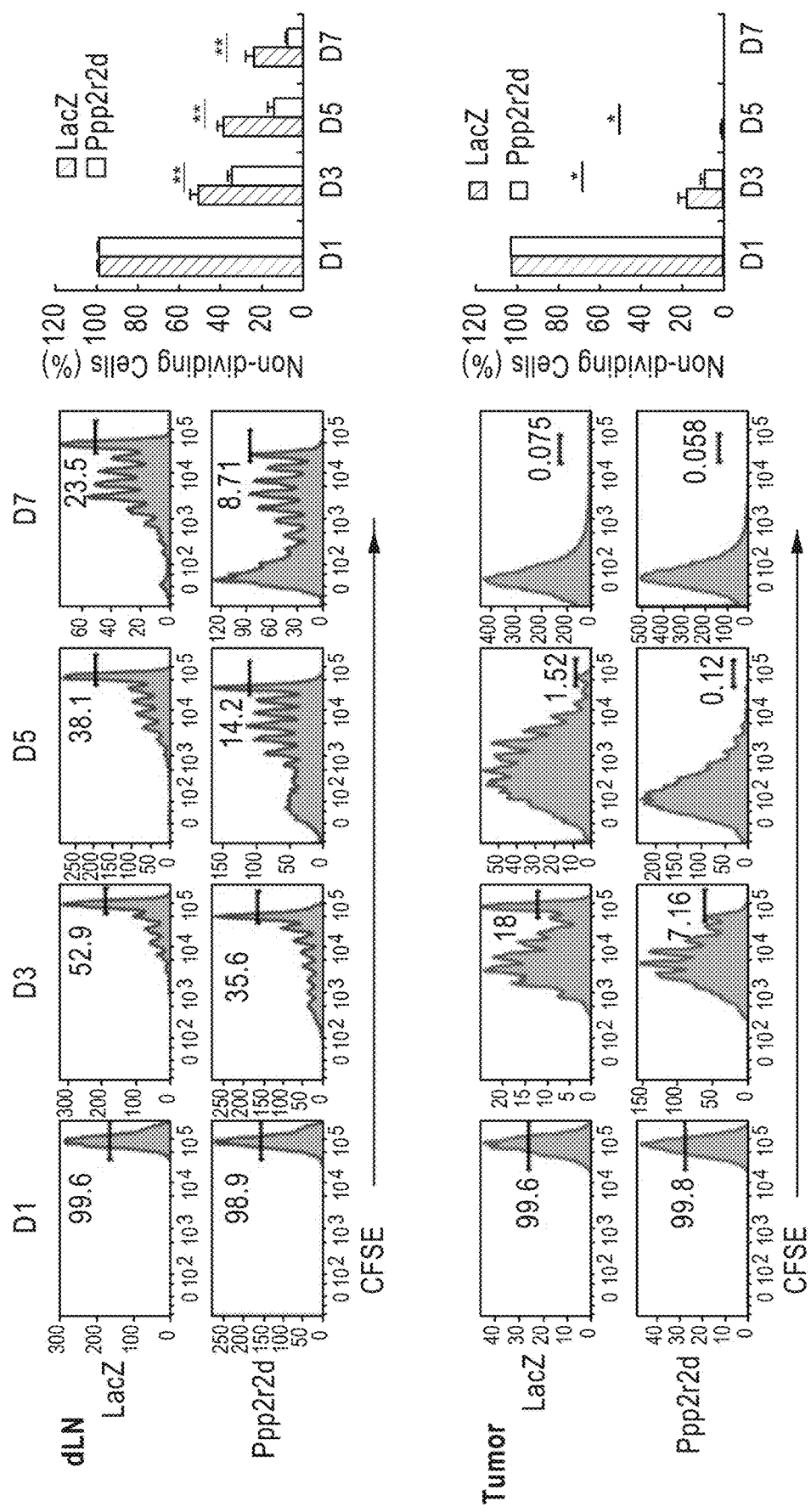
FIG. 20a are graphs showing representative flow cytometry plots demonstrating proliferation of Ppp2r2d shRNA-expressing T cells in tumors and tumor-draining lymph nodes. OTI T cells expressing Ppp2r2d or LacZ shRNAs were labeled with CFSE and injected into B16-Ova tumor-bearing mice. T cells were isolated from the indicated organs on days 1, 3, 5 and 7 to examine the extent of T cell proliferation based on CFSE dilution. T cells that had not diluted CFSE (nondividing cells) were quantified (right).
Figure 20C:
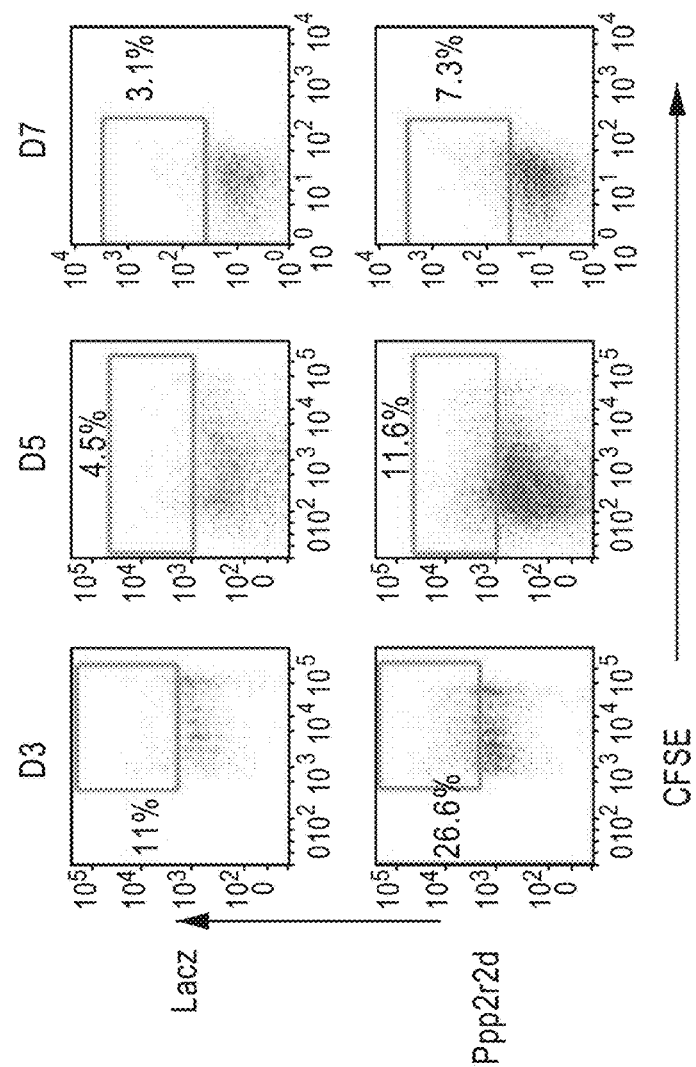
FIG. 20c are graphs showing representative flow cytometry plots demonstrating intracellularcytokine staining for IFNγ by LacZ and Ppp2r2d shRNA-expressing T cells harvested from B16-Ova tumors; T cells were labeled with CFSE prior to injection. Data for all experiments are representative of two independent trials. Statistical analysis was performed on biological replicates (n=3); *P<0.05, **P<0.01, two-sided Student's t-test. Each value represents mean+/–s.d.
Figure 20B:
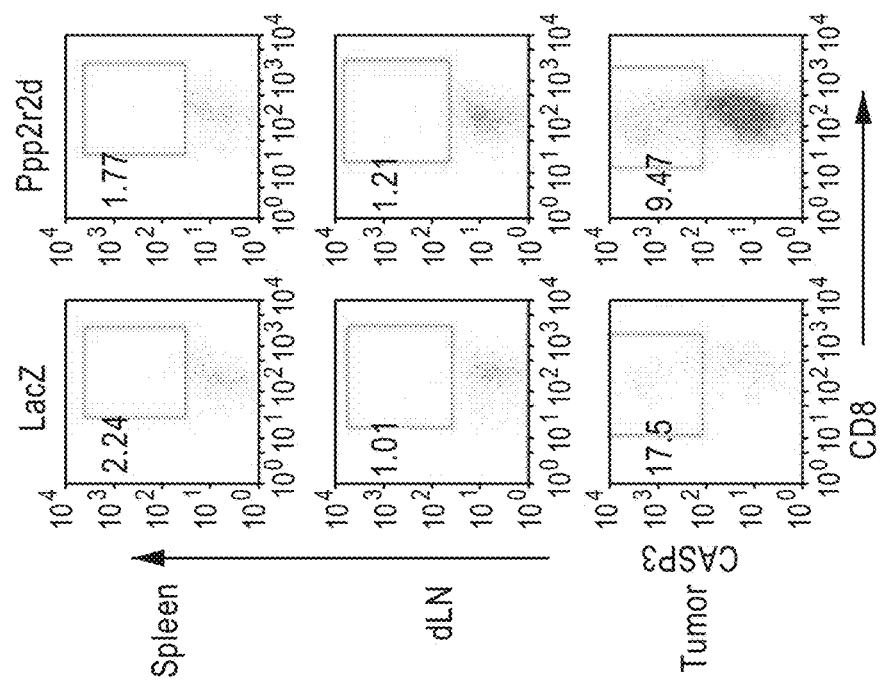
FIG. 20b are graphs showing representative flow cytometry plots demonstrating viability of tumor-infiltrating T cells. OT-I T cells expressing Pp2r2d or LacZ shRNAs were injected into B16-Ova tumor-bearing mice. T cells were isolated on day 7 and apoptosis was assessed by intracellular staining with an antibody specific for activated caspase-3 (some T cell death may have been caused by the isolation procedure from tumors).

For this example, the cellular mechanisms driving T cell accumulation by a Ppp2r2d shRNA in tumors—specifically T cell infiltration, accumulation and apoptosis were examined. T cell infiltration into tumors was assessed by transfer of OT-I CD8 T cells labeled with a cytosolic dye, CFSE. OT-I T cells expressing Ppp2r2d or LacZ shRNAs were labeled with CFSE and injected into B16-Ova tumor-bearing mice. Twenty-four hours later transduced T cells were isolated from tumors and spleens and quantified by flow cytometry. OT-I T cells expressing LacZ or Ppp2r2d shRNAs were purified using the Thy1.1 reporter and cultured in complete RPMI media without added cytokines for 24 hours. Live cells isolated by Ficoll density gradient centrifugation (Sigma) were labeled with CFSE (carboxyfluorescein diacetate, succinimidyl ester, Invitrogen), and 2×10$^6$ labeled cells were injected into mice bearing day 14 B16-Ova tumors. CFSE dilution was quantified by flow cytometry at 24 hours and days 3, 5 and 7 following transfer. In addition, intracellular staining was performed on days 3, 5 and 7 for IFN$\gamma$, TNF$\alpha$ and isotype controls (BD). No differences were observed in the frequency of Ppp2r2d or LacZ shRNA-transduced CD8 T cells in tumors on day 1, arguing against a substantial effect on T cell infiltration (FIG. 13a). However, analysis of later time points (days 3 and 5) demonstrated a higher degree of proliferation (based on CFSE dilution) by Ppp2r2d compared to LacZ shRNA-transduced T cells (FIG. 13b, FIG. 20a). Ppp2r2d shRNA-transduced T cells also produced higher levels of interferon-$\gamma$, a cytokine critical for anti-tumor immunity (FIG. 13e). The action of Ppp2r2d was downstream of T cell receptor activation because T cell accumulation was enhanced in tumors and to a lesser extent in tumor-draining lymph nodes. In contrast, no accumulation was observed in irrelevant lymph nodes or the spleen where the relevant antigen is not presented to T cells (FIG. 15). A substantial degree of T cell accumulation was even observed for LacZ shRNA-transduced T cells (complete dilution of CFSE dye by day 7), despite the presence of small numbers of such cells in tumors. This suggested that LacZ shRNA-transduced T cells were lost by apoptosis. Indeed, a larger percentage of tumor-infiltrating T cells were labeled with an antibody specific for active caspase-3 when the LacZ control shRNA (rather than Ppp2r2d shRNA) was expressed (FIG. 13g, FIG. 20b). Furthermore, co-culture of CD8 T cells with B16-Ova tumor cells showed that the majority of LacZ shRNA expressing T cells became apoptotic (65.7%) while most Ppp2r2d shRNA-transduced T cells were viable (89.5%, FIG. 13c).

Figure 14:
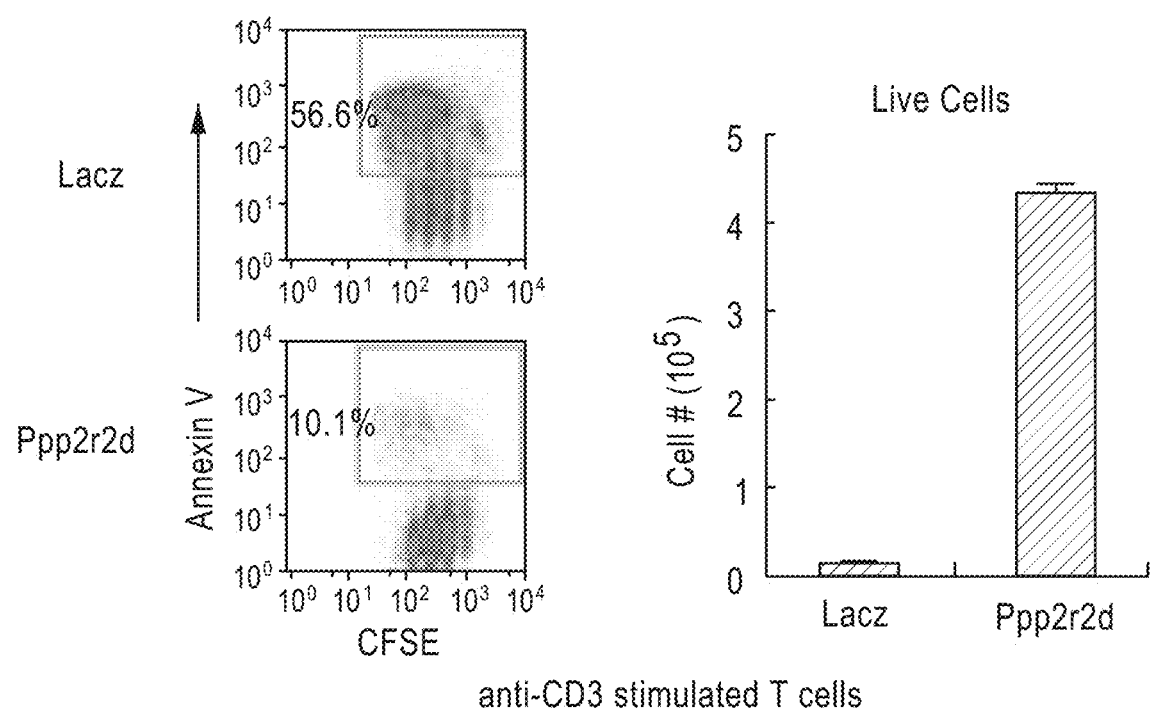
FIG. 14 is a set of graphs demonstrating OT-I T cells expressing LacZ or Ppp2r2d shRNAs labeled with CFSE and stimulated with CD3 antibody for 72 h. Cells were then stained with CD8 and annexin V and analyzed by flow cytometry.

OT-I T cells expressing LacZ or Ppp2r2d shRNAs were purified based on Thy1.1 expression and labeled with CFSE, as described above. CFSE labeled OT-I T cells (1-10$^5$) were co-cultured with 5×10$^4$ B16-Ova cells per well in a 96-well plate for 72 h. Prior to the assay, B16-Ova cells were exposed to 1 ng/mL IFN$\gamma$ for 48 hours (to induce MHC class I, which is not expressed in vitro) and washed three times. Apoptosis of OT-I T cells was detected by annexin V labeling of CD8$^+$ cells. (FIG. 13c) Intracellular staining of phospho-AKT (Ser473), phopsho-Bad (Ser 112), Bcl-2 and isotype control was performed at 48 hours using a BD intracellular staining kit. Co-culture of CD8 T cells with B16-Ova tumor cells indeed showed that the majority of LacZ shRNA expressing T cells were apoptotic (65.7%) while the majority of Ppp2r2d shRNA-transduced T cells were viable (89.5%, FIG. 13c). A similar phenotype was observed when Ppp2r2d and LacZ shRNA-expressing T cells were stimulated with immobilized CD3 antibody in the absence of CD28 costimulation (FIG. 14). Specifically, B16-Ova cells (2×10$^5$) were injected s.c. into female C57BL/6 mice (10 weeks of age). On day 12, mice bearing tumors of similar size were divided into 7 groups (7-8 mice/group). Anti-CD3/CD28 bead activated CD4 TRP-1 or/and CD8 OT-I T cells infected with Ppp2r2d or LacZ shRNA vectors (2×10$^6$ T cells each) were injected i.v. on days 12 and day 17. For the treatment of B16 tumors, mice were treated at day 10 with anti-CD3/CD28 bead activated CD4 TRP-1 and CD8 pmel-1 T cells expressing Ppp2r2d or LacZ shRNAs (3×10$^6$ T cells each). Tumor size was measured every three days following transfer and calculated as length×width. Mice with tumors ≥20 mm on the longest axis were sacrificed.

These results suggested the possibility that Ppp2r2d shRNA-transduced CD8 T cells may be able to proliferate and survive even when they recognize their antigen directly presented by B16-Ova tumor cells. This idea was tested by implantation of tumor cells into b2m−/− mice which are deficient in expression of MHC class I proteins[24]. In such mice, only tumor cells but not professional antigen presenting cells of the host could present tumor antigens to T cells. Indeed, Ppp2r2d shRNA-transduced OT-I CD8 T cells showed massive accumulation within B16-Ova tumors in b2m−/− mice (FIG. 12f) while there were very small numbers of T cells in contralateral B16 tumors that lacked expression of the Ova antigen. T cells expressing a Ppp2r2d shRNA could thus effectively proliferate and survive in response to tumor cells, despite a lack of suitable co-stimulatory signals and an inhibitory microenvironment.

Figure 21A:
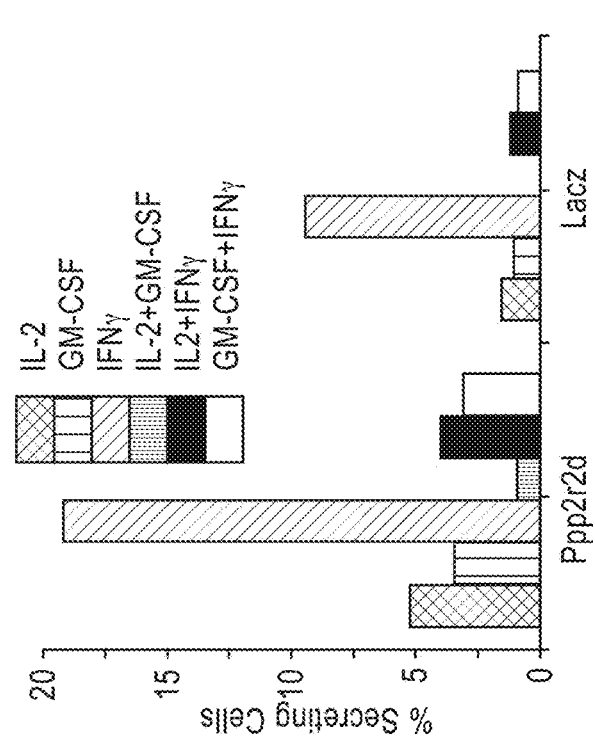
FIGS. 21a-c are a series of graphs demonstrating ex vivo analysis of cytokine production by tumor-infiltrating OT-I T cells at a single-cell level using a nanowell device (84,672 wells of picoliter volume). a, Representative single cells in nanowells and corresponding patterns of cytokine secretion. b, Percentage of T cells secreting indicated cytokines. c, Cytokine secretion rates calculated from standard curves (mean+/–s.d., Mann Whitney test *P<0.05).
Figure 21B:
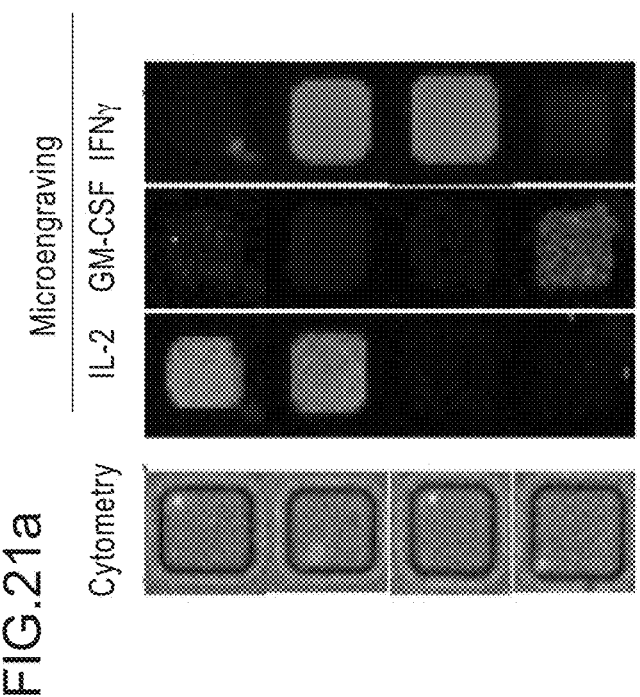
Figure 21C:
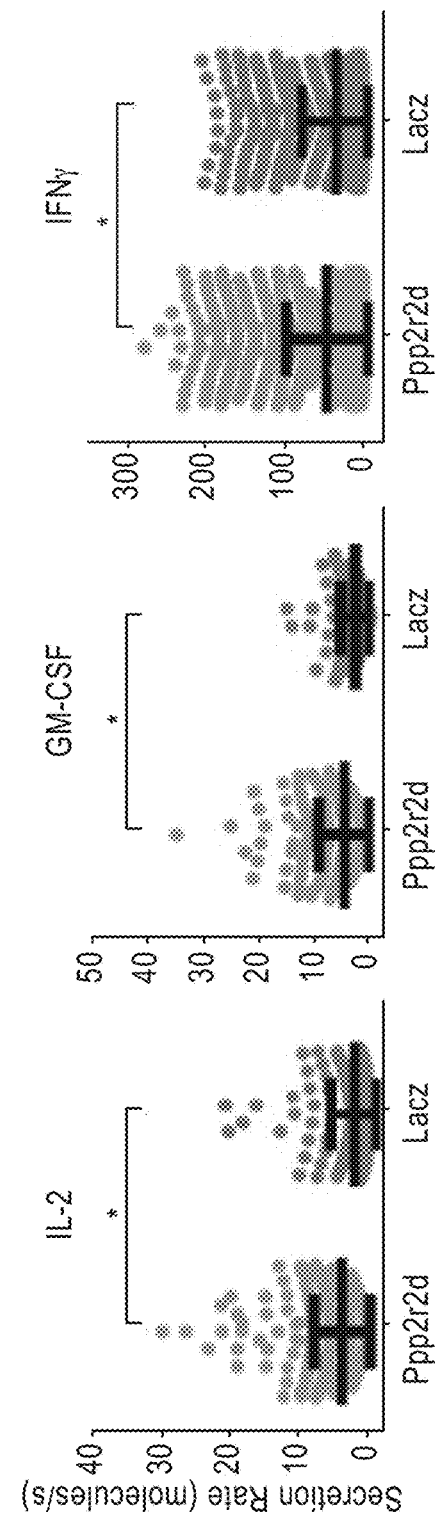

Ex vivo analysis of tumor-infiltrating T cells at a single-cell level using a nanowell device also demonstrated that Ppp2r2d silencing increased cytokine production by T cells (FIG. 21a-c). T cells were activated for 3 hours by CD3/CD28 antibodies on lipid bilayers, followed by 1 hour cytokine capture on antibody-coated slides. CD8 T cells showed a higher secretion rate for IFNγ, IL-2 and GM-CSF, and a larger fraction of T cells more than one cytokine (FIG. 21b, c). The presence of larger numbers of IFNγ-producing T cells was confirmed by intracellular cytokine staining (FIG. 21d, FIG. 20).

PP2A phosphatase is composed of a catalytic and scaffolding subunit, and its substrate specificity is determined by one of many regulatory subunits[7]. Ppp2r2d directs PP2A to Cdk1 substrates during interphase and anaphase; it thereby inhibits entry into mitosis and induces exit from mitosis[25]. PP2A plays a gatekeeper role for BAD-mediated apoptosis. Phosphorylated BAD is sequestered in its inactive form in the cytosol by 14-3-3, while dephosphorylated BAD is targeted to mitochondria where it causes cell death by binding Bcl-XL and Bcl-2[26]. PP2A phosphatases have also been shown to interact with the cytoplasmic domains of CD28 and CTLA-4 as well as Carma1 (upstream of the NF-κB pathway), but it is not known which regulatory subunits are required for these activities; Ppp2r2d antibodies suitable for the required biochemical studies are currently not available.

Figure 16A:
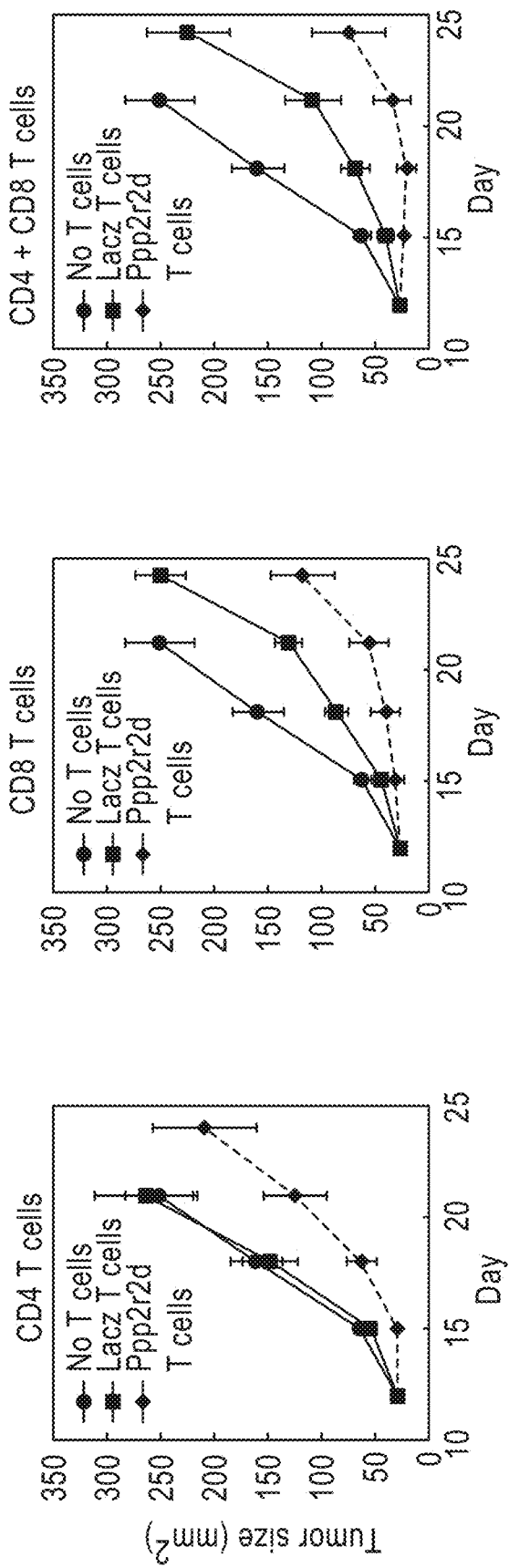
FIGS. 16a-c are a set of graphs demonstrating that the silencing of Ppp2r2d enhances anti-tumor activity of CD4 and CD8 T cells. T cells were activated with anti-CD3/CD28 beads, infected with lentiviruses driving LacZ or Ppp2r2d shRNA expression and injected into B16-Ova (a,b) or B16 (c) tumor-bearing mice. Tumor size was measured every three days following T cell transfer using calipers on the two longest axes. a,b CD4$^+$ TRP-1 and/or CD8$^+$ OT-I T cells ($2 \times 10^6$) were transferred (day 12 and 17) into mice bearing day 12 B16-Ova tumors. Tumor burden (a) and survival (b) were assessed. c, CD4$^+$ TRP-1 and CD8$^+$ pmel-1 T cells ($3 \times 10^6$ CD4$^+$ TRP-1 plus $3 \times 10^6$ CD8$^+$ pmel-1) were transferred (day 10 and 15) into mice with day 10 B16 tumors. Log-rank (Mantel-Cox) test was performed using GraphPad Prism version 6 comparing survival of mice treated with LacZ versus Ppp2r2d shRNA-expressing T cells.
Figure 16B:
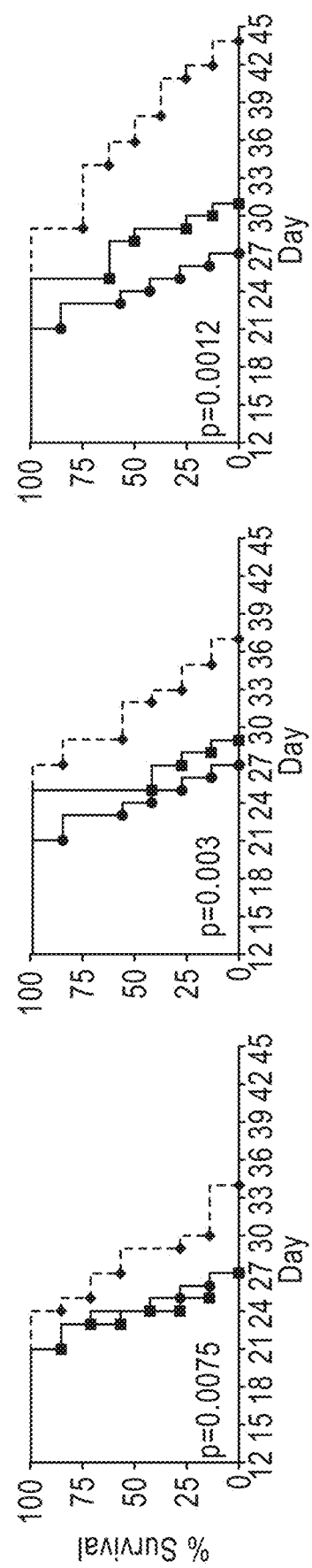
Figure 16C:
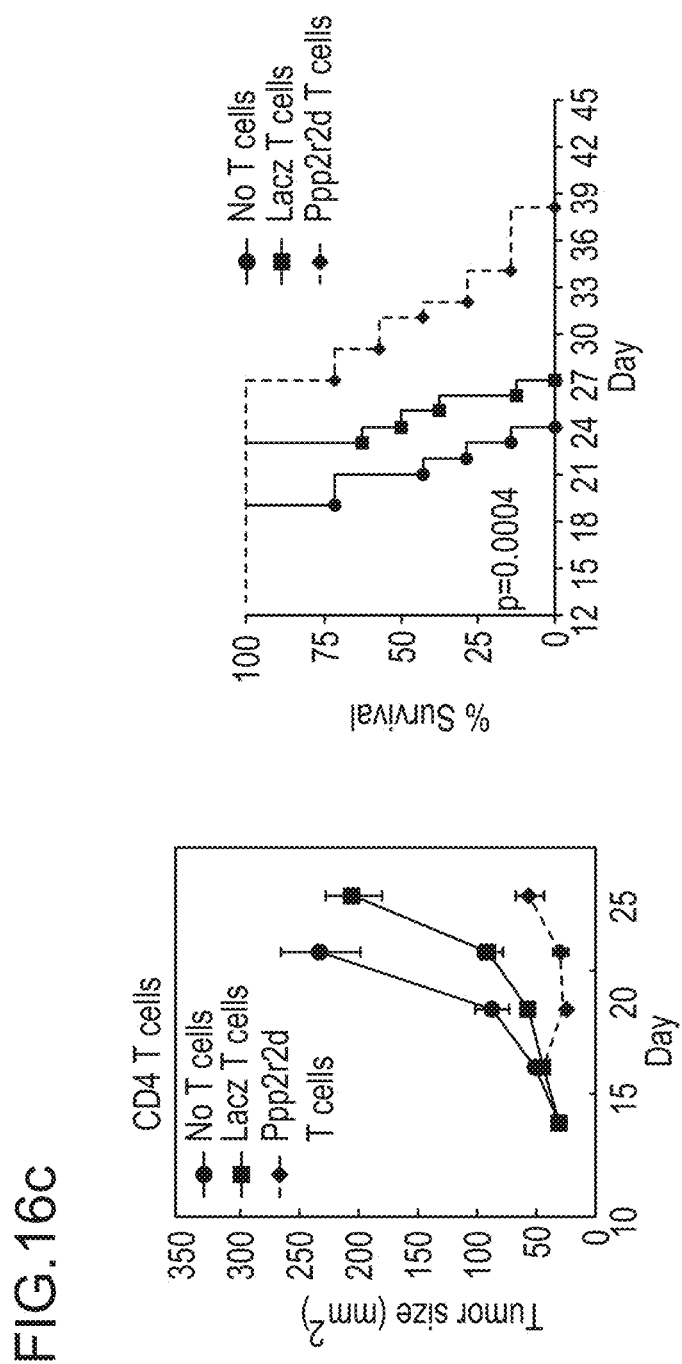

Example 4: Silencing of Ppp2r2d Enhances Anti-Tumor Activity of CD4 and CD8 T Cells The ability of a Ppp2r2d shRNA to enhance the efficacy of adoptive T cell therapy was assesed. B16-Ova tumor cells ($2 \times 10^5$) were injected subcutaneously into female C57BL/6 mice (10 weeks of age). On day 12, mice bearing tumors of similar size were divided into seven groups (7-8 mice/group), either receiving no T cells, $2 \times 10^6$ shRNA-transduced TRP-1 CD4 T cells, $2 \times 10^6$ shRNA infected OT-I CD8 T cells, or both CD4 and CD8 T cells (days 12 and day 17). According to group, anti-CD3/CD28 bead activated CD4 TRP-1 or/and CD8 OT-I T cells infected with Ppp2r2d or LacZ shRNA vectors ($2 \times 10^6$ T cells each) were injected i.v. on days 12 and day 17. For the treatment of B16 tumors, mice were treated at day 10 with anti-CD3/CD28 bead activated CD4 TRP-1 and CD8 pmel-1 T cells expressing Ppp2r2d or LacZ shRNAs ($3 \times 106$ T cells each). Tumor size was measured every three days following transfer and calculated as length×width. Mice with tumors ≥20 mm on the longest axis were sacrificed. Ppp2r2d-silencing improved the therapeutic activity of CD4 and CD8 T cells, and a synergistic effect was observed when Ppp2r2d shRNA-transduced CD4 and CD8 T cells were co-administered (FIG. 16a, b). A Ppp2r2d shRNA also enhanced anti-tumor responses when introduced into T cells specific for endogenous tumor antigens (pmel-1 CD8 T cells and TRP-1 CD4 T cells) (FIG. 16c).

Figure 22B:
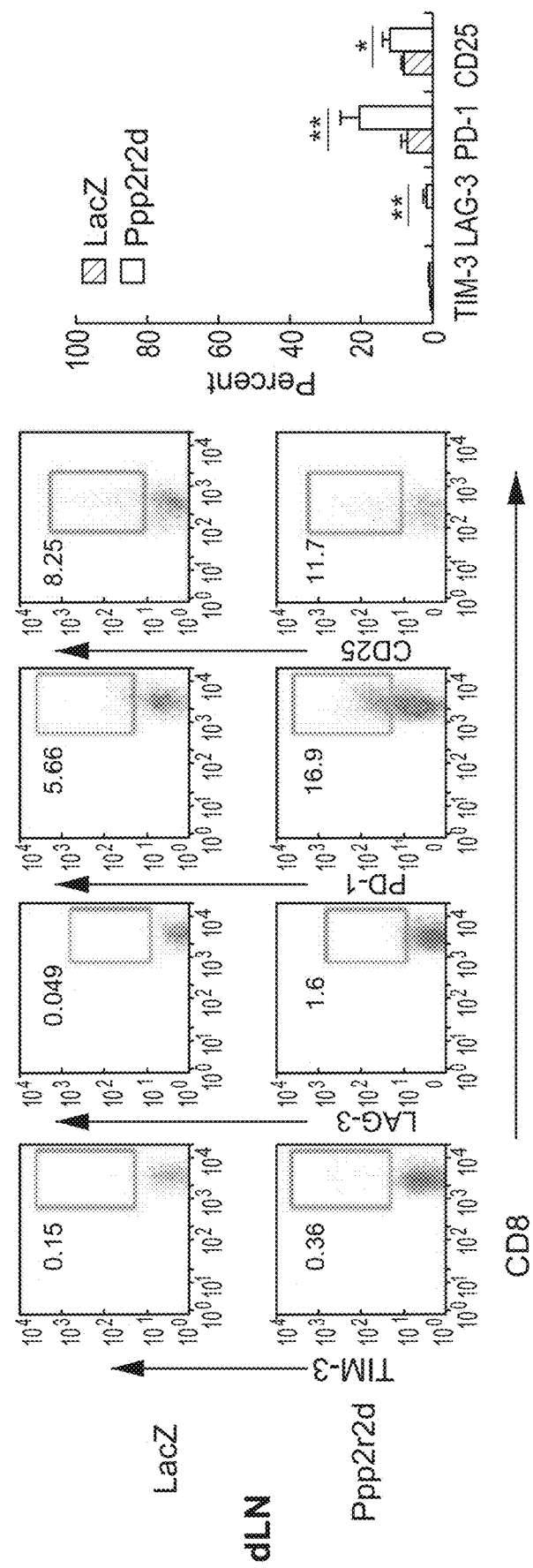
FIG. 22b is a set of graphs showing representative flow cytometry plots demonstrating analysis of exhaustion markers. OT-I cells were harvested from draining lymph nodes and tumors of mice and stained with antibodies specific for TIM-3, LAG-3, PD-1 and CD25. For all experiments (n=3 biological replicates; *P<0.05, **P<0.01, Two-sided Student's t-test); each value represents mean+/–s.d.
Figure 22B:
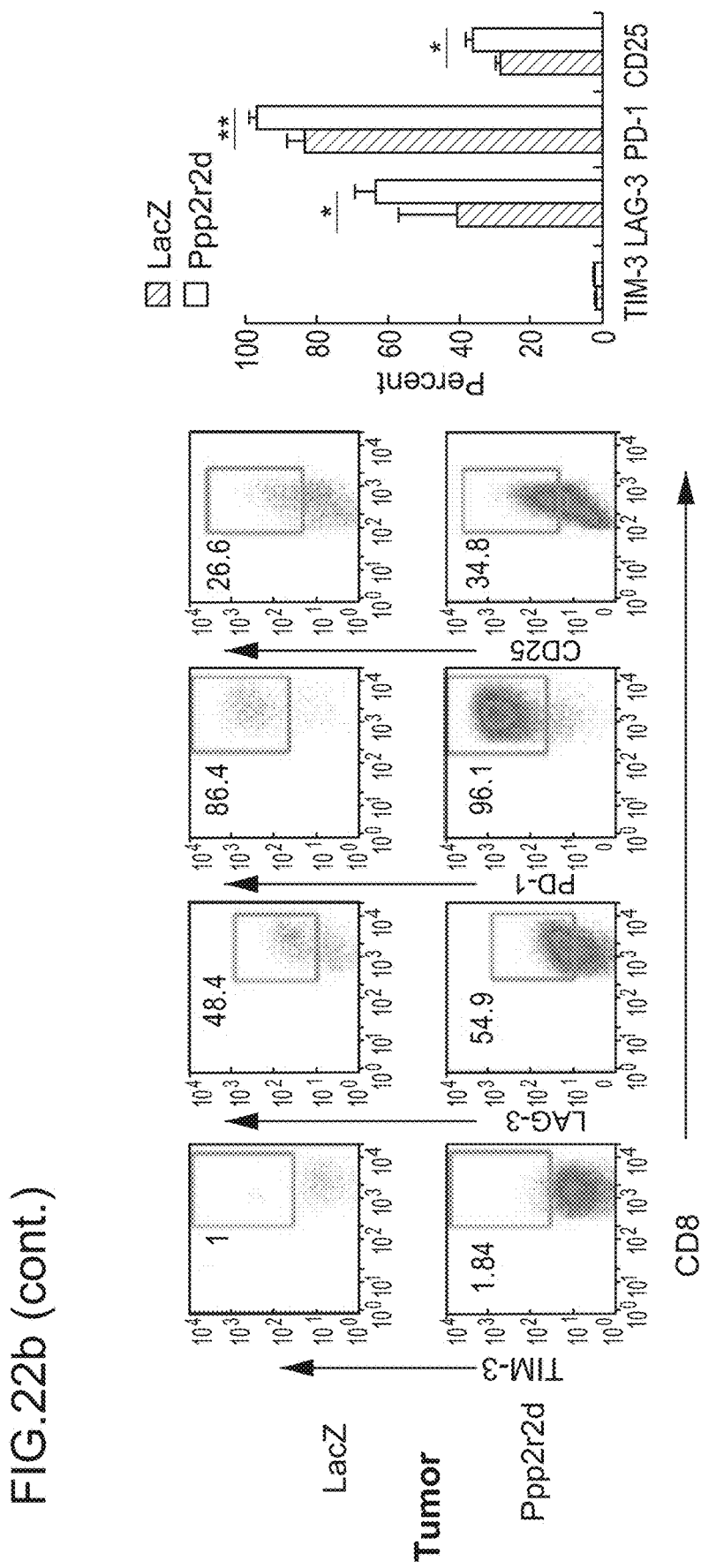
Figure 23A:
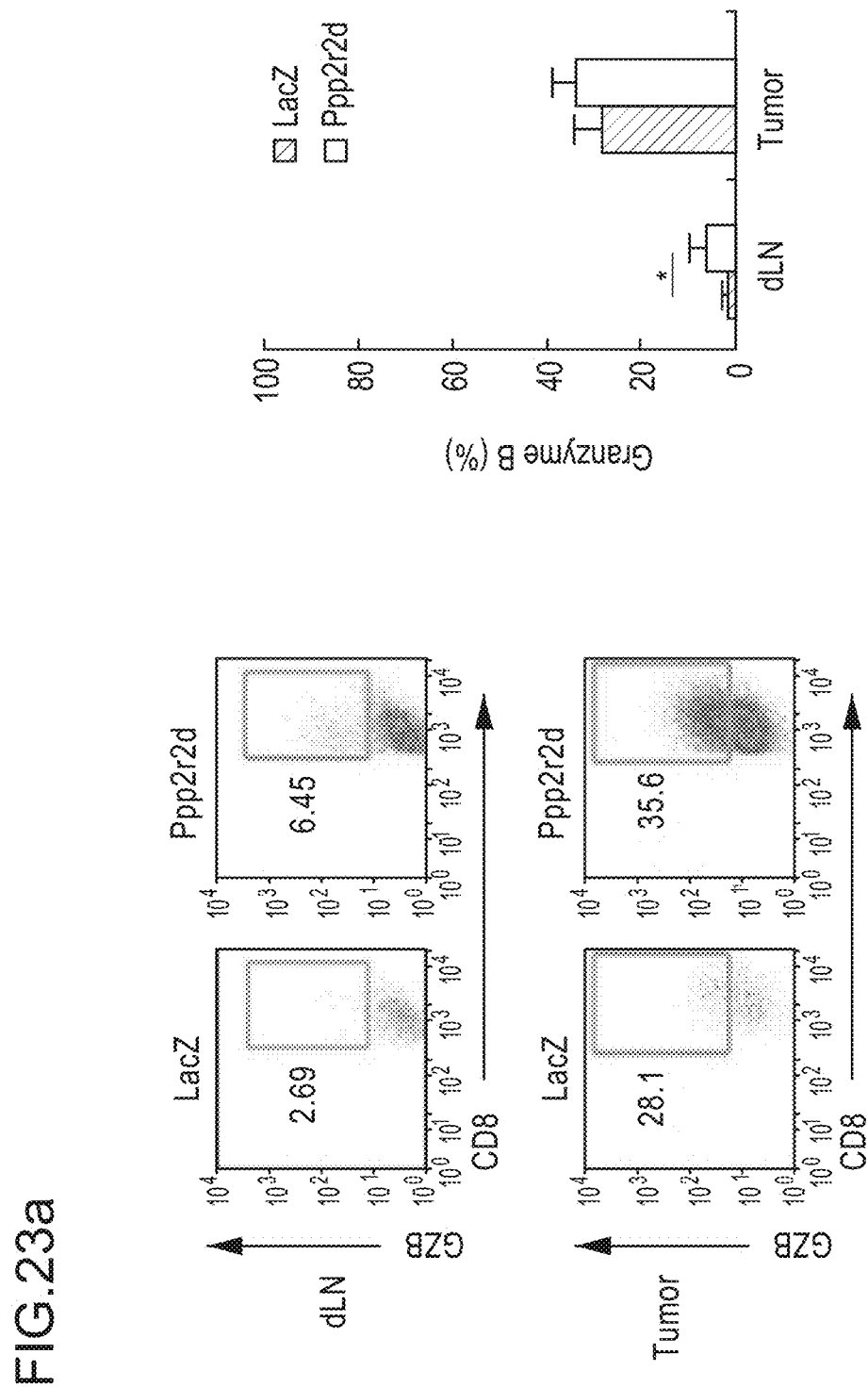
FIG. 23a is a set of graphs showing demonstrating intracellular staining for granzyme B by OT-I T cells in tumor-draining lymph nodes and tumors.
Figures 23B, 23C:
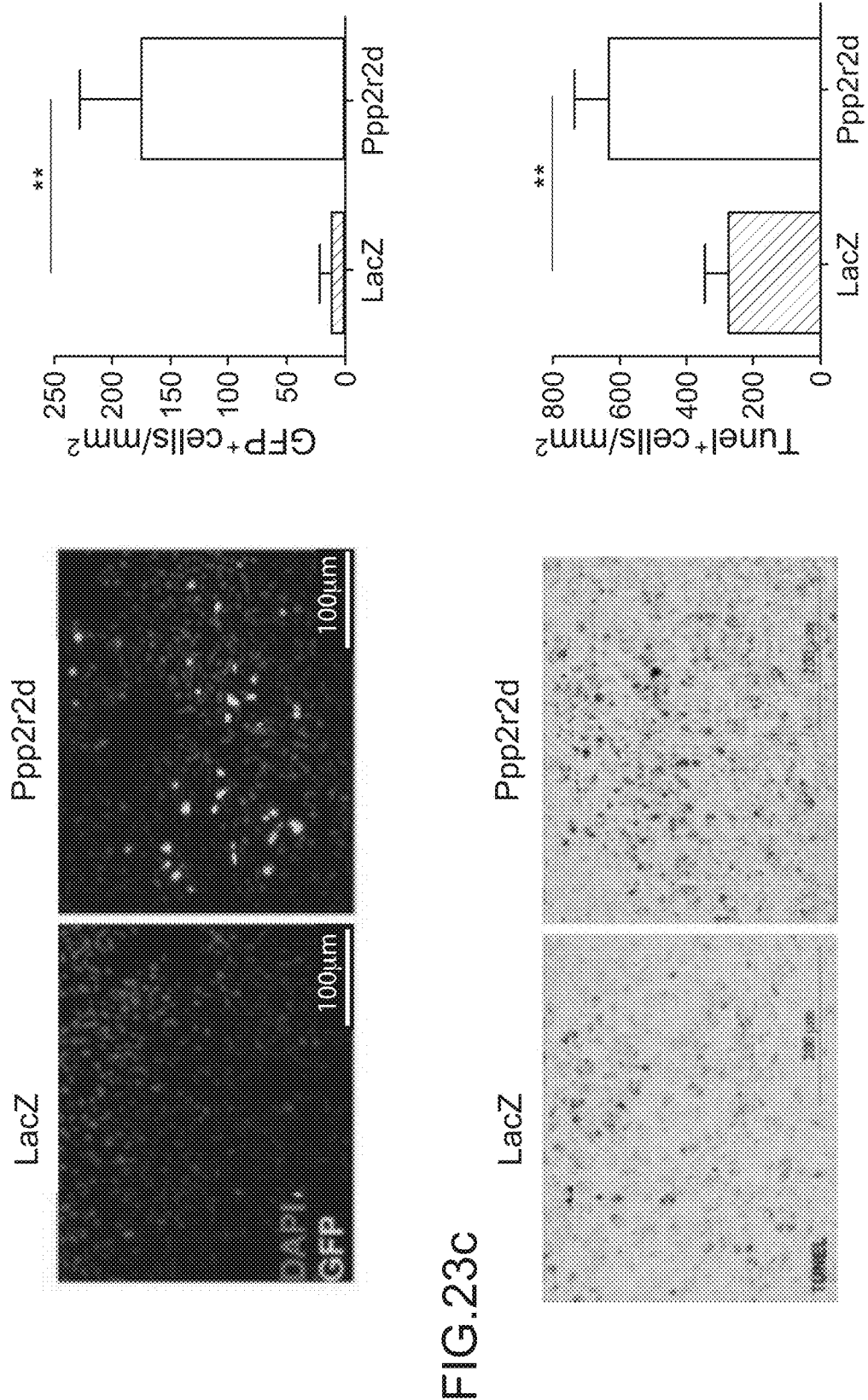
FIG. 23b is a pair of images and a graph demonstrating infiltration of shRNA-expressing T cells into tumors. OT-I T cells were transduced with LacZ or Ppp2r2d shRNA vectors encoding a GFP reporter and injected into B6-Ova tumor-bearing mice. After 7 days, tumors were excised and frozen sections stained with anti-GFP and DAPI to enumerate shRNAexpressing OT-I T cells in tumors.
FIG. 23c is a pair of images and a graph demonstrating TUNEL immunohistochemistry performed on tissue sections and apoptotic cells were quantified.
Figure 23D:
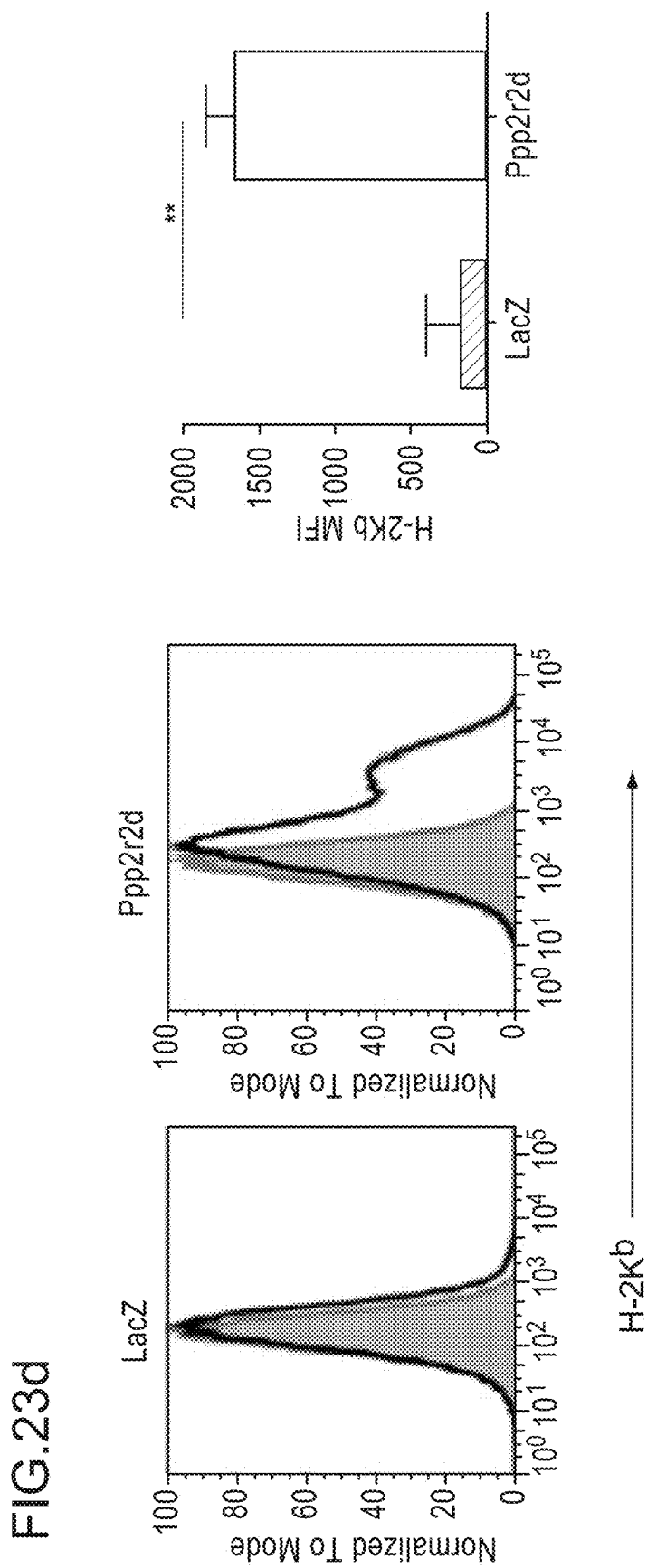
FIG. 23d is a set of graphs demonstrating MHC class I expression by tumor cells. Tumors were digested with collagenase and stained with CD45.2 and H-2Kb antibodies. FACS analysis for H-2Kb expression was performed by gating on CD45.2-negative melanoma cells. Data represent biological replicates (n=3), each value represents mean+/–s.d.

Ppp2r2d-silenced T cells acquired an effector phenotype in tumors (FIG. 22a) and >30% of the cells expressed granzyme B (FIG. 23a). Consistent with greatly increased numbers of such effector T cells in tumors (FIG. 23b), TUNEL staining demonstrated increased apoptosis in tumors when Ppp2r2d rather than LacZ shRNA expressing T cells were present (FIG. 23c). B16 melanomas are highly aggressive tumors in part because MHC class I expression is very low. Interestingly, Ppp2r2d but not LacZ shRNA-expressing T cells significantly increased MHC class I expression (H-2Kb) by tumor cells (FIG. 23d), possibly due to the observed increase in IFNγ secretion by T cells (FIG. 21a-c, FIG. 13e). A Ppp2r2d shRNA did not reduce expression of inhibitory PD-1 or LAG-3 receptors on tumor-infiltrating T cells, demonstrating that its mechanism of action is distinct from these known negative regulators of T cell function (FIG. 22b). This finding suggests combination approaches targeting these intracellular and cell surface molecules.

These results establish the feasibility of in vivo discovery of novel targets for immunotherapy in complex tissue microenvironments. The inventors have shown that it is possible to discover genes with differential action across tissues, as exemplified by T cell accumulation in tumors compared to secondary lymphoid organs. For genes with tissue-selective action, T cell accumulation and survival are likely to be under the control of the T cell receptor and therefore do not occur in tissues lacking presentation of a relevant antigen. Many variations of the approach presented here can be envisioned to investigate control of particular immune cell functions in vivo. For example, fluorescent reporters for expression of cytokines or cytotoxic molecules (granzyme B, perforin) could be integrated into our approach to discover genes that control critical T cell effector functions in tumors.

Targeting of key regulatory switches may offer new approaches to modify the activity of T cells in cancer and other pathologies. The efficacy of such T cell-based therapies could be enhanced by shRNA-mediated silencing of genes that inhibit T cell function in the tumor microenvironment.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Galon, J., et al. Type, density, and location of immune cells within human colorectal tumors predict clinical outcome. *Science* 313, 1960-1964 (2006).
2. Hamanishi, J., et al. Programmed cell death 1 ligand 1 and tumor-infiltrating CD8+T lymphocytes are prognostic factors of human ovarian cancer. *Proceedings of the National Academy of Sciences of the United States of America* 104, 3360-3365 (2007).
3. Mahmoud, S. M., et al. Tumor-Infiltrating CD8+ Lymphocytes Predict Clinical Outcome in Breast Cancer. *J Clin Oncol* 29, 1949-1955 (2011).
4. Topalian, S. L., et al. Safety, activity, and immune correlates of anti-PD-1 antibody in cancer. *The New England journal of medicine* 366, 2443-2454 (2012).
5. Brahmer, J. R., et al. Safety and activity of anti-PD-L1 antibody in patients with advanced cancer. *The New England journal of medicine* 366, 2455-2465 (2012).

6. Hodi, F. S., et al. Improved Survival with Ipilimumab in Patients with Metastatic Melanoma. *N Engl J Med* (2011).
7. Barr, F. A., Elliott, P. R. & Gruneberg, U. Protein phosphatases and the regulation of mitosis. *J Cell Sci* 124, 2323-2334 (2011).
8. Pages, F., et al. In situ cytotoxic and memory T cells predict outcome in patients with early-stage colorectal cancer. *J Clin Oncol* 27, 5944-5951 (2009).
9. Shiao, S. L., Ganesan, A. P., Rugo, H. S. & Coussens, L. M. Immune microenvironments in solid tumors: new targets for therapy. *Genes Dev* 25, 2559-2572 (2011).
10. Gabrilovich, D. I. & Nagaraj, S. Myeloid-derived suppressor cells as regulators of the immune system. *Nat Rev Immunol* 9, 162-174 (2009).
11. Topalian, S. L., Drake, C. G. & Pardoll, D. M. Targeting the PD-1/B7-H1(PD-L1) pathway to activate anti-tumor immunity. *Current opinion in immunology* 24, 207-212 (2012).
12. Westbrook, T. F., et al. A genetic screen for candidate tumor suppressors identifies REST. *Cell* 121, 837-848 (2005).
13. Luo, B., et al. Highly parallel identification of essential genes in cancer cells. *Proceedings of the National Academy of Sciences of the United States of America* 105, 20380-20385 (2008).
14. Zender, L., et al. An oncogenomics-based in vivo RNAi screen identifies tumor suppressors in liver cancer. *Cell* 135, 852-864 (2008).
15. Fidler, I. J. Biological behavior of malignant melanoma cells correlated to their survival in vivo. *Cancer research* 35, 218-224 (1975).
16. Hogquist, K. A., et al. T cell receptor antagonist peptides induce positive selection. *Cell* 76, 17-27 (1994).
17. Bellone, M., et al. Relevance of the tumor antigen in the validation of three vaccination strategies for melanoma. *Journal of immunology* 165, 2651-2656 (2000).
18. Overwijk, W. W., et al. Tumor regression and autoimmunity after reversal of a functionally tolerant state of self-reactive CD8+ T cells. *The Journal of experimental medicine* 198, 569-580 (2003).
19. Paolino, M. & Penninger, J. M. Cbl-b in T-cell activation. *Semin Immunopathol* 32, 137-148 (2010).
20. Zheng, Y., Zha, Y. & Gajewski, T. F. Molecular regulation of T-cell anergy. *EWBO Rep* 9, 50-55 (2008).
21. Doody, K. M., Bourdeau, A. & Tremblay, M. L. T-cell protein tyrosine phosphatase is a key regulator in immune cell signaling: lessons from the knockout mouse model and implications in human disease. *Immunological reviews* 228, 325-341 (2009).
22. Tamiya, T., Kashiwagi, I., Takahashi, R., Yasukawa, H. & Yoshimura, A. Suppressors of cytokine signaling (SOCS) proteins and JAK/STAT pathways: regulation of T-cell inflammation by SOCS1 and SOCS3. *Arterioscler Thromb Vasc Biol* 31, 980-985 (2011).
23. Muranski, P., et al. Tumor-specific Th17-polarized cells eradicate large established melanoma. *Blood* 112, 362-373 (2008).
24. Koller, B. H., Marrack, P., Kappler, J. W. & Smithies, O. Normal development of mice deficient in beta 2M, MHC class I proteins, and CD8+ T cells. *Science* 248, 1227-1230 (1990).
25. Mochida, S., Maslen, S. L., Skehel, M. & Hunt, T. Greatwall phosphorylates an inhibitor of protein phosphatase 2A that is essential for mitosis. *Science* 330, 1670-1673 (2010).
26. Chiang, C. W., et al. Protein phosphatase 2A dephosphorylation of phosphoserine 112 plays the gatekeeper role for BAD-mediated apoptosis. *Mol Cell Biol* 23, 6350-6362 (2003).
27. Turtle, C. J., Hudecek, M., Jensen, M. C. & Riddell, S. R. Engineered T cells for anti-cancer therapy. *Current opinion in immunology* 24, 633-639 (2012).
28. Restifo, N. P., Dudley, M. E. & Rosenberg, S. A. Adoptive immunotherapy for cancer: harnessing the T cell response. *Nature reviews. Immunology* 12, 269-281 (2012).
29. Bollard, C. M., Rooney, C. M. & Heslop, H. E. T-cell therapy in the treatment of post-transplant lymphoproliferative disease. *Nat Rev Clin Oncol* 9, 510-519 (2012).
30. Ashton, J. M., et al. Gene sets identified with oncogene cooperativity analysis regulate in vivo growth and survival of leukemia stem cells. *Cell Stem Cell* 11, 359-372 (2012).
31. Wherry, E. J., et al. Molecular signature of CD8+ T cell exhaustion during chronic viral infection. *Immunity* 27, 670-684 (2007).
32. Parish, I. A., et al. The molecular signature of CD8+ T cells undergoing deletional tolerance. *Blood* 113, 4575-4585 (2009).
33. Macian, F., et al. Transcriptional mechanisms underlying lymphocyte tolerance. *Cell* 109, 719-731 (2002).
34. Zha, Y., et al. T cell anergy is reversed by active Ras and is regulated by diacylglycerol kinase-alpha. *Nat Immunol* 7, 1166-1173 (2006).
35. Lopes, A. R., et al. Bim-mediated deletion of antigen-specific CD8 T cells in patients unable to control HBV infection. *The Journal of clinical investigation* 118, 1835-1845 (2008).
36. Kurella, S., et al. Transcriptional modulation of TCR, Notch and Wnt signaling pathways in SEB-anergized CD4+ T cells. *Genes Immun* 6, 596-608 (2005).
37. Xu, T., et al. Microarray analysis reveals differences in gene expression of circulating CD8(+) T cells in melanoma patients and healthy donors. *Cancer research* 64, 3661-3667 (2004).
38. Gorer, P. A. Studies in antibody response of mice to tumour inoculation. *Br. J Cancer* 4, 372-379 (1950).

What is claimed is:

1. An immunoresponsive cell having tumor specificity comprising a vector, the vector comprising a sequence encoding a shRNA,
wherein the shRNA comprises contiguous nucleotides complementary to a nucleic acid sequence of SEQ ID NO: 612, selected from a group consisting of SEQ ID NOS: 58-72 and 645-652.

2. The immunoresponsive cell of claim 1, wherein the immunoresponsive cell is selected from the group consisting of a tumor-infiltrating lymphocyte (TIL), a Natural Killer T cell (NKT), a cytotoxic T lymphocyte (CTL), and a CD4T cell.

3. The immunoresponsive cell of claim 1, wherein the immunoresponsive cell expresses a tumor-specific T-cell receptor.

4. The immunoresponsive cell of claim 1, wherein the immunoresponsive cell further comprises a vector encoding a chimeric antigen receptor (CAR),
wherein the CAR comprises an antigen binding domain, a transmembrane domain, and a stimulatory domain.

5. The immunoresponsive cell of claim 1, wherein the shRNA sequence reduces expression of Cblb.

6. The immunoresponsive cell of claim 4, wherein the CAR is directed to a tumor antigen comprising prostate-specific membrane antigen (PSMA).

7. The immunoresponsive cell of claim 4, wherein the CAR further comprises a costimulatory domain.

8. A composition comprising the immunoresponsive cell of claim 1 and a pharmaceutically acceptable carrier.

9. The composition of claim 8, further comprising an inhibitor of Cblb.

10. The immunoresponsive cell of claim 1, wherein the sequence encoding the shRNA comprises a first sequence comprising 15-25 nucleotides complementary to SEQ ID NO: 612 and a second sequence that is the reverse complement of the first sequence with one or no mismatches, and a third sequence of 5-9 nucleotides positioned between the first and second sequences.

11. The immunoresponsive cell of claim 10, wherein the first sequence comprises 19-25 nucleotides complementary to SEQ ID NO: 612.

12. A method of treating cancer associated with a regulatory subunit of Cblb in a subject, the method comprising administering to the subject an autologous T cell modified to express a tumor specific T-cell receptor or chimeric antigen receptor (CAR) and an shRNA,
wherein the shRNA comprises contiguous nucleotides complementary a nucleic acid sequence of SEQ ID NO: 612, selected from a group consisting of SEQ ID NOS: 58-72 and 645-652; and
wherein the CAR comprises an antigen binding domain, a transmembrane domain, a stimulatory domain, and a co-stimulatory domain.

13. The method of claim 12, wherein the autologous T cell is selected from the group consisting of a tumor-infiltrating lymphocyte (TIL), a Natural Killer T cell (NKT), a cytotoxic T lymphocyte (CTL), and a CD4T cell.

14. The method of claim 12, wherein the autologous T cell expresses a tumor-specific T-cell receptor.

15. The method of claim 12, wherein the CAR is directed to a tumor antigen comprising prostate-specific membrane antigen (PSMA).

16. A method of treating cancer associated with a regulatory subunit of Cblb in a subject in need thereof by silencing genes that inhibit T cell function comprising
administering to the subject an immunoresponsive cell comprising a vector, the vector encoding a tumor-specific T-cell receptor or a chimeric antigen receptor (CAR) and a shRNA sequence,
wherein the shRNA sequences comprise a sequence at least 12 contiguous nucleotides complementary to the mRNA sequence encoded by a nucleic acid sequence of SEQ ID NO: 612, selected from a group consisting of SEQ ID NOS: 58-72 and 645-652.

17. The method of claim 16, wherein the CAR comprises an antigen binding domain, a transmembrane domain, a stimulatory domain, and a co-stimulatory domain.

18. The method of claim 16, wherein the immunoresponsive cell is selected from the group consisting of a tumor-infiltrating lymphocyte (TIL), a Natural Killer T cell (NKT), a cytotoxic T lymphocyte (CTL), and a CD4T cell.

19. The method of claim 16, wherein the immunoresponsive cell expresses a tumor-specific T-cell receptor.

20. The method of claim 16, wherein the CAR is directed to a tumor antigen comprising prostate-specific membrane antigen (PSMA).

* * * * *

SEQUENCE LISTING

<160> NUMBER OF SEQ ID NOS: 681

<210> SEQ ID NO 1
<211> LENGTH: 21
<212> TYPE: DNA
<213> ORGANISM: Homo sapiens

<400> SEQUENCE: 1
cgaaaccgca ggcttatgat g                                          21

```
<210> SEQ ID NO 2
<211> LENGTH: 21
<212> TYPE: DNA
<213> ORGANISM: Homo sapiens

<400> SEQUENCE: 2
cagactgctc agacaacagt g                                         21

<210> SEQ ID NO 3
<211> LENGTH: 21
<212> TYPE: DNA
<213> ORGANISM: Homo sapiens

<400> SEQUENCE: 3
ccacaaggaa cacttcaaat a                                         21

<210> SEQ ID NO 4
<211> LENGTH: 21
<212> TYPE: DNA
<213> ORGANISM: Homo sapiens

<400> SEQUENCE: 4
agacctctac cggtcaagct a                                         21

<210> SEQ ID NO 5
<211> LENGTH: 21
<212> TYPE: DNA
<213> ORGANISM: Homo sapiens

<400> SEQUENCE: 5
atagaggcta cgagaactat g                                         21

<210> SEQ ID NO 6
<211> LENGTH: 21
<212> TYPE: DNA
<213> ORGANISM: Homo sapiens

<400> SEQUENCE: 6
ccagaacatc atacccgagt a                                         21

<210> SEQ ID NO 7
<211> LENGTH: 21
<212> TYPE: DNA
<213> ORGANISM: Homo sapiens

<400> SEQUENCE: 7
ttagatatga tgccgcactt g                                         21

<210> SEQ ID NO 8
<211> LENGTH: 21
<212> TYPE: DNA
<213> ORGANISM: Homo sapiens

<400> SEQUENCE: 8
cccacctgtg attatggata t                                         21

<210> SEQ ID NO 9
<211> LENGTH: 21
<212> TYPE: DNA
<213> ORGANISM: Homo sapiens

<400> SEQUENCE: 9
```

```
ggcgagaatc ctttcactga c                                              21

<210> SEQ ID NO 10
<211> LENGTH: 21
<212> TYPE: DNA
<213> ORGANISM: Homo sapiens

<400> SEQUENCE: 10
cgagaactat ggttatggct a                                              21

<210> SEQ ID NO 11
<211> LENGTH: 21
<212> TYPE: DNA
<213> ORGANISM: Homo sapiens

<400> SEQUENCE: 11
caaataccgg accttctatg a                                              21

<210> SEQ ID NO 12
<211> LENGTH: 21
<212> TYPE: DNA
<213> ORGANISM: Homo sapiens

<400> SEQUENCE: 12
gatatctgaa gggcgagaat c                                              21

<210> SEQ ID NO 13
<211> LENGTH: 21
<212> TYPE: DNA
<213> ORGANISM: Homo sapiens

<400> SEQUENCE: 13
accggtcaag ctatgactat g                                              21

<210> SEQ ID NO 14
<211> LENGTH: 21
<212> TYPE: DNA
<213> ORGANISM: Homo sapiens

<400> SEQUENCE: 14
ttggatttgg caatggcatg a                                              21

<210> SEQ ID NO 15
<211> LENGTH: 21
<212> TYPE: DNA
<213> ORGANISM: Homo sapiens

<400> SEQUENCE: 15
ccgaaaccac tttgcagtct a                                              21

<210> SEQ ID NO 16
<211> LENGTH: 21
<212> TYPE: DNA
<213> ORGANISM: Homo sapiens

<400> SEQUENCE: 16
acctagagga gaatcacttt a                                              21

<210> SEQ ID NO 17
<211> LENGTH: 21
<212> TYPE: DNA
<213> ORGANISM: Homo sapiens

<400> SEQUENCE: 17
```
gccttcatgg aagggatatt t                                              21

<210> SEQ ID NO 18
<211> LENGTH: 21
<212> TYPE: DNA
<213> ORGANISM: Homo sapiens

<400> SEQUENCE: 18
cgggcctgta taccggataa t                                              21

<210> SEQ ID NO 19
<211> LENGTH: 21
<212> TYPE: DNA
<213> ORGANISM: Homo sapiens

<400> SEQUENCE: 19
gtggagccac ctacgtgttt a                                              21

<210> SEQ ID NO 20
<211> LENGTH: 21
<212> TYPE: DNA
<213> ORGANISM: Homo sapiens

<400> SEQUENCE: 20
ggaatctgac ctggacgatg a                                              21

<210> SEQ ID NO 21
<211> LENGTH: 21
<212> TYPE: DNA
<213> ORGANISM: Homo sapiens

<400> SEQUENCE: 21
cttcgttgta ccctcgctct t                                              21

<210> SEQ ID NO 22
<211> LENGTH: 21
<212> TYPE: DNA
<213> ORGANISM: Homo sapiens

<400> SEQUENCE: 22
gaagggatat ttacctctaa a                                              21

<210> SEQ ID NO 23
<211> LENGTH: 21
<212> TYPE: DNA
<213> ORGANISM: Homo sapiens

<400> SEQUENCE: 23
ccgggatatt gctgctagaa a                                              21

<210> SEQ ID NO 24
<211> LENGTH: 21
<212> TYPE: DNA
<213> ORGANISM: Homo sapiens

<400> SEQUENCE: 24
gcatcgcatt ggaggctata a                                              21

<210> SEQ ID NO 25
<211> LENGTH: 21
<212> TYPE: DNA
<213> ORGANISM: Homo sapiens

```
<400> SEQUENCE: 25
gggcctgtat accggataat g                                              21

<210> SEQ ID NO 26
<211> LENGTH: 21
<212> TYPE: DNA
<213> ORGANISM: Homo sapiens

<400> SEQUENCE: 26
cggaggatat ataggtggca a                                              21

<210> SEQ ID NO 27
<211> LENGTH: 21
<212> TYPE: DNA
<213> ORGANISM: Homo sapiens

<400> SEQUENCE: 27
atcgaatacg gtccagtagt a                                              21

<210> SEQ ID NO 28
<211> LENGTH: 21
<212> TYPE: DNA
<213> ORGANISM: Homo sapiens

<400> SEQUENCE: 28
tgcttccgcg tagtcagaaa t                                              21

<210> SEQ ID NO 29
<211> LENGTH: 21
<212> TYPE: DNA
<213> ORGANISM: Homo sapiens

<400> SEQUENCE: 29
cctgcggcaa tgtcaactat g                                              21

<210> SEQ ID NO 30
<211> LENGTH: 21
<212> TYPE: DNA
<213> ORGANISM: Homo sapiens

<400> SEQUENCE: 30
cccgaacgtc aactatggtt a                                              21

<210> SEQ ID NO 31
<211> LENGTH: 21
<212> TYPE: DNA
<213> ORGANISM: Homo sapiens

<400> SEQUENCE: 31
ggcgaggaga cgattcttga a                                              21

<210> SEQ ID NO 32
<211> LENGTH: 21
<212> TYPE: DNA
<213> ORGANISM: Homo sapiens

<400> SEQUENCE: 32
tggtacatat cctcgtaaat t                                              21

<210> SEQ ID NO 33
<211> LENGTH: 21
<212> TYPE: DNA
<213> ORGANISM: Homo sapiens
```

```
<400> SEQUENCE: 33
attgcaatca gtatatcatt c                                              21

<210> SEQ ID NO 34
<211> LENGTH: 21
<212> TYPE: DNA
<213> ORGANISM: Homo sapiens

<400> SEQUENCE: 34
gatcatgaac gtaaccataa a                                              21

<210> SEQ ID NO 35
<211> LENGTH: 21
<212> TYPE: DNA
<213> ORGANISM: Homo sapiens

<400> SEQUENCE: 35
tgataatagc agcaactaaa t                                              21

<210> SEQ ID NO 36
<211> LENGTH: 21
<212> TYPE: DNA
<213> ORGANISM: Homo sapiens

<400> SEQUENCE: 36
agcatgactg gagaggttta a                                              21

<210> SEQ ID NO 37
<211> LENGTH: 21
<212> TYPE: DNA
<213> ORGANISM: Homo sapiens

<400> SEQUENCE: 37
tgatagtcag aatcgaatta t                                              21

<210> SEQ ID NO 38
<211> LENGTH: 21
<212> TYPE: DNA
<213> ORGANISM: Homo sapiens

<400> SEQUENCE: 38
gaactggttc atgggtatat a                                              21

<210> SEQ ID NO 39
<211> LENGTH: 21
<212> TYPE: DNA
<213> ORGANISM: Homo sapiens

<400> SEQUENCE: 39
gcaagctcta agaggagtat t                                              21

<210> SEQ ID NO 40
<211> LENGTH: 21
<212> TYPE: DNA
<213> ORGANISM: Homo sapiens

<400> SEQUENCE: 40
cctgatcctt tgattccata t                                              21

<210> SEQ ID NO 41
<211> LENGTH: 21
<212> TYPE: DNA
```

<213> ORGANISM: Homo sapiens

<400> SEQUENCE: 41
acagatcctc ttggtattat a                                              21

<210> SEQ ID NO 42
<211> LENGTH: 21
<212> TYPE: DNA
<213> ORGANISM: Homo sapiens

<400> SEQUENCE: 42
gcacgattta atgtcaacat t                                              21

<210> SEQ ID NO 43
<211> LENGTH: 21
<212> TYPE: DNA
<213> ORGANISM: Homo sapiens

<400> SEQUENCE: 43
ctcagtccca ctacagtaat g                                              21

<210> SEQ ID NO 44
<211> LENGTH: 21
<212> TYPE: DNA
<213> ORGANISM: Homo sapiens

<400> SEQUENCE: 44
tgaccacatc cggatgcata a                                              21

<210> SEQ ID NO 45
<211> LENGTH: 21
<212> TYPE: DNA
<213> ORGANISM: Homo sapiens

<400> SEQUENCE: 45
gcctcaccac caatgagtat g                                              21

<210> SEQ ID NO 46
<211> LENGTH: 21
<212> TYPE: DNA
<213> ORGANISM: Homo sapiens

<400> SEQUENCE: 46
tgagaaatga cacaaataga g                                              21

<210> SEQ ID NO 47
<211> LENGTH: 21
<212> TYPE: DNA
<213> ORGANISM: Homo sapiens

<400> SEQUENCE: 47
tgcaagagtc agggctgaaa t                                              21

<210> SEQ ID NO 48
<211> LENGTH: 21
<212> TYPE: DNA
<213> ORGANISM: Homo sapiens

<400> SEQUENCE: 48
ggaagctgtc atcgtgctac t                                              21

<210> SEQ ID NO 49
<211> LENGTH: 21

```
<212> TYPE: DNA
<213> ORGANISM: Homo sapiens

<400> SEQUENCE: 49
gcataagatt ctgcaagagt c                                          21

<210> SEQ ID NO 50
<211> LENGTH: 21
<212> TYPE: DNA
<213> ORGANISM: Homo sapiens

<400> SEQUENCE: 50
cctcagtccc actacagtaa t                                          21

<210> SEQ ID NO 51
<211> LENGTH: 21
<212> TYPE: DNA
<213> ORGANISM: Homo sapiens

<400> SEQUENCE: 51
tcgagggtca tatccaagca t                                          21

<210> SEQ ID NO 52
<211> LENGTH: 21
<212> TYPE: DNA
<213> ORGANISM: Homo sapiens

<400> SEQUENCE: 52
gaacatcgtg acagccatga a                                          21

<210> SEQ ID NO 53
<211> LENGTH: 21
<212> TYPE: DNA
<213> ORGANISM: Homo sapiens

<400> SEQUENCE: 53
ccaatgagta tgacggacac a                                          21

<210> SEQ ID NO 54
<211> LENGTH: 21
<212> TYPE: DNA
<213> ORGANISM: Homo sapiens

<400> SEQUENCE: 54
gagggtcatg catcctgaga a                                          21

<210> SEQ ID NO 55
<211> LENGTH: 21
<212> TYPE: DNA
<213> ORGANISM: Homo sapiens

<400> SEQUENCE: 55
taggagacca accactaact g                                          21

<210> SEQ ID NO 56
<211> LENGTH: 21
<212> TYPE: DNA
<213> ORGANISM: Homo sapiens

<400> SEQUENCE: 56
gctgaaatac gtggcagtga t                                          21

<210> SEQ ID NO 57
```

```
<211> LENGTH: 21
<212> TYPE: DNA
<213> ORGANISM: Homo sapiens

<400> SEQUENCE: 57
cggatgcata agattctgca a                                          21

<210> SEQ ID NO 58
<211> LENGTH: 21
<212> TYPE: DNA
<213> ORGANISM: Homo sapiens

<400> SEQUENCE: 58
tctacatcga tagtctcatg a                                          21

<210> SEQ ID NO 59
<211> LENGTH: 21
<212> TYPE: DNA
<213> ORGANISM: Homo sapiens

<400> SEQUENCE: 59
ctacacctca cgatcatata a                                          21

<210> SEQ ID NO 60
<211> LENGTH: 21
<212> TYPE: DNA
<213> ORGANISM: Homo sapiens

<400> SEQUENCE: 60
tgagcgagaa tgagtacttt a                                          21

<210> SEQ ID NO 61
<211> LENGTH: 21
<212> TYPE: DNA
<213> ORGANISM: Homo sapiens

<400> SEQUENCE: 61
atcgaacatc ccagatttag g                                          21

<210> SEQ ID NO 62
<211> LENGTH: 21
<212> TYPE: DNA
<213> ORGANISM: Homo sapiens

<400> SEQUENCE: 62
taaagtgtac tggtccatta g                                          21

<210> SEQ ID NO 63
<211> LENGTH: 21
<212> TYPE: DNA
<213> ORGANISM: Homo sapiens

<400> SEQUENCE: 63
cttgtactcc agtaccataa t                                          21

<210> SEQ ID NO 64
<211> LENGTH: 21
<212> TYPE: DNA
<213> ORGANISM: Homo sapiens

<400> SEQUENCE: 64
gtatgagaca gaaggactga g                                          21
```

```
<210> SEQ ID NO 65
<211> LENGTH: 21
<212> TYPE: DNA
<213> ORGANISM: Homo sapiens

<400> SEQUENCE: 65
ccagatttag gcatctattt g                                              21

<210> SEQ ID NO 66
<211> LENGTH: 21
<212> TYPE: DNA
<213> ORGANISM: Homo sapiens

<400> SEQUENCE: 66
tcagcacttg agacttatat t                                              21

<210> SEQ ID NO 67
<211> LENGTH: 21
<212> TYPE: DNA
<213> ORGANISM: Homo sapiens

<400> SEQUENCE: 67
tacacctcac gatcatataa a                                              21

<210> SEQ ID NO 68
<211> LENGTH: 21
<212> TYPE: DNA
<213> ORGANISM: Homo sapiens

<400> SEQUENCE: 68
aacacagacg ccatgatttg c                                              21

<210> SEQ ID NO 69
<211> LENGTH: 21
<212> TYPE: DNA
<213> ORGANISM: Homo sapiens

<400> SEQUENCE: 69
aagatgtcaa gattgagcct t                                              21

<210> SEQ ID NO 70
<211> LENGTH: 21
<212> TYPE: DNA
<213> ORGANISM: Homo sapiens

<400> SEQUENCE: 70
ccctgattta accggattat g                                              21

<210> SEQ ID NO 71
<211> LENGTH: 21
<212> TYPE: DNA
<213> ORGANISM: Homo sapiens

<400> SEQUENCE: 71
agccaggtcc aattccattt c                                              21

<210> SEQ ID NO 72
<211> LENGTH: 21
<212> TYPE: DNA
<213> ORGANISM: Homo sapiens

<400> SEQUENCE: 72
cgagcgatcc ggctctttaa a                                              21
```

```
<210> SEQ ID NO 73
<211> LENGTH: 21
<212> TYPE: DNA
<213> ORGANISM: Homo sapiens

<400> SEQUENCE: 73
cttggtgaag ttcgtgcgat c                                              21

<210> SEQ ID NO 74
<211> LENGTH: 21
<212> TYPE: DNA
<213> ORGANISM: Homo sapiens

<400> SEQUENCE: 74
cgctctggct ttcgtgaaca t                                              21

<210> SEQ ID NO 75
<211> LENGTH: 21
<212> TYPE: DNA
<213> ORGANISM: Homo sapiens

<400> SEQUENCE: 75
gatgatgatg ggcaacgttc a                                              21

<210> SEQ ID NO 76
<211> LENGTH: 21
<212> TYPE: DNA
<213> ORGANISM: Homo sapiens

<400> SEQUENCE: 76
tcccaagagc agagctaaat c                                              21

<210> SEQ ID NO 77
<211> LENGTH: 21
<212> TYPE: DNA
<213> ORGANISM: Homo sapiens

<400> SEQUENCE: 77
tcttggtgaa gttcgtgcga t                                              21

<210> SEQ ID NO 78
<211> LENGTH: 21
<212> TYPE: DNA
<213> ORGANISM: Homo sapiens

<400> SEQUENCE: 78
acgggcatag cttcagctca a                                              21

<210> SEQ ID NO 79
<211> LENGTH: 21
<212> TYPE: DNA
<213> ORGANISM: Homo sapiens

<400> SEQUENCE: 79
gctcggctgg atgtgcgcga t                                              21

<210> SEQ ID NO 80
<211> LENGTH: 21
<212> TYPE: DNA
<213> ORGANISM: Homo sapiens

<400> SEQUENCE: 80
ttgaggctag agaggatctt g                                              21
```

<210> SEQ ID NO 81
<211> LENGTH: 21
<212> TYPE: DNA
<213> ORGANISM: Homo sapiens

<400> SEQUENCE: 81
catcaagaca tcgtgcgata t                                              21

<210> SEQ ID NO 82
<211> LENGTH: 21
<212> TYPE: DNA
<213> ORGANISM: Homo sapiens

<400> SEQUENCE: 82
gtgaacatgt tgttgaggct a                                              21

<210> SEQ ID NO 83
<211> LENGTH: 21
<212> TYPE: DNA
<213> ORGANISM: Homo sapiens

<400> SEQUENCE: 83
gtctttgtgt accgctggga a                                              21

<210> SEQ ID NO 84
<211> LENGTH: 21
<212> TYPE: DNA
<213> ORGANISM: Homo sapiens

<400> SEQUENCE: 84
ctagcgatgc tagcgtgtct a                                              21

<210> SEQ ID NO 85
<211> LENGTH: 21
<212> TYPE: DNA
<213> ORGANISM: Homo sapiens

<400> SEQUENCE: 85
gtgatgatga tgggcaacgt t                                              21

<210> SEQ ID NO 86
<211> LENGTH: 21
<212> TYPE: DNA
<213> ORGANISM: Homo sapiens

<400> SEQUENCE: 86
gctcaactac ggtgcagatt c                                              21

<210> SEQ ID NO 87
<211> LENGTH: 21
<212> TYPE: DNA
<213> ORGANISM: Homo sapiens

<400> SEQUENCE: 87
tcaagacatc gtgcgatatt t                                              21

<210> SEQ ID NO 88
<211> LENGTH: 21
<212> TYPE: DNA
<213> ORGANISM: Homo sapiens

<400> SEQUENCE: 88

```
gagctaagta aggtggtata t                                              21

<210> SEQ ID NO 89
<211> LENGTH: 21
<212> TYPE: DNA
<213> ORGANISM: Homo sapiens

<400> SEQUENCE: 89
gcgatgtact gaaggtcttt g                                              21

<210> SEQ ID NO 90
<211> LENGTH: 21
<212> TYPE: DNA
<213> ORGANISM: Homo sapiens

<400> SEQUENCE: 90
tcagtgatgt gtactgctac t                                              21

<210> SEQ ID NO 91
<211> LENGTH: 21
<212> TYPE: DNA
<213> ORGANISM: Homo sapiens

<400> SEQUENCE: 91
gtatatctcg accgatggtt c                                              21

<210> SEQ ID NO 92
<211> LENGTH: 21
<212> TYPE: DNA
<213> ORGANISM: Homo sapiens

<400> SEQUENCE: 92
tgatgcgagt ggccgaatat c                                              21

<210> SEQ ID NO 93
<211> LENGTH: 21
<212> TYPE: DNA
<213> ORGANISM: Homo sapiens

<400> SEQUENCE: 93
cctaggattt gaacaattca t                                              21

<210> SEQ ID NO 94
<211> LENGTH: 21
<212> TYPE: DNA
<213> ORGANISM: Homo sapiens

<400> SEQUENCE: 94
aaagattctc aaggatatag a                                              21

<210> SEQ ID NO 95
<211> LENGTH: 21
<212> TYPE: DNA
<213> ORGANISM: Homo sapiens

<400> SEQUENCE: 95
gagggatgtt ccatcacctt c                                              21

<210> SEQ ID NO 96
<211> LENGTH: 21
<212> TYPE: DNA
<213> ORGANISM: Homo sapiens

<400> SEQUENCE: 96
```

| | |
|---|---|
| tacagacatc cttacacaac c | 21 |

<210> SEQ ID NO 97
<211> LENGTH: 21
<212> TYPE: DNA
<213> ORGANISM: Homo sapiens

<400> SEQUENCE: 97

| | |
|---|---|
| gccgaatatc tagactggga t | 21 |

<210> SEQ ID NO 98
<211> LENGTH: 21
<212> TYPE: DNA
<213> ORGANISM: Homo sapiens

<400> SEQUENCE: 98

| | |
|---|---|
| cggctggaag tggtaggaat a | 21 |

<210> SEQ ID NO 99
<211> LENGTH: 21
<212> TYPE: DNA
<213> ORGANISM: Homo sapiens

<400> SEQUENCE: 99

| | |
|---|---|
| gttcctcagt tccggatatt g | 21 |

<210> SEQ ID NO 100
<211> LENGTH: 21
<212> TYPE: DNA
<213> ORGANISM: Homo sapiens

<400> SEQUENCE: 100

| | |
|---|---|
| cctgagctgt aacttctgta a | 21 |

<210> SEQ ID NO 101
<211> LENGTH: 21
<212> TYPE: DNA
<213> ORGANISM: Homo sapiens

<400> SEQUENCE: 101

| | |
|---|---|
| tgcgaacaga gcattagcct t | 21 |

<210> SEQ ID NO 102
<211> LENGTH: 21
<212> TYPE: DNA
<213> ORGANISM: Homo sapiens

<400> SEQUENCE: 102

| | |
|---|---|
| tgttcctcag ttccggatat t | 21 |

<210> SEQ ID NO 103
<211> LENGTH: 21
<212> TYPE: DNA
<213> ORGANISM: Homo sapiens

<400> SEQUENCE: 103

| | |
|---|---|
| caccttccac agcaaggaga t | 21 |

<210> SEQ ID NO 104
<211> LENGTH: 21
<212> TYPE: DNA
<213> ORGANISM: Homo sapiens

```
<400> SEQUENCE: 104
atcgtggtgc atacccaatg c                                              21

<210> SEQ ID NO 105
<211> LENGTH: 21
<212> TYPE: DNA
<213> ORGANISM: Homo sapiens

<400> SEQUENCE: 105
cctggatgtc tttaacaact a                                              21

<210> SEQ ID NO 106
<211> LENGTH: 21
<212> TYPE: DNA
<213> ORGANISM: Homo sapiens

<400> SEQUENCE: 106
cgagtagtgt gtgacggaat g                                              21

<210> SEQ ID NO 107
<211> LENGTH: 21
<212> TYPE: DNA
<213> ORGANISM: Homo sapiens

<400> SEQUENCE: 107
cacatctggt ttgagaccaa c                                              21

<210> SEQ ID NO 108
<211> LENGTH: 21
<212> TYPE: DNA
<213> ORGANISM: Homo sapiens

<400> SEQUENCE: 108
gagaagttca acagccgctt t                                              21

<210> SEQ ID NO 109
<211> LENGTH: 21
<212> TYPE: DNA
<213> ORGANISM: Homo sapiens

<400> SEQUENCE: 109
actgtgcagg caccatgccc t                                              21

<210> SEQ ID NO 110
<211> LENGTH: 21
<212> TYPE: DNA
<213> ORGANISM: Homo sapiens

<400> SEQUENCE: 110
agaagctgtt cagatctagg g                                              21

<210> SEQ ID NO 111
<211> LENGTH: 21
<212> TYPE: DNA
<213> ORGANISM: Homo sapiens

<400> SEQUENCE: 111
gtggacttca aagaattcat t                                              21

<210> SEQ ID NO 112
<211> LENGTH: 21
<212> TYPE: DNA
<213> ORGANISM: Homo sapiens
```

<400> SEQUENCE: 112
actacgaggc tctacattat g                                            21

<210> SEQ ID NO 113
<211> LENGTH: 21
<212> TYPE: DNA
<213> ORGANISM: Homo sapiens

<400> SEQUENCE: 113
agtacataat ttgaggattc t                                            21

<210> SEQ ID NO 114
<211> LENGTH: 21
<212> TYPE: DNA
<213> ORGANISM: Homo sapiens

<400> SEQUENCE: 114
cgaggctcta cattatgaca a                                            21

<210> SEQ ID NO 115
<211> LENGTH: 21
<212> TYPE: DNA
<213> ORGANISM: Homo sapiens

<400> SEQUENCE: 115
cctgtaagat cgtggtgcat a                                            21

<210> SEQ ID NO 116
<211> LENGTH: 21
<212> TYPE: DNA
<213> ORGANISM: Homo sapiens

<400> SEQUENCE: 116
gaaaccgcag tgcatcgtct t                                            21

<210> SEQ ID NO 117
<211> LENGTH: 21
<212> TYPE: DNA
<213> ORGANISM: Homo sapiens

<400> SEQUENCE: 117
cagcatcacg gattcgaatt g                                            21

<210> SEQ ID NO 118
<211> LENGTH: 21
<212> TYPE: DNA
<213> ORGANISM: Homo sapiens

<400> SEQUENCE: 118
aggatccttc agcattctta t                                            21

<210> SEQ ID NO 119
<211> LENGTH: 20
<212> TYPE: DNA
<213> ORGANISM: Homo sapiens

<400> SEQUENCE: 119
agctctggct gacacaccag                                              20

<210> SEQ ID NO 120
<211> LENGTH: 21
<212> TYPE: DNA

<213> ORGANISM: Homo sapiens

<400> SEQUENCE: 120
ccaggatcct tcagcattct t                                    21

<210> SEQ ID NO 121
<211> LENGTH: 21
<212> TYPE: DNA
<213> ORGANISM: Homo sapiens

<400> SEQUENCE: 121
gctgtatatt tctgcctatt a                                    21

<210> SEQ ID NO 122
<211> LENGTH: 21
<212> TYPE: DNA
<213> ORGANISM: Homo sapiens

<400> SEQUENCE: 122
actattgtgg ccgcaagttt g                                    21

<210> SEQ ID NO 123
<211> LENGTH: 21
<212> TYPE: DNA
<213> ORGANISM: Homo sapiens

<400> SEQUENCE: 123
agcgggtact accgtttatt t                                    21

<210> SEQ ID NO 124
<211> LENGTH: 21
<212> TYPE: DNA
<213> ORGANISM: Homo sapiens

<400> SEQUENCE: 124
ctgtatattt ctgcctatta a                                    21

<210> SEQ ID NO 125
<211> LENGTH: 21
<212> TYPE: DNA
<213> ORGANISM: Homo sapiens

<400> SEQUENCE: 125
gtgaccacct tactactcac a                                    21

<210> SEQ ID NO 126
<211> LENGTH: 21
<212> TYPE: DNA
<213> ORGANISM: Homo sapiens

<400> SEQUENCE: 126
gtttgccagg agtgacgaaa g                                    21

<210> SEQ ID NO 127
<211> LENGTH: 21
<212> TYPE: DNA
<213> ORGANISM: Homo sapiens

<400> SEQUENCE: 127
ccttcaccta catgggcaaa t                                    21

<210> SEQ ID NO 128
<211> LENGTH: 21

```
<212> TYPE: DNA
<213> ORGANISM: Homo sapiens

<400> SEQUENCE: 128
ccagaaggta tcatcaatat t                                       21

<210> SEQ ID NO 129
<211> LENGTH: 21
<212> TYPE: DNA
<213> ORGANISM: Homo sapiens

<400> SEQUENCE: 129
ccactctcta ccatccgtaa t                                       21

<210> SEQ ID NO 130
<211> LENGTH: 21
<212> TYPE: DNA
<213> ORGANISM: Homo sapiens

<400> SEQUENCE: 130
ccgtgccaga gagatccaca c                                       21

<210> SEQ ID NO 131
<211> LENGTH: 21
<212> TYPE: DNA
<213> ORGANISM: Homo sapiens

<400> SEQUENCE: 131
caataggttg ggagttgctg a                                       21

<210> SEQ ID NO 132
<211> LENGTH: 21
<212> TYPE: DNA
<213> ORGANISM: Homo sapiens

<400> SEQUENCE: 132
actctctacc atccgtaatt t                                       21

<210> SEQ ID NO 133
<211> LENGTH: 21
<212> TYPE: DNA
<213> ORGANISM: Homo sapiens

<400> SEQUENCE: 133
ccatgagttc atctggaaca a                                       21

<210> SEQ ID NO 134
<211> LENGTH: 21
<212> TYPE: DNA
<213> ORGANISM: Homo sapiens

<400> SEQUENCE: 134
catagctcct tctcctgaaa g                                       21

<210> SEQ ID NO 135
<211> LENGTH: 21
<212> TYPE: DNA
<213> ORGANISM: Homo sapiens

<400> SEQUENCE: 135
gatgactgca attacgctat c                                       21

<210> SEQ ID NO 136
```

```
<211> LENGTH: 21
<212> TYPE: DNA
<213> ORGANISM: Homo sapiens

<400> SEQUENCE: 136
gtcgccattt atgtcggtag t                                              21

<210> SEQ ID NO 137
<211> LENGTH: 21
<212> TYPE: DNA
<213> ORGANISM: Homo sapiens

<400> SEQUENCE: 137
tggaaacaac tactcccata a                                              21

<210> SEQ ID NO 138
<211> LENGTH: 21
<212> TYPE: DNA
<213> ORGANISM: Homo sapiens

<400> SEQUENCE: 138
gtgacccatc tgcactaatt t                                              21

<210> SEQ ID NO 139
<211> LENGTH: 21
<212> TYPE: DNA
<213> ORGANISM: Homo sapiens

<400> SEQUENCE: 139
gcatgatggc aaccattatg t                                              21

<210> SEQ ID NO 140
<211> LENGTH: 21
<212> TYPE: DNA
<213> ORGANISM: Homo sapiens

<400> SEQUENCE: 140
atcccgatat ctaacagatt t                                              21

<210> SEQ ID NO 141
<211> LENGTH: 21
<212> TYPE: DNA
<213> ORGANISM: Homo sapiens

<400> SEQUENCE: 141
tgtcgccgat gggatagtga t                                              21

<210> SEQ ID NO 142
<211> LENGTH: 21
<212> TYPE: DNA
<213> ORGANISM: Homo sapiens

<400> SEQUENCE: 142
gccactttga acttcggtat a                                              21

<210> SEQ ID NO 143
<211> LENGTH: 21
<212> TYPE: DNA
<213> ORGANISM: Homo sapiens

<400> SEQUENCE: 143
ccatacgata acggttacta t                                              21
```

```
<210> SEQ ID NO 144
<211> LENGTH: 21
<212> TYPE: DNA
<213> ORGANISM: Homo sapiens

<400> SEQUENCE: 144
cctctactgt tcactcagaa a                                             21

<210> SEQ ID NO 145
<211> LENGTH: 21
<212> TYPE: DNA
<213> ORGANISM: Homo sapiens

<400> SEQUENCE: 145
catacgataa cggttactat c                                             21

<210> SEQ ID NO 146
<211> LENGTH: 21
<212> TYPE: DNA
<213> ORGANISM: Homo sapiens

<400> SEQUENCE: 146
cgtgacccat ctgcactaat t                                             21

<210> SEQ ID NO 147
<211> LENGTH: 21
<212> TYPE: DNA
<213> ORGANISM: Homo sapiens

<400> SEQUENCE: 147
gcctgtttga tgatacaagt t                                             21

<210> SEQ ID NO 148
<211> LENGTH: 21
<212> TYPE: DNA
<213> ORGANISM: Homo sapiens

<400> SEQUENCE: 148
gaatgtaagt gagctctatg g                                             21

<210> SEQ ID NO 149
<211> LENGTH: 21
<212> TYPE: DNA
<213> ORGANISM: Homo sapiens

<400> SEQUENCE: 149
ccgaactgat accaacatcc a                                             21

<210> SEQ ID NO 150
<211> LENGTH: 21
<212> TYPE: DNA
<213> ORGANISM: Homo sapiens

<400> SEQUENCE: 150
cccatgcttt aacccaggat a                                             21

<210> SEQ ID NO 151
<211> LENGTH: 21
<212> TYPE: DNA
<213> ORGANISM: Homo sapiens

<400> SEQUENCE: 151
ccttggtttc acctctatct t                                             21
```

<210> SEQ ID NO 152
<211> LENGTH: 21
<212> TYPE: DNA
<213> ORGANISM: Homo sapiens

<400> SEQUENCE: 152
ccaaggacat tcaggtttca a                                              21

<210> SEQ ID NO 153
<211> LENGTH: 21
<212> TYPE: DNA
<213> ORGANISM: Homo sapiens

<400> SEQUENCE: 153
caggaacaga gttggctaag c                                              21

<210> SEQ ID NO 154
<211> LENGTH: 21
<212> TYPE: DNA
<213> ORGANISM: Homo sapiens

<400> SEQUENCE: 154
ttaacccagg atacgagaag g                                              21

<210> SEQ ID NO 155
<211> LENGTH: 21
<212> TYPE: DNA
<213> ORGANISM: Homo sapiens

<400> SEQUENCE: 155
actatctcag ccatggcttt g                                              21

<210> SEQ ID NO 156
<211> LENGTH: 21
<212> TYPE: DNA
<213> ORGANISM: Homo sapiens

<400> SEQUENCE: 156
ttcaagtggt ggcgtcctta a                                              21

<210> SEQ ID NO 157
<211> LENGTH: 21
<212> TYPE: DNA
<213> ORGANISM: Homo sapiens

<400> SEQUENCE: 157
gactttgggc tacatgctga a                                              21

<210> SEQ ID NO 158
<211> LENGTH: 21
<212> TYPE: DNA
<213> ORGANISM: Homo sapiens

<400> SEQUENCE: 158
ggcatgcgct tgcttagaat g                                              21

<210> SEQ ID NO 159
<211> LENGTH: 21
<212> TYPE: DNA
<213> ORGANISM: Homo sapiens

<400> SEQUENCE: 159
gcactggaga ctacgaacag t                                              21

<210> SEQ ID NO 160
<211> LENGTH: 21
<212> TYPE: DNA
<213> ORGANISM: Homo sapiens

<400> SEQUENCE: 160
gtggattact attaactatc t                                              21

<210> SEQ ID NO 161
<211> LENGTH: 21
<212> TYPE: DNA
<213> ORGANISM: Homo sapiens

<400> SEQUENCE: 161
gctcctggga acagattcat t                                              21

<210> SEQ ID NO 162
<211> LENGTH: 21
<212> TYPE: DNA
<213> ORGANISM: Homo sapiens

<400> SEQUENCE: 162
accatttgat cagtttcgaa t                                              21

<210> SEQ ID NO 163
<211> LENGTH: 21
<212> TYPE: DNA
<213> ORGANISM: Homo sapiens

<400> SEQUENCE: 163
gctgattccc aggactatat t                                              21

<210> SEQ ID NO 164
<211> LENGTH: 21
<212> TYPE: DNA
<213> ORGANISM: Homo sapiens

<400> SEQUENCE: 164
gtatcgctgt ataactatgt a                                              21

<210> SEQ ID NO 165
<211> LENGTH: 19
<212> TYPE: DNA
<213> ORGANISM: Homo sapiens

<400> SEQUENCE: 165
attgacctgc acctactct                                                 19

<210> SEQ ID NO 166
<211> LENGTH: 19
<212> TYPE: DNA
<213> ORGANISM: Homo sapiens

<400> SEQUENCE: 166
gccgggagga aactgttgt                                                 19

<210> SEQ ID NO 167
<211> LENGTH: 21
<212> TYPE: DNA
<213> ORGANISM: Homo sapiens

<400> SEQUENCE: 167
cctggttcaa ggacgggata t    21

<210> SEQ ID NO 168
<211> LENGTH: 21
<212> TYPE: DNA
<213> ORGANISM: Homo sapiens

<400> SEQUENCE: 168
ttcggtgtac actgctcaat c    21

<210> SEQ ID NO 169
<211> LENGTH: 21
<212> TYPE: DNA
<213> ORGANISM: Homo sapiens

<400> SEQUENCE: 169
caccgggtaa gaaggtcatt t    21

<210> SEQ ID NO 170
<211> LENGTH: 21
<212> TYPE: DNA
<213> ORGANISM: Homo sapiens

<400> SEQUENCE: 170
acttgcatgg tctccgagga a    21

<210> SEQ ID NO 171
<211> LENGTH: 21
<212> TYPE: DNA
<213> ORGANISM: Homo sapiens

<400> SEQUENCE: 171
gtaacactga ttctccttgg a    21

<210> SEQ ID NO 172
<211> LENGTH: 21
<212> TYPE: DNA
<213> ORGANISM: Homo sapiens

<400> SEQUENCE: 172
gttataacag ccagatcaca g    21

<210> SEQ ID NO 173
<211> LENGTH: 21
<212> TYPE: DNA
<213> ORGANISM: Homo sapiens

<400> SEQUENCE: 173
tagctgcaca ggatgccttc a    21

<210> SEQ ID NO 174
<211> LENGTH: 21
<212> TYPE: DNA
<213> ORGANISM: Homo sapiens

<400> SEQUENCE: 174
ggtttgccta tagccgtgga t    21

<210> SEQ ID NO 175
<211> LENGTH: 21
<212> TYPE: DNA
<213> ORGANISM: Homo sapiens

<400> SEQUENCE: 175
cctatagccg tggatacttt g                                           21

<210> SEQ ID NO 176
<211> LENGTH: 21
<212> TYPE: DNA
<213> ORGANISM: Homo sapiens

<400> SEQUENCE: 176
ctccgttgtc catttgcctt a                                           21

<210> SEQ ID NO 177
<211> LENGTH: 21
<212> TYPE: DNA
<213> ORGANISM: Homo sapiens

<400> SEQUENCE: 177
ccaccctctg aatattcctg g                                           21

<210> SEQ ID NO 178
<211> LENGTH: 21
<212> TYPE: DNA
<213> ORGANISM: Homo sapiens

<400> SEQUENCE: 178
catcccgaac tacaacaact t                                           21

<210> SEQ ID NO 179
<211> LENGTH: 21
<212> TYPE: DNA
<213> ORGANISM: Homo sapiens

<400> SEQUENCE: 179
cctttggaaa cccaagaggt a                                           21

<210> SEQ ID NO 180
<211> LENGTH: 21
<212> TYPE: DNA
<213> ORGANISM: Homo sapiens

<400> SEQUENCE: 180
tctgagacag aagcgtgtta t                                           21

<210> SEQ ID NO 181
<211> LENGTH: 21
<212> TYPE: DNA
<213> ORGANISM: Homo sapiens

<400> SEQUENCE: 181
gctcggttga ttgaagacaa t                                           21

<210> SEQ ID NO 182
<211> LENGTH: 21
<212> TYPE: DNA
<213> ORGANISM: Homo sapiens

<400> SEQUENCE: 182
ttgacaatgg tggatactat a                                           21

<210> SEQ ID NO 183
<211> LENGTH: 21
<212> TYPE: DNA
<213> ORGANISM: Homo sapiens -continued

<400> SEQUENCE: 183
tcttcacctg attcaactaa a    21

<210> SEQ ID NO 184
<211> LENGTH: 21
<212> TYPE: DNA
<213> ORGANISM: Homo sapiens

<400> SEQUENCE: 184
gctctgaagt tgccaaacct t    21

<210> SEQ ID NO 185
<211> LENGTH: 21
<212> TYPE: DNA
<213> ORGANISM: Homo sapiens

<400> SEQUENCE: 185
cactgtttgt ggcgctttat g    21

<210> SEQ ID NO 186
<211> LENGTH: 21
<212> TYPE: DNA
<213> ORGANISM: Homo sapiens

<400> SEQUENCE: 186
catcgagcgc atgaattata t    21

<210> SEQ ID NO 187
<211> LENGTH: 21
<212> TYPE: DNA
<213> ORGANISM: Homo sapiens

<400> SEQUENCE: 187
cctgtatgga aggttcacaa t    21

<210> SEQ ID NO 188
<211> LENGTH: 20
<212> TYPE: DNA
<213> ORGANISM: Homo sapiens

<400> SEQUENCE: 188
tcgatgttat gtcaaaggcc    20

<210> SEQ ID NO 189
<211> LENGTH: 20
<212> TYPE: DNA
<213> ORGANISM: Homo sapiens

<400> SEQUENCE: 189
accacacaaa cttcctgtat    20

<210> SEQ ID NO 190
<211> LENGTH: 21
<212> TYPE: DNA
<213> ORGANISM: Homo sapiens

<400> SEQUENCE: 190
acagctcctg tcctttggaa a    21

<210> SEQ ID NO 191
<211> LENGTH: 21
<212> TYPE: DNA
<213> ORGANISM: Homo sapiens

```
<400> SEQUENCE: 191
gcagcgaaac tgacagagga g                                              21

<210> SEQ ID NO 192
<211> LENGTH: 21
<212> TYPE: DNA
<213> ORGANISM: Homo sapiens

<400> SEQUENCE: 192
acactgtttg tggcgcttta t                                              21

<210> SEQ ID NO 193
<211> LENGTH: 21
<212> TYPE: DNA
<213> ORGANISM: Homo sapiens

<400> SEQUENCE: 193
tgactaccac agcctatgtg a                                              21

<210> SEQ ID NO 194
<211> LENGTH: 21
<212> TYPE: DNA
<213> ORGANISM: Homo sapiens

<400> SEQUENCE: 194
cgagaaacag atcttggaga a                                              21

<210> SEQ ID NO 195
<211> LENGTH: 21
<212> TYPE: DNA
<213> ORGANISM: Homo sapiens

<400> SEQUENCE: 195
ctaaccttgc ttagcaactg t                                              21

<210> SEQ ID NO 196
<211> LENGTH: 21
<212> TYPE: DNA
<213> ORGANISM: Homo sapiens

<400> SEQUENCE: 196
aggaatgagc gctacacgtt c                                              21

<210> SEQ ID NO 197
<211> LENGTH: 21
<212> TYPE: DNA
<213> ORGANISM: Homo sapiens

<400> SEQUENCE: 197
tcttggagaa agtgaacagt a                                              21

<210> SEQ ID NO 198
<211> LENGTH: 21
<212> TYPE: DNA
<213> ORGANISM: Homo sapiens

<400> SEQUENCE: 198
gcgcctgtta tttcgtgagt t                                              21

<210> SEQ ID NO 199
<211> LENGTH: 21
<212> TYPE: DNA
```

```
<213> ORGANISM: Homo sapiens

<400> SEQUENCE: 199
gaacagttct ctacagttaa a                                              21

<210> SEQ ID NO 200
<211> LENGTH: 21
<212> TYPE: DNA
<213> ORGANISM: Homo sapiens

<400> SEQUENCE: 200
caggctattt attgcaagga t                                              21

<210> SEQ ID NO 201
<211> LENGTH: 21
<212> TYPE: DNA
<213> ORGANISM: Homo sapiens

<400> SEQUENCE: 201
gagcttagcc tacgcctatg a                                              21

<210> SEQ ID NO 202
<211> LENGTH: 21
<212> TYPE: DNA
<213> ORGANISM: Homo sapiens

<400> SEQUENCE: 202
gcaaaggcaa gagcaagaaa t                                              21

<210> SEQ ID NO 203
<211> LENGTH: 21
<212> TYPE: DNA
<213> ORGANISM: Homo sapiens

<400> SEQUENCE: 203
ccatggctct caacgagaaa c                                              21

<210> SEQ ID NO 204
<211> LENGTH: 21
<212> TYPE: DNA
<213> ORGANISM: Homo sapiens

<400> SEQUENCE: 204
tctatgctgc tgagatctgc t                                              21

<210> SEQ ID NO 205
<211> LENGTH: 21
<212> TYPE: DNA
<213> ORGANISM: Homo sapiens

<400> SEQUENCE: 205
gccgactaat gcagaacttt c                                              21

<210> SEQ ID NO 206
<211> LENGTH: 21
<212> TYPE: DNA
<213> ORGANISM: Homo sapiens

<400> SEQUENCE: 206
cgcctgttat ttcgtgagtt c                                              21

<210> SEQ ID NO 207
<211> LENGTH: 21
```

```
<212> TYPE: DNA
<213> ORGANISM: Homo sapiens

<400> SEQUENCE: 207
cgccgactaa tgcagaactt t                                             21

<210> SEQ ID NO 208
<211> LENGTH: 21
<212> TYPE: DNA
<213> ORGANISM: Homo sapiens

<400> SEQUENCE: 208
ctacctgcaa tcacgctact a                                             21

<210> SEQ ID NO 209
<211> LENGTH: 21
<212> TYPE: DNA
<213> ORGANISM: Homo sapiens

<400> SEQUENCE: 209
agcggagggt tcacatgtat g                                             21

<210> SEQ ID NO 210
<211> LENGTH: 21
<212> TYPE: DNA
<213> ORGANISM: Homo sapiens

<400> SEQUENCE: 210
caaccagtac agcactatta t                                             21

<210> SEQ ID NO 211
<211> LENGTH: 21
<212> TYPE: DNA
<213> ORGANISM: Homo sapiens

<400> SEQUENCE: 211 tacctttct ctggctaatt c                                              21

<210> SEQ ID NO 212
<211> LENGTH: 21
<212> TYPE: DNA
<213> ORGANISM: Homo sapiens

<400> SEQUENCE: 212
agcctgaagg cgaggtctaa t                                             21

<210> SEQ ID NO 213
<211> LENGTH: 21
<212> TYPE: DNA
<213> ORGANISM: Homo sapiens

<400> SEQUENCE: 213
cattggcacc cgtactatca t                                             21

<210> SEQ ID NO 214
<211> LENGTH: 21
<212> TYPE: DNA
<213> ORGANISM: Homo sapiens

<400> SEQUENCE: 214
gcttcagaat acgatcagat t                                             21

<210> SEQ ID NO 215
```

```
<211> LENGTH: 21
<212> TYPE: DNA
<213> ORGANISM: Homo sapiens

<400> SEQUENCE: 215
gaagactctt aaccaccaat t                                              21

<210> SEQ ID NO 216
<211> LENGTH: 21
<212> TYPE: DNA
<213> ORGANISM: Homo sapiens

<400> SEQUENCE: 216
atacgatcag attcgctata t                                              21

<210> SEQ ID NO 217
<211> LENGTH: 21
<212> TYPE: DNA
<213> ORGANISM: Homo sapiens

<400> SEQUENCE: 217
ctgtcataca tttggtctct t                                              21

<210> SEQ ID NO 218
<211> LENGTH: 21
<212> TYPE: DNA
<213> ORGANISM: Homo sapiens

<400> SEQUENCE: 218
gctactagcc ctgagttctt a                                              21

<210> SEQ ID NO 219
<211> LENGTH: 21
<212> TYPE: DNA
<213> ORGANISM: Homo sapiens

<400> SEQUENCE: 219
tataactttg tccgttctta t                                              21

<210> SEQ ID NO 220
<211> LENGTH: 21
<212> TYPE: DNA
<213> ORGANISM: Homo sapiens

<400> SEQUENCE: 220
ctcgctgcta aactaccaat c                                              21

<210> SEQ ID NO 221
<211> LENGTH: 21
<212> TYPE: DNA
<213> ORGANISM: Homo sapiens

<400> SEQUENCE: 221
gccaatcatc attccagata c                                              21

<210> SEQ ID NO 222
<211> LENGTH: 21
<212> TYPE: DNA
<213> ORGANISM: Homo sapiens

<400> SEQUENCE: 222
cgctccaaat acaagcacaa a                                              21
```

```
<210> SEQ ID NO 223
<211> LENGTH: 21
<212> TYPE: DNA
<213> ORGANISM: Homo sapiens

<400> SEQUENCE: 223
gcttagaggt tcctggataa a                                        21

<210> SEQ ID NO 224
<211> LENGTH: 21
<212> TYPE: DNA
<213> ORGANISM: Homo sapiens

<400> SEQUENCE: 224
cctttggttc acacaccaga a                                        21

<210> SEQ ID NO 225
<211> LENGTH: 21
<212> TYPE: DNA
<213> ORGANISM: Homo sapiens

<400> SEQUENCE: 225
ctgttagtga cctgacgttg a                                        21

<210> SEQ ID NO 226
<211> LENGTH: 21
<212> TYPE: DNA
<213> ORGANISM: Homo sapiens

<400> SEQUENCE: 226
cggatctcct atccatacat t                                        21

<210> SEQ ID NO 227
<211> LENGTH: 21
<212> TYPE: DNA
<213> ORGANISM: Homo sapiens

<400> SEQUENCE: 227
gtatcggaca aggctcacat t                                        21

<210> SEQ ID NO 228
<211> LENGTH: 21
<212> TYPE: DNA
<213> ORGANISM: Homo sapiens

<400> SEQUENCE: 228
ttcgagacac aatcgtgaga t                                        21

<210> SEQ ID NO 229
<211> LENGTH: 21
<212> TYPE: DNA
<213> ORGANISM: Homo sapiens

<400> SEQUENCE: 229
cggatctcct atccatacat t                                        21

<210> SEQ ID NO 230
<211> LENGTH: 21
<212> TYPE: DNA
<213> ORGANISM: Homo sapiens

<400> SEQUENCE: 230
ctcaagcttg tattccaact t                                        21
```

```
<210> SEQ ID NO 231
<211> LENGTH: 21
<212> TYPE: DNA
<213> ORGANISM: Homo sapiens

<400> SEQUENCE: 231
atataaggga ctgtctagat a                                              21

<210> SEQ ID NO 232
<211> LENGTH: 21
<212> TYPE: DNA
<213> ORGANISM: Homo sapiens

<400> SEQUENCE: 232
cgagtccttc acgattcata a                                              21

<210> SEQ ID NO 233
<211> LENGTH: 21
<212> TYPE: DNA
<213> ORGANISM: Homo sapiens

<400> SEQUENCE: 233
ccgagtcctt cacgattcat a                                              21

<210> SEQ ID NO 234
<211> LENGTH: 21
<212> TYPE: DNA
<213> ORGANISM: Homo sapiens

<400> SEQUENCE: 234
cgtccgactg gttgggatta t                                              21

<210> SEQ ID NO 235
<211> LENGTH: 21
<212> TYPE: DNA
<213> ORGANISM: Homo sapiens

<400> SEQUENCE: 235
cccagatggt acagttctga a                                              21

<210> SEQ ID NO 236
<211> LENGTH: 21
<212> TYPE: DNA
<213> ORGANISM: Homo sapiens

<400> SEQUENCE: 236
cgaggctctg tgggttctat a                                              21

<210> SEQ ID NO 237
<211> LENGTH: 21
<212> TYPE: DNA
<213> ORGANISM: Homo sapiens

<400> SEQUENCE: 237
ttgccgtgct tcggagtatt t                                              21

<210> SEQ ID NO 238
<211> LENGTH: 21
<212> TYPE: DNA
<213> ORGANISM: Homo sapiens

<400> SEQUENCE: 238
gatgcgattg ccgccagtat t                                              21
```

<210> SEQ ID NO 239
<211> LENGTH: 21
<212> TYPE: DNA
<213> ORGANISM: Homo sapiens

<400> SEQUENCE: 239
cctaacgaaa gagaccctga a                                              21

<210> SEQ ID NO 240
<211> LENGTH: 21
<212> TYPE: DNA
<213> ORGANISM: Homo sapiens

<400> SEQUENCE: 240
atattctagc tagcatattt g                                              21

<210> SEQ ID NO 241
<211> LENGTH: 21
<212> TYPE: DNA
<213> ORGANISM: Homo sapiens

<400> SEQUENCE: 241
ggccagagtt tgaccatata a                                              21

<210> SEQ ID NO 242
<211> LENGTH: 21
<212> TYPE: DNA
<213> ORGANISM: Homo sapiens

<400> SEQUENCE: 242
gagtccttca cgattcataa t                                              21

<210> SEQ ID NO 243
<211> LENGTH: 21
<212> TYPE: DNA
<213> ORGANISM: Homo sapiens

<400> SEQUENCE: 243
attgccgtgc ttcggagtat t                                              21

<210> SEQ ID NO 244
<211> LENGTH: 21
<212> TYPE: DNA
<213> ORGANISM: Homo sapiens

<400> SEQUENCE: 244
agcggaagta cggatgatag a                                              21

<210> SEQ ID NO 245
<211> LENGTH: 21
<212> TYPE: DNA
<213> ORGANISM: Homo sapiens

<400> SEQUENCE: 245
gaggctctgt gggttctata t                                              21

<210> SEQ ID NO 246
<211> LENGTH: 21
<212> TYPE: DNA
<213> ORGANISM: Homo sapiens

<400> SEQUENCE: 246

```
tgcccaaata ctacggcgtc t                                              21

<210> SEQ ID NO 247
<211> LENGTH: 21
<212> TYPE: DNA
<213> ORGANISM: Homo sapiens

<400> SEQUENCE: 247
cggcaaggac aaagtgggca t                                              21

<210> SEQ ID NO 248
<211> LENGTH: 21
<212> TYPE: DNA
<213> ORGANISM: Homo sapiens

<400> SEQUENCE: 248
ctagcaacac agtcgatgag g                                              21

<210> SEQ ID NO 249
<211> LENGTH: 21
<212> TYPE: DNA
<213> ORGANISM: Homo sapiens

<400> SEQUENCE: 249
accaaacgat gtgtacctaa a                                              21

<210> SEQ ID NO 250
<211> LENGTH: 21
<212> TYPE: DNA
<213> ORGANISM: Homo sapiens

<400> SEQUENCE: 250
accctgtata atggacgtga a                                              21

<210> SEQ ID NO 251
<211> LENGTH: 21
<212> TYPE: DNA
<213> ORGANISM: Homo sapiens

<400> SEQUENCE: 251
cctgtataat ggacgtgaag a                                              21

<210> SEQ ID NO 252
<211> LENGTH: 21
<212> TYPE: DNA
<213> ORGANISM: Homo sapiens

<400> SEQUENCE: 252
caccaaacga tgtgtaccta a                                              21

<210> SEQ ID NO 253
<211> LENGTH: 21
<212> TYPE: DNA
<213> ORGANISM: Homo sapiens

<400> SEQUENCE: 253
gaacaggtgg cacagcttaa g                                              21

<210> SEQ ID NO 254
<211> LENGTH: 21
<212> TYPE: DNA
<213> ORGANISM: Homo sapiens

<400> SEQUENCE: 254
```

```
cggctacagt aacccctaaga t                                              21

<210> SEQ ID NO 255
<211> LENGTH: 21
<212> TYPE: DNA
<213> ORGANISM: Homo sapiens

<400> SEQUENCE: 255
ctacgccaac ctcagcaact t                                               21

<210> SEQ ID NO 256
<211> LENGTH: 21
<212> TYPE: DNA
<213> ORGANISM: Homo sapiens

<400> SEQUENCE: 256
cggtgcctac ggctacagta a                                               21

<210> SEQ ID NO 257
<211> LENGTH: 21
<212> TYPE: DNA
<213> ORGANISM: Homo sapiens

<400> SEQUENCE: 257
gcttaagcag aaagtcatga a                                               21

<210> SEQ ID NO 258
<211> LENGTH: 21
<212> TYPE: DNA
<213> ORGANISM: Homo sapiens

<400> SEQUENCE: 258
agcgcatgag gaaccgcatt g                                               21

<210> SEQ ID NO 259
<211> LENGTH: 21
<212> TYPE: DNA
<213> ORGANISM: Homo sapiens

<400> SEQUENCE: 259
cctatcgaca tggagtctca g                                               21

<210> SEQ ID NO 260
<211> LENGTH: 21
<212> TYPE: DNA
<213> ORGANISM: Homo sapiens

<400> SEQUENCE: 260
gaagcgcatg aggaaccgca t                                               21

<210> SEQ ID NO 261
<211> LENGTH: 21
<212> TYPE: DNA
<213> ORGANISM: Homo sapiens

<400> SEQUENCE: 261
attcgatctc attcagtatt a                                               21

<210> SEQ ID NO 262
<211> LENGTH: 21
<212> TYPE: DNA
<213> ORGANISM: Homo sapiens
```

```
<400> SEQUENCE: 262
ggatcgctcg gctagaggaa a                                              21

<210> SEQ ID NO 263
<211> LENGTH: 21
<212> TYPE: DNA
<213> ORGANISM: Homo sapiens

<400> SEQUENCE: 263
gcggatcaag gcagagagga a                                              21

<210> SEQ ID NO 264
<211> LENGTH: 21
<212> TYPE: DNA
<213> ORGANISM: Homo sapiens

<400> SEQUENCE: 264
ggcatgtgct gtgatcattt a                                              21

<210> SEQ ID NO 265
<211> LENGTH: 21
<212> TYPE: DNA
<213> ORGANISM: Homo sapiens

<400> SEQUENCE: 265
acgcagcagt tgcaaacgtt t                                              21

<210> SEQ ID NO 266
<211> LENGTH: 21
<212> TYPE: DNA
<213> ORGANISM: Homo sapiens

<400> SEQUENCE: 266
gcgggctaac tgcaataaga t                                              21

<210> SEQ ID NO 267
<211> LENGTH: 21
<212> TYPE: DNA
<213> ORGANISM: Homo sapiens

<400> SEQUENCE: 267
cagtaaccct aagatcctaa a                                              21

<210> SEQ ID NO 268
<211> LENGTH: 21
<212> TYPE: DNA
<213> ORGANISM: Homo sapiens

<400> SEQUENCE: 268
gctaacgcag cagttgcaaa c                                              21

<210> SEQ ID NO 269
<211> LENGTH: 21
<212> TYPE: DNA
<213> ORGANISM: Homo sapiens

<400> SEQUENCE: 269
gaaagtcatg aaccacgtta a                                              21

<210> SEQ ID NO 270
<211> LENGTH: 21
<212> TYPE: DNA
<213> ORGANISM: Homo sapiens
```

```
<400> SEQUENCE: 270
agcaacaaca ggaaggtata t                                          21

<210> SEQ ID NO 271
<211> LENGTH: 21
<212> TYPE: DNA
<213> ORGANISM: Homo sapiens

<400> SEQUENCE: 271
gcatccacga acaagaccat a                                          21

<210> SEQ ID NO 272
<211> LENGTH: 21
<212> TYPE: DNA
<213> ORGANISM: Homo sapiens

<400> SEQUENCE: 272
ttgagaccaa gcgtcactta t                                          21

<210> SEQ ID NO 273
<211> LENGTH: 21
<212> TYPE: DNA
<213> ORGANISM: Homo sapiens

<400> SEQUENCE: 273
ccgcaagagc ttgattgtaa c                                          21

<210> SEQ ID NO 274
<211> LENGTH: 21
<212> TYPE: DNA
<213> ORGANISM: Homo sapiens

<400> SEQUENCE: 274
gctggttctg aagagtggaa a                                          21

<210> SEQ ID NO 275
<211> LENGTH: 21
<212> TYPE: DNA
<213> ORGANISM: Homo sapiens

<400> SEQUENCE: 275
gatattacgg aagcggttat c                                          21

<210> SEQ ID NO 276
<211> LENGTH: 21
<212> TYPE: DNA
<213> ORGANISM: Homo sapiens

<400> SEQUENCE: 276
gcctcattac gtcacactat t                                          21

<210> SEQ ID NO 277
<211> LENGTH: 21
<212> TYPE: DNA
<213> ORGANISM: Homo sapiens

<400> SEQUENCE: 277
cctcattacg tcacactatt t                                          21

<210> SEQ ID NO 278
<211> LENGTH: 21
<212> TYPE: DNA
```

<213> ORGANISM: Homo sapiens

<400> SEQUENCE: 278
acgaatacca cggtcccaaa t                                            21

<210> SEQ ID NO 279
<211> LENGTH: 21
<212> TYPE: DNA
<213> ORGANISM: Homo sapiens

<400> SEQUENCE: 279
gtggaaacaa ggtatcaatt t                                            21

<210> SEQ ID NO 280
<211> LENGTH: 21
<212> TYPE: DNA
<213> ORGANISM: Homo sapiens

<400> SEQUENCE: 280
gaagtgtgct atccgggaaa g                                            21

<210> SEQ ID NO 281
<211> LENGTH: 21
<212> TYPE: DNA
<213> ORGANISM: Homo sapiens

<400> SEQUENCE: 281
acttgtatga gggtcatatt g                                            21

<210> SEQ ID NO 282
<211> LENGTH: 21
<212> TYPE: DNA
<213> ORGANISM: Homo sapiens

<400> SEQUENCE: 282
cgaatgagaa accaatccct t                                            21

<210> SEQ ID NO 283
<211> LENGTH: 21
<212> TYPE: DNA
<213> ORGANISM: Homo sapiens

<400> SEQUENCE: 283
gcatcaaacc tggttcgaat g                                            21

<210> SEQ ID NO 284
<211> LENGTH: 21
<212> TYPE: DNA
<213> ORGANISM: Homo sapiens

<400> SEQUENCE: 284
ccctgtcaac aaagtaatca a                                            21

<210> SEQ ID NO 285
<211> LENGTH: 21
<212> TYPE: DNA
<213> ORGANISM: Homo sapiens

<400> SEQUENCE: 285
ggaggaaaca ggcaagataa a                                            21

<210> SEQ ID NO 286
<211> LENGTH: 21

```
<212> TYPE: DNA
<213> ORGANISM: Homo sapiens

<400> SEQUENCE: 286
tgatgcggga ccagtccatt t                                      21

<210> SEQ ID NO 287
<211> LENGTH: 21
<212> TYPE: DNA
<213> ORGANISM: Homo sapiens

<400> SEQUENCE: 287
tgtaatgagg acaatacgga g                                      21

<210> SEQ ID NO 288
<211> LENGTH: 21
<212> TYPE: DNA
<213> ORGANISM: Homo sapiens

<400> SEQUENCE: 288
tcctgaccct ctgcaacatt g                                      21

<210> SEQ ID NO 289
<211> LENGTH: 21
<212> TYPE: DNA
<213> ORGANISM: Homo sapiens

<400> SEQUENCE: 289
tgacatggac tgcggcatca t                                      21

<210> SEQ ID NO 290
<211> LENGTH: 21
<212> TYPE: DNA
<213> ORGANISM: Homo sapiens

<400> SEQUENCE: 290
cgaagcatgt aatgaggaca a                                      21

<210> SEQ ID NO 291
<211> LENGTH: 21
<212> TYPE: DNA
<213> ORGANISM: Homo sapiens

<400> SEQUENCE: 291
gacatcagta agaagagtaa a                                      21

<210> SEQ ID NO 292
<211> LENGTH: 21
<212> TYPE: DNA
<213> ORGANISM: Homo sapiens

<400> SEQUENCE: 292
tgccaagtga caggttataa a                                      21

<210> SEQ ID NO 293
<211> LENGTH: 21
<212> TYPE: DNA
<213> ORGANISM: Homo sapiens

<400> SEQUENCE: 293
tgcaacattg tcctgggaca a                                      21

<210> SEQ ID NO 294
```

```
<211> LENGTH: 21
<212> TYPE: DNA
<213> ORGANISM: Homo sapiens

<400> SEQUENCE: 294
atcgtcagac tgtctagaaa t                                        21

<210> SEQ ID NO 295
<211> LENGTH: 21
<212> TYPE: DNA
<213> ORGANISM: Homo sapiens

<400> SEQUENCE: 295
ccgtggagaa tcacaagata t                                        21

<210> SEQ ID NO 296
<211> LENGTH: 21
<212> TYPE: DNA
<213> ORGANISM: Homo sapiens

<400> SEQUENCE: 296
gtttatctat tggaggttaa a                                        21

<210> SEQ ID NO 297
<211> LENGTH: 21
<212> TYPE: DNA
<213> ORGANISM: Homo sapiens

<400> SEQUENCE: 297
gaagagtaaa gtaaatgctg t                                        21

<210> SEQ ID NO 298
<211> LENGTH: 21
<212> TYPE: DNA
<213> ORGANISM: Homo sapiens

<400> SEQUENCE: 298
cgccggatgt atgtggttta a                                        21

<210> SEQ ID NO 299
<211> LENGTH: 21
<212> TYPE: DNA
<213> ORGANISM: Homo sapiens

<400> SEQUENCE: 299
gccggatgta tgtggtttaa t                                        21

<210> SEQ ID NO 300
<211> LENGTH: 21
<212> TYPE: DNA
<213> ORGANISM: Homo sapiens

<400> SEQUENCE: 300
cttggtctct cccatcatat a                                        21

<210> SEQ ID NO 301
<211> LENGTH: 21
<212> TYPE: DNA
<213> ORGANISM: Homo sapiens

<400> SEQUENCE: 301
acagcaactg gcaccatatc t                                        21
```

<210> SEQ ID NO 302
<211> LENGTH: 21
<212> TYPE: DNA
<213> ORGANISM: Homo sapiens

<400> SEQUENCE: 302
gataccttgg gaggccgatt t                                    21

<210> SEQ ID NO 303
<211> LENGTH: 21
<212> TYPE: DNA
<213> ORGANISM: Homo sapiens

<400> SEQUENCE: 303
ggccaatgag atcgtgcttc t                                    21

<210> SEQ ID NO 304
<211> LENGTH: 21
<212> TYPE: DNA
<213> ORGANISM: Homo sapiens

<400> SEQUENCE: 304
gtagcctttg accctcaaat c                                    21

<210> SEQ ID NO 305
<211> LENGTH: 21
<212> TYPE: DNA
<213> ORGANISM: Homo sapiens

<400> SEQUENCE: 305
caatggagct gctgatcaac g                                    21

<210> SEQ ID NO 306
<211> LENGTH: 21
<212> TYPE: DNA
<213> ORGANISM: Homo sapiens

<400> SEQUENCE: 306
gacagcaact ggcaccatat c                                    21

<210> SEQ ID NO 307
<211> LENGTH: 21
<212> TYPE: DNA
<213> ORGANISM: Homo sapiens

<400> SEQUENCE: 307
ttggtctctc ccatcatata c                                    21

<210> SEQ ID NO 308
<211> LENGTH: 21
<212> TYPE: DNA
<213> ORGANISM: Homo sapiens

<400> SEQUENCE: 308
ataccttggg aggccgattt g                                    21

<210> SEQ ID NO 309
<211> LENGTH: 21
<212> TYPE: DNA
<213> ORGANISM: Homo sapiens

<400> SEQUENCE: 309
cctgtcagtt tcaggacttt g                                    21

```
<210> SEQ ID NO 310
<211> LENGTH: 21
<212> TYPE: DNA
<213> ORGANISM: Homo sapiens

<400> SEQUENCE: 310
tccgcaacaa ctacatgtac g                                              21

<210> SEQ ID NO 311
<211> LENGTH: 21
<212> TYPE: DNA
<213> ORGANISM: Homo sapiens

<400> SEQUENCE: 311
ataagctggt agaggccttt g                                              21

<210> SEQ ID NO 312
<211> LENGTH: 21
<212> TYPE: DNA
<213> ORGANISM: Homo sapiens

<400> SEQUENCE: 312
cggtgccgtc atctgcatca t                                              21

<210> SEQ ID NO 313
<211> LENGTH: 21
<212> TYPE: DNA
<213> ORGANISM: Homo sapiens

<400> SEQUENCE: 313
caagccacac ggcatcctta t                                              21

<210> SEQ ID NO 314
<211> LENGTH: 21
<212> TYPE: DNA
<213> ORGANISM: Homo sapiens

<400> SEQUENCE: 314
tcaagccaca cggcatcctt a                                              21

<210> SEQ ID NO 315
<211> LENGTH: 21
<212> TYPE: DNA
<213> ORGANISM: Homo sapiens

<400> SEQUENCE: 315
ttggacttgc ctgaacgtct t                                              21

<210> SEQ ID NO 316
<211> LENGTH: 21
<212> TYPE: DNA
<213> ORGANISM: Homo sapiens

<400> SEQUENCE: 316
tttgacgggc aggatcataa a                                              21

<210> SEQ ID NO 317
<211> LENGTH: 21
<212> TYPE: DNA
<213> ORGANISM: Homo sapiens

<400> SEQUENCE: 317
gccaatggaa acatcaagat t                                              21
```

<210> SEQ ID NO 318
<211> LENGTH: 21
<212> TYPE: DNA
<213> ORGANISM: Homo sapiens

<400> SEQUENCE: 318
gtgtagtgac tgccattatt t                                              21

<210> SEQ ID NO 319
<211> LENGTH: 21
<212> TYPE: DNA
<213> ORGANISM: Homo sapiens

<400> SEQUENCE: 319
ccaaggtgtg cagcttcttc a                                              21

<210> SEQ ID NO 320
<211> LENGTH: 21
<212> TYPE: DNA
<213> ORGANISM: Homo sapiens

<400> SEQUENCE: 320
cctgatccgg tggctgttaa t                                              21

<210> SEQ ID NO 321
<211> LENGTH: 21
<212> TYPE: DNA
<213> ORGANISM: Homo sapiens

<400> SEQUENCE: 321
gggctcatca agtcgcctaa a                                              21

<210> SEQ ID NO 322
<211> LENGTH: 21
<212> TYPE: DNA
<213> ORGANISM: Homo sapiens

<400> SEQUENCE: 322
ccgaaaggca ttctcaagaa a                                              21

<210> SEQ ID NO 323
<211> LENGTH: 21
<212> TYPE: DNA
<213> ORGANISM: Homo sapiens

<400> SEQUENCE: 323
gtcgcctaaa cctctgatga a                                              21

<210> SEQ ID NO 324
<211> LENGTH: 21
<212> TYPE: DNA
<213> ORGANISM: Homo sapiens

<400> SEQUENCE: 324
ccgaggcgat ctgtatgatt a                                              21

<210> SEQ ID NO 325
<211> LENGTH: 21
<212> TYPE: DNA
<213> ORGANISM: Homo sapiens

<400> SEQUENCE: 325

```
gaagtctcga cagcgtgaat c                                              21

<210> SEQ ID NO 326
<211> LENGTH: 21
<212> TYPE: DNA
<213> ORGANISM: Homo sapiens

<400> SEQUENCE: 326
tcggaccgct gtttgacttc a                                              21

<210> SEQ ID NO 327
<211> LENGTH: 21
<212> TYPE: DNA
<213> ORGANISM: Homo sapiens

<400> SEQUENCE: 327
tagcagcaag attgtgattg t                                              21

<210> SEQ ID NO 328
<211> LENGTH: 21
<212> TYPE: DNA
<213> ORGANISM: Homo sapiens

<400> SEQUENCE: 328
agtctcgaca gcgtgaatct g                                              21

<210> SEQ ID NO 329
<211> LENGTH: 21
<212> TYPE: DNA
<213> ORGANISM: Homo sapiens

<400> SEQUENCE: 329
cccaaggaaa ggcatcctta a                                              21

<210> SEQ ID NO 330
<211> LENGTH: 21
<212> TYPE: DNA
<213> ORGANISM: Homo sapiens

<400> SEQUENCE: 330
gatggcagat actcctcaat g                                              21

<210> SEQ ID NO 331
<211> LENGTH: 21
<212> TYPE: DNA
<213> ORGANISM: Homo sapiens

<400> SEQUENCE: 331
gggaatggat ggcagatact c                                              21

<210> SEQ ID NO 332
<211> LENGTH: 21
<212> TYPE: DNA
<213> ORGANISM: Homo sapiens

<400> SEQUENCE: 332
ctccctcacc tctctagaat c                                              21

<210> SEQ ID NO 333
<211> LENGTH: 21
<212> TYPE: DNA
<213> ORGANISM: Homo sapiens

<400> SEQUENCE: 333
```
tgcaatcgtc ttcgccgtca a                                              21

<210> SEQ ID NO 334
<211> LENGTH: 21
<212> TYPE: DNA
<213> ORGANISM: Homo sapiens

<400> SEQUENCE: 334
cattgctgtc gctgtgttct t                                              21

<210> SEQ ID NO 335
<211> LENGTH: 21
<212> TYPE: DNA
<213> ORGANISM: Homo sapiens

<400> SEQUENCE: 335
acaagaatgc ctacgagaat g                                              21

<210> SEQ ID NO 336
<211> LENGTH: 21
<212> TYPE: DNA
<213> ORGANISM: Homo sapiens

<400> SEQUENCE: 336
ttcttggtcc ttgttgcaat c                                              21

<210> SEQ ID NO 337
<211> LENGTH: 21
<212> TYPE: DNA
<213> ORGANISM: Homo sapiens

<400> SEQUENCE: 337
ggagcacagt gatgatcatt g                                              21

<210> SEQ ID NO 338
<211> LENGTH: 21
<212> TYPE: DNA
<213> ORGANISM: Homo sapiens

<400> SEQUENCE: 338
actgctctac aggaatctac t                                              21

<210> SEQ ID NO 339
<211> LENGTH: 21
<212> TYPE: DNA
<213> ORGANISM: Homo sapiens

<400> SEQUENCE: 339
ctgtcaacaa ggtctaggaa a                                              21

<210> SEQ ID NO 340
<211> LENGTH: 21
<212> TYPE: DNA
<213> ORGANISM: Homo sapiens

<400> SEQUENCE: 340
cctcattgct gtcgctgtgt t                                              21

<210> SEQ ID NO 341
<211> LENGTH: 21
<212> TYPE: DNA
<213> ORGANISM: Homo sapiens -continued

```
<400> SEQUENCE: 341
tctacaggaa tctactgaaa c                                              21

<210> SEQ ID NO 342
<211> LENGTH: 21
<212> TYPE: DNA
<213> ORGANISM: Homo sapiens

<400> SEQUENCE: 342
caagtcctat gaccctaatt t                                              21

<210> SEQ ID NO 343
<211> LENGTH: 21
<212> TYPE: DNA
<213> ORGANISM: Homo sapiens

<400> SEQUENCE: 343
ggtggacacc actcagtatt a                                              21

<210> SEQ ID NO 344
<211> LENGTH: 21
<212> TYPE: DNA
<213> ORGANISM: Homo sapiens

<400> SEQUENCE: 344
ccaactcaac atcaccgtaa a                                              21

<210> SEQ ID NO 345
<211> LENGTH: 21
<212> TYPE: DNA
<213> ORGANISM: Homo sapiens

<400> SEQUENCE: 345
acacaatacc acgcatattt a                                              21

<210> SEQ ID NO 346
<211> LENGTH: 21
<212> TYPE: DNA
<213> ORGANISM: Homo sapiens

<400> SEQUENCE: 346
ggccgcttca aatatgaaat a                                              21

<210> SEQ ID NO 347
<211> LENGTH: 21
<212> TYPE: DNA
<213> ORGANISM: Homo sapiens

<400> SEQUENCE: 347
ttcactagga gtggcatatt c                                              21

<210> SEQ ID NO 348
<211> LENGTH: 21
<212> TYPE: DNA
<213> ORGANISM: Homo sapiens

<400> SEQUENCE: 348
catctataag ggtagtcttt c                                              21

<210> SEQ ID NO 349
<211> LENGTH: 21
<212> TYPE: DNA
<213> ORGANISM: Homo sapiens
```

```
<400> SEQUENCE: 349
gttattacct ctcttgtttc t                                              21

<210> SEQ ID NO 350
<211> LENGTH: 21
<212> TYPE: DNA
<213> ORGANISM: Homo sapiens

<400> SEQUENCE: 350
gtagtctacc ctgtctattt g                                              21

<210> SEQ ID NO 351
<211> LENGTH: 21
<212> TYPE: DNA
<213> ORGANISM: Homo sapiens

<400> SEQUENCE: 351
gccctgtacc tttcaaccaa t                                              21

<210> SEQ ID NO 352
<211> LENGTH: 21
<212> TYPE: DNA
<213> ORGANISM: Homo sapiens

<400> SEQUENCE: 352
catgtcatcg agtactcttt a                                              21

<210> SEQ ID NO 353
<211> LENGTH: 21
<212> TYPE: DNA
<213> ORGANISM: Homo sapiens

<400> SEQUENCE: 353
caactgatgg tgtcctatat a                                              21

<210> SEQ ID NO 354
<211> LENGTH: 21
<212> TYPE: DNA
<213> ORGANISM: Homo sapiens

<400> SEQUENCE: 354
ccatcattga aggtggctca t                                              21

<210> SEQ ID NO 355
<211> LENGTH: 21
<212> TYPE: DNA
<213> ORGANISM: Homo sapiens

<400> SEQUENCE: 355
gcttcactac tcttcctgct t                                              21

<210> SEQ ID NO 356
<211> LENGTH: 21
<212> TYPE: DNA
<213> ORGANISM: Homo sapiens

<400> SEQUENCE: 356
cgctcgcact ttcagcaata a                                              21

<210> SEQ ID NO 357
<211> LENGTH: 21
<212> TYPE: DNA
```

<213> ORGANISM: Homo sapiens

<400> SEQUENCE: 357
gaggatgata aagacaaagt a					21

<210> SEQ ID NO 358
<211> LENGTH: 21
<212> TYPE: DNA
<213> ORGANISM: Homo sapiens

<400> SEQUENCE: 358
gctttcctca gcccattaca a					21

<210> SEQ ID NO 359
<211> LENGTH: 21
<212> TYPE: DNA
<213> ORGANISM: Homo sapiens

<400> SEQUENCE: 359
gagatgatgg tccctggaat g					21

<210> SEQ ID NO 360
<211> LENGTH: 21
<212> TYPE: DNA
<213> ORGANISM: Homo sapiens

<400> SEQUENCE: 360
tgaccacaga ggaagtcatt a					21

<210> SEQ ID NO 361
<211> LENGTH: 21
<212> TYPE: DNA
<213> ORGANISM: Homo sapiens

<400> SEQUENCE: 361
gatgccttct tggctattga t					21

<210> SEQ ID NO 362
<211> LENGTH: 21
<212> TYPE: DNA
<213> ORGANISM: Homo sapiens

<400> SEQUENCE: 362
ccatggatgg acgagtcaat g					21

<210> SEQ ID NO 363
<211> LENGTH: 21
<212> TYPE: DNA
<213> ORGANISM: Homo sapiens

<400> SEQUENCE: 363
tgacgcgata tgggcagaac t					21

<210> SEQ ID NO 364
<211> LENGTH: 21
<212> TYPE: DNA
<213> ORGANISM: Homo sapiens

<400> SEQUENCE: 364
gctaccatga ctattgaaga g					21

<210> SEQ ID NO 365
<211> LENGTH: 21

<212> TYPE: DNA
<213> ORGANISM: Homo sapiens

<400> SEQUENCE: 365
tggcaaagct ttagatatgt c                                              21

<210> SEQ ID NO 366
<211> LENGTH: 21
<212> TYPE: DNA
<213> ORGANISM: Homo sapiens

<400> SEQUENCE: 366
catggatgga cgagtcaatg g                                              21

<210> SEQ ID NO 367
<211> LENGTH: 21
<212> TYPE: DNA
<213> ORGANISM: Homo sapiens

<400> SEQUENCE: 367
cttcggttat tgtcatccat t                                              21

<210> SEQ ID NO 368
<211> LENGTH: 21
<212> TYPE: DNA
<213> ORGANISM: Homo sapiens

<400> SEQUENCE: 368
tgcctgtgct ctgttgtgtt g                                              21

<210> SEQ ID NO 369
<211> LENGTH: 21
<212> TYPE: DNA
<213> ORGANISM: Homo sapiens

<400> SEQUENCE: 369
caaattagtg agcccggtac t                                              21

<210> SEQ ID NO 370
<211> LENGTH: 21
<212> TYPE: DNA
<213> ORGANISM: Homo sapiens

<400> SEQUENCE: 370
gccttgtact gtgccaaata t                                              21

<210> SEQ ID NO 371
<211> LENGTH: 21
<212> TYPE: DNA
<213> ORGANISM: Homo sapiens

<400> SEQUENCE: 371
catgacgtgc atcatcattt g                                              21

<210> SEQ ID NO 372
<211> LENGTH: 21
<212> TYPE: DNA
<213> ORGANISM: Homo sapiens

<400> SEQUENCE: 372
acttcgagac ccatttagaa t                                              21

<210> SEQ ID NO 373

```
<211> LENGTH: 21
<212> TYPE: DNA
<213> ORGANISM: Homo sapiens

<400> SEQUENCE: 373
cagaagatcc cagcagtaga t                                              21

<210> SEQ ID NO 374
<211> LENGTH: 21
<212> TYPE: DNA
<213> ORGANISM: Homo sapiens

<400> SEQUENCE: 374
gccaccaata acttgtatat a                                              21

<210> SEQ ID NO 375
<211> LENGTH: 21
<212> TYPE: DNA
<213> ORGANISM: Homo sapiens

<400> SEQUENCE: 375
atagtgatca tgaaacatat c                                              21

<210> SEQ ID NO 376
<211> LENGTH: 21
<212> TYPE: DNA
<213> ORGANISM: Homo sapiens

<400> SEQUENCE: 376
atatgtacgc cggtcaatta g                                              21

<210> SEQ ID NO 377
<211> LENGTH: 21
<212> TYPE: DNA
<213> ORGANISM: Homo sapiens

<400> SEQUENCE: 377
atgctcatac atatcacata a                                              21

<210> SEQ ID NO 378
<211> LENGTH: 21
<212> TYPE: DNA
<213> ORGANISM: Homo sapiens

<400> SEQUENCE: 378
tcatctccac cgttgagttt a                                              21

<210> SEQ ID NO 379
<211> LENGTH: 21
<212> TYPE: DNA
<213> ORGANISM: Homo sapiens

<400> SEQUENCE: 379
gatctgagaa ttaacctatg g                                              21

<210> SEQ ID NO 380
<211> LENGTH: 21
<212> TYPE: DNA
<213> ORGANISM: Homo sapiens

<400> SEQUENCE: 380
ccatttagaa ttacggcact a                                              21
```

```
<210> SEQ ID NO 381
<211> LENGTH: 21
<212> TYPE: DNA
<213> ORGANISM: Homo sapiens

<400> SEQUENCE: 381
cggttcagac agtgccatta t                                              21

<210> SEQ ID NO 382
<211> LENGTH: 21
<212> TYPE: DNA
<213> ORGANISM: Homo sapiens

<400> SEQUENCE: 382
caccgttgag tttaactact c                                              21

<210> SEQ ID NO 383
<211> LENGTH: 21
<212> TYPE: DNA
<213> ORGANISM: Homo sapiens

<400> SEQUENCE: 383
gctcaataaa ggccattact c                                              21

<210> SEQ ID NO 384
<211> LENGTH: 21
<212> TYPE: DNA
<213> ORGANISM: Homo sapiens

<400> SEQUENCE: 384
gagaattaac ctatggcatt t                                              21

<210> SEQ ID NO 385
<211> LENGTH: 21
<212> TYPE: DNA
<213> ORGANISM: Homo sapiens

<400> SEQUENCE: 385
ccacagtggt cgatacatga t                                              21

<210> SEQ ID NO 386
<211> LENGTH: 21
<212> TYPE: DNA
<213> ORGANISM: Homo sapiens

<400> SEQUENCE: 386
cccacatcag tgcaatgtat t                                              21

<210> SEQ ID NO 387
<211> LENGTH: 21
<212> TYPE: DNA
<213> ORGANISM: Homo sapiens

<400> SEQUENCE: 387
cccgaggtct agaccgaatt a                                              21

<210> SEQ ID NO 388
<211> LENGTH: 21
<212> TYPE: DNA
<213> ORGANISM: Homo sapiens

<400> SEQUENCE: 388
tcacagtgtg tggtgatgtt c                                              21
```

```
<210> SEQ ID NO 389
<211> LENGTH: 21
<212> TYPE: DNA
<213> ORGANISM: Homo sapiens

<400> SEQUENCE: 389
gctgtatcta tggagcttaa a                                          21

<210> SEQ ID NO 390
<211> LENGTH: 21
<212> TYPE: DNA
<213> ORGANISM: Homo sapiens

<400> SEQUENCE: 390
cctatgagca aatcacattt a                                          21

<210> SEQ ID NO 391
<211> LENGTH: 21
<212> TYPE: DNA
<213> ORGANISM: Homo sapiens

<400> SEQUENCE: 391
aggaatgtcg gatcaagtat t                                          21

<210> SEQ ID NO 392
<211> LENGTH: 21
<212> TYPE: DNA
<213> ORGANISM: Homo sapiens

<400> SEQUENCE: 392
cggctaactt tgaaggaagt t                                          21

<210> SEQ ID NO 393
<211> LENGTH: 21
<212> TYPE: DNA
<213> ORGANISM: Homo sapiens

<400> SEQUENCE: 393
cggatgaaga aatgaacgta a                                          21

<210> SEQ ID NO 394
<211> LENGTH: 21
<212> TYPE: DNA
<213> ORGANISM: Homo sapiens

<400> SEQUENCE: 394
acctagtaat actcgctacc t                                          21

<210> SEQ ID NO 395
<211> LENGTH: 21
<212> TYPE: DNA
<213> ORGANISM: Homo sapiens

<400> SEQUENCE: 395
ctgtatctat ggagcttaaa g                                          21

<210> SEQ ID NO 396
<211> LENGTH: 21
<212> TYPE: DNA
<213> ORGANISM: Homo sapiens

<400> SEQUENCE: 396
agaaatgaac gtaaccgatg a                                          21
```

```
<210> SEQ ID NO 397
<211> LENGTH: 21
<212> TYPE: DNA
<213> ORGANISM: Homo sapiens

<400> SEQUENCE: 397
caaacaactt aaacttggag g                                       21

<210> SEQ ID NO 398
<211> LENGTH: 21
<212> TYPE: DNA
<213> ORGANISM: Homo sapiens

<400> SEQUENCE: 398
tgtaattcag tcgcatttat t                                       21

<210> SEQ ID NO 399
<211> LENGTH: 21
<212> TYPE: DNA
<213> ORGANISM: Homo sapiens

<400> SEQUENCE: 399
ggacaattct ttgacctgat g                                       21

<210> SEQ ID NO 400
<211> LENGTH: 21
<212> TYPE: DNA
<213> ORGANISM: Homo sapiens

<400> SEQUENCE: 400
cgaggtctag accgaattaa t                                       21

<210> SEQ ID NO 401
<211> LENGTH: 21
<212> TYPE: DNA
<213> ORGANISM: Homo sapiens

<400> SEQUENCE: 401
ttccgtcact tattacgatt t                                       21

<210> SEQ ID NO 402
<211> LENGTH: 21
<212> TYPE: DNA
<213> ORGANISM: Homo sapiens

<400> SEQUENCE: 402
ctgtggttac cagtcagctt g                                       21

<210> SEQ ID NO 403
<211> LENGTH: 21
<212> TYPE: DNA
<213> ORGANISM: Homo sapiens

<400> SEQUENCE: 403
gtatgtcacc acgctgctgt a                                       21

<210> SEQ ID NO 404
<211> LENGTH: 21
<212> TYPE: DNA
<213> ORGANISM: Homo sapiens

<400> SEQUENCE: 404
```

```
ccctcaccta ctccaagtta t                                                  21

<210> SEQ ID NO 405
<211> LENGTH: 21
<212> TYPE: DNA
<213> ORGANISM: Homo sapiens

<400> SEQUENCE: 405
tatgagttca cggagtttat t                                                  21

<210> SEQ ID NO 406
<211> LENGTH: 21
<212> TYPE: DNA
<213> ORGANISM: Homo sapiens

<400> SEQUENCE: 406
cgcaacccat cgctacaaga a                                                  21

<210> SEQ ID NO 407
<211> LENGTH: 21
<212> TYPE: DNA
<213> ORGANISM: Homo sapiens

<400> SEQUENCE: 407
catcgctaca agaagaagta t                                                  21

<210> SEQ ID NO 408
<211> LENGTH: 21
<212> TYPE: DNA
<213> ORGANISM: Homo sapiens

<400> SEQUENCE: 408
caattggagc accaagatcc c                                                  21

<210> SEQ ID NO 409
<211> LENGTH: 21
<212> TYPE: DNA
<213> ORGANISM: Homo sapiens

<400> SEQUENCE: 409
agtgggttca tgatccgtca g                                                  21

<210> SEQ ID NO 410
<211> LENGTH: 21
<212> TYPE: DNA
<213> ORGANISM: Homo sapiens

<400> SEQUENCE: 410
accgttatcc gctggtctga a                                                  21

<210> SEQ ID NO 411
<211> LENGTH: 21
<212> TYPE: DNA
<213> ORGANISM: Homo sapiens

<400> SEQUENCE: 411
gatctgagga gagattcaaa t                                                  21

<210> SEQ ID NO 412
<211> LENGTH: 21
<212> TYPE: DNA
<213> ORGANISM: Homo sapiens

<400> SEQUENCE: 412
```
cttaacaagg acacgaatat t        21

<210> SEQ ID NO 413
<211> LENGTH: 21
<212> TYPE: DNA
<213> ORGANISM: Homo sapiens

<400> SEQUENCE: 413
ctctgataaa gagtcataat g        21

<210> SEQ ID NO 414
<211> LENGTH: 21
<212> TYPE: DNA
<213> ORGANISM: Homo sapiens

<400> SEQUENCE: 414
cgctgctgta taagcccatc t        21

<210> SEQ ID NO 415
<211> LENGTH: 21
<212> TYPE: DNA
<213> ORGANISM: Homo sapiens

<400> SEQUENCE: 415
cttacggtca agaaatgtat g        21

<210> SEQ ID NO 416
<211> LENGTH: 21
<212> TYPE: DNA
<213> ORGANISM: Homo sapiens

<400> SEQUENCE: 416
cattaaggac agtgtgatgg t        21

<210> SEQ ID NO 417
<211> LENGTH: 21
<212> TYPE: DNA
<213> ORGANISM: Homo sapiens

<400> SEQUENCE: 417
tccgaacaca tgctgccatt t        21

<210> SEQ ID NO 418
<211> LENGTH: 21
<212> TYPE: DNA
<213> ORGANISM: Homo sapiens

<400> SEQUENCE: 418
gccaagattg acagacacct a        21

<210> SEQ ID NO 419
<211> LENGTH: 21
<212> TYPE: DNA
<213> ORGANISM: Homo sapiens

<400> SEQUENCE: 419
agactattct gcagctataa a        21

<210> SEQ ID NO 420
<211> LENGTH: 21
<212> TYPE: DNA
<213> ORGANISM: Homo sapiens

```
<400> SEQUENCE: 420
ccgttatact tggaaattcg a                                              21

<210> SEQ ID NO 421
<211> LENGTH: 21
<212> TYPE: DNA
<213> ORGANISM: Homo sapiens

<400> SEQUENCE: 421
agtatcgaat gggacttatt c                                              21

<210> SEQ ID NO 422
<211> LENGTH: 21
<212> TYPE: DNA
<213> ORGANISM: Homo sapiens

<400> SEQUENCE: 422
ttatattaat gccagcttag t                                              21

<210> SEQ ID NO 423
<211> LENGTH: 21
<212> TYPE: DNA
<213> ORGANISM: Homo sapiens

<400> SEQUENCE: 423
atgttcatga cttgagacta t                                              21

<210> SEQ ID NO 424
<211> LENGTH: 21
<212> TYPE: DNA
<213> ORGANISM: Homo sapiens

<400> SEQUENCE: 424
atatgatcac agtcgtgtta a                                              21

<210> SEQ ID NO 425
<211> LENGTH: 21
<212> TYPE: DNA
<213> ORGANISM: Homo sapiens

<400> SEQUENCE: 425
cggtggaaag aactttctaa a                                              21

<210> SEQ ID NO 426
<211> LENGTH: 21
<212> TYPE: DNA
<213> ORGANISM: Homo sapiens

<400> SEQUENCE: 426
ccatatctca cttccattat a                                              21

<210> SEQ ID NO 427
<211> LENGTH: 21
<212> TYPE: DNA
<213> ORGANISM: Homo sapiens

<400> SEQUENCE: 427
tctcctacat ggccataata g                                              21

<210> SEQ ID NO 428
<211> LENGTH: 21
<212> TYPE: DNA
<213> ORGANISM: Homo sapiens
```

```
<400> SEQUENCE: 428
cggtggaaag aactttctaa a                                              21

<210> SEQ ID NO 429
<211> LENGTH: 21
<212> TYPE: DNA
<213> ORGANISM: Homo sapiens

<400> SEQUENCE: 429
tatcgaatgg gacttattca g                                              21

<210> SEQ ID NO 430
<211> LENGTH: 21
<212> TYPE: DNA
<213> ORGANISM: Homo sapiens

<400> SEQUENCE: 430
cctgtcttgt tctgatggaa a                                              21

<210> SEQ ID NO 431
<211> LENGTH: 21
<212> TYPE: DNA
<213> ORGANISM: Homo sapiens

<400> SEQUENCE: 431
tcgctgcagt cagtgtacag g                                              21

<210> SEQ ID NO 432
<211> LENGTH: 21
<212> TYPE: DNA
<213> ORGANISM: Homo sapiens

<400> SEQUENCE: 432
ggccttctac ctggcttact a                                              21

<210> SEQ ID NO 433
<211> LENGTH: 21
<212> TYPE: DNA
<213> ORGANISM: Homo sapiens

<400> SEQUENCE: 433
ctgcaatgat tctcctagaa c                                              21

<210> SEQ ID NO 434
<211> LENGTH: 21
<212> TYPE: DNA
<213> ORGANISM: Homo sapiens

<400> SEQUENCE: 434
agtggtgggt tcctgcatga c                                              21

<210> SEQ ID NO 435
<211> LENGTH: 21
<212> TYPE: DNA
<213> ORGANISM: Homo sapiens

<400> SEQUENCE: 435
atatgccagc tagaaataag c                                              21

<210> SEQ ID NO 436
<211> LENGTH: 21
<212> TYPE: DNA
```

```
<213> ORGANISM: Homo sapiens

<400> SEQUENCE: 436
gtgatgatat gccagctaga a                                              21

<210> SEQ ID NO 437
<211> LENGTH: 21
<212> TYPE: DNA
<213> ORGANISM: Homo sapiens

<400> SEQUENCE: 437
catatttcta cagagtttac a                                              21

<210> SEQ ID NO 438
<211> LENGTH: 21
<212> TYPE: DNA
<213> ORGANISM: Homo sapiens

<400> SEQUENCE: 438
tcaataatga aggccagaat a                                              21

<210> SEQ ID NO 439
<211> LENGTH: 21
<212> TYPE: DNA
<213> ORGANISM: Homo sapiens

<400> SEQUENCE: 439
gctgccaggt tgtggtcatc a                                              21

<210> SEQ ID NO 440
<211> LENGTH: 21
<212> TYPE: DNA
<213> ORGANISM: Homo sapiens

<400> SEQUENCE: 440
tgatgatatg ccagctagaa a                                              21

<210> SEQ ID NO 441
<211> LENGTH: 21
<212> TYPE: DNA
<213> ORGANISM: Homo sapiens

<400> SEQUENCE: 441
caaggttggc aacgattctt t                                              21

<210> SEQ ID NO 442
<211> LENGTH: 21
<212> TYPE: DNA
<213> ORGANISM: Homo sapiens

<400> SEQUENCE: 442
gagcctgttc caaagcacat t                                              21

<210> SEQ ID NO 443
<211> LENGTH: 21
<212> TYPE: DNA
<213> ORGANISM: Homo sapiens

<400> SEQUENCE: 443
ccaaagcaca ttcccactga a                                              21

<210> SEQ ID NO 444
<211> LENGTH: 21
```

```
<212> TYPE: DNA
<213> ORGANISM: Homo sapiens

<400> SEQUENCE: 444
cattagccga gccaaagtga t                                              21

<210> SEQ ID NO 445
<211> LENGTH: 21
<212> TYPE: DNA
<213> ORGANISM: Homo sapiens

<400> SEQUENCE: 445
gcctccataa ttgtcaataa t                                              21

<210> SEQ ID NO 446
<211> LENGTH: 21
<212> TYPE: DNA
<213> ORGANISM: Homo sapiens

<400> SEQUENCE: 446
catactgtta gtcggcttga a                                              21

<210> SEQ ID NO 447
<211> LENGTH: 21
<212> TYPE: DNA
<213> ORGANISM: Homo sapiens

<400> SEQUENCE: 447
atgacatgca agcgcaattg g                                              21

<210> SEQ ID NO 448
<211> LENGTH: 21
<212> TYPE: DNA
<213> ORGANISM: Homo sapiens

<400> SEQUENCE: 448
gcctacaggt agattagatt a                                              21

<210> SEQ ID NO 449
<211> LENGTH: 21
<212> TYPE: DNA
<213> ORGANISM: Homo sapiens

<400> SEQUENCE: 449
agttcaattg gtgaggcata a                                              21

<210> SEQ ID NO 450
<211> LENGTH: 21
<212> TYPE: DNA
<213> ORGANISM: Homo sapiens

<400> SEQUENCE: 450
ctagcaaaga gagtgatatt g                                              21

<210> SEQ ID NO 451
<211> LENGTH: 21
<212> TYPE: DNA
<213> ORGANISM: Homo sapiens

<400> SEQUENCE: 451
cctggtttat gatttggatt t                                              21

<210> SEQ ID NO 452
```

```
<211> LENGTH: 21
<212> TYPE: DNA
<213> ORGANISM: Homo sapiens

<400> SEQUENCE: 452
cgggagttac aagatcaact t                                              21

<210> SEQ ID NO 453
<211> LENGTH: 21
<212> TYPE: DNA
<213> ORGANISM: Homo sapiens

<400> SEQUENCE: 453
ccgtgcaaag taagttacga t                                              21

<210> SEQ ID NO 454
<211> LENGTH: 21
<212> TYPE: DNA
<213> ORGANISM: Homo sapiens

<400> SEQUENCE: 454
gcagaaataa tgaatcgcaa a                                              21

<210> SEQ ID NO 455
<211> LENGTH: 21
<212> TYPE: DNA
<213> ORGANISM: Homo sapiens

<400> SEQUENCE: 455
atcaagatca gatcgtggaa g                                              21

<210> SEQ ID NO 456
<211> LENGTH: 21
<212> TYPE: DNA
<213> ORGANISM: Homo sapiens

<400> SEQUENCE: 456
ttcaattggt gaggcataaa t                                              21

<210> SEQ ID NO 457
<211> LENGTH: 21
<212> TYPE: DNA
<213> ORGANISM: Homo sapiens

<400> SEQUENCE: 457
gcagtgtctc aaaattgagaa a                                             21

<210> SEQ ID NO 458
<211> LENGTH: 21
<212> TYPE: DNA
<213> ORGANISM: Homo sapiens

<400> SEQUENCE: 458
tgtgggatgc tacctgataa a                                              21

<210> SEQ ID NO 459
<211> LENGTH: 21
<212> TYPE: DNA
<213> ORGANISM: Homo sapiens

<400> SEQUENCE: 459
ctacaggtag attagattaa t                                              21
```

```
<210> SEQ ID NO 460
<211> LENGTH: 21
<212> TYPE: DNA
<213> ORGANISM: Homo sapiens

<400> SEQUENCE: 460
caactttcta agcagatata a                                          21

<210> SEQ ID NO 461
<211> LENGTH: 21
<212> TYPE: DNA
<213> ORGANISM: Homo sapiens

<400> SEQUENCE: 461
cagtatgtta ctcgtaagaa g                                          21

<210> SEQ ID NO 462
<211> LENGTH: 21
<212> TYPE: DNA
<213> ORGANISM: Homo sapiens

<400> SEQUENCE: 462
gcagtatgtt actcgtaaga a                                          21

<210> SEQ ID NO 463
<211> LENGTH: 21
<212> TYPE: DNA
<213> ORGANISM: Homo sapiens

<400> SEQUENCE: 463
tgctaagttg tttctagaac c                                          21

<210> SEQ ID NO 464
<211> LENGTH: 21
<212> TYPE: DNA
<213> ORGANISM: Homo sapiens

<400> SEQUENCE: 464
cgatactatg accaccgaat g                                          21

<210> SEQ ID NO 465
<211> LENGTH: 21
<212> TYPE: DNA
<213> ORGANISM: Homo sapiens

<400> SEQUENCE: 465
cgagaggaat ccaccaactt t                                          21

<210> SEQ ID NO 466
<211> LENGTH: 21
<212> TYPE: DNA
<213> ORGANISM: Homo sapiens

<400> SEQUENCE: 466
gcgatactat gaccaccgaa t                                          21

<210> SEQ ID NO 467
<211> LENGTH: 21
<212> TYPE: DNA
<213> ORGANISM: Homo sapiens

<400> SEQUENCE: 467
ctaacttatt gtggtgtcat g                                          21
```

<210> SEQ ID NO 468
<211> LENGTH: 21
<212> TYPE: DNA
<213> ORGANISM: Homo sapiens

<400> SEQUENCE: 468
tcttgctgga ctctgattat g                                    21

<210> SEQ ID NO 469
<211> LENGTH: 21
<212> TYPE: DNA
<213> ORGANISM: Homo sapiens

<400> SEQUENCE: 469
ggctagatga gggcacaatt c                                    21

<210> SEQ ID NO 470
<211> LENGTH: 21
<212> TYPE: DNA
<213> ORGANISM: Homo sapiens

<400> SEQUENCE: 470
gaagacaaca cgtcgcgttt a                                    21

<210> SEQ ID NO 471
<211> LENGTH: 21
<212> TYPE: DNA
<213> ORGANISM: Homo sapiens

<400> SEQUENCE: 471
tacggaattg catctcctat g                                    21

<210> SEQ ID NO 472
<211> LENGTH: 21
<212> TYPE: DNA
<213> ORGANISM: Homo sapiens

<400> SEQUENCE: 472
cacgcggaca tctatgacaa a                                    21

<210> SEQ ID NO 473
<211> LENGTH: 21
<212> TYPE: DNA
<213> ORGANISM: Homo sapiens

<400> SEQUENCE: 473
ttaccacata ccgcgtcatc t                                    21

<210> SEQ ID NO 474
<211> LENGTH: 21
<212> TYPE: DNA
<213> ORGANISM: Homo sapiens

<400> SEQUENCE: 474
ccctacagca atgtgtccaa t                                    21

<210> SEQ ID NO 475
<211> LENGTH: 21
<212> TYPE: DNA
<213> ORGANISM: Homo sapiens

<400> SEQUENCE: 475
gactttgtcg tccgcatgat g                                    21

<210> SEQ ID NO 476
<211> LENGTH: 21
<212> TYPE: DNA
<213> ORGANISM: Homo sapiens

<400> SEQUENCE: 476
agatcagtgg gacacaacag g       21

<210> SEQ ID NO 477
<211> LENGTH: 21
<212> TYPE: DNA
<213> ORGANISM: Homo sapiens

<400> SEQUENCE: 477
tggtgttcaa tcgcatacta t       21

<210> SEQ ID NO 478
<211> LENGTH: 21
<212> TYPE: DNA
<213> ORGANISM: Homo sapiens

<400> SEQUENCE: 478
gtaattacat cccagaaaca c       21

<210> SEQ ID NO 479
<211> LENGTH: 21
<212> TYPE: DNA
<213> ORGANISM: Homo sapiens

<400> SEQUENCE: 479
cggttagatg agcttgagaa a       21

<210> SEQ ID NO 480
<211> LENGTH: 21
<212> TYPE: DNA
<213> ORGANISM: Homo sapiens

<400> SEQUENCE: 480
ccagtagtag tgcctgaagt a       21

<210> SEQ ID NO 481
<211> LENGTH: 21
<212> TYPE: DNA
<213> ORGANISM: Homo sapiens

<400> SEQUENCE: 481
taacccgaat gtgcaccata a       21

<210> SEQ ID NO 482
<211> LENGTH: 21
<212> TYPE: DNA
<213> ORGANISM: Homo sapiens

<400> SEQUENCE: 482
cccaactgta accagagata c       21

<210> SEQ ID NO 483
<211> LENGTH: 21
<212> TYPE: DNA
<213> ORGANISM: Homo sapiens

<400> SEQUENCE: 483
ccactgtaga aatgacaaga a       21

<210> SEQ ID NO 484
<211> LENGTH: 21
<212> TYPE: DNA
<213> ORGANISM: Homo sapiens

<400> SEQUENCE: 484
cctccgtcgt agtattcatg t       21

<210> SEQ ID NO 485
<211> LENGTH: 21
<212> TYPE: DNA
<213> ORGANISM: Homo sapiens

<400> SEQUENCE: 485
gccagtggtg aagagacttc t       21

<210> SEQ ID NO 486
<211> LENGTH: 21
<212> TYPE: DNA
<213> ORGANISM: Homo sapiens

<400> SEQUENCE: 486
ctcggcacac ggagattcta a       21

<210> SEQ ID NO 487
<211> LENGTH: 21
<212> TYPE: DNA
<213> ORGANISM: Homo sapiens

<400> SEQUENCE: 487
gacagtatcc caaaggttat t       21

<210> SEQ ID NO 488
<211> LENGTH: 21
<212> TYPE: DNA
<213> ORGANISM: Homo sapiens

<400> SEQUENCE: 488
gagtgcgctt gtattacata g       21

<210> SEQ ID NO 489
<211> LENGTH: 21
<212> TYPE: DNA
<213> ORGANISM: Homo sapiens

<400> SEQUENCE: 489
ctaagtgata gtgcaatctt t       21

<210> SEQ ID NO 490
<211> LENGTH: 21
<212> TYPE: DNA
<213> ORGANISM: Homo sapiens

<400> SEQUENCE: 490
tgcctaagtg atagtgcaat c       21

<210> SEQ ID NO 491
<211> LENGTH: 21
<212> TYPE: DNA
<213> ORGANISM: Homo sapiens

<400> SEQUENCE: 491
tttcgagctg ctggagcact a									21

<210> SEQ ID NO 492
<211> LENGTH: 21
<212> TYPE: DNA
<213> ORGANISM: Homo sapiens

<400> SEQUENCE: 492
tcgagctgct ggagcactac g									21

<210> SEQ ID NO 493
<211> LENGTH: 21
<212> TYPE: DNA
<213> ORGANISM: Homo sapiens

<400> SEQUENCE: 493
tcgccaacgg aactgcttct t									21

<210> SEQ ID NO 494
<211> LENGTH: 21
<212> TYPE: DNA
<213> ORGANISM: Homo sapiens

<400> SEQUENCE: 494
acttctggct ggagacctca t									21

<210> SEQ ID NO 495
<211> LENGTH: 21
<212> TYPE: DNA
<213> ORGANISM: Homo sapiens

<400> SEQUENCE: 495
gcgagacctt cgactgcctt t									21

<210> SEQ ID NO 496
<211> LENGTH: 21
<212> TYPE: DNA
<213> ORGANISM: Homo sapiens

<400> SEQUENCE: 496
cgacactcac ttccgcacct t									21

<210> SEQ ID NO 497
<211> LENGTH: 21
<212> TYPE: DNA
<213> ORGANISM: Homo sapiens

<400> SEQUENCE: 497
ctacctgagt tccttcccct t									21

<210> SEQ ID NO 498
<211> LENGTH: 21
<212> TYPE: DNA
<213> ORGANISM: Homo sapiens

<400> SEQUENCE: 498
ttccgctccc actccgatta c									21

<210> SEQ ID NO 499
<211> LENGTH: 21
<212> TYPE: DNA
<213> ORGANISM: Homo sapiens

<400> SEQUENCE: 499
taacccggta ctccgtgact a					21

<210> SEQ ID NO 500
<211> LENGTH: 21
<212> TYPE: DNA
<213> ORGANISM: Homo sapiens

<400> SEQUENCE: 500
tactccgtga ctacctgagt t					21

<210> SEQ ID NO 501
<211> LENGTH: 21
<212> TYPE: DNA
<213> ORGANISM: Homo sapiens

<400> SEQUENCE: 501
cttccgctcc cactccgatt a					21

<210> SEQ ID NO 502
<211> LENGTH: 21
<212> TYPE: DNA
<213> ORGANISM: Homo sapiens

<400> SEQUENCE: 502
gcgcgacagt cgccaacgga a					21

<210> SEQ ID NO 503
<211> LENGTH: 21
<212> TYPE: DNA
<213> ORGANISM: Homo sapiens

<400> SEQUENCE: 503
tggacgcctg cggcttctat t					21

<210> SEQ ID NO 504
<211> LENGTH: 21
<212> TYPE: DNA
<213> ORGANISM: Homo sapiens

<400> SEQUENCE: 504
cgcatccctc ttaacccggt a					21

<210> SEQ ID NO 505
<211> LENGTH: 21
<212> TYPE: DNA
<213> ORGANISM: Homo sapiens

<400> SEQUENCE: 505
tacatattcc cagtatcttt g					21

<210> SEQ ID NO 506
<211> LENGTH: 21
<212> TYPE: DNA
<213> ORGANISM: Homo sapiens

<400> SEQUENCE: 506
gcgccttatt atttcttatt a					21

<210> SEQ ID NO 507
<211> LENGTH: 21
<212> TYPE: DNA
<213> ORGANISM: Homo sapiens

```
<400> SEQUENCE: 507
ccgtgactac ctgagttcct t                                              21

<210> SEQ ID NO 508
<211> LENGTH: 21
<212> TYPE: DNA
<213> ORGANISM: Homo sapiens

<400> SEQUENCE: 508
ggagggtctc tggcttcatt t                                              21

<210> SEQ ID NO 509
<211> LENGTH: 21
<212> TYPE: DNA
<213> ORGANISM: Homo sapiens

<400> SEQUENCE: 509
ttcgcgctca gcgtgaagat g                                              21

<210> SEQ ID NO 510
<211> LENGTH: 21
<212> TYPE: DNA
<213> ORGANISM: Homo sapiens

<400> SEQUENCE: 510
atccctctta acccggtact c                                              21

<210> SEQ ID NO 511
<211> LENGTH: 21
<212> TYPE: DNA
<213> ORGANISM: Homo sapiens

<400> SEQUENCE: 511
cgagaagatt ccgctggtac t                                              21

<210> SEQ ID NO 512
<211> LENGTH: 21
<212> TYPE: DNA
<213> ORGANISM: Homo sapiens

<400> SEQUENCE: 512
gctgcaggag agcggattct a                                              21

<210> SEQ ID NO 513
<211> LENGTH: 21
<212> TYPE: DNA
<213> ORGANISM: Homo sapiens

<400> SEQUENCE: 513
ggctaggaga ctcgccttaa a                                              21

<210> SEQ ID NO 514
<211> LENGTH: 21
<212> TYPE: DNA
<213> ORGANISM: Homo sapiens

<400> SEQUENCE: 514
gctaggagac tcgccttaaa t                                              21

<210> SEQ ID NO 515
<211> LENGTH: 21
<212> TYPE: DNA
```

```
<213> ORGANISM: Homo sapiens

<400> SEQUENCE: 515
gagagcttac tacatctatt c                                              21

<210> SEQ ID NO 516
<211> LENGTH: 21
<212> TYPE: DNA
<213> ORGANISM: Homo sapiens

<400> SEQUENCE: 516
gggagttcct ggatcagtat g                                              21

<210> SEQ ID NO 517
<211> LENGTH: 21
<212> TYPE: DNA
<213> ORGANISM: Homo sapiens

<400> SEQUENCE: 517
caagagagct tactacatct a                                              21

<210> SEQ ID NO 518
<211> LENGTH: 21
<212> TYPE: DNA
<213> ORGANISM: Homo sapiens

<400> SEQUENCE: 518
cagtatgatg ctccacttta a                                              21

<210> SEQ ID NO 519
<211> LENGTH: 21
<212> TYPE: DNA
<213> ORGANISM: Homo sapiens

<400> SEQUENCE: 519
caagctggtg caccactaca t                                              21

<210> SEQ ID NO 520
<211> LENGTH: 21
<212> TYPE: DNA
<213> ORGANISM: Homo sapiens

<400> SEQUENCE: 520
acctggactc ctatgagaaa g                                              21

<210> SEQ ID NO 521
<211> LENGTH: 21
<212> TYPE: DNA
<213> ORGANISM: Homo sapiens

<400> SEQUENCE: 521
cttcttcacg ttgagcgtca a                                              21

<210> SEQ ID NO 522
<211> LENGTH: 21
<212> TYPE: DNA
<213> ORGANISM: Homo sapiens

<400> SEQUENCE: 522
tcgggagttc ctggatcagt a                                              21

<210> SEQ ID NO 523
<211> LENGTH: 21
```

-continued

<212> TYPE: DNA
<213> ORGANISM: Homo sapiens

<400> SEQUENCE: 523
tgcaggagag cggattctac t                                            21

<210> SEQ ID NO 524
<211> LENGTH: 21
<212> TYPE: DNA
<213> ORGANISM: Homo sapiens

<400> SEQUENCE: 524
cctggtggga caataccttt g                                            21

<210> SEQ ID NO 525
<211> LENGTH: 21
<212> TYPE: DNA
<213> ORGANISM: Homo sapiens

<400> SEQUENCE: 525
gatcagtatg atgctccact t                                            21

<210> SEQ ID NO 526
<211> LENGTH: 21
<212> TYPE: DNA
<213> ORGANISM: Homo sapiens

<400> SEQUENCE: 526
tcttcacgtt gagcgtcaag a                                            21

<210> SEQ ID NO 527
<211> LENGTH: 21
<212> TYPE: DNA
<213> ORGANISM: Homo sapiens

<400> SEQUENCE: 527
cgcttcgact gtgtactcaa g                                            21

<210> SEQ ID NO 528
<211> LENGTH: 21
<212> TYPE: DNA
<213> ORGANISM: Homo sapiens

<400> SEQUENCE: 528
ggagcaaaag ggtcagaggg g                                            21

<210> SEQ ID NO 529
<211> LENGTH: 21
<212> TYPE: DNA
<213> ORGANISM: Homo sapiens

<400> SEQUENCE: 529
agtgggactt tggaagcttg t                                            21

<210> SEQ ID NO 530
<211> LENGTH: 21
<212> TYPE: DNA
<213> ORGANISM: Homo sapiens

<400> SEQUENCE: 530
catctggact gactcggaaa t                                            21

<210> SEQ ID NO 531

-continued

<211> LENGTH: 21
<212> TYPE: DNA
<213> ORGANISM: Homo sapiens

<400> SEQUENCE: 531
atgctgcggg tggagaaatt t                                        21

<210> SEQ ID NO 532
<211> LENGTH: 21
<212> TYPE: DNA
<213> ORGANISM: Homo sapiens

<400> SEQUENCE: 532
tatctgaata tttctcaagt g                                        21

<210> SEQ ID NO 533
<211> LENGTH: 21
<212> TYPE: DNA
<213> ORGANISM: Homo sapiens

<400> SEQUENCE: 533
tttacctgag ttagccgaaa t                                        21

<210> SEQ ID NO 534
<211> LENGTH: 21
<212> TYPE: DNA
<213> ORGANISM: Homo sapiens

<400> SEQUENCE: 534
gttaactcat acatcaccat t                                        21

<210> SEQ ID NO 535
<211> LENGTH: 21
<212> TYPE: DNA
<213> ORGANISM: Homo sapiens

<400> SEQUENCE: 535
cctataccat aactctatta c                                        21

<210> SEQ ID NO 536
<211> LENGTH: 21
<212> TYPE: DNA
<213> ORGANISM: Homo sapiens

<400> SEQUENCE: 536
ctcaactatg atcccattac c                                        21

<210> SEQ ID NO 537
<211> LENGTH: 21
<212> TYPE: DNA
<213> ORGANISM: Homo sapiens

<400> SEQUENCE: 537
agacctccaa gtcctcctgt a                                        21

<210> SEQ ID NO 538
<211> LENGTH: 21
<212> TYPE: DNA
<213> ORGANISM: Homo sapiens

<400> SEQUENCE: 538
gctgtggtta gacaatgtat a                                        21

```
<210> SEQ ID NO 539
<211> LENGTH: 21
<212> TYPE: DNA
<213> ORGANISM: Homo sapiens

<400> SEQUENCE: 539
tattggcata atagcgtata t                                              21

<210> SEQ ID NO 540
<211> LENGTH: 21
<212> TYPE: DNA
<213> ORGANISM: Homo sapiens

<400> SEQUENCE: 540
gcttgtttca tcctgaggaa a                                              21

<210> SEQ ID NO 541
<211> LENGTH: 21
<212> TYPE: DNA
<213> ORGANISM: Homo sapiens

<400> SEQUENCE: 541
tcctcaacta tgatcccatt a                                              21

<210> SEQ ID NO 542
<211> LENGTH: 21
<212> TYPE: DNA
<213> ORGANISM: Homo sapiens

<400> SEQUENCE: 542
gcagaagcta aggacgaatt t                                              21

<210> SEQ ID NO 543
<211> LENGTH: 21
<212> TYPE: DNA
<213> ORGANISM: Homo sapiens

<400> SEQUENCE: 543
cagaataaca ttgttcacct t                                              21

<210> SEQ ID NO 544
<211> LENGTH: 21
<212> TYPE: DNA
<213> ORGANISM: Homo sapiens

<400> SEQUENCE: 544
tgcccagcgc agacttaatg a                                              21

<210> SEQ ID NO 545
<211> LENGTH: 21
<212> TYPE: DNA
<213> ORGANISM: Homo sapiens

<400> SEQUENCE: 545
cgtgacactc tgggaaatgt t                                              21

<210> SEQ ID NO 546
<211> LENGTH: 21
<212> TYPE: DNA
<213> ORGANISM: Homo sapiens

<400> SEQUENCE: 546
gtgtcccacc atatctcatc c                                              21
```

```
<210> SEQ ID NO 547
<211> LENGTH: 21
<212> TYPE: DNA
<213> ORGANISM: Homo sapiens

<400> SEQUENCE: 547
agtagcaata ccggatcact g                                             21

<210> SEQ ID NO 548
<211> LENGTH: 21
<212> TYPE: DNA
<213> ORGANISM: Homo sapiens

<400> SEQUENCE: 548
gcgggaagta tctgtcatga t                                             21

<210> SEQ ID NO 549
<211> LENGTH: 21
<212> TYPE: DNA
<213> ORGANISM: Homo sapiens

<400> SEQUENCE: 549
agaggatgcg aggcatttcc a                                             21

<210> SEQ ID NO 550
<211> LENGTH: 21
<212> TYPE: DNA
<213> ORGANISM: Homo sapiens

<400> SEQUENCE: 550
ggacagagag aaggcaacgt t                                             21

<210> SEQ ID NO 551
<211> LENGTH: 21
<212> TYPE: DNA
<213> ORGANISM: Homo sapiens

<400> SEQUENCE: 551
agaattgggt gtacaagata c                                             21

<210> SEQ ID NO 552
<211> LENGTH: 21
<212> TYPE: DNA
<213> ORGANISM: Homo sapiens

<400> SEQUENCE: 552
ccacctatta tctgcaactc t                                             21

<210> SEQ ID NO 553
<211> LENGTH: 21
<212> TYPE: DNA
<213> ORGANISM: Homo sapiens

<400> SEQUENCE: 553
gcctctgatg tgtggatgtt t                                             21

<210> SEQ ID NO 554
<211> LENGTH: 21
<212> TYPE: DNA
<213> ORGANISM: Homo sapiens

<400> SEQUENCE: 554
tgcagaggat gcgaggcatt t                                             21
```

<210> SEQ ID NO 555
<211> LENGTH: 21
<212> TYPE: DNA
<213> ORGANISM: Homo sapiens

<400> SEQUENCE: 555
tggcgtgaca ctctgggaaa t                                              21

<210> SEQ ID NO 556
<211> LENGTH: 21
<212> TYPE: DNA
<213> ORGANISM: Homo sapiens

<400> SEQUENCE: 556
cagacttaat gaagccctga a                                              21

<210> SEQ ID NO 557
<211> LENGTH: 21
<212> TYPE: DNA
<213> ORGANISM: Homo sapiens

<400> SEQUENCE: 557
gtgttgtaca tcgagggtta t                                              21

<210> SEQ ID NO 558
<211> LENGTH: 21
<212> TYPE: DNA
<213> ORGANISM: Homo sapiens

<400> SEQUENCE: 558
ccagaacttc ggcgtacaag a                                              21

<210> SEQ ID NO 559
<211> LENGTH: 21
<212> TYPE: DNA
<213> ORGANISM: Homo sapiens

<400> SEQUENCE: 559
gaagtatcag cggtatcatt t                                              21

<210> SEQ ID NO 560
<211> LENGTH: 21
<212> TYPE: DNA
<213> ORGANISM: Homo sapiens

<400> SEQUENCE: 560
atggattgtt atcgcttata t                                              21

<210> SEQ ID NO 561
<211> LENGTH: 21
<212> TYPE: DNA
<213> ORGANISM: Homo sapiens

<400> SEQUENCE: 561
gcttggaaag ggtcttatta a                                              21

<210> SEQ ID NO 562
<211> LENGTH: 21
<212> TYPE: DNA
<213> ORGANISM: Homo sapiens

<400> SEQUENCE: 562
attgaatccc ttgagcaaat t                                              21

<210> SEQ ID NO 563
<211> LENGTH: 21
<212> TYPE: DNA
<213> ORGANISM: Homo sapiens

<400> SEQUENCE: 563
ccttatcaaa ccctattgaa t                                              21

<210> SEQ ID NO 564
<211> LENGTH: 21
<212> TYPE: DNA
<213> ORGANISM: Homo sapiens

<400> SEQUENCE: 564
ccaaagatca agaacccatt t                                              21

<210> SEQ ID NO 565
<211> LENGTH: 21
<212> TYPE: DNA
<213> ORGANISM: Homo sapiens

<400> SEQUENCE: 565
tagaggtaat gttctcattg a                                              21

<210> SEQ ID NO 566
<211> LENGTH: 21
<212> TYPE: DNA
<213> ORGANISM: Homo sapiens

<400> SEQUENCE: 566
accggattgg ttacgagata g                                              21

<210> SEQ ID NO 567
<211> LENGTH: 21
<212> TYPE: DNA
<213> ORGANISM: Homo sapiens

<400> SEQUENCE: 567
acctggtgca ggaccattaa c                                              21

<210> SEQ ID NO 568
<211> LENGTH: 21
<212> TYPE: DNA
<213> ORGANISM: Homo sapiens

<400> SEQUENCE: 568
tagactttct agccgtaaat c                                              21

<210> SEQ ID NO 569
<211> LENGTH: 21
<212> TYPE: DNA
<213> ORGANISM: Homo sapiens

<400> SEQUENCE: 569
ctagactttc tagccgtaaa t                                              21

<210> SEQ ID NO 570
<211> LENGTH: 21
<212> TYPE: DNA
<213> ORGANISM: Homo sapiens

<400> SEQUENCE: 570

| | |
|---|---|
| cctcaggatg agtcatcaga t | 21 |

<210> SEQ ID NO 571
<211> LENGTH: 21
<212> TYPE: DNA
<213> ORGANISM: Homo sapiens

<400> SEQUENCE: 571

| | |
|---|---|
| cctggtataa ggtcatatta a | 21 |

<210> SEQ ID NO 572
<211> LENGTH: 21
<212> TYPE: DNA
<213> ORGANISM: Homo sapiens

<400> SEQUENCE: 572

| | |
|---|---|
| gctcagaatc ttattgatga t | 21 |

<210> SEQ ID NO 573
<211> LENGTH: 21
<212> TYPE: DNA
<213> ORGANISM: Homo sapiens

<400> SEQUENCE: 573

| | |
|---|---|
| gccctaacag tagatacatt g | 21 |

<210> SEQ ID NO 574
<211> LENGTH: 21
<212> TYPE: DNA
<213> ORGANISM: Homo sapiens

<400> SEQUENCE: 574

| | |
|---|---|
| cttactcaca tggcaattat t | 21 |

<210> SEQ ID NO 575
<211> LENGTH: 21
<212> TYPE: DNA
<213> ORGANISM: Homo sapiens

<400> SEQUENCE: 575

| | |
|---|---|
| gcacaactga agcatcactc t | 21 |

<210> SEQ ID NO 576
<211> LENGTH: 21
<212> TYPE: DNA
<213> ORGANISM: Homo sapiens

<400> SEQUENCE: 576

| | |
|---|---|
| gcacaagtgg atgaactgaa a | 21 |

<210> SEQ ID NO 577
<211> LENGTH: 21
<212> TYPE: DNA
<213> ORGANISM: Homo sapiens

<400> SEQUENCE: 577

| | |
|---|---|
| ttacggttca agagcacaaa c | 21 |

<210> SEQ ID NO 578
<211> LENGTH: 21
<212> TYPE: DNA
<213> ORGANISM: Homo sapiens

```
<400> SEQUENCE: 578
taagagccta gacaaagtga t                                        21

<210> SEQ ID NO 579
<211> LENGTH: 21
<212> TYPE: DNA
<213> ORGANISM: Homo sapiens

<400> SEQUENCE: 579
agccatgtgt atgaagaata t                                        21

<210> SEQ ID NO 580
<211> LENGTH: 21
<212> TYPE: DNA
<213> ORGANISM: Homo sapiens

<400> SEQUENCE: 580
tccaggagcc catacaagta a                                        21

<210> SEQ ID NO 581
<211> LENGTH: 21
<212> TYPE: DNA
<213> ORGANISM: Homo sapiens

<400> SEQUENCE: 581
ataaactaac ttactcacat g                                        21

<210> SEQ ID NO 582
<211> LENGTH: 21
<212> TYPE: DNA
<213> ORGANISM: Homo sapiens

<400> SEQUENCE: 582
gccgccacat ttcgttgtaa a                                        21

<210> SEQ ID NO 583
<211> LENGTH: 21
<212> TYPE: DNA
<213> ORGANISM: Homo sapiens

<400> SEQUENCE: 583
gcacttcctt atgctatgaa t                                        21

<210> SEQ ID NO 584
<211> LENGTH: 21
<212> TYPE: DNA
<213> ORGANISM: Homo sapiens

<400> SEQUENCE: 584
gccttaagat atgcaatgtt a                                        21

<210> SEQ ID NO 585
<211> LENGTH: 21
<212> TYPE: DNA
<213> ORGANISM: Homo sapiens

<400> SEQUENCE: 585
ctgaaaggaa taatggtcag a                                        21

<210> SEQ ID NO 586
<211> LENGTH: 21
<212> TYPE: DNA
<213> ORGANISM: Homo sapiens
```

```
<400> SEQUENCE: 586
ctccttgtaa atgatacaca a                                              21

<210> SEQ ID NO 587
<211> LENGTH: 21
<212> TYPE: DNA
<213> ORGANISM: Homo sapiens

<400> SEQUENCE: 587
ctttgcctgt catatagttt g                                              21

<210> SEQ ID NO 588
<211> LENGTH: 21
<212> TYPE: DNA
<213> ORGANISM: Homo sapiens

<400> SEQUENCE: 588
tcgagccatg tgtatgaaga a                                              21

<210> SEQ ID NO 589
<211> LENGTH: 21
<212> TYPE: DNA
<213> ORGANISM: Homo sapiens

<400> SEQUENCE: 589
atccctagca attacgtagt g                                              21

<210> SEQ ID NO 590
<211> LENGTH: 21
<212> TYPE: DNA
<213> ORGANISM: Homo sapiens

<400> SEQUENCE: 590
tggttatatc cctagcaatt a                                              21

<210> SEQ ID NO 591
<211> LENGTH: 21
<212> TYPE: DNA
<213> ORGANISM: Homo sapiens

<400> SEQUENCE: 591
tatgcttcac tcggcatgtt t                                              21

<210> SEQ ID NO 592
<211> LENGTH: 21
<212> TYPE: DNA
<213> ORGANISM: Homo sapiens

<400> SEQUENCE: 592
attccagata cggttactca a                                              21

<210> SEQ ID NO 593
<211> LENGTH: 21
<212> TYPE: DNA
<213> ORGANISM: Homo sapiens

<400> SEQUENCE: 593
tttaagaagg gtgaacgatt t                                              21

<210> SEQ ID NO 594
<211> LENGTH: 21
<212> TYPE: DNA
```

<213> ORGANISM: Homo sapiens

<400> SEQUENCE: 594
cacgaccaga gctcagtttg a                                              21

<210> SEQ ID NO 595
<211> LENGTH: 21
<212> TYPE: DNA
<213> ORGANISM: Homo sapiens

<400> SEQUENCE: 595
caggtatggt aaaccgtgaa g                                              21

<210> SEQ ID NO 596
<211> LENGTH: 21
<212> TYPE: DNA
<213> ORGANISM: Homo sapiens

<400> SEQUENCE: 596
ggagtggaac atgctacagt t                                              21

<210> SEQ ID NO 597
<211> LENGTH: 21
<212> TYPE: DNA
<213> ORGANISM: Homo sapiens

<400> SEQUENCE: 597
cctcattctc agtggtgtca a                                              21

<210> SEQ ID NO 598
<211> LENGTH: 21
<212> TYPE: DNA
<213> ORGANISM: Homo sapiens

<400> SEQUENCE: 598
tcgagaatca ttgcgactag a                                              21

<210> SEQ ID NO 599
<211> LENGTH: 21
<212> TYPE: DNA
<213> ORGANISM: Homo sapiens

<400> SEQUENCE: 599
ccaggtacaa tgatgccaga a                                              21

<210> SEQ ID NO 600
<211> LENGTH: 21
<212> TYPE: DNA
<213> ORGANISM: Homo sapiens

<400> SEQUENCE: 600
gcggaaagat tacttctgaa t                                              21

<210> SEQ ID NO 601
<211> LENGTH: 21
<212> TYPE: DNA
<213> ORGANISM: Homo sapiens

<400> SEQUENCE: 601
gctgctctgt atggtcgatt t                                              21

<210> SEQ ID NO 602
<211> LENGTH: 21

<212> TYPE: DNA
<213> ORGANISM: Homo sapiens

<400> SEQUENCE: 602
ccttgtatga ttatgaagct a                                              21

<210> SEQ ID NO 603
<211> LENGTH: 21
<212> TYPE: DNA
<213> ORGANISM: Homo sapiens

<400> SEQUENCE: 603
gccagtcatt atggagtgga a                                              21

<210> SEQ ID NO 604
<211> LENGTH: 2466
<212> TYPE: DNA
<213> ORGANISM: Homo sapiens

<400> SEQUENCE: 604
gtgtccggcc aagcggcgcc ctgaaggcgt gtccggccgc agcttaggct ctccgggagt    60
ccccggagag taggggcggc cggcggcgct agtcttctgg ggagcgccgg gtgcacaccg   120
gaccactgcg ggaggcctag ggccgagggc cgaggagctg gcctgcgccc ggcgaccccg   180
gcttccctcc gcagtcgccc aggcgtccct tcccccctac agccgagcgg cgccgggcgc   240
aggcgcattg ggcgccccg gcagcccccg cggcccgccc cgtccgctgc ccgtccgagg    300
aggcggaggg cgatgacgtc atcgagcggg gcgacgggca ttgggcgcca ttttgaaaag   360
ggaaaaaaat ccctccccgg cggcggcggc ggcggcggcc gcgccggcgg tggtggcggc   420
cccggggctg agcgctcggc tgcagcggcg cggaggccgt ctccctggtc tgccgcggtc   480
cccgcccgtc ccgccgccgg ctgccatggc aggagccgga ggcggcggct gccccgcggg   540
cggcaacgac ttccagtggt gcttctcgca ggtcaagggg gccatcgacg aggacgtggc   600
cgaagcggac atcatttcca ccgttgagtt taattactct ggagatcttc ttgcaacagg   660
agacaagggc ggcagagttg ttatttttca gcgtgaacaa gagaataaaa gccgccctca   720
ttctagggga gaatataatg tttacagcac cttttcaaagt catgaaccgg agtttgacta   780
tttgaaaagt ctagaaattg aggaaaaaat taataaaatt aggtggttac cacaacagaa   840
tgctgctcat tttctactgt ctacaaatga taaaactata aaattatgga aaataagtga   900
acgggataaa agagcagaag gttataacct gaaagacgaa gatggaagac ttcgagaccc   960
atttaggatc acggcgctac gggtcccaat attgaagccc atggatctta tggtagaagc  1020
gagtccacgg cgaatttttg caaatgctca cacatatcat ataaattcca tttcagtaaa  1080
tagtgatcat gaaacatatc tttctgcaga tgacctgaga attaatttat ggcacttaga  1140
aatcacagat agaagcttta acatcgtgga catcaagcct gctaacatgg aggagctgac  1200
cgaagtcatc actgcagccg agttccaccc gcaccagtgc aacgtgttcg tctacagcag  1260
tagcaaaggg accatccgcc tgtgtgacat gcgctcctcg gccctgtgcg acagacactc  1320 caagttttttt gaagagcctg aagatcccag cagtaggtcc ttcttctcag aaataatttc  1380
atccatatcc gatgtaaaat tcagtcatag tgggcggtac atgatgacca gagactacct  1440
gtcggtgaag gtgtgggacc tcaacatgga gagcaggccg gtggagaccc accaggtcca  1500
cgagtacctg cgcagcaagc tctgctctct ctatgagaac gactgcatct ttgacaagtt  1560
tgagtgttgc tggaacggtt cggatagcgc catcatgacc gggtcctata caacttctt   1620

```
caggatgttt gatagagaca cgcggaggga tgtgaccctg gaggcctcga gagagagcag    1680
caaaccgcgc gccagcctca aaccccggaa ggtgtgtacg gggggtaagc ggaggaaaga    1740
cgagatcagt gtggacagtc tggacttcaa caagaagatc ctgcacacag cctggcaccc    1800
cgtggacaat gtcattgccg tggctgccac caataacttg tacatattcc aggacaaaat    1860
caactagaga cgcgaacgtg aggaccaagt cttgtcttgc atagttaagc cggacatttt    1920
tctgtcagag aaaaggcatc attgtccgct ccattaagaa cagtgacgca cctgctactt    1980
cccttcacag acacaggaga aagccgcctc cgctggaggc ccggtgtggt tccgcctcgg    2040
cgaggcgcga gacaggcgct gctgctcacg tggagacgct ctcgaagcag agttgacgga    2100
cactgctccc aaaaggtcat tactcagaat aaatgtattt atttcagtcc gagccttcct    2160
ttccaattta tagaccaaaa aattaacatc aagagaaaa gttattgtca gataccgctc     2220
tttctccaac tttccctctt tctctgccat cacacttggg ccttcactgc agcgtggtgt    2280
ggccaccgtc cgtgtcctct cggccttcct ccgagtccag gtggactctg tggatgtgtg    2340
gatgtggccc gagcaggctc aggcggcccc actcacccac agcatccgcc gccacccctt    2400
cgggtgtgag cgctcaataa aaacaacaca ctataaagtg ttttaaatc caaaaaaaa      2460 aaaaaa                                                               2466

<210> SEQ ID NO 605
<211> LENGTH: 4665
<212> TYPE: DNA
<213> ORGANISM: Homo sapiens

<400> SEQUENCE: 605
ggaaagtcca ccttccccaa caaggccagc ctgggaacat ggagtggcag cggccgcagc      60
caatgagaga gcaaacgcgc ggaaagtttg ctcaatgggc gatgtccgag ataggctgtc     120
actcaggtgg cagcggcaga ggccgggctg agacgtggcc aggggaacac ggctggctgt     180
ccaggccgtc ggggcggcag tagggtccct agcacgtcct tgccttcttg ggagctccaa     240
gcggcgggag aggcaggcgt cagtggctgc gcctccatgc ctgcgcgcgg ggcgggacgc     300
tgatggagcg cgccatcagc ccggggctgc tggtacgggc gctgctgctg ctgctgctgc     360
tgctggggct cgcggcaagg acggtggccg cggggcgcgc ccgtggcctc ccagcgccga     420
cggcggaggc ggcgttcggc ctcggggcgg ccgctgctcc cacctcagcg acgcgagtac     480
cggcggcggg cgccgtggct gcggccgagg tgactgtgga ggacgctgag cgctgccgg     540 cagccgcggg agagcaggag cctcggggtc cggaaccaga cgatgagaca gagttgcgac     600
cgcgcggcag gtcattagta attatcagca ctttagatgg gagaattgct gccttggatc     660
ctgaaaatca tggtaaaaag cagtgggatt tggatgtggg atccggttcc ttggtgtcat     720
ccagccttag caaaccagag gtatttggga ataagatgat cattccttcc ctggatggag     780
ccctcttcca gtgggaccaa gaccgtgaaa gcatggaaac agttcctttc acagttgaat     840
cacttcttga atcttcttat aaatttggag atgatgttgt tttggttgga ggaaaatctc     900
tgactacata tggactcagt gcatatagtg aaaggtgag gtatatctgt tcagctctgg     960
gttgtcgcca atgggatagt gacgaaatgg aacaagagga agacatcctg cttctacagc    1020
gtacccaaaa aactgttaga gctgtcggac ctcgcagtgg caatgagaag tggaatttca    1080
gtgttggcca ctttgaactt cggtatattc cagacatgga aacgagagcc ggatttattg    1140
aaagcacctt taagcccaat gagaacacag aagagtctaa aattatttca gatgtggaag    1200
aacaggaagc tgccataatg gacatagtga taaaggtttc ggttgctgac tggaaagtta    1260
```

```
tggcattcag taagaaggga ggacatctgg aatgggagta ccagttttgt actccaattg    1320
catctgcctg gttacttaag gatgggaaag tcattcccat cagtcttttt gatgatacaa    1380
gttatacatc taatgatgat gttttagaag atgaagaaga cattgtagaa gctgccagag    1440
gagccacaga aaacagtgtt tacttgggaa tgtatagagg ccagctgtat ctgcagtcat    1500
cagtcagaat tcagaaaag ttccttcaa gtcccaaggc tttggaatct gtcactaatg    1560
aaaacgcaat tattccttta ccaacaatca aatggaaacc cttaattcat tctccttcca    1620
gaactcctgt cttggtagga tctgatgaat ttgacaaatg tctcagtaat gataagtttt    1680
ctcatgaaga atatagtaat ggtgcactt caatcttgca gtatccatat gataatggtt    1740
attatctacc atactacaag agggagagga acaaacgaag cacacagatt acagtcagat    1800
tcctcgacaa cccacattac aacaagaata tccgcaaaaa ggatcctgtt cttcttttac    1860
actggtggaa agaaatagtt gcaacgattt tgttttgtat catagcaaca acgtttattg    1920
tgcgcaggct tttccatcct catcctcaca ggcaaaggaa ggagtctgaa actcagtgtc    1980
aaactgaaaa taaatatgat tctgtaagtg gtgaagccaa tgacagtagc tggaatgaca    2040
taaaaaactc tggatatata tcacgatatc taactgattt tgagccaatt caatgcctgg    2100
gacgtggtgg cttggagtt gtttttgaag ctaaaaacaa agtagatgac tgcaattatg    2160
ctatcaagag gatccgtctc cccaataggg aattggctcg ggaaaaggta atgcgagaag    2220
ttaaagcctt agccaagctt gaacacccgg gcattgttag atatttcaat gcctggctcg    2280
aagcaccacc agagaagtgg caagaaaaga tggatgaaat ttggctgaaa gatgaaagca    2340
cagactggcc actcagctct cctagcccaa tggatgcacc atcagttaaa atacgcagaa    2400
tggatccttt cgctacaaaa gaacatattg aaatcatagc tccttcacca caaagaagca    2460 ggtcttttc agtagggatt tcctgtgacc agacaagttc atctgagagc cagttctcac    2520
cactggaatt ctcaggaatg gaccatgagg acatcagtga gtcagtggat gcagcataca    2580
acctccagga cagttgcctt acagactgtg atgtggaaga tgggactatg gatggcaatg    2640 atgagggca ctcctttgaa cttgtcctt ctgaagcttc tccttatgta aggtcaaggg    2700
agagaacctc ctcttcaata gtatttgaag attctggctg tgataatgct tccagtaaag    2760
aagagccgaa aactaatcga ttgcatattg gcaaccattg tgctaataaa ctaactgctt    2820
tcaagcccac cagtagcaaa tcttcttctg aagctcatt gtctatttct cctccaagac    2880
caaccacttt aagtttagat ctcactaaaa acaccacaga aaaactccag cccagttcac    2940
caaaggtgta tctttacatt caaatgcagc tgtgcagaaa agaaaacctc aaagactgga    3000
tgaatggacg atgtaccata gaggagagag agaggagcgt gtgtctgcac atcttcctgc    3060
agatcgcaga ggcagtggag tttcttcaca gtaaaggact gatgcacagg gacctcaagc    3120
catccaacat attctttaca atggatgatg tggtcaaggt tggagacttt gggttagtga    3180
ctgcaatgga ccaggatgag gaagagcaga cggttctgac cccaatgcca gcttatgcca    3240
gacacacagg acaagtaggg accaaactgt atatgagccc agagcagatt catggaaaca    3300
gctattctca taaagtggac atcttttctt taggcctgat tctatttgaa ttgctgtatc    3360
cattcagcac tcagatggag agagtcagga ccttaactga tgtaagaaat ctcaaatttc    3420
caccattatt tactcagaaa tatccttgtg agtacgtgat ggttcaagac atgctctctc    3480
catcccccat ggaacgacct gaagctataa acatcattga aaatgctgta tttgaggact    3540
tggactttcc aggaaaaaca gtgctcagac agaggtctcg ctccttgagt tcatcgggaa    3600
```

| | |
|---|---|
| caaaacattc aagacagtcc aacaactccc atagcccttt gccaagcaat tagccttaag | 3660 |
| ttgtgctagc aaccctaata ggtgatgcag ataatagcct acttcttaga atatgcctgt | 3720 |
| ccaaaattgc agacttgaaa agtttgttct tcgctcaatt tttttgtgga ctacttttt | 3780 |
| tatatcaaat ttaagctgga tttgggggca taacctaatt tgagccaact cctgagtttt | 3840 |
| gctatactta aggaaagggc tatctttgtt ctttgttagt ctcttgaaac tggctgctgg | 3900 |
| ccaagcttta tagccctcac catttgccta aggaggtagc agcaatccct aatatatata | 3960 |
| tatagtgaga actaaaatgg atatatttt ataatgcaga agaaggaaag tccccctgtg | 4020 |
| tggtaactgt attgttctag aaatatgctt tctagagata tgatgatttt gaaactgatt | 4080 |
| tctagaaaaa gctgactcca ttttgtccc tggcgggtaa attaggaatc tgcactattt | 4140 |
| tggaggacaa gtagcacaaa ctgtataacg gttatgtcc gtagttttat agtcctattt | 4200 |
| gtagcattca atagctttat ccttagatg gttctagggt gggtttacag cttttgtac | 4260 |
| ttttacctcc aataaaggga aaatgaagct tttatgtaa attggttgaa aggtctagtt | 4320 |
| ttgggaggaa aaaagccgta gtaagaaatg gatcatatat attacaacta acttcttcaa | 4380 |
| ctatggactt tttaagccta atgaaatctt aagtgtctta tatgtaatcc tgtaggttgg | 4440 |
| tacttccccc aaactgatta taggtaacag tttaatcatc tcacttgcta acatgttttt | 4500 |
| atttttcact gtaaatatgt ttatgtttta tttataaaaa ttctgaaatc aatccatttg | 4560 |
| ggttggtggt gtacagaaca cacttaagtg tgttaacttg tgacttcttt caagtctaaa | 4620 |
| tgatttaata aaacttttt taaattaaaa aaaaaaaaa aaaaa | 4665 |

<210> SEQ ID NO 606
<211> LENGTH: 9604
<212> TYPE: DNA
<213> ORGANISM: Homo sapiens

<400> SEQUENCE: 606

| | |
|---|---|
| ctcggtgagc gcgccgagga agagaggcga gcggagagtg gaggaggagg cggcggcggc | 60 |
| gggagcggtc cccaggaatg tcgctgccgc cgccaccgcc ggggccgctg ccgttgagga | 120 |
| ggagacggag gagaccgacg ttgttaggaa gatgatccct atgatcttga agatgtttct | 180 |
| gcacagaaat gagggaaata caaagaacca atacagttc tgaaatttgg gatctgtatt | 240 |
| ttgagatgat tttatttca gaatgagaag catatctggt tacctttatg aatgtagaga | 300 |
| catgagaaga gagttatgat ggcaaaaaac aaagagcctc gtcccccatc ctataccatc | 360 |
| agtatagttg gactctctgg gactgaaaaa gacaaaggta actgtggagt tggaaagtct | 420 |
| tgtttgtgca atagatttgt acgctcaaaa gcagatgaat attatccaga gcatacttct | 480 |
| gtgcttagca ccattgactt tggaggacga gtagtaaaca atgatcactt tttgtactgg | 540 |
| ggtgacataa tacaaaatag tgaagatgga gtagaatgca aaattcatgt cattgaacaa | 600 |
| acagagttca ttgatgacca gactttcttg cctcatcgga gtacgaattt gcaaccatat | 660 |
| ataaaacgtg cagctgcatc taaattgcag tcagcagaaa aactaatgta catttgcact | 720 |
| gatcagctag gcttagaaca agactttgaa cagaagcaaa tgcctgaagg gaagctcaac | 780 |
| gtagatggat tttattatg cattgatgta agtcaaggat gcaataggaa gtttgatgat | 840 |
| caacttaaat ttgtgaataa ccttttgtc cagttatcaa aatcaaaaaa acctgtaata | 900 |
| atagcagcaa ctaaatgtga tgaatgcgtg atcattatc ttagagaagt tcaggcattt | 960 |
| gcttcaaata aaaagaacct tcttgtagtg gaaacatcag cacgatttaa tgtcaacatt | 1020 |
| gaaacatgtt ttactgcact ggtacaaatg ttggataaaa ctcgtagcaa gcctaaaatt | 1080 |

```
attccctatt tggatgctta taaaacacag agacaacttg ttgtcacagc aacagataag    1140
tttgaaaaac ttgtgcagac tgtgagagat tatcatgcaa cttggaaaac tgttagtaat    1200
aaattaaaaa atcatcctga ttatgaagaa tacatcaact tagagggaac aagaaaggcc    1260
agaaatacat tctcaaaaca tatagaacaa cttaaacagg aacatataag aaaaaggaga    1320
gaagagtata taaatacttt accaagagct tttaacactc ttttgccaaa tctagaagag    1380
attgaacatt tgaattggtc agaagctttg aagttaatgg aaaagagagc agatttccag    1440
ttatgttttg tggtgctaga aaaaactcct tgggatgaaa ctgaccatat agacaaaatt    1500
aatgataggc ggattccatt tgacctcctg agcactttag aagctgaaaa agtctatcag    1560
aaccatgtac agcatctgat atccgagaag aggagggtgg aaatgaagga aaaattcaaa    1620
aagactttgg aaaaaattca attcatttca ccagggcagc catgggagga agttatgtgc    1680
tttgttatgg aggatgaagc ctacaaatat atcactgagg ctgatagcaa agaggtatat    1740
ggtaggcatc agcgagaaat agttgaaaaa gccaaagaag agtttcaaga aatgcttttt    1800
gagcattctg aacttttta tgatttagat cttaatgcaa cacctagttc agataaaatg    1860
agtgaaattc atacagttct gagtgaagaa cctagatata aagctttaca gaaacttgca    1920
cctgataggg aatcccttct acttaagcat ataggatttg tttatcatcc cactaaagaa    1980
acatgtctta gtggccaaaa ttgtacagac attaaagtgg agcagttact tgctagtagt    2040
cttttacagt tggatcatgg ccgcttaaga ttatatcacg atagtaccaa tatagataaa    2100
gttaaccttt ttattttagg gaaggatggc cttgcccaag aactagcaaa tgagataagg    2160
acacaatcca ctgatgatga gtatgcctta gatggaaaaa tttatgaact tgatcttcgg    2220
ccggttgatg ccaaatcgcc ttacttttg agtcagttat ggactgccgc ctttaaacca    2280
catgggtgct tctgtgtatt taattccatt gagtcattga gttttattgg ggaatttatt    2340
gggaaaataa gaactgaagc ttctcagatc agaaaagata atacatggc taatcttcca    2400 tttacattaa ttctggctaa tcagagagat tccattagta agaatctacc aattctcagg    2460
caccaagggc agcagttggc aaacaagttg caatgtcctt ttgtagatgt acctgctggt    2520
acatatcctc gtaaatttaa tgaaacccaa ataaagcaag ctctcagagg agtattggaa    2580
tcagttaaac acaatttgga tgtggtgagc ccaattcctg ccaataagga cttatcagaa    2640
gctgacttga gaattgtcat gtgcgccatg tgtggagatc catttagtgt ggatcttatt    2700
ctttcaccct tccttgattc tcattcttgc agtgctgctc aagctggaca gaataattcc    2760
ctaatgcttg ataaaatcat tggtgaaaaa aggaggcgaa tacagatcac aatattatca    2820
taccactctt caattggagt aagaaaagat gaactagttc atgggtatat attagtttac    2880
tctgcaaaac ggaaagcttc gatgggaatg cttcgagcat ttctatcaga agttcaagac    2940
accattcctg tacagctggt ggcagttact gacagccaag cagattttt tgaaaatgag    3000 gctatcaaag agttaatgac tgaaggagaa cacattgcaa ctgagatcac tgctaaattt    3060
acagcactgt attctttatc tcagtatcat cggcaaactg aggtctttac tctgttttt    3120 agtgatgttc tagagaaaaa aaatatgata gaaaattctt atttgtctga ataacaagg    3180 gaatcaaccc atcaaagtga agatgttttt ctaccatctc ccagagactg tttcccctat    3240
aataactacc ctgattcaga tgatgacaca gaagcaccac ctccttatag tccaattggg    3300
gatgatgtac agttgcttcc aacacctagt gaccgttcca gatatagatt agatttggaa    3360
ggaaatgagt atccctattca tagtacccca aactgtcatg accatgaacg caaccataaa    3420
```

```
gtgcctccac ctattaaacc taaaccagtt gtacctaaga caaatgtgaa aaaactcgat    3480 ccaaacctttt taaaaacaat tgaagctggt attggtaaaa atccaagaaa gcagacttcc    3540
cgggtgcctt tggcacatcc tgaagatatg gatccttcag ataactatgc ggaacccatt    3600 gatacaatt tcaaacagaa gggctattct gatgagattt atgttgtccc agatgatagt    3660
caaaatcgta ttaaaattcg aaactcattt gtaaataaca cccaaggaga tgaagaaaat    3720
gggttttctg atagaacctc aaaaagtcat ggggaacgga ggccttcaaa atacaaatat    3780
aaatctaaaa ccttgtttag taaagccaag tcatactata gaagaacaca ttcagatgcc    3840
agtgatgatg aggctttcac cacttctaaa acaaaaagaa aaggaagaca tcgtggaagt    3900
gaagaagatc cacttctttc tcctgttgaa acttggaaag gtggtattga taatcctgca    3960
atcacttctg accaggagtt agatgataag aagatgaaga agaaaaccca caaagtgaaa    4020
gaagataaaa agcagaaaaa gaaaactaag aacttcaatc caccaacacg tagaaattgg    4080
gaaagtaatt actttgggat gcccctccag gatctggtta cagctgagaa gcccatacca    4140
ctatttgttg agaaatgtgt ggaatttatt gaagatacag ggttatgtac cgaaggactc    4200
taccgtgtca gcgggaataa aactgaccaa gacaatattc aaaagcagtt tgatcaagat    4260
cataatatca atctagtgtc aatggaagta acagtaaatg ctgtagctgg agcccttaaa    4320
gctttctttg cagatctgcc agatcctta attccatatt ctcttcatcc agaactattg    4380
gaagcagcaa aaatcccgga taaaacagaa cgtcttcatg ccttgaaaga aattgttaag    4440
aaatttcatc ctgtaaacta tgatgtattc agatacgtga taacacatct aaacagggtt    4500
agtcagcaac ataaaatcaa cctaatgaca gcagacaact tatccatctg tttttggcca    4560
accttgatga gacctgattt tgaaaatcga gagtttctgt ctactactaa gattcatcaa    4620
tctgttgttg aaacattcat tcagcagtgt cagttttctct tttacaatgg agaaattgta    4680
gaaacgacaa acattgtggc tcctccacca ccttcaaacc caggacagtt ggtggaacca    4740
atggtgccac ttcagttgcc gccaccattg caacctcagc tgatcaaacc acaattacaa    4800
acggatcctc ttggtattat atgagtagga agtgattgca acaggctgg attttggacaa    4860 aaagcaaatc tagacatgca tgtttcaggg ttcagtagta acttcatgt ttcatacaga    4920 taattcacat tcaaaattac attttctctt tgaactagat ggtattcctt attcacttac    4980
attacaaatc taagaccatg tgataagcat gactggagag gtttaatttt tataaacaaa    5040
aatagctata aagtacaaag ctgctgctgc atgcaaccct attgcaatca gtatatcatt    5100
cctgtggcaa tttctgtcac cttatattgt gaataaaatt tttctataga aattaaatga    5160
tttaaaaact cacctatatg aaacatttaa tgcttttcag cctgctttct ggctgatttt    5220
gttatttgat gtgctaattt gggcaactta atttacattc tggcagtcgg tgtagataac    5280
taaaagccca gttaagtatt ttataatttc aggctactga ggccatgctt gggatgttgt    5340
ttgaaagaaa gaaaaaatac acttgacata tttcacattt ctgtaccttc atctttactt    5400
ccaagtaaac ccgtggatga tttgatgagg gataaatgaa cctatttctt ttacacacat    5460
accaaggaca tgcttgtggc taaagtgagt tgataatgtt gtgcaaagga tagttgtcac    5520
caactcattt ctttatggtc cataatgaaa taaaatttt gtatactgtt aattctgtaa    5580
acagatgcat gttcaaaaga tctatgatgg tcttgtaatc ttaatctaat atattttaga    5640
tattttaatt ttttcccttct tggggaacac atttagtata gtgtagaaaa tacttccatg    5700
acattttcat ataaggttat ataacttttc atacataaac atgaaatttg ttgtagaaaa    5760
ttctttaaac caaacatttta aatctaggac ttcaatttaa tttgttcctt gaatctattt    5820
```

-continued

| | | |
|---|---|---|
| ttatgtggcc cttaaaaaat atccaaaaaa cccattgcta atatagcaat aaaaatactt | 5880 |
| tgggtactga cagactcttt ggagtgttta tattacaaat ttgtattcat attcttttct | 5940 |
| gtgatgtgtt gtactaaaat ccaaaatggc ttttgcacca ttttttaagcc aattttttcc | 6000 |
| tttgatgttg gtaccagaat tactataagt gactgctgct tttgggggta aacattttgt | 6060 |
| tagtgaagat aaaaccagaa cactaaatta tggataaaat tttcagaata ggtggcacag | 6120 |
| gtaaatttca ctaggttata ttttgtgtag taaagaaaaa aattatttgg tcaatgttat | 6180 |
| cttaattcat actacaattt aagattatct tatgtgtatt atagtaaata gatgattttc | 6240 |
| agattcaagg ctcctaagag tttgatttgc tctgtttttt cctaaaataa atattgtctc | 6300 |
| tcccaactgt taagttctag gtattgtact tccaattttta acttcagaac caagatgttg | 6360 |
| gcatgaacca ggctgctgtt gaagtacatg tatattataa attatcttat ttgtgttata | 6420 |
| ctcttacatg ttatcttttc taagaaaaca aagtccctat tattcctatt gcaaagcaca | 6480 |
| caggaattaa gaaagtacag taattttaaa aaaaaaatcc ggtaaatgta gtattcttaa | 6540 |
| cctgttctat attacttata cctattgtct atatagcttt aatttatagt tgtcagttta | 6600 |
| actattggca tgtctggcaa agaaaattaa actttaagag ttttataaac tgtttctagg | 6660 |
| ttgctaaaga atttattttt ctactatata tggtatagac aaagcatcaa actatgtaca | 6720 |
| ggaaaaaagc ctgactattt ctatttggaa gtaggctgaa aagagaattt tcaaaactgt | 6780 |
| tcgtgtcttc agttcattct gtcataactt tgctattgta atatgtgaat accagtttat | 6840 |
| ttaagctgtt ctcttttata ctgtattaat ttaatgttca tctgcgttta gtaccatttt | 6900 |
| tgttattaaa actggcattt accgttttc acattaaccc accttgcacc ttcccccaaa | 6960 |
| cttatctcca cttttctatg cattctatca ttgatttgac acacttcata gtgagtcatt | 7020 |
| taaatactct acgtttggtt caattaacca gtaggttaca gttattgaaa attaaagtac | 7080 |
| agtttaaagc tcagtctgtt acactgaatt gattgtgttt gttttttgcca agggtttaga | 7140 |
| tatgctttta aatattagaa acatctaaga acagaataac ataattaaac ttttttctgg | 7200 |
| taagttactg gaaggtttca ctgtttaggg acctatcata tgagacttct taaaggatta | 7260 |
| aaagaatagg atagtctcat aattgtgagt aaacatcaag gcattatatt ttacaatact | 7320 |
| gaataaaatt tcatctacac acatgttgcc attgtttcat ttaaggttca gtgcttatag | 7380 |
| ttaactacaa tattggacct aacaggatct agattagcaa tataaagaag catagtggta | 7440 |
| ctctgtttca cactttcagt agatttatta gaagtcaaat tctattcaac agacacttat | 7500 |
| taggatatac aactaatta agaataaaat tccaggcaca atatatttt tttaaatggt | 7560 |
| atttgttagt agtgcttctt ccccttaaca tttacagtgt aaatactgca ggtaaccgca | 7620 |
| atctaagtta gccaaaaagc agctttttt cccatactgt atgtaaataa tgtagacctg | 7680 |
| ggttttttg tttatttggg tttgtttttt tttttgaggt actggaatct aattaatatc | 7740 |
| tcttaggtat caacaaaagg gaacaattgg aatgagaatt taggccttag cttccatggt | 7800 |
| gattttttagt ttttttataca gtaataattg tgatgctatt tgtcaactgg atataaatac | 7860 |
| acatataatt ttaaaaagtc aaagtgcttt tgtttctttt gtttaatgta atttttgtgc | 7920 |
| ttcacctaca ggatgctgca gtaaattaaa tatcagtgaa gcttctgatg tataaagaat | 7980 |
| gctatgaata aaacattaag aagctgtgta attttaagtt atagttgcct ctattttttac | 8040 |
| catttcattg gtaaaaatta gctaattttt ttcaagtgaa atgaaaaata aaatatataaa | 8100 |
| tttatcaata tgatggaaat cttattaagg agatgtatta ttgaattttc actgtacctg | 8160 |

```
aaaaggagat tcaaaatttt ttctggggat gtatataggt gaaaatttga ttttttaaat      8220
tatcaggaaa acaagataat gcacagattt ctaagactaa gatcttacct ggatgtgatt      8280
tttgagctgt ggctagacat tctttagagc cactggaaat attttgaaaa ctattctagt      8340
tatagcagag ctgctaatat taacgaatat atttgtgtct tcatggtttg tgactattag      8400
gccaaatttt gtggtatatg ttgtcagtct ggatctggtg aggtctgttc aacatgaatc      8460
tttgtgttat cttgaattta gtagtttcaa ggtacttaaa ttcttaacag tttctaatttt     8520 gtttcaatac atatgggaca tggttgattt ttttactgta ttagaactct tggaagttct      8580 tagcctttc aggttatgaa atacctgaaa gtaaaatttt ctaagattta ataagggaag       8640
atactattca aatcattttc ttaggatagc atctttacat acaatgagag gattgtacaa      8700
gcattaatct catattccaa catccagtta cttgatgtga tccaagtacc ctggtctttt      8760
tgaagcagtt aaaatctaat taattaactt tgggagtctt cactattcaa ttgatcctca     8820
tcattgtcct atttgcatga ctccattttt tcctccacta tatgagtttt ctttgtcagg     8880
gggagaggag tgggaagagt cacagaatct catattcaca tcttaattaa attgtgtgaa      8940
attagtcttt tgtggaaatt ctgtaggcag tatgattttg aaaagctaac caatgataat      9000
tagcatttta gttaatacta aatgcataaa attataaccc ttgaaattaa tttggtgctg      9060
gcagttctgg tttagtcatt tttaccagta gttagtagta ttaagacctg cagtatatgc      9120 acttttgag tagctgtcaa ataattgtag ttgagaaaca acttgtttat tctcacaatt       9180
cagattttct attcagtttt gtctcaaata gtaagttatt gtgaacaatt taataacggc      9240
cctcctgttc tagtttgcct aatatttag ttaagattta gtgttttaac ctattttttt       9300
aagtttattt tttgtattag attttatttg aataagttat gtgggtttag taattgacct      9360
atttattcat tgcttcacta attcatccag attagtttta agtgtgtata tgtatttgct      9420
caccagatca ttttcttggg accttgaact gtgaatgttt tgtcctaacc atttaatatt      9480
ttctaggtac ttgctgcaag ttcttgaact attttaccag ctttaacttt ggggctctta     9540 gtttctttc tccagattct tgttatttta tttatccaa ataaatattt aggtgttcta        9600
agaa                                                                   9604

<210> SEQ ID NO 607
<211> LENGTH: 10551
<212> TYPE: DNA
<213> ORGANISM: Homo sapiens

<400> SEQUENCE: 607
cggccgggag gcggggcggg ccgtaggcaa agggaggtgg ggaggcggtg gccggcgact        60
ccccgcgccc cgctcgcccc ccggcccttc ccgcggtgct cggcctcgtt cctttcctcc       120
tccgctccct ccgtcttcca tacccgcccc gcgcggcttt cggccggcgt gcctcgcgcc       180
ctaacgggcg gctggaggcg ccaatcagcg ggcggcaggg tgccagcccc ggggctgcgc       240
cggcgaatcg gcggggcccg cggcccaggg tgcaggcgg gtctacccgc gcggccgcgg        300
cggcggagaa gcagctcgcc agccagcagc ccgccagccg ccgggaggtt cgatacaaga       360
ggctgttttc ctagcgtggc ttgctgcctt tggtaagaac atgtcgtcca tcttgccatt      420
cacgccgcca gttgtgaaga gactgctggg atggaagaag tcagctggtg ggtctggagg      480
agcaggcgga ggagagcaga atgggcagga agaaaagtgg tgtgagaaag cagtgaaaag      540
tctggtgaaa aagctaaaga aaacaggacg attagatgag cttgagaaag ccatcaccac      600
tcaaaactgt aatactaaat gtgttaccat accaagcact tgctctgaaa tttggggact      660
```

-continued

```
gagtacacca aatacgatag atcagtggga tacaacaggc ctttacagct tctctgaaca      720
aaccaggtct cttgatggtc gtctccaggt atcccatcga aaaggattgc cacatgttat      780
atattgccga ttatggcgct ggcctgatct tcacagtcat catgaactca aggcaattga      840
aaactgcgaa tatgctttta atcttaaaaa ggatgaagta tgtgtaaacc cttaccacta      900
tcagagagtt gagacaccag ttttgcctcc agtattagtg ccccgacaca ccgagatcct      960
aacagaactt ccgcctctgg atgactatac tcactccatt ccagaaaaca ctaacttccc     1020
agcaggaatt gagccacaga gtaattatat tccagaaacg ccacctcctg gatatatcag     1080
tgaagatgga gaaacaagtg accaacagtt gaatcaaagt atggacacag gctctccagc     1140
agaactatct cctactactc ttcccctgt taatcatagc ttggatttac agccagttac      1200
ttactcagaa cctgcatttt ggtgttcgat agcatattat gaattaaatc agagggttgg     1260
agaaaccttc catgcatcac agccctcact cactgtagat ggctttacag acccatcaaa     1320
ttcagagagg ttctgcttag gtttactctc caatgttaac cgaaatgcca cggtagaaat     1380
gacaagaagg catataggaa gaggagtgcg cttatactac ataggtgggg aagtttttgc     1440
tgagtgccta agtgatagtg caatctttgt gcagagcccc aattgtaatc agagatatgg     1500
ctggcaccct gcaacagtgt gtaaaattcc accaggctgt aatctgaaga tcttcaacaa     1560
ccaggaattt gctgctcttc tggctcagtc tgttaatcag ggttttgaag ccgtctatca     1620
gctaactaga atgtgcacca taagaatgag ttttgtgaaa gggtggggag cagaataccg     1680
aaggcagacg gtaacaagta ctccttgctg gattgaactt catctgaatg gacctctaca     1740
gtggttggac aaagtattaa ctcagatggg atccccttca gtgcgttgct caagcatgtc     1800
ataaagcttc accaatcaag tcccatgaaa agacttaatg taacaactct tctgtcatag     1860
cattgtgtgt ggtccctatg gactgtttac tatccaaaag ttcaagagag aaaacagcac     1920
ttgaggtctc atcaattaaa gcaccttgtg aatctgtttt cctatatttg aatattagat     1980
gggaaaatta gtgtctagaa atactctccc attaaagagg aagagaagat tttaaagact     2040
taatgatgtc ttattgggca taaaactgag tgtcccaaag gtttattaat aacagtagta     2100
gttatgtgta caggtaatgt atcatgatcc agtatcacag tattgtgctg tttatataca     2160 ttttagttt gcatagatga ggtgtgtgtg tgcgctgctt cttgatctag gcaaaccttt      2220
ataaagttgc agtacctaat ctgttattcc cacttctctg ttatttttgt gtgtcttttt     2280
taatatataa tatatatcaa gattttcaaa ttatttagaa gcagattttc ctgtagaaaa     2340
actaattttt ctgcctttta ccaaaaataa actcttgggg gaagaaaagt ggattaactt     2400
ttgaaatcct tgaccttaat gtgttcagtg gggcttaaac agtcattctt tttgtggttt     2460 tttgttttt tttgttttt ttttaactg ctaaatctta ttataaggaa accatactga       2520
aaacctttcc aagcctcttt tttccattcc cattttgtc ctcataatca aacagcata      2580 acatgacatc atcaccagta atagttgcat tgatactgct ggcaccagtt aattctggga     2640
tacagtaaga attcatatgg agaaagtccc tttgtcttat gcccaaattt caacaggaat     2700
aattggcttg tataatctag cagtctgttg atttatcctt ccactcata aaaaatgcat      2760 aggtggcagt ataattattt tcagggatat gctagaatta cttccacata tttatccctt     2820
tttaaaaaag ctaatctata aataccgttt ttccaaaggt attttacaat atttcaacag     2880
cagaccttct gctcttcgag tagtttgatt tggtttagta accagattgc attatgaaat     2940
gggccttttg taaatgtaat tgtttctgca aaatacctag aaaagtgatg ctgaggtagg     3000
```

```
atcagcagat atgggccatc tgtttttaaa gtatgttgta ttcagtttat aaattgattg    3060
ttattctaca cataattatg aattcagaat tttaaaaatt gggggaaaag ccatttattt    3120
agcaagtttt ttagcttata agttacctgc agtctgagct gttcttaact gatcctggtt    3180
ttgtgattga caatatttca tgctctgtag tgagaggaga tttccgaaac tctgttgcta    3240
gttcattctg cagcaaataa ttattatgtc tgatgttgac tcattgcagt ttaaacattt    3300
cttcttgttt gcatcttagt agaaatggaa ataaccact cctggtcgtc ttttcataaa    3360
ttttcatatt tttgaagctg tctttggtac ttgttctttg aaatcatatc cacctgtctc    3420
tataggtatc atttttcaata cttttcaacat ttggtggttt tctattgggt actccccatt    3480
ttcctatatt tgtgtgtata tgtatgtgtt catgtaaatt tggtatagta attttttatt    3540
cattcaacaa atatttattg ttcacctgtt tgtaccagga acttttctta gtctttgggt    3600
aaaggtgaac aagacaacta cagttcctgc ctttgctgag acagcagtta cactaacccct    3660 taattatctt acttgtctat gaaggagata acagggtac tgtactggag aataacagat    3720
gggatgcttc aggtaggaca tcaaggaaag cctctaagga aaggatgcat gagctaacac    3780
ctgacattaa agaagcaagc caagtgagga gccaggggag ataagcattc ctggcaaaga    3840
gaatagcatc aaatgcaaaa aggttcacac taaaggaaac tcctgattag gtattaatgc    3900
tttatacaga aacctctata caaatccaaa cttgaagatc agaatggttc tacagttcat    3960
aacattttga aggtggcctt attttgtgat agtctgcttc atgtgattct cactaacata    4020
tctccttcct caacctttgc tgtaaaaatt tcatttgcac cacatcagta ctacttaatt    4080
taacaagctt ttgttgtgta agctctcact gttttagtgc cctgctgctt gcttccagac    4140
tttgtgctgt ccagtaatta tgtcttccac tacccatctt gtgagcagag taaatgtcct    4200
aggtaatacc actatcaggc ctgtaggaga tactcagtgg agcctctgcc cttctttttc    4260
ttacttgaga acttgtaatg gtgttaggga acagttgtag gggcagaaaa caactctgaa    4320
agtggtagaa ggtcctgatc ttggtggtta ctcttgcatt actgtgttag gtcaagcagt    4380
gcctactatg ctgtttcagt agtggagcgc atctctacag ttctgatgcg atttttctgt    4440
acagtatgaa attgggactc aactctttga aaacacctat tgagcagtta tacctgttga    4500
gcagtttact tcctggttgt aattacattt gtgtgaatgt gtttgatgct ttttaacgag    4560
atgatgtttt ttgtattta tctactgtgg cctgattttt tttttgtttt ctgcccctcc    4620
ccccatttat aggtgtggtt ttcatttttc taagtgatag aatcccctct tgttgaatt     4680 tttgtcttta tttaaattag caacattact taggatttat tcttcacaat actgttaatt    4740
ttctaggaat gatgacctga gaaccgaatg gccatgcttt ctatcacatt tctaagatga    4800
gtaatatttt ttccagtagg ttccacagag acaccttggg ggctggctta ggggaggctg    4860
ttggagttct cactgactta gtggcatatt tattctgtac tgaagaactg catggggttt    4920
cttttggaaa gagtttcatt gctttaaaaa gaagctcaga aagtctttat aaccactggt    4980
caacgattag aaaaatataa ctggatttag gcctaccttc tggaataccg ctgattgtgc    5040 tcttttatc ctactttaaa gaagctttca tgattagatt tgagctatat cagttatacc     5100
gattatacct tataatacac attcagttag taaacattta ttgatgcctg ttgtttgccc    5160
agccactgtg atggatattg aataataaaa agatgactag gacgggccc tgacccttga     5220 gctgtgcttg gtcttgtaga ggttgtgttt ttttcctca ggacctgtca ctttggcaga    5280
aggaaatctg cctaattttt cttgaaagct aaatttcttt tgtaagtttt tacaaattgt    5340
ttaataccta gttgtatttt ttaccttaag ccacattgag ttttgcttga tttgtctgtc    5400
```

```
ttttaaacac tgtcaaatgc tttcccttt  gttaaaatta ttttaatttc acttttttg     5460 tgcccttgtc aatttaagac taagactttg aaggtaaaac aaacaaacaa acatcagtct    5520
tagtctcttg ctagttgaaa tcaaataaaa gaaatatat  acccagttgg tttctctacc    5580
tcttaaaagc ttcccatata tacctttaag atccttctct tttttcttta actactaaat    5640
aggttcagca tttattcagt gttagatacc ctcttcgtct gagggtggcg taggtttatg    5700
ttgggatata aagtaacaca agacaatctt cactgtacat aaaatatgtc ttcatgtaca    5760
gtctttactt taaaagctga acattccaat ttgcgccttc cctcccaagc ccctgcccac    5820
caagtatctc tttagatatc tagtctgtgg acatgaacaa tgaatacttt ttcttactc     5880 tgatcgaagg cattgatact tagacatatc aaacatttct tcctttcata tgctttactt    5940
tgctaaatct attatattca ttgcctgaat tttattcttc ctttctacct gacaacacac    6000
atccaggtgg tacttgctgg ttatcctctt tcttgttagc cttgtttttt gttttttttt    6060
tttttttttg agagggagtc tcgctctgtt gcccaacctg gagtgcagtg gtgcgatctt    6120
ggttcactgc aagctccgcc tcccgggttc acgccatgct tctgcctcag cctcccaagt    6180
agctgggact acaggcgccc accaccacac tcggctaatt ttttgtattt ttagtagaga    6240
cggggtttca ccgtgttggc caggatggtc tcgatctcct gacctcgtga tctgtccacc    6300
tcggcttccc aaagtgctgg gattacaggc atgagccacc gcgcccagcc tagccatatt    6360
tttatctgca tatatcagaa tgtttctctc ctttgaactt attaacaaaa aaggaacatg    6420
cttttcatac ctagagtcct aatttcttca tcatgaaggt tgctattcaa attgatcaat    6480
cattttaatt ttacaaatgg ctcaaaaatt ctgttcagta aatgtctttg tgactggcaa    6540
atggcataaa ttatgtttaa gattatgaac ttttctgaca gttgcagcca atgttttccc    6600
tacgatacca gatttccatc ttggggcata ttggattgtt gtatttaaga cagtcagaat    6660
aatgatagtg tgtggtctcc agaggtagtc agaatcctgc tattgagttc ttttatatc    6720 ttccttttca atttttattt accatttgt  ttgtttagac tacactttgt agggattgag    6780
gggcaaatta tctcttggag tggaattcct gtgttttgag ccttacaacc aggaaatatg    6840
agctatacta gatagcctca tgatagcatt tacgataaga acttatctcg tgtgttcatg    6900
taattttttg agtaggaact gttttatctt gaatattgta gctaactata tatagcagaa    6960
ctgcctcagt ctttttaaga aggaaataaa taatatatgt gtatgaattt atatatacat    7020
atacactcat agacaaactt aacagttggg gtcattctaa cagttaaaac aattgttcca    7080
ttgtttaaat ctcagatcct ggtaaaatgt tcttaatttg tctgtgtaca ttttcctttc    7140
atggacagac cattggagta cattaatttt cttaatctgc catttggcag ttcatttaat    7200 ataccattt  ttggcaactt ggtaactaag aatcacagcc aaaatttgtt aacatcaaag    7260
aaagctctgc catataccc  gttactaaat tattatacat ccagcagatt ctgggatgta    7320
ctaacttagg gttaactttg ttgttgttga taatactaga ttgctccctc tttaattctt    7380
cttctggtgc aaggttgctg cttaagttac cctgggaaat actactacaa ggtcaaattt    7440
tctagtatct tacagcctga ttgaaggtga ttcagatctt tgctcaatat aaatggattt    7500
tccaagattc tctgggccat ccttgaccca caggtgatct cgctggagta tattaactta    7560
acttcagtgc cagttggttt ggtgccatga gatccataat gaatccagaa cttcaccatt    7620
gcttagatat aagagtccct tggaagaata atgccactga tgatggggt  cagaaggtgt    7680 attaactcaa catagagggc ttttagattt ttcttcaaaa aaatttcgag aaaagtattc    7740
```

```
ttttaccctc caaacagtta acagctctta gtttctccaa atatgctctt tgatttactt    7800
atttttaatt aaagatggta atttattgaa caatgaaatc cgtaatatat tgatttaagg    7860
acaaaagtga agttttagaa ttataaaagt acttaaatat tatatatttt ccatttcata    7920
attgttttcc tttctctgtg gctttaaagt ttttgactat tttacaatgt taatcactag    7980
gtaacttgcc atatttctgg ttctatatta agttctatcc tttataatgc tgttattata    8040
aagctggttt ttagcatttg tctgtagcaa tagaaatttt actaagtctc tgttctccca    8100
gtaagttttt tcttttctca gtaagtccct aagaaaacat ttgtttgcca ctcttactat    8160
tcccaatctt ggattgttcg agctgaaaaa aaatttgatg agaaacagga ggatcctttt    8220
ctggtgaata taggttcctg ctttaagaat gtggaaatcc attgctttat ataactaata    8280
tacacacaga ttaattaaaa ttgtgagaaa taattcacac atgacaagta ggtaacatgc    8340
atgagttttg aatttttta aaacccaac tgtttgacaa aatatagaac ccaaattggt    8400
actttcttag accagtgtaa cctcacacct cagttttgct tttccaaccc tgacttgaaa    8460
ggcatatttg tatcttttta ttagtgatag tgaagctgtg acactaacct tttatacaaa    8520
agagtaaaga aagaaaaact acagcgatta agatgagaac agttctgcag ttgttgaact    8580
agatcacagc attgtaggca gaataaaaaa tgttcatatc tgagaatatt cctttcgcca    8640
tcttttccca aggccagacc tcctggtgga gcacagttaa aagtaacatt ctgggccttt    8700
gtaatcggag ggctgtgtct ccagctggca gcctttgttt taatatataa tgcaggactg    8760
tggaaaacag ttggcataga atattttcac ctaaaaaga aagaaaagac atacaaaact    8820
ggattaattg caaaaagaga atacagtaaa ataccatata actggacaaa gctagaagaa    8880
cctttagaag atttgtctga aaacagattt caagagtgag cttttataca ctgctcacta    8940
atttgcttga ttactaccaa ctcttcttaa agttaacacg tttaaggtat ttctggactt    9000
cctagccttt tagcaagctt agaggaacta gccattagct agtgatgtaa aaatatttg    9060 gggactgatg ccccttaaagg ttatgcccct gaaagttctt accttttctc tagtgatatt    9120
aaggaacgag tgggtagtgt tctcagggtg accagctgcc ctaaagtgcc tgggattgag    9180
ggtttccctg gatgcgggac tttccctgga tacaaaactt ttagcagagt tttgtatata    9240
tgtggatttt tctgataagt agcacatcag aggccttaac cactgcccaa aagcgattct    9300
ccattgagag tacatatctt gaacttaaga aattcatttg ctctgatttt taatcttgta    9360 aagttttttgc taaactcaaa acaagtccca ggcacaccag aaggagctga ccaccttagg    9420
tgttcttgtg atttatcctt acttcccctat gttgtcatag ttgcttctaa actcagctgc    9480
actatggctg tcaacatttc tgatacttat tgggatatgt gccatccagt catttagtac    9540
tttgaatgga acatgagatt tataacacag gtaatagctg aaggtaccag tatggtggtg    9600
agactcacac ttagtgatcc agctaaggta actgatgtta taatggaaca gagaagaggc    9660
caactagata gctaagttct tctgaaccta tgtgtatatg taagtacaaa tcatgcgtcc    9720
ttatggggtt aaacttaatc tgaaatttac attttcata gtaaaaggaa accaattgtt    9780
gcagatttct tttcttgtga ggaaatacat ggcctttgat gctctggcgt ctactgcatt    9840
tcccagtctg ttctgctcga gaagccagaa tgtgttgtta acattttcc gtgaatgttg    9900 tgttaaaatg attaaatgca tcagccaatg gcaagtgaag gaattgggtg tcctgatgca    9960
gactgagcag tttctctcaa ttgtagccta atactcataa ggtgcttacc agctagaaca   10020
ttgagcacgt gaggtgagat tttttttctc tgatggcatt aactttgtaa tgcaatatga   10080
tggatgcaga ccctgttctt gtttccctct ggaagtcctt agtggctgca tccttggtgc   10140
```

```
actgtgatgg agatattaaa tgtgttcttt gtgagctttc gttctatgat tgtcaaaagt    10200
acgatgtggt tccttttta ttttattaa acaatgagct gaggctttat tacagctggt     10260
tttcaagtta aaattgttga atactgatgt ctttctccca cctacaccaa atattttagt   10320
ctatttaaag tacaaaaaaa gttctgctta agaaaacatt gcttacatgt cctgtgattt   10380
ctggtcaatt tttatatata tttgtgtgca tcatctgtat gtgctttcac ttttacctt   10440 gtttgctctt acctgtgtta acagccctgt caccgttgaa aggtggacag ttttcctagc   10500
attaaaagaa agccatttga gttgtttacc atgttaaaaa aaaaaaaaaa a           10551
```

<210> SEQ ID NO 608
<211> LENGTH: 2136
<212> TYPE: DNA
<213> ORGANISM: Homo sapiens

<400> SEQUENCE: 608

```
gtgtgtggag gggaccctgt ggttagcagc agctatcgca gcgtcggatg ttcagagcag      60
cagaagccgg cgtcgtcgga tgttgtgttg cccgccacca tgagctacac aggctttgtc    120
cagggatctg aaaccacttt gcagtcgaca tactcggata ccagcgctca gcccacctgt    180
gattatggat atggaacttg gaactctggg acaaatagag gctacgaggg ctatggctat    240
ggctatggct atggccagga taacaccacc aactatgggt atggtatggc cacttcacac    300
tcttgggaaa tgcctagctc tgcacacaat gcaaacacta gtgcctcggg tagcgccagt    360
gccgattccg ttttatccag aattaaccag cgcttagata tggtgccgca tttggagaca    420
gacatgatgc aaggaggcgt gtacggctca ggtggagaaa ggtatgactc ttatgagtcc    480
tgcgactcga gggccgtcct gagtgagcgc gacctgtacc ggtcaggcta tgactacagc    540
gagcttgacc ctgagatgga aatggcctat gagggccaat acgatgccta ccgcgaccag    600
ttccgcatgc gtggcaacga caccttcggt cccagggcac agggctgggc ccgggatgcc    660
cggagcggcc ggccaatggc ctcaggctat gggcgcatgt gggaagaccc catggggcc    720 cggggccagt gcatgtctgg tgcctctcgg ctgccctccc tcttctccca gaacatcatc    780
cccgagtacg gcatgttcca gggcatgcga ggtgggggcg ccttcccggg cggctcccgc   840
tttggtttcg ggtttggcaa tggcatgaag cagatgaggc ggacctggaa gacctggacc   900
acagccgact tccgaaccaa gaagaagaag agaaagcagg gcggcagtcc tgatgagcca   960
gatagcaaag ccacccgcac ggactgctcg gacaacagcg actcagacaa tgatgagggc  1020
accgaggggg aagccacaga gggccttgaa ggcaccgagg ctgtggagaa gggctccaga  1080
gtggacggag aggatgagga gggaaaagag gatgggagag aagaaggcaa agaggatcca  1140 gagaagggg ccctaaccac ccaggatgaa aatggccaga ccaagcgcaa gttgcaggca   1200
ggcaagaaga gtcaggacaa gcagaaaaag cggcagcgag accgcatggt ggaaaggatc  1260
cagtttgtgt gttctctgtg caaataccgg accttctatg aggacgagat ggccagccat  1320
cttgacagca agttccacaa ggaacacttt aagtacgtag gcaccaagct ccctaagcag  1380
acggctgact ttctgcagga gtacgtcact aacaagacca agaagacaga ggagctccga  1440
aaaaccgtgg aggaccttga tggcctcatc caccaaatct acagagacca ggatctgacc  1500
caggaaattg ccatggagca ttttgtgaag aaggtggagg cagcccattg tgcagcctgc  1560
gacctcttca ttcccatgca gtttgggatc atccagaagc atctgaagac catggatcac  1620
aaccggaacc gcaggctcat gatggagcag tccaagaagt cctcctcat ggtggcccgc  1680
```

| | |
|---|---|
| agtattctca caacaagct catcagcaag aagctggagc gctacctgaa gggcgagaac | 1740 |
| cctttcaccg acagccccga ggaggagaag gagcaggagg aggctgaggg cggtgccctg | 1800 |
| gacgaggggg cgcagggcga agcggcaggg atctcggagg gcgcagaggg cgtgccggcg | 1860 |
| cagcctcccg tgcccccaga gccagccccc ggggccgtgt cgccgccacc gccgccgccc | 1920 |
| ccagaggagg aggaggaggg cgccgtgccc ttgctgggag gggcgctgca acgccagatc | 1980 |
| cgcggcatcc cgggcctcga cgtggaggac gacgaggagg cggcgggggg cgccccgtga | 2040 |
| cccgagctcg gggcgggcgg agcccgcgtg gccgaagctg gaaaccaaac ctaataaagt | 2100 |
| tttcccatcc caccaaaaaa aaaaaaaaaa aaaaaa | 2136 |

<210> SEQ ID NO 609
<211> LENGTH: 1196
<212> TYPE: DNA
<213> ORGANISM: Homo sapiens

<400> SEQUENCE: 609

| | |
|---|---|
| acctttgagc gatggcggcg tctggggaac cccagaggca gtggcaagag gaggtggcgg | 60 |
| cggtggtagt ggtgggctcc tgcatgaccg acctggtcag tcttacttct cgtttgccaa | 120 |
| aaactggaga aaccatccat ggacataagt ttttattgg ctttggaggg aaaggtgcca | 180 |
| accagtgtgt ccaagctgct cggcttggag caatgacgtc catggtgtgt aaggttggca | 240 |
| aagattcttt tggcaatgat tatatagaaa acttaaaaca gaatgatatt tctacagaat | 300 |
| ttacatatca gactaaagat gctgctacag gaactgcttc tataattgtc aataatgaag | 360 |
| gccagaatat cattgtcata gtggctggag caaatttact tttgaatacg gaggatctga | 420 |
| gggcagcagc caatgtcatt agcagagcca agtcatggt ctgccagctc gaaataactc | 480 |
| cagcaacttc tttggaagcc ctaacaatgg cccgcaggag tggagtgaaa accttgttca | 540 |
| atccagcccc tgccattgct gacctggatc cccagttcta caccctctca gatgtgttct | 600 |
| gctgcaatga aagtgaggct gagattttaa ctggcctcac ggtgggcagc gctgcagatg | 660 |
| ctggggaggc tgcattagtg ctcttgaaaa ggggctgcca ggtggtaatc attacccttag | 720 |
| gggctgaagt atgtgtggtg ctgtcacaga cagaacctga gccaaagcac attcccacag | 780 |
| agaaagtcaa ggctgtggat accacgggtg ctggtgacag cttttgtggga gctctggcct | 840 |
| tctacctggc ttactatcca aatctgtcct tggaagacat gctcaacaga tccaatttca | 900 |
| ttgcagcagt cagtgtccag gctgcaggaa cacagtcatc ttacccttac aaaaaagacc | 960 |
| ttccgcttac tctgttttga ttgctattag tcccaaaata aatatacctg gaataaaat | 1020 |
| gtacttgggg gtggctgctc ctggctaatg cttattagaa aatgtcctcg tccctttct | 1080 |
| ttgcaaatat tagttctttt acgaagtcat cctcaagctt caatttattt ataacgatga | 1140 |
| ttcttttgct ttccatgcat ttgcacaaaa caaccagaat taaagattcc acaacc | 1196 |

<210> SEQ ID NO 610
<211> LENGTH: 2992
<212> TYPE: DNA
<213> ORGANISM: Homo sapiens

<400> SEQUENCE: 610

| | |
|---|---|
| aactgagcga ggagcaattg attaatagct cggcgagggg actcactgac tgttataata | 60 |
| acactacacc agcaactcct ggcttcccag cagccggaac acagacagga gagagtcagt | 120 |
| ggcaaataga catttttctt atttcttaaa aaacagcaac ttgtttgcta cttttatttc | 180 |
| tgttgatttt ttttttcttgg tgtgtgtggt ggttgttttt aagtgtggag ggcaaaagga | 240 |

```
gataccatcc caggctcagt ccaacccctc tccaaaacgg cttttctgac actccaggta    300
gcgagggagt tgggtctcca ggttgtgcga ggagcaaatg atgaccgcca aggccgtaga    360
caaaatccca gtaactctca gtggttttgt gcaccagctg tctgacaaca tctacccggt    420
ggaggacctc gccgccacgt cggtgaccat ctttcccaat gccgaactgg gaggccccctt   480 tgaccagatg aacggagtgg ccggagatgg catgatcaac attgacatga ctggagagaa    540
gaggtcgttg gatctcccat atcccagcag ctttgctccc gtctctgcac ctagaaacca    600
gaccttcact tacatgggca agttctccat tgaccctcag taccctggtg ccagctgcta    660
cccagaaggc ataatcaata ttgtgagtgc aggcatcttg caagggtgtca cttccccagc    720 ttcaaccaca gcctcatcca gcgtcacctc tgcctccccc aacccactgg ccacaggacc    780
cctgggtgtg tgcaccatgt cccagaccca gcctgacctg gaccacctgt actctccgcc    840
accgcctcct cctccttatt ctggctgtgc aggagacctc taccaggacc cttctgcgtt    900
cctgtcagca gccaccacct ccacctcttc ctctctggcc tacccaccac ctccttccta    960
tccatccccc aagccagcca cggacccagg tctcttccca atgatcccag actatcctgg   1020 attcttttcca tctcagtgcc agagagacct acatggtaca gctggcccag accgtaagcc   1080 cttttccctgc ccactggaca ccctgcgggt gcccctcca ctcactccac tctctacaat    1140
ccgtaacttt accctggggg gccccagtgc tggggtgacc ggaccagggg ccagtggagg   1200
cagcgaggga ccccggctgc ctggtagcag ctcagcagca gcagcagccg ccgccgccgc   1260
cgcctataac ccacaccacc tgccactgcg gcccattctg aggcctcgca agtaccccaa   1320
cagacccagc aagacgccgg tgcacgagag gccctacccg tgcccagcag aaggctgcga   1380
ccggcggttc tcccgctctg acgagctgac acggcacatc cgaatccaca ctgggcataa   1440
gcccttccag tgtcggatct gcatgcgcaa cttcagccgc agtgaccacc tcaccaccca   1500
tatccgcacc cacaccggtg agaagccctt cgcctgtgac tactgtggcc gaaagtttgc   1560
ccggagtgat gagaggaagc gccacaccaa gatccacctg agacagaaag agcggaaaag   1620
cagtgccccc tctgcatcgg tgccagcccc ctctacagcc tcctgctctg ggggcgtgca   1680
gcctgggggt accctgtgca gcagtaacag cagcagtctt ggcggagggc cgctcgcccc   1740
ttgctcctct cggacccgga caccttgaga tgagactcag gctgatacac cagctcccaa   1800
aggtcccgga ggccctttgt ccactggagc tgcacaacaa acactaccac cctttcctgt   1860
ccctctctcc ctttgttggg caaagggctt tggtggagct agcactgccc cctttccacc   1920
tagaagcagg ttcttcctaa aacttagccc attctagtct ctcttaggtg agttgactat   1980
caacccaagg caaaggggag gctcagaagg aggtggtgtg gggacccctg gccaagaggg   2040
ctgaggtctg accctgcttt aaagggttgt ttgactaggt tttgctaccc cacttcccct   2100
tattttgacc catcacaggt ttttgaccct ggatgtcaga gttgatctaa gacgttttct   2160
acaataggtt gggagatgct gatcccttca gtggggaca gcaaaaagac aagcaaaact   2220
gatgtgcact ttatggcttg ggactgattt ggggacatt gtacagtgag tgaagtatag   2280
cctttatgcc acactctgtg gccctaaaat ggtgaatcag agcatatcta gttgtctcaa   2340
cccttgaagc aatatgtatt ataaactcag agaacagaag tgcaatgtga tgggaggaac   2400
atagcaatat ctgctccttt tcgagttgtt tgagaaatgt aggctatttt ttcagtgtat   2460
atccactcag attttgtgta tttttgatgt acactgttct ctaaattctg aatctttggg   2520
aaaaaatgta aagcatttat gatctcagag gttaacttat ttaaggggga tgtacatata   2580
```

| | |
|---|---|
| ttctctgaaa ctaggatgca tgcaattgtg ttggaagtgt ccttggtgcc ttgtgtgatg | 2640 |
| tagacaatgt tacaaggtct gcatgtaaat gggttgcctt attatggaga aaaaaatcac | 2700 |
| tccctgagtt tagtatggct gtatatttct gcctattaat atttggaatt ttttttagaa | 2760 |
| agtatatttt tgtatgcttt gttttgtgac ttaaaagtgt tacctttgta gtcaaatttc | 2820 |
| agataagaat gtacataatg ttaccggagc tgatttgttt ggtcattagc tcttaatagt | 2880 |
| tgtgaaaaaa taaatctatt ctaacgcaaa accactaact gaagttcaga taatggatgg | 2940 |
| tttgtgacta tagtgtaaat aaatactttt caacaataaa aaaaaaaaa aa | 2992 |

<210> SEQ ID NO 611
<211> LENGTH: 2756
<212> TYPE: DNA
<213> ORGANISM: Homo sapiens

<400> SEQUENCE: 611

| | |
|---|---|
| agttcctgcc agtgagtccc taggcctcca tctctctccc ttgctgtacc accttcacca | 60 |
| ccatccatgc gaccccaaga gccttaatga ctctagaaga gactccaggc aggggaagct | 120 |
| gaaaggacct ttcactccct acttttggcc agggccttct gtgccacctg ccaagaccag | 180 |
| caggcctacc ctctgaagag gtccaagcaa cggaagtact actacgaagc tgcctttctg | 240 |
| gccatccttg agaaaaatag acagatggcc aaggagaggg cctaataag ccccagtgat | 300 |
| tttgcccagc tgcaaaaata catggaatac tccaccaaaa aggtcagtga tgtcctaaag | 360 |
| ctcttcgagg atggcgagat ggctaaatat gtccaaggag atgccattgg gtacgaggga | 420 |
| ttccagcaat tcctgaaaat ctatctcgaa gtggataatg ttcccagaca cctaagcctg | 480 |
| gcactgtttc aatcctttga gactggtcac tgcttaaatg agacaaatgt gacaaaagat | 540 |
| gtggtgtgtc tcaatgatgt ttcctgctac ttttcccttc tggagggtgg tcggccagaa | 600 |
| gacaagttag aattcacctt caagctgtac gacacggaca gaaatgggat cctggacagc | 660 |
| tcagaagtgg acaaaattat cctacagatg atgcgagtgg ctgaatacct ggattgggat | 720 |
| gtgtctgagc tgaggccgat tcttcaggag atgatgaaag agattgacta tgatggcagt | 780 |
| ggctctgtct ctcaagctga gtgggtccgg gctggggcca ccaccgtgcc actgctagtg | 840 |
| ctgctgggtc tggagatgac tctgaaggac gacggacagc acatgtggag gcccaagagg | 900 |
| ttccccagac cagtctactg caatctgtgc gagtcaagca ttggtcttgg caaacaggga | 960 |
| ctgagctgta acctctgtaa gtacactgtt cacgaccagt gtgccatgaa agccctgcct | 1020 |
| tgtgaagtca gcacctatgc caagtctcgg aaggacattg tgtccaatc acatgtgtgg | 1080 |
| gtgcgaggag gctgtgagtc cgggcgctgc gaccgctgtc agaaaaagat ccggatctac | 1140 |
| cacagtctga ccgggctgca ttgtgtatgg tgccacctag atccacga tgactgcctg | 1200 |
| caagcggtgg gccatgagtg tgactgtggg ctgctccggg atcacatcct gcctccatct | 1260 |
| tccatctatc ccagtgtcct ggcctctgga ccggatcgta aaaatagcaa acaagccag | 1320 |
| aagaccatgg atgatttaaa tttgagcacc tctgaggctc tgcggattga ccctgttcct | 1380 |
| aacacccacc cacttctcgt ctttgtcaat cctaagagtg gcgggaagca ggggcaaagg | 1440 |
| gtgctctgga agttccagta tatattaaac cctcgacagg tgttcaacct cctaaaggat | 1500 |
| ggtcctgaga tagggctccg attattcaag gatgttcctg atagccggat tttggtgtgt | 1560 |
| ggtggagacg gcacagtagg ctggattcta gagaccattg acaaagctaa cttgccagtt | 1620 |
| ttgcctcctg ttgctgtgtt gccccctggg actggaaatg atctggctcg atgcctaaga | 1680 |
| tggggaggag gttatgaagg acagaatctg gcaaagatcc tcaaggattt agagatgagt | 1740 |

```
aaagtggtac atatggatcg atggtctgtg gaggtgatac ctcaacaaac tgaagaaaaa   1800
agtgacccag tccccctttca aatcatcaat aactacttct ctattggcgt ggatgcctct   1860
attgctcatc gattccacat catgcgagag aaatatccgg agaagttcaa cagcagaatg   1920
aagaacaagc tatggtactt cgaatttgcc acatctgaat ccatcttctc aacatgcaaa   1980
aagctggagg agtctttgac agttgagatc tgtgggaaac cgctggatct gagcaacctg   2040
tccctagaag gcatcgcagt gctaaacatc cctagcatgc atggtggctc caacctctgg   2100
ggtgatacca ggagacccca tggggatatc tatgggatca accaggcctt aggtgctaca   2160
gctaaagtca tcaccgaccc tgatatcctg aaaacctgtg taccagacct aagtgacaag   2220
agactggaag tggttgggct ggagggtgca attgagatgg ccaaatcta taccaagctc   2280 aagaatgctg acgtcggct ggccaagtgc tctgagatca ccttccacac cacaaaaacc   2340
cttcccatgc aaattgacgg agaaccctgg atgcagacgc cctgtacaat caagatcacc   2400
cacaagaacc agatgcccat gctcatgggc ccaccccccc gctccaccaa tttctttggc   2460
ttcttgagct aaggggaca cccttggcct ccaagccagc cttgaaccca cctccctgtc   2520
cctggactct actcccgagg ctctgtacat tgctgccaca tactcctgcc agcttggggg   2580
agtgttcctt caccctcaca gtatttatta tcctgcacca cctcactgtt ccccatgcgc   2640
acacacatac acacacccca aaacacatac attgaaagtg cctcatctga ataaaatgac   2700
ttgtgtttcc cctttgggat ctgctaaaaa aaaaaaaaa aaaaaaaaa aaaaaa   2756

<210> SEQ ID NO 612
<211> LENGTH: 3976
<212> TYPE: DNA
<213> ORGANISM: Homo sapiens

<400> SEQUENCE: 612
ctgggtcctg tgtgtgccac aggggtgggg tgtccagcga gcggtctcct cctcctgcta     60
gtgctgctgc ggcgtcccgc ggcctccccg agtcgggcgg gaggggagag cgggtgtgga    120
tttgtcttga cggtaattgt tgcgtttcca cgtctcggag gcctgcgcgc tgggttgctc    180
cttcttcggg agcgagctgt tctcagcgat cccactccca gccggggctc cccacacaca    240
ctgggctgcg tgcgtgtgga gtgggacccg cgcacgcgcg tgtctctgga cagctacggc    300
gccgaaagaa ctaaaattcc agatggcaaa ctcaatgaat ggcagaaacc ctggtggtcg    360
aggaggaaat ccccgaaaag gtcgaatttt gggtattatt gatgctattc aggatgcagt    420 tggacccct aagcaagctg ccgcagatcg caggaccgtg agaagacttt ggaagctcat    480
ggacaaagtg gtaagactgt gccaaaatcc caaacttcag ttgaaaaata gcccaccata    540
tatacttgat attttgcctg atacatatca gcatttacga cttatattga gtaaatatga    600
tgacaaccag aaacttgccc aactcagtga gaatgagtac tttaaaatct acattgatag    660
ccttatgaaa aagtcaaaac gggcaataag actctttaaa gaaggcaagg agagaatgta    720
tgaagaacag tcacaggaca gacgaaatct cacaaaactg tcccttatct tcagtcacat    780
gctggcagaa atcaaagcaa tcttcccaa tggtcaattc cagggagata actttcgtat    840
cacaaaagca gatgctgctg aattctggag aaagttttt ggagacaaaa ctatcgtacc    900
atggaaagta ttcagacagt gccttcatga ggtccaccag attagctctg gcctggaagc    960
aatggctcta aaatcaacaa ttgatttaac ttgcaatgat tacatttcag tttttgaatt   1020 tgatatttttt accaggctgt ttcagccttg gggctctatt ttgcggaatt ggaatttctt   1080
```

```
agctgtgaca catccaggtt acatggcatt tctcacatat gatgaagtta aagcacgact    1140
acagaaatat agcaccaaac ccggaagcta tattttccgg ttaagttgca ctcgattggg    1200
acagtgggcc attggctatg tgactgggga tgggaatatc ttacagacca tacctcataa    1260 caagcccttta tttcaagccc tgattgatgg cagcagggaa ggattttatc tttatcctga    1320
tgggaggagt tataatcctg atttaactgg attatgtgaa cctacacctc atgaccatat    1380
aaaagttaca caggaacaat atgaattata ttgtgaaatg gctccactt ttcagctctg     1440 taagatttgt gcagagaatg acaaagatgt caagattgag ccttgtgggc atttgatgtg    1500
cacctcttgc cttacggcat ggcaggagtc ggatggtcag ggctgccctt tctgtcgttg    1560
tgaaataaaa ggaactgagc ccataatcgt ggacccctttt gatccaagag atgaaggctc   1620
caggtgttgc agcatcattg acccctttgg catgccgatg ctagacttgg acgacgatga   1680
tgatcgtgag gagtccttga tgatgaatcg gttggcaaac gtccgaaagt gcactgacag   1740
gcagaactca ccagtcacat caccaggatc ctctcccctt gcccagagaa gaaagccaca   1800
gcctgaccca ctccagatcc cacatctaag cctgccaccc gtgcctcctc gcctggatct   1860
aattcagaaa ggcatagtta gatctccctg tggcagccca acgggttcac caaagtcttc   1920
tccttgcatg gtgagaaaac aagataaacc actcccagca ccacctcctc ccttaagaga   1980
tcctcctcca ccgccacctg aaagacctcc accaatccca ccagacaata gactgagtag   2040
acacatccat catgtggaaa gcgtgccttc cagagacccg ccaatgcctc ttgaagcatg   2100
gtgccctcgg gatgtgtttg ggactaatca gcttgtggga tgtcgactcc taggggaggg   2160
ctctccaaaa cctggaatca cagcgagttc aaatgtcaat ggaaggcaca gtagagtggg   2220
ctctgaccca gtgcttatgc ggaaacacag acgccatgat ttgcctttag aaggagctaa   2280 ggtctttttcc aatggtcacc ttggaagtga agaatatgat gttcctcccc ggctttctcc   2340
tcctcctcca gttaccaccc tcctccctag cataaagtgt actggtccgt tagcaaattc   2400
tctttcagag aaaacaagag acccagtaga ggaagatgat gatgaataca agattccttc   2460
atcccaccct gtttccctga attcacaacc atctcattgt cataatgtaa aacctcctgt   2520
tcggtcttgt gataatggtc actgtatgct gaatggaaca catggtccat cttcagagaa   2580
gaaatcaaac atccctgact taagcatata tttaaaggga gatgttttttg attcagcctc   2640 tgatcccgtg ccattaccac ctgccaggcc tccaactcgg gacaatccaa agcatggttc   2700
ttcactcaac aggacgccct ctgattatga tcttctcatc cctccattag gtgaagatgc   2760
ttttgatgcc ctccctccat ctctcccacc tcccccacct cctgcaaggc atagtctcat   2820
tgaacattca aaacctcctg gctccagtag ccggccatcc tcaggacagg atcttttttct   2880 tcttccttca gatcccttttg ttgatctagc aagtggccaa gttcctttttgc ctcctgctag  2940 aaggttacca ggtgaaaatg tcaaaactaa cagaacatca caggactatg atcagcttcc   3000
ttcatgttca gatggttcac aggcaccagc cagaccccct aaaccacgac cgcgcaggac   3060
tgcaccagaa attcaccaca gaaaacccca tgggcctgag gcggcattgg aaaatgtcga   3120
tgcaaaaatt gcaaaactca tgggagaggg ttatgccttt gaagaggtga agagagcctt   3180
agagatagcc cagaataatg tcgaagttgc ccggagcatc ctccgagaat ttgccttccc   3240
tcctccagta tccccacgtc taaatctata gcagccagaa ctgtagacac caaaatggaa   3300
agcaatcgat gtattccaag agtgtggaaa taaagagaac tgagatggaa ttcaagagag   3360
aagtgtctcc tcctcgtgta gcagcttgag aagaggcttg ggagtgcagc ttctcaaagg   3420
agaccgatgc ttgctcagga tgtcgacagc tgtggcttcc ttgttttttgc tagccatatt   3480
```

| | |
|---|---|
| tttaaatcag ggttgaactg acaaaaataa tttaaagacg tttacttccc ttgaactttg | 3540 |
| aacctgtgaa atgctttacc ttgtttacag tttggcaaag ttgcagtttg ttcttgtttt | 3600 |
| tagtttagtt ttgttttggt gttttgatac ctgtactgtg ttcttcacag acccttgta | 3660 |
| gcgtggtcag gtctgctgta acatttccca ccaactctct tgctgtccac atcaacagct | 3720 |
| aaatcattta ttcatatgga tctctaccat ccccatgcct tgcccaggtc cagttccatt | 3780 |
| tctctcattc acaagatgct ttgaaggttc tgattttcaa ctgatcaaac taatgcaaaa | 3840 |
| aaaaaaaagt atgtattctt cactactgag tttcttcttt ggaaaccatc actattgaga | 3900 |
| gatgggaaaa acctgaatgt ataaagcatt tatttgtcaa taaactgcct tttgtaaggg | 3960 |
| gttttcacat aacata | 3976 |

<210> SEQ ID NO 613
<211> LENGTH: 5312
<212> TYPE: DNA
<213> ORGANISM: Homo sapiens

<400> SEQUENCE: 613

| | |
|---|---|
| cccaggccgg ctctggcctc ctgacccaga cagcgcaggg cgcgagggat cgcgcggccg | 60 |
| agcccgggtc gcgccgctcc cagcatcggg gccgctagcc aagagttcga ggccttcccg | 120 |
| atccggatgt gatgaaaaag agcaacagag ggagaagtgt ttcaggattg taggagtgga | 180 |
| agagggaaa gagaggcaga gaggggaag gcccctcgc aggggagccg gctggagtga | 240 |
| gctggctgga aagaggggc ggagtgcgcg gagtcagagc cgccaccgct gccgcagttg | 300 |
| ccgccactgc ggcgtctggg ctgagccgga gggaggcggg aggacgcgca ggggcggccg | 360 |
| ccgccgtcgt caggccaccg gggcgaaaat gcggccgctg ccggaggctc gctaactttc | 420 |
| cggggcggaa gaggaggagg aggaggagga aggggcttgg agcgactacg gggggatgcg | 480 |
| gagaagcagt cagttccctg cacccagcac ctcacagccc ttcctccgtg cgccctgccg | 540 |
| ggcggcgagc taggcggcag cggcgcggcg cgggctcggc ggagcggccc atgtccggcg | 600 |
| cgggcgaagc cctcgctccc gggccgtgg ggccgcagcg cgtggccgag gcgggcggcg | 660 |
| gccagctggg ctccacagcc cagggaaaat gtgataaaga caatactgag aaagatataa | 720 |
| ctcaagctac caatagccac ttcacacatg gagagatgca agaccagtcc atttggggaa | 780 |
| atccttcgga tggtgaactc attagaaccc aacctcagcg cttgcctcag cttcagactt | 840 |
| cagcccaggt gccaagtggt gaggaaatag gcaagataaa gaacggccac acaggtctga | 900 |
| gcaatggaaa tggaattcac cacggggcca aacacggatc cgcagataat cgcaaacttt | 960 |
| cagcacctgt ttctcaaaaa atgcatagaa aaattcagtc cagcttgtct gtaaacagcg | 1020 |
| atatcagtaa gaagagcaaa gtaaatgctg tcttttccca aaagacaggc tcttcacctg | 1080 |
| aagattgttg tgtccactgt atcctggctt gcttgttctg cgaattcctg accctttgca | 1140 |
| acattgtcct gggacaagcg tcatgtggca tctgcacctc agaagcctgc tgctgttgct | 1200 |
| gtggtgacga gatgggggat gattgtaact gcccttgtga tatggactgt ggcatcatgg | 1260 |
| atgcctgttg tgaatcatca gactgcttgg aaatctgtat ggaatgctgt ggaatttgtt | 1320 |
| ttccttcata aatatttatc ttttgttttgt gttaaaactg gagagtgttt aaaaatttcc | 1380 |
| ttttgggggg aagaaaagca cattgtaaga ttctcatgaa acaacatgga atttgcactg | 1440 |
| ttaactcatt attgtaagta atctctgaaa gcctttttac tttaaccaaa tctacatggt | 1500 |
| ttaatatgtg aaatttttaac tactttaact agttttataa atttcttaat atgttacaat | 1560 |

```
aacttaggga cattttgaca ccccccttcc caaatgttaa atgccttctc cttttttaccg   1620
atatttctgt ttcttttaac cgttctcagg agcactttgc tccaaatata ttatttttca   1680
gtgtgtattt aaacgaggca gtttattttg atatgtatct attcatgatt gaaaggaagc   1740
agtcttggcc aggcacggtg gcttacacct gtaaccctgg cattttggga ggccaaggtg   1800
ggcagattgc ctgagctcag gagttcgaga ccagccaggg caacatggtg aaaccccatc   1860
tctactaaaa tacaaaaagt tagctgggct tggcggtgtg cgcctgtagt cccagctact   1920
caggaggctg aggcaggaga attgcttgaa cccgagaggc ggaagttgca gtgagccgag   1980
attgtgccac tgaactccaa cctgcactcc agcctgggca acagagcgag actccatctc   2040
taaataaata aataaataaa taaataaata aataaataaa taaacaaacc agtctttatt   2100
ttaaaagaaa ctttaggaaa caaacccaca taatagttgg gaaccagtgt tgatctctct   2160
cccttacctt ctccacttgt tcaacagact ctgaatgccg actgtgtgga ctctcttcct   2220
cagactgtgg ggacagatac aattccactc ctgtccacag gaacatgaga tttagcagac   2280
taaggagatc tgtaaagaat gaaccatacc acaaggcata ctgaagtgag gattataaga   2340
gaaataaact caaaatgctg ttggaatatg cagagaattg ctaccagaat attcagtaag   2400
gtttcaggga gaatgtggca tttgaggact ctcttagaat gagtgattca cctgctattt   2460
aaatgaatta tttagatttt tgacaaagat ttaggtggac accctaaaact gtgtgtgcct   2520
ttaaccagtt aaaagaacag tgccttcagc atacttttt attagttgta ggaatacagc   2580
tttttgaaaa agctataaag tttaaattaa ctaaaaatat gcattttctt acacataatt   2640
taaatgttat catacttttt tgatgaaaac ataatgcctt agtaaaatag ctctatttaa   2700
taaagaagat tgagtactct gacacatttc atttaaatta ggaaattttt aatattaaaa   2760
tcccagtgtt ctgagttatt gaaaggcttt cttttatttt gagagcttta ggtctttttg   2820
ggatgagaac attttagttg tttagtttgt tcttaagca gtgctatttt ttgtaaacac   2880
agataaatgg aaaccattct tttcaatgca gaagaaatct agatatcccc tactgtgacc   2940
aaatttctgt attacgattt tatgttaaat taaactaata tggcaggtta taatgatcct   3000
taagtgtaaa gaaatcagtc aattacaaga gtaattgtat agttattgag acctatagtg   3060
tgtggcttag atgaaaggga gagtaaattt tcataccatg ctctctccta ctcagtttga   3120
tctctctaaa attgtagttt ggtttgattt aatataattc ttagtagaaa ttttgaaagt   3180
atgctttggg attaataatt attttttaatt tttctggctg aatatcaaat tgatagtaac   3240
aacagaagca taattttagg aaggctttcg caaacctagc cttttaagag aggtttttaa   3300
cctgaagcat gagaatatat cacctgtggt ttttcctttg agatgaaacg tagtttctag   3360
ttatatcatt acttaaaggg cttaaaaaga aaaacttag caaacttttg aatcttcctt   3420
ttattgctat ttacacatac atacacacat acaaaacctt taaattttgg gatctgaata   3480
taattctggt aaacagctgt cttcattttt ctcctctaaa gaacttaatt catttgttac   3540
ataaaatata aggaaatctt tatactattt tacagtaacc acaatctaaa tatttacata   3600
tacccaaaat taacttatgc tcatatatta ggatgtgaga atatcatctg tttatggaca   3660
catgaaacct cctaatgacc tggaattgtt agaatatttg acttttata tgcaaagttt   3720
ttcaaccaag tggtttgtct aatatttaaa catgtactgg cacaatttgt gatgaaaata   3780
ttagcacatt tgcaataatg tttctccata acagagaatg ttaatggata ccagaatttt   3840
attttttgtat ttatgttcat agtacttttc ctcttgtcta ctccagacag ttattccata   3900
aagcatttgt ataattaaaa ggaaaacaga aaaaggaaaa gtaggcaaat gtgaaaatag   3960
```

```
tttcaatata tcttatgatt tcttaatgta aaatgttttg ttgaagtata tggctatcat    4020
gactaagtgc tagaatttat agttacaggc ggtgtccttt aaatgtgga aaggctttta    4080 aaatatttta aaactggacc tgtattatcc tgaatacact attttgaaaa ttttaaaaa    4140 tgacttcttt attttgcttt accgtatgtt tatatctaat tgacatattg actaatgttt    4200
gaaagaattc aaccataagt taaaatctga aggttatctt tatcatgttt catccctgtc    4260
tgaagatttc ctagtcttct tatgtaaatc acatgactca tgtccgtaaa tgaactatga    4320
aagatatcga tcagtttatg atcattgaca tgtgatttca aaacacagtg ttcttttaaa    4380
aatctataat atgtcaaaat acaagttttt tttttttaca tcgttttagt aagttaattt    4440
catttattta ctttggagct atatttccac ttagaaaaac taaggtaatt ttacaatata    4500
tgctgagatt aaaaaccaag gtaaaaatga tcaaacatat atgaaattga gtcttagatt    4560
taatgaattt cactcgaaaa taaatgatca gaagaatttt catctaaggc atagagtggc    4620 gaaattttg taaatgctcg cagttagcat ctaactaaaa caatacagta tgactttatt    4680
taggagaagg cttttatt agaaaattat ttttcattt ttacagtgta tcaactgtat    4740 ccatttcct cacctggata gtcaatgtta tctgagcagt tcaaggagta accaaggcaa    4800
ccttatgtaa taactttcca ttctttatcc atacaaactc tttcagtgcc ctagattcta    4860
atgttataaa cgtcaaacat cactgcccaa cataaataag actcgagact tattaacata    4920
aataagtatc ttgccttctt gaatgctagt taaatgctta gatttaccta actgcctaat    4980
gaatcaggtt atttgttaat aagattatt ttcaaattat ttaagacctt tatgccccctt    5040 ccaattactt gtgatttgta ggcctgtagg attgttgcat ctaatctgac tggcaacaga    5100
aaatgtcatc aaatactata atatccattt tgttttcttt tgcactaata caacagaaca    5160
tatcattttt gttttaaaca atggttaata tattaatagg gtttgttcca cacttactat    5220 ttatagttttt tataatcaag cattgggtat aaaagagaa tcctttcaac ccttcatctt    5280
cgtatgctta tacaataaat tgcagtgagt gt                                 5312
```

<210> SEQ ID NO 614
<211> LENGTH: 12739
<212> TYPE: DNA
<213> ORGANISM: Homo sapiens

<400> SEQUENCE: 614

```
agggaagaag ggagaaagag agagagattt gaatatacat tgcttcaagg atgcaaaaaa     60
ttacaacctg gaaaaggctt cgagtaactt taggaaaatg agctgctgga ctcctcagtc    120
aatctgtcct ttctagtcaa tgaaaagac agggtttgag gttccttccg aaacggggcc    180
ggctaattta gccctccca cgagcccaag ggtctgttat atctctgttt ccttgaggac    240
ctctctcacg gagacggacc acagcaagca gaggctgggg gggggaaaga cgaggaaaga    300
ggaggaaaac aaaagctgct acttatggaa gatacaaagg agtctaacgt gaagacattt    360
tgctccaaga atatcctagc catccttggc ttctcctcta tcatagctgt gatagctttg    420
cttgctgtgg ggttgaccca gaacaaagca ttgccagaaa acgttaagta tgggattgtg    480
ctggatgcgg gttcttctca cacaagttta tacatctata agtggccagc agaaaaggag    540
aatgacacag gcgtggtgca tcaagtagaa gaatgcaggg ttaaaggtcc tggaatctca    600
aaatttgttc agaagtaaa tgaaataggc atttacctga ctgattgcat ggaaagagct    660
agggaagtga ttccaaggtc ccagcaccaa gagacacccg tttacctggg agccacggca    720
```

```
ggcatgcggt tgctcaggat ggaaagtgaa gagttggcag acagggttct ggatgtggtg    780
gagaggagcc tcagcaacta cccctttgac ttccagggtg ccaggatcat tactggccaa    840
gaggaaggtg cctatggctg gattactatc aactatctgc tgggcaaatt cagtcagaaa    900
acaaggtggt tcagcatagt cccatatgaa accaataatc aggaaacctt ggagctttg     960
gaccttgggg gagcctctac acaagtcact tttgtacccc aaaaccagac tatcgagtcc   1020
ccagataatg ctctgcaatt tcgcctctat ggcaaggact acaatgtcta cacacatagc   1080
ttcttgtgct atgggaagga tcaggcactc tggcagaaac tggccaagga cattcaggtt   1140
gcaagtaatg aaattctcag ggacccatgc tttcatcctg atataagaa ggtagtgaac    1200
gtaagtgacc tttacaagac cccctgcacc aagagatttg agatgactct tccattccag   1260
cagtttgaaa tccagggtat tggaaactat caacaatgcc atcaaagcat cctggagctc   1320
ttcaacacca gttactgccc ttactcccag tgtgccttca atgggatttt cttgccacca   1380
ctccaggggg attttgggc attttcagct ttttactttg tgatgaagtt tttaaacttg    1440
acatcgagaa agtctctcag gaaaaggtga ctgagatgat gaaaaagttc tgtgctcagc   1500
cttgggagga gataaaaaca tcttacgctg gagtaaagga gaagtacctg agtgaatact   1560
gcttttctgg tacctacatt ctctcccctcc ttctgcaagg ctatcatttc acagctgatt   1620
cctgggagca catccatttc attggcaaga tccagggcag cgacgccggc tggactttgg   1680
gctacatgct gaacctgacc aacatgatcc cagctgagca accattgtcc cacctctct    1740
cccactccac ctatgtcttc ctcatggttc tattctccct ggtccttttc acagtggcca   1800
tcataggctt gcttatcttt cacaagcctt catatttctg gaaagatatg gtatagcaaa   1860
agcagctgaa atatgctggc tggagtgagg aaaaaaatcg tccagggagc attttcctcc   1920
atcgcagtgt tcaaggccat ccttccctgt ctgccagggc cagtcttgac gagtgtgaag   1980
cttccttggc ttttactgaa gccttttcttt tggaggtatt caatatcctt tgcctcaagg   2040
acttcggcag atactgtctc tttcatgagt ttttcccagc tacacctttc tcctttgtac   2100
tttgtgcttg tataggttttt aaagacctga cacctttcat aatctttgct ttataaaga    2160
acaatattga ctttgtctag aagaactgag agtcttgagt cctgtgatag gaggctgagc   2220
tggctgaaag aagaatctca ggaactggtt cagttgtact ctttaagaac cccttctct    2280
ctcctgtttg ccatccatta agaaagccat atgatgcctt tggagaaggc agacacacat   2340
tccattccca gcctgctctg tgggtaggag aatttctac agtaggcaaa tatgtgctaa     2400
agccaaagag ttttataagg aaatatatgt gctcatgcag tcaatacagt tctcaatccc   2460
acccaaagca ggtatgtcaa taaatcacat attcctaggt gatacccaaa tgctacagag   2520
tggaacactc agacctgaga tttgcaaaaa gcagatgtaa atatatgcat tcaaacatca   2580
gggcttacta tgaggtaggt ggtatataca tgtcacaaat aaaaatacag ttacaactca   2640
gggtcacaaa aaatgcatct tccaatgcat attttttatta tggtaaaata tacataaata   2700
taattcacca ttttaacatt taattcatat taaatacgta caaatcagtg acatttagta   2760
cattcacagt gttgtgccac catcaccact atttagttcc agaacatttg catcatcaat   2820
acattgtcta gagacaagac tatcctgggt aggcagaaac catagatctt ttgtgtttac   2880
agctatggaa accaactgta ccataaagat agttcactga gttttaaagc caagccacat   2940
cttatttttc caaggtttaa tttagtgaga gggcagcatt agtgtggagt ggcatgcttt   3000
tgccctatcg tggaatttac acatcagaat gtgcaggatc caagtctgaa agtgttgcca   3060
cccgtcacac aacatgggct tgtttgctt attccatgaa gcagcagcta tagaccttac    3120
```

```
catggaaaca tgaagagacc ctgcacccct ttccttaagg attgctgcaa gagttacctg    3180
ttgagcagga ttgactggtg atgtttcatt ctgaccttgt cccaagctct ccatctctag    3240
atctggggac tgactgttga gctgatgggg aagaaaagc tctcacacaa accggaagcc    3300
aaatgtcccc tatctcttga atgatcaagt cacttttgac aacatccagg tgaatataaa    3360
aacttaataa agctgtggaa aggaactctt aatcttcttt tctgctactt aggttaaatt    3420
cactagatct tgattaggaa tcaaaattcg aattgggaca tgttcaaatt ctttcttgtg    3480
gtagttgcct atactgtcat cgctgctgtt ggttgagcat tgtggtgta ccacgctgtg    3540 tgctcaaggg tattacattc atcttctcat ttaatcctca caacaatctg aagaaggtag    3600
gtattacaat tcccacttca tagaaacaga aactgaggtt cagagaggtt aagtcatttg    3660
cccaaatggc tgagccaaag cctaccatgt acctaacctt tattttcttt cccgaacata    3720
ccaggctgtc tcctcataac ttccaagcat gcacttaaaa ctccacatga atacaaggtt    3780
catgggactt ggtattcata gaagggagg cagaaagctg gtctgttcct gataggcttg    3840
taatttaata tcattctgtt catgtgcttt ggatggaagc acatctggca tatgatgcta    3900
atcagtggtt cccataccc tggcttccta atttttaatgt ttgctcacag catagtagat    3960
tgacatcaaa tagtggccga tgatgatgaa aataaaggtc aaataagttg agccaataac    4020
agccgctttt ttccttctgt ctgcgtatac aaagcactgt catgcacaca atctattctg    4080
accctcacaa caacccataa gggtgtaaat agtatttcca ttttacaaat gaggatcaca    4140
caaactacta catggcagag cagatactcc aactcatgtc ttctggttga agcctattgc    4200
tttttctttt ctaaacactt tccctcagca agttggaatt agacttcaca agtctccttc    4260
agagaacaca aatcttttct tattccattc ctgtttggtt gcctacgtcc aatctccccc    4320
tccccagaga tgccaaaaaa aaaatccttt aaggtatttg ggagccaaac tcaacttgtt    4380
aaaatctcaa attatggaga caatcagcag acacaaccta accccaatta ttttggcagg    4440
aaggttggtt tagaggcaga tccagcaatc tgctttgggc cactctgggt ggggtaggtg    4500
aaataagatt ggtcactgtt aactaatttt aatattggat tggccattgg ttatcactga    4560
ttaccattct cccctggatt ttcacccagg actcaaaact tggttctgct aaccctgttc    4620
ctttatgagg aaccttttaa agattccttt ataaggtggg agttttttt ctatgaacct    4680 ataggggaga aaaagatca gcagaagtca ttacttttt tttttttttt tttttttttt    4740
gagagagagt ctcactccat tgcccaggct ggagtgcagt ggtgctatct cggctcactg    4800
caacctccgc ctcctgggtt caagcaattc tcctgcctca gcctcccgag tagctgggat    4860
tgcaggtgcc caccaccaca cccggctaat ttttgtattt ttagtaaaga cagggtttca    4920
ccatgttggc caggctggtc tccaactccc aatctcaggt gatcctattg cctcgggctc    4980
ccaaagtgct gggattacag gagtgagcca ccatgcctgg ccagaagtgg ttacttctgt    5040
agacaaaaga ataatgctac ttaatcaggc tttctgtgtg acaagaaaga gaaagaaaat    5100
aaagaagttt caattcatcc aattcttaat aagaaatatg taaataaaat tttttaaaat    5160
tacacttcat tttaatgttg tatcagtcaa ggtccctgca agagatggat ggtatggtac    5220
actcaaactg ggtaacacag gagagttttc agaaagcaac taaatccaaa atactatcaa    5280
ggaatcaata taaaaattgt taatattttt ctcatactaa attttcaaaa tattttgtgt    5340
ctattacatt tacagcacat cttaattagg actagctgtg tgttcacctc acatgtggct    5400
tgtagctacc atactggaca gcacatgtcc aaaaaatac acgtaaagtt aaagtttaaa    5460
```

```
agacacagga actaagccct cattgtcttt cccttgggag gtagtttaaa gagctataga    5520
tgctgtaaca ttcttgctat tatttattat atatgacatt attcctaaaa aagcttttga    5580
gatcctaggt tgtattcctc aggttttgtt gccttcccat gaagatgtga aggcagggat    5640
gcctgttatt cagtccaaga tgcatgacaa gagaccttgg gaaagtttca tctggattta    5700
aagattaatt cttgatgctt acattccata ctcaaaatgt aaatttgaat attaaaataa    5760
agatgatttt ttttttggag ctagtcttgc tctgttgccc aggctggaat gcagtggcat    5820
gatcatggct cactgcagcc tcgacctccc aagctcaagc aaggctacag gtgtgcacct    5880
aagtagctag gactacaggt gtgcaccacc atgtctagct attttttttt ctgtagagac    5940
agggttttcc tatgttgtcc aggctggtct cgaactcctg ccctcaagca atcctcctgc    6000
cttggcctcc caaagtgttg agattacagg cgtaagccac tgcacctggc caagatgaat    6060
attttaatag ctcacagaac aaagtttgcc acataatgat aaaattacta tgaaaatata    6120 ttcccttat tgtcagttta aaagatgaac tgagtttcac ccaaactggt ctggcccctc     6180
tctgattcaa ataccaatag ttgctctgat tcaaattcca actgttagaa catgacagct    6240
gctcataact agctttgctt actaaccatg tttctttcca tttgtattag gtcctttact    6300
ttttataaca gcctcaaagt ttcatgaatt gctgcagtaa acattgattt tcatgtttgt    6360
gagtctgcaa gccagctggg cagctctact tcaggtggta agggtggatc agacctattc    6420 catataccto ttgttctcct tgtccagtgg tttctaggga tatgttctca tgatgaaccc    6480
cgcagaggct cgtgaaagtg agaggaaact aggatgcctc ttaaggtctt ggtcaggatg    6540
gggtctcctg tcacttctgt cacaggctat tgtaagtcat atgagcaagc tcaataaaat    6600
ataaacaagt cagataaaca gtgggaggaa tggcaaagtc atatggccaa ggccatgagt    6660
gattaatttt aacacaggaa aaagtaaag cattaaatgc gattatttaa tatacaatgt     6720
cttattaact gaaatataaa atgtgtttac tgtaaaatat aatctgttta tctcaccaaa    6780
gaaatattat ctttaaaaaa tgtcattact tctaagacat catcagtctg caacttcttt    6840
ccatagcctt aatcaggatg ctgtggcagc tcccacatta gcctcgcatt ctaaactggt    6900
agatgtccta ggaaaccata catctatgta ttttcttat tttatacgtt taggacaatg     6960
tatagctaat tacccaactt tttatttgca tacaaatcta atacaactga acacaatcag    7020
ttttatcaca ggtataatgg attttttcaat agtgaggagg tgcctccatg agccttctct   7080
ttagaaaagt ggcattcaag actcttcatt tgaagtgaag attgctatgt cttttgcatt    7140
gctctatttt acataaatta agttataaat tgacactata atcaactgac accatgatca    7200
gtgatgatga tcaccctcat cagcactaga gttgacttgt ttttataacc cctttgcatg    7260
tatgttgaat agcaaagttc atcagagaac atgtattagt caatggtaag taagatactc    7320
tcatctaaga aataacatca cctcttctaa tgaagttcta agaagagagg gaagaaaaag    7380
tcttgggagc tagtcaggga atagtgtgta tttgcaatta cctaaactga actctaccat    7440
tactcctaac ccagttcctc ctcctgtgtt ttacatgatt aatgccaccc ctgcctcaat    7500
gaaccaagat cagctccatc actgggacct ccccattctg cctgtgcaat atttttcttt    7560
tttatttctc cttctaatat tactgttatt gctccagtaa agagctgtaa tatatttac    7620 ctggactgat accaggaatg gtggtgttgc ttccaatctg ttgctgctag attaatcttt    7680
gcaaagcaca ggcttaattt cattgctgct caactaaaac cactggtggc tttccattgc    7740
ctacaaaata aagtcaacct ccccatcaga cattcaaggc tttcaatgat ccatggccgc    7800
cagctctctc caggctcata tcccactcca ctcctctgat gtttcctaca ctacactaca    7860
```

```
ctatactaca ctacagccag gtagaatgac tgttcaccca acaccactca ggttgtcttc   7920
tcaacttgga atactcttgc accttcaaag ctcatttcaa atgccccttc atttgtgaag   7980
ccttctccaa atttccaagt cagaatgtct cttccttgtg ctaccacaac cctttaactg   8040
agcctccatt agtgcactga gaccattctg ttcagtgtct gggtgaagct tcctggtgaa   8100
aaatatgtta cctatttctt tctgaaaagt tggattcagg gatattatca cggacctaag   8160
gtaatagttc tagccaacct ccctgtccac tgccaggccg actacaaacc cttctgttgc   8220
tggcgagctg gtccgcacca ctagttctgc ttcactctat ttatctcttg atgtaaccat   8280
cttctttctc caggttttaa gaaccagccc aactcctggt tccctgatga gctttttatt   8340
cccctagcca catggaactt ttcctttttg gaacatgcct ttagtttctg tgtagtttgc   8400
catgcagcac ttcattgtac acattattaa aacagaattt taaggattag aatgaacctt   8460
aaaagatcat gcatctcaaa atttaatgta catacaaatt acccagggat tttgttgaaa   8520
taaaaattat ttaattttaa ttaatataaa taattcagta ggtctggggt gaggcctgag   8580
gttttacatt tccaacaagc tgccaggtaa agccaataca tctgtccagg aatcacactt   8640
tgcgtatcaa aggtctagat gacattatca ttccaaagag tttcttttac aggctctcag   8700
atcagtgttc atccactacc tgactactgt cattcacagg cattctgttc cacagcaggc   8760
cagctaacgt ggtatttaca aagctcactc ctcttataca acaatccaag tgtttctttt   8820
gtcagttgtc tgtgccccag gagatccctc tctgccttgc cttgccctct gcctttggag   8880
accagcacct catactcagt gaaggcctgg agtgcttaag agggatttct tccagctctc   8940
ttgccctggt cttcagtgta ttagatgtat tacctccatg ctctcagtag aggcccatag   9000
gaaagagtag gtaggttatg ccagctcaca cgcatccttt aaaaatggtt tagaagttta   9060 gctggttttct tattactcct gtctatggat gttttccttct gtcactctac tagggatgaa   9120
acagctaatc atgttcaata gttacattta gattggtttt taaaaactat gattgtatta   9180
gttcgtttcc atgctgctga taaagacata tctgagactg gaaacaaaaa gggtttaatt   9240
ggacttacag ttccacatgg ctggggaggc ctcaaaatca ggtgggaggc aaaaggtact   9300
tcttacgtgg tggcatcaag agcaaaatga ggaagaagca aaagcagaaa ctcttcataa   9360
acccaccaga tcttgtggga cttattatca cgagaatagc acagaaaaga ctggcctcca   9420
tgattcaatt acctcccact gcgtccctcc acaacatgt gggaattctg ggagatacaa   9480
ttcaagttga gatttgggtg gggacacagc caaaccatat cattcctccc tgggctcctc   9540
caaatttcat aatcctcaca tttcaaaacc aatcattcct tcccaacagt tccccaaagt   9600
cttaactcat ttcagcatta acccaaaagt ccacagtcca aagtctcatc tgagacaagg   9660
caagtccctt ccacttacaa gcctgtaaaa gcaagctagt tacctcctag atacaatggg   9720
gggtacaggt attgggtaaa tacagctgtt ccaaatgaga gaaattggcc aaaacaaagg   9780
ggttacaggg tccatgcaag tctgaaatcc agtggggcag tcaaatttta aagctccata   9840
atgatctcct ttgactccat gtctcacatt caggtcatgc tgatgcaaga gataggttcc   9900
catggtcttg tgcagctccg cccctgtggc tttgcagagt acagcctccc tcctggctgc   9960
tttctcaggc tgatgttgag tgtctgtagc ttttccaggc acaagatgca agttggtggt  10020
tgatctacca ttctggggtc taccattctg gggtctaccg ttctgggact gtggccttct  10080
tctcacagct ccactaggca gtgccccaac agggactctg tgtgggggct ctgccccaca  10140
tttcccttcc acactgccct aggagaggtt cccatgagg gctctgcccc tgcagcaaac  10200
```

```
ttttgcctgg acatccaggt gtttccatat atattctgaa atctaggcag aggttcccaa    10260
atctcaattc ttgacatctc tgcacccaca ggctcaacat cacatggaag ctgccaatgc    10320
ttggggcctc taccctctga agccacagcc caagctctat gttggctcct ttcagccatg    10380
gctggagcag ctgggacaca gggcaccaag tccctaggct gcacacagca cagagaccct    10440
gggcccagcc cacaaaacca cttttcctc ctgggcctct gggcctgtga tgggaggggc     10500
tgccatgaag gtctctgaca tgacctggag acattttccc catggtcttg gggattaaca    10560
ttaggctcct tgctgcttat gcaaatttct gcagccagct tgaatttctc cttaaaaaaa    10620
atgggttttt cttttctact gcatcatcag gctgcagatt ttccacattt atgctcttgt    10680
ttccctttta aaacagaatg tttttaacag cacccaagtc acctttgaa tgctttgctg      10740
cttagaaatt tattccacca gatacccaa gtcatctctc tcaagctcta agttccacaa     10800
atctctaggg caagggtgaa atgctgccag tctccttgct aaaacataac aagggtcacc    10860
tttacttcag ttcccaacaa ggtcttcatc tccatctgag accacctcag cctggacctt    10920
attgttcata tcactatcag tatttttgtc aatgccattc acagtctcta ggaggttcca    10980
aactttccta catttccta tcttcttctg agccctccag attatttcaa cacccagttc     11040
caaagttgct tccacatttt cgggtatctt ttcagcaatg ccccactcta ctggtactat    11100
tagtccattt tcatgctgct gataaagaca tacctgagac tgggaacaaa agaggttta     11160
attggactta tagttccacc tggctgggga ggcctcagaa tcatggcagg aggtgaaagg    11220
catttcttac acggcagcag caagagaaaa atgaagaagc agcaaaagca gaaaccctg     11280
ataaaaccat cagatctcgt gagacttatt cactatcaca agaatagcat gggaaagacc    11340
agcccccttg attcaattac ctccccctgg gtcctgtggg aattctggaa ggtacaattc    11400
aagttgagat ttgggtgggg acacagccaa accatatcaa tgattttgta ctttaaccag    11460
ctgaatggaa gtacaatctc ttgctatatg acacaataat tatttgcaaa atgagtaaac    11520
atatcataag gaaattattt ttacaaggtt tgaaacctga aatgcagtct attatcatac    11580
ataactaaaa atagagcctc aataaacaga ttcccagttt tgaaaatgca acatttgtac    11640
tccacattgt cagttttctt aggtatattt ataaatactc ctataaaaat gtaaagaaac    11700
acataatgta gattgctaat tttataataa cacaagttga ttttgacatc caacttatta    11760
attatgaaat gacttttggc ctagtaacaa tgaaaatggg ggcaaataca gataaatggt    11820
aattcttaga atgaactact cagcaccaat tctaagtttt tcttgatggt aaatcataat    11880
gttccctttc tcctcggttc tgcaatctat aggcatacca taattgtaat caatagctta    11940
aaaatatgtc tctctgtcct attctgtatc tgtatctctt ggatttttac ctttgcaata    12000
gtcaactgaa ccatcttctt ggagtactca tgaagatgga agtctacatg gagaatacag    12060
gatgaatcca ctctgtctcc tgcagtgaag tctgtttgaa ggatgtattt ggctgtcttc    12120
tggacaggcc attctaataa cagaaacaaa caagttattt taaaacttat tggaatattc    12180
aaatattaac caaagtagaa aaatataata cacatccatg tgcccatcac agaacttcac    12240
tgattatcat catttagcca gtcttgaaga agcaagtgct aattacaatc acaaatgaaa    12300
caagattcag acttcatgaa gagcactgcg ctataataaa agaagaaatg agcacataca    12360
ttctttact gacagtcaaa tggtgaaggt gggcagaatc attatgtgat gcaacatggc     12420
aaaagtatac agacagtgca tccagaggaa ggcaccttgc tgaatgacta gaatggaagt    12480
aggagacatt ttgcaggccc ccttcatcct gcagggagaa ccagaccac agcagctcta     12540
tttgcctatt cctctttaaa ttacaaagtt aaaatttggg agtagtagaa aatcaattgg    12600
```

-continued

| | |
|---|---|
| ttatcttata gagtctccta gaatatttca ttggcattga gaaggtggaa aatgcaaatt | 12660 |
| atatacttta aaatgtaatt tttgcttttc acatatgctt aaagcctaaa acctcttaat | 12720 |
| aaacttcttc tgaaatata | 12739 |

<210> SEQ ID NO 615
<211> LENGTH: 3824
<212> TYPE: DNA
<213> ORGANISM: Homo sapiens

<400> SEQUENCE: 615

| | |
|---|---|
| ggagagtgtc tctaaggtga cactcgggtg cgcggcagca gcggcggttg caggagctcg | 60 |
| ctctccgccc gggctccggc tccgctccag ccgtccgggg ggcgccgcgg cgcgcagagc | 120 |
| gcagcacccc gactccagcc aggagccccc gccccccggg agcgcaggag daccccggcc | 180 |
| cgcctctccc aggcgcagcg cccagcatct cgctgctcct gtcgtctaag cgtcggcgtc | 240 |
| gctagggacc tgcggaaccc ggcgctcccc tccctccccg cctcgcgtcc ccggcccggg | 300 |
| cggactggag actcgaactt gagcgggtgc ccgaaaggcc gcaggagccg cgggcggaag | 360 |
| gcggccgcac gatggccgag gggcagggcg gcggagggca gcgctgggac tgggctggcg | 420 |
| gcggccgggc agccgaggag gaggtggtgc ggcggcgatg ccggcgcggg gaggaggccc | 480 |
| aggtcgcgca gccctggccc gagggttccc ggggcacggc cgctgggccc ccggtggagg | 540 |
| agcgtttccg ccagctgcac ctacgaaagc aggtgtctta caggaaagcc atcaccaagt | 600 |
| cgggcctcca gcacctggcc cccctccgc ccacccctgg ggcccgtgc agcgagtcag | 660 |
| agcggcagat ccggagtaca gtggactgga gcgagtcagc gacatatggg gagcacatct | 720 |
| ggttcgagac caacgtgtcc ggggacttct gctacgttgg ggagcagtac tgtgtagcca | 780 |
| ggatgctgaa gtcagtgtct cgaagaaagt gcgcagcctg caagattgtg gtgcacacgc | 840 |
| cctgcatcga gcagctggag aagataaatt ccgctgtaa gccgtccttc cgtgaatcag | 900 |
| gctccaggaa tgtccgcgag ccaaccttg tacggcacca ctgggtacac agacgacgcc | 960 |
| aggacggcaa gtgtcggcac tgtgggaagg gattccagca gaagttcacc ttccacagca | 1020 |
| aggagattgt ggccatcagc tgctcgtggt gcaagcaggc ataccacagc aaggtgtcct | 1080 |
| gcttcatgct gcagcagatc gaggagccgt gctcgctggg ggtccacgca gccgtggtca | 1140 |
| tcccgcccac ctggatcctc cgcgcccgga ggccccagaa tactctgaaa gcaagcaaga | 1200 |
| agaagaagag ggcatccttc aagaggaagt ccagcaagaa agggcctgag gagggccgct | 1260 |
| ggagaccctt catcatcagg cccaccccct cccgctcat gaagcccctg ctggtgtttg | 1320 |
| tgaaccccaa gagtgggggc aaccagggtg caaagatcat ccagtctttc ctctggtatc | 1380 |
| tcaatcccg acaagtcttc gacctgagcc agggagggcc caaggaggcg ctggagatgt | 1440 |
| accgcaaagt gcacaacctg cggatcctgg cgtgcggggg cgacggcacg gtgggctgga | 1500 |
| tcctctccac cctggaccag ctacgcctga agcgccacc ccctgttgcc atcctgcccc | 1560 |
| tgggtactgg caacgacttg gcccgaaccc tcaactgggg tggggctac acagatgagc | 1620 |
| ctgtgtccaa gatcctctcc cacgtggagg aggggaacgt ggtacagctg gaccgctggg | 1680 |
| acctccacgc tgagcccaac cccgaggcag ggcctgagga ccgagatgaa ggcgccaccg | 1740 |
| accggttgcc cctggatgtc ttcaacaact acttcagcct gggctttgac gcccacgtca | 1800 |
| ccctggagtt ccacgagtct cgagaggcca cccagagaa attcaacagc cgcttcggt | 1860 |
| ataagatgtt ctacgccggg acagctttct ctgacttcct gatgggcagc tccaaggacc | 1920 |

| | |
|---|---:|
| tggccaagca catccgagtg gtgtgtgatg aatggactt gactcccaag atccaggacc | 1980 |
| tgaaacccca gtgtgttgtt ttcctgaaca tccccaggta ctgtgcgggc accatgccct | 2040 |
| ggggccaccc tggggagcac cacgactttg agcccagcg gcatgacgac ggctacctcg | 2100 |
| aggtcattgg cttcaccatg acgtcgttgg ccgcgctgca ggtgggcgga cacggcgagc | 2160 |
| ggctgacgca gtgtcgcgag gtggtgctca ccacatccaa ggccatcccg gtgcaggtgg | 2220 |
| atggcgagcc ctgcaagctt gcagcctcac gcatccgcat cgccctgcgc aaccaggcca | 2280 |
| ccatggtgca gaaggccaag cggcggagcg ccgccccct gcacagcgac cagcagccgg | 2340 |
| tgccagagca gttgcgcatc caggtgagtc gcgtcagcat gcacgactat gaggccctgc | 2400 |
| actacgacaa ggagcagctc aaggaggcct ctgtgccgct gggcactgtg gtggtcccag | 2460 |
| gagacagtga cctagagctc tgccgtgccc acattgagag actccagcag gagcccgatg | 2520 |
| gtgctggagc caagtccccg acatgccaga aactgtcccc caagtggtgc ttcctggacg | 2580 |
| ccaccactgc cagccgcttc tacaggatcg accgagccca ggagcacctc aactatgtga | 2640 |
| ctgagatcgc acaggatgag atttatatcc tggaccctga gctgctgggg gcatcggccc | 2700 |
| ggcctgacct cccaaccccc acttcccctc tccccacctc accctgctca cccacgcccc | 2760 |
| ggtcactgca aggggatgct gcacccccctc aaggtgaaga gctgattgag gctgccaaga | 2820 |
| ggaacgactt ctgtaagctc caggagctgc accgagctgg gggcgacctc atgcaccgag | 2880 |
| acgagcagag tcgcacgctc ctgcaccacg cagtcagcac tggcagcaag gatgtggtcc | 2940 |
| gctacctgct ggaccacgcc cccccagaga tccttgatgc ggtggaggaa acggggaga | 3000 |
| cctgtttgca ccaagcagcg gccctgggcc agcgcaccat ctgccactac atcgtggagg | 3060 |
| ccggggcctc gctcatgaag acagaccagc agggcgacac tccccggcag cgggctgaga | 3120 |
| aggctcagga caccgagctg gccgcctacc tggagaaccg gcagcactac cagatgatcc | 3180 |
| agcgggagga ccaggagacg gctgtgtagc gggccgccca cgggcagcag gagggacaat | 3240 |
| gcggccaggg gacgagcgcc ttccttgccc acctcactgc cacattccag tgggacggcc | 3300 |
| acggggggac ctaggcccca gggaaagagc cccatgccgc cccctaagga gccgcccaga | 3360 |
| cctaggctg gactcaggag ctgggggggc ctcacctgtt cccctgagga ccccgccgga | 3420 |
| cccgaggct cacagggaac aagacacggc tgggttggat atgcctttgc cggggttctg | 3480 |
| gggcagggcg ctccctggcc gcagcagatg ccctcccagg agtggagggg ctggagaggg | 3540 |
| ggaggccttc gggaagaggc ttcctgggcc ccctggtctt cggccgggtc cccagcccc | 3600 |
| gctcctgccc cacccccacct cctccggct tcctccccgga aactcagcgc ctgctgcact | 3660 |
| tgcctgccct gccttgcttg gcacccgctc cggcgaccct cccgctccc ctgtcatttc | 3720 |
| atcgcggact gtgcggcctg ggggtggggg gcgggactct cacggtgaca tgtttacagc | 3780 |
| tgggtgtgac tcagtaaagt ggatttttt ttctttaaaa aaaa | 3824 |

<210> SEQ ID NO 616
<211> LENGTH: 2664
<212> TYPE: DNA
<213> ORGANISM: Homo sapiens

<400> SEQUENCE: 616

| | |
|---|---:|
| attggaggag cgctcccact cccaagaggc cacgcgtaga cggggcgctt catgcggaag | 60 |
| tcagcggcgt ccggtcccag cctcctctgg gagcgggcag ttggcgaccc tgcactgacc | 120 |
| cgcgtccctc cgtcccgagc ccgcgcgccc tcagagggtg cccggacaga ctgaagccat | 180 |
| ggcgattctt tttgctgttg ttgccagggg gaccactatc cttgccaaac atgcttggtg | 240 |

```
tggaggaaac ttcctggagg tgacagagca gattctggct aagataccett        300
                                            ctgaaaataa caaactaacg tactcacatg gcaattattt gtttcattac atctgccaag         360
                                            acaggattgt atatctttgt atcactgatg atgattttga acgttcccga gcctttaatt        420
                                            ttctgaatga gataaagaag aggttccaga ctacttacgg ttcaagagca cagacagcac         480
                                            ttccatatgc catgaatagc gagttctcaa gtgtcttagc tgcacagctg aagcatcact        540
                                            ctgagaataa gggcctagac aaagtgatgg agactcaagc ccaagtggat gaactgaaag         600
                                            gaatcatggt cagaaacata gatctggtag ctcagcgagg agaaagattg gaattattga        660
                                            ttgacaaaac agaaaatctt gtggattctt ctgtcacctt caaaactacc agcagaaatc         720
                                            ttgctcgagc catgtgtatg aagaacctca agctcactat tatcatcatc atcgtatcaa        780
                                            ttgtgttcat ctatatcatt gtttcacctc tctgtggtgg atttacatgg ccaagctgtg         840
                                            tgaagaaata ggaaagaaga agttaccatt aaccaaggat atgagagaac aaggagttaa        900
                                            aagcaatcca tgtgactcaa gcctttcaca tactgacaga tggtatctgc cagtctcttc         960
                                            aaccctcttc tcactttta aaatcttgtt ccatgcctcc aggtttatct ttgtcttatc        1020
                                           taccagttta ttcctgtgaa cttcagattg aaccattcat tgcagcagta gccttaaaaa        1080
                                           ggcttttgtt tatttctttg gtttgttaac tagtgtcatc tatttagaga acatttttg         1140
                                           tttttaattg ctcaaagctg tcgccgctag tcttatgagc tatctactaa aactatggag        1200
                                           aaactttgta tgtgcacaca aaagtattca agagacagta ttgctaacat ctcatcttaa        1260
                                           tgtctttgt tattgagaag ttttaggtgc ttcaaaacaa tataaatgga taatagttgt        1320
                                           tatttgggga attgtaatga tgttggtgct gcttccttct aagagctcag acaagtaaag        1380
                                           tatgaaacat tcttatttca gttagatggg gaacattttg ctagcccatt agaagcacac        1440
                                           agaattatcc ttgtcctcct aatattgact ttcaggaata agttcagtg tgctgatcat         1500
                                           tcacaataca gtggatagct tgatatcttc tgttttccca ttgcagttga tttgagaaga        1560
                                           tgaaggttta aatattgttg aaagttgcag ttttttaaat gtgttccttt tcttctgtg         1620
                                           aatatttagg gcaatcgtgt cgctaataga atatgtagta gaggggtgg ggaggtaaat         1680
                                           tcctctgact tgccaaagaa aaagaaggga accacagtgg atatgctagc attttagctg        1740
                                           tgcaaaggga ggtagtgtgg gaaaagtgtt tccattctgg gaaaagccca aaccgaatac        1800
                                           ggtcagcagt caactccagg gtttgggctt gattcctgtt gaataatagt tttgagcatt        1860
                                           ctttgtggtt aaataaattc ttaaatctgc ctagttttga tgaattcttt tgtgaaactt        1920
                                           gaaagagaat agacagtatg acatatagaa ttaatacaaa acagtttaac aaccatttaa        1980
                                           ctgcagtgta agaaaattgg actgtaatca tatcgctact ggcatctgtt atctagtatg        2040
                                           catttctggt gtgtatctga aaggaagaca ttttctaccc tagatccaat tgcatttatt        2100
                                           tatcaataag tgccattaaa ttgaaattat attacatttt acactttctc aatgaatgaa        2160
                                           caaattagtc tgtagaatct agccacctgt ttagcctagt catgtgcctt gaacatatat        2220
                                           gtgtcccata atctggctca tggtacctgt tcttctatcc aaaccttca attcatgcta         2280
                                           cctgattcat ttatttgaca tagatcttag gcccacttga actcttttct tgtttatcta        2340
                                           gcatagcaca aacgttttc cagtcttctt tatcaacact aatgcctcta attgcatca          2400
                                           gtatttccta ttggaaaata catctgttcc agaaaaacat ttggcattcc tgaataattt        2460
                                           ccaaatgttt ttaatccaaa gaaaaggtt taagcttat ttccctttct tatacacacc          2520
                                           tgaataaaat tgatgtgcat gttttaggga tcaattacct aactgttcct tggtctattt        2580
                                           atgtataaga
```

| | |
|---|---:|
| atgcttttta aagcacatgt ctcattttaa atgacgcaca aactgaagat gttaataaaa | 2640 |
| tttaagagta atacaatgaa aaaa | 2664 |

<210> SEQ ID NO 617
<211> LENGTH: 8155
<212> TYPE: DNA
<213> ORGANISM: Homo sapiens

<400> SEQUENCE: 617

| | |
|---|---:|
| gcagagtctg cagtgcggag ggggcgggaa gtccaggccc cgcactcgat ccacgctggc | 60 |
| tccctacgga ggcccaccta ctcgaggccc accgactcct actgcaatca gtactatgcg | 120 |
| atcgtcctag agagtccatt cagctgcact tccgcctcag tatggcatca cagctgcaag | 180 |
| tgttttcgcc cccatcagtg tcgtcgagtg ccttctgcag tgcgaagaaa ctgaaaatag | 240 |
| agccctctgg ctgggatgtt tcaggacaga gtagcaacga caaatattat acccacagca | 300 |
| aaaccctccc agccacacaa gggcaagcca actcctctca ccaggtagca aatttcaaca | 360 |
| tccctgctta cgaccagggc ctcctcctcc cagctcctgc agtggagcat attgttgtaa | 420 |
| cagccgctga tagctcgggc agtgctgcta catcaacctt ccaaagcagc cagaccctga | 480 |
| ctcacagaag caacgtttct ttgcttgagc catatcaaaa atgtggattg aaacgaaaaa | 540 |
| gtgaggaagt tgacagcaac ggtagtgtgc agatcataga agaacatccc cctctcatgc | 600 |
| tgcaaaacag gactgtggtg ggtgctgctg ccacaaccac cactgtgacc acaaagagta | 660 |
| gcagttccag cggagaaggg gattaccagc tggtccagca tgagatcctt tgctctatga | 720 |
| ccaatagcta tgaagtcttg gagttcctag gccgggggac atttggacag gtggctaagt | 780 |
| gctggaagag gagcaccaag gaaattgtgg ctattaaaat cttgaagaac caccctcct | 840 |
| atgccagaca aggacagatt gaagtgagca tcctttcccg cctaagcagt gaaaatgctg | 900 |
| atgagtataa ttttgtccgt tcatacgagt gctttcagca taagaatcac acctgccttg | 960 |
| tttttgaaat gttggagcag aacttatatg attttctaaa gcaaaacaaa tttagcccac | 1020 |
| tgccactcaa gtacatcaga ccaatcttgc agcaggtggc cacagccttg atgaagctca | 1080 |
| agagtcttgg tctgatccac gctgacctta agcctgaaaa catcatgctg ttgatccag | 1140 |
| ttcgccagcc ctaccgagtg aaggtcattg actttggttc tgctagtcac gtttccaaag | 1200 |
| ctgtgtgctc aacctactta cagtcacgtt actacagagc tcctgaaatt attcttgggt | 1260 |
| taccattttg tgaagctatt gatatgtggt cactgggctg tgtgatagct gagctgttcc | 1320 |
| tgggatggcc tctttatcct ggtgcttcag aaatatgatca gattcgttat atttcacaaa | 1380 |
| cacaaggctt gccagctgaa tatcttctca gtgccggaac aaaaacaacc aggttttca | 1440 |
| acagagatcc taatttgggg tacccactgt ggaggcttaa gacacctgaa gaacatgaac | 1500 |
| tggagactgg aataaaatca aagaagctc ggaagtacat tttaattgc ttagatgaca | 1560 |
| tggctcaggt gaatatgtct acagacctgg agggaacaga catgttggca gagaaggcag | 1620 |
| accgaagaga atacattgat ctgttaaaga aaatgctcac aattgatgca gataagagaa | 1680 |
| ttacccctct aaaaactctt aaccatcagt ttgtgacaat gactcacctt ttggatttc | 1740 |
| cacatagcaa tcatgttaag tcttgttttt agaacatgga gatctgcaag cggagggttc | 1800 |
| acatgtatga tacagtgagt cagatcaaga gtcccttcac tacacatgtt gccccaaata | 1860 |
| caagcacaaa tctaaccatg agcttcagca atcagctcaa tacagtgcac aatcaggcca | 1920 |
| gtgttctagc ttccagttct actgcagcag ctgctactct ttctctggct aattcagatg | 1980 |
| tctcactact aaactaccag tcagctttgt acccatcatc tgctgcacca gttcctggag | 2040 |

```
ttgcccagca gggtgtttcc ttgcagcctg gaaccaccca gatttgcact cagacagatc    2100
cattccaaca gacatttata gtatgtccac ctgcgtttca aactggacta caagcaacaa    2160
caaagcattc tggattccct gtgaggatgg ataatgctgt accgattgta ccccaggcac    2220
cagctgctca gccactacag attcagtcag gagttctcac gcagggaagc tgtacaccac    2280
taatggtagc aactctccac cctcaagtag ccaccatcac accgcagtat gcggtgccct    2340
ttactctgag ctgcgcagcc ggccggccgg cgctggttga acagactgcc gctgtactgc    2400
aggcgtggcc tggagggact cagcaaattc tcctgccttc aacttggcaa cagttgcctg    2460
gggtagctct acacaactct gtccagccca cagcaatgat tccagaggcc atggggagtg    2520
gacagcagct agctgactgg aggaatgccc actctcatgg caaccagtac agcactatca    2580
tgcagcagcc atccttgctg actaaccatg tgacattggc cactgctcag cctctgaatg    2640
ttggtgttgc ccatgttgtc agacaacaac aatccagttc cctcccttcg aagaagaata    2700
agcagtcagc tccagtctct tccaagtcct ctctagatgt tctgccttcc caagtctatt    2760
ctctggttgg gagcagtccc ctccgcacca catcttctta taattccttg gtccctgtcc    2820
aagatcagca tcagcccatc atcattccag atactcccag ccctcctgtg agtgtcatca    2880
ctatccgaag tgacactgat gaggaagagg acaacaaata caagcccagt agctctggac    2940
tgaagccaag gtctaatgtc atcagttatg tcactgtcaa tgattctcca gactctgact    3000
cttctttgag cagcccttat tccactgata ccctgagtgc tctccgaggc aatagtggat    3060
ccgttttgga ggggcctggc agagttgtgg cagatggcac tggcacccgc actatcattg    3120
tgcctccact gaaaactcag cttggtgact gcactgtagc aacccaggcc tcaggtctcc    3180
tgagcaataa gactaagcca gtcgcttcag tgagtgggca gtcatctgga tgctgtatca    3240
cccccacagg gtatcgagct caacgcgggg ggaccagtgc agcacaacca ctcaatctta    3300
gccagaacca gcagtcatcg gcggctccaa cctcacagga gagaagcagc aacccagccc    3360
cccgcaggca gcaggcgttt gtggcccctc tctcccaagc cccctacacc ttccagcatg    3420
gcagcccgct acactcgaca gggcaccac accttgcccc ggcccctgct cacctgccaa    3480
gccaggctca tctgtatacg tatgctgccc cgacttctgc tgctgcactg gctcaaccac    3540
gctccattgc tcatcttttc tccccacagg gttcctcaag gcatgctgca gcctatacca    3600
ctcaccctag cactttggtg caccaggtcc ctgtcagtgt tgggcccagc ctcctcactt    3660
ctgccagcgt ggcccctgct cagtaccaac accagtttgc cacccaatcc tacattgggt    3720
cttcccgagg ctcaacaatt tacactggat acccgctgag tcctaccaag atcagccagt    3780
attcctactt atagttggtg agcatgaggg aggaggaatc atggctacct tctcctggcc    3840
ctgcgttctt aatattgggc tatggagaga tcctcctta ccctcttgaa atttcttagc    3900
cagcaacttg ttctgcaggg gcccactgaa gcagaaggtt tttctctggg ggaacctgtc    3960
tcagtgttga ctgcattgtt gtagtcttcc caaagtttgc cctatttta aattcattat    4020 ttttgtgaca gtaattttgg tacttggaag agttcagatg cccatcttct gcagttacca    4080
aggaagagag attgttctga agttaccctc tgaaaaatat tttgtctctc tgacttgatt    4140
tctataaatg ctttaaaaa caagtgaagc ccctctttat ttcattttgt gttattgtga    4200
ttgctggtca ggaaaaatgc tgatagaagg agttgaaatc tgatgacaaa aaagaaaaa    4260 ttacttttg tttgttata aactcagact tgcctatttt atttaaaag cggcttacac    4320 aatctcccctt ttgtttattg gacatttaaa cttacagagt ttcagttttg ttttaatgtc    4380
```

```
atattatact taatgggcaa ttgttatttt tgcaaaactg gttacgtatt actctgtgtt    4440
actattgaga ttctctcaat tgctcctgtg tttgttataa agtagtgttt aaaaggcagc    4500
tcaccatttg ctggtaactt aatgtgagag aatccatatc tgcgtgaaaa caccaagtat    4560
tcttttaaa tgaagcacca tgaattcttt tttaaattat ttttaaaag tctttctctc     4620
tctgattcag cttaaatttt tttatcgaaa aagccattaa ggtggttatt attacatggt    4680
ggtggtggtt ttattatatg caaaatctct gtctattatg agatactggc attgatgagc    4740
tttgcctaaa gattagtatg aattttcagt aatacacctc tgttttgctc atctctccct    4800
tctgtttat gtgatttgtt tggggagaaa gctaaaaaaa cctgaaacca gataagaaca     4860
tttcttgtgt atagcttta tacttcaaag tagcttcctt tgtatgccag cagcaaattg     4920
aatgctctct tattaagact tatataataa gtgcatgtag gaattgcaaa aaatatttta    4980
aaaatttatt actgaattta aaaatatttt agaagttttg taatggtggt gttttaatat    5040
tttacataat taaatatgta catattgatt agaaaaatat aacaagcaat ttttcctgct    5100
aacccaaaat gttatttgta atcaaatgtg tagtgattac acttgaattg tgtacttagt    5160
gtgtatgtga tcctccagtg ttatcccgga gatggattga tgtctccatt gtatttaaac    5220
caaaatgaac tgatacttgt tggaatgtat gtgaactaat tgcaattata ttagagcata    5280
ttactgtagt gctgaatgag caggggcatt gcctgcaagg agaggagacc cttggaattg    5340
ttttgcacag gtgtgtctgg tgaggagttt ttcagtgtgt gtctcttcct tcccttcct    5400
cctccttccc ttattgtagt gccttatatg ataatgtagt ggttaataga gtttacagtg    5460
agcttgcctt aggatggacc agcaagcccc cgtggaccct aagttgttca ccgggattta    5520
tcagaacagg attagtagct gtattgtgta atgcattgtt ctcagtttcc ctgccaacat    5580
tgaaaaataa aaacagcagc ttttctcctt taccaccacc tctaccccctt tccatttggg   5640
attctcggct gagttctcac agaagcattt tccccatgtg gctctctcac tgtgcgttgc    5700
taccttgctt ctgtgagaat tcaggaagca ggtgagagga gtcaagccaa tattaaatat    5760
gcattctttt aaagtatgtg caatcacttt tagaatgaat ttttttttcc ttttcccatg    5820
tggcagtcct tcctgcacat agttgacatt cctagtaaaa tatttgcttg ttgaaaaaaa    5880
catgttaaca gatgtgttta taccaaagag cctgttgtat tgcttaccat gtccccatac    5940
tatgaggaga agttttgtgg tgccgctggt gacaaggaac tcacagaaag gtttcttagc    6000
tggtgaagaa tatagagaag gaaccaaagc ctgttgagtc attgaggctt tgaggtttc    6060
tttttaaca gcttgtatag tcttgggggcc cttcaagctg tgaaattgtc cttgtactct    6120
cagctcctgc atggatctgg gtcaagtaga aggtactggg gatggggaca ttcctgccca    6180
taaaggattt ggggaaagaa gattaatcct aaaatacagg tgtgttccat ctgaattgaa    6240
aatgatatat ttgagatata attttaggac tggttctgtg tagatagaga tggtgtcaag    6300
gaggtgcagg atggagatgg gagatttcat ggagcctggt cagccagctc tgtaccaggt    6360
tgaacaccga ggagctgtca aagtatttgg agtttcttca ttgtaaggag taagggcttc    6420
caagatgggg caggtagtcc gtacagccta ccaggaacat gttgtgtttt ctttattttt    6480
taaaatcatt atattgagtt gtgttttcag cactatattg gtcaagatag ccaagcagtt    6540
tgtataattt ctgtcactag tgtcatacag ttttctggtc aacatgtgtg atctttgtgt    6600
ctccttttg ccaagcacat tctgattttc ttgttggaac acaggtctag tttctaaagg     6660
acaaattttt tgttccttgt ctttttttctg taagggacaa gatttgttgt ttttgtaaga    6720
aatgagatgc aggaaagaaa accaaatccc attcctgcac cccagtccaa taagcagata    6780
```

```
ccacttaaga taggagtcta aactccacag aaaaggataa taccaagagc ttgtattgtt      6840
accttagtca cttgcctagc agtgtgtggc tttaaaaact agagatttt cagtcttagt      6900 ctgcaaactg gcatttccga ttttccagca taaaaatcca cctgtgtctg ctgaatgtgt     6960
atgtatgtgc tcactgtggc tttagattct gtccctgggg ttagccctgt tggccctgac    7020
aggaagggag gaagcctggt gaatttagtg agcagctggc ctgggtcaca gtgacctgac    7080
ctcaaaccag cttaaggctt taagtcctct ctcagaactt ggcatttcca acttcttcct    7140
ttccgggtga gagaagaagc ggagaagggt tcagtgtagc cactctgggc tcatagggac    7200
acttggtcac tccagagttt ttaatagctc ccaggaggtg atattatttt cagtgctcag    7260
ctgaaatacc aaccccagga ataagaactc catttcaaac agttctggcc attctgagcc    7320
tgcttttgtg attgctcatc cattgtcctc cactagaggg gctaagcttg actgccctta    7380
gccaggcaag cacagtaatg tgtgttttgt tcagcattat tatgcaaaaa ttcactagtt    7440
gagatggttt gttttaggat aggaaatgaa attgcctctc agtgacagga gtggcccgag    7500
cctgcttcct attttgattt tttttttttt taactgatag atggtgcagc atgtctacat    7560
ggttgtttgt tgctaaactt tatataatgt gtggtttcaa ttcagcttga aaaataatct    7620
cactacatgt agcagtacat tatatgtaca ttatatgtaa tgttagtatt tctgctttga    7680
atccttgata ttgcaatgga attcctactt tattaaatgt atttgatatg ctagttattg    7740
tgtgcgattt aaactttttt tgctttctcc cttttttgg ttgtgcgctt tcttttacaa     7800
caagcctcta gaaacagata gtttctgaga attactgagc tatgtttgta atgcagatgt    7860
acttagggag tatgtaaaat aatcatttta acaaagaaa tagatattta aatttaata     7920 ctaactatgg gaaagggtc cattgtgtaa aacatagttt atctttggat tcaatgtttg     7980
tctttggttt tacaaagtag cttgtatttt cagtattttc tacataatat ggtaaaatgt    8040
agagcaattg caatgcatca ataaaatggg taaatttct gacttatgtg gctgttttg     8100 acttctgtta taggatataa aggggatcaa taaatgacat ctttgaaagt gaaaa         8155

<210> SEQ ID NO 618
<211> LENGTH: 3443
<212> TYPE: DNA
<213> ORGANISM: Homo sapiens

<400> SEQUENCE: 618
gtgctttact gcgcgctctg gtactgctgt ggctccccgt cctggtgcgg gacctgtgcc       60
ccgcgcttca gccctccccg cacagcctac tgattcccct gccgcccttg ctcacctcct      120
gctcgccatg gagtcgctgg ttttcgcgcg gcgctccggc cccactccct cggccgcaga     180
gctagcccgg ccgctggcgg aagggctgat caagtcgccc aagcccctaa tgaagaagca     240
ggcggtgaag cggcaccacc acaagcacaa cctgcggcac cgctacgagt tcctggagac     300
cctgggcaaa ggcacctacg ggaaggtgaa gaaggcgcgg gagagctcgg ggcgcctggt     360
ggccatcaag tcaatccgga aggacaaaat caaagatgag caagatctga tgcacatacg     420
gagggagatt gagatcatgt catcactcaa ccaccctcac atcattgcca tccatgaagt     480
gtttgagaac agcagcaaga tcgtgatcgt catggagtat gccagccggg gcgaccttta     540
tgactacatc agcgagcggc agcagctcag tgagcgcgaa gctaggcatt tcttccggca     600
gatcgtctct gccgtgcact attgccatca gaacagagtt gtccaccgag atctcaagct     660
ggagaacatc ctcttggatg ccaatgggaa tatcaagatt gctgacttcg gcctctccaa     720
```

```
cctctaccat caaggcaagt tcctgcagac attctgtggg agcccctct atgcctcgcc      780
agagattgtc aatgggaagc cctacacagg cccagaggtg acagctggt ccctgggtgt      840
tctcctctac atcctggtgc atggcaccat gcccttgat gggcatgacc ataagatcct      900
agtgaaacag atcagcaacg gggcctaccg ggagccacct aaaccctctg atgcctgtgg     960
cctgatccgg tggctgttga tggtgaaccc cacccgccgg gccaccctgg aggatgtggc    1020
cagtcactgg tgggtcaact ggggctacgc cacccgagtg ggagagcagg aggctccgca    1080
tgagggtggg caccctggca gtgactctgc ccgcgcctcc atggctgact ggctccggcg    1140
ttcctcccgc cccctcctgg agaatggggc caaggtgtgc agcttcttca agcagcatgc    1200
acctggtggg ggaagcacca cccctggcct ggagcgccag cattcgctca agaagtcccg    1260
caaggagaat gacatggccc agtctctcca cagtgacacg gctgatgaca ctgcccatcg    1320
ccctggcaag agcaacctca agctgccaaa gggcattctc aagaagaagg tgtcagcctc    1380
tgcagaaggg gtacaggagg accctccgga gctcagccca atccctgcga gcccagggca    1440
ggctgccccg ctgctcccca agaagggcat tctcaagaag cccgacagc gcgagtctgg     1500
ctactactcc tctcccgagc ccagtgaatc tggggagctc ttggacgcag gcgacgtgtt    1560
tgtgagtggg gatcccaagg agcagaagcc tccgcaagct tcagggctgc tcctccatcg    1620
caaaggcatc ctcaaactca atggcaagtt ctcccagaca gccttggagc tcgcggcccc    1680
caccaccttc ggctccctgg atgaactcgc cccacctcgc cccctggccc gggccagccg    1740
accctcaggg gctgtgagcg aggacagcat cctgtcctct gagtcctttg accagctgga    1800
cttgcctgaa cggctcccag agcccccact gcggggctgt gtgtctgtgg acaacctcac    1860
ggggcttgag gagcccccct cagagggccc tggaagctgc ctgaggcgct ggcggcagga    1920
tcctttgggg gacagctgct tttccctgac agactgccag gaggtgacag cgacctaccg    1980
acaggcactg agggtctgct caaagctcac ctgagtggag taggcattgc cccagcccgg    2040
tcaggctctc agatgcagct ggttgcaccc cgaggggaga tgccttctcc cccacctccc    2100
aggacctgca tcccagctca gaaggctgag agggtttgca gtggagccct gagcagggct    2160
ggatatggga agtaggcaaa tgaaatgcgc caagggttca gtgtctgtct tcagccctgc    2220
tgaacgaaga ggatactaaa gagaggggaa cgggaatgcc cgcgacagag tccacattgc    2280
ctgtttcttg tgtacatggg ggggccacag agacctggaa agagaactct cccagggccc    2340
atctcctgca tcccatgaat actctgtaca catggtgcct tctaaggaca gctccttccc    2400
tactcattcc ctgcccaagt ggggccagac ctctttacac acacattccc gttcctacca    2460
accaccagaa ctggatggtg cacccctaa tgtgcatgag gcatcctggg aatggtctgg     2520
agtaacgctt cgttattttt atttttattt ttatttattt atttattttt ttgagacgga    2580
gtttcgctct tggtgcccag gctagagtgc aatggcgcga tctcagctca cctcaacctc    2640
cgcctcccgg gttcaagcga ttctcctgcc tcagcctccc tagtagctgg gattacaggc    2700
gcccgccacc atgcccggct aattttgtat ttttagtaga cagggtttt ctccatgttg      2760
gtcaggctgg tctcaaactc ccgacctcag gtgatccacc cacctcggcc tcccaaagtg    2820
ctgggattac aggcgtgagc caccgcgccc cacctaaccc ttccttattt agcctaggag    2880
taagagaaca caatctctgt ttcttcaatg gttctcttcc cttttccatc ctccaaacct    2940
ggcctgagcc tcctgaagtt gctgctgtga atctgaaaga cttgaaaagc ctccgcctgc    3000
tgtgtggact tcatctcaag gggcccagcc tcctctggac tccaccttgg acctcagtga    3060
ctcagaactt ctgcctctaa gctgctctaa agtccagact atggatgtgt tctctaggcc    3120
```

| | | | | |
|---|---|---|---|---|
| ttcaggactc | tagaatgtcc | atatttattt | ttatgttctt | ggctttgtgt | tttaggaaaa | 3180 |
| gtgaatcttg | ctgttttcaa | taatgtgaat | gctatgttct | gggaaaatcc | actatgacat | 3240 |
| ctaagttttg | tgtacagaga | gatattttg | caactatttc | cacctcctcc | cacaaccccc | 3300 |
| cacactccac | tccacactct | tgagtctctt | tacctaatgg | tctctaccta | atggacctcc | 3360 |
| gtggccaaaa | agtaccatta | aaaccagaaa | ggtgattgga | aaaaaaaaa | aaaaaaaaa | 3420 |
| aaaaaaaaa | aaaaaaaaa | aaa | | | | 3443 |

<210> SEQ ID NO 619
<211> LENGTH: 6267
<212> TYPE: DNA
<213> ORGANISM: Homo sapiens

<400> SEQUENCE: 619

| | | | | | | |
|---|---|---|---|---|---|---|
| agctgcaagt | ggcgggcgcc | caggcagatg | cgatccagcg | gctctggggg | cggcagcggt | 60 |
| ggtagcagct | ggtacctccc | gccgcctctg | ttcggagggt | cgcggggcac | cgaggtgctt | 120 |
| tccggccgcc | ctctggtcgg | ccacccaaag | ccgcgggcgc | tgatgatggg | tgaggagggg | 180 |
| gcggcaagat | ttcgggcgcc | cctgccctga | acgccctcag | ctgctgccgc | cggggccgct | 240 |
| ccagtgcctg | cgaactctga | ggagccgagg | cgccggtgag | agcaaggacg | ctgcaaactt | 300 |
| gcgcagcgcg | gggctggga | ttcacgccca | gaagttcagc | aggcagacag | tccgaagcct | 360 |
| tcccgcagcg | gagagatagc | ttgagggtgc | gcaagacggc | agcctccgcc | ctcggttccc | 420 |
| gcccagaccg | ggcagaagag | cttggaggag | ccaaaaggaa | cgcaaaaggc | ggccaggaca | 480 |
| gcgtgcagca | gctgggagcc | gccgttctca | gccttaaaag | ttgcagagat | tggaggctgc | 540 |
| cccgagaggg | gacagacccc | agctccgact | gcgggggca | ggagaggacg | gtacccaact | 600 |
| gccacctccc | ttcaaccata | gtagttcctc | tgtaccgagc | gcagcgagct | acagacgggg | 660 |
| gcgcggcact | cggcgcggag | agcgggaggc | tcaaggtccc | agccagtgag | cccagtgtgc | 720 |
| ttgagtgtct | ctggactcgc | ccctgagctt | ccaggtctgt | ttcatttaga | ctcctgctcg | 780 |
| cctccgtgca | gttggggaa | agcaagagac | ttgcgcgcac | gcacagtcct | ctggagatca | 840 |
| ggtggaagga | gccgctgggt | accaaggact | gttcagagcc | tcttcccatc | tcggggagag | 900 |
| cgaagggtga | ggctgggccc | ggagagcagt | gtaaacggcc | tcctccggcg | gatgggagc | 960 |
| catcgggctc | ctgtggctcc | tgccgctgct | gctttccacg | gcagctgtgg | gctccggat | 1020 |
| ggggaccggc | cagcgcgcgg | gctccccagc | tgcggggccg | ccgctgcagc | ccgggagcc | 1080 |
| actcagctac | tcgcgcctgc | agaggaagag | tctggcagtt | gacttcgtgg | tgccctcgct | 1140 |
| cttccgtgtc | tacgcccggg | acctactgct | gccaccatcc | tcctcggagc | tgaaggctgg | 1200 |
| caggcccgag | gccgcggct | cgctagctct | ggactgcgcc | ccgctgctca | ggttgctggg | 1260 |
| gccggcgccg | ggggtctcct | ggaccgccgg | ttcaccagcc | ccggcagagg | cccggacgct | 1320 |
| gtccaggggtc | tgaagggcg | gctccgtgcg | caagctccgg | cgtgccaagc | agttggtgct | 1380 |
| ggagctgggc | gaggaggcga | tcttggaggg | ttgcgtcggg | cccccggg | aggcggctgt | 1440 |
| ggggctgctc | cagttcaatc | tcagcgagct | gttcagttgg | tggattcgcc | aaggcgaagg | 1500 |
| gcgactgagg | atccgcctga | tgcccagaa | gaaggcgtcg | gaagtgggca | gagagggaag | 1560 |
| gctgtccgcg | gcaattcgcg | cctcccagcc | ccgccttctc | ttccagatct | cgggactgg | 1620 |
| tcatagctcc | ttggaatcac | caacaaacat | gccttctcct | tctcctgatt | attttacatg | 1680 |
| gaatctcacc | tggataatga | aagactccctt | ccctttcctg | tctcatcgca | gccgatatgg | 1740 |

-continued

```
tctggagtgc agctttgact tcccctgtga gctggagtat tcccctccac tgcatgacct    1800
caggaaccag agctggtcct ggcgccgcat cccctccgag gaggcctccc agatggactt    1860
gctggatggg cctggggcag agcgttctaa ggagatgccc agaggctcct ttctccttct    1920
caacacctca gctgactcca agcacaccat cctgagtccg tggatgagga gcagcagtga    1980
gcactgcaca ctggccgtct cggtgcacag gcacctgcag ccctctggaa ggtacattgc    2040
ccagctgctg ccccacaacg aggctgcaag agagatcctc ctgatgccca ctccagggaa    2100
gcatggttgg acagtgctcc agggaagaat cgggcgtcca gacaacccat ttcgagtggc    2160
cctggaatac atctccagtg gaaaccgcag cttgtctgca gtggacttct ttgccctgaa    2220
gaactgcagt gaaggaacat ccccaggctc aagatggcc ctgcagagct ccttcacttg     2280
ttggaatggg acagtcctcc agcttgggca ggcctgtgac ttccaccagg actgtgccca    2340
gggagaagat gagagccaga tgtgccggaa actgcctgtg ggtttttact gcaactttga    2400
agatggcttc tgtggctgga cccaaggcac actgtcaccc cacactcctc aatggcaggt    2460
caggacccta aaggatgccc ggttccagga ccaccaagac catgctctat tgctcagtac    2520
cactgatgtc cccgcttctg aaagtgctac agtgaccagt gctacgtttc ctgcaccgat    2580
caagagctct ccatgtgagc tccgaatgtc ctggctcatt cgtggagtct tgaggggaaa    2640
cgtgtccttg gtgctagtgg agaacaaaac cgggaaggag caaggcagga tggtctggca    2700
tgtcgccgcc tatgaaggct tgagcctgtg gcagtggatg tgttgcctc tcctcgatgt     2760
gtctgacagg ttctggctgc agatggtcgc atggtgggga caaggatcca gagccatcgt    2820
ggcttttgac aatatctcca tcagcctgga ctgctacctc accattagcg gagaggacaa    2880
gatcctgcag aatacagcac ccaaatcaag aaacctgttt gagagaaacc caaacaagga    2940
gctgaaaccc gggaaaaatt caccaagaca gaccccccatc tttgacccta cagttcattg    3000
gctgttcacc acatgtgggg ccagcggggcc ccatggcccc acccaggcac agtgcaacaa    3060
cgcctaccag aactccaacc tgagcgtgga ggtggggagc gagggcccccc tgaaaggcat   3120
ccagatctgg aaggtgccag ccaccgacac ctacagcatc tcgggctacg agctgctgg     3180
cgggaaaggc gggaagaaca ccatgatgcg gtcccacggc gtgtctgtgc tgggcatctt    3240
caacctggag aaggatgaca tgctgtacat cctggttggg cagcagggag aggacgcctg    3300
ccccagtaca aaccagttaa tccagaaagt ctgcattgga gagaacaatg tgatagaaga    3360
agaaatccgt gtgaacagaa gcgtgcatga gtgggcagga ggcggaggag gagggggtgg    3420
agccacctac gtatttaaga tgaaggatgg agtgccggtg cccctgatca ttgcagccgg    3480
aggtggtggc agggcctacg gggccaagac agacacgttc cacccagaga gactggagaa    3540
taactcctcg gttctagggc taaacggcaa ttccggagcc gcaggtggtg gaggtggctg    3600
gaatgataac acttccttgc tctgggccgg aaaatctttg caggagggtg ccaccggagg    3660
acattcctgc ccccaggcca tgaagaagtg gggggtggggag acaagagggg gtttcggagg   3720
gggtggaggg gggtgctcct caggtggagg aggcggagga tatataggcg gcaatgcagc    3780
ctcaaacaat gaccccgaaa tggatgggga agatgggggtt tccttcatca gtccactggg   3840
catcctgtac acccccagctt taaaagtgat ggaaggccac ggggaagtga atattaagca    3900
ttatctaaac tgcagtcact gtgaggtaga cgaatgtcac atggaccctg aaagccacaa    3960
ggtcatctgc ttctgtgacc acgggacggt gctggctgag gatggcgtct cctgcattgt    4020
gtcacccacc ccggagccac acctgccact ctcgctgatc ctctctgtgg tgacctctgc    4080
cctcgtggcc gccctggtcc tggctttctc cggcatcatg attgtgtacc gccggaagca    4140
```

-continued

```
ccaggagctg caagccatgc agatggagct gcagagccct gagtacaagc tgagcaagct    4200
ccgcacctcg accatcatga ccgactacaa ccccaactac tgctttgctg caagacctc     4260
ctccatcagt gacctgaagg aggtgccgcg gaaaaacatc accctcattc ggggtctggg    4320
ccatggcgcc tttggggagg tgtatgaagg ccaggtgtcc ggaatgccca acgacccaag    4380
ccccctgcaa gtggctgtga agacgctgcc tgaagtgtgc tctgaacagg acgaactgga    4440
tttcctcatg gaagccctga tcatcagcaa attcaaccac cagaacattg ttcgctgcat    4500
tggggtgagc ctgcaatccc tgccccggtt catcctgctg gagctcatgg cggggggaga    4560
cctcaagtcc ttcctccgag agacccgccc tcgcccgagc cagccctcct ccctggccat    4620
gctggacctt ctgcacgtgg ctcgggacat tgcctgtggc tgtcagtatt ggaggaaaa     4680
ccacttcatc caccgagaca ttgctgccag aaactgcctc ttgacctgtc caggccctgg    4740
aagagtggcc aagattggag acttcgggat ggcccgagac atctacaggg cgagctacta    4800
tagaaaggga ggctgtgcca tgctgccagt taagtggatg cccccagagg ccttcatgga    4860
aggaatattc acttctaaaa cagacacatg gtcctttgga gtgctgctat gggaaatctt    4920
ttctcttgga tatatgccat accccagcaa aagcaaccag gaagttctgg agtttgtcac    4980
cagtggaggc cggatggacc cacccaagaa ctgccctggg cctgtatacc ggataatgac    5040
tcagtgctgg caacatcagc ctgaagacag gcccaacttt gccatcattt tggagaggat    5100
tgaatactgc acccaggacc cggatgtaat caacaccgct tgccgatag aatatggtcc      5160
acttgtggaa gaggaagaga agtgcctgt gaggcccaag gaccctgagg gggttcctcc      5220
tctcctggtc tctcaacagg caaaacggga ggaggagcgc agcccagctg ccccaccacc    5280
tctgcctacc acctcctctg gcaaggctgc aaagaaaccc acagctgcag agatctctgt    5340
tcgagtccct agagggccgg ccgtggaagg gggacacgtg aatatggcat ctctcagtc     5400
caaccctcct tcggagttgc acaaggtcca cggatccaga aacaagccca ccagcttgtg    5460
gaacccaacg tacggctcct ggtttacaga gaaacccacc aaaaagaata atcctatagc    5520
aaagaaggag ccacacgaca ggggtaacct ggggctggag ggaagctgta ctgtcccacc    5580
taacgttgca actgggagac ttccgggggc ctcactgctc ctagagccct cttcgctgac    5640
tgccaatatg aaggaggtac ctctgttcag gctacgtcac ttcccttgtg gaatgtcaa     5700
ttacggctac cagcaacagg gcttgccctt agaagccgct actgccctg gagctggtca    5760
ttacgaggat accattctga aaagcaagaa tagcatgaac cagcctgggc cctgagctcg    5820
gtcgcacact cacttctctt ccttgggatc cctaagaccg tggaggagag agaggcaatg    5880
gctccttcac aaaccagaga ccaaatgtca cgttttgttt tgtgccaacc tattttgaag    5940
taccaccaaa aaagctgtat tttgaaaatg ctttagaaag gttttgagca tgggttcatc    6000
ctattctttc gaaagaagaa aatatcataa aaatgagtga taaatacaag gcccagatgt    6060
ggttgcataa ggtttttatg catgtttgtt gtatacttcc ttatgcttct ttcaaattgt    6120
gtgtgctctg cttcaatgta gtcagaatta gctgcttcta tgtttcatag ttggggtcat    6180
agatgtttcc ttgccttgtt gatgtggaca tgagccattt gaggggagag ggaacggaaa    6240
taaaggagtt atttgtaatg actaaaa                                        6267
```

<210> SEQ ID NO 620
<211> LENGTH: 894
<212> TYPE: DNA
<213> ORGANISM: Homo sapiens

```
<400> SEQUENCE: 620
gcccgtcttc gtgtctcctc cctccctcgc cttcctcctt cctagctcct ctcctccagg      60
gccagactga gcccaggttg atttcaggcg gacaccaata gactccacag cagctccagg     120
agcccagaca ccggcggcca gaagcaaggc taggagctgc tgcagccatg tcggccctca     180
gcctcctcat tctgggcctg ctcacggcag tgccacctgc cagctgtcag caaggcctgg     240
ggaaccttca gccctggatg cagggcctta tcgcggtggc cgtgttcctg gtcctcgttg     300
caatcgcctt tgcagtcaac cacttctggt gccaggagga gccggagcct gcacacatga     360
tcctgaccgt cggaaacaag gcagatggag tcctggtggg aacagatgga aggtactctt     420
cgatggcggc cagtttcagg tccagtgagc atgagaatgc ctatgagaat gtgcccgagg     480
aggaaggcaa ggtccgcagc accccgatgt aaccttctct gtggctccaa ccccaagact     540
cccaggcaca tgggatggat gtccagtgct accacccaag cccctccttt ctttgtgtgg     600
aatctgcaat agtgggctga ctccctccag ccccatgccg gccctacccg cccttgaagt     660
atagccagcc aaggttggag ctcagaccgt gtctaggttg gggctcggct gtggccctgg     720
ggtctcctgc tcagctcaga agagccttct ggagaggaca gtcagctgag cacctcccat     780
cctgctcaca cgtccttccc cataactatg gaaatggccc taatttctgt gaaataaaga     840 cttttttgtat ttctggggct gaggctcagc aacagcccct caggcttcca gtga           894

<210> SEQ ID NO 621
<211> LENGTH: 21
<212> TYPE: DNA
<213> ORGANISM: Homo sapiens

<400> SEQUENCE: 621
gcgctaatca cgacgcgctg t                                                21

<210> SEQ ID NO 622
<211> LENGTH: 21
<212> TYPE: DNA
<213> ORGANISM: Homo sapiens

<400> SEQUENCE: 622
ggaagccgac atcatctcca c                                                21

<210> SEQ ID NO 623
<211> LENGTH: 20
<212> TYPE: DNA
<213> ORGANISM: Homo sapiens

<400> SEQUENCE: 623
gtgagcgcgg cctttattct                                                  20

<210> SEQ ID NO 624
<211> LENGTH: 23
<212> TYPE: DNA
<213> ORGANISM: Homo sapiens

<400> SEQUENCE: 624
ggtcgcattt tggggattat tga                                              23

<210> SEQ ID NO 625
<211> LENGTH: 22
<212> TYPE: DNA
<213> ORGANISM: Homo sapiens

<400> SEQUENCE: 625
```
tttggcacag tcttaccact tt                                           22

<210> SEQ ID NO 626
<211> LENGTH: 20
<212> TYPE: DNA
<213> ORGANISM: Homo sapiens

<400> SEQUENCE: 626
ctgtgaaggg aatcaaggga                                              20

<210> SEQ ID NO 627
<211> LENGTH: 20
<212> TYPE: DNA
<213> ORGANISM: Homo sapiens

<400> SEQUENCE: 627
tgtcgaatta ccactgctgg                                              20

<210> SEQ ID NO 628
<211> LENGTH: 10
<212> TYPE: PRT
<213> ORGANISM: Homo sapiens

<400> SEQUENCE: 628

Phe Phe Glu Glu Pro Glu Asp Pro Ser Ser
1               5                   10

<210> SEQ ID NO 629
<211> LENGTH: 9
<212> TYPE: PRT
<213> ORGANISM: Homo sapiens

<400> SEQUENCE: 629

Gly Tyr Ser Phe Thr Thr Thr Ala Glu
1               5

<210> SEQ ID NO 630
<211> LENGTH: 24
<212> TYPE: DNA
<213> ORGANISM: Homo sapiens

<400> SEQUENCE: 630
ggatccatgg caggagctgg aggc                                         24

<210> SEQ ID NO 631
<211> LENGTH: 44
<212> TYPE: DNA
<213> ORGANISM: Homo sapiens

<400> SEQUENCE: 631
gctagcatta attttgtcct ggaatatata caagttattg gtgg                   44

<210> SEQ ID NO 632
<211> LENGTH: 21
<212> TYPE: DNA
<213> ORGANISM: Homo sapiens

<400> SEQUENCE: 632
cccacatcag tgcaatgtat t                                            21

<210> SEQ ID NO 633
<211> LENGTH: 21
<212> TYPE: DNA

<213> ORGANISM: Homo sapiens

<400> SEQUENCE: 633
tccccaccaa tgtaacgtgt t                                          21

<210> SEQ ID NO 634
<211> LENGTH: 45
<212> TYPE: DNA
<213> ORGANISM: Homo sapiens

<400> SEQUENCE: 634
tccatcccca ccaatgtaac gtgtttgttt acagcagcag caagg                45

<210> SEQ ID NO 635
<211> LENGTH: 45
<212> TYPE: DNA
<213> ORGANISM: Homo sapiens

<400> SEQUENCE: 635
aaacaaacac gttacattgg tggggatgga actctgcggc agtga                45

<210> SEQ ID NO 636
<211> LENGTH: 21
<212> TYPE: DNA
<213> ORGANISM: Homo sapiens

<400> SEQUENCE: 636
cccgcaccag tgcaacgtgt t                                          21

<210> SEQ ID NO 637
<211> LENGTH: 21
<212> TYPE: DNA
<213> ORGANISM: Homo sapiens

<400> SEQUENCE: 637
tcatagtggg cggtacatga t                                          21

<210> SEQ ID NO 638
<211> LENGTH: 21
<212> TYPE: DNA
<213> ORGANISM: Homo sapiens

<400> SEQUENCE: 638
gagaattaat ttatggcact t                                          21

<210> SEQ ID NO 639
<211> LENGTH: 21
<212> TYPE: DNA
<213> ORGANISM: Homo sapiens

<400> SEQUENCE: 639
ccatttagga tcacggcgct a                                          21

<210> SEQ ID NO 640
<211> LENGTH: 21
<212> TYPE: DNA
<213> ORGANISM: Homo sapiens

<400> SEQUENCE: 640
gccaccaata acttgtacat a                                          21

<210> SEQ ID NO 641
<211> LENGTH: 21

-continued

<212> TYPE: DNA
<213> ORGANISM: Homo sapiens

<400> SEQUENCE: 641
cggttcggat agcgccatca t                                              21

<210> SEQ ID NO 642
<211> LENGTH: 21
<212> TYPE: DNA
<213> ORGANISM: Homo sapiens

<400> SEQUENCE: 642
tcatttccac cgttgagttt a                                              21

<210> SEQ ID NO 643
<211> LENGTH: 21
<212> TYPE: DNA
<213> ORGANISM: Homo sapiens

<400> SEQUENCE: 643
atgctcacac atatcatata a                                              21

<210> SEQ ID NO 644
<211> LENGTH: 20
<212> TYPE: DNA
<213> ORGANISM: Homo sapiens

<400> SEQUENCE: 644
cgggcaataa gactctttaa                                                20

<210> SEQ ID NO 645
<211> LENGTH: 22
<212> TYPE: DNA
<213> ORGANISM: Homo sapiens

<400> SEQUENCE: 645
tgcccaggtc cagttccatt tc                                             22

<210> SEQ ID NO 646
<211> LENGTH: 21
<212> TYPE: DNA
<213> ORGANISM: Homo sapiens

<400> SEQUENCE: 646
tcctgattta actggattat g                                              21

<210> SEQ ID NO 647
<211> LENGTH: 21
<212> TYPE: DNA
<213> ORGANISM: Homo sapiens

<400> SEQUENCE: 647
atcaaacatc cctgacttaa g                                              21

<210> SEQ ID NO 648
<211> LENGTH: 21
<212> TYPE: DNA
<213> ORGANISM: Homo sapiens

<400> SEQUENCE: 648
ctacacctca tgaccatata a                                              21

<210> SEQ ID NO 649

<210> SEQ ID NO 649
<211> LENGTH: 21
<212> TYPE: DNA
<213> ORGANISM: Homo sapiens

<400> SEQUENCE: 649
tacacctcat gaccatataa a                                         21

<210> SEQ ID NO 650
<211> LENGTH: 21
<212> TYPE: DNA
<213> ORGANISM: Homo sapiens

<400> SEQUENCE: 650
tcagtgagaa tgagtacttt a                                         21

<210> SEQ ID NO 651
<211> LENGTH: 21
<212> TYPE: DNA
<213> ORGANISM: Homo sapiens

<400> SEQUENCE: 651
cctgacttaa gcatatattt a                                         21

<210> SEQ ID NO 652
<211> LENGTH: 21
<212> TYPE: DNA
<213> ORGANISM: Homo sapiens

<400> SEQUENCE: 652
tctacattga tagccttatg a                                         21

<210> SEQ ID NO 653
<211> LENGTH: 4469
<212> TYPE: DNA
<213> ORGANISM: Homo sapiens

<400> SEQUENCE: 653
aaatgtagtc actgtcccgg aacctggggc agcggagtcc cgtgcgccct gtggtgacag      60
ctcaggaggg tgtgtgcgct cagcaggggc cagcatggac cagtctgtgg caatccagga     120
gacgctggct gagggggaat actgcgtcat cgcggtgcaa ggtgtgctgt gtgaggggga     180
cagccggcag agccgcctcc tgggactcgt gcgctaccgc ctggagcacg gcggccagga     240
acacgctctc ttcctctata cgcaccggag gatggccatt accggggacg atgtctctct     300
ggaccagata gtgccagtct cgcgggattt tacgctggaa gaagtgtccc cagatggtga     360
actctacatc cttggctcag atgtgaccgt ccagctggac acagcagagc ttagcctcgt     420
attccaactg ccctttggtt cacaaaccag gatgttcctc cacgaagttg ccagggcctg     480
tccaggcttc gattctgcga cccgggatcc tgaattcctg tggctgtctc ggtataggtg     540
cgcagagctg gagctggaga tgccaacgcc gcgcggttgt aactcggccc tagttacctg     600
gccagggtac gcgacaattg gcggaggtgg ttctaacttt gatggtttga gaccaaatgg     660
gaagggagtg cctatggacc aaagctccag gggtcaagat aaaccagaaa gcttgcaacc     720
aagacagaat aaatccaagt ccgaaattac tgacatggtt cgctcctcca ctatcacagt     780
gtcggacaag gctcatattt tatccatgca gaagtttgga ctgcgagata caattgtgaa     840
atcacatcta ctacagaaag aagaggatta cacctatatc cagaacttca gttttttgc      900 gggaacatac aatgtaaatg ggcagtcccc caaagaatgc ctccggctgt ggctgagcaa     960
tggtatccag gccccagatg tctattgtgt agggttccag gagcttgatc tgagtaagga    1020

```
agcttttttc tttcacgata ccccaaagga ggaagagtgg ttcaaagctg tgtcagaggg    1080
tcttcatcca gatgccaaat atgcaaaggt gaagcttatc cgactggttg ggattatgct    1140
gctgttatat gtcaaacagg agcatgcagc ttatatctca gaagtggaag ccgagactgt    1200
ggggacagga atcatgggga ggatgggcaa caagggaggc gtggcgatca ggttccagtt    1260
ccacaacacc agcatctgcg ttgtgaattc tcacttggca gcccacattg aagagtatga    1320
gaggaggaac caggactata aggacatttg ttctcgaatg cagttttgtc agcctgaccc    1380
aagccttccc cctctcacca tcagcaacca tgatgtgatc ttgtggctgg gggacctcaa    1440
ctacaggata gaagagctgg atgtggaaaa agtgaaaaag ctcatcgaag agaaggactt    1500
tcaaatgctg tatgcatatg atcagctgaa aattcaggtg gccgcaaaga ctgtctttga    1560
aggcttcaca gagggtgagc tcacattcca gcctacttac aagtatgata cgggctctga    1620
cgactgggat accagtgaga agtgccgtgc tcctgcctgg tgtgatcgga ttctctggaa    1680
agggaagaac atcactcagc tgagttacca gagccacatg gccctgaaga ccagtgacca    1740
caagcctgtc agctcagtgt tgacatcgg ggtgagggtc gtaaatgacg agctttaccg    1800
gaagacactg gaggaaattg ttcgctccct ggataagatg gaaaatgcca acattccttc    1860
tgtgtccctg tccaagcgag agttctgttt tcagaatgtg aagtacatgc aattgaaagt    1920
agaatccttt acaattcata atggacaagt accctgtcat tttgaattca tcaacaagcc    1980
tgatgaagag tcttactgta agcagtggct gaatgccaac cccagcagag cttcctcct    2040 gccagattct gatgttgaga ttgacttgga gctcttcgta aataagatga cagctacaaa    2100
gctcaactcg ggtgaagaca aaattgagga cattctggtt ctgcacttgg acaggggaaa    2160
ggattacttt ttgtctgtgt ctgggaacta cctgcccagc tgttttgggt ctcccattca    2220
tacactgtgt tacatgagag agccaatctt ggacctacca cttgaaacca ttagtgagct    2280
gactctgatg ccagtatgga ctggagatga tgggagccag ttggatagcc ccatggaaat    2340
ccccaaagag ctctggatga tggttgatta cctgtaccga aatgctgtcc agcaggaaga    2400
tctgtttcag caaccaggcc tgaggtcaga atttgaacat atcagggact gcttggatac    2460
tggaatgatt gataacctct ctgccagcaa tcattctgta gccgaagccc tgctgctttt    2520
cctggagagc cttccagagc ctgtcatctg ttacagcacc taccataact gcttggagtg    2580
ttctggcaac tacacagcaa gcaaacaggt catttctact ctccccatat tccacaaaaa    2640
tgtcttccac tacttgatgg cgttttgcg agaactgctg aaaaattcag caaaaaatca    2700 tttgatgag aatattctag ctagcatatt tggcagctta ttgcttcgaa cccagctgg    2760 tcaccaaaag cttgatatga cagagaagaa gaaggctcaa gaatttattc accagttcct    2820
ctgcaaccca ctctgagcct ctctctcctc ctattttact tgaggctgcc aattaccagc    2880
cccacctgtt tcagctcaag agatgcctta agataattat gtgaggccac ttggtagcaa    2940
gaatggcagc tatttcctga gcctagtacc ccaattaagc ccaccattgg ttagcacact    3000
cagcgctgtg agtcgtgaag acacgggaga aaatccacca taataaaact gacattcaat    3060
tttcaacttt agttatttaa cacagatttt tttattttt atttttttt attttgagac    3120 ggagttttgc tctgtcgcgc agggtggagt gcggtggcac gatctcggct cactgcaacc    3180
tctgcctcct gggtgcaagc aattatcctg cctcagcctc ccgagtagct gggactgcag    3240
gcacacactg ccacgcccag ctaatttttt gcatttagt agagacgggg tttcaccgtg    3300
ttgcccaggc tgttctaaaa ctcctgaact caggtaatct gcctgcctcg gcctccccaa    3360
```

| | |
|---|---:|
| gtgctaggat tacagatgtg agccaccacg cccggccttt ttttttttt tttcttttt | 3420 |
| gagatggagt ttcactcttg ttgcccaggc tggagtgcgt tggcgtggtc ttggctcact | 3480 |
| gcaacctctg cctccttggt tcaagcaatt ctcctgcctc agcctctcga gtagctggga | 3540 |
| ttataggcgt ccgccaccat gcctggctaa ttttttttgtg tgttttttagt atagacacgg | 3600 |
| tttcaccatg ttggccaggc tggtctcgaa tgcctggcct caggtgatcc acctgccttg | 3660 |
| gcctcccaaa gtgctgggat tacaggcatg aaccaccacg cctggcctaa aatgttttta | 3720 |
| aataactgta cttgtactca ctcaccctac ctccagggca tagtcagtct gggctgagat | 3780 |
| ccccatgatc agatatttga tggaaagtcc tgaaaggcca atgagttgga tgcaagaat | 3840 |
| gcaggcagaa gctgctggat aaaataggct acagccacct cagatgcttt cagtgctctg | 3900 |
| tctgaggatg tgtatatgca tatgcaaact cgaccccccgt tcctgcccag ataatggctc | 3960 |
| aataactctg aggctggttg ctcagcctct gagggcaata caggcattta aaaaattaaa | 4020 |
| atgaccaggc acagtggctc acgcctgtaa tctcggcact ttgggagact gaggtgggag | 4080 |
| catcacttga gaccaggagt ttgggaccag gctgggcaac acaggagac ccctctcta | 4140 |
| caaaaacatt tttaaaaaat tagctgggtg tggtgatgca tgcctgtggt cccagttact | 4200 |
| tgggaggctg acgtgggtgg ctcacttgag cacaggagtt tgaggctgca gtgacctatg | 4260 |
| accacatcac tgtacgccag cccgggtgag agagggagac ccgtctctcta aaaataaaat | 4320 |
| gtaaaatcac tgaaaaatg agtgttcggt gaaacaagtg ggattttctg ggccagcaag | 4380 |
| tcttccaaac tgtatatgat gcatcctgtc tccatgtgta atatattta atgataaatg | 4440 |
| tattttaac agtgaaaaa aaaaaaaaa | 4469 |

<210> SEQ ID NO 654
<211> LENGTH: 1216
<212> TYPE: DNA
<213> ORGANISM: Homo sapiens

<400> SEQUENCE: 654

| | |
|---|---:|
| ggcagctgca cggctcctgg ccccggagca tgcgcgagag ccgccccgga gcgccccgga | 60 |
| gcccccccgcc gtcccgcccg cggcgtcccg cgccccgccg ccagcgcacc cccggacgct | 120 |
| atggcccacc cctccggctg gcccccttctg taggatggta gcacacaacc aggtggcagc | 180 |
| cgacaatgca gtctccacag cagcagagcc ccgacggcgg ccagaacctt cctcctcttc | 240 |
| ctcctcctcg cccgcggccc ccgcgcgccc gcggcgtgc ccgcgcggtcc cggccccggc | 300 |
| ccccggcgac acgcacttcc gcacattccg ttcgcacgcc gattaccggc gcatcacgcg | 360 |
| cgccagcgcg ctcctggacg cctgcggatt ctactggggg cccctgagcg tgcacggggc | 420 |
| gcacgagcgg ctgcgcgccg agcccgtggg caccttcctg gtgcgcgaca gccgccagcg | 480 |
| gaactgcttt ttcgccctta gcgtgaagat ggcctcggga cccacgagca tccgcgtgca | 540 |
| cttcaggcc ggccgctttc acctggatgg cagccgcgag agcttcgact gcctcttcga | 600 |
| gctgctggag cactacgtgg cggcgccgcg ccgcatgctg ggggccccgc tgcgccagcg | 660 |
| ccgcgtgcgg ccgctgcagg agctgtgccg ccagcgcatc gtggccaccg tgggccgcga | 720 |
| gaacctggct cgcatccccc tcaacccccgt cctccgcgac tacctgagct ccttcccctt | 780 |
| ccagatttga ccggcagcgc ccgccgtgca cgcagcatta actgggatgc cgtgttattt | 840 |
| tgttattact tgcctggaac catgtgggta ccctcccccgg cctgggttgg agggagcgga | 900 |
| tgggtgtagg ggcgaggcgc ctcccgccct cggctggaga cgaggccgca gaccccttct | 960 |
| cacctcttga gggggtcctc cccctcctgg tgctccctct gggtccccct ggttgttgta | 1020 |

```
gcagcttaac tgtatctgga gccaggacct gaactcgcac ctcctacctc ttcatgttta    1080 catatacccca gtatctttgc acaaaccagg ggttggggga gggtctctgg ctttattttt    1140
ctgctgtgca gaatcctatt ttatattttt taaagtcagt ttaggtaata aactttatta    1200
tgaaagtttt tttttt                                                    1216

<210> SEQ ID NO 655
<211> LENGTH: 3337
<212> TYPE: DNA
<213> ORGANISM: Homo sapiens

<400> SEQUENCE: 655
gacatcatgg gctattttta ggggttgact ggtagcagat aagtgttgag ctcgggctgg      60
ataagggctc agagttgcac tgagtgtggc tgaagcagcg aggcgggagt ggaggtgcgc     120
ggagtcaggc agacagacag acacagccag ccagccaggt cggcagtata gtccgaactg     180
caaatcttat tttctttttca ccttctctct aactgcccag agctagcgcc tgtggctccc    240
gggctggtgt tcgggagtg tccagagagc ctggtctcca gccgccccg ggaggagagc       300 cctgctgccc aggcgctgtt gacagcggcg gaaagcagcg gtacccacgc gcccgccggg     360
ggaagtcggc gagcggctgc agcagcaaag aactttcccg gctgggagga ccggagacaa     420
gtggcagagt cccggagcga acttttgcaa gcctttcctg cgtcttaggc ttctccacgg     480
cggtaaagac cagaaggcgg cggagagcca cgcaagagaa gaaggacgtg cgctcagctt     540
cgctcgcacc ggttgttgaa cttgggcgag cgcgagccgc ggctgccggg cgcccctcc     600 ccctagcagc ggaggagggg acaagtcgtc ggagtccggg cggccaagac ccgccgccgg     660
ccggccactg cagggtccgc actgatccgc tccgcgggga gagccgctgc tctgggaagt     720
gagttcgcct gcggactccg aggaaccgct gcgcccgaag agcgctcagt gagtgaccgc     780
gacttttcaa agccgggtag cgcgcgcgag tcgacaagta agagtgcggg aggcatctta     840
attaaccctg cgctccctgg agcgagctgg tgaggagggc gcagcgggga cgacagccag     900
cgggtgcgtg cgctcttaga gaaactttcc ctgtcaaagg ctccgggggg gcgcgggtgtc    960 ccccgcttgc cagagccctg ttgcggcccc gaaacttgtg cgcgcagccc aaactaacct    1020
cacgtgaagt gacggactgt tctatgactg caaagatgga aacgaccttc tatgacgatg    1080
ccctcaacgc ctcgttcctc ccgtccgaga gcggaccttta tggctacagt aaccccaaga   1140
tcctgaaaca gagcatgacc ctgaacctgg ccgacccagt gggagcctga gccgcacct    1200 ccgcgccaag aactcggacc tcctcacctc gcccgacgtg gggctgctca gctggcgtc    1260 gcccgagctg gagcgcctga taatccagtc cagcaacggg cacatcacca ccacgccgac    1320
ccccacccag ttcctgtgcc caagaacgt gacagatgag caggagggct tcgccgaggg    1380
cttcgtgcgc gccctggccg aactgcacag ccagaacacg ctgcccagcg tcacgtcggc    1440
ggcgcagccg gtcaacgggg caggcatggt ggctcccgcg gtagcctcgg tggcagggggg   1500 cagcggcagc ggcggcttca gcgccagcct gcacagcgag ccgccggtct acgcaaacct    1560
cagcaacttc aacccaggcg cgctgagcag cggcggcggg gcgccctcct acggcgcggc    1620
cggcctggcc tttcccgcgc aaccccagca gcagcagcag ccgccgcacc acctgcccca    1680
gcagatgccc gtgcagcacc cgcggctgca ggccctgaag gaggagcctc agacagtgcc    1740
cgagatgccc ggcgagacac cgcccctgtc ccccatcgac atggagtccc aggagcggat    1800
caaggcggag aggaagcgca tgaggaaccg catcgctgcc tccaagtgcc gaaaaaggaa    1860
```

| | |
|---|---:|
| gctggagaga atcgcccggc tggaggaaaa agtgaaaacc ttgaaagctc agaactcgga | 1920 |
| gctggcgtcc acggccaaca tgctcaggga acaggtggca cagcttaaac agaaagtcat | 1980 |
| gaaccacgtt aacagtgggt gccaactcat gctaacgcag cagttgcaaa cattttgaag | 2040 |
| agagaccgtc gggggctgag gggcaacgaa gaaaaaaat aacacagaga gacagacttg | 2100 |
| agaacttgac aagttgcgac ggagagaaaa aagaagtgtc cgagaactaa agccaagggt | 2160 |
| atccaagttg gactgggttg cgtcctgacg gcgcccccag tgtgcacgag tgggaaggac | 2220 |
| ttggcgcgcc ctcccttggc gtggagccag ggagcggccg cctgcgggct gccccgcttt | 2280 |
| gcggacgggc tgtccccgcg cgaacggaac gttggacttt tcgttaacat tgaccaagaa | 2340 |
| ctgcatggac ctaacattcg atctcattca gtattaaagg gggagggggg aggggttac | 2400 |
| aaactgcaat agagactgta gattgcttct gtagtactcc ttaagaacac aaagcggggg | 2460 |
| gagggttggg gagggcggc aggagggagg tttgtgagag cgaggctgag cctacagatg | 2520 |
| aactctttct ggcctgcctt cgttaactgt gtatgtacat atatatattt tttaatttga | 2580 |
| tgaaagctga ttactgtcaa taaacagctt catgcctttg taagttattt cttgtttgtt | 2640 |
| tgtttgggta tcctgcccag tgttgtttgt aaataagaga tttggagcac tctgagttta | 2700 |
| ccatttgtaa taaagtatat aattttttta tgttttgttt ctgaaaattc cagaaaggat | 2760 |
| atttaagaaa atacaataaa ctattggaaa gtactcccct aacctctttt ctgcatcatc | 2820 |
| tgtagatact agctatctag gtggagttga aagagttaag aatgtcgatt aaaatcactc | 2880 |
| tcagtgcttc ttactattaa gcagtaaaaa ctgttctcta ttagacttta gaaataaatg | 2940 |
| tacctgatgt acctgatgct atggtcaggt tatactcctc ctcccccagc tatctatatg | 3000 |
| gaattgctta ccaaaggata gtgcgatgtt tcaggaggct ggaggaaggg gggttgcagt | 3060 |
| ggagagggac agcccactga gaagtcaaac atttcaaagt ttggattgta tcaagtggca | 3120 |
| tgtgctgtga ccatttataa tgttagtaga aattttacaa taggtgctta ttctcaaagc | 3180 |
| aggaattggt ggcagatttt acaaaagatg tatccttcca atttggaatc ttctctttga | 3240 |
| caattcctag ataaaaagat ggcctttgct tatgaatatt tataacagca ttcttgtcac | 3300 |
| aataaatgta ttcaaatacc aaaaaaaaaa aaaaaaa | 3337 |

<210> SEQ ID NO 656
<211> LENGTH: 5831
<212> TYPE: DNA
<213> ORGANISM: Homo sapiens

<400> SEQUENCE: 656

| | |
|---|---:|
| cggccgcggc gacagctcca gctccggctc cggctccggc tccggctccg gctccgcgc | 60 |
| ctgcccccgct cggcccagcg cgcccgggct ccgcgcccg accccgccgc cgcgcctgcc | 120 |
| gggggcctcg ggcgccccg ccgcccgcct cacgctgaag ttcctggccg tgctgctggc | 180 |
| cgcgggcatg ctggcgttcc tcggtgccgt catctgcatc atcgccagcg tgcccctggc | 240 |
| ggccagcccg gcgcgggcgc tgcccggcgg cgccgacaat gcttcggtcg cctcgggcgc | 300 |
| cgccgcgtcc ccgggcccgc agcggagcct gagcgcgctg cacggcgcgg gcggttcagc | 360 |
| cgggcccccc gcgctgcccg gggcacccgc ggccagcgcg cacccgctgc cgcccgggcc | 420 |
| cctgttcagc cgcttcctgt gcacgccgct ggctgctgcc tgcccgtcgg ggcccagca | 480 |
| ggggacgcg gcgggcgctg cgccgggcga gcgcgaagag ctgctgctgc tgcagagcac | 540 |
| ggccgagcag ctgcgccaga cggcgctgca gcaggagggcg cgcatccgcg ccgaccagga | 600 |
| caccatccgt gagctcaccg gcaagctggg ccgctgcgag agcggcctgc cgcgcgggcct | 660 |

```
ccagggcgcc gggccccgcc gcgacaccat ggccgacggg ccctgggact cgcctgcgct    720
cattctggag ctggaggacg ccgtgcgcgc cctgcgggac cgcatcgacc gcctggagca    780
ggagcttcca gcccgtgtga acctctcagc tgccccagcc ccagtctctg ctgtgcccac    840
cggcctacac tccaagatgg accagctgga ggggcagctg ctggcccagg tgctggcact    900
ggagaaggag cgtgtggccc tcagccacag cagccgccgg cagaggcagg aagtggaaaa    960
ggagttggac gtcctgcagg tcgtgtggc tgagctggag cacgggtcct cagcctacag    1020
tcctccagat gccttcaaga tcagcatccc catccgtaac aactacatgt acgcccgcgt    1080
gcggaaggct ctgcccgagc tctacgcatt caccgcctgc atgtggctgc ggtccaggtc    1140
cagcggcacc ggccagggca ccccttctc ctactcagtg cccgggcagg ccaacgagat    1200
tgtactgcta gaggcgggcc atgagcccat ggagctgctg atcaacgaca aggtggccca    1260
gctgcccctg agcctgaagg acaatggctg gcaccacatc tgcatcgcct ggaccacaag    1320
ggatggccta tggtctgcct accaggacgg ggagctgcag ggctccggtg agaacctggc    1380
tgcctggcac cccatcaagc ctcatgggat ccttatcttg ggccaggagc aggataccct    1440
gggtggccgt tttgatgcca cccaggcctt tgtcggtgac attgcccagt ttaacctgtg    1500
ggaccacgcc ctgacaccag cccaggtcct gggcattgcc aactgcactg cgccactgct    1560
gggcaacgtc cttccctggg aagacaagtt ggtggaggcc tttggggtg caacaaaggc    1620 tgccttcgat gtctgcaagg ggagggccaa ggcatgaggg gccacctcat ccagggcccc    1680
tcccttgcct gccactttgg ggacttgagg ggggtcatat tccctcctca gcctgcccac    1740
gcactggcct tcctcctgc cccactcctg gctgtgcctc ccatttcccc tcacctgtac    1800
ccacacctcc agaatgccct gccctgcgag tgtgtccct gtcccacct gagtggggag    1860 gagcgtctca agtgaacagt gggagcctgc ccacctggca ctgcactgga gttgtctctt    1920
acccccacct ccctgcccat caactgtatc tgatttcact aattttgaca gcaccccag    1980 tagggtagga ttgtgtatga gggggacccc actatctcag tggtgggggt ggccgcccgc    2040
ccccttgtcc cccatgcaac aggcccagtg gcttcccctt cagggccaca acaggctgta    2100 gaagggggatg acgaggacat cagaggttag acttaccctc ctccctcttt ccaccagctg    2160
ccagtcaagg gcagtgggat ctcgatggag cctcccccc cccccaccca tgcctccctc    2220
ttcctcctct ttcctcctct ctttgtgtgt agcggtttga atgttggttc catgcctggc    2280
ccagccccac ctcagtctcc aggacattcc tttcccagct ccagcctgga gggaagggga    2340
caaagacccc aggaggccaa agggctgcag tcaccccttg tgctcaccca tagtgatggc    2400
cactggtata gtcatcgctc tccctccatg ccaaggacag gacttggacc gcttcagcct    2460
gggctgggag cagccctaag gtagaggcct catggcccag gagaccccac ctctggcaga    2520
gccacattac ctaccctgtg catggtcctg gggcagcaag gaagaagctc agagggtggg    2580
gagaagcatg aagcagtgag cagagcactg ggtgagaggg agaagacctt ggttcctagc    2640
cagccctgct aatgtgctgt gtggccttct gtaagtccct gccctctctg ggcctggcct    2700
tcctcattcg tgagctgagg ccctcgcttt ggtcatttgc tctccagatt gggtgtgagc    2760
ttctctgtga ttccaggtgg atatgtgggg aaagctctgg tgaccctggg cttcgcaggg    2820
gtagatccca ggactcggca gtggatggga tgcagccagt catgggttag ggtcagcaga    2880
gactcagagt ccagggcaag gttcaaggca gactaacctc atgcatggat tgtaaaaaac    2940
cagctccctt tggatcaacc cagcctggca cccttgcctg tctgagagtg tctcaaaggg    3000
```

```
ctgatggctt cctggtcccc ttgagtcatc accagcttcc ccaagagagt gtcagaatct   3060
taagagctga gaggccgggc acggtggctc acgcctgtaa tcccagcact ttgggaggct   3120
gagacaggca gatcacttga ggtcaggagt tcgaagtcag cctggccaac gtggtgaaac   3180
cccatcttca ctaaaaatac aaaacttagc tggttaggtg gtgcatgcct gtagtcccag   3240
ctactcggga ggccgaggca gaagaatctc ttgaactgag gaggtggagg ttgcagtgag   3300
ccgagatcac gccattgcac tccagcctgg gcaacagagc aagactccat ctcaaaaaaa   3360
taataataat cttaaagatg agaaaagcca ccccatctgg caccacagct gcatcttgct   3420
tgtgagaaat ggggaagagt tcagggagga cacgtgacct gcacaggatc acagagcatg   3480
gggcagagcc aggactagag ctcagggcat ctgactccct cttcagtgtt cttccccctc   3540
catgttgcct gccccctgaag acctttgagt tcagtctaca cctaagcagg tagacatccg   3600
cgaggtcaga tgctttccaa catgacacct gaacatcttc ctttatgcaa cacccaaaca   3660
tcttggcatc cccaccccag gaagtgcggg gaggaggtta tgatccctgg gcgcttcggc   3720
agaatggaga gctgaggtgt ccctcccctg ctagtcacct accaggtgtc tgagcagctg   3780
catgctccct ggctcaagtg ggcactgtac cttttgcctg cctttttgtt ccctatctcc   3840
actccctgag gccacttagc ctgagacatg atgcaagagc tgcaggccgg ggggctcagt   3900
gccatggaag ctactccaag ttgcattgcc tcccgcgccc agatcctgct ttccatttcg   3960
agaacataaa tagattgccc agccctcca gtacaatccc actggaagaa aaggcaatgg   4020
cgggcttcag ccagacctgc tgagacctag gttgccacgg taacagccaa agacatcaac   4080
ccaagtgctg ggtcaagtgt ctcatcatac tggcactgtt gctggggtga cggcagaatt   4140
cagaacttca atttcagtga cgccaagctt gatgtgtttc tgttattgtt ttgaagaagg   4200
tagctcttgt ggaggacttg ggagaaggat ggggtcttag gaaggaggtg acagcacttg   4260
catggtcact tgagcccaca cacacgctca accccaagtc ctttatgctt tgtcacagtg   4320
aagatgagac ctctgacgtc caagccttgt tcctgtgctg catcacccac tcagccttcc   4380
aaagggaaca ggaacaaatt tccccagcac cactgtttgg gtcccgcttt tcctatcttc   4440 tgctgccct gagcacatcc aagcagacag ggaaagagga gtcagacatg cccagtcac   4500 atcctgagct gctcctggct gataaccacg atggagcccg tgtttgtcct gccatctggc   4560
actgcactga gtgtggcaca ggcaccgtcc tgttgatctc acaacacagt tctaagttag   4620
gacgttcttg gctccgttag acaggtgagg aaactggggc acagagaggt gatgtcatct   4680
gcctggtgtc aatcagctag caagtgatgg agcccagatt tcaaaccaaa gggggttacg   4740 tccagggget gagttcccac tcacctgtgt agagtgccat ctgggcacca ttgctccaga   4800
cgtgttccga ccccttttccc agcccacagg gcttgaagtg aaggaacaga ggcaggggt   4860 gggccagccc cagggccagg gtccccttgg tgaagccgtg ccagggggct cagctgcttc   4920
agggaatgtg tccctcccac catgggccag agcttcagcc cttctttagc tcagctagag   4980
ttcacaggag agccaaaaaa gaaaaggaag ctgagcatct cccgagtcct gggcagggaa   5040 gggagggaa attgctgctt ctccaactct tgcttgggc caagccctgc accagttgct   5100
tcccagctgt tatctgccag atcttcccat cttgtggcat gtggtgcccc caccaacatc   5160
ccaaggggac caatccccctt gccaccactt tgcatcacct gggaccacag atttggacag   5220
gaagggctct gagaagaggc caaagccctc attttacaga tgaggaagct gaagcccggg   5280
gaggggagcg accctcaagg ccacccagct ggacacggga gacttgagcc cagccttctg   5340
actgcattca gccctctcta ggacgcagca gcctctcccc agcactgagt cccccctcct   5400
```

```
ttgtgtgtcc cagcacccct tggcctgagta aacttggaaa gggctcccct cccagagaag    5460
ggactactct cttcacccct ttattccagc tgcctgccac cccagacccc cacctcccac    5520
cctgaccccc gacccctggg tggggaaggg gctcacatgg gcccaggctg agtgtgagtg    5580
agcatgtcaa gttgtctgac actgtgacat tagtgcaccc tactgacaac ccctcccag    5640
ccttgcccct ttctcctctc cctgttttgt acataaattg acatgagctg caacatgtgt    5700
gcgtgtgtgt gcgtgtgtgt gtgtgtgtat gtgtgtgtga tctgtgtcat ggttttgtta    5760
ccttttttgtt tttgtaaact tgaatgttca aaataaacat gctgtttact ctgagaaaaa    5820
aaaaaaaaaa a                                                         5831
```

<210> SEQ ID NO 657
<211> LENGTH: 2737
<212> TYPE: DNA
<213> ORGANISM: Homo sapiens

<400> SEQUENCE: 657

```
gcggctccga cttggactcc ctgctccgct gctgccgctt cggccccgca cgcagccagc      60
cgccagccgc ccgcccggcc cagctcccgc cgcggcccct tgccgcggtc cctctcctgg     120
tccctcccg gttggtccgg gggtgcgcag ggggcagggc gggcgcccag gggaagctcg     180
agggacgcgc gcgcgaaggc tcctttgtgg acttcacggc cgccaacatc tgggcgcagc     240
gcgggccacc gctggccgtc tcgccgccgc gtcgccttgg ggacccgagg gggctcagcc     300
ccaaggacgg agacttcgat tcggaccag cccccggga tgcggtagcg gccgctgtgc     360
ggaggccgcg aagcagctgc agccgccgcc gcgcagatcc acgctggctc cgtgcgccat     420
ggtcacccac agcaagtttc cgccgccggg atgagccgc cccctggaca ccagcctgcg     480
cctcaagacc ttcagctcca agagcgagta ccagctggtg gtgaacgcag tgcgcaagct     540
gcaggagagc ggcttctact ggagcgcagt gaccggcggc gaggcgaacc tgctgctcag     600
tgccgagccc gccggcacct ttctgatccg cgacagctcg gaccagcgcc acttcttcac     660
gctcagcgtc aagacccagt ctgggaccaa gaacctgcgc atccagtgtg aggggggcag     720
cttctctctg cagagcgatc cccggagcac gcagcccgtg ccccgcttcg actgcgtgct     780
caagctggtg caccactaca tgccgccccc tggagccccc tccttcccct cgccacctac     840
tgaaccctcc tccgaggtgc ccgagcagcc gtctgcccag ccactccctg ggagtccccc     900
cagaagagcc tattacatct actccggggg cgagaagatc cccctggtgt gagccggcc     960
cctctcctcc aacgtggcca ctcttcagca tctctgtcgg aagaccgtca acggccacct    1020
ggactcctat gagaaagtca cccagctgcc ggggcccatt cgggagttcc tggaccagta    1080
cgatgccccg ctttaagggg taaagggcgc aaagggcatg ggtcgggaga ggggacgcag    1140
gccctctcc tccgtggcac atggcacaag cacaagaagc caaccaggag agagtcctgt    1200
agctctgggg ggaaagaggg cggacaggcc cctccctctg ccctctccct gcagaatgtg    1260
gcaggcggac ctggaatgtg ttggagggaa ggggagtac cacctgagtc tccagcttct    1320
ccggaggagc cagctgtcct ggtgggacga tagcaaccac aagtggattc tccttcaatt    1380
cctcagcttc ccctctgcct ccaaacaggg gacacttcgg gaatgctgaa ctaatgagaa    1440
ctgccaggga atcttcaaac tttccaacgg aacttgtttg ctctttgatt tggtttaaac    1500
ctgagctggt gtggagcct gggaaaggtg aagagagag aggtcctgag gccccaggg    1560
ctgcgggctg gcgaaggaaa tggtcacacc cccgcccac cccaggcgag gatcctggtg    1620
```

```
acatgctcct ctccctggct ccggggagaa gggcttgggg tgacctgaag ggaaccatcc    1680
tggtacccca catcctctcc tccgggacag tcaccgaaaa cacaggttcc aaagtctacc    1740
tggtgcctga gagcccaggg cccttcctcc gttttaaggg ggaagcaaca tttggagggg    1800
atggatgggc tggtcagctg gtctcctttt cctactcata ctataccttc ctgtacctgg    1860
gtggatggag cgggaggatg gaggagacgg gacatctttc acctcaggct cctggtagag    1920
aagacagggg attctactct gtgcctcctg actatgtctg gctaagagat tcgccttaaa    1980
tgctccctgt cccatggaga gggacccagc ataggaaagc cacatactca gcctggatgg    2040
gtggagaggc tgagggactc actggagggc accaagccag cccacagcca gggaagtggg    2100
gagggggggc ggaaacccat gcctcccagc tgagcactgg gaatgtcagc ccagtaagta    2160
ttggccagtc aggcgcctcg tggtcagagc agagccacca ggtcccactg ccccgagccc    2220
tgcacagccc tccctcctgc ctgggtgggg gaggctggag gtcattggag aggctggact    2280
gctgccaccc cgggtgctcc cgctctgcca tagcactgat cagtgacaat ttacaggaat    2340
gtagcagcga tggaattacc tggaacagtt ttttgttttt gttttgttt ttgttttgt     2400 gggggggggc aactaaacaa acacaaagta ttctgtgtca ggtattgggc tggacagggc    2460
agttgtgtgt tggggtggtt ttttctcta tttttttgtt tgtttcttgt tttttaataa    2520
tgtttacaat ctgcctcaat cactctgtct tttataaaga ttccacctcc agtcctctct    2580
cctcccccct actcaggccc ttgaggctat taggagatgc ttgaagaact caacaaaatc    2640
ccaatccaag tcaaactttg cacatattta tatttatatt cagaaaagaa acatttcagt    2700
aatttataat aaagagcact attttttaat gaaaaac                             2737

<210> SEQ ID NO 658
<211> LENGTH: 4830
<212> TYPE: DNA
<213> ORGANISM: Homo sapiens

<400> SEQUENCE: 658
gaggcagctc ctgtggggaa aggcgccagt gcgccgaggc ggggagtggc ggcggggtaa      60
cacctggccg aggtgactcg ttctgaagag cagcggttcc ttacaccaat cggaacgtgc     120
aggggtgggg agctggccaa tcaggcgcgg agggcggggc cggcgggggt tccacctggc     180
ggctggctct cagtcccctc gctgtagtcg cggagctgtg tctgttccca ggagtccttc     240
ggcggctgtt gtgtcgggag cctgatcgcg atggggacaa aggcgcaagt cgagaggaaa     300
ctgttgtgcc tcttcatatt ggcgatcctg ttgtgctccc tggcattggg cagtgttaca     360
gtgcactctt ctgaacctga agtcagaatt cctgagaata atcctgtgaa gttgtcctgt     420
gcctactcgg gcttttcttc tccccgtgtg gagtggaagt ttgaccaagg agacaccacc     480
agactcgttt gctataataa caagatcaca gcttcctatg aggaccgggt gaccttcttg     540
ccaactggta tcaccttcaa gtccgtgaca cgggaagaca ctgggacata cacttgtatg     600
gtctctgagg aaggcggcaa cagctatggg gaggtcaagg tcaagctcat cgtgcttgtg     660
cctccatcca agcctacagt taacatcccc tcctctgcca ccattgggaa ccggcagtg     720 ctgacatgct cagaacaaga tggttcccca ccttctgaat acacctggtt caaagatggg     780
atagtgatgc ctacgaatcc caaaagcacc cgtgccttca gcaactcttc ctatgtcctg     840
aatcccacaa caggagagct ggtctttgat cccctgtcag cctctgatac tggagaatac     900
agctgtgagc cacggaatgg gtatgggaca cccatgactt caaatgctgt gcgcatggaa     960
gctgtggagc ggaatgtggg ggtcatcgtg gcagccgtcc ttgtaaccct gattctcctg    1020
```

```
ggaatcttgg ttttggcat  ctggtttgcc tatagccgag gccactttga cagaacaaag   1080
aaagggactt cgagtaagaa ggtgattac  agccagccta gtgcccgaag tgaaggagaa   1140
ttcaaacaga cctcgtcatt cctggtgtga gcctggtcgg ctcaccgcct atcatctgca   1200
tttgccttac tcaggtgcta ccggactctg gcccctgatg tctgtagttt cacaggatgc   1260
cttatttgtc ttctacaccc cacagggccc cctacttctt cggatgtgtt tttaataatg   1320
tcagctatgt gccccatcct ccttcatgcc ctccctccct ttcctaccac tgctgagtgg   1380
cctggaactt gtttaaagtg tttattcccc atttctttga gggatcagga aggaatcctg   1440
ggtatgccat tgacttccct tctaagtaga cagcaaaaat ggcgggggtc gcaggaatct   1500
gcactcaact gcccacctgg ctggcaggga tctttgaata ggtatcttga gcttggttct   1560
gggctctttc cttgtgtact gacgaccagg gccagctgtt ctagagcggg aattagaggc   1620
tagagcggct gaaatggttg tttggtgatg acactggggt ccttccatct ctggggccca   1680
ctctcttctg tcttcccatg ggaagtgcca ctgggatccc tctgccctgt cctcctgaat   1740
acaagctgac tgacattgac tgtgtctgtg gaaaatggga gctcttgttg tggagagcat   1800
agtaaatttt cagagaactt gaagccaaaa ggatttaaaa ccgctgctct aaagaaaaga   1860
aaactggagg ctgggcgcag tggctcacgc ctataatccc agaggctgag gcaggcggat   1920
cacctgaggt caggagttca agatcagcct gaccaacatg gagaaaccct actaaaaata   1980
caaagttagc caggcatagt ggtgcatgcc tgtaatccca gctgctcagg agcctggcaa   2040
caagagcaaa actccagctc aaaaaaaaaa agaaagaaaa gaaagctgga gctggtggct   2100
taggccatca cccttccctt ggctggaact actggacaga ccctttgag  atgtgcctgt   2160 ggtgctgtgg agatgtgtgt agtggtctta gctctttgtt gagcttgtgt gtgtgttgtg   2220
tagtcttagc tgtatgctga aattgggcgt gtgttggagg gcttcttagc tctttggtga   2280
gattgtattt ctatgtgttt gtatcagctg aatgttgctg gaataaaaac cttggtttgt   2340
caaggctctt ttttgtggga agtaagtagg ggaaaaggtc tttgagggtt cctaggctcc   2400
tttgtacaac aggaaaatgc ctcaaagcct tgcttcccag caacctgggg ctggttccca   2460
gtgcctggtc ctgcccttc  ctggttctta tctcaaggca gagcttctga atttcaggcc   2520
ttcattccag agccctcttg tggccaggcc ttcctttgct ggaggaaggt acacagggtg   2580
aagctgatgc tgtactgggg gatctccttt ggcctgttcc accaagtgag agaaggtact   2640
tactcttgta cctcctgttc agccaggtgc attaacagac ctccctacag ctgtaggaac   2700
tactgtccca gagctgaggc aaggggattt ctcaggtcat ttggagaaca agtgctttag   2760
tagtagttta aagtagtaac tgctactgta tttagtgggg tggaattcag aagaaatttg   2820
aagaccagat catgggtggt ctgcatgtga atgaacagga atgagccgga cagcctggct   2880
gtcattgctt tcttcctccc catttggacc cttctctgcc cttacatttt tgtttctcca   2940
tctaccacca tccaccagtc tatttattaa cttagcaaga ggacaagtaa agggccctct   3000
tggcttgatt ttgcttcttt ctttctgtgg aggatatact aagtgcgact ttgccctatc   3060
ctatttggaa atccctaaca gaattgagtt ttctattaag gatccaaaaa gaaaacaaa    3120 atgctaatga agccatcagt caagggtcac atgccaataa acaataaatt ttccagaaga   3180
aatgaaatcc aactagacaa ataaagtaga gcttatgaaa tggttcagta aagatgagtt   3240
tgttgttttt tgttttgttt tgttttgttt tttaaagac  ggagtctcgc tctgtcaccc   3300
aggctggagt gcagtggtat gatcttggct cactgtaacc tccgcctccc gggttcaagc   3360
```

| | |
|---|---|
| cattctcctg cctcagtctc ctgagtagct gggattacgg gtgcgtgcca ccatgcctgg | 3420 |
| ctaattttg tgttttagt agagacaggg tttcaccatg ttggtcgggc tggtctcaaa | 3480 |
| ctcctgacct cttgatccgc ctgccttggc ctcccaaagt gatgggatta cagatgtgag | 3540 |
| ccaccgtgcc tagccaagga tgagattttt aaagtatgtt tcagttctgt gtcatggttg | 3600 |
| gaagacagag taggaaggat atggaaaagg tcatggggaa gcagaggtga ttcatggctc | 3660 |
| tgtgaatttg aggtgaatgg ttccttattg tctaggccac ttgtgaagaa tatgagtcag | 3720 |
| ttattgccag ccttggaatt tacttctcta gcttacaatg gaccttttga actggaaaac | 3780 |
| accttgtctg cattcacttt aaaatgtcaa aactaatttt tataataaat gtttattttc | 3840 |
| acattgagtt tgtttaaatc ctgaagttct taccttaaga gaattgggac tcctagagtg | 3900 |
| attggacatt caaatattc ctgatagtct tgttaattaa gagattagga tatctttcca | 3960 |
| ttaccttgat aattacgttt taatttagct tttttcattg gcctgtgttt aaatgcaaat | 4020 |
| aaccccacaa tggacatttc ctatgttaaa gtgacattta ggggataaaa atgagagca | 4080 |
| gttccatgga ttttggtgtt tcccctgaga catgaactca gcataatctg ggataaaatg | 4140 |
| attgagtgtt aaggatgtgt ttgttgttcc tgtcgttttt ttattttctt caaagtatac | 4200 |
| aacatggttt gatatgcaca tacatttgtg taatgattgc catggtcaat taacacatca | 4260 |
| ccattttgt gtgtgtgtgt gtgtgtgtgt gtgagggagt cttgctccgt tgccaggctg | 4320 |
| gagtgcaatg gtacaacctt ggctcactgc aacctccacc tcctgggttc aagcaattct | 4380 |
| cttgcctcag cctcctaagt agctgggact ataggcgtgt gccaccatgc ccagctaatt | 4440 |
| tttgtatttt tagtagagac gggggtttcac catgttggcc aggatgatct cgatcccttg | 4500 |
| acctcatgat ccgcccacct cggcctccca agtgctggg attacaggcg tgagtcactg | 4560 |
| cacccggcca catcacctcc catgttctat cttacgtatt cagaacttgt tcatcttgta | 4620 |
| actgaaagcg tgtacccttt gaccaacact gttttcctg tcttaacagg atctacagat | 4680 |
| caaggacagg ggaggggata gtggaggaaa acggagttag tctgtttcta aatgaggga | 4740 |
| cagtatgttt cttggggcct gaggacagct taataaagta gacaaatgaa gaaaacaac | 4800 |
| aatttgcatt aaaaaatatc caattctta | 4830 |

<210> SEQ ID NO 659
<211> LENGTH: 3628
<212> TYPE: DNA
<213> ORGANISM: Homo sapiens

<400> SEQUENCE: 659

| | |
|---|---|
| agagcatcag caagagtagc agcgagcagc cgcgctggtg gcggcggcgc gtcgttgcag | 60 |
| ttgcgccatc tgtcaggagc ggagccggc aggaggggc tgccgcgggc gaggaggagg | 120 |
| ggtcgccgcg agccgaaggc cttcgagacc cgcccgccgc ccggcggcga gagtagaggc | 180 |
| gaggttgttg tgcgagcggc gcgtcctctc ccgcccggcc gcgccgcgct tctcccagcg | 240 |
| caccgaggac cgccccgggcg cacacaaagc cgccgcccgc cgcaccgc ccggcggccg | 300 |
| ccgcccgcgc cagggaggga ttcggccgcc gggccgggga caccccggcg ccgcccctc | 360 |
| ggtgctctcg gaaggcccac cggctccegg gccgccgggg accccccgg agccgcctcg | 420 |
| gccgcgccgg aggagggcgg ggagaggacc atgtgagtgg gctccggagc ctcagcgccg | 480 |
| cgcagttttt ttgaagaagc aggatgctga tctaaacgtg gaaaagacc agtcctgcct | 540 |
| ctgttgtaga agacatgtgg tgtatataaa gtttgtgatc gttggcggac attttggaat | 600 |
| ttagataatg ggctgtgtgc aatgtaagga taaagaagca acaaaactga cggaggagag | 660 |

```
ggacggcagc ctgaaccaga gctctgggta ccgctatggc acagacccca ccactcagca    720
ctaccccagc ttcggtgtga cctccatccc aactacaac aacttccacg cagccggggg     780
ccaaggactc accgtctttg gaggtgtgaa ctcttcgtct catacgggga ccttgcgtac    840
gagaggagga acaggagtga cactctttgt ggcccttat gactatgaag cacggacaga     900
agatgacctg agttttcaca aaggagaaaa atttcaaata ttgaacagct cggaaggaga    960
ttggtgggaa gcccgctcct tgacaactgg agagacaggt tacattccca gcaattatgt   1020
ggctccagtt gactctatcc aggcagaaga gtggtacttt ggaaaacttg ccgaaaaga    1080
tgctgagcga cagctattgt cctttggaaa cccaagaggg acctttctta tccgcgagag   1140
tgaaaccacc aaaggtgcct attcactttc tatccgtgat gggatgata tgaaaggaga    1200
ccatgtcaaa cattataaaa ttcgcaaact tgacaatggt ggatactaca ttaccacccg   1260
ggcccagttt gaaacacttc agcagcttgt acaacattac tcagagagag ctgcaggtct   1320
ctgctgccgc ctagtagttc cctgtcacaa agggatgcca aggcttaccg atctgtctgt   1380
caaaaccaaa gatgtctggg aaatccctcg agaatccctg cagttgatca agagactggg   1440
aaatgggcag tttggggaag tatggatggg tacctggaat ggaaacacaa aagtagccat   1500
aaagactctt aaaccaggca caatgtcccc cgaatcattc cttgaggaag cgcagatcat   1560
gaagaagctg aagcacgaca agctggtcca gctctatgca gtggtgtctg aggagcccat   1620
ctacatcgtc accgagtata tgaacaaagg aagtttactg gatttcttaa aagatggaga   1680
aggaagagct ctgaaattac caaatcttgt ggacatggca gcacaggtgg ctgcaggaat   1740
ggcttacatc gagcgcatga attatatcca tagagatctg cgatcagcaa acattctagt   1800
ggggaatgga ctcatatgca agattgctga cttcggattg gcccgattga tagaagacaa   1860
tgagtacaca gcaagacaag gtgcaaagtt ccccatcaag tggacggccc ccgaggcagc   1920
cctgtacggg aggttcacaa tcaagtctga cgtgtggtct tttggaatct tactcacaga   1980
gctggtcacc aaaggaagag tgccatacc aggcatgaac aaccgggagg tgctggagca   2040
ggtggagcga ggctacagga tgcccctgcc gcaggactgc cccatctctc tgcatgagct   2100
catgatccac tgctggaaaa aggaccctga agaacgcccc acttttgagt acttgcagag   2160
cttcctggaa gactacttta ccgcgacaga gccccagtac caacctggtg aaaacctgta   2220
aggcccgggt ctgcgagag aggccttgtc ccagaggctg ccccacccct ccccattagc    2280
tttcaattcc gtagccagct gctccccagc agcggaaccg cccaggatca gattgcatgt   2340
gactctgaag ctgacgaact tccatggccc tcattaatga cacttgtccc caaatccgaa   2400
cctcctctgt gaagcattcg agacagaacc ttgttatttc tcagactttg gaaaatgcat   2460
tgtatcgatg ttatgtaaaa ggccaaacct ctgttcagtg taaatagtta ctccagtgcc   2520
aacaatccta gtgctttcct tttttaaaaa tgcaaatcct atgtgatttt aactctgtct   2580
tcacctgatt caactaaaaa aaaaaagta ttattttcca aaagtggcct ctttgtctaa    2640
aacaataaaa ttttttttca tgttttaaca aaaaccaatc aggacaggtg tttgttttg    2700
ttttcttttt tataaatatg aatatatata atatatatgt ccctgtacat atacaatgtg   2760
ggtgctaatg tggagactgt ggccggcctg agccaccaag ctgcgggacc cagagggagg   2820
attttactgc aagtcagcat caaagcaccg gtgttattct gaaaacacca gtggcctcat   2880
ttttggcttt tgcaaagcat gaatttttc atttggattg cactttcctg gttcatgact   2940
gtacctgtag gtggttgtta ctttgactct tttcaggaac cacccccaa gctgaattta   3000
```

| | | | |
|---|---|---|---|
| caagttctgt | tagcactatt | tgcttcaact | tactgcgatt tgttctcaaa acttaaaaat | 3060 |
| aagcaagcaa | atggctgata | ctaccaagag | aactggaaga tggataccac acaaacttct | 3120 |
| tgtataaaaa | tatgaatgct | gaaatgtttc | agacattttt aatttaataa acctgtaacc | 3180 |
| acatttaagt | gatctaaaac | ccatagcatt | gtagtcatgg caacccgcta aactttctca | 3240 |
| tgcaactaaa | atttctgggg | gaaatgaggg | tgggggttgt acatttccca ttgtaaaata | 3300 |
| agtgttttaa | atgtcctgta | ctgctaacga | atgactttct atatgtccag gagttctcca | 3360 |
| gtggaataac | tatgcactac | tttacatttc | atggggatgc acaaaacaa aaaagtatta | 3420 |
| cattttagt | tgctgtttgt | accaacctta | aattacatat gtttaacaac aacaaatcaa | 3480 |
| aaatcctatt | tctattgagt | ttttaatact | gactagcaac tctgaagtct taattccttt | 3540 |
| tttgttatga | tttatttgtg | agtttacatt | tttaaattgt ttaactttct taatttagta | 3600 |
| attaaaaaga | gagcatttta | catttgaa | | 3628 |

<210> SEQ ID NO 660
<211> LENGTH: 5242
<212> TYPE: DNA
<213> ORGANISM: Homo sapiens

<400> SEQUENCE: 660

| | | | |
|---|---|---|---|
| gccgcggcgg | tggcggagac | tgtggcttta | agagcgtgcc gggagcccga gccccagccg | 60 |
| ggccgcgctt | cgccgctgcg | caccccagcg | gagccaagcc ccacgctggc cggacagggc | 120 |
| cgcctgtcgc | cgggctgctg | agaactagcc | ctagacctct gcgtgagggt tcttctgccg | 180 |
| aagacatcac | cagtgtgtgg | agcctgccac | acccacccgc tgccaaacca cggccttac | 240 |
| ctgtgtcttc | cggtgtttcc | cgtgcgaccc | atcctgtggg agtgcctcgt gggctgcccc | 300 |
| agagttcacc | ccacactcag | cagcaccaat | ggtgaagatg acaagatcga agactttcca | 360 |
| ggcatatctg | ccctcctgcc | accggaccta | cagctgcatt cactgcagag ctcacttggc | 420 |
| caatcatgat | gaactaattt | ccaagtcatt | ccaaggaagt caaggacgag catacctctt | 480 |
| taactcagta | gttaatgtgg | gctgtgggcc | tgcagaagag cgagtgttgc taacaggact | 540 |
| gcatgcagtc | gcagacattt | actgtgaaaa | ctgcaaaacc actctgggct ggaaatacga | 600 |
| acatgctttt | gaaagcagcc | agaaatataa | agaaggcaaa tacatcattg aactagcaca | 660 |
| catgatcaag | gacaatggct | gggactgatt | ggacagcatc tacccaaccc agtgtccacg | 720 |
| tgaacgccat | tcaaccgaac | attcttccca | agcgtgagag agtgactgac acttggttcc | 780 |
| atccatttag | gggccttgcc | atccggggca | tcctcccacc ctgacgccat ctttctggtg | 840 |
| accggcctct | aaatcgctgt | ctctctgtct | ctttgctttg tatctgtttg tgagttgatc | 900 |
| ctggcttctc | tctctgttct | agttttggct | gaaaacaaaa caacaaaagg aacagatcct | 960 |
| tgaccgcatg | gcggcagccc | accttggtaa | gggccccagg gcccatgcga gagctgcctg | 1020 |
| atggcctctt | gtcaggagag | cagtggcacg | gggcgtgag gaagagggaa aggggaaact | 1080 |
| ctaagggtcc | tggcgcgggg | aaggggtgga | agggtggagg taggaacaaa attgcgccgc | 1140 |
| tcctggagac | ctgataactt | aggcttgaaa | taattgactt gtctaaaagg acaaagagaa | 1200 |
| aaaaaaaata | cctcatgact | gcattctctc | tgactagaag cttctgttcc tgacaccaaa | 1260 |
| tgtgccaggt | tagcaaatga | gcacaagatg | tggccctgat tctagttggt ggggcaaggg | 1320 |
| cctggttctc | ctgggctgag | tgggggagtg | tcctggcagc agcgagtgac ctgggcagtg | 1380 |
| gccaggtggg | tgcgatgact | ctgatgcctc | actcagtctc tggcaatca tcatctttgc | 1440 |
| ctctagccac | cgtagataag | gtgtgaaggg | actgctgttt gcaatgggct taccatccaa | 1500 |

```
atatcccaaa ggctttgacc agcaaccaag taaaatcagt aattgaggag agcagggcac    1560 aaagggctg cagtttggga gctcctgaag aaatggctca gatattgagt cagagaaata     1620
aaaagtagga tcagttagca attctaactg cccttccttc tgaccoctca taagaggagt    1680 gtggtgaggg aggggactgg gtaggggtca tcccaggagg aggggtttac attggaacca    1740
gttcaggttc ggtgcatctt tcctcttcgg ttttacagtg gcttccgtgg gatcgtcaat    1800
ttcttgttct tagagtttcg ggtgtttttc tccagtcttg ttactgtaga ctgtagaaag    1860
cacgggcccc aggctctgag cttagtaata acctggctgg tagattcctc atgcccctaa    1920
ttgtcccact taggcctgaa tgtcttgcat ggagagaaat ctcctgtcag tgtggtccag    1980
cagcagggag gagttctgcc caaattccga tatcacccct tcccccatcc aagcatcctt    2040
cgattaggga agtggagagc acatccctgt aaggcccata agagaaagag gagtttgtta   2100
catttaatca acactgtgaa gtctgttcta cagcaattca gccattacac agtatatgac   2160
tgaaactcat ttaactgggt taatttcatt tcttagactg aatatattat tgttaagata   2220
cgtgtgcgtg ttaggtaatt ctcagcatct cctccaagta ggccgacctt ctcggaaaat   2280
tcaccctaaa agtctcacaa agaatgagt tcatggggag attctgtaaa gtgatgaact   2340
gagatgaaag cagccaacag cccaggagct tttcagaata gcgtctgcag cagaaccagt   2400
ttccattcag agcgcgtcct tggtggaaat gcttttttgt gtgtctccac gcgctgatgg   2460
tggaatggga gccccaagac gtgtgggctt agaaatcaac ttttgttccc caaggcttct   2520
tgtccagatc tttccagtgc tttcatagcc ctgggagatc aagttgttct ccccacttta   2580
ctgcaaggta gactgaagtt cagaagaaat actgaatttc tgctcccaga agaatagttt   2640
ctctggctca caggcccaag ttctcaatga aatcgttttt taactttcac attcctaagc   2700
tggcttcccg gcacagaagc catggatttc ccctctctcc cttcccctc tcaaggaaa     2760 tagtcttcct ttatggattt tcattggact cttttcctcag cgattgtcct ggctgtttat   2820
tgatagtcct tcccataaga aaatgggtt aaacatgggg taggtatttt gtctttcaaa    2880
ctacaaatgg aatgtggtga cataaactag acatggggtg ccctcaagtt tccaagggga   2940
ccaatgtgcc actgttcttc cttggggatg aggcctttga ctgttggatg gatcagagca   3000
ggctccagtc agaccctggt tctgaatgtt ttttttttcg gtgactatcc agtgagcctt   3060
cagtgggtgc aaggcgccat acttgctgtg agagagctga gtagagtgtt ggttttccca   3120
taactacagg gggaaaaaaa gtcattaggc tttcccttg tgtcagtgaa accaaaagtg     3180
cttcttacaa cgttcgctct gttcatgggt tgtctatcta acattgagca gcattggaga    3240
ggccacagct gagctatgga gatgctaaat taactcatgg cctcagtcag ttcattcttt    3300
aatttcctca ccaaattatt gacttagagc ataaccaaag acctcattca ttcaccccag    3360
gtgggttggg gtaattggag tttgttggtg aagtttgggg gcggggtgtt gggagtagag    3420
acagggtaag gggacgtgag aaaggaaaag gcatgaagtt ctatacctca gccagcagct    3480
gccttcgttt ggaactgaag tccagccagc agactctcta gctccatctc ccctgtgcca    3540
ccctaggtca tatgaccttg gccaccttgg agtagaccca gaccctcgg gacccgggac     3600 attagtctca ggctgctgat ggattgattt gacatgaacc aaacacagcc aaactcgata    3660
cccacaagct gtcagctgaa cctgactgag tgttcttcct gagttcacga ggataggcta    3720
gagtgcattt ttactggtgg atcagtgtgt gcgaaagaga tgacccttta taagagatt     3780 ttcaagtgga tatatataaa agaaacagtt gcttgtaaaa tatactttg taaataatat    3840
```

```
ttaattttttt aaataatata tttggtgctg ttttctcaga tccccctgaga gcactttttta    3900 ttttccttttt aaattctatg gtttcctttg catttcttga agtatatttt aagggaaaca     3960
gtgatcacca atacatgttt tcagtttttt ttttttttaa ggtctctatc actttaatct     4020
ggatcaaggc tttgaagcaa tgcctctctg cattttttcc ccagtggaac agactctgca     4080
gtacattaat caggttgaga attgaaatat tttcttgcat cagtattggc tagaaaagaa     4140
aataaataaa accaagttaa tttagtagta acaacttaca gtgattcttc ctgttggaag     4200
aatttccaac aaatcagaat cacgttttta gttgtgcgtg tgcgcgcaca cgtgtgtaaa     4260
aagcactttc gattgtgcct cctgttttct cgagtgggga cactttaact acagtttaca    4320
cctcgggcgc ataaagtttt tcttctcttt ctctctggtt gtttctgttt ctgagtggac     4380
caacagcaga acccacgagg atttgttttg agtatggagc tgttgcgggt ttgctccttt     4440
ttcttgcttt gcgtgctcag tttttacaga ctgtaaagga gatgtgttgt ttgtgaagat     4500
ggagcagagt caaatctgtg cttctaactg agatgagagt gtattaatca cgtatcgcag     4560
ggctccagct gttttagaag ccacatcatg ttaaacatta actggtttgg attaaaagaa    4620
cattaatatt ataatacaca tatcttagtg gtaaacagct ttttttttttt aaggtcagat    4680 tgcctcaggt ttagaaagag gctgagaaat caaatcttga acacaatcaa cttacatatt    4740 ttaaggaat ctgcctcaaa tgagaaaata tgctagttat ctagatagag gaaagagata    4800 tttactttttt taaaaattaa aatagttatg aaatctggca gaaaaggtaa agcctagaag    4860
aaactatgaa agctattctc atgttaccaa attctatctg cgcatatgtt tttgtataac    4920
atttcggtga cagtgggagt cggttcccct tcccaacctg cagagactat cttccaatac     4980
agaatctgtc tatttatgct tgtgtttaca aactgtatt gttgggtttg ggttttgtt      5040 ttctttggtg gcattttca ggtcactttg cttctataac aaaggtaatt gttttcaaat    5100
aatttgtctt cacctttttcc tgtatttgta catagtgatt cagtattaga gaaaagtgca   5160
ttgtttctgt catatttcca atctgtgttg gtgctcattt gagaaaataa aagttttcaa    5220
atattaactc ttaaaaaaaa aa                                              5242

<210> SEQ ID NO 661
<211> LENGTH: 3679
<212> TYPE: DNA
<213> ORGANISM: Homo sapiens

<400> SEQUENCE: 661
ccctcccctc ccgatcctca tccccttgcc ctcccccagc ccagggactt ttccggaaag      60
tttttatttt ccgtctgggc tctcggagaa agaagctcct ggctcagcgg ctgcaaaact     120
ttcctgctgc cgcgccgcca gccccgcccc tccgctgccc ggccctgcgc ccgccgagc     180 gatgagcgcc cctccggtcc tgcggccgcc cagtccgctg ctgcccgtgg cggcggcagc     240
tgccgcagcg gccgccgcac tggtcccagg gtccgggccc gggcccgcgc cgttcttggc     300
tcctgtcgcg gccccggtcg ggggcatctc gttccatctg cagatcggcc tgagccgtga    360
gccggtgctg ctgctgcagg actcgtccgg ggactacagc ctggcgcacg tccgcgagat     420
ggcttgctcc attgtcgacc agaagttccc tgaatgtggt ttctacggaa tgtatgataa    480
gatcctgctt tttcgccatg accctacctc tgaaaacatc cttcagctgg tgaaagcggc     540
cagtgatatc caggaaggcg atcttattga agtggtcttg tcagcttccg ccacctttga     600
agactttcag attcgtcccc acgctctctt tgttcattca tacagagctc cagctttctg    660
tgatcactgt ggagaaatgc tgtgggggct ggtacgtcaa ggtcttaaat gtgaagggtg    720
```

```
tggtctgaat taccataaga gatgtgcatt taaaataccc aacaattgca gcggtgtgag    780
gcggagaagg ctctcaaacg tttccctcac tggggtcagc accatccgca catcatctgc    840
tgaactctct acaagtgccc ctgatgagcc ccttctgcaa aaatcaccat cagagtcgtt    900
tattggtcga gagaagaggt caaattctca atcatacatt ggacgaccaa ttcaccttga    960
caagattttg atgtctaaag ttaaagtgcc gcacacattt gtcatccact cctacacccg   1020
gcccacagtg tgccagtact gcaagaagct tctgaagggg cttttcaggc agggcttgca   1080
gtgcaaagat tgcagattca actgccataa acgttgtgca ccgaaagtac caacaactg    1140 ccttggcgaa gtgaccatta tggagattt gcttagccct ggggcagagt ctgatgtggt    1200
catggaagaa gggagtgatg acaatgatag tgaaaggaac agtgggctca tggatgatat   1260
ggaagaagca atggtccaag atgcagagat ggcaatggca gagtgccaga cgacagtgg    1320 cgagatgcaa gatccagacc cagaccacga ggacgccaac agaaccatca gtccatcaac   1380
aagcaacaat atcccactca tgagggtagt gcagtctgtc aaacacacga agaggaaaag   1440
cagcacagtc atgaaagaag gatggatggt ccactacacc agcaaggaca cgctgcggaa   1500
acggcactat tggagattgg atagcaaatg tattaccctc tttcagaatg acacaggaag   1560
caggtactac aaggaaattc ctttatctga aattttgtct ctggaaccag taaaaacttc   1620
agctttaatt cctaatgggg ccaatcctca ttgtttcgaa atcactacgg caaatgtagt   1680
gtattatgtg ggagaaaatg tggtcaatcc ttccagccca tcaccaaata acagtgttct   1740
caccagtggc gttggtgcag atgtggccag gatgtgggag atagccatcc agcatgccct   1800
tatgcccgtc attcccaagg gctcctccgt gggtacagga accaacttgc acagagatat   1860
ctctgtgagt atttcagtat caaattgcca gattcaagaa aatgtggaca tcagcacagt   1920
atatcagatt tttcctgatg aagtactggg ttctggacag tttggaattg tttatggagg   1980
aaaacatcgt aaaacaggaa gagatgtagc tattaaaatc attgacaaat tacgatttcc   2040
aacaaaacaa gaaagccagc ttcgtaatga ggttgcaatt ctacagaacc ttcatcaccc   2100
tggtgttgta aatttggagt gtatgtttga gacgcctgaa agagtgtttg ttgttatgga   2160
aaaactccat ggagacatgc tggaaatgat cttgtcaagt gaaaagggca ggttgccaga   2220
gcacataacg aagttttaa ttactcagat actcgtggct ttgcggcacc ttcattttaa    2280
aaatatcgtt cactgtgacc tcaaaccaga aaatgtgttg ctagcctcag ctgatccttt   2340
tcctcaggtg aaactttgtg attttggttt tgcccggatc attggagaga agtctttccg   2400
gaggtcagtg gtgggtaccc ccgcttacct ggctcctgag gtcctaagga caagggcta    2460 caatcgctct ctagacatgt ggtctgttgg ggtcatcatc tatgtaagcc taagcggcac   2520
attcccattt aatgaagatg aagacataca cgaccaaatt cagaatgcag ctttcatgta   2580
tccaccaaat ccctggaagg aaatatctca tgaagccatt gatcttatca acaatttgct   2640
gcaagtaaaa atgagaaagc gctacagtgt ggataagacc ttgagccacc cttggctaca   2700
ggactatcag acctggttag atttgcgaga gctggaatgc aaaatcgggg agcgctacat   2760
cacccatgaa agtgatgacc tgaggtggga gaagtatgca ggcgagcagg ggctgcagta   2820
ccccacacac ctgatcaatc caagtgctag ccacagtgac actcctgaga ctgaagaaac   2880
agaaatgaaa gccctcggtg agcgtgtcag catcctctga gttccatctc ctataatctg   2940
tcaaaacact gtggaactaa taatacata cggtcaggtt taacatttgc cttgcagaac   3000
tgccattatt ttctgtcaga tgagaacaaa gctgttaaac tgttagcact gttgatgtat   3060
```

| | |
|---|---|
| ctgagttgcc aagacaaatc aacagaagca tttgtatttt gtgtgaccaa ctgtgttgta | 3120 |
| ttaacaaaag ttccctgaaa cacgaaactt gttattgtga atgattcatg ttatatttaa | 3180 |
| tgcattaaac ctgtctccac tgtgcctttg caaatcagtg ttttcttac tggagcttca | 3240 |
| ttttggtaag agacagaatg tatctgtgaa gtagttctgt ttggtgtgtc ccattggtgt | 3300 |
| tgtcattgta aacaaactct tgaagagtcg attatttcca gtgttctatg aacaactcca | 3360 |
| aaacccatgt gggaaaaaaa tgaatgagga gggtagggaa taaaatccta agacacaaat | 3420 |
| gcatgaacaa gttttaatgt atagttttga atcctttgcc tgcctggtgt gcctcagtat | 3480 |
| atttaaactc aagacaatgc acctagctgt gcaagaccta gtgctcttaa gcctaaatgc | 3540 |
| cttagaaatg taaactgcca tatataacag atacatttcc ctctttctta taatactctg | 3600 |
| ttgtactatg gaaaatcagc tgctcagcaa ccttttcacct ttgtgtattt ttcaataata | 3660 |
| aaaaatattc ttgtcaaaa | 3679 |

```
<210> SEQ ID NO 662
<211> LENGTH: 3418
<212> TYPE: DNA
<213> ORGANISM: Homo sapiens

<400> SEQUENCE: 662
```

| | |
|---|---|
| gctcgggcgc cgagtctgcg cgctgacgtc cgacgctcca ggtactttcc ccacggccga | 60 |
| cagggcttgg cgtgggggcg gggcgcggcg cgcagcgcgc atgcgccgca cgccagcgc | 120 |
| tctccccgga tcgtgcgggg cctgagcctc tccgccggcg caggctctgc tcgcgccagc | 180 |
| tcgctcccgc agccatgccc accaccatcg agcgggagtt cgaagagttg atactcagc | 240 |
| gtcgctggca gccgctgtac ttggaaattc gaaatgagtc ccatgactat cctcatagag | 300 |
| tggccaagtt tccagaaaac agaaatcgaa acagatacag agatgtaagc ccatatgatc | 360 |
| acagtcgtgt taaactgcaa aatgctgaga atgattatat taatgccagt ttagttgaca | 420 |
| tagaagaggc acaaaggagt tacatcttaa cacagggtcc acttcctaac acatgctgcc | 480 |
| atttctggct tatggtttgg cagcagaaga ccaaagcagt tgtcatgctg aaccgcattg | 540 |
| tggagaaaga atcggttaaa tgtgcacagt actggccaac agatgaccaa gagatgctgt | 600 |
| ttaaagaaac aggattcagt gtgaagctct tgtcagaaga tgtgaagtcg tattatacag | 660 |
| tacatctact acaattagaa aatatcaata gtggtgaaac cagaacaata tctcactttc | 720 |
| attatactac ctggccagat tttggagtcc ctgaatcacc agcttcattt ctcaatttct | 780 |
| tgtttaaagt gagagaatct ggctccttga acctgacca tgggcctgcg gtgatccact | 840 |
| gtagtgcagg cattgggcgc tctggcacct tctctctggt agacacttgt cttgttttga | 900 |
| tggaaaaagg agatgatatt aacataaaac aagtgttact gaacatgaga aaataccgaa | 960 |
| tgggtcttat tcagacccca gatcaactga gattctcata catggctata atagaaggag | 1020 |
| caaaatgtat aaagggagat tctagtatac agaaacgatg gaaagaactt tctaaggaag | 1080 |
| acttatctcc tgcctttgat cattcaccaa acaaaataat gactgaaaaa tacaatggga | 1140 |
| acagaatagg tctagaagaa gaaaaactga caggtgaccg atgtacagga ctttcctcta | 1200 |
| aaatgcaaga tacaatggag gagaacagtg agagtgctct acggaaacgt attcgagagg | 1260 |
| acagaaaggc caccacagct cagaaggtgc agcagatgaa acagaggcta atgagaatg | 1320 |
| aacgaaaaag aaaaaggtgg ttatattggc aacctattct cactaagatg gggtttatgt | 1380 |
| cagtcatttt ggttggcgct tttgttggct ggacactgtt tttcagcaa aatgccctat | 1440 |
| aaacaattaa ttttgcccag caagcttctg cactagtaac tgacagtgct acattaatca | 1500 |

```
tagggggtttg tctgcagcaa acgcctcata tcccaaaaac ggtgcagtag aatagacatc   1560
aaccagataa gtgatattta cagtcacaag cccaacatct caggactctt gactgcaggt   1620
tcctctgaac cccaaactgt aaatggctgt ctaaaataaa gacattcatg tttgttaaaa   1680
actggtaaat tttgcaactg tattcataca tgtcaaacac agtatttcac ctgaccaaca   1740
ttgagatatc ctttatcaca ggatttgttt ttggaggcta tctggatttt aacctgcact   1800
tgatataagc aataaatatt gtggttttat ctacgttatt ggaaagaaaa tgacatttaa   1860
ataatgtgtg taatgtataa tgtactattg acatgggcat caacacttt attcttaagc    1920 atttcagggt aaatatattt tataagtatc tatttaatct tttgtagtta actgtactttt  1980 ttaagagctc aatttgaaaa atctgttact aaaaaaataa attgtatgtc gattgaattg   2040
tactggatac attttccatt tttctaaaga aagtttgat atgagcagtt agaagttgga    2100
ataagcaatt tctactatat attgcatttc ttttatgttt tacagttttc cccatttaa    2160 aaagaaaagc aaacaaagaa acaaagtttt ttcctaaaaa tatctttgaa ggaaaattct   2220
ccttactggg atagtcaggt aaacagttgg tcaagacttt gtaaagaaat tggtttctgt   2280
aaatcccatt attgatatgt ttattttca tgaaaatttc aatgtagttg gggtagatta    2340
tgatttagga agcaaaagta agaagcagca ttttatgatt cataattttca gtttactaga   2400 ctgaagtttt gaagtaaaca ctttttcagtt tctttctact tcaataaata gtatgattat  2460
atgcaaacct tacattgtca tttaactta atgaatattt tttaaagcaa actgtttaat    2520
gaatttaact gctcatttga atgctagctt tcctcagatt tcaacattcc attcagtgtt   2580
taatttgtct tacttaaact tgaaattgtt gttacaaatt taattgctag gaggcatgga   2640
tagcatacat tattatggat agcataccct atttcagtgg ttttcaaact atgctcattg   2700
gatgtccagg tgggtcaaga ggttactttc aaccacagca tctctgcctt gtctctttat   2760
atgccacata agatttctgc ataaggctta agtattttaa aggggcagt tatcattaaa    2820 aaacagtttg gtcgggcgcg gtggctcatg cctgtaatcc cagcactttg ggaggctgaa   2880
gtgggcagat cacctgaggt caggagttca agaccagcct ggccaacgtg gtgaaacacc   2940
atctctacta aaaatgcaaa aattagctgg gcatggtgga gggcacctgt aatctcagct   3000
actcaggagg ctgaggtagg agaattgctt gaacccagga gatggaggtt gcagtgagct   3060
gagatcacgt cactgcactc cagccagggc gacagagcga gactccatct caaaagaaac   3120
aaacaaaaaa aacagtttgg gccgggtgtg gtggctcacg cttgtaatcc cagcacttcg   3180
gaaggccaag gcgggcggat cacgaggtca agagatggag actgtcctgg ccaacatggt   3240
gaaatccctt cttactaaaa aatacaaaaa ttatctgggc gtggtggtgc atgcctgtag   3300
tcccagctcc ttgggaggct aaggcaggag aatcacttga acccgggagg cagaggttgc   3360
agtgagccga gattgcacca ctgcactcca gcctggcaac agagcaagac ttcgtctc     3418
```

<210> SEQ ID NO 663
<211> LENGTH: 2950
<212> TYPE: DNA
<213> ORGANISM: Homo sapiens

<400> SEQUENCE: 663

```
cggctggctg cggcggccgg ggaggccggg gaggccgcgg cgcggtcact gcgagccgag     60
ccgagccgcg ccgagccgcg ccgatcgcca tccggcctcg gcactcgcgc gcgatcccgg   120
ccggcggcgc ggcccggcgg gccaggcggc gccacagccc atggagctcg agaacatcgt   180
```

-continued

| | | | | |
|---|---|---|---|---|
| agcgaacacg | gtgctactca | aggcccggga | aggtggcggt | ggaaatcgca | aaggcaaaag | 240 |
| caagaaatgg | cggcagatgc | tccagttccc | tcacatcagc | cagtgcgaag | agctgcggct | 300 |
| cagcctcgag | cgtgactatc | acagcctgtg | cgagcggcag | cccattgggc | gcctgctgtt | 360 |
| ccgagagttc | tgtgccacga | ggccggagct | gagccgctgc | gtcgccttcc | tggatggggt | 420 |
| ggccgagtat | gaagtgaccc | cggatgacaa | gcggaaggca | tgtgggcggc | agctaacgca | 480 |
| gaattttctg | agccacacgg | gtcctgacct | catccctgag | gtcccccggc | agctggtgac | 540 |
| gaactgcacc | cagcggctgg | agcagggtcc | ctgcaaagac | cttttccagg | aactcacccg | 600 |
| gctgacccac | gagtacctga | gcgtggcccc | ttttgccgac | tacctcgaca | gcatctactt | 660 |
| caaccgtttc | ctgcagtgga | agtggctgga | aaggcagcca | gtgaccaaaa | acaccttcag | 720 |
| gcaataccga | gtcctgggca | aggtggctt | tggggaggtg | tgcgcctgcc | aggtgcgggc | 780 |
| cacaggtaag | atgtatgcct | gcaagaagct | agagaaaaag | cggatcaaga | agcggaaagg | 840 |
| ggaggccatg | cgcgctgaacg | agaagcagat | cctggagaaa | gtgaacagta | ggtttgtagt | 900 |
| gagcttggcc | tacgcctatg | agaccaagga | cgcgctgtgc | ctggtgctga | cactgatgaa | 960 |
| cggggggcgac | ctcaagttcc | acatctacca | catgggccag | gctggcttcc | ccgaagcgcg | 1020 |
| ggccgtcttc | tacgccgccg | agatctgctg | tggcctggag | gacctgcacc | gggagcgcat | 1080 |
| cgtgtacagg | gacctgaagc | ccgagaacat | cttgctggat | gaccacggcc | acatccgcat | 1140 |
| ctctgacctg | ggactagctg | tgcatgtgcc | cgagggccag | accatcaaag | ggcgtgtggg | 1200 |
| caccgtgggt | tacatggctc | cggaggtggt | gaagaatgaa | cggtacacgt | tcagccctga | 1260 |
| ctggtgggcg | ctcggctgcc | tcctgtacga | gatgatcgca | ggccagtcgc | ccttccagca | 1320 |
| gaggaagaag | aagatcaagc | gggaggaggt | ggagcggctg | gtgaaggagg | tccccgagga | 1380 |
| gtattccgag | cgcttttccc | cgcaggcccg | ctcactttgc | tcacagctcc | tctgcaagga | 1440 |
| ccctgccgaa | cgcctggggt | gtcgtggggg | cagtgcccgc | gaggtgaagg | agcaccccct | 1500 |
| ctttaagaag | ctgaacttca | gcggctggg | agctggcatg | ctggagccgc | cgttcaagcc | 1560 |
| tgacccccag | gccatttact | gcaaggatgt | tctggacatt | gaacagttct | ctacggtcaa | 1620 |
| gggcgtggag | ctggagccta | ccgaccagga | cttctaccag | aagtttgcca | caggcagtgt | 1680 |
| gcccatcccc | tggcagaacg | agatggtgga | gaccgagtgc | ttccaagagc | tgaatgtctt | 1740 |
| tgggctggat | ggctcagttc | ccccagacct | ggactggaag | ggccagccac | ctgcacctcc | 1800 |
| taaaaaggga | ctgctgcaga | gactcttcag | tcgccaagat | tgctgtggaa | actgcagcga | 1860 |
| cagcgaggaa | gagctcccca | cccgcctcta | gcccccagcc | cgaggccccc | accagcagtt | 1920 |
| ggcggtagca | gctactccga | gcgccgttta | cagttttgca | cagtgatctt | ccccattgtc | 1980 |
| cactcaagtc | gtggcctggg | gaacacagac | ggagctgtcc | ccagtgtcct | ccgtccctca | 2040 |
| gccccctggcc | tggctgagtt | tggcagggcc | tgggccatcc | ctgggacaaa | ggtgcgtccc | 2100 |
| ttcagctctt | ctccgtggag | ctcggggctt | tctgtattta | tgtatttgta | cgaatgtata | 2160 |
| tagcgaccag | agcattctta | attcccgccg | cagacctggc | gcccccgcct | ggctcctgg | 2220 |
| gggcagccag | ccctggctgg | gagagcggga | gctggcagag | gagccactgc | caaactcaag | 2280 |
| gctcctctgg | cccagcttgg | atggctgagg | tggtcacac | ccctgagcct | tcagcactgt | 2340 |
| gctggccacc | ccggcctctg | agtaagactc | gtgcctcccc | ctgctgccct | gggctcaggc | 2400 |
| tgctacccctc | tgggggccaa | agctgtccct | tctcagtgct | tgtcagcgct | gggtctgggg | 2460 |
| cctctgtatg | ccctaggcct | gtgccaaagt | ggccagagat | tgggctgcct | gtgatacccca | 2520 |
| tcagcccact | gccccggccg | gcccagatag | gtctgcctct | gccttccagc | tcccacagcc | 2580 |

```
tggtccctga tactgggctc tgtcctgcag acacctcttt cagaaacgcc caagcccagc    2640
ccctaggagg gggtgggqca tccctggtca accctcaaac attccggact ccccctcataa    2700 caatagacac atgtgcccag caataatccg ccccttcctg tgtgcgcctg tggggtgcgt    2760
gcgcgcgcgt gtgtacctgt gtgggtgaag gggatagggc gaggctgtgc ctgtgcccca    2820
ggtcccagcc ctggcccttc ccagactgtg atggccatcc tggtcccagt gttagggtag    2880
catgggatta cagggccctg ttttttccat atttaaagcc aattttattt actcgttttg    2940
tccaacgtaa                                                           2950

<210> SEQ ID NO 664
<211> LENGTH: 1267
<212> TYPE: DNA
<213> ORGANISM: Homo sapiens

<400> SEQUENCE: 664
cgagggctgc ttccggctgg tgccccgggg ggagacccaa cctggggcga cttcaggggt     60
gccacattcg ctaagtgctc ggagttaata gcacctcctc cgagcactcg ctcacggcgt    120
ccccttgcct ggaaagatac cgcggtccct ccagaggatt tgaggacag ggtcggaggg     180 ggctcttccg ccagcaccgg aggaagaaag aggaggggct ggctggtcac cagagggtgg    240
ggcggaccgc gtgcgctcgg cggctgcgga gaggggggaga gcaggcagcg ggcggcgggg   300
agcagcatgg agccggcggc ggggagcagc atggagcctt cggctgactg gctggccacg    360
gccgcggccc ggggtcgggt agaggaggtg cgggcgctgc tggaggcggg ggcgctgccc    420
aacgcaccga atagttacgg tcggaggccg atccaggtca tgatgatggg cagcgcccga    480
gtggcggagc tgctgctgct ccacggcgcg gagcccaact cgccgacccc cgccactctc    540
acccgacccg tgcacgacgc tgcccgggag ggcttcctgg acacgctggt ggtgctgcac    600
cgggccgggg cgcggctgga cgtgcgcgat gcctggggcc gtctgcccgt ggacctggct    660
gaggagctgg gccatcgcga tgtcgcacgg tacctgcgcg cggctgcggg gggcaccaga    720
ggcagtaacc atgcccgcat agatgccgcg gaaggtccct cagacatccc cgattgaaag    780
aaccagagag gctctgagaa acctcgggaa acttagatca tcagtcaccg aaggtcctac    840
agggccacaa ctgcccccgc cacaacccac cccgctttcg tagttttcat ttagaaaata    900
gagcttttaa aaatgtcctg cctttaacg tagatatatg ccttccccca ctaccgtaaa     960
tgtccattta tatcattttt tatatattct tataaaatg taaaaagaa aaacaccgct      1020 tctgccttt cactgtgttg gagttttctg gagtgagcac tcacgcccta agcgcacatt     1080
catgtgggca tttcttgcga gcctcgcagc ctccggaagc tgtcgacttc atgacaagca    1140
ttttgtgaac tagggaagct caggggggtt actggcttct cttgagtcac actgctagca    1200
aatggcagaa ccaaagctca ataaaaata aaataatttt cattcattca ctcaaaaaaa    1260
aaaaaaa                                                             1267

<210> SEQ ID NO 665
<211> LENGTH: 8033
<212> TYPE: DNA
<213> ORGANISM: Homo sapiens

<400> SEQUENCE: 665
gggcgggccg gctggctggg aagatggcgg cgggaacctg gccgccgcc gccgccgccg      60 ccgccgccgc ggagcgaacc aggggtgtcc ggggtgcgcg gtccagggcc ggggccgggc    120
```

```
catgagcgcg ccgtcctcga gtccccgagc cgcggagccc gcccgcgccc ctcgggccgc    180
cccgcgtccc tcgccatggc gcggctcgcg gactacttcg tgctggtggc gttcgggccg    240 caccccgcgcg ggagtgggga aggccagggc cagattctgc agcgcttccc agagaaggac    300
tgggaggaca acccattccc ccagggcatc gagctgtttt gccagcccag cgggtggcag    360
ctgtgtcccg agaggaatcc accgaccttc tttgttgctg tcctcaccga catcaactcc    420
gagcgccact actgcgcctg cttgaccttc tgggagccag cggagccttc acaggaaacg    480
acgcgcgtgg aggatgccac agagagggag gaagaggggg atgagggagg ccagacccac    540
ctgtctccca cagcacctgc cccatctgcc cagctgtttg caccgaagac gctggtactg    600
gtgtcgcgac tcgaccacac ggaggtgttc aggaacagcc ttggcctcat ctatgccatc    660
cacgtggagg gcctgaatgt gtgcctggag aacgtgattg gaacctgct gacgtgcact    720 gtgcccctgg ctgggggctc gcagaggacg atctctttgg gggctggtga ccggcaggtc    780
atccagactc cactggccga ctcgctgccc gtcagccgct gcagcgtggc cctgctcttc    840
cgccagctag gcatcaccaa cgtgctgtct ttgttctgtg ccgccctcac ggagcacaag    900
gttctcttcc tgtcccggag ctaccagcgg ctcgccgatg cctgtagggg cctcctggca    960
ctgctgtttc ctctcagata cagcttcacc tatgtgccca tcctgccggc tcagctgctg   1020
gaggtcctca gcacacccac gcccttcatc attgggggtca acgcggcctt ccaggcagag   1080
acccaggagc tgctcgatgt gattgttgct gatctgatg gagggacggt caccattcct   1140
gagtgtgtgc acattccacc cttgccagag ccactgcaga gtcagacgca cagtgtgctg   1200
agcatggtcc tggaccccga gctggagttg gctgacctcg ccttccctcc gcccacgaca   1260
tccacctcct ccctgaagat gcaggacaag gagctgcgcg cggtcttcct gcggctgttc   1320
gctcagctgc tgcagggcta tcgctggtgc ctgcacgtcg tgcgcatcca cccggagcct   1380
gtcatccgct tccataaggc agccttcctg ggccagcgtg ggctggtaga ggacgatttc   1440
ctgatgaagg tgctggaggg catggccttt gctggctttg tgtcagagcg tggggtccca   1500
taccgcccta cggacctgtt cgatgagctg gtggcccacg aggtggcaag gatgcgggcg   1560
gatgagaacc accccagcg tgtcctgcgt cacgtccagg aactggcaga gcagctctac   1620
aagaacgaga cccgtaccc agccgtggcg atgcacaagg tacagaggcc cggtgagagc   1680
agccacctgc gacgggtgcc ccgacccttc ccccggctgg atgagggcac cgtgcagtgg   1740
atcgtggacc aggctgcagc caagatgcag ggtgcacccc cagctgtgaa ggccgagagg   1800
aggaccaccg tgccctcagg gccccccatg actgccatac tggagcggtg cagtgggctg   1860
catgtcaaca gcgcccggcg gctggaggtt gtgcgcaact gcatctccta cgtgtttgag   1920
gggaaaatgc ttgaggccaa gaagctgctc cagccgtgt tgaggccct gaaggggcga   1980 gctgcccgcc gctgcctcgc ccaggagctg cacctgcatg tgcagcagaa ccgtgcggtc   2040
ctggaccacc agcagtttga ctttgtcgtc cgtatgatga actgctgcct gcaggactgc   2100
acttctctgg acgagcatgg cattgcgcg gctctgctgc ctctggtcac agccttctgc   2160
cggaagctga gcccggggggt gacgcagttt gcatacagct gtgtgcagga gcacgtggtg   2220
tggagcacgc cacagttctg ggaggccatg ttctatgggg atgtgcagac tcacatccgg   2280
gccctctacc tggagcccac ggaggacctg gccccgcccc aggaggttgg ggaggcacct   2340
tcccaggagg acgagcgctc tgccctagac gtggcttctg agcagcggcg cttgtggcca   2400
actctgagtc gtgagaagca gcaggagctg gtgcagaagg aggagagcac ggtgttcagc   2460
caggccatcc actatgccaa ccgcatgagc tacctcctcc tgcccctgga cagcagcaag   2520
```

```
agccgcctac ttcgggagcg tgccgggctg ggcgacctgg agagcgccag caacagcctg    2580
gtcaccaaca gcatggctgg cagtgtggcc gagagctatg acacggagag cggcttcgag    2640
gatgcagaga cctgcgacgt agctggggct gtggtccgct tcatcaaccg ctttgtggac    2700
aaggtctgca cggagagtgg ggtcaccagc gaccacctca aggggctgca tgtcatggtg    2760
ccagacattg tccagatgca catcgagacc ctggaggccg tgcagcggga gagccggagg    2820
ctgccgccca tccagaagcc caagctgctg cggccgcgcc tgctgccggg tgaggagtgt    2880
gtgctggacg gcctgcgcgt ctacctgctg ccggatgggc gtgaggaggg cgcggggggc    2940
agtgctgggg gaccagcatt gctcccagct gagggcgccg tcttcctcac cacgtaccgg    3000
gtcatcttca cggggatgcc cacggacccc ctggttgggg agcaggtggt ggtccgctcc    3060
ttcccggtgg ctgcgctgac caaggagaag cgcatcagcg tccagacccc tgtgaccag    3120 ctcctgcagg acgggctcca gctgcgctcc tgcacattcc agctgctgaa aatggccttt    3180
gacgaggagg tggggtctga cagcgccgag ctcttccgta agcagctgca taagctgcgg    3240
tacccgccgg acatcagggc cacctttgcg ttcaccttgg gctctgccca cacacctggc    3300
cggccaccgc gagtcaccaa ggacaagggt ccttccctca gaaccctgtc ccggaacctg    3360
gtcaagaacg ccaagaagac catcgggcgg cagcatgtca ctcgcaagaa gtacaacccc    3420
cccagctggg agcaccgggg ccagccgccc cctgaggacc aggaggacga gatctcagtg    3480
tcggaggagc tggagcccag cacgctgacc ccgtcctcag ccctgaagcc ctccgaccgc    3540
atgaccatga gcagcctggt ggaaagggct tgctgtcgcg actaccagcg cctcggtctg    3600
ggcaccctga gcagcagcct gagccgggcc aagtctgagc ccttccgcat ttctccggtc    3660
aaccgcatgt atgccatctg ccgcagctac ccagggctgc tgatcgtgcc ccagagtgtc    3720
caggacaacg ccctgcagcg cgtgtcccgc tgctaccgcc agaaccgctt ccccgtggtc    3780
tgctggcgca gcgggcggtc caaggcggtg ctgctgcgct ctggaggcct gcatggcaaa    3840
ggtgtcgtcg gcctcttcaa ggcccagaac gcaccttctc caggccagtc ccaggcggac    3900
tcgagtagcc tggagcagga gaagtacctg caggctgtgg tcagctccat gccccgctac    3960
gccgacgcgt cgggacgcaa cacgcttagc ggcttctcct cagcccacat gggcagtcac    4020
gttcccagcc ccagagccag ggtcaccacg ctgtccaacc ccatggcggc ctcggcctcc    4080
agacggaccg caccccgagg taagtggggc agtgtccgga ccagtggacg cagcagtggc    4140
cttggcaccg atgtgggctc ccggctagct ggcagagacg cgctggcccc accccaggcc    4200
aacgggggcc ctcccgaccc gggcttcctg cgtccgcagc gagcagccct ctatatcctt    4260
ggggacaaag cccagctcaa gggtgtgcgg tcagacccccc tgcagcagtg ggagctggtg    4320
cccattgagg tattcgaggc acggcaggtg aaggctagct tcaagaagct gctgaaagca    4380
tgtgtcccag gctgccccgc tgctgagccc agcccagcct ccttcctgcg ctcactggag    4440
gactcagagt ggctgatcca gatccacaag ctgctgcagg tgtctgtgct ggtggtggag    4500
ctcctggatt caggctcctc cgtgctggtg ggcctggagg atggctggga catcaccacc    4560 cagtggtat ccttggtgca gctgctctca gacccccttct accgcacgct ggagggcttt    4620
cgcctgctgg tggagaagga gtggctgtcc ttcggccatc gcttcagcca ccgtggagct    4680
cacaccctgg ccgggcagag cagcggcttc acacccgtct tcctgcagtt cctggactgc    4740
gtacaccagg tccacctgca gttccccatg gagtttgagt tcagccagtt ctacctcaag    4800
ttcctcggct accaccatgt gtcccgccgt ttccggacct tcctgctcga ctctgactat    4860
```

```
gagcgcattg agctggggct gctgtatgag gagaaggggg aacgcagggg ccaggtgccg   4920
tgcaggtctg tgtgggagta tgtggaccgg ctgagcaaga ggacgcctgt gttccacaat   4980
tacatgtatg cgcccgagga cgcagaggtc ctgcggccct acagcaacgt gtccaacctg   5040
aaggtgtggg acttctacac tgaggagacg ctggccgagg ccctccccta tgactgggaa   5100
ctggcccagg ggcccctga accccagag gaagaacggt ctgatggagg cgctccccag   5160
agcaggcgcc gcgtggtgtg gccctgttac gacagctgcc cgcgggccca gcctgacgcc   5220
atctcacgcc tgctggagga gctgcagagg ctggagacag agttgggcca accgctgag   5280
cgctggaagg acacctggga ccgggtgaag gctgcacagc gcctcgaggg ccggccagac   5340
ggccgtggca cccctagctc cctccttgtg tccaccgcac cccaccaccg tcgctcgctg   5400
ggtgtgtacc tgcaggaggg gcccgtgggc tccaccctga gcctcagcct ggacagcgac   5460
cagagtagtg gctcaaccac atccggctcc cgtcaggctg cccgccgcag caccagcacc   5520
ctgtacagcc agttccagac agcagagagt gagaacaggt cctacgaggg cactctgtac   5580
aagaagggg ccttcatgaa gccttggaag gcccgctggt tcgtgctgga caagaccaag   5640
caccagctgc gctactacga ccaccgtgtg gacacagagt gcaagggtgt catcgacttg   5700
gcggaggtgg aggctgtggc acctggcacg cccactatgg gtgcccctaa gactgtggac   5760
gagaaggcct tctttgacgt gaagacaacg cgtcgcgttt acaacttctg tgcccaggac   5820
gtgccctcgg cccagcagtg ggtggaccgg atccagagct gcctgtcgga cgcctgagcc   5880
tcccagccct gcccggctgc tctgcttccg gtcgttaccg accactaggg gtgggcaggg   5940
ccgcccggc catgtttaca gccccggccc tcgacagtat tgaggccccg agcccccagc   6000
acttgtgtgt acagcccccg tccccgcccc gccccgcccg gccggcccta acttatttg   6060
gcgtcacagc tgagcaccgt gccgggaggt ggccaaggta cagcccgcaa tgggcctgta   6120
aatagtccgg ccccgtcagc gtgtgctggt ccagccagcg gctgcaggcg agtttctaga   6180
accagagtct atataaagag agaactaacg ccacgctcct gtgcctgcct tccccactcc   6240
ccggctgcct gctctcggcc tacccagagg gtcccatctg cccctatcca ggcccacctg   6300
gcgggaggtt ggcatctttc tcgtgagcct cctcctggtgc ctgggtccac ccagctcggc   6360
ctgcatgtcc ctgggagtga cttttgctctg ggggcggatc gagcaggagg cttcactggg   6420
gacttgcttg attccctcca cgcctcaggg ctggtctagg ggccggcacg gctggagagg   6480
aagcccccat ccctacccag gggatgcaga agctgacctc acagaggctt gggggtgaaa   6540
gggtgggtgg tcatttgacc ccagaaggct gttgcaggtc cagaggacac ttgaggtgga   6600
cgtcagtttc tggctagacc cgagctgaag ggatggaggc cggaggcggg gggggggggg   6660
ggacagtggg ctcccagggg aatgcaggtt gaccacatct ggctcctgcc aggcaacgag   6720
cagcatctgg cagagtaagg ggccaacgcc catgggggat ggaccctctc agttcttggg   6780
aattctgccc caaaagtcct ttccctgggg tctcagaggg cccccgtcct tcccttcttg   6840
gtgtcactgt ggcccctcac tgctcttttc ctattcaaac ctgagtccca ccaggcccag   6900
ggcttcacct gctgagctgt tgtgtccttg cctgtgacga ggcctggcca ggggtgcagg   6960
agcagaaggt ggggagggtt atagacgctg caaaggccaa gagaacatct gagagtggca   7020
gctggtgacc tggccagagg ggctggtgag gggcagagaa cctggctaga ggctgggtcc   7080
ctcaggtggt cctctcaggt gggaggcgag cagcaggtgt gggtgagggg aaggttctga   7140
tgacagctgc agaggcaggg cccagtgctg gcaggtgggg ggccaagacc ctcccctggt   7200
gggacgttga agccaaggat ggccttggac cctgtcaggc ccagcatggt cccgccacct   7260
```

-continued

```
ccccacccc acaggtggtg ttgggacacc tgggcgagat gtgagggtgg gctcacttga      7320
gccactgaaa ccagccaggt cttccctcag gccggacaga tggcgcctga ccgaagttcc      7380
tggcacctgg aaaacccaca ggtcagagta aggggagaaa ggaccctgcc ctccctgttc      7440
cacgtctgtg gggggagagg acaaatgcca ggcacaggt aggcggcgag aacaaggcac       7500
tcaatgtgta gctggggcag agactcggcc tctggggagc tgagcgggtt ccctccaccc      7560
ccaaccgtgt tggaaagaca agctcgctgg ggcggggtgg gggtctggtc tccacctgcc      7620
cctcccactc agccactgag gacaaggtgg ggcccaggct tctgggaggg ggagctggca      7680
caaaaggaag tcctgggggtt gatgtgtttg agcgttaggc gaagtggttc cccccatccc      7740
ccaaacggaa aaatgtcagt atttgctaag ctgtagagac ctgatgccgt gatgtggcct      7800
gttccgcctc cacccattac acggggataa cgctgggggg tggcgggccc acaaaagagg      7860
tgctggagga gactctccca cccctggccg ggccggggct ttggggccgg aaggttcaca      7920
gtacgcggtt tgtccgaacg tcacggcttt tattgggagt tgggggtttg gggtgccctg      7980
tcaggtgatc agaacattaa aaatggactc aacgtaaaaa aaaaaaaaaa aaa            8033
```

<210> SEQ ID NO 666
<211> LENGTH: 6133
<212> TYPE: DNA
<213> ORGANISM: Homo sapiens

<400> SEQUENCE: 666

```
gccgtcaggg ccccagggag cgcggggcgc cgctgctgct gttcttcggc tcggttctgt        60
ctaccgggca gcgccggggc cggcggctgc ggcggcagag gaacaggagc cgggagccgc       120
gttccgccga gagttgggca gaggagcgcc cgcgccccgg cggcgtcatg ggccccctcc       180
ccgcgcttca gagggcacca gccgcgggaa ccccgggcc tcctcgcgcc cgagcctgag        240
cgaccctcgg gttctccggc gcccctccc tcgccctatt ttttttccta ctctcgctgc        300
cgttaccgct tctgctctcc gttatggcaa cagagccacc atccccctc cgggtcgagg        360 cgccgggccc cccagaaatg cggacctcac cggcgatcga gtccacccct gagggcaccc       420
cgcagccggc gggcggcaga ctccgcttcc tcaacggctg cgtgccctc tcgcatcagg        480 tggccgggca catgtacggg aaggacaaag tgggtatact gcaacatcca gatggcacag       540
ttttgaaaca gttacaacca cctccaaggg cccaagaga gctggaattc tataatatgg       600
tttatgctgc tgactgtttt gatggtgttc ttctagagct acgaaaatat ttgccaaaat       660 attatgcat ctggtcacct cccactgcac caaacgattt taacctaaaa ctggaagatg       720
tgacccataa atttaataag ccctgtataa tggatgtaaa gatagggcaa aaaagctatg      780
atccttttgc ctcatctgag aagattcagc aacaggtcag caagtaccca ttaatggaag      840
agattgggtt cttggtgctt ggcatgaggg tttatcatgt tcattccgat agctatgaga      900
cagaaaacca gcattacgga agaagcttaa caaaagaaac tataaaggat ggagtctcca      960
gatttttcca taatgggtac tgcttaagaa aagatgctgt tgctgccagt attcagaaga     1020
ttgagaaaat tctgcagtgg tttgaaaacc agaagcagct taatttttac gcaagttcat     1080
tactctttgt ttatgaaggt tcatctcagc caaccactac aaaattgaat gacagaactt     1140
tggcagaaaa gtttttgtcc aaaggacaac tgtcagacac agaagtacta gagtacaata     1200 ataacttca tgtgttaagt tccacagcta atggaaaaat agagtcttca gtgggcaaaa      1260
gcttgtccaa gatgtatgcg cgtcacagga aaatatatac aaaaaagcat cacagtcaga     1320
```

```
cttcattgaa agttgaaaat ctggagcaag acaatgggtg gaaaagcatg tcacaggaac   1380
atttaaatgg aaatgtactt tcccaactgg aaaaagtttt ctaccatctt cccactggtt   1440
gccaagagat tgctgaagta gaagtgcgaa tgatagattt tgctcatgtg ttccctagca   1500
acacaataga tgagggatat gtttatgggc taaagcattt aatttctgta cttcgaagta   1560
ttttagacaa ttgaatcctc tgttgcagtc ttttttaaggg gtgggccaat cataatgaag   1620
agggcagtc aatatctgca cctttaatgc tatgtaaaaa atttgtatta tgagtcgaca   1680
ttttatttgt ctttatactt ttggaagaat ggttaacttt tttataatct tactcaggaa   1740
aactaactat ttgttcatta gaaaactatg aagaataaag aaacttagga atgttaagca   1800
gggaatgtgg tggtacatgg cttaaacatc ttttttggct caagcaaaat gcaaaccatt   1860
attcagtcat taagagttta gttagctttc tgtagccaat tcatgaaatc tctgtccacc   1920
cagccttgac aatgagccat atctaaaata ttacattatt agaacaccta ccaaaatctc   1980
gaaagcacag gttgatgtcc ttagtattgc tatgtatgaa gttactaaaa ctggagaaaa   2040
ttctacttca gaaataagta ctgtttaggt tttatattaa aagttcagac cagcatatca   2100
aagggtgctc cttagtgaaa tgatttagaa ttgttgcatt ccaaaagcag gttttctctt   2160
taatttttac atctctctct caaaatatta tacttcatga aaaagacaat tgatgtggat   2220
gacaacaaca aagtcttgaa attaagggca cactaattgt ccttactggg gttaggggaa   2280
gagagatatt attttcaagg aacaaaatat tttcctttac aatctttcat tcatgagaaa   2340
attggaatat aaatttatta cattgtgaaa gtatcataaa ccatatacct ttgtatctaa   2400
atgcagcttc aaaaaagtaa ataattgaag ttttatttct cctctaaata acttgaattt   2460
ttttctttaa aaatttatgt atttatatgt ccccatttag ttaagtggta gtgtaaatgt   2520
atgttgttaa aaacagtttc tcagaattat agtaagcaat gaaagacaat atctaattag   2580
gttgttatca aaaatactgt gtgtaaatta gtccgtaata tagggtttgg tgcgtatcta   2640
tattcatgct tctatttcac tcttcctcaa aacagtttta tattatgttg accagtgaaa   2700
ttgtaactta atttcatggg gacaggggca gtgctacagt tcctggaaaa attagatttg   2760
tattatcttt gtttccacacc caccaccttta aaaaaaaatc aactagttat ttgtcattta   2820
aaacatttaa aactttgagt cttcaaatac atttgatgtt aatgctgcca ttacttgcac   2880
ttccattcac taataacatt tctaggtagt tatcagtttt gtcatattcc tggaaaatat   2940
tttggggttg taaattcttt ctcctctttt tcttctggag ttacaaattg aattttttaaa   3000
tccgagcacc tttattgtgg tgtggagaaa attatcacaa ttttatgttt attttacctt   3060
ctcagccttc tctgagggca ctttgcaaat acctgagtcc aaacagaagt accaactaaa   3120
tgctctatga actctatcct tagtaaatct attaaacctg aataatttaa aagatcatgt   3180
tcattttgta atagcaaaat ttgattttaa ttttttattt agaattggtg tatttatcat   3240
agggacttcc aattttttctt cacttttgga atggatattg gctatagttt tatgttttaa   3300
cgggaatgaa tttcaagtca taataatcag aatttttagt tttactttt ttcttttacaa   3360
tatggatttt gttgttattt ggatagtggt tcaataaatc ttaagctcag ataattaaac   3420
actatttga atcttaacaa gatactgagg ctttttttgt atgggatgat atcaacctat   3480
gtacaatgaa tttaataaac ttaagtattg tcagattttt tgcacatttt agctcaataa   3540
aatcttaatg ttcaagattt ttttatctgc atttggaaat acaatttgt aaaatcaatg   3600
tcttaccttt tgatacaat agatcatgtt ttgttttaa taaagcaaga agcccttta   3660
tctgttgttt ttcagggaag ggattaacat ttaattctgt ttgtttacat ttgttatcat   3720
```

```
tgttatccaa tgctcatttt atgttgcttt ataagtaggc ttaggtataa cagaataagt    3780
atctgtttat ctaatctaca tgtgactatc ttagtctctc tcggtcactt aatattatgc    3840
tgaaatttac cactgtgggg atgaatgatc gctattcacc aagtatattt gaacatgtaa    3900
atgcttaaga aataagcata atgcggatat agtttgggtt aataggattc tcatagtttt    3960
ttttccccta tgaaacataa gtaatgattt tagtgtattt cttatggaat acactcattt    4020
aaaaaggact ttaagaaatt gtggatgtga ataatacctt tctctaataa aaatttaaat    4080
tgtataatag ttttataata tttacattaa ttgatatttt aatatggata gacattgcat    4140
agattcaaat aaattaaaat caatgataaa tgctaaatat tttatctaaa tagttttttca   4200 agaaacagtt atggaaatgt gtatattaaa tggctctaat gtggagcttg tggtatttca    4260
actcagtatt cattattagt tgtgtgtctg gaaagattgt acttactttt cctctttaca    4320
ctacagtttg ctcttatggg gctctaaact gtttaactga agaaccttcg tctgtatttt    4380
gattgagcat aatttagtat tttatgattt ccaagatgat gttcttatgt ctatcaagtc    4440
tatgtatcaa atttataaca tcatttaaga aaaaggaatt tccacagata cttcagttgc    4500 aatttttttgt ttcatgctac tgaaaataca tttgtttcta ggggttggaa tattatagaa    4560
gatgtaggat gaaagaaaac gatagaacaa cgaaagaatt ctgtttatga aattacagga    4620
attgtgtcca ctatggtaaa gcattgtcat tttagtacat tttctcttag tagtttggca    4680
ttttatactt taaaacttgt tttgctttaa aaattgttta taatgcttac cttctttctc    4740
cagtgccttt agtcttgatt tgatatgttt gtaccctcag ttacccttttc tattacatgt    4800 ttttgatgtt ttcatagcct aggaaacatc gattccttttt taataattgt caatctgatt    4860
atttaaagag gtaacaatta tctgttaatg ctttggaaaa acaagtaggg ttgcctttgg    4920
aggccaggct tcttagttca ttcaaaaata ttccttggat ttatgccatg tattaagcat    4980
ttttagcccc cagtattaca actgtgaacc aaacggataa ggccctaacc attttcagca    5040
ttctctttgg atggggtggg attggggact taattaaaat agagatatag aaaaataggc    5100
atctaaataa gataataagt gtggggttga aatgaagcat ctaacaatag ttgaagttag    5160
aagtaatatt ttacagtatt gtaacctcta tttaagtttg ggtattagtt acagatagca    5220
taaaaaagcc ttaattttc actttccttg ctggcaaagg tacatttatt tagactgtcc    5280
atttaaagta atgtttaaca taaacattac tgtgaaaaac attccattac atattcccaa    5340
gcaaatgagc tgcatcttct ttactgtatt ttacaattta gtacaacagt tttaggcctc    5400
aatcttaaca tcactggtat tttaaatttg gcaatgaata tgaaattact tttgacttac    5460
agattgatta tattattact ttgaaaatgc attaatttct tagaaaagtt tggagcctct    5520 atctttttt gagttaatac ttaaattctc attacttata ttaatagcct gtactaagtg    5580
aaaatattat ttatgcaagt aaacaagtca ctataggctt ttaagacttt tctttaattt    5640
tagattttgt catcaaagtt taaattttt acctactgtc cacttaaata taatttaaca    5700
gtttgtaaag tgaaatagtt ttaagtatga tgtatgatgc acctgcatat aaatgaaaat    5760
ggcgtgcaca aagacacttt actatgggaa ctgtactgga agatttatga aagcatgtga    5820
aattgcacct aaaattgtgt tattagtgac tataagcagc aatgctaaat ttattgtact    5880
tgatgaatga atgtatttag tcacagttac tttggtttaa atgtataaat gtctttaggg    5940 tttttttttta aatgtgtttg taatttgtac tattgtgggg gtatacttgg actgcagggg    6000
ttattgtcaa tgtgtgattt gtgttttttat tttatagaat catctaatgt gatataccaa    6060
``` ttttttataag tgatatttac ataattctaa taactgtata tttgacaacc tattaaaatg    6120
ttttgcattg gaa    6133

<210> SEQ ID NO 667
<211> LENGTH: 6650
<212> TYPE: DNA
<213> ORGANISM: Homo sapiens

<400> SEQUENCE: 667
gctggttccc cttccgagcg tccgcgcccc gcatgcgcag tctgccccgg cggtctccgt    60
ttgtttgaac aggaaggcgg acatattagt ccctctcagc cccctcgcc ccaccccca    120 ggcattcgcc gccgcgactc gccctttccc cggctgggac cgcagcccct cccagaagct    180
cccccatcag cagccgccgg gacccaacta tcgtcttcct cttcgcccgc tctccagcct    240
ttcctctgct aagtctccat cgggcatcga cctcgccctg cccaccgga caccgtagca    300 gcagccccag cagcgacggg acaaaatggg agagtgaggc tgtcctgcgt ggaccagctc    360
gtggccgaga ctgatcggtg cgtcgggccg ggccgagtag agccgggac gcggggctag    420 accgtctaca gcgcctctga gcggagcggg cccggcccgt ggcccgagcg gcggccgcag    480
ctggcacagc tcctcacccg ccctttgctt tcgccttttcc tcttctccct cccttgttgc    540
ccggagggag tctccaccct gcttctcttt ctctacccgc tcctgcccat ctcgggacgg    600
ggacccctcc atggcgacgg cggccggggc ccgctagact gaagcacctc gccggagcga    660
cgaggctggt ggcgacggcg ctgtcggctg tcgtgagggg ctgccggtg ggatgcgact    720 tgggcgtcc gagcggctgt gggtcgctgt tgccccccggc ccggggtctg gagagcggag    780
gtcccctcag tgaggggaag acgggggaac cgggcgcacc tggtgaccct gaggttccgg    840
ctcctccgcc ccgcggctgc gaacccaccg cggaggaagt tggttgaaat tgctttccgc    900
tgctggtgct ggtaagaggg cattgtcaca gcagcagcaa catgtcgact ggggacagtt    960
ttgagactcg atttgaaaaa atggacaacc tgctgcggga tcccaaatcg aagtgaatt    1020 cggattgttt gctggatgga ttggatgctt tggtatatga tttggatttt cctgccttaa    1080
gaaaaaacaa aaatattgac aacttttaa gcagatataa agacacaata ataaaaatca    1140
gagatttacg aatgaaagct gaagattatg aagtagtgaa ggtgattggt agaggtgcat    1200
ttggagaagt tcaattggta aggcataaat ccaccaggaa ggtatatgct atgaagcttc    1260
tcagcaaatt tgaaatgata aagagatctg attctgcttt tttctgggaa gaaagggaca    1320
tcatggcttt tgccaacagt ccttgggttg ttcagctttt ttatgcattc caagatgatc    1380
gttatctcta catggtgatg gaatacatgc ctggtggaga tcttgtaaac ttaatgagca    1440
actatgatgt gcctgaaaaa tgggcacgat tctatactgc agaagtagtt cttgcattgg    1500
atgcaatcca ttccatgggt tttattcaca gagatgtgaa gcctgataac atgctgctgg    1560
ataaatctgg acatttgaag ttagcagatt ttggtacttg tatgaagatg aataaggaag    1620
gcatggtacg atgtgataca gcggttggaa cacctgatta tatttcccct gaagtattaa    1680
aatcccaagg tggtgatggt tattatggaa gagaatgtga ctggtggtcg gttggggtat    1740
ttttatacga aatgcttgta ggtgatacac cttttatgc agattctttg gttggaactt    1800
acagtaaaat tatgaaccat aaaaattcac ttacctttcc tgatgataat gacatatcaa    1860
aagaagcaaa aaaccttatt tgtgccttcc ttactgacag ggaagtgagg ttagggcgaa    1920
atggtgtaga agaaatcaaa cgacatctct tcttcaaaaa tgaccagtgg gcttgggaaa    1980
cgctccgaga cactgtagca ccagttgtac ccgatttaag tagtgacatt gatactagta    2040

```
attttgatga cttggaagaa gataaaggag aggaagaaac attccctatt cctaaagctt    2100
tcgttggcaa tcaactacct tttgtaggat ttacatatta tagcaatcgt agatacttat    2160
cttcagcaaa tcctaatgat aacagaacta gctccaatgc agataaaagc ttgcaggaaa    2220
gtttgcaaaa aacaatctat aagctggaag aacagctgca taatgaaatg cagttaaaag    2280
atgaaatgga gcagaagtgc agaacctcaa acataaaact agacaagata atgaagaat     2340
tggatgaaga gggaaatcaa agaagaaatc tagaatctac agtgtctcag attgagaagg    2400
agaaaatgtt gctacagcat agaattaatg agtaccaaag aaaagctgaa caggaaaatg    2460
agaagagaag aaatgtagaa aatgaagttt ctacattaaa ggatcagttg gaagacttaa    2520
agaaagtcag tcagaattca cagcttgcta atgagaagct gtcccagtta caaaagcagc    2580
tagaagaagc caatgactta cttaggacag aatcggacac agctgtaaga ttgaggaaga    2640
gtcacacaga gatgagcaag tcaattagtc agttagagtc cctgaacaga gagttgcaag    2700
agagaaatcg aattttagag aattctaagt cacaaacaga caaagattat taccagctgc    2760
aagctatatt agaagctgaa cgaagagaca gaggtcatga ttctgagatg attggagacc    2820
ttcaagctcg aattacatct ttacaagagg aggtgaagca tctcaaacat aatctcgaaa    2880
aagtggaagg agaaagaaaa gaggctcaag acatgcttaa tcactcagaa aaggaaaaga    2940
ataatttaga gatagattta aactacaaac ttaaatcatt acaacaacgg ttagaacaag    3000
aggtaaatga acacaaagta accaaagctc gtttaactga caaacatcaa tctattgaag    3060
aggcaaagtc tgtggcaatg tgtgagatgg aaaaaaagct gaaagaagaa agagaagctc    3120
gagagaaggc tgaaaatcgg gttgttcaga ttgagaaaca gtgttccatg ctagacgttg    3180
atctgaagca atctcagcag aaactagaac atttgactgg aaataaagaa aggatggagg    3240
atgaagttaa gaatctaacc ctgcaactgg agcaggaatc aaataagcgg ctgttgttac    3300
aaaatgaatt gaagactcaa gcatttgagg cagacaattt aaaaggttta gaaaagcaga    3360
tgaaacagga aataaatact ttattggaag caaagagatt attagaattt gagttagctc    3420
agcttacgaa acagtataga ggaaatgaag gacagatgcg ggagctacaa gatcagcttg    3480
aagctgagca atatttctcg acactttata aaacccaggt aaaggaactt aaagaagaaa    3540
ttgaagaaaa aaacagagaa aatttaaaga aaatacagga actacaaaat gaaaagaaa    3600
ctcttgctac tcagttggat ctagcagaaa caaaagctga gtctgagcag ttggcgcgag    3660
gccttctgga agaacagtat tttgaattga cgcaagaaag caagaaagct gcttcaagaa    3720
atagacaaga gattacagat aaagatcaca ctgttagtcg gcttgaagaa gcaaacagca    3780
tgctaaccaa agatattgaa atattaagaa gagagaatga agagctaaca gagaaaatga    3840
agaaggcaga ggaagaatat aaactggaga aggaggagga gatcagtaat cttaaggctg    3900
cctttgaaaa gaatatcaac actgaacgaa cccttaaaac acaggctgtt aacaaattgg    3960
cagaataat gaatcgaaaa gatttaaaa ttgatagaaa gaaagctaat acacaagatt     4020
tgagaaagaa agaaaaggaa aatcgaaagc tgcaactgga actcaaccaa gaaagagaga    4080
aattcaacca gatggtagtg aaacatcaga aggaactgaa tgacatgcaa gcgcaattgg    4140
tagaagaatg tgcacatagg aatgagcttc agatgcagtt ggccagcaaa gagagtgata    4200
ttgagcaatt gcgtgctaaa cttttggacc tctcggattc tacaagtgtt gctagttttc    4260
ctagtgctga tgaaactgat ggtaacctcc cagagtcaag aattgaaggt tggctttcag    4320
taccaaatag aggaaatatc aaacgatatg gctggaagaa acagtatgtt gtggtaagca    4380
```

```
gcaaaaaaat tttgttctat aatgacgaac aagataagga gcaatccaat ccatctatgg    4440
tattggacat agataaactg tttcacgtta gacctgtaac ccaaggagat gtgtatagag    4500
ctgaaactga agaaattcct aaaatattcc agatactata tgcaaatgaa ggtgaatgta    4560
gaaaagatgt agagatggaa ccagtacaac aagctgaaaa aactaatttc caaaatcaca    4620
aaggccatga gtttattcct acactctacc actttcctgc caattgtgat gcctgtgcca    4680
aacctctctg gcatgttttt aagccacccc ctgccctaga gtgtcgaaga tgccatgtta    4740
agtgccacag agatcactta gataagaaag aggacttaat ttgtccatgt aaagtaagtt    4800
atgatgtaac atcagcaaga gatatgctgc tgttagcatg ttctcaggat gaacaaaaaa    4860
aatgggtaac tcatttagta aagaaaatcc ctaagaatcc accatctggt tttgttcgtg    4920
cttcccctcg aacgctttct acaagatcca ctgcaaatca gtctttccgg aaagtggtca    4980
aaaatacatc tggaaaaact agttaaccat gtgactgagt gccctgtgga atcgtgtggg    5040
atgctacctg ataaaccagg cttctttaac catgcagagc agacaggctg tttctttgac    5100
acaaatatca caggcttcag ggttaagatt gctgtttttc tgtccttgct ttggcacaac    5160
acactgaggg tttttttttat tgcgggtttg cctacaggta gattagatta attattacta    5220
tgtaatgcaa gtacagttgg gggaaagctt aggtagatat atttttttta aaaggtgctg    5280
cctttttgga tttataagaa aatgcctgtc agtcgtgata gaacagagtt ttcctcatat    5340
gagtaagagg aagggacttt cactttcaag tggaacagcc atcactatca agatcagctc    5400
atggaaggag taaagaaaat atctcaaaat gagacaaact gaagttttgt ttttttttta    5460
atgacttaag ttttttgtgct cttgcaagac tatacaaaac tattttaaga aagcagtgat    5520
atcacttgaa cttcagtgcc ctcactgtag aatttaaaag ccttactgtt gattgcccat    5580
gttggacttg atgagaaat taaatatctt tcattatgct ttacaaaata ctgtatatgt    5640
ttcagcaagt ttggggaatg ggagaggaca aaaaaaagtt acatttaatc tatgcatttt    5700
tgccaagcca tattgagtta ttttactact agagacatta ggaaactaac tgtacaaaag    5760
aaccaagttt aaaagcattt tgtggggtac atcatttcta aattgtata atgtatttct     5820
ttgtggtttt aaatgataaa gacattaagt taacaaacat ataagaaatg tatgcactgt    5880
ttgaaatgta aattattctt agaacacttt caatgggggt tgcattgtcc ttttagtgcc    5940
ttaatttgag ataattattt tactgccatg agtaagtata gaaatttcaa aaaatgtatt    6000
ttcaaaaaat tatgtgtgtc agtgagtttt tcattgataa ttggtttaat ttaaaatatt    6060
tagaggtttg ttggactttc ataaattgag tacaatcttt gcatcaaact acctgctaca    6120
ataatgactt tataaaactg caaaaaatgt agaaggttgc accaacataa aaggaaata    6180
tggcaataca tccatgatgt tttccagtta acataggaat taccagataa atactgttaa    6240
actcttgtcc agtaacaaga gttgattcat atggacagta tgatttattg tttattttt    6300
taaccaaata cctcctcagt aatttataat ggctttgcag taatgtgtat cagataagaa    6360
gcactggaaa accgatcgtc tctaggatga tatgcatgtt tcaagtggta ttgaaagccg    6420
cactgatgga tatgtaataa taaacatatc tgttattaat atactaatga ctctgtgctc    6480
atttaatgag aaataaaagt aatttatgga tgggtatctt taattttttac tgcaatgtgt    6540
tttctcatgg ctgaaatgaa tggaaaacat acttcaaatt agtctctgat tgtatataaa    6600
tgtttgtgaa attccatggt tagattaaag tgtattttta aaagataaaa                 6650
```

<210> SEQ ID NO 668
<211> LENGTH: 5324

<212> TYPE: DNA
<213> ORGANISM: Homo sapiens

<400> SEQUENCE: 668

```
gaacggcgat gccccagacg cggctgcagt tttcaaaccg cgactgcaag cttcggtagt    60
cctctccgct gctgtcgcca ggagtcactt cacgagaagc caggtcacaa ccgtcggccc   120
ttgtctggaa aagtaaaagt ggatcctgcc acgttcggag ctccctggcg cctcgcccgg   180
ctggagctag agaactcgtc ctgtggcggc cccggcgtg gggcgggaca gcggcccct    240
ggaggggca gtcccgggag aacctgcggc ggccggagcg gtaaaaataa gtgactaaag   300
aagcagacct gggaatcacc taacatgtcg aggaggagat tgattgccg aagtatttca    360
ggcctactaa ctacaactcc tcaaattcca ataaaaatgg aaaactttaa taatttctat   420
atacttacat ctaaagagct agggagagga aaatttgctg tggttagaca atgtatatca   480
aaatctactg gccaagaata tgctgcaaaa tttctaaaaa agagaagaag aggacaggat   540
tgtcgagcag aaattttaca cgagattgct gtgcttgaat tggcaaagtc ttgtccccgt   600
gttattaatc ttcatgaggt ctatgaaaat acaagtgaaa tcattttgat attggaatat   660
gctgcaggtg gagaaatttt cagcctgtgt ttacctgagt tggctgaaat ggtttctgaa   720
aatgatgtta tcagactcat taaacaaata cttgaaggag tttattatct acatcagaat   780
aacattgtac accttgattt aaagccacag aatatattac tgagcagcat ataccctctc   840
ggggacatta aaatagtaga ttttggaatg tctcgaaaaa tagggcatgc gtgtgaactt   900
cgggaaatca tgggaacacc agaatattta gctccagaaa tcctgaacta tgatcccatt   960
accacagcaa cagatatgtg gaatattggt ataatagcat atatgttgtt aactcacaca  1020
tcaccatttg tgggagaaga taatcaagaa acatacctca atatttctca agttaatgta  1080
gattattcgg aagaaacttt ttcatcagtt tcacagctgg ccacagactt tattcagagc  1140
cttttagtaa aaaatccaga gaaaagacca acagcagaga tatgcctttc tcattcttgg  1200
ctacagcagt gggactttga aaacttgttt caccctgaag aaacttccag ttcctctcaa  1260
actcaggatc attctgtaag gtcctctgaa gacaagactt ctaaatcctc ctgtaatgga  1320
acctgtggtg atagagaaga caaagagaat atcccagagg atagcagcat ggtttccaaa  1380
agatttcgtt tcgatgactc attacccaat ccccatgaac ttgtttcaga tttgctctgt  1440
tagcactttt ttctttgact catttggact gaatttgaaa ttttatatcc actccagtga  1500
gattatgatt tgtagcttca tatatgacat gtttatattg taaatgcact tttccatgga  1560
ataatttagg gaagtgtttt aatgttaaat tactagttgc tagcatgtta tgatttcata  1620
tcctgagata gctctgcaga taagaaaata tttaaatata tgacaaaaag taaaattgta  1680
catgtgagtt tacatgttaa tgaaataatt caacttcaaa tgaacttacc agaatgtttt  1740
gcatatcaac aaaaaagtg gcttgagttt tattatagtt ggtgtaaact gaacacagtg  1800
aagacattgg aatttaatag gttctctctc taaggtgact cttataccat gcctctatca  1860
acataatttg tttaggaaag cagtatgaag tttaagccaa aataatttct actttataga  1920
tgctcaagag acatttttaca attgaaaatg tctttcaatt acaaatattt tgaaacttcg  1980
taagattttc attctctgtg gtctgttata tgagagagat cctttaacta gagcaaagag  2040
ggagttagaa acctgatcag ggatattctt tacaagttgg agcagaggaa agagtagcat  2100
gccttcgtat tttaacgcaa atgtcttttt cctcctccca acctacttga gatctgataa  2160
ggtctggaag atggagatat ttggtatgca agtgtagagt tttttaatcc tccagaattt  2220
```

```
ctagagtaga agatacttag gtatagttaa atattctgta ttttagtca aacatattta    2280
ttaattgaat atagaagaaa atgttgacac actcagacag cttactgaat tttagatgtc    2340
ttctgcatct tagaatacaa gccagtcatt cagagttcta aaagtatgca taaaaaatta    2400
cagcaccggt aggtctatta acacagtgcc cgagtcagcg gtagcaagac tgatgtgatc    2460
ataaaacatg acatcaggct cgtctgaagt tcttgtgtga aattcctagt gagtgaggag    2520
gctcagctta aagccatctg cagagtggcc cctcattgtg gtcttttgct gggaccaatg    2580
caagagacta gggagagcaa atgtttgct tatggctaga gactatatcc agccctaatg     2640
atggggaaag ttagtccttt tcgggtaatc ttttatgaat tttcacctga tgaccgttat    2700
attggtctgt tatcatgtta cgataactgt gatctcatga ccatgttgct gtatcagaag    2760
aaatagtttg acaaatggta acaacaacct gatgttcccc ctttagacct taacttctc     2820
aaaattttgg taagtttcca aattctttaa taataactta aaacttttg aataactatc     2880
aggtcacttt atttgaccac atggtgaatt cctttaatgt cttcagcatt tgttaaggaa    2940
aagttttctc tacttgtgtg tgtatgtgtg cacatgtgtg tatgtacagg tgtatgtata    3000
tatctataga tagatacaat acattcttta gacacttttc aagattcttt gctgtggtat    3060
attgtgctca actcaggtgc caaaggagct tttttttttt ttttttttt ttgagatgga     3120
gttttgctct gtctctcagg ctggagtgca gtggcatgat ctcagctcac ggcaacctct    3180
gcctcccggg ttcaagcaat tctcctgtct cagcctcctg agtagttggg attacaggcg    3240
catgccaccg tgcccagcta attttgtat ttttagtaga gacggggttt caccatgttg     3300
gccaggctgt tcacaaactc ctgacttcaa gtgatccacc cgcctcggcc tcccaaagtg    3360
ctgggattac aggcgtgagc cactgcgccc ccgcccagga gctcttttct tatgacatat    3420
aaattatgac atttatattc tttatatgac tttatgttct cttcttatga catttaaatt    3480
ctttaagtag tttgttggtc caataaacta gacgttgtat aatctaaatt gagcccttgt    3540
atatctaaaa ctgatgagtt gtttctaaat tgttgattgt ccattacctt gcctttggta    3600
ttaagataat gcaagtaaag tttagtaagt cattggataa tgaaatgatt atgtttctga    3660
agaccatatt atatttttaa tttttagagg aatcatgcca tcccccaaaa aatcaagaaa    3720
tatttgaatt ttaaattata agttcatttg ttaaaagaca ttttacaaa tgtctgaaaa     3780
tcttaaaata cttacatct accttttaagt agtagaatac agagctgtaa atttccatgc    3840
cttttttcct gatattaagt tttatagtaa aaaagcaact agtgattgca caagaatat     3900
aaaaatccac tcttttttaca aaggtgtgaa tttaaataac gttattgatt ggaatatgaa    3960
aatagaccaa tcatttaaga gcttttagc aaatgattca attcttactc ttttctccc      4020
aagattgaaa agcataatgt atttctctaa gtaggaatc tagagagccc ctgtgagtgg     4080
acaaatgtca gtaacacttg aacacatgag aagataagtg ttatgttgtg ataattaaa     4140
gttaaatttg cttttgggt aggatcccta aatagatggg attttaaat agatgatata      4200
tagatgacaa ttgcaattgt cattttaatt attttcccta cagtaaagaa cctagctctg    4260
agcagtgaaa ttgtaatggc actttaaagg aagtaagccg ttaactgttc tctagtggag    4320
cgatctccaa ctgttttggc actagggacg ggttttgtgg aagaaaattt ttccacagga    4380
ctgggggttt aggggatgg tttcaggatg attcaagtac attacattta tcattagatt     4440
ctcataagga gcatgcaacc tagatctctt gcacgtgtgg ttcacagcag gattcgagct    4500
cctttgagaa tctaatgcca tggctgatct aacaggaaac tgagctcagg cagtaatgct    4560
tggcaccgcc ccccaccttc tatgcagccc ggtcgtggcc tggggactgg gaccccctgc    4620
```

```
tctagtcagt aataaggtac ttgtgccaga atataaatca acacattgct tcctttatca    4680
aagaagtctt gttatttaaa aaaagtcaac tgagccagta tgattagtga tgtaattgat    4740
tttcattctg gcacaagcct ctttcattct ggacagctca caaatagtta atggaccatg    4800
ctttgaatag ccttcctcta agcaacattt ataaatactg atattttaga actgtttaca    4860
tttcttctgt ttatttttga attttcagtt tgatatcttg tccttattca ttgttgtata    4920
aacaactgta ctttaatttc aagtagtatt aaaagtattt cacttcagtt tgggggggatt    4980 attatcaatt tataatttta taaaagtatt ttaaagaata attgtaaatt ttccataaat    5040
tacaacttcc tgccatattt tattaaataa taatcttgct taaggcatat agacagacat    5100
tattatgagt attccagtaa aaaaaatcta catcaacttg accattctgg ctaaaaatta    5160
aaaagcactt ttttatatct gtggttgtca tttgtttcaa agcatttcta aatttattgt    5220
tcttaaaagt atgtctgcat gttctagcct ttgacctagg tcatctatga accctctttg    5280
tgtctaataa acatatctgt aaaggcaaaa aaaaaaaaaa aaaa                     5324
```

<210> SEQ ID NO 669
<211> LENGTH: 5756
<212> TYPE: DNA
<213> ORGANISM: Homo sapiens

<400> SEQUENCE: 669

```
taggcaggcg gctgagccgg cggcgggtgg cctgcccaac gtgtgctggg tgggagaagg      60
cgaggcgtca gcgatgctgt ctcttccgtg aggagcgcag aggaggtcgc ggcgccggag     120
gccccagaag gctcgaaggc gccgcgggct ggggtcggtg gcttagggag cccgtccggc     180
catggtggcc gcgggtggtg gttggcgcgg ctgcgctgcg gcccggggca gtgcggagcc     240
gggacagtcg cggcgctgac gcccgcgggc cccagctgca gatatgaagc ggagccgctg     300
ccgcgaccga ccgcagccgc cgccgcccga ccgccgggag gatggagttc agcgggcagc     360
ggagctgtct cagtctttgc cgccgcgccg gcgagcgccg cccgggaggc agcggctgga     420
ggagcggacg ggccccgcgg ggcccgaggg caaggagcag gatgtagtaa ctggagttag     480 tccccctgctc ttcaggaaac tcagtaatcc tgacatattt tcatccactg gaaaagttaa     540
acttcagcga caactgagtc aggatgattg taagttatgg agaggaaacc tggccagctc     600
tctatcgggt aagcagctgc tccctttgtc cagcagtgta catagcagtg tgggacaggt     660
gacttggcag tcgtcaggag aagcatcaaa cctggttcga atgagaaacc agtcccttgg     720
acagtctgca ccttctctta ctgctggcct gaaggagttg agccttccaa gaagaggcag     780
cttttgtcgg acaagtaacc gcaagagctt gattgtgacc tctagcacat cacctacact     840
accacggcca cactccaccac tccatggcca cacaggtaac agtcctttgg acagcccccg     900
gaatttctct ccaaatgcac ctgctcactt ttcttttgtt cctgcccgta ggactgatgg     960
gcggcgctgt tctttggcct ctttgcccctc ttcaggatat ggaactaaca ctcctagctc    1020
cactgtctca tcatcatgct cctcacagga aaagctgcat cagttgcctt tccagcctac    1080
agctgatgag ctgcactttt tgacgaagca tttcagcaca gagagcgtac cagatgagga    1140
aggacggcag tccccagcca tgcggcctcg ctcccggagc ctcagtcccg gacgatcccc    1200
agtatccttt gacagtgaaa taataatgat gaatcatgtt tacaaagaaa gattcccaaa    1260
ggccaccgca caaatggaag agcgactagc agagtttatt tcctccaaca ctccagacag    1320
cgtgctgccc ttggcagatg gagccctgag ctttattcat catcaggtga ttgagatggc    1380
```

```
ccgagactgc ctggataaat ctcggagtgg cctcattaca tcacaatact tctacgaact   1440
tcaagataat ttgagaaaac ttttacaaga tgctcatgag cgctcagaga gctcagaagt   1500
ggcttttgtg atgcagctgg tgaaaaagct gatgattatc attgcccgcc cagcacgtct   1560
cctggaatgc ctggagtttg accctgaaga gttctaccac cttttagaag cagctgaggg   1620
ccacgccaaa gagggacaag ggattaaatg tgacattccc cgctacatcg ttagccagct   1680
gggcctcacc cgggatcccc tagaagaaat ggcccagttg agcagctgtg acagtcctga   1740
cactccagag acagatgatt ctattgaggg ccatgggca tctctgccat ctaaaaagac   1800
accctctgaa gaggacttcg agaccattaa gctcatcagc aatggcgcct atggggctgt   1860
atttctggtg cggcacaagt ccacccggca gcgctttgcc atgaagaaga tcaacaagca   1920
gaacctgatc ctacggaacc agatccagca ggccttcgtg gagcgtgaca tactgacttt   1980
cgctgagaac ccctttgtgg tcagcatgtt ctgctccttt gataccaagc gccacttgtg   2040
catggtgatg gagtacgttg aagggggaga ctgtgccact ctgctgaaga atattggggc   2100
cctgcctgtg gacatggtgc gtctatactt tgcggaaact gtgctggccc tggagtactt   2160
acacaactat ggcatcgtgc accgtgacct caagcctgac aacctcctaa ttacatccat   2220
ggggcacatc aagctcacgg actttggact gtccaaaatt ggcctcatga gtctgacaac   2280
gaacttgtat gagggtcata ttgaaaagga tgcccgggaa ttcctggaca gcaggtatg   2340 cgggaccca gaatacattg cgcctgaggt gatcctgcgc cagggctatg gaagccagt   2400 ggactggtgg gccatgggca ttatcctgta tgagttcctg gtgggctgcg tcccttttt   2460 tggagatact ccgagggagc tctttgggca ggtgatcagt gatgagattg tgtggcctga   2520
gggtgatgag gcactgcccc cagacgccca ggacctcacc tccaaactgc tccaccagaa   2580
ccctctggag agacttggca caggcagtgc ctatgaggtg aagcagcacc cattctttac   2640
tggtctggac tggacaggac ttctccgcca gaaggctgaa tttattcctc agttggagtc   2700
agaggatgat actagctatt ttgacacccg ctcagagcga taccaccaca tggactcgga   2760
ggatgaggaa gaagtgagtg aggatggctg ccttgagatc cgccagttct cttcctgctc   2820
tccaaggttc aacaaggtgt acagcagcat ggagcggctc tcactgctcg aggagcgccg   2880
gacaccaccc ccgaccaagc gcagcctgag tgaggagaag gaggaccatt cagatggcct   2940
ggcagggctc aaaggccgag accggagctg ggtgattggc tcccctgaga tattacggaa   3000
gcggctgtcg gtgtctgagt catcccacac agagagtgac tcaagccctc caatgacagt   3060
gcgacgccgc tgctcaggcc tcctggatgc gcctcggttc ccggagggcc ctgaggaggc   3120
cagcagcacc ctcaggaggc aaccacagga gggtatatgg gtcctgacac ccccatctgg   3180 agaggggta tctgggcctg tcactgaaca ctcaggggag cagcggccaa agctggatga   3240
ggaagctgtt ggccggagca gtggttccag tccagctatg gagacccgag gccgtgggac   3300
ctcacagctg gctgagggag ccacagccaa ggccatcagt gacctggctg tgcgtagggc   3360
ccgccaccgg ctgctctctg ggactcaac agagaagcgc actgctcgcc ctgtcaacaa   3420
agtgatcaag tccgcctcag ccacagccct ctcactcctc attccttcgg aacaccacac   3480
ctgctccccg ttggccagcc ccatgtcccc acattctcag tcgtccaacc catcatcccg   3540
ggactcttct ccaagcaggg acttcttgcc agcccttggc agcatgaggc ctcccatcat   3600
catccaccga gctggcaaga agtatggctt caccctgcgg gccattcgcg tctacatggg   3660
tgactccgat gtctacaccg tgcaccatat ggtgtggcac gtggaggatg gaggtccggc   3720
cagtgaggca gggcttcgtc aaggtgacct catcacccat gtcaatgggg aacctgtgca   3780
```

```
tggcctggtg cacacggagg tggtagagct gatcctgaag agtggaaaca aggtggccat    3840
ttcaacaact cccctggaga acacatccat taaagtgggg ccagctcgga agggcagcta    3900
caaggccaag atggcccgaa ggagcaagag gagccgcggc aaggatgggc aagaaagcag    3960
aaaaaggagc tccctgttcc gcaagatcac caagcaagca tccctgctcc acaccagccg    4020
cagcctttct tcccttaacc gctccttgtc atcagggag agtgggccag gctctcccac    4080
acacagccac agcctttccc cccgatctcc cactcaaggc taccgggtga ccccgatgc     4140 tgtgcattca gtgggaggga attcatcaca gagcagctcc cccagctcca gcgtgcccag    4200
ttccccagcc ggctctgggc acacggccc cagctccctc cacggtctgg cacccaagct    4260
ccaacgccag taccgctctc cacggcgcaa gtcagcaggc agcatcccac tgtcaccact    4320
ggcccacacc ccttctcccc caccccccaac agcttcacct cagcggtccc catcgccct     4380 gtctggccat gtagcccagg ccttccccac aaagcttcac ttgtcacctc ccctgggcag    4440
gcaactctca cggcccaaga gtgcggagcc accccgttca ccactactca agagggtgca    4500
gtcggctgag aaactggcag cagcacttgc cgcctctgag aagaagctag ccacttctcg    4560
caagcacagc cttgacctgc cccactctga actaaagaag gaactgccgc caggggaagt    4620
gagccctctg gaggtagttg gagccaggag tgtgctgtct ggcaaggggg ccctgccagg    4680
gaagggggtc ctgcagcctg ctccctcacg ggcctaggc accctccggc aggaccgagc     4740
cgaacgacgg gagtcgctgc agaagcaaga agccattcgt gaggtggact cctcagagga    4800
cgacaccgag gaagggcctg agaacagcca gggtgcacag gagctgagct tggcacctca    4860
cccagaagtg agccagagtg tggcccctaa aggagcagga gagagtgggg aagaggatcc    4920
tttcccgtcc agagaccta ggagcctggg cccaatggtc ccaagcctat tgacagggat     4980
cacactgggg cctcccagaa tggaaagtcc cagtggtccc cacaggaggc tcgggagccc    5040
acaagccatt gaggaggctg ccagctcctc ctcagcaggc cccaacctag gtcagtctgg    5100
agccacagac cccatccctc ctgaaggttg ctggaaggcc cagcacctcc acacccaggc    5160
actaacagca ctttctccca gcacttcggg actcacccc accagcagtt gctctcctcc    5220
cagctccacc tctgggaagc tgagcatgtg gtcctggaaa tcccttattg agggcccaga    5280
cagggcatcc ccaagcagaa aggcaaccat ggcaggtggg ctagccaacc tccaggattt    5340 ggaaacaca actccagccc agcctaagaa cctgtctccc agggagcagg ggaagacaca     5400
gccacctagt gccccagac tggcccatcc atcttatgag gatcccagcc agggctggct    5460
atgggagtct gagtgtgcac aagcagtgaa agaggatcca gccctgagca tcacccaagt    5520
gcctgatgcc tcaggtgaca gaaggcagga cgttccatgc cgaggctgcc ccctcaccca    5580
gaagtctgag cccagcctca ggaggggcca agaaccaggg ggccatcaaa agcatcggga    5640
tttggcattg gttccagatg agcttttaaa gcaaacatag cagttgtttg ccatttcttg    5700
cactcagacc tgtgtaatat atgctcctgg aaaccatcaa aaaaaaaaaa aaaaaa        5756

<210> SEQ ID NO 670
<211> LENGTH: 4373
<212> TYPE: DNA
<213> ORGANISM: Homo sapiens

<400> SEQUENCE: 670
agagtgggca ggccggggggt gagggctcgc gctccgggag ctgcacgggg ctgcgtggaa      60
agagcgccga gcggtggcgt cgttgtcgcc ccctcctcgt cgggaagaat cgtttggtct     120
```

```
cctgccgtgc ccggttcgta ttccctactc cctgccacga gccgcccgt ccgggatcct      180 ccacccgtcc aaagttgtga gggggcgccg ggcgtgctcg cggatcggcg gccgcgggcg      240
tgcggagggc tggacgagcc ctggagcgcc aggagaatgt gtgtgtgtcc cgggcccaga      300
cgaattggaa tcccagtcag aagttccagc ctgccactgt tctctgatgc catgccagca      360
ccaactcaac tgttttttcc tctcatccgt aactgtgaac tgagcaggat ctatggcact      420
gcatgttact gccaccacaa acatctctgt tgttcctcat cgtacattcc tcagagtcga      480
ctgagataca cacctcatcc agcatatgct acctttgca ggccaaagga gaactggtgg       540
cagtacaccc aaggaaggag atatgcttcc acaccacaga aatttaccct cacacctcca      600
caagtcaata gcatccttaa agctaatgaa tacagtttca aagtgccaga atttgacggc      660
aaaaatgtca gttctatcct tggatttgac agcaatcagc tgcctgcaaa tgcacccatt      720
gaggaccgga gaagtgcagc aacctgcttg cagaccagag ggatgctttt gggggttttt      780
gatggccatg caggttgtgc ttgttcccag gcagtcagtg aaagactctt ttattatatt      840
gctgtctctt tgttaccca  tgagactttg ctagagattg aaaatgcagt ggagagcggc      900
cgggcactgc tacccattct ccagtggcac aagcacccca atgattactt tagtaaggag      960
gcatccaaat tgtactttaa cagcttgagg acttactggc aagagcttat agacctcaac     1020
actggtgagt cgactgatat tgatgttaag gaggctctaa ttaatgcctt caagaggctt     1080
gataatgaca tctccttgga ggcgcaagtt ggtgatccta attctttct caactacctg      1140 gtgcttcgag tggcattttc tggagccact gcttgtgtgg cccatgtgga tggtgttgac     1200
cttcatgtgg ccaatactgg cgatagcaga gccatgctgg gtgtgcagga agaggacggc     1260
tcatggtcag cagtcacgct gtctaatgac cacaatgctc aaaatgaaag agaactagaa     1320
cggctgaaat tggaacatcc aaagagtgag gccaagagtg tcgtgaaaca ggatcggctg     1380
cttggcttgc tgatgccatt tagggcattt ggagatgtaa agttcaaatg gagcattgac     1440
cttcaaaaga gagtgataga atctggccca gaccagttga atgacaatga atataccaag     1500
tttattcctc ctaattatca cacacctcct tatctcactg ctgagccaga ggtaacttac     1560
caccgattaa ggccacagga taagtttctg tgttggcta ctgatgggtt gtgggagact      1620
atgcataggc aggatgtggt taggattgtg ggtgagtacc taactggcat gcatcaccaa     1680
cagccaatag ctgttggtgg ctacaaggtg actctgggac agatgcatgg ccttttaaca     1740
gaaaggagaa ccaaaatgtc ctcggtattt gaggatcaga acgcagcaac ccatctcatt     1800
cgccacgctg tgggcaacaa cgagtttggg actgttgatc atgagcgcct ctctaaaatg     1860
cttagtcttc ctgaagagct tgctcgaatg tacagagatg acattacaat cattgtagtt     1920
cagttcaatt ctcatgttgt aggggcgtat caaaaccaag aatagtgagt ggctctttca     1980
ctggcaattc tcaaatgata tacatttaaa gggcagattt tttaaaaaga tactactata     2040 ataacattt ccagttggtc attctaagca tttacccttt tgatactcta gctagtcagg       2100
tactccaaat tgactttgca gcagggtggc agggtcagga gagtctggtc ctgcctagct     2160
cagatttcat ggcacctgca cttgaagcaa gtcacttctt tatcacaggt gtcttgaaac     2220
attagcttct tttaccaacc tgagaaaatt aggatgacct ggcaaataag atcttgaata     2280
ggccaaaagc aagtatcttg ctgtgtgtag tctcttggtt aaagtgaaga aacagtactg     2340
ttcacacctt tcttcactga gattccagtg tacatgagaa catatattta ttgcatgatt     2400
ttctagatac acagtctatg cattattcat atacatttat tttagcctaa agtggttttc     2460
aaatccagtt cttcaagcca taaatgacca agatccaagc aatctgaatt tgttttttgtg     2520
```

```
attatttgac tggaatgctt cttaagtgga ataactatac tccgttatcc acccgatttc    2580
ctaatgtaat tgaaagattt tctattttgc cacacacttg gagacaataa gggtttttag    2640
ttttatctac tcttctattg aagttaaaga aagaaaaaaa gattttttta tttgtattaa    2700
tgaaaagctt tagtttaaaa taaggagatc cagaataaaa agaagagact gatctcttca    2760
attattgtca tctgtagcca ccagcacatc actcttatgt aatccccaaa ggcttggcat    2820
gccgtaagtg tgtggtgggt agactgctgc cggggaatcg tacttcttat ttagtaatga    2880
taagactttt cattattttt ggaattttaa agatgacata aataagttta aatatcaatt    2940
tggggagtaa ggtttaatat tgccatcggg tattgagaca ggaggaagtt tctgtttttc    3000
tccatttaga cataggtcaa ttaaaatatt tgggtttaaa atgactaaat gctttaaaca    3060
tattgtagct taagatatat gtgttaagat atatacatga gaaactttaa aaggtaacta    3120
ctgtgcatgc ctgatgctta atagaatact tagtggcatc aaatgtttgc agcagtctcc    3180
ataattatat tcagtcccctt ctaatactgt atcaatgtaa atgaaataaa tatattcaaa    3240
ttggcttttt gatatgcatc aagtggcatt ttgttcctgt gtttaatagt gatctgtata    3300
cagctgtgca catattgtca tcacttattc tagcatcact gttaaggctg tgattatgtt    3360
tgatattcac ctggatttta atacaagcca atatcagctt cccattgtgt aataacttgg    3420
gtgtttagga gtcttttcac attttttggg gatatgaact agatgttcaa gaactccttc    3480
tggactgtgg atactgaatc agtgtactat tggctgcaga atttgtttca attgaaaata    3540
gactcaggaa gattgctgct cagaatatca tataatgttt attttttgag gtgttttgt     3600 ttttatttgt gtgtttttttt ttttttaagt cagcttggaa cttttttcct gggtagtatt    3660
tgggagaggg aaaggctgta ctatatattt atttctaaat gttttgactg gcatttttc     3720 ttttaatgaa atatgtggac tgctctagca acccctattt tcagctacta tttgaatatt    3780
cttgaacacc accactgaag agtttcatat acaccaaata atgtctcatc tctatagtac    3840
agggaatata aaattggttt cctgtggtca tgatcaagat agtagtatta ttacacaaga    3900
aacttggtct gcagtctgga agcttgtctg ctctatagaa atgaaaatgc agcatgaagt    3960
tgacattgtg gaaatgaaag taattgggta ttagaaatct gaaagtactg tcatctaaaa    4020
gcaattgtga ttttattgta attggttgtc actgttgtac ggtgtctaga attaaagaat    4080
acatgtaaac tttcatggta tttagccttt cttaaatttt tttaaaattt aaactttcta    4140
acctatgtat tcaacttctg tatttatatt taatcagtgg ttcatgttat ataatacacc    4200
cttaactagt taaatggaat gttggtatgg tacagagtac catattgcta agaaaactgt    4260
cttataaaag atgtatatgt gtgaagacat gaaagtttaa tgtacagaat ggttggagaa    4320
atgcctatgg tgaattaaag cttcatatct gctttctgaa aaaaaaaaaa aaa           4373
```

<210> SEQ ID NO 671
<211> LENGTH: 4685
<212> TYPE: DNA
<213> ORGANISM: Homo sapiens

<400> SEQUENCE: 671

```
ggaggaggtg gagagtgagg ccgaggcgtg gggagcccgg gaactccctc ctcctgaagt      60
aacgcgtccc gggccggctc tgccgtcgtt gctgccgccg ggcgccccgg gacgaggagg     120
tggaggaggg agagggcccg cgggcctcgc ctccgccctc cgccacctcg agctgcggta     180
gcagcgactc atgagagcgc ggccggagga cagatttgat aatgggctgc attaaaagta     240
```

```
aagaaaacaa aagtccagcc attaaataca gacctgaaaa tactccagag cctgtcagta    300
caagtgtgag ccattatgga gcagaaccca ctacagtgtc accatgtccg tcatcttcag    360
caaagggaac agcagttaat ttcagcagtc tttccatgac accatttgga ggatcctcag    420
gggtaacgcc ttttggaggt gcatcttcct cattttcagt ggtgccaagt tcatatcctg    480
ctggtttaac aggtggtgtt actatatttg tggccttata tgattatgaa gctagaacta    540
cagaagacct ttcatttaag aagggtgaaa gatttcaaat aattaacaat acggaaggag    600
attggtggga agcaagatca atcgctacag gaaagaatgg ttatatcccg agcaattatg    660
tagcgcctgc agattccatt caggcagaag aatggtattt tggcaaaatg gggagaaaag    720
atgctgaaag attactttg aatcctggaa atcaacgagg tattttctta gtaagagaga    780
gtgaaacaac taaggtgct tattcccttt ctattcgtga ttgggatgag ataagggtg     840 acaatgtgaa acactacaaa attaggaaac ttgacaatgg tggatactat atcacaacca    900
gagcacaatt tgatactctg cagaaattgg tgaaacacta cacagaacat gctgatggtt    960
tatgccacaa gttgacaact gtgtgtccaa ctgtgaaacc tcagactcaa ggtctagcaa   1020
aagatgcttg ggaaatccct cgagaatctt tgcgactaga ggttaaacta ggacaaggat   1080
gtttcggcga agtgtggatg ggaacatgga atggaaccac gaaagtagca atcaaaacac   1140
taaaaccagg tacaatgatg ccagaagctt tccttcaaga agctcagata atgaaaaaat   1200
taagacatga taaacttgtt ccactatatg ctgttgtttc tgaagaacca atttacattg   1260
tcactgaatt tatgtcaaaa ggaagcttat tagatttcct taaggaagga gatggaaagt   1320
atttgaagct tccacagctg gttgatatgg ctgctcagat tgctgatggt atggcatata   1380
ttgaaagaat gaactatatt caccgagatc ttcgggctgc taatattctt gtaggagaaa   1440
atcttgtgtg caaatagca gactttggtt tagcaaggtt aattgaagac aatgaataca   1500
cagcaagaca aggtgcaaaa tttccaatca aatggacagc tcctgaagct gcactgtatg   1560
gtcggtttac aataaagtct gatgtctggt cattggaat tctgcaaaca gaactagtaa   1620
caaagggccg agtgccatat ccaggtatgg tgaaccgtga agtactagaa caagtggagc   1680
gaggatacag gatgccgtgc cctcagggct gtccagaatc cctccatgaa ttgatgaatc   1740
tgtgttggaa gaaggaccct gatgaaagac caacatttga atatattcag tccttcttgg   1800
aagactactt cactgctaca gagccacagt accagccagg agaaaattta taattcaagt   1860
agcctatttt atatgcacaa atctgccaaa atataaagaa cttgtgtaga ttttctacag   1920
gaatcaaaag aagaaaatct tctttactct gcatgttttt aatggtaaac tggaatccca   1980
gatatggttg cacaaaacca cttttttttc cccaagtatt aaactctaat gtaccaatga   2040
tgaatttatc agcgtatttc agggtccaaa caaaatagag ctaagatact gatgacagtg   2100
tgggtgacag catggtaatg aaggacagtg aggctcctgc ttatttataa atcatttcct   2160
ttcttttttt ccccaaagtc agaattgctc aagaaaatt atttattgtt acagataaaa   2220
cttgagagat aaaaagctat accataataa aatctaaaat taaggaatat catgggacca   2280
aataattcca ttccagtttt ttaaagtttc ttgcatttat tattctcaaa gttttttct    2340 aagttaaaca gtcagtatgc aatcttaata tatgctttct tttgcatgga catgggccag   2400 gttttcaaa aggaatataa acaggatctc aaacttgatt aaatgttaga ccacagaagt    2460
ggaatttgaa agtataatgc agtacattaa tattcatgtt catggaactg aaagaataag   2520 aacttttca cttcagtcct tttctgaaga gtttgactta gaataatgaa ggtaactaga    2580
aagtgagtta atcttgtatg aggttgcatt gatttttta ggcaatatat aattgaaact    2640
```

```
actgtccaat caaaggggaa atgttttgat ctttagatag catgcaaagt aagacccagc   2700
attttaaaag ccctttttaa aaactagact tcgtactgtg agtattgctt atatgtcctt   2760
atggggatgg gtgccacaaa tagaaaatat gaccagatca gggacttgaa tgcacttttg   2820
ctcatggtga atatagatga acagagagga aaatgtattt aaaagaaata cgagaaaaga   2880
aagtgaaagt tttacaagtt agagggatgg aaggtaatgt ttaatgttga tgtcatggag   2940
tgacagaatg gctttgctgg cactcagagc tcctcactta gctatattct gagactttga   3000
agagttataa agtataacta taaaactaat ttttcttaca cactaaatgg gtatttgttc   3060
aaaataatga agttatggct tcacattcat tgcagtggga tatggttttt atgtaaaaca   3120
tttttagaac tccagttttc aaatcatgtt tgaatctaca ttcactttt tttgttttct   3180 tttttgagac ggagtctcgc tctgtcgccc aggctggagt gcagtggcgc gatctcggct   3240
cactgcaagc tctgcctccc aggttcacac cattctcctg cctcagcctc ccgagtagct   3300
gggactacag gtgcccacca ccacgcctgg ctagtttttt gtattttag tagagacgca   3360 gtttcaccgt gttagccagg atggtctcga tctcctgacc ttgtgatctg cccgcctcgg   3420
cctcccaaag tgctgggatt acaggcgtga gccaccgcgc ccagcctaca ttcacttcta   3480
aagtctatgt aatggtggtc attttttccc ttttagaata cattaaatgg ttgatttggg   3540
gaggaaaact tattctgaat attaacggtg gtgaaagggg acagtttttt accctaaagt   3600
gcaaaagtga aacatacaaa ataagactaa tttttaagag taactcagta atttcaaaat   3660
acagatttga atagcagcat tagtggtttg agtgtctagc aaaggaaaaa ttgatgaata   3720
aaatgaaggt ctggtgtata tgttttaaaa tactctcata tagtcacact ttaaattaag   3780
ccttatatta ggcccctcta ttttcaggat ataattctta actatcatta tttacctgat   3840
tttaatcatc agattcgaaa ttctgtgcca tggcatatat gttcaaattc aaaccatttt   3900
taaaatgtga agatggactt catgcaagtt ggcagtggtt ctggtactaa aaattgtggt   3960
tgttttttct gtttacgtaa cctgcttagt attgacactc tctaccaaga gggtcttcct   4020
aagaagagtg ctgtcattat ttcctcttat caacaacttg tgacatgaga tttttttaagg   4080 gctttatgtg aactatgata ttgtaatttt tctaagcata ttcaaagggg tgacaaaatt   4140
acgtttatgt actaaatcta atcaggaaag taaggcagga aaagttgatg gtattcatta   4200
ggttttaact gaatggagca gttccttata taataacaat tgtatagtag ggataaaaca   4260
ctaacttaat gtgtattcat tttaaattgt tctgtatttt taaattgcca agaaaaacaa   4320
ctttgtaaat ttggagatat tttccaacag cttttcgtct tcagtgtctt aatgtggaag   4380 ttaacccctta ccaaaaaagg aagttggcaa aaacagcctt ctagcacact ttttaaatg   4440 aataatggta gcctaaactt aatattttta taaagtattg taatattgtt ttgtggataa   4500
ttgaaataaa aagttctcat tgaatgcacc tattaatcgt tttagttgct attcatattc   4560
tcattcgttt tttaaaaact gatatattct gaatttattc ttccattgag aaaaaaatgt   4620
tcagttactt gtaactactg agcagaattt aatcaatcct ttattaaatt cagaacatta   4680
ttgaa                                                              4685
```

<210> SEQ ID NO 672
<211> LENGTH: 6695
<212> TYPE: DNA
<213> ORGANISM: Homo sapiens

<400> SEQUENCE: 672

| | |
|---|---|
| gccctcgccg cccgcggcgc cccgagcgct ttgtgagcag atgcggagcc gagtggaggg | 60 |
| cgcgagccag atgcggggcg acagctgact tgctgagagg aggcggggag gcgcggagcg | 120 |
| cgcgtgtggt ccttgcgccg ctgacttctc cactggttcc tgggcaccga aagataaacc | 180 |
| tctcataatg aaggcccccg ctgtgcttgc acctggcatc ctcgtgctcc tgtttacctt | 240 |
| ggtgcagagg agcaatgggg agtgtaaaga ggcactagca aagtccgaga tgaatgtgaa | 300 |
| tatgaagtat cagcttccca acttcaccgc ggaaacaccc atccagaatg tcattctaca | 360 |
| tgagcatcac attttccttg gtgccactaa ctacatttat gttttaaatg aggaagacct | 420 |
| tcagaaggtt gctgagtaca agactgggcc tgtgctggaa cacccagatt gtttcccatg | 480 |
| tcaggactgc agcagcaaag ccaatttatc aggaggtgtt tggaaagata acatcaacat | 540 |
| ggctctagtt gtcgacacct actatgatga tcaactcatt agctgtggca gcgtcaacag | 600 |
| agggacctgc cagcgacatg tctttcccca caatcatact gctgacatac agtcggaggt | 660 |
| tcactgcata ttctccccac agatagaaga gcccagccag tgtcctgact gtgtggtgag | 720 |
| cgccctggga gccaaagtcc tttcatctgt aaaggaccgg ttcatcaact tctttgtagg | 780 |
| caataccata aattcttctt atttcccaga tcatccattg cattcgatat cagtgagaag | 840 |
| gctaaaggaa acgaaagatg gttttatgtt tttgacggac cagtcctaca ttgatgtttt | 900 |
| acctgagttc agagattctt accccattaa gtatgtccat gcctttgaaa gcaacaattt | 960 |
| tatttacttc ttgacggtcc aaagggaaac tctagatgct cagacttttc acacaagaat | 1020 |
| aatcaggttc tgttccataa actctggatt gcattcctac atggaaatgc ctctggagtg | 1080 |
| tattctcaca gaaaagagaa aaagagatc cacaaagaag gaagtgttta atatacttca | 1140 |
| ggctgcgtat gtcagcaagc ctggggccca gcttgctaga caaataggag ccagcctgaa | 1200 |
| tgatgacatt cttttcgggg tgttcgcaca aagcaagcca gattctgccg aaccaatgga | 1260 |
| tcgatctgcc atgtgtgcat tccctatcaa atatgtcaac gacttcttca acaagatcgt | 1320 |
| caacaaaaac aatgtgagat gtctccagca ttttttacgga cccaatcatg agcactgctt | 1380 |
| taataggaca cttctgagaa attcatcagg ctgtgaagcg cgccgtgatg aatatcgaac | 1440 |
| agagtttacc acagctttgc agcgcgttga cttattcatg ggtcaattca gcgaagtcct | 1500 |
| cttaacatct atatccacct tcattaaagg agacctcacc atagctaatc ttgggacatc | 1560 |
| agagggtcgc ttcatgcagg ttgtggtttc tcgatcagga ccatcaaccc ctcatgtgaa | 1620 |
| ttttctcctg gactcccatc cagtgtctcc agaagtgatt gtggagcata cattaaacca | 1680 |
| aaatggctac acactggtta tcactgggaa gaagatcacg aagatcccat gaatggctt | 1740 |
| gggctgcaga catttccagt cctgcagtca atgcctctct gccccaccct tgttcagtg | 1800 |
| tggctggtgc cacgacaaat gtgtgcgatc ggaggaatgc ctgagcggga catggactca | 1860 |
| acagatctgt ctgcctgcaa tctacaaggt tttcccaaat agtgcacccc ttgaaggagg | 1920 |
| gacaaggctg accatatgtg gctgggactt tggatttcgg aggaataata aatttgattt | 1980 |
| aaagaaaact agagttctcc ttggaaatga gagctgcacc ttgactttaa gtgagagcac | 2040 |
| gatgaataca ttgaaatgca cagttggtcc tgccatgaat aagcatttca atatgtccat | 2100 |
| aattatttca aatggccacg ggacaacaca atacagtaca ttctcctatg tggatcctgt | 2160 |
| aataacaagt atttcgccga aatacggtcc tatggctggt ggcactttac ttactttaac | 2220 |
| tggaaattac ctaaacagtg ggaattctag acacatttca attggtggaa aaacatgtac | 2280 |
| tttaaaaagt gtgtcaaaca gtattcttga atgttatacc ccagcccaaa ccatttcaac | 2340 |
| tgagtttgct gttaaattga aaattgactt agccaaccga gagacaagca tcttcagtta | 2400 |

```
ccgtgaagat cccattgtct atgaaattca tccaaccaaa tcttttatta gtacttggtg    2460
gaaagaacct ctcaacattg tcagttttct attttgcttt gccagtggtg ggagcacaat    2520
aacaggtgtt gggaaaaacc tgaattcagt tagtgtcccg agaatggtca taaatgtgca    2580
tgaagcagga aggaacttta cagtggcatg tcaacatcgc tctaattcag agataatctg    2640
ttgtaccact ccttccctgc aacagctgaa tctgcaactc ccctgaaaa ccaaagcctt     2700 tttcatgtta gatgggatcc tttccaaata ctttgatctc atttatgtac ataatcctgt    2760
gtttaagcct tttgaaaagc cagtgatgat ctcaatgggc aatgaaaatg tactggaaat    2820
taagggaaat gatattgacc ctgaagcagt taaaggtgaa gtgttaaaag ttggaaataa    2880
gagctgtgag aatatacact tacattctga agccgtttta tgcacggtcc ccaatgacct    2940
gctgaaattg aacagcgagc taaatataga gtggaagcaa gcaatttctt caaccgtcct    3000
tggaaaagta atagttcaac cagatcagaa tttcacagga ttgattgctg gtgttgtctc    3060
aatatcaaca gcactgttat tactacttgg gttttcctg tggctgaaaa agagaaagca     3120
aattaaagat ctgggcagtg aattagttcg ctacgatgca agagtacaca ctcctcattt    3180
ggataggctt gtaagtgccc gaagtgtaag cccaactaca gaaatggttt caaatgaatc    3240
tgtagactac cgagctactt ttccagaaga tcagtttcct aattcatctc agaacggttc    3300
atgccgacaa gtgcagtatc ctctgacaga catgtccccc atcctaacta gtggggactc    3360
tgatatatcc agtccattac tgcaaaatac tgtccacatt gacctcagtg ctctaaatcc    3420
agagctggtc caggcagtgc agcatgtagt gattgggccc agtagcctga ttgtgcattt    3480
caatgaagtc ataggaagag ggcattttgg ttgtgtatat catgggactt tgttggacaa    3540
tgatggcaag aaaattcact gtgctgtgaa atccttgaac agaatcactg acataggaga    3600
agtttcccaa tttctgaccg agggaatcat catgaaagat tttagtcatc ccaatgtcct    3660
ctcgctcctg ggaatctgcc tgcgaagtga agggtctccg ctggtggtcc taccatacat    3720
gaaacatgga gatcttcgaa atttcattcg aaatgagact cataatccaa ctgtaaaaga    3780
tcttattggc tttggtcttc aagtagccaa aggcatgaaa tatcttgcaa gcaaaaagtt    3840
tgtccacaga gacttggctg caagaaactg tatgctggat gaaaaattca cagtcaaggt    3900
tgctgatttt ggtcttgcca gagacatgta tgataaagaa tactatagtg tacacaacaa    3960
aacaggtgca aagctgccag tgaagtggat ggctttggaa agtctgcaaa ctcaaaagtt    4020
taccaccaag tcagatgtgt ggtccttttgg cgtgctcctc tgggagctga tgacaagagg    4080
agccccacct tatcctgacg taaacacctt tgatataact gtttacttgt tgcaagggag    4140
aagactccta caacccgaat actgcccaga ccccttatat gaagtaatgc taaaatgctg    4200
gcaccctaaa gccgaaatgc gcccatcctt ttctgaactg gtgtcccgga tatcagcgat    4260
cttctctact ttcattgggg agcactatgt ccatgtgaac gctacttatg tgaacgtaaa    4320
atgtgtcgct ccgtatcctt ctctgttgtc atcagaagat aacgctgatg atgaggtgga    4380
cacacgacca gcctccttct gggagacatc atagtgctag tactatgtca aagcaacagt    4440
ccacactttg tccaatggtt ttttcactgc ctgacctttta aaaggccatc gatattcttt    4500
gctcttgcca aaattgcact attataggac ttgtattgtt atttaaatta ctggattcta    4560
aggaatttct tatctgacag agcatcagaa ccagaggctt ggtcccacag gccacggacc    4620
aatggcctgc agccgtgaca acactcctgt catattggag tccaaaactt gaattctggg    4680
ttgaattttt taaaaatcag gtaccacttg atttcatatg ggaaattgaa gcaggaaata    4740
```

| | |
|---|---|
| ttgagggctt cttgatcaca gaaaactcag aagagatagt aatgctcagg acaggagcgg | 4800 |
| cagccccaga acaggccact catttagaat tctagtgttt caaaacactt ttgtgtgttg | 4860 |
| tatggtcaat aacatttttc attactgatg gtgtcattca cccattaggt aaacattccc | 4920 |
| ttttaaatgt ttgtttgttt tttgagacag gatctcactc tgttgccagg gctgtagtgc | 4980 |
| agtggtgtga tcatagctca ctgcaacctc cacctcccag gctcaagcct cccgaatagc | 5040 |
| tgggactaca ggcgcacacc accatccccg gctaatttttt gtattttttg tagagacggg | 5100 |
| gttttgccat gttgccaagg ctggtttcaa actcctggac tcaagaaatc cacccacctc | 5160 |
| agcctcccaa agtgctagga ttacaggcat gagccactgc gcccagccct tataaatttt | 5220 |
| tgtatagaca ttcctttggt tggaagaata tttataggca atacagtcaa agtttcaaaa | 5280 |
| tagcatcaca caaacatgt ttataaatga acaggatgta atgtacatag atgacattaa | 5340 |
| gaaaatttgt atgaaataat ttagtcatca tgaaatattt agttgtcata taaaaaccca | 5400 |
| ctgtttgaga atgatgctac tctgatctaa tgaatgtgaa catgtagatg ttttgtgtgt | 5460 |
| atttttttaa atgaaaactc aaaataagac aagtaatttg ttgataaata tttttaaaga | 5520 |
| taactcagca tgtttgtaaa gcaggataca ttttactaaa aggttcattg gttccaatca | 5580 |
| cagctcatag gtagagcaaa gaaagggtgg atggattgaa aagattagcc tctgtctcgg | 5640 |
| tggcaggttc ccacctcgca agcaattgga aacaaaactt tggggagtt ttattttgca | 5700 |
| ttagggtgtg tttatgtta agcaaaacat actttagaaa caaatgaaaa aggcaattga | 5760 |
| aaatcccagc tatttcacct agatggaata gccaccctga gcagaacttt gtgatgcttc | 5820 |
| attctgtgga attttgtgct tgctactgta tagtgcatgt ggtgtaggtt actctaactg | 5880 |
| gttttgtcga cgtaaacatt taaagtgtta tattttttat aaaaatgttt atttttaatg | 5940 |
| atatgagaaa aattttgtta ggccacaaaa acactgcact gtgaacattt tagaaaaggt | 6000 |
| atgtcagact gggattaatg acagcatgat tttcaatgac tgtaaattgc gataaggaaa | 6060 |
| tgtactgatt gccaatacac cccaccctca ttacatcatc aggacttgaa gccaggggtt | 6120 |
| aacccagcaa gctacaaaga gggtgtgtca cactgaaact caatagttga gtttggctgt | 6180 |
| tgttgcagga aaatgattat aactaaaagc tctctgatag tgcagagact taccagaaga | 6240 |
| cacaaggaat tgtactgaag agctattaca atccaaatat tgccgtttca taaatgtaat | 6300 |
| aagtaatact aattcacaga gtattgtaaa tggtggatga caaaagaaaa tctgctctgt | 6360 |
| ggaaagaaag aactgtctct accagggtca agagcatgaa cgcatcaata gaaagaactc | 6420 |
| gggaaacat cccatcaaca ggactacaca cttgtatata cattcttgag aacactgcaa | 6480 |
| tgtgaaaatc acgtttgcta tttataaact tgtccttaga ttaatgtgtc tggacagatt | 6540 |
| gtgggagtaa gtgattcttc taagaattag atacttgtca ctgcctatac ctgcagctga | 6600 |
| actgaatggt acttcgtatg ttaatagttg ttctgataaa tcatgcaatt aaagtaaagt | 6660 |
| gatgcaacat cttgtaaaaa aaaaaaaaa aaaaa | 6695 |

```
<210> SEQ ID NO 673
<211> LENGTH: 2302
<212> TYPE: DNA
<213> ORGANISM: Homo sapiens

<400> SEQUENCE: 673
```

| | |
|---|---|
| agttgctaag gaaatgactg cccgcagcgc ctggccccgc cgcgcaggcc gggcggggtc | 60 |
| tggagcggcg ccgtttccgc ttccgctccc tcacagctcc cgtccgtta ccgcctcctg | 120 |
| gccggcctcg cgcctttcac cggcaccttg cgtcggtcgc gccgcggggc ctgctcctgc | 180 |

```
cgcgcgcacc cccggggctt cggctccggc acgggtcgcg cccagctttc ctgcacctga      240
ggccgccggc cagccgccgc catgggtgcc tacctctccc agcccaacac ggtgaagtgc      300
tccggggacg gggtcggcgc cccgcgcctg ccgctgccct acggcttctc cgccatgcaa      360
ggctggcgcg tctccatgga ggatgctcac aactgtattc ctgagctgga cagtgagaca      420
gccatgtttt ctgtctacga tggacatgga ggggaggaag ttgccttgta ctgtgccaaa      480
tatcttcctg atatcatcaa agatcagaag gcctacaagg aaggcaagct acagaaggct      540
ttagaagatg ccttcttggc tattgacgcc aaattgacca ctgaagaagt cattaaagag      600
ctggcacaga ttgcagggcg acccactgag gatgaagatg aaaaagaaaa agtagctgat      660
gaagatgatg tggacaatga ggaggctgca ctgctgcatg aagaggctac catgactatt      720
gaagagctgc tgacacgcta cgggcagaac tgtcacaagg gccctcccca cagcaaatct      780
ggaggtggga caggcgagga accagggtcc cagggcctca atggggaggc aggacctgag      840
gactcaacta gggaaactcc ttcacaagaa aatggcccca cagccaaggc ctacacaggc      900 tttcctcca actcggaacg tgggactgag gcaggccaag ttggtgagcc tggcattccc      960
actggtgagg ctgggccttc ctgctcttca gcctctgaca agctgcctcg agttgctaag     1020
tccaagttct ttgaggacag tgaggatgag tcagatgagg cggaggaaga agaggaagac     1080
agtgaggaat gcagcgagga agaggatggc tacagcagtg aggaggcaga gaatgaggaa     1140
gatgaggatg acaccgagga ggctgaagag gacgatgaag aagaagaaga agagatgatg     1200
gtgccaggga tggaaggcaa agaggagcct ggctctgaca gtggtacaac agcggtggtg     1260
gccctgatac gagggaagca gttgattgta gccaacgcag gagactctcg ctgtgtggta     1320
tctgaggctg gcaaagcttt agacatgtcc tatgatcaca accagaggga tgaagtagaa     1380
ctagcacgca tcaagaatgc tggtggcaag gtcaccatgg atgggcgagt caacggggc      1440 ctcaacctct ccagagccat tggggaccac ttctataaga gaaacaagaa cctgccacct     1500
gaggaacaga tgatttcagc ccttcctgac atcaaggtgc tgactctcac tgacgaccat     1560
gaattcatgg tcattgcctg tgatggcatc tggaatgtga tgagcagcca ggaagttgta     1620
gatttcattc aatcaaagat cagccagcgt gatgaaaatg gggagcttcg gttattgtca     1680
tccattgtgg aagagctgct ggatcagtgc ctggcaccag acacttctgg ggatggtaca     1740
gggtgtgaca acatgacctg catcatcatt gcttcaagc cccgaaacac agcagagctc     1800
cagccagaga gtggcaagcg aaaactagag gaggtgctct ctactgaggg ggctgaagaa     1860
aatggcaaca gcgacaagaa gaagaaggcc aagcgagact agcagtcatc cagacccctg     1920
cccacctaga ctgttttctg agccctccgg acctgagact gagtttttgtc tttttccttt     1980 agccttagca gtgggtatga ggtgtgcagg gggagctggg tggcttcact ccgcccattc     2040
caaagagggc tctccctcca cactgcagcc gggagcctct gctgtccttc ccagccgcct     2100
ctgctcctcg ggctcatcac cggttctgtg cctgtgctct gttgtgttgg agggaaggac     2160
tggcggttct ggttttttact ctgtgaactt tatttaagga cattcttttt tattggcggc     2220
tccatggccc tcggccgctt gcacccgctc tctgttgtac actttcaatc aacactttt      2280 cagactaaag gccaaaacct aa                                              2302

<210> SEQ ID NO 674
<211> LENGTH: 874
<212> TYPE: DNA
<213> ORGANISM: Homo sapiens
```

<400> SEQUENCE: 674

```
ggcgtggccc ttcgagccag ctccgccccg ttgttcctgg cttgagtagg gcagagagca     60
ccgcccagca gccagtgggt tcccgcgcgt gccgagactc tgaggccttg caccccacg     120
atcccgtacg atggccgtca agaagatcgc gatcttcggc gccactggcc agaccgggct    180
caccaccctg gcgcaggcgg tgcaagcagg ttacgaagtg acagtgctgg tgcgggactc    240
ctccaggctg ccatcagagg ggccccggcc ggcccacgtg gtagtgggag atgttctgca    300
ggcagccgat gtggacaaga ccgtggctgg gcaggacgct gtcatcgtgc tgctgggcac    360
ccgcaatgac ctcagtccca cgacagtgat gtccgagggc gcccggaaca ttgtggcagc    420
catgaaggct catggtgtgg acaaggtcgt ggcctgcacc tcggctttcc tgctctggga    480
ccctaccaag gtgcccccac gactgcaggc tgtgactgat gaccacatcc ggatgcacaa    540
ggtgctgcgg gaatcaggcc tgaagtacgt ggctgtgatg ccgccacaca taggagacca    600
gccactaact ggggcgtaca cagtgaccct ggatggacga gggccctcaa gggtcatctc    660
caaacatgac ctgggccatt tcatgctgcg ctgcctcacc accgatgagt acgacggaca    720
cagcacctac ccctcccacc agtaccagta gcactctgtc cccatctggg agggtggcat    780
tctgggacat gaggagcaaa ggaaggggc aataaatgtt gagccaagag cttcaaatta    840
ctctagagaa accgacaaaa aaaaaaaaaa aaaa                                874
```

<210> SEQ ID NO 675
<211> LENGTH: 2927
<212> TYPE: DNA
<213> ORGANISM: Homo sapiens

<400> SEQUENCE: 675

```
ggaactcggg gtgcggccct cgccggcccc gggccagcgg ccaggtcccc gccctccgcg     60
ggatttactc ctgtcccgcc tcctcggatt tagcccaggc agcctgggag gttccgcagt    120
cgccgcttcc gccttgacca ggtggagctg agacctggt ctctctaggg cctaccctga    180
gctcaccatc tgaaggagag tgccatcatc cttaggaact ccttctccag acatgcttcc    240
tgaggctggc tccctgtggc tactgaagct gctccgggac atccagttgg cccagttta    300
ctggcccatc cttgaggagc ttaatgtcac tcggccagag cacttcgact ttgtaaagcc    360
tgaggacctg gacggcattg gcatgggccg gcctgcccag cgcagactgt ccgaagctct    420
gaaaaggcta cgttctgggc ctaagtctaa gaactgggtc tacaagatcc ttggaggttt    480
tgccccctgag cacaaggagc ccaccctgcc ctcggacagc ccacggcacc tccctgagcc    540
agagggggc ctcaagtgtc tgatcccaga gggtgctgtt tgcagagggg agctgctggg    600
ttcaggctgc ttcggtgtgg tgcaccgagg gctgtgacg ctgcccagtg gcaagagtgt    660
cccagtggct gtcaagtccc tccgggtagg tcccgaaggc ccgatgggca cagaactggg    720
ggacttcctg cgagaggtat cggtcatgat gaacttggag cacccacacg tgctgcgtct    780
gcacggcctt gtactgggcc agcctctgca gatggtgatg gagctggcgc cactgggctc    840
cctgcacgcg cgcctaacgg ccccggcccc gacaccccg ctgctcgtgg ccctgctctg    900
cctcttcctg cggcagctgg cgggagccat ggcgtacctg ggggcccgcg gctggtgca    960
ccgagacctc gctacgcgca acctactgct ggcgtcgccg cgcaccatca aggtggctga   1020
cttcgggctg gtgcggcctc tggcggtgc ccggggccgc tacgtcatgg gcgggccccg   1080
ccctatcccc tacgcctggt gtgccccaga gagcctgcgc cacggagcct tctcgtctgc   1140
ctcggacgtg tggatgtttg gggtgacgct gtgggagatg ttctccgggg gcgaggaacc   1200
```

-continued

```
ctgggccggg gtcccaccgt acctcatcct gcagcggctg gaggacagag cccggctgcc    1260
taggcctccc ctctgctcca gggccctcta ctccctcgcc ttgcgctgct ggccccccca    1320
ccctgccgac cggcctagct tttcccacct ggaggggctg ctgcaagagg ccgggccttc    1380
ggaagcatgt tgtgtgaggg atgtcacaga accaggcgcc ctgaggatgg agactggtga    1440
ccccatcaca gtcatcgagg gcagctcctc tttccacagc cccgactcca caatctggaa    1500
gggccagaat ggtcgcacct tcaaagtggg cagcttccca gcctcggcag tgacgctggc    1560
agatgcgggg ggcttgccag ccacccgtcc agtccacaga ggcacccctg cccggggaga    1620
tcaacaccca ggaagcatag atggagacag aaagaaggca aatctttggg atgcgccccc    1680
agcacggggc cagaggagga acatgcccct ggagaggatg aaaggcattt ccaggagtct    1740
ggagtcagtt ctgtccctcg gtcctcgtcc cacaggggt ggttcaagcc ccctgaaat     1800 tcgacaagcc agagctgtgc cccagggacc tccaggcctg cctccacgcc cacctttatc    1860
ctctagctct cctcagccca gccagccctc taggagagg cttccctggc caaaagaaa     1920 acccccacac aatcacccca tgggaatgcc tggagcccgt aaagccgctg ccctctctgg    1980
aggcctcttg tccgatcctg agttgcagag gaagattatg gaggtggagc tgagtgtgca    2040
tggggtcacc caccaggagt gccagacagc actaggagcc actggggag atgtggtttc     2100 tgccatccgg aacctcaagg tagatcagct cttccacctg agtagccggt ccagagctga    2160
ctgctggcgc atcctggagc attaccagtg ggacctctca gctgccagcc gctatgtcct    2220
ggccaggccc tgagctcagc ttctgcgggc acagacacca gcatgaaaag cctaggcccc    2280
tgagggcctg gccacatggg accaagcgga accagaacaa ggtcccgaca ggggtagacg    2340
ttccacctgg ggagatccca cctgccgtag gcacatggag gaggagccca gagttgggca    2400
ctggcaaatg tctcctccct cccatgctcc ttggcttctg aaggctgaag ctcctttggc    2460
tgggccaaga aggatctagt ctgcccacta cattctcaaa caagaggact tggaggaaaa    2520
gagctgctat acatcatatg cagaggaagc ttctacgcgc tagagaggat caaggggcca    2580
cactggacca tgtgaacagc catcctgaac tgccatcagc taccacactg gactctgcag    2640
ggcagccatc ctggatgatg aagccacca tattgacttg gggtataggc ccaaactgcc      2700
ttcgtttggt ccagggccat cgtgggtgat gacgattgct ctcttgcact caaggacatt    2760
tgatgctggt agtatggatt atgagatgga ctagcccctg cccagccca gctctcacat      2820 tccccttgt ttttcccat accaactgct tctaccctcc cctattacat acatctttca       2880
atgtccaaaa agttacaaag tttatatgaa tgtaacatat aaaaaaa                    2927
```

<210> SEQ ID NO 676
<211> LENGTH: 5475
<212> TYPE: DNA
<213> ORGANISM: Homo sapiens

<400> SEQUENCE: 676

```
actgggcgga ctccgcgccg ccggccttgt agccatttta ggaggaatcg ctggtcgcca    60 gcgagggtg cggcttcaat ttcaataact ttattggtgg cctgatctgc agaacagcca      120
tcacatcagt ggcccttgga ggaggagcg catcgcccga ggtggtcccc gacgagctgc     180
agccatggga aacaccacca gcgaccgggt gtccggggag cgccacggcg ccaaggctgc    240
acgctccgag ggcgcaggcg gccatgcccc ggggaaggag cacaagatca tggtggggag    300 tacgacgac cccagcgtgt tcagcctccc tgactccaag ctccctgggg acaaagagtt      360
```

```
tgtatcatgg cagcaggatt tggaggactc cgtaaagccc acacagcagg cccggcccac    420
tgttatccgc tggtctgaag gaggcaagga ggtcttcatc tctgggtcct tcaacaattg    480
gagcaccaag attccactga ttaagagcca taatgacttt gttgccatcc tggacctccc    540
tgagggagag caccaataca agttctttgt ggatggacag tgggttcatg atccatcaga    600
gcctgtggtt accagtcagc ttggcacaat taacaatttg atccatgtca agaaatctga    660
ttttgaggtg ttcgatgctt taaagttaga ttctatggaa agttctgaga catcttgtag    720
agacctttcc agctcacccc cagggcctta tggtcaagaa atgtatgcgt ttcgatctga    780
ggaaagattc aaatccccac ccatccttcc tcctcatcta cttcaagtta ttcttaacaa    840
agacactaat atttcttgtg acccagcctt actccctgag cccaaccatg ttatgctgaa    900
ccatctctat gcattgtcca ttaaggacag tgtgatggtc cttagcgcaa cccatcgcta    960
caagaagaag tatgttacta ctctgctata caagcccatt tgaagggatc ccttcttgcc   1020
tctaaggatt caggagaagc atctcccttg catttctgga ctgaaccagt cttacctgag   1080
actggaaggc tgatttgctt tgaggctgat atgtgtgttt cagagcctct gagtaggatg   1140
ctctgctttt gcatttgatt gcagatgaga gctttatgag ttcacggaat ttattttaag   1200
aaaaaaaaat atacatatga gaagaaggta atggaagcc tcctagcccc agctagaagt   1260
attgtttctg cctgtgggtt ttcaccaaga cctgtttggg ggcgctgcag gaataactat   1320
ataggaagat ttttcctaaa atgaaagaac agcaaactct taggatcctt gttgggtgga   1380
gattctatca ctgctacctt ggctctccaa ggaatgggct tgtgctagac cgctgcccta   1440
cttaacagct gcctcattgc aagggcagtt tttcttgcat gggttctcta tattcccaga   1500
gtatgtggca aatctgtgt tgtttatatg ataccagatg ccccacaaga acccttattc   1560
ctctcatttc acattcttcc tttaatagcc tccttcagat cccatacctg accctctct   1620 aacacaaaac ttattgggta agtgactttg aaaagttttg tggcacctga cccaccccag   1680
acactagggc tatcagaagg tctcctttt agcccagcac aggcccaggc cactttgtcg   1740
tgtttgtttt aacttctaaa gaaaatatgt ttcagcatta taagaaaggc agaatgcaga   1800
acacctacat ttttgttta gtttggtgcc aaggctcagg ctgtattggc aaattcccga   1860
aagttttccc actttgcctg gccctgcttc tgtctttct ttctcagtaa acagttctga   1920
aggcaggagt ggaacccggg agtattttca tgtctttcat ccttgaaaga ttttatgtg    1980 cctgcatttt ttttttaatt aaaaaatgcc ttttcattgg tcttaagaga ccgcattgga   2040
gaatttcagg cttttgataa atgcttcttc aaagagattt tcttctctag tctagccttc   2100
cacattctta gattaatatg gccaaccctg tacacatcac tacactaaac actgctctag   2160
ataaactgct caagttcatt taactcattt gatgcaccta aaggggttcc tcattttaaa   2220
gatttgttag gccaagaagc aagagagtat tcctagtatt cccaaccatg aaaagtatca   2280
ttctttgcac caaatgttaa caaaatcatt tgttctcct gcctcttctt tttaaaggtg   2340
tttgatgatt aagtggggtc actgaattcc atttgtggac tgaaaagtat tcaatccact   2400
tttggggttc agagataaaa cattttttcc caagtagctg gggctcttcc attttgcaga   2460
taagtcaaat aatcaacact aaaggaggct aaactgttga tgaatgagag actccctgac   2520
tgctcagatg accctagcca cactgaaagg gcacctacag gtcagtttag ctacctcctg   2580
tctttcccat gcaaagctga taacacagtt gtctttggac ttgtagacct cttggattcc   2640
aggtgtgatg gagtaaagtg tgggattgtt gttttgctgg gatgcaaata actaaatgct   2700
ttggtggtta attgctaaga gtaaatacta ctttagccat ccaaggccac cttctgcagc   2760
```

```
aaaaggcttt tgtggagaac cttttatgtt cccaaccact ttttgaatgg tgtgccattt    2820
aaaaatccag gccagatcct attataacca actctcagga tttacagcct tcagttgtac    2880
tagaattttg tttttatcca atactcatta aataagtggg ccacttagga agattcaaaa    2940
tcttggttat tacatgaagt ttgttatatt tcttgtcaac agtattgaaa tgtaatatgt    3000
atgtgttcat gtatgaaaat ttttactcca cacaggtgtt tcagtagagt ggggcaggaa    3060
aagagatctc ttcgatttct ttcaggcctg aggcttttgt gaaatgcgtc agcccctgt    3120 gacagtaggt tttgatgcta gtgatcttca gatctttctc tctggaaatg tgcagagagt    3180
gtcagtttcc caagttctga ggtaactctc agcccagatg tgaaatggga gcctaccagc    3240
tggtatagaa gggaatgggt aggaggcact gggtgctgac tcattcagca ctgtcccttt    3300
tctatactgc tgatacatcc catggttctg agaagcctta tctcagtcta tttggaagag    3360
agggaggaag agaaggaagt aacccaaagt actactcatt tatcattgta tattgattag    3420
ttaaagggat aattaattta atgctgagga gagtttgaca gattttgaaa atgagtaaag    3480
gcaaaaaaaa tttttttagc ctttattttg cttttgggaa ttttacagag tcaaagtagg    3540
cagaataaga aaatagttct tcaggagggc cgacctttaa agaacttcaa catagtttcg    3600
gaattgtggg gaagagaaga gtgactgagc tgagaagtaa taatagaata aagggttgag    3660
taacttacaa ctgaaaatga tctcttttaa aaagaaatta aatcagacac cacatggtgg    3720
tgtccttgga tctcactgta cagaattagc agtgtataac catcttctct tttcatcttg    3780
ttccaattct ctcctctttc ctttccattc tgctttaagc tcatgtgtca ggcagacttt    3840
accagagtgt cagacattac ctaaaacaca tacgttagcc atgctgctgg tatggagaaa    3900
ttccacacca tgattattag cctcctttaa gctgaatggg atttaaccat tctaggcaac    3960
acccctgaag ggcataccta acctcaatag tgttggcttt taaaacgtat gtttgtatgg    4020
tagagaaact ttgtaaaaga agaatccaag agaagtttgt gaggatccta caaacccagg    4080
cccactcact ttgctctaat tcttttctagt atcttgtaga tctaatgggt ctgggataaa    4140
aactttgaaa agtgtcaata ttccatgtat gctgctgaaa tgaagttaag tttggaaaga    4200
agtgatacct ctagactggg tttatattaa tctgggatat aaatgaagaa gacatactaa    4260
tagaactcct tgcttttaat tggggaaata gggctttaat aattttgacc tcaactaaaa    4320
atgatatgca atagtctctg tgtgtgtttg aaatacattg tgttctcaga gatttctaca    4380
ttctcacgtt ctagtgattt ggggcatggg cttaatagca gatgtacagt gtattcctgc    4440
attattgtga ttcccttaa agcccagttc ttgctgtctt ctaccagggg ctgctgactc    4500
cagttaccca tggaatgcag gacctgggag gggtagccat tagggtcttt caaaactctt    4560
tggatctaag catttgtctc tccttaagtg ccaatcacaa ttggatatgg aaggactgtg    4620
atttctgcaa tgaacccaaa cttttagagt aaaaagccaa atttaaatta taagaaagaa    4680
gggaaaaaag agaaaaactc aagtctatta cttgtagagt ccaattctta gcaatggaat    4740
cgctctagga ttctagtttg ggctttgtct ggatttgctt ttctcagttg tgctttgaag    4800
tgaataagct ttgttacaaa ttaattttt attagttcca atattagttg gagttaactt    4860
gaattgattg tatgtagcac agcacttttg cagtaagatt ggtgtgaaat actaaacact    4920
atggattttg taggtgtcag gttaaatggt caagggatac ctacattaag tcatatatta    4980
ggtattgatg atcttacttc ttttctgttc ccctgtacaa aacacttacc taacccagct    5040
tgtggtttta ggacagccaa agctcactgt tgttggttag tcctaatcac tacacgggtc    5100
```

| | |
|---|---|
| tcataaatga gacttgtttg aattttggta cattggagca tgttggttgg tattacacgg | 5160 |
| cagcatttcg aatgagtgca gctctgtgtc tgtcagaaag gagagataag actactttga | 5220 |
| agggaattaa atatgtgagt cctctttta atggtgcttt ttgtaacctt taatgctgag | 5280 |
| gtacagagct gcttttcaat atttcataaa ggagtggcag acaagagtgg attttaaagc | 5340 |
| tgttcttcaa acgtaatttg tcactggact ctgacacacc tggaaattat atgatatgat | 5400 |
| acatacagaa atgttgtggg ttttttccat aaaactttaa taaagtatt atacagcaat | 5460 |
| aaaaaaaaaa aaaaa | 5475 |

<210> SEQ ID NO 677
<211> LENGTH: 10404
<212> TYPE: DNA
<213> ORGANISM: Homo sapiens

<400> SEQUENCE: 677

| | |
|---|---|
| gcgccgctca cgtggtccgt ccccagcccc gtcgccggcg gaggcgggcg cgggcgcgtc | 60 |
| cctgtggcca gtcacccgga ggagttggtc gcacaattat gaaagactcg gcttctgctg | 120 |
| ctagcgccgg agctgagtta gttctgagaa ggtttccctg ggcgttcctt gtccggcggc | 180 |
| ctctgctgcc gcctccggag acgcttcccg atagatggct acaggccgcg gaggaggagg | 240 |
| aggtggagtt gctgcccttc cggagtccgc cccgtgagga aatgtccca gaaatcctgg | 300 |
| atagaaagca ctttgaccaa gagggaatgt gtatatatta taccaagttc caaggaccct | 360 |
| cacagatgcc ttccaggatg tcaaatttgt cagcaactcg tcaggtgttt ttgtggtcgc | 420 |
| ttggtcaagc aacatgcttg ttttactgca agtcttgcca tgaaatactc agatgtgaaa | 480 |
| ttgggtgacc attttaatca ggcaatagaa gaatggtctg tggaaaagca tacagaacag | 540 |
| agcccaacga atgcttatgg agtcataaat tttcaagggg gttctcattc ctacagagct | 600 |
| aagtatgtga ggctatcata tgacaccaaa cctgaagtca ttctgcaact tctgcttaaa | 660 |
| gaatggcaaa tggagttacc caaacttgtt atctctgtac atgggggcat gcagaaattt | 720 |
| gagcttcacc cacgaatcaa gcagttgctt ggaaaaggtc ttattaaagc tgcagttaca | 780 |
| actggagcct ggatttttaac tggaggagta acacaggtg tggcaaaaca tgttggagat | 840 |
| gccctcaaag aacatgcttc cagatcatct cgaaagattt gcactatcgg aatagctcca | 900 |
| tggggagtga ttgaaaacag aaatgatctt gttgggagag atgtggttgc tccttatcaa | 960 |
| accttattga accccctgag caaattgaat gttttgaata atctgcattc ccatttcata | 1020 |
| ttggtggatg atggcactgt tggaaagtat ggggcggaag tcagactgag aagagaactt | 1080 |
| gaaaaaacta ttaatcagca aagaattcat gctaggattg ccagggtgt ccctgtggtg | 1140 |
| gcacttatat ttgagggtgg gccaaatgtt atcctcacag ttcttgaata ccttcaggaa | 1200 |
| agcccccctg ttccagtagt tgtgtgtgaa ggaacaggca gagctgcaga tctgctagcg | 1260 |
| tatattcata acaaacaga agaaggaggg aatcttcctg atgcagcaga gcccgatatt | 1320 |
| atttccacta tcaaaaaaac atttaacttt ggccagaatg aagcacttca tttatttcaa | 1380 |
| acactgatgg agtgcatgaa agaaaggag cttatcactg ttttccatat gggtcagat | 1440 |
| gaacatcaag atatagatgt agcaatactt actgcactgc taaaaggtac taatgcatct | 1500 |
| gcatttgacc agcttatcct tacattggca tgggatagag ttgacattgc caaaaatcat | 1560 |
| gtatttgttt atggacagca gtggctggtt ggatccttgg aacaagctat gcttgatgct | 1620 |
| cttgtaatgg atagagttgc atttgtaaaa cttcttattg aaaatggagt aagcatgcat | 1680 |
| aaattcctta ccattccgag actggaagaa ctttacaaca ctaaacaagg tccaactaat | 1740 |

-continued

```
ccaatgctgt tcatcttgt tcgagacgtc aaacagggaa atcttcctcc aggatataag    1800
atcactctga ttgatatagg acttgttatt gaatatctca tgggaggaac ctacagatgc    1860
acctatacta ggaaacgttt tcgattaata tataatagtc ttggtggaaa taatcggagg    1920
tctggccgaa atacctccag cagcactcct cagttgcgaa agagtcatga atcttttggc    1980
aatagggcag ataaaaagga aaaatgagg cataaccatt tcattaagac agcacagccc    2040
taccgaccaa agattgatac agttatgaa gaaggaaaga agaaaagaac caaagatgaa    2100
attgtagaca ttgatgatcc agaaaccaag cgctttcctt atccacttaa tgaactttta    2160
atttgggctt gccttatgaa gaggcaggtc atggcccgtt ttttatggca acatggtgaa    2220
gaatcaatgg ctaaagcatt agttgcctgt aagatctatc gttcaatggc atatgaagca    2280
aagcagagtg acctggtaga tgatacttca gaagaactaa aacagtattc caatgatttt    2340
ggtcagttgg ccgttgaatt attagaacag tccttcagac aagatgaaac catggctatg    2400
aaattgctca cttatgaact gaagaactgg agtaattcaa cctgccttaa gttagcagtt    2460
tcttcaagac ttagaccttt tgtagctcac acctgtacac aaatgttgtt atctgatatg    2520
tggatgggaa ggctgaatat gaggaaaaat tcctggtaca aggtcatact aagcatttta    2580
gttccacctg ccatattgct gttagagtat aaaactaagg ctgaaatgtc ccatatccca    2640
caatctcaag atgctcatca gatgacaatg gatgacagcg aaaacaactt tcagaacata    2700
acagaagaga tccccatgga agtgtttaaa gaagtacgga ttttggatag taatgaagga    2760
aagaatgaga tggagataca aatgaaatca aaaaagcttc caattacgcg aaagtttat    2820 gccttttatc atgcaccaat tgtaaaattc tggtttaaca cgttggcata tttaggattt    2880
ctgatgcttt atacatttgt ggttcttgta caaatggaac agttaccttc agttcaagaa    2940
tggattgtta ttgcttatat ttttacttat gccattgaga agtccgtga gatctttatg    3000 tctgaagctg ggaaagtaaa ccagaagatt aaagtatggt ttagtgatta cttcaacatc    3060
agtgatacaa ttgccataat ttctttcttc attggatttg gactaagatt tggagcaaaa    3120
tggaactttg caaatgcata tgataatcat gttttttgtgg ctggaagatt aatttactgt    3180
cttaacataa tattttggta tgtgcgtttg ctagattttc tagctgtaaa tcaacaggca    3240
ggaccttatg taatgatgat tggaaaaatg gtggccaata tgttctacat tgtagtgatt    3300
atggctcttt tattacttag ttttggtgtt cccagaaagg caatacttta tcctcatgaa    3360
gcaccatctt ggactcttgc taaagatata gttttttcacc catactggat gattttggt    3420 gaagtttatg catacgaaat tgatgtgtgt gcaaatgatt ctgttatccc tcaaatctgt    3480
ggtcctggga cgtggttgac tccatttctt caagcagtct acctctttgt acagtatatc    3540
attatggtta atcttcttat tgcatttttc aacaatgtgt atttacaagt gaaggcaatt    3600
tccaatattg tatggaagta ccagcgttat catttttatta tggcttatca tgagaaacca    3660
gttctgcctc ctccacttat cattcttagc catatagttt tctctgttttg ctgcatatgt    3720 aagagaagaa agaaagataa gacttccgat ggaccaaaac ttttcttaac agaagaagat    3780
caaaagaaac ttcatgattt tgaagagcag tgtgttgaaa tgtatttcaa tgaaaaagat    3840
gacaaatttc attctgggag tgaagagaga attcgtgtcc cttttgaaag agtggaacag    3900
atgtgcattc agattaaaga agttggagat cgtgtcaact acataaaaag atcattacaa    3960
tcattagatt ctcaaattgg ccatttgcaa gatctttcag ccctgacggt agatacatta    4020 aaacactca ctgcccagaa agcgtcggaa gctagcaaag ttcataatga aatcacacga    4080
```

```
gaactgagca tttccaaaca cttggctcaa aaccttattg atgatggtcc tgtaagacct    4140
tctgtatgga aaaagcatgg tgttgtaaat acacttagct cctctcttcc tcaaggtgat    4200
cttgaaagta ataatccttt tcattgtaat attttaatga agatgacaa agatccccag     4260 tgtaatatat ttggtcaaga cttacctgca gtacccaga gaaaagaatt taattttcca    4320
gaggctggtt cctcttctgg tgccttattc ccaagtgctg tttcccctcc agaactgcga    4380
cagagactac atggggtaga actcttaaaa atatttaata aaaatcaaaa attaggcagt    4440
tcatctacta gcataccaca tctgtcatcc ccaccaacca aattttttgt tagtacacca    4500
tctcagccaa gttgcaaaag ccacttggaa actggaacca agatcaaga aactgtttgc     4560 tctaaagcta cagaaggaga taatacagaa tttggagcat tgtaggaca cagagatagc     4620 atggatttac agaggtttaa agaaacatca aacaagataa aaatactatc aataacaat    4680 acttctgaaa acactttgaa acgagtgagt tctcttgctg gatttactga ctgtcacaga     4740
acttccattc ctgttcattc aaaacaagca gaaaaaatca gtagaaggcc atctaccgaa     4800
gacactcatg aagtagattc caaagcagct ttaataccgg attggttaca agatagacca    4860
tcaaacagag aaatgccatc tgaagaagga acattaaatg gtctcacttc tccatttaag    4920
ccagctatgg atacaaatta ctattattca gctgtggaaa gaaataactt gatgaggtta    4980
tcacagagca ttccatttac acctgtgcct ccaagagggg agcctgtcac agtgtatcgt    5040
ttggaagaga gttcacccaa catactaaat aacagcatgt cttcttggtc acaactaggc    5100
ctctgtgcca aaatagagtt tttaagcaaa gaggagatgg gaggaggttt acgaagagct    5160
gtcaaagtac agtgtacctg gtcagaacat gatatcctca aatcagggca tctttatatt    5220
atcaaatctt ttcttccaga ggtggttaat acatggtcaa gtatttacaa agaagataca    5280
gttctgcatc tctgtctgag agaaattcaa aacagagag cagcacaaaa gcttacgttt    5340
gcctttaatc aaatgaaacc caaatccata ccatattctc caaggttcct tgaagttttc    5400
ctgctgtatt gccattcagc aggacagtgg tttgctgtgg aagaatgtat gactggagaa    5460
tttagaaaat acaacaataa taatggagat gagattattc caactaatac tctggaagag    5520
atcatgctag cctttagcca ctggacttac gaatatacaa gagggagtt actggtactt    5580 gatttgcaag gtgttggtga aaatttgact gacccatctg tgataaaagc agaagaaaag    5640
agatcctgtg atatggtttt tggcccagca aatctaggag aagatgcaat taaaaacttc    5700
agagcaaaac atcactgtaa ttcttgctgt agaaagctta aacttccaga tctgaagagg    5760
aatgattata cgcctgataa aattatattt cctcaggatg agccttcaga tttgaatctt    5820
cagcctggaa attccaccaa agaatcagaa tcaactaatt ctgttcgtct gatgttataa    5880
tattaatatt actgaatcat tggttttgcc tgcacctcac agaaatgtta ctgtgtcact    5940
tttccctcgg gaggaaattg tttggtaata tagaaaggtg tatgcaagtt gaatttgctg    6000
actccagcac agttaaaagg tcaatattct tttgacctga ttaatcagtc agaaagtccc    6060
tataggatag agctggcagc tgagaaattt taaaggtaat tgataattag tatttataac    6120
tttttaaagg gctctttgta tagcagagga tctcatttga cttgttttg atgagggtga    6180 tgctctctct tatgtggtac aataccatta accaaggta ggtgtccatg cagattttat     6240
tggcagctgt tttattgcca ttcaactagg gaaatgaaga aatcacgcag ccttttggtt    6300
aaatggcagt caaattttc ctcagtgtat ttagtgtgtt cagtgatgat atcactggtt     6360
cccaactaga tgcttgttgg ccacgggaag ggaaatgact tgttctaatt ctaggttcac    6420
agaggtatga gaagcctgaa ctgaagacca ttttcaagag ggacggtatt tatgaatcag    6480
```

```
ggttaggctc catatttaaa gatagagcca gttttttttt ttaaatagaa cccaaattgt   6540
gtaaaaatgt taattgggtt ttttaaacat tgttttatca agtcactgtt aagtagaaga   6600
aagccatggt aaactgatac ataacctaaa ttataaaagc agaaacctaa ctcactcgtc   6660
aagggaagtt acctttgag gaaagttaaa gtactttttt ccctatctgt atctatagca    6720
acaacccaga acttacaaac ttctccaaag attttattga ttgttatatc aaatcagaat   6780
gtaaacatga actcttgcat atatttaaaa ttgtgttgga acatttgaac atgaatgctg   6840
tttgtggtac ttaagaaatt aattcagttg gattatcatt atgtgatact ggcagattgc   6900
agtgcaacct tatgccaata aaatgtaatt taacagcccc agatattgtt gaatattcaa   6960
caataacaag aaaagctttt catctaagtt ttatgcttta attttttttc tttttttttc   7020 ttttctttt gtttccttgg tactaatttt aatttttatt tggaagggag cagtataaag    7080
cttatttgta tttagtagtg tatctcatag atacagacaa ggcaagagat gataagctgt   7140
ttaaatagtg tttaatattg attggggtg gggagaaaga aaaagtgtat tacttaaaga    7200
tactatatac gttttgtata tcattaaatc tttaaagaa atgaaataaa tttattgttt     7260
acagatgttt agtgagttta atcattctga aaaattatct gacattttca gggtgtcaat   7320
ttgagtatca gttttttaa atgaaccatt tgtatacctg tgcttttgat ctcctgtcct    7380
gtacaatgtt taaattaata ctgatttctt actgtcttct tagaaatctg ttttttgtta   7440
ggccaaaaaa gggcaatatg ggctgtctgt tgatttttaa ttttatattg attattttca   7500
caggattata atagtagcta tactttttt tttttttttt tttttgagac ggagtctcgc    7560
tctgttgctt gggctggagt gcagtggtgc gatctcagct caccacaacc gccgccttcc   7620
gggtttaagt gattctcctg cctcagcctc ccgagtagct gggactacag gcacacgcca   7680
ccatgcccag ctaattttta tattttagt agagacaggg tttcactatg ttggccagtg    7740
tggtcacaaa ctcctgacct tgtgagccac cgcacctggc tgctaacact tatttagtgc   7800
ctactgtgta ccagacatta tctaagtat ttcacatata ttaacctact taatccttat    7860
aacaatgtta taagaaata ggtgttatta tcctgttttg cagatttgaa agtcaaggtg    7920
ctagagaggt aaagtaacgt ccataagatt cttacgttta tttaataata agtagcaacg   7980
gtaggatttg aacccaggct ggctgccttt catctatact gttttgtttt tgtttgttt    8040 tgtttgtttt tgttttgttt gtcttggtgg ggcatggtgg ctcatgcctg taatcccagc   8100
acttcgggag gccaaggcag gtggatcact tgggctcagg agtttgagac cagcctgggc   8160
aacatggcaa aatcctatct ctgctaaaaa aaaaaataca aaaattaggc caggtgcagt   8220
ggctcatgcc tgtaatccca gcactttggg aggccaaggt gggcggatca caaggtcagg   8280
agttcgagac cagcctgacc aacatagtga accccgtct ctactaaaaa tacaaaaaat    8340
tagctgggca tggcggtgag tgcctgtaat cccagctact caggagtctg aggcaggaga   8400
attgcttgaa cctgggaggt ggaggttgca gtgagctgag atcgtgccat tgcgctccag   8460
cctgggcaac agtgcgagac tccgtcaaaa aaaaaaaat aactggatgt gatggtgtgc    8520
acctgtagtt ccagctactt gggagactga ggtgggagga tcacttgagc ctgggagact   8580
gaggcagcag tgagctgaga tcatgccact gctttccaac ctgggcaaca gagtgagatc   8640
ctgtctcaga aagaaaaaaa aaaaaagac aacctcttgc tctgttgccc aggctggagt    8700
gtagtagcgt gatcatagct cactgcagcc gtaaactcct gggctcaagc aatcctcctg   8760
ccactgcctc ttgattaggt ggaaccacag gcatgcacca ccacacgtac ctaatttat    8820
```

```
atatatattt ttttatttt catttttatt tattttgtt tttttgagtt gaagtctcac    8880
tctgttgccc aggccggagt acagtggcac aatcttggct cactgcaacc tctgcctccc   8940
aagatcaagc aattctcgtg cttcagcctc caaagtagct gagattacag gtacccacca   9000
taatgcctgg ctgattttg tattttcgt agagacaagg tttcaccttg ttggccaggc    9060
tgatctcaaa ctcctgacct caagtgatcc acctccccg gctacccaaa gtactgggat   9120
tataggtgtg agccaccatg cctgggtaac acccaactaa tttaaatat atatttgta   9180
gagatggggt ctagccttgt tgcccacgct ggtctcaaat tcctgggctc aagtgatcct   9240
ctcgcctgag cttcccaaag tggtagaatt gcaggcatga attgctgcac ccagcctcat   9300
ctgtgctgtg aattatgtgc tgtattgact ctcaagcatg atgaccattg gtggtttctg   9360
taccatttcc tgttacttta ctgaaacaca cctactccat taacttcttg ggttaagtct   9420
agaaagtaac agtttacttg taaaccacat ttcttatccc caataagtat ttttttaaga   9480
ttattaaagt tcattattac taccctatga tgtgaaagtg tcatttgctt aatcttttta   9540
atttttatt ctcaacctca tcttactgaa gagaataaaa ctctttacc atattcttaa    9600
aatgtggaat tctcggccag gtgcagtggc tcacgcctgt aattccatca ctttgggagg   9660
ccaaggtggg tggatcatct gaggtcagga gttcaagacc agcctggcca acatggtgaa   9720
accccgtctc tactaaaaat acaaaaatta tctgggtgtg gtggcgcgtg cctgtaggcc   9780
cagctactca ggaggctgag gcaggagaat tgcttgaacc caagaggtgg aggttgcagt   9840
gagcctagat tgctgccact gcactccagc ctgggtgaca gcagaactct gtctcaaaaa   9900
aaagatgtgg aattcttttc tgcaaatgtt ctctaatagt ataccttctt cagtctgtcg   9960
atatatgtat gctattattt tacaagtaat acatgttgat tgtattggaa attatagaaa  10020
agattatatt ggattgttta gaaaatattt ttaaatgtga agaaaaatat aaaaattact  10080
cccttgttcc actttcccca ctctcaagtc agactatgtt gttttcatag ttagtagcta  10140
gcagtctacc ccactagatt atatgcttca cagagggaag ggaccctcaa gacttcactg  10200
gattgagtag cacccaatac cttgcttgct gcctggtttg tgatgggcat actgtaagaa  10260
aaaaaaatct gaatgacaaa atgttttttcc ataataccag acttcctctt gaagagatgg  10320
gtcgtaatgt tgtagtctta catgcttacg tagacaatca aagcaagaat actcaataaa  10380
tggctattta ccacttgaaa gaaa                                         10404

<210> SEQ ID NO 678
<211> LENGTH: 2361
<212> TYPE: DNA
<213> ORGANISM: Homo sapiens

<400> SEQUENCE: 678
aaggcggaag ggtggggagg gcggcgctcg gggcggagg cccggccggg tccgctagga      60
cagcggggcc gctgggaagt tgtgagagcg gcgctcgggg gcgcgcttgc gtgcacgagg    120
gcccgggccg cgagcagccg cggccgtccc ggtcgccacc cttagcagcg gtcgcggtcg    180
gtgccgaagc ggtgttcccc gccttagccg ctggcgcctc caagagagc ggccggtggg    240
ccctcgtcct gtcagtggcg tcggaggccg gcgctgcggt ggccgcgccc ttctggtgct    300
cggacaccgc tgaggagccg gggccgggca cggctggctg acggctccgg gcagctaagg    360
ctgcccgagg agaaggcggc ggccgcggcg taggcgcacg tccggcgggc tcctggagcc    420
tggaggaggc cgagggggacc atgtccggga ggcgcttcca cctctccacc accgaccgcg    480
tcatcaaagc tgtcccctt cctccaaccc aacggcttac tttcaaggaa gtatttgaga    540
```

```
atgggaaacc taaagttgat gttttaaaaa accatttggt aaaggaagga cgactggaag    600
aggaagtagc cttaaagata atcaatgatg gggctgccat cctgaggcaa gagaagacta    660
tgatagaagt agatgctcca atcacagtat gtggtgatat tcatggacaa ttctttgacc    720
taatgaagtt atttgaagtt ggaggatcac ctagtaacac acgctacctc tttctgggtg    780
actatgtgga cagaggctat ttcagtatag agtgtgtgct gtatttatgg agtttaaaga    840
ttaatcatcc caaaacattg tttctgcttc ggggaaatca tgaatgcagg catcttacag    900
actatttcac cttcaaacag gaatgtcgaa tcaaatattc ggaacaggtg tatgatgcct    960
gtatggagac atttgactgt cttcctcttg ctgccctctt aaaccagcag tttctctgtg   1020
tacatggagg aatgtcacct gaaattactt ctttagatga cattaggaaa ttagacaggt   1080
ttacggaacc tcccgccttt ggacctgtgt gtgacctgct ttggtctgat ccctcagagg   1140
attatggcaa tgagaagacc ttggagcact atacccacaa cactgtccga gggtgctctt   1200
atttctacag ttaccctgca gtttgtgaat ttttgcagaa caataattta ctatcaatta   1260
tcagagccca tgaagcccaa gatgctgggt atcgaatgta caggaagagc caagccacag   1320
gctttccatc acttattaca attttctctg cccccaatta cctagatgtc tataacaata   1380
aagctgctgt gttgaaatat gaaaacaatg tcatgaatat caggcagttt aactgttctc   1440
cacaccccta ctggcttcca aactttatgg atgttttcac atggtctttg ccttttgttg   1500
gggaaaaagt cacagagatg ctggtaaatg tgctcaacat atgctctgat gacgaactga   1560
tttctgatga tgaagcagaa gatcactaca ttccaagcta tcagaaagga agcactacag   1620
ttcgtaagga gatcatcagg aataagatca gagccattgg gaagatggca cgggtctttt   1680
caattcttcg gcaagaaagt gagagtgtgc tgactctcaa gggcctgact cccacaggca   1740
cactccctct gggcgtcctc tcaggaggca agcagactat cgagacagcc acagtagaag   1800
cggtagaggc ccgggaagcc atcagagggt tctcgcttca gcacaagatc cggagttttg   1860
aagaagcgcg aggtctggac cgaattaatg agcgaatgcc accccgaaag gatagcatac   1920
acgctggtgg gccaatgaaa tctgtaacct cagcacactc acatgctgcg cacaggagcg   1980
accaagggaa gaaagcccat tcatgactta gagtcctgcc gtggctcagg tggatctaaa   2040
actcaagaac aaattctatt tatttattat tggaaaatga aaagcaactc aaaacaactt   2100
caacgtggag gtgcatttat aattcagtct gcatttattc tgtaaaaagg tggctgtttt   2160
ataaattctt ttaatttatg ttcaatatat ataaaaagtg catctgtttt gttttttccct   2220 tttttctcca taatttaag aaatgaatct gattgttgtc aacacatttg tgaagtcttg   2280
tgctataaag gggaacttcc cctaataaaa gggccttgga aacctcaaac ctgggtttct   2340
gacttgaaaa aaaaaaaaa a                                              2361
```

<210> SEQ ID NO 679
<211> LENGTH: 24
<212> TYPE: DNA
<213> ORGANISM: Homo sapiens

<400> SEQUENCE: 679
cacccacatc agtgcaatgt attt                                            24

<210> SEQ ID NO 680
<211> LENGTH: 8
<212> TYPE: PRT
<213> ORGANISM: Homo sapiens

```
<400> SEQUENCE: 680

His Pro His Gln Cys Asn Val Phe
1               5

<210> SEQ ID NO 681
<211> LENGTH: 24
<212> TYPE: DNA
<213> ORGANISM: Artificial Sequence
<220> FEATURE:
<223> OTHER INFORMATION: Mutant Ppp2r2d cDNA

<400> SEQUENCE: 681
catccccacc aatgtaacgt gttt                                          24
```